US011421231B2

(12) United States Patent
Hung et al.

(10) Patent No.: US 11,421,231 B2
(45) Date of Patent: Aug. 23, 2022

(54) MODULATION OF HUNTINGTON EXPRESSION

(71) Applicant: Ionis Pharmaceuticals, Inc., Carlsbad, CA (US)

(72) Inventors: Gene Hung, Carlsbad, CA (US); C. Frank Bennett, Carlsbad, CA (US); Susan M. Freier, San Diego, CA (US); Holly Kordasiewicz, San Diego, CA (US); Lisa Stanek, Cambridge, MA (US); Don W. Cleveland, Del Mar, CA (US); Seng H. Cheng, Natick, MA (US); Lamya Shihabuddin, Brighton, MA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 123 days.

(21) Appl. No.: 17/068,185

(22) Filed: Oct. 12, 2020

(65) Prior Publication Data
US 2021/0139900 A1 May 13, 2021

Related U.S. Application Data

(60) Division of application No. 16/801,431, filed on Feb. 26, 2020, now Pat. No. 10,837,016, which is a division of application No. 16/270,983, filed on Feb. 8, 2019, now Pat. No. 10,619,158, which is a continuation of application No. 15/596,249, filed on May 16, 2017, now Pat. No. 10,202,603, which is a continuation of application No. 15/005,712, filed on Jan. 25, 2016, now Pat. No. 9,683,236, which is a continuation of application No. 14/528,656, filed on Oct. 30, 2014, now Pat. No. 9,273,315, which is a continuation of application No. 13/395,188, filed as application No. PCT/US2010/048532 on Sep. 10, 2010, now Pat. No. 8,906,873.

(60) Provisional application No. 61/241,853, filed on Sep. 11, 2009.

(51) Int. Cl.
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/113* (2013.01); *C12N 2310/315* (2013.01); *C12N 2310/321* (2013.01); *C12N 2310/3341* (2013.01); *C12N 2310/341* (2013.01); *C12N 2310/345* (2013.01); *C12N 2310/346* (2013.01)

(58) Field of Classification Search
None
See application file for complete search history.

(56) References Cited

U.S. PATENT DOCUMENTS

| 5,595,756 | A | 1/1997 | Bally et al. |
|---|---|---|---|
| 5,686,288 | A | 11/1997 | MacDonald et al. |
| 5,700,922 | A | 12/1997 | Cook |
| 5,801,154 | A | 9/1998 | Baracchini et al. |
| 5,998,148 | A | 12/1999 | Bennett et al. |
| 6,043,060 | A | 3/2000 | Imanishi |
| 6,147,200 | A | 11/2000 | Manoharan et al. |
| 6,582,908 | B2 | 6/2003 | Fodor et al. |
| 6,670,461 | B1 | 12/2003 | Wengel et al. |
| 7,320,965 | B2 | 1/2008 | Sah et al. |
| 7,374,927 | B2 | 5/2008 | Palma et al. |
| 2001/0053519 | A1 | 12/2001 | Fodor et al. |
| 2003/0109476 | A1 | 6/2003 | Kmiec |
| 2003/0144242 | A1 | 7/2003 | Ward et al. |
| 2003/0228597 | A1 | 12/2003 | Cowsert et al. |
| 2004/0092465 | A1 | 5/2004 | Dobie |
| 2004/0096880 | A1 | 5/2004 | Kmiec |
| 2004/0137471 | A1 | 7/2004 | Vickers et al. |
| 2004/0146902 | A1 | 7/2004 | Ecker et al. |
| 2005/0042646 | A1 | 2/2005 | Davidson |
| 2005/0096284 | A1 | 5/2005 | McSwiggen |
| 2005/0101013 | A1 | 5/2005 | Freier et al. |
| 2005/0191638 | A1 | 9/2005 | McSwiggen |
| 2005/0245475 | A1 | 11/2005 | Khvorova et al. |
| 2005/0255086 | A1 | 11/2005 | Davidson |
| 2005/0255487 | A1 | 11/2005 | Khvorova et al. |
| 2006/0051769 | A1 | 3/2006 | Barts |
| 2007/0031844 | A1 | 2/2007 | Khvorova et al. |
| 2007/0099860 | A1 | 5/2007 | Sah |
| 2007/0299027 | A1 | 12/2007 | Hung et al. |
| 2008/0015158 | A1 | 1/2008 | Ichiro |
| 2008/0039415 | A1 | 2/2008 | Stewart et al. |
| 2008/0039418 | A1 | 2/2008 | Freier |

(Continued)

FOREIGN PATENT DOCUMENTS

| CA | 2526893 | 11/2004 |
|---|---|---|
| JP | 2009-513144 | 4/2009 |

(Continued)

OTHER PUBLICATIONS

Anderson et al., "An Overview of Psychiatric Symptoms in Huntington's Disease" Current Psychiatry Reports (2001) 3:379-388.

(Continued)

*Primary Examiner* — Kimberly Chong
(74) *Attorney, Agent, or Firm* — McDonnell Boehnen Hulbert & Berghoff LLP

(57) ABSTRACT

Provided herein are methods, compounds, and compositions for reducing expression of huntingtin mRNA and protein in an animal. Such methods, compounds, and compositions are useful to treat, prevent, delay, or ameliorate Huntington's disease, or a symptom thereof.

16 Claims, 10 Drawing Sheets

Specification includes a Sequence Listing.

(56) References Cited

U.S. PATENT DOCUMENTS

| | | |
|---|---|---|
| 2008/0274989 A1 | 11/2008 | Davidson et al. |
| 2009/0092981 A1 | 4/2009 | Swayze et al. |

FOREIGN PATENT DOCUMENTS

| | | |
|---|---|---|
| JP | 2009-524431 | 7/2009 |
| RU | 2297833 | 4/2007 |
| WO | WO 1994/026764 | 11/1994 |
| WO | WO 1999/050409 | 10/1999 |
| WO | WO 2000/003720 | 1/2000 |
| WO | WO 2001/079283 | 10/2001 |
| WO | WO 2003/013437 | 2/2003 |
| WO | WO 2003/009835 | 8/2003 |
| WO | WO 2003/064625 | 8/2003 |
| WO | WO 2004/044123 | 5/2004 |
| WO | WO 2004/048601 | 6/2004 |
| WO | WO 2004/101787 | 11/2004 |
| WO | WO 2004/013280 | 12/2004 |
| WO | WO 2005/027980 | 3/2005 |
| WO | WO 2005/045032 | 5/2005 |
| WO | WO 2005/083436 | 9/2005 |
| WO | WO 2005/105995 | 11/2005 |
| WO | WO 2005/116204 | 12/2005 |
| WO | WO 2006/128141 | 11/2006 |
| WO | WO 2007/022470 | 2/2007 |
| WO | WO 2007/051045 | 5/2007 |
| WO | WO 2007/120883 | 10/2007 |
| WO | WO 2007089584 | 11/2007 |
| WO | WO 2008/005562 | 1/2008 |
| WO | WO 2008/018795 | 2/2008 |
| WO | WO 2009/008725 | 1/2009 |
| WO | WO 2011/097388 | 8/2011 |

OTHER PUBLICATIONS

Bennett et al., "Antisense oligonucleoties as a tool for gene functionalization and target validation" Biochimica Biophysica Acta (1999) 1489:19-30.
Boado et al., "Antisense-mediated down-regulation of the human huntington gene" Journal of Pharmacology and Experimental Therapeutics (2000) 295:239-243.
Boffa et al., "Isolation of active genes containing CAG repeats by DNA strands invasion by a peptide nucleic acid" PNAS (1995) 92:1901-5.
Borovecki et al., "Genome-wide expression profiling of human blood reveals biomarkers for Huntington's disease" Proc. Natl. Acad. Sci. USA (2005) 102:11023-11028.
Branch et al., "A good antisense molecule is hard to find," TIBS (1998) 23:45-50.
Caplen et al., "Rescue ofpolyglutamine-mediated cytotoxicity by double-stranded RNA-mediated RNA interference" Human Molecular Genetics (2002) II (2): 175-184.
Chang et al., "Structural Analysis of Complementary DNA and Amino Acid Sequences of Human and Rat Androgen Receptors" PNAS (1988) 85:7211-7215.
Chin "On the Preparation and Utilization ofIsolated and Purififed Oligonucleotides." Document purportedly located on a CD-ROM and contributed to the public collection of the Katherine R. Everett Law Library of the University ofNorth Carolina on Mar. 14, 2002.
Crooke et al., "Basic Principles of Antisense Therapeutics" Antisense Research and Application (1998) Chapter 1:1-50.
Davidson et al., "Molecular medicine for the brain: silencing of disease genes with RNA interference" Lancet Neural. (2004) 3:145-149.
Diaz-Hernandez et al., "Full Motor Recovery Despite Striatal Neuron Loss and Formation of Irreversible Amyloid-Like Inclusions in a Conditional Mouse Model of Huntington's Disease" J Neurosci(2005) 25:9773-9781.
Drouet et al., "Sustained effects of nonallele-specific Huntingtin silencing" Ann Neural. (2009) 65(3): 276-285.

Eder et al., "Inhibition of LNCaP Prostate Cancer Cells by Means of Androgen Receptor Antisense Oligonucleotides" Cancer Gene Therapy (2000) 7(7):997-1007.
Gagnon et al., "HD Therapeutics—CHDI Fifth Annual Conference" IDrugs 13( 4): 219-223 (2010).
Gonzalez-Alegre et al., "Technology Insight: therapeutic RNA interference—how far from the neurology clinic?" Nature Clinical Practice 3:394-404, 2007.
Gryaznov et al., "Oligodeoxyribonucleotide N3'->P5' Phosphoramidates Synthesis and Hybridization Properties" JAm. Chem. Soc. (1994) 116:3143-3144.
Haque et al., "Antisense gene therapy for neurodegenerative disease" Experimental Neurology (1997) 144:139-146.
Harper et al., "Ten years ofpresymptomatic testing for Huntington's disease: the experience of the UK Huntington's Disease Prediction Consortium" J. Med. Genet. 37:567-571, 2000.
Harper et al., "RNA interference improves motor and neuropathological abnormalities in a Huntington'sdisease mouse model" PNAS (2005) I 02:5820-5825.
Hasholt et al., "Antisense downregulation of mutant huntingtin in a cell model" Journal of Gene Medicine (2003) 5:528-538.
Hersch et al., "Translating Therapies for Huntington's Disease from Genetic Animal Models to Clinical Trials" NeuroRX (2004) 1:298-306.
Hersch et al., "Neuroprotection for Huntington's disease: Ready, set, slow" Neurotherapeutics (2008) 5(2):226-236.
Liu et al., "Specific inhibition of Huntington's disease gene expression by siRNAs in cultures cells" Proceedings of the Japan Academy. Series B, Physical and Biological Sciences (2003) 79B:293-298.
Macdonald et al., "A novel gene containing a trinucleotide repeat that is expanded and unstable on Huntington's disease chromosomes" Cell (1993) 72(6):971-983.
Machida et al., "rAAV-mediated shRNA ameliorated neuropathology in Huntington disease model mouse" Biochem. Biophys. Res. Commun. (2006) 343:190-197.
Macmillan et al., "Molecular analysis and clinical correlations oftheHuntington's disease mutation" Lancet (1993) 342:954-958.
Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.
Martin et al., "38. Ein neuer Zugang zu 2'-0-Alkylribonucleosiden und Eigenschaften deren Oligonucleotide" Helv. Chim. Acta (1995) 78:486-504.
Nellemann et al., "Inhibition of Huntington synthesis by antisense oligonucleotides" Molecular and Cellular Neurosciences (2000) 16:313-323.
New England BioLabs, Inc. Catalogue (1998): 121, 284.
Nguyen et al., "Clioquinol down-regulates mutant huntingtin expression in vitro and mitigates pathology in a Huntington's disease mouse model" PNAS (2005) 102:11840-11845.
Nikiforov et al., "The Use ofPhosphorothioate Primers and Exonuclease Hydrolysis for the Preparation of Single-stranded PCR Products and their Detection by Solid-phase Hybridization" PCR Methods and Applications (1994) 3:285-291.
Pakula et al., "Genetic analysis of protein stability and function" Annual review of genetics 23: 289-310 (1989).
Reynolds et al., "Rational siRNA design for RNA interference" Nature Biotechnology (2004) 22:326-330.
Sanghvi et al., "Heterocyclic Base Modifications in Nucleic Acids and Their Applications in Antisense Oligonucleotides" Antisense Research and Applications (1993) pp. 273-288.
Sewell et al., "Phase I Trial of ISIS 104838, a 2'-Methoxyexthyl Modified Antisense Oligonucleotide Targeting Tumor Necrosis Factor-Alpha" The Journal of Pharmacology and Experimental Therapeutics (2002) 303(3):1334-1343.
Sheehan et al., "Biochemical properties ofphosphonoacetate and thiophosphonoacetate oligodeoxyribonucleotides" Nucleic Acids Research (2003) 31 :4109-4118.
Uhlmann et al., "Antisense oligonucleotides: a new therapeutic principle" Chemical Reviews (1990) 90:543-584.

(56) References Cited

OTHER PUBLICATIONS

Vickers et al., "Efficient Reduction of Target RNAs by Small Interfering RNA and Rnase H-dependent Antisense Agents. A comparative analysis." J Bioi. Chem. (2003) 278:7108-7118.

Wang et al., "Clinico-pathological rescue of a model mouse of Huntington's disease by siRNA" Neurosci. Res. (2005) 53:241-249.

Woolf et al., "Specificity of antisense oligonucleotides in vivo" Proc. Natl. Acad. Sci. USA (1992) 89:7305-7309.

Yen et al., "Sequence-specific cleavage ofHuntingtin mRNA by catalytic DNA" Annals ofNeurology (1999) 46 (3):366-373.

International Search Report for Application No. PCT/US2007/002215 dated Nov. 16, 2007.

International Search Report for Application No. PCT/US2007/002171 dated Sep. 26, 2007.

International Search Report for Application # PCT /US2010/048532 dated Jan. 26, 2011.

Karaki S. et al., "Antisense Oligonucleotides, A Novel Developing Targeting Therapy" Antisense Therapy, pp. (Jan. 19, 2019).

MODULATION OF HUNTINGTON EXPRESSION

SEQUENCE LISTING

The present application is being filed along with a Sequence Listing in electronic format. The Sequence Listing is provided as a file entitled BIOL0113USC3SEQ_ST25.txt created May 15, 2017, which is 488 Kb in size. The information in the electronic format of the sequence listing is incorporated herein by reference in its entirety.

FIELD OF THE INVENTION

Provided herein are methods, compounds, and compositions for reducing expression of huntingtin mRNA and protein in an animal. Such methods, compounds, and compositions are useful, for example, to treat, prevent, or ameliorate Huntington's disease.

BACKGROUND

Huntington's disease (HD) is a devastating autosomal dominant, neurodegenerative disease caused by a CAG trinucleotide repeat expansion encoding an abnormally long polyglutamine (PolyQ) tract in the huntingtin protein. The Huntington disease gene was first mapped in 1993 (The Huntington's Disease Collaborative Research Group. Cell. 1993, 72:971-83), consisting of a gene, IT15, which contained a polymorphic trinucleotide repeat that is expanded and unstable on HD chromosomes. Although CAG repeats in the normal size range are usually inherited as Mendelian alleles, expanded HD repeats are unstable through meiotic transmission and are found to be expanded beyond the normal size range (6-34 repeat units) in HD patients.

Both normal and variant huntingtin protein are localized chiefly in the cytoplasm of neurons (DiFiglia et al., Neuron 1995, 14:1075-81). As a result of excessive polyglutamine length, huntingtin protein forms aggregates in the cytoplasm and nucleus of CNS neurons (Davies et al., Cell 1997, 90:537-548). Both transgenic animals and genetically modified cell lines have been used to investigate the effects of expanded polyQ repeats on the localization and processing of huntingtin. However, it is still unclear whether the formation of aggregates per se is the essential cytotoxic step or a consequence of cellular dysfunction.

HD is characterized by progressive chorea, psychiatric changes and intellectual decline. This dominant disorder affects males and females equally, and occurs in all races (Gusella and MacDonald, Curr. Opin. Neurobiol. 1995 5:656-62). Symptoms of HD are due to the death of neurons in many brain regions, but is most apparent in the striatum, particularly in the caudate nucleus, which suffers a progressive gradient of cell loss that ultimately decimates the entire structure. Although the gene encoding huntingtin is expressed ubiquitously (Strong, T. V. et al., Nat. Genet. 1995, 5:259-263), selective cell loss and fibrillary astrocytosis is observed in the brain, particularly in the caudate and putamen of the striatum and in the cerebral cortex of HD patients (Vonsattel, J-P. et al., Neuropathol. Exp. Neurol. 1985, 44:559-577), and, to a lesser extent, in the hippocampus (Spargo, E. et al., J. Neurol. Neurosurg. Psychiatry 1993, 56:487-491) and the subthalamus (Byers, R. K. et al., Neurology 1973, 23:561-569).

Huntingtin is crucial for normal development and may be regarded as a cell survival gene (Nasir et al., Human Molecular Genetics, Vol 5, 1431-1435). The normal function of huntingtin remains incompletely characterized, but based upon protein-protein interactions, it appears to be associated with the cytoskeleton and required for neurogenesis (Walling et al., J. Neurosci Res. 1998, 54:301-8). Huntingtin is specifically cleaved during apoptosis by a key cysteine protease, apopain, known to play a pivotal role in apoptotic cell death. The rate of cleavage is enhanced by longer polyglutamine tracts, suggesting that inappropriate apoptosis underlies HD.

Antisense technology is emerging as an effective means for reducing the expression of specific gene products and may therefore prove to be uniquely useful in a number of therapeutic, diagnostic, and research applications for the modulation of huntingtin expression. (See U.S. Patent Publication Nos. 2008/0039418 and 2007/0299027)

Antisense compounds for modulating expression of huntingtin are disclosed in the aforementioned published patent applications. However, there remains a need for additional such compounds.

SUMMARY OF THE INVENTION

Provided herein are methods, compounds, and compositions for modulating expression of huntingtin and treating, preventing, delaying or ameliorating Huntington's disease and/or a symptom thereof.

Figure 1:
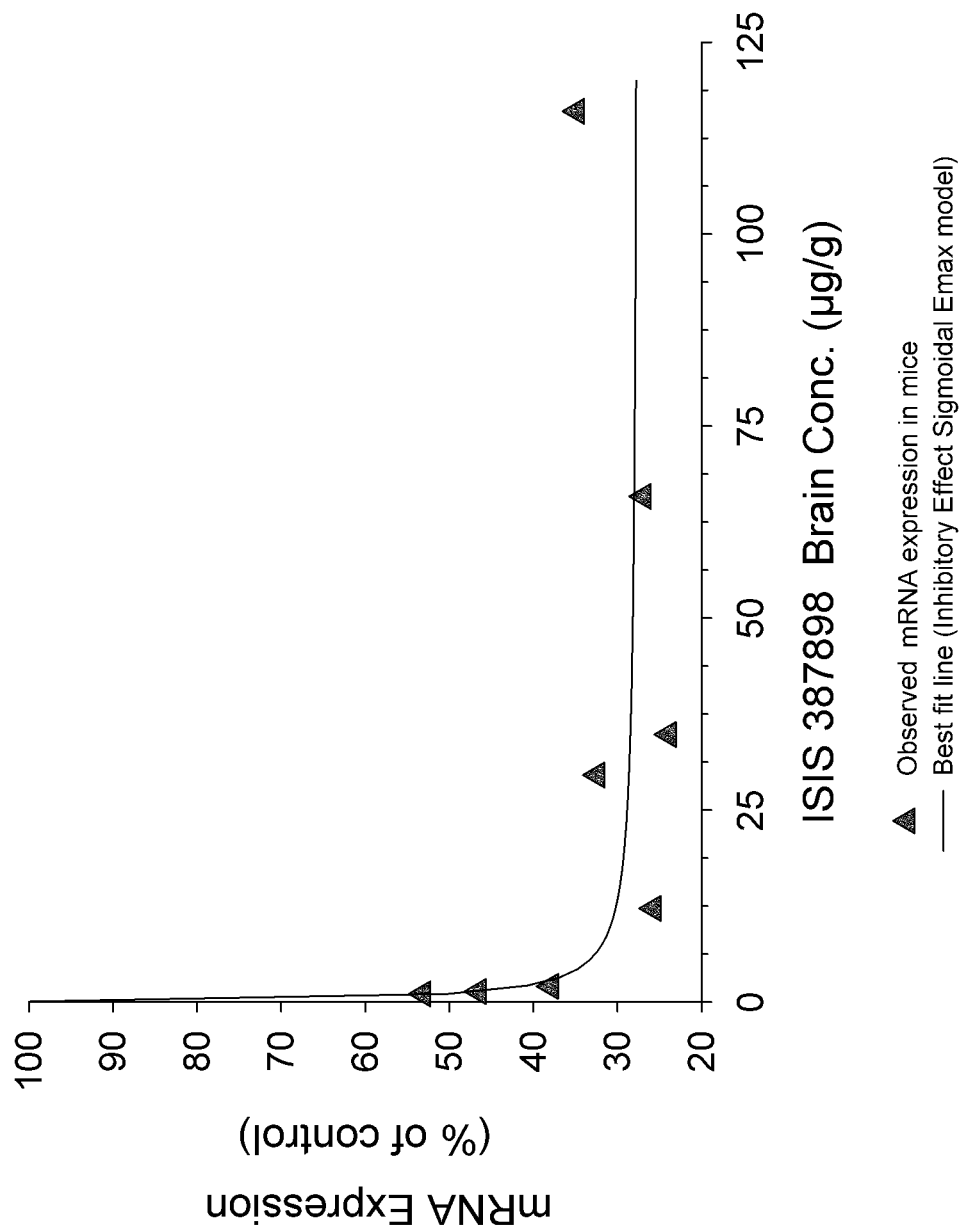
FIG. 1.

The PK/PD relationship of huntingtin mRNA expression in intrastriatal tissue with ISIS 387898 concentration in mouse brain. C57/BL6 mice were administered a single bolus of 50 µg of ISIS 387898 and huntingtin mRNA expression as well as the concentration of the antisense oligonucleotide in the tissue were measured. The $EC_{50}$ of ISIS 387898 was also calculated.

FIG. 2:

Comparison of huntingtin mRNA expression in intrastriatal tissue and ISIS 387898 concentrations at various time points. C57/BL6 mice were administered a single bolus of 50 µg of ISIS 387898 and huntingtin mRNA expression as well as the concentration of the antisense oligonucleotide in the tissue were measured. The duration of action (as measured by htt mRNA expression) of ISIS 387898 (dashed line) was observed to be longer even after the concentration of the oligonucleotide (solid line) in the tissue.

FIG. 3:

The PK/PD relationship of huntingtin mRNA expression in the anterior cortex tissue with ISIS 387898 concentration in mouse brain. BACHD mice were administered an intracerebroventricular infusion of 75 µg of ISIS 387898 for 2 weeks and huntingtin mRNA expression as well as the concentration of the antisense oligonucleotide in the tissue were measured. The $EC_{50}$ of ISIS 387898 was also calculated.

FIG. 4:

Comparison of huntingtin mRNA expression in anterior cortex tissue and ISIS 387898 concentrations at various time points. BACHD mice were administered intracerebroventricular infusion of 75 µg of ISIS 387898 for 2 weeks, and huntingtin mRNA expression as well as the concentration of the antisense oligonucleotide in the tissue were measured. The duration of action (as measured by htt mRNA expression) of ISIS 387898 (dashed line) was observed to be longer even after the concentration of the oligonucleotide (solid line) in the tissue.

FIG. 5:

Comparison of huntingtin mRNA expression in posterior cortex tissue and ISIS 388241 concentrations at various time points. BACHD mice were administered intracerebroventricular infusion of 50 µg of ISIS 388241 for 2 weeks, and huntingtin mRNA expression as well as the concentration of the antisense oligonucleotide in the tissue were measured. The duration of action (as measured by htt mRNA expression) of ISIS 388241 (dashed line) was observed to be longer even after the concentration of the oligonucleotide (solid line) in the tissue.

FIG. 6:

Comparison of huntingtin mRNA expression in posterior cortex tissue and ISIS 443139 concentrations at various time points. BACHD mice were administered intracerebroventricular infusion of 50 µg of ISIS 443139 for 2 weeks, and huntingtin mRNA expression as well as the concentration of the antisense oligonucleotide in the tissue were measured. The duration of action (as measured by htt mRNA expression) of ISIS 443139 (dashed line) was observed to be longer even after the concentration of the oligonucleotide (solid line) in the tissue.

FIG. 7.

Effect of antisense oligonucleotide treatment on the motor performance of BACHD mice using the Rotarod assay. BACHD mice were treated with 50 µg/day ICV of ISIS 388241 or PBS for two weeks. Control groups of non-transgenic littermates were similarly treated with ISIS 388241 or PBS. The accelerating Rotarod assay was then performed. Animals were placed on the Rotarod at a speed of 2 RPM; the Rotarod accelerated to 40 RPM over 5 minutes. The duration to fall was recorded. Baseline values at 6 months age were taken before the treatment and the time points given are the age of the mice at which the assay was conducted. The bars represent the duration to fall in seconds by BACHD mice treated with ISIS 388241 (black); by BACHD mice treated with PBS (hashed); and by non-transgenic littermates treated with PBS (white). ISIS 388241-treated mice displayed increased duration of fall and, therefore, improved motor performance on the Rotarod, compared to the PBS control.

FIG. 8.

Effect of antisense oligonucleotide treatment on brain weight of R6/2 mice. Six-month old R6/2 mice were treated with 50 µg/day ICV of ISIS 388817 or control oligonucleotide ISIS 141923 or PBS for 4 weeks. Control groups of non-transgenic littermates were similarly treated with ISIS 388817 or PBS. A control group of eight-week old pre-symptomatic R6/2 mice were included in the study and not given any treatment. The bars represent the brain weights of eight-week old untreated R6/2 mice; R6/2 mice treated with ISIS 141923; R6/2 mice treated with PBS; R6/2 mice treated with ISIS 388817; non-transgenic littermates treated with PBS; and non-transgenic littermates treated with ISIS 388817. There was an increase in brain weight of R6/2 mice treated with ISIS 388817 compared to the PBS control.

FIG. 9

Behavioral characterization of antisense oligonucleotide-treated YAC128 mice using the Open Field assay. Five month old YAC128 mice were treated with 50 µg/day ICV of ISIS 388241 or control oligonucleotide ISIS 141923 or PBS for 14 days. A control group of non-transgenic FVB/NJ littermates were included in the study and not given any treatment. Mice were placed in an open field arena that uses photobeam breaks to measure horizontal and vertical movement over a 30 min test session. Data was analyzed using Activity Monitor software to examine total ambulatory movement within the arena and movement within the center of the arena as a measure of anxiety. The bars represent time in seconds spent at the center of the field by FVB/NJ mice, YAC128 treated with PBS, and, YAC128 mice treated with ISIS 388241. YAC128 mice treated with ISIS 388241 spent more time in the center and were therefore deemed less anxiety-prone than the PBS control.

FIG. 10

Behavioral characterization of antisense oligonucleotide-treated YAC128 mice using the Elevated Plus Maze assay. Five month old YAC128 mice were treated with 50 µg/day ICV of ISIS 388241 or control oligonucleotide ISIS 141923 or with PBS for 14 days. A control group of non-transgenic FVB/NJ littermates were included as untreated control. Mice were placed in the center of an apparatus which consisted of two open arms and two closed arms each measuring 65×6.25 cm and elevated 50 cm above the ground. The location of the mice on the apparatus and amount of time spent in the open arms was recorded over a 5 minute test session as a measure of anxiety. The bars represent the percentage of time spent in the open arms by FVB/NJ control, YAC128 treated with PBS, and YAC128 mice treated with ISIS 388241. YAC128 mice treated with ISIS 388241 spent more time in the open arms and were therefore deemed less anxiety-prone than the PBS control.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to huntingtin is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Huntingtin nucleic acid" means any nucleic acid encoding huntingtin. For example, in certain embodiments, a huntingtin nucleic acid includes a DNA sequence encoding huntingtin, an RNA sequence transcribed from DNA encoding huntingtin (including genomic DNA comprising introns and exons), and an mRNA sequence encoding huntingtin. "Huntingtin mRNA" means an mRNA encoding a huntingtin protein.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid may also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting huntingtin expression.

Certain embodiments provide antisense compounds targeted to a huntingtin nucleic acid. In certain embodiments, the huntingtin nucleic acid is any of the sequences set forth in GENBANK Accession No. NM_002111.6 (incorporated herein as SEQ ID NO: 1), GENBANK Accession No. NT_006081.17 truncated from nucleotides 462000 to 634000 (incorporated herein as SEQ ID NO: 2), GENBANK Accession No. NM_010414.1 (incorporated herein as SEQ ID NO: 3), the complement of GENBANK Accession No. NW_001109716.1 truncated at nucleotides 698000 to 866000 (incorporated herein as SEQ ID NO: 4), and GENBANK Accession No. NM_024357.2 (incorporated herein as SEQ ID NO: 5).

Certain embodiments provide compounds comprising a modified oligonucleotide consisting of 12 to 30 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the modified oligonucleotide comprises at least 9, at least 10, at least 11, or at least 12 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, or at least 12 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 15 to 25 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the modified oligonucleotide comprises at least 9, at least 10, at least 11, at least 12, at least 13, at least 14 or at least 15 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, at least 12, at least 13, at least 14 or at least 15 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 18 to 21 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, and 32. In certain embodiments, the modified oligonucleotide comprises at least 9, at least 10, at least 11, at least 12, at least 13, at least 14, at least 15, at least 16, at least 17 or at least 18 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, at least 12, at least 13, at least 14, at least 15, at least 16, at least 17, or at least 18 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 12-30 linked nucleosides wherein the linked nucleosides comprise at least an 8 contiguous nucleobase portion that is complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828, 4928-4947 of SEQ ID NO: 1. In certain embodiments the region is selected from 4384-4403, 4609-4628, 4610-4629, 4860-4877, 4862-4881, 4925-4944, 4928-4947, 4931-4950, 4955-4974, and 5809-5828 of SEQ ID NO: 1. In certain embodiments the region is selected from 4862-4881, 4609-4628, 5809-5828, 5809-5826, 5801-5820, and 4955-4974. In certain embodiments, the modified oligonucleotide has at least a 9, at least a 10, at least an 11, or at least a 12 contiguous nucleobase portion of which is complementary within a region described herein.

Certain embodiments provide compounds comprising a modified oligonucleotide consisting of 15-25 linked nucleosides wherein the linked nucleosides comprise at least an 8 contiguous nucleobase portion that is complementary within the region selected from nucleotides 4384-4403, 4609-4628, 4610-4629, 4860-4877, 4862-4881, 4925-4944, 4928-4947, 4931-4950, 4955-4974, and 5809-5829 of SEQ ID NO: 1. In certain embodiments, the modified oligonucleotide has at least a 9, at least a 10, at least an 11, at least a 12, at least a 13, or at least a 15 contiguous nucleobase portion of which is complementary within a region described herein.

Certain embodiments provide compounds comprising a modified oligonucleotide consisting of 15-25 linked nucleosides wherein the linked nucleosides comprise at least an 8 contiguous nucleobase portion that is complementary within the region selected from nucleotides 4862-4881, 4609-4628, 5809-5828, 5809-5826, 5801-5820, and 4955-4974. In certain embodiments, the modified oligonucleotide has at least a 9, at least a 10, at least an 11, at least a 12, at least a 13, or at least a 15 contiguous nucleobase portion of which is complementary within a region described herein.

Certain embodiments provide compounds comprising a modified oligonucleotide consisting of 18-21 linked nucleosides wherein the linked nucleosides comprise at least an 8 contiguous nucleobase portion that is complementary within the region selected from nucleotides 4384-4403, 4609-4628, 4610-4629, 4860-4877, 4862-4881, 4925-4944, 4928-4947, 4931-4950, 4955-4974, and 5809-5829 of SEQ ID NO: 1. In certain embodiments, the modified oligonucleotide has at least a 9, at least a 10, at least an 11, at least a 12, at least a 13, at least a 14, at least a 15, at least a 16, at least a 17, or at least an 18 contiguous nucleobase portion of which is complementary within a region described herein.

Certain embodiments provide compounds comprising a modified oligonucleotide consisting of 18-21 linked nucleosides wherein the linked nucleosides comprise at least an 8 contiguous nucleobase portion that is complementary within the region selected from nucleotides 4862-4881, 4609-4628, 5809-5828, 5809-5826, 5801-5820, and 4955-4974. In certain embodiments, the modified oligonucleotide has at least a 9, at least a 10, at least an 11, at least a 12, at least a 13, at least a 14, at least a 15, at least a 16, at least a 17, or at least an 18 contiguous nucleobase portion of which is complementary within a region described herein.

In certain embodiments, the modified oligonucleotide consists of a single-stranded modified oligonucleotide.

In certain embodiments, the modified oligonucleotide consists of 20 linked nucleosides.

In certain embodiments, the nucleobase sequence of the modified oligonucleotide is at least 90% complementary over its entire length to a nucleobase sequence of SEQ ID NO: 1, 2, 3, 4 or 5. In certain embodiments, the nucleobase sequence of the modified oligonucleotide is at least 95% complementary over its entire length to a nucleobase sequence of SEQ ID NO: 1, 2, 3, 4 or 5. In certain embodiments, the modified oligonucleotide is at least 99% complementary over its entire length to SEQ ID NO: 1, 2, 3, 4 or 5. In certain embodiments, the nucleobase sequence of the modified oligonucleotide is 100% complementary over its entire length to a nucleobase sequence of SEQ ID NO: 1, 2, 3, 4 or 5.

In certain embodiments, the compound has at least one modified internucleoside linkage. In certain embodiments, the internucleoside linkage is a phosphorothioate internucleoside linkage.

In certain embodiments, the compound has at least one nucleoside comprising a modified sugar. In certain embodiments, the at least one modified sugar is a bicyclic sugar. In certain embodiments, the at least one bicyclic sugar comprises a 4'-CH(CH3)-O-2' bridge. In certain embodiments, the at least one modified sugar comprises a 2'-O-methoxyethyl.

In certain embodiments, the compound comprises at least one at least one tetrahydropyran modified nucleoside wherein a tetrahydropyran ring replaces the furanose ring. In certain embodiments, the at least one tetrahydropyran modified nucleoside has the structure:

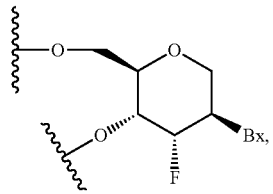

wherein Bx is an optionally protected heterocyclic base moiety.

In certain embodiments, the compound has at least one nucleoside comprising a modified nucleobase. In certain embodiments, the modified nucleobase is a 5-methylcytosine.

In certain embodiments, the modified oligonucleotide of the compound comprises:
(i) a gap segment consisting of linked deoxynucleosides;
(ii) a 5' wing segment consisting of linked nucleosides;
(iii) a 3' wing segment consisting of linked nucleosides, wherein the gap segment is positioned between the 5' wing segment and the 3' wing segment and wherein each nucleoside of each wing segment comprises a modified sugar.

In certain embodiments, the modified oligonucleotide of the compound comprises:
(i) a gap segment consisting of ten linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
(i) a gap segment consisting of eight linked deoxynucleosides;
(ii) a 5' wing segment consisting of six linked nucleosides;
(iii) a 3' wing segment consisting of six linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
(i) a gap segment consisting of eight linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32 or a salt thereof and a pharmaceutically acceptable carrier or diluent.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 12, 22, 28, 30, 32, and 33 or a salt thereof and a pharmaceutically acceptable carrier or diluent.

Certain embodiments provide methods of treating, preventing, or ameliorating Huntington's disease.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 12, 22, 28, 30, 32, and 33.

In certain embodiments, the animal is a human.

In certain embodiments, the administering prevents, treats, ameliorates, or slows progression Huntington's disease as described herein.

In certain embodiments, the compound is co-administered with a second agent.

In certain embodiments, the compound and the second agent are administered concomitantly.

In certain embodiments, the administering is parenteral administration. In certain embodiments, the parenteral administration is intracranial administration. In certain embodiments, the intracranial administration is intrathecal or intracerebroventricular administration.

Certain embodiments further provide a method to reduce huntingtin mRNA or protein expression in an animal comprising administering to the animal a compound or composition as described herein to reduce huntingtin mRNA or protein expression in the animal. In certain embodiments, the animal is a human. In certain embodiments, reducing huntingtin mRNA or protein expression prevents, treats, ameliorates, or slows progression of Huntington's disease.

Certain embodiments provide a method for treating a human with Huntington's disease comprising identifying the human with the disease and administering to the human a therapeutically effective amount of a compound or composition as described herein. In certain embodiments, the treatment reduces a symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, sleep disturbances, impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination, dementia, a anxiety, depression, blunted affect, egocentrisms, aggression, compulsive behavior, irritability, suicidal ideation, reduced brain mass, muscle atrophy, cardiac failure, impaired glucose tolerance, weight loss, osteoporosis, and testicular atrophy.

Further provided is a method for reducing or preventing Huntington's disease comprising administering to a human a therapeutically effective amount compound or composition as described herein, thereby reducing or preventing Huntington's disease.

Further provided is a method for ameliorating a symptom of Huntington's disease, comprising administering to a human in need thereof a compound comprising a modified oligonucleotide consisting of 12 to 30 linked nucleosides, wherein said modified oligonucleotide specifically hybridizes to SEQ ID NO:1, 2, 3, 4 or 5, thereby ameliorating a symptom of Huntington's disease in the human.

Further provided is a method for reducing the rate of progression of a symptom associated with Huntington's Disease, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby reducing the rate of progression a symptom of Huntington's disease in the human.

Further provided is a method for reversing degeneration indicated by a symptom associated with Huntington's disease, administering to a human in need thereof a compound comprising a modified oligonucleotide consisting of 12 to 30 linked nucleosides, wherein said modified oligonucleotide specifically hybridizes to SEQ ID NO:1, 2, 3, 4 or 5, thereby reversing degeneration indicated by a symptom of Huntington's disease in the human.

In certain embodiments, the symptom is a physical, cognitive, psychiatric, or peripheral symptom. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

Also provided are methods and compounds for the preparation of a medicament for the treatment, prevention, or amelioration of Huntington's disease.

Certain embodiments provide the use of a compound as described herein in the manufacture of a medicament for treating, ameliorating, or preventing Huntington's disease.

Certain embodiments provide a compound as described herein for use in treating, preventing, or ameliorating Huntington's disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating Huntington's disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating Huntington's disease as described herein in a patient who is subsequently administered an additional agent or therapy as described herein.

Certain embodiments provide a kit for treating, preventing, or ameliorating Huntington's disease as described herein wherein the kit comprises:
(i) a compound as described herein; and alternatively
(ii) an additional agent or therapy as described herein.

A kit as described herein may further include instructions for using the kit to treat, prevent, or ameliorate Huntington's disease as described herein by combination therapy as described herein.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 6, 9, 10, 11, 12, 13, 14, 15, 18, 19, 20, 21, 22, 23, 24, 25, 26, 27, 28, 29, 30, 32, 33, 35, or 36, for use in treating an animal having a disease or condition associated with huntingtin by administering to the animal a therapeutically effective amount of the compound so that expression of huntingtin is inhibited. In certain embodiments, the disease or condition is a neurological disorder. In certain embodiments, the disease or condition is Huntington's Disease. In certain embodiments, the animal is a human.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 6, 9, 10, 11, 12, 13, 14, 15, 18, 19, 20, 21, 22, 23, 24, 25, 26, 27, 28, 29, 30, 32, 33, 35, or 36, for use in an animal having a disease or condition associated with huntingtin by administering to the animal a therapeutically effective amount of the compound to prevent, treat, ameliorate, or slow progression of Huntington's disease.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 12, 22, 28, 30, 32, or 33, for use in an animal having a disease or condition associated with huntingtin by administering to the animal a therapeutically effective amount of the compound so that expression of huntingtin is inhibited. In certain embodiments, the disease or condition is a neurological disorder. In certain embodiments, the disease or condition is Huntington's Disease. In certain embodiments, the animal is a human.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 12, 22, 28, 30, 32, or 33, for use in an animal having a disease or condition associated with huntingtin by administering to the animal a therapeutically effective amount of the compound to prevent, treat, ameliorate, or slow progression of Huntington's disease.

Certain embodiments provide compounds comprising a modified oligonucleotide consisting of 12-30 linked nucleosides, wherein the linked nucleosides at least an 8, at least a 9, at least a 10, at least an 11, at least a 12, at least a 13, at least a 14, at least a 15, at least a 16, at least a 17, at least a 18, at least a 19, or at least a 20 contiguous nucleobase portion complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 and 4928-4947 of SEQ ID NO: 1, for use in an animal having a disease or condition associated with huntingtin by administering to the animal a therapeutically effective amount of the compound so that expression of huntingtin is inhibited.

Certain embodiments provide compounds comprising a modified oligonucleotide consisting of 12-30 linked nucleosides, wherein the linked nucleosides comprise at least an 8, at least a 9, at least a 10, at least an 11, at least a 12, at least a 13, at least a 14, at least a 15, at least a 16, at least a 17, at least a 18, at least a 19, or at least a 20 contiguous nucleobase portion complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 and 4928-4947 of SEQ ID NO: 1, for use in an animal having a disease or condition associated with huntingtin by administering to the animal a therapeutically effective amount of the compound to prevent, treat, ameliorate, or slow progression of Huntington's disease.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a huntingtin nucleic acid is 12 to 30 nucleotides in length. In other words, antisense compounds are from 12 to 30 linked nucleobases. In other embodiments, the antisense compound comprises a modified oligonucleotide consisting of 8 to 80, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide may have two nucleosides deleted from the 5' end, or alternatively may have two subunits deleted from the 3' end. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the 5' or 3' end of the oligonucleotide. When two or more additional nucleosides are present, the added nucleosides may be adjacent to each other, for example, in an oligonucleotide having two nucleosides added to the 5' end (5' addition), or alternatively to the 3' end (3' addition), of the oligonucleotide. Alternatively, the added nucleoside may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a huntingtin nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH_2)_n$-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6 or 5-8-5.

In certain embodiments, the antisense compound as a "wingmer" motif, having a wing-gap or gap-wing configuration, i.e. an X-Y or Y-Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, or 5-13.

In certain embodiments, antisense compounds targeted to a huntingtin nucleic acid possess a 5-10-5 gapmer motif.

In certain embodiments, antisense compounds targeted to a huntingtin nucleic acid possess a 6-8-6 gapmer motif.

In certain embodiments, antisense compounds targeted to a huntingtin nucleic acid possess a 5-8-5 gapmer motif In certain embodiments, an antisense compound targeted to a huntingtin nucleic acid has a gap-widened motif.

In certain embodiments, a gap-widened antisense oligonucleotide targeted to a huntingtin nucleic acid has a gap segment of ten 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a huntingtin nucleic acid has a gap segment of eight 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a huntingtin nucleic acid has a gap segment of eight 2'-deoxyribonucleotides positioned immediately adjacent to and between wing segments of six chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences

Nucleotide sequences that encode huntingtin include, without limitation, the following: GENBANK Accession No. NM_002111.6, first deposited with GENBANK® on May 31, 2006 incorporated herein as SEQ ID NO: 1; GENBANK Accession No. NT_006081.17 truncated from nucleotides 462000 to 634000, first deposited with GENBANK® on Aug. 19, 2004, and incorporated herein as SEQ ID NO: 2; GENBANK Accession No. NM_010414.1, first deposited with GENBANK® on Mar. 23, 2004, incorporated herein as SEQ ID NO: 3; the complement of GENBANK Accession No. NW_001109716.1 truncated at nucleotides 698000 to 866000, first deposited with GENBANK® on Jun. 14, 2006, incorporated herein as SEQ ID NO: 4, and GENBANK Accession No. NM_024357.2, first deposited with GENBANK® on Jun. 5, 2008, incorporated herein as SEQ ID NO: 5.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for huntingtin can be obtained by accession number from sequence databases such as NCBI and such information is incorporated herein by reference. In certain embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in huntingtin mRNA levels are indicative of inhibition of huntingtin expression.

Reductions in levels of a huntingtin protein are also indicative of inhibition of target mRNA expression. Further, phenotypic changes are indicative of inhibition of huntingtin expression. For example, increase in brain size to normal, improvement in motor coordination, decrease in continual muscular spasms (dystonia), decrease in irritability and/or anxiety, improvement of memory, or an increase in energy, among other phenotypic changes that may be assayed. Other phenotypic indications, e.g., symptoms associated with Huntington's disease, may also be assessed as described below.

Hybridization

In some embodiments, hybridization occurs between an antisense compound disclosed herein and a huntingtin nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a huntingtin nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a huntingtin nucleic acid).

An antisense compound may hybridize over one or more segments of a huntingtin nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a huntingtin nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a huntingtin nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a huntingtin nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a huntingtin nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The nonidentical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a huntingtin nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or C(R1)(R)2 (R=H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH3 and 2'-O(CH2)2OCH$_3$ substituent groups. The substituent at the 2' position can also be selected from allyl, amino, azido, thio, O-allyl, O—C1-C10 alkyl, OCF3, O(CH2)2SCH3, O(CH2)2-O—N(Rm)(Rn), and O—CH2-C(=O)—N(Rm)(Rn), where each Rm and Rn is, independently, H or substituted or unsubstituted C1-C10 alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH2)-O-2' (LNA); 4'-(CH2)-S-2; 4'-(CH2)-O-2' (LNA); 4'-(CH2)2-O-2' (ENA); 4'-C(CH3)2-O-2' (see PCT/US2008/068922); 4'-CH(CH3)¬-O-2' and 4'-C¬H (CH2OCH3)¬-O-2' (see U.S. Pat. No. 7,399,845, issued on Jul. 15, 2008); 4'-CH2-N(OCH3)-2' (see PCT/US2008/064591); 4'-CH2-O—N(CH3)-2' (see published U.S. Patent Application US2004-0171570, published Sep. 2, 2004); 4'-CH2-N(R)—O-2' (see U.S. Pat. No. 7,427,672, issued on Sep. 23, 2008); 4'-CH2-C(CH3)-2' and 4'-CH2-C¬(=CH2)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

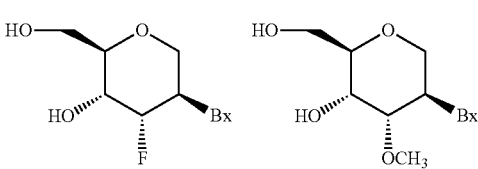

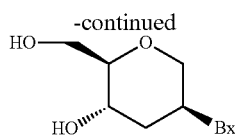

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds targeted to a huntingtin nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a huntingtin nucleic acid comprise one or more modified nucleobases. In certain embodiments, gap-widened antisense oligonucleotides targeted to a huntingtin nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a huntingtin nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a huntingtin nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of huntingtin nucleic acids can be tested in vitro in a variety of cell types. Cell types used for such analyses are available from commercial vendors (e.g. American Type Culture Collection, Manassas, Va.; Zen-Bio, Inc., Research Triangle Park, NC; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a huntingtin nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a huntingtin nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of huntingtin nucleic acids can be assessed by measuring huntingtin protein levels. Protein levels of huntingtin can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat huntingtin are commercially available.

In Vivo Testing of Antisense Compounds

Antisense compounds, for example, antisense oligonucleotides, are tested in animals to assess their ability to inhibit expression of huntingtin and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in huntingtin nucleic acid expression are measured. Changes in huntingtin protein levels are also measured.

Certain Compounds

About seventeen hundred newly designed antisense compounds of various lengths, motifs and backbone composition were tested for their effect on human huntingtin mRNA in vitro in several cell types. The new compounds were compared with about two hundred and fifty previously designed compounds including ISIS 387916 which had previously been determined to be one of the most potent antisense compounds in vitro (see e.g., U.S. Patent Publication Nos. 2008/0039418 and 2007/0299027. Of the about seventeen hundred newly designed antisense compounds, about sixty compounds were selected for further study based on in vitro potency compared to ISIS 387916. The selected compounds were tested for systemic tolerability (see Example 3) and activity and tolerability in the brain of BACHD mice (see Example 4) compared to previously designed ISIS 388241 and ISIS 387916. From these studies, compounds having a nucleobase sequence of a sequence recited in SEQ ID NO: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 or 32 were selected as having high tolerability and high in vivo potency. By virtue of their complementary sequence, the compounds are complementary to the regions 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 or 4928-4947 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 419628, ISIS 419637, ISIS 419640, ISIS 419641, ISIS 451541, ISIS 419642, ISIS 436665, ISIS 436671, ISIS 436684, ISIS 436689, ISIS 436754, ISIS 437168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663.

Compounds described above as having high in vivo potency and tolerability were then tested by CNS bolus injection in rat to further assess neurotoxicity (see Example 5) along with several additional compounds having a nucleobase sequence of a sequence recited in SEQ ID NO: 7, 8, 11, 16, 17. Of these, ten compounds having a nucleobase sequence of a sequence recited in SEQ ID NO: 24, 25, 26, 6, 12, 28, 21, 22, 32 or 13 were selected as having high tolerability. By virtue of their complementary sequence, the compounds are complementary to the regions 4384-4403, 4609-4628, 4610-4629, 4860-4877, 4862-4881, 4925-4944, 4928-4947, 4931-4950, 4955-4974, or 5809-5829 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 419640, ISIS 419641, ISIS 419642, ISIS 436665, ISIS 436671, ISIS 436689, ISIS 437507, ISIS 443139, ISIS 444591, and ISIS 444661. Selected compounds were compared with previously designed compound ISIS 388241 by ICV administration in BACHD mice.

Additional studies were then run on compounds described above as having high in vivo potency and tolerability. The additional studies were designed to further assess neurotoxicity. Studies included ICV administration in wild-type mouse (see Example 16) and bolus administration in rat (see Example 17). SEQ ID NOs: 12, 22, 28, 30, 32, and 33 were selected as having high neurotolerability. By virtue of their complementary sequence, the compounds are complementary to the regions 4862-4881, 4609-4628, 5809-5828, 5809-5826, 5801-5820, and 4955-4974 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by ISIS 388241, ISIS 443139, ISIS 436671, ISIS 444591, ISIS 437527, ISIS 444584, ISIS 444652, and ISIS 436689.

Accordingly, provided herein are antisense compounds with improved characteristics. In certain embodiments, provided herein are compounds comprising a modified oligonucleotide as further described herein targeted to or specifically hybridizable with the region of nucleotides of SEQ ID NO: 1.

In certain embodiments, the compounds as described herein are efficacious by virtue of having at least one of an in vitro $IC_{50}$ of less than 7 uM, less than 6 uM, less than 5, uM, less than 4 uM, less than 3 uM, less than 2 uM, less than 1 uM when delivered to a human fibroblast cell line as described herein or an $ED_{50}$ of less than 10 µg, less than 9 µg, less than 8 µg, less than 7.5 µg, less than 7.4 µg, less than 7.0 µg, less than 6 µg, less than 5 µg, less than 4 µg, less than 3 µg, or less than 2 µg by bolus injection. As described herein, ICV infusion can result in 3 to 4 fold higher $ED_{50}$ values for the compounds described herein. In certain embodiments, the compounds as described herein are highly tolerable as demonstrated by having at least one of an increase an ALT or AST value of no more than 4 fold, 3 fold, or 2 fold over saline treated animals; an increase in liver, spleen or kidney weight of no more than 30%, 20%, 15%, 12%, 10%, 5% or 2%; or an increase AIF1 levels by no more than 350%, 300%, 275%, 250% 200%, 150% or 100% over control.

Certain Indications

In certain embodiments, provided herein are methods of treating an individual comprising administering one or more pharmaceutical compositions as described herein. In certain embodiments, the individual has Huntington's disease.

As shown in the examples below, compounds targeted to huntingtin as described herein have been shown to reduce the severity of physiological symptoms of Huntington's disease. In certain of the experiments, the compounds reduced rate of degeneration, e.g., the animals continued to experience symptoms, but the symptoms were less severe compared to untreated animals. In other of the experiments, however, the compounds appear to result in regeneration of function over time; e.g., animals treated for a longer period of time experienced less severe symptoms than those administered the compounds for a shorter period of time. As discussed above, Huntington's disease is a degenerative disease with a progression typified by increased severity of symptoms over time. The ability of the compounds exemplified below to restore function therefore demonstrates that symptoms of the disease may be reversed by treatment with a compound as described herein.

Accordingly, provided herein are methods for ameliorating a symptom associated with Huntington's disease in a subject in need thereof. In certain embodiments, provided is a method for reducing the rate of onset of a symptom associated with Huntington's disease. In certain embodiments, provided is a method for reducing the severity of a symptom associated with Huntington's disease. In certain embodiments, provided is a method for regenerating neurological function as shown by an improvement of a symptom associated with Huntington's disease. In such embodiments, the methods comprise administering to an individual in need thereof a therapeutically effective amount of a compound targeted to a huntingtin nucleic acid.

Huntington's disease is characterized by numerous physical, neurological, psychiatric, and/or peripheral symptoms. Any symptom known to one of skill in the art to be associated with Huntington's disease can be ameliorated or otherwise modulated as set forth above in the methods described above. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

In certain embodiments, the symptom is restlessness. In certain embodiments, the symptom is lack of coordination. In certain embodiments, the symptom is unintentionally initiated motions. In certain embodiments, the symptom is unintentionally uncompleted motions. In certain embodiments, the symptom is unsteady gait. In certain embodiments, the symptom is chorea. In certain embodiments, the symptom is rigidity. In certain embodiments, the symptom is writhing motions. In certain embodiments, the symptom is abnormal posturing. In certain embodiments, the symptom is instability. In certain embodiments, the symptom is abnormal facial expressions. In certain embodiments, the symptom is difficulty chewing. In certain embodiments, the symptom is difficulty swallowing. In certain embodiments, the symptom is difficulty speaking. In certain embodiments, the symptom is seizures. In certain embodiments, the symptom is sleep disturbances.

In certain embodiments, the symptom is impaired planning. In certain embodiments, the symptom is impaired flexibility. In certain embodiments, the symptom is impaired abstract thinking. In certain embodiments, the symptom is impaired rule acquisition. In certain embodiments, the symptom is impaired initiation of appropriate actions. In certain embodiments, the symptom is impaired inhibition of inappropriate actions. In certain embodiments, the symptom is impaired short-term memory. In certain embodiments, the symptom is impaired long-term memory. In certain embodiments, the symptom is paranoia. In certain embodiments, the symptom is disorientation. In certain embodiments, the symptom is confusion. In certain embodiments, the symptom is hallucination. In certain embodiments, the symptom is dementia.

In certain embodiments, the symptom is anxiety. In certain embodiments, the symptom is depression. In certain embodiments, the symptom is blunted affect. In certain embodiments, the symptom is egocentrism. In certain embodiments, the symptom is aggression. In certain embodiments, the symptom is compulsive behavior. In certain embodiments, the symptom is irritability. In certain embodiments, the symptom is suicidal ideation.

In certain embodiments, the symptom is reduced brain mass. In certain embodiments, the symptom is muscle atrophy. In certain embodiments, the symptom is cardiac failure. In certain embodiments, the symptom is impaired glucose tolerance. In certain embodiments, the symptom is weight loss. In certain embodiments, the symptom is osteoporosis. In certain embodiments, the symptom is testicular atrophy.

In certain embodiments, symptoms of Huntington's disease may be quantifiable. For example, osteoporosis may be measured and quantified by, for example, bone density scans. For such symptoms, in certain embodiments, the symptom may be reduced by about 15, 20, 25, 30, 35, 40, 45, 50, 55, 60, 65, 70, 75, 80, 85, 90, 95 or 99%, or a range defined by any two of these values.

In certain embodiments, provided are methods of treating an individual comprising administering one or more pharmaceutical compositions as described herein. In certain embodiments, the individual has Huntington's disease.

In certain embodiments, administration of an antisense compound targeted to a huntingtin nucleic acid results in reduction of huntingtin expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to huntingtin are used for the preparation of a medicament for treating a patient suffering or susceptible to Huntington's disease.

In certain embodiments, the methods described herein include administering a compound comprising a modified oligonucleotide having a contiguous nucleobases portion as described herein of a sequence recited in SEQ ID NO: 6, 9, 10, 11, 12, 13, 14, 15, 18, 19, 20, 21, 22, 23, 24, 25, 26, 27, 28, 29, 30, 32, 33, 35, 36, 10, 11, 12, 13, 18, 22 or 32. In certain embodiments, the methods described herein include administering a compound comprising a modified oligonucleotide having a contiguous nucleobases portion as described herein of a sequence recited in SEQ ID NOs: 12, 22, 28, 30, 32, and 33.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

The median effective concentration ($EC_{50}$) of an antisense compounds for inhibiting huntingtin mRNA expression was calculated after either ICV infusion or bolus injection (see Examples 9 and 10). The $EC_{50}$ for the compound after intrastriatal injection was determined to be 0.45 µg/g. The $EC_{50}$ after ICV administration was determined to be 26.4 µg/g.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration ($EC_{50}$) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration ($EC_{50}$) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing $EC_{50}$ is desirable because it reduces the dose required to achieve a pharmacological result in a patient in need thereof.

The half-life of MOE gapmer oligonucleotides in brain tissue is about 20 days (see Examples 9-11). The duration of action as measured by inhibition of huntingtin mRNA is prolonged in the brain (see Examples 9 and 10). Intracerebroventricular infusion of antisense oligonucleotides for 2 weeks results in inhibition of huntingtin mRNA by at least 50% in striatal tissue of BACHD mice for at least 91 days after termination of dosing. Administration by bolus injection resulted in a similar duration of action.

In certain embodiments, delivery of a compound or composition, as described herein, to the CNS results in 47% down-regulation of a target mRNA and/or target protein for at least 91 days. In certain embodiments, delivery of a compound or composition results in at least 25%, at least 30%, at least 35%, at least 40%, at least 45%, at least 50%, at least 55%, at least 60%, at least 65%, at least 70%, or at least 75% down-regulation of a target mRNA and/or target protein for at least 20 days, at least 30 days, at least 40 days, at least 50 days, at least 60 days, at least 70 days, at least 80 days, at least 85 days, at least 90 days, at least 95 days, at least 100 days, at least 110 days, at least 120 days.

In certain embodiments, delivery to the CNS is by intraparenchymal administration, intrathecal administration, or intracerebroventricular administration.

In certain embodiments, an antisense oligonucleotide is delivered by injection or infusion once every month, every two months, every 90 days, every 3 months, every 6 months, twice a year or once a year.

Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [1231]MNI-420, atomoxetine, tetrabenazine, digoxin, detromethorphan, warfarin, alprozam, ketoconazole, omeprazole, and minocycline.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Oligonucleotides Targeted to Human Huntingtin Gene Sequences About seventeen hundred newly designed antisense compounds of various lengths, motifs and backbone composition targeting the human huntingtin gene sequence were tested for their effect on human huntingtin mRNA in vitro in several cell types. These gapmers were further designed with internucleoside linkages that are either only phosphorothioate linkages (described in Table 1) or that are phosphorothioate and phosphodiester linkages (described in Table 5). A number of the newly designed oligos and two benchmark oligonucleotides (previously designed and disclosed) are provided in Tables 1 and 5.

Gapmers with Fully Phosphorothioate Internucleoside Linkages

Certain of the compounds presented in Table 1 have a motif of 5-10-5 MOE, 6-8-6 MOE, or 5-8-5 MOE. The 5-10-5 gapmers have twenty linked nucleosides, wherein the central gap segment has ten 2'-deoxynucleosides and is flanked on both sides (in the 5' and 3' directions) by wings having five nucleosides each. The 6-8-6 gapmer has twenty linked nucleosides, wherein the central gap segment has eight 2'-deoxynucleosides and is flanked on both sides (in the 5' and 3' directions) by wings having six nucleosides each. The 5-8-5 gapmers have eighteen linked nucleosides, wherein the central gap segment has eight 2'-deoxynucleosides and is flanked on both sides (in the 5' and 3' directions) by wings having five nucleosides each. For all gapmers listed in Table 1, each nucleoside in the 5' wing segment and each nucleoside in the 3' wing segment has a 2'-MOE modification. The internucleoside linkages throughout each gapmer are phosphorothioate (P=S) internucleoside linkages. All cytosines throughout each gapmer are 5-methylcytosines. Each gapmer in Table 1 is targeted to SEQ ID NO: 1 (GENBANK Accession No. NM_002111.6) or SEQ ID NO: 2 (GENBANK Accession No. NT 006081.17 truncated from nucleotides 462000 to 634000). 'Start site' indicates the 5'-most nucleotide to which the gapmer is targeted in the human gene sequence. 'Stop site' indicates the 3'-most nucleotide to which the gapmer is targeted in the human gene sequence.

TABLE 1

Chimeric antisense oligonucleotides with phosphorothioate internucleoside linkages targeting human huntingtin gene sequences (SEQ ID NOs: 1 and 2)

| Start Site | Stop Site | Target SEQ ID NO. | ISIS No. | Sequence (5' to 3') | Motif | SEQ ID NO. |
|---|---|---|---|---|---|---|
| 4384 | 4403 | 1 | 436665 | TAGCATTCTTATCTGCACGG | 5-10-5 | 6 |
| 4511 | 4530 | 1 | 436668 | ACCCGTAACTGAACCAGCTG | 5-10-5 | 7 |
| 4599 | 4618 | 1 | 419627 | TTCCCTGAACTGGCCCACTT | 5-10-5 | 8 |
| 4605 | 4624 | 1 | 419628 | CTCTGATTCCCTGAACTGGC | 5-10-5 | 9 |
| 4607 | 4626 | 1 | 444607 | GCCTCTGATTCCCTGAACTG | 5-10-5 | 10 |
| 4608 | 4627 | 1 | 419629 | TGCCTCTGATTCCCTGAACT | 5-10-5 | 11 |
| 4608 | 4627 | 1 | 444578 | TGCCTCTGATTCCCTGAACT | 6-8-6 | 11 |
| 4609 | 4628 | 1 | 436671 | TTGCCTCTGATTCCCTGAAC | 5-10-5 | 12 |
| 4610 | 4629 | 1 | 444608 | ATTGCCTCTGATTCCCTGAA | 5-10-5 | 13 |
| 4617 | 4636 | 1 | 444615 | TGGAATGATTGCCTCTGATT | 5-10-5 | 14 |

TABLE 1-continued

Chimeric antisense oligonucleotides with phosphorothioate internucleoside linkages targeting human huntingtin gene sequences (SEQ ID NOs: 1 and 2)

| Start Site | Stop Site | Target SEQ ID NO. | ISIS No. | Sequence (5' to 3') | Motif | SEQ ID NO. |
|---|---|---|---|---|---|---|
| 4622 | 4639 | 1 | 437168 | GTTTGGAATGATTGCCTC | 5-8-5 | 15 |
| 4679 | 4698 | 1 | 419630 | CCAATGATCTGTTTTGAATG | 5-10-5 | 16 |
| 4733 | 4752 | 1 | 419636 | GCCTTCCTTCCACTGGCCAT | 5-10-5 | 17 |
| 4813 | 4832 | 1 | 444618 | CTGCATCAGCTTTATTTGTT | 5-10-5 | 18 |
| 4814 | 4833 | 1 | 419637 | CCTGCATCAGCTTTATTTGT | 5-10-5 | 19 |
| 4823 | 4842 | 1 | 444627 | AGCTCTTTTCCTGCATCAGC | 5-10-5 | 20 |
| 4860 | 4877 | 1 | 437507 | GTAACATTGACACCACCA | 5-8-5 | 21 |
| 4862 | 4881 | 1 | 388241 | CTCAGTAACATTGACACCAC | 5-10-5 | 22 |
| 4868 | 4887 | 1 | 436684 | ATGAGTCTCAGTAACATTGA | 5-10-5 | 23 |
| 4925 | 4944 | 1 | 419640 | TCCTTGTGGCACTGCTGCAG | 5-10-5 | 24 |
| 4928 | 4947 | 1 | 419641 | TTCTCCTTGTGGCACTGCTG | 5-10-5 | 25 |
| 4931 | 4950 | 1 | 419642 | TCATTCTCCTTGTGGCACTG | 5-10-5 | 26 |
| 4931 | 4948 | 1 | 437442 | ATTCTCCTTGTGGCACTG | 5-8-5 | 27 |
| 4955 | 4974 | 1 | 436689 | CGAGACAGTCGCTTCCACTT | 5-8-5 | 28 |
| 4960 | 4977 | 1 | 437175 | TGTCGAGACAGTCGCTTC | 5-8-5 | 29 |
| 5801 | 5820 | 1 | 444584 | TTGCACATTCCAAGTTTGGC | 5-10-5 | 30 |
| 5807 | 5826 | 1 | 387916 | TCTCTATTGCACATTCCAAG | 5-10-5 | 31 |
| 5809 | 5828 | 1 | 444591 | TTTCTCTATTGCACATTCCA | 5-10-5 | 32 |
| 5809 | 5826 | 1 | 437527 | TCTCTATTGCACATTCCA | 5-8-5 | 33 |
| 1446 | 1465 | 2 | 388817 | GCAGGGTTACCGCCATCCCC | 5-10-5 | 34 |
| 101088 | 101105 | 2 | 437441 | ACCTTATCTGCACGGTTC | 5-8-5 | 35 |
| 115066 | 115085 | 2 | 436754 | CTCTCTGTGTATCACCTTCC | 5-10-5 | 36 |

The complementarity of the gapmers in Table 1 with mouse, rhesus monkey and rat huntingtin gene sequences is further described in Tables 2, 3, and 4.

The gapmers of Table 2 are complementary with mouse huntingtin mRNA (GENBANK Accession No. NM_010414.1, designated herein as SEQ ID NO: 3). 'Mouse target start site' indicates the 5'-most nucleotide to which the gapmer is targeted in the mouse mRNA. 'Mouse target stop site' indicates the 3'-most nucleotide to which the gapmer is targeted in the mouse mRNA. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the mouse mRNA sequence.

TABLE 2

Complementarity of antisense oligonucleotides having phosphorothioate linkages with murine mRNA (SEQ ID NO: 3)

| Human Start Site | Human Stop Site | Human Target SEQ ID NO. | ISIS No. | Mouse Start Site | Mouse Stop Site | No. of mismatches | SEQ ID NO. |
|---|---|---|---|---|---|---|---|
| 4384 | 4403 | 1 | 436665 | 4343 | 4362 | 0 | 6 |
| 4511 | 4530 | 1 | 436668 | 4470 | 4489 | 1 | 7 |
| 4599 | 4618 | 1 | 419627 | 4558 | 4577 | 0 | 8 |
| 4605 | 4624 | 1 | 419628 | 4564 | 4583 | 0 | 9 |
| 4607 | 4626 | 1 | 444607 | 4566 | 4585 | 0 | 10 |
| 4608 | 4627 | 1 | 419629 | 4567 | 4586 | 0 | 11 |
| 4608 | 4627 | 1 | 444578 | 4567 | 4586 | 0 | 11 |

TABLE 2-continued

Complementarity of antisense oligonucleotides having phosphorothioate linkages with murine mRNA (SEQ ID NO: 3)

| Human Start Site | Human Stop Site | Human Target SEQ ID NO. | ISIS No. | Mouse Start Site | Mouse Stop Site | No. of mismatches | SEQ ID NO. |
|---|---|---|---|---|---|---|---|
| 4609 | 4628 | 1 | 436671 | 4568 | 4587 | 0 | 12 |
| 4610 | 4629 | 1 | 444608 | 4569 | 4588 | 0 | 13 |
| 4617 | 4636 | 1 | 444615 | 4576 | 4595 | 1 | 14 |
| 4622 | 4639 | 1 | 437168 | 4581 | 4598 | 2 | 15 |
| 4679 | 4698 | 1 | 419630 | 4638 | 4657 | 0 | 16 |
| 4733 | 4752 | 1 | 419636 | 4692 | 4711 | 0 | 17 |
| 4813 | 4832 | 1 | 444618 | 4772 | 4791 | 0 | 18 |
| 4814 | 4833 | 1 | 419637 | 4773 | 4792 | 0 | 19 |
| 4823 | 4842 | 1 | 444627 | 4782 | 4801 | 1 | 20 |
| 4925 | 4944 | 1 | 419640 | 4884 | 4903 | 0 | 24 |
| 4928 | 4947 | 1 | 419641 | 4887 | 4906 | 0 | 25 |
| 4931 | 4950 | 1 | 419642 | 4890 | 4909 | 0 | 26 |
| 4931 | 4948 | 1 | 437442 | 4890 | 4907 | 0 | 27 |
| 4955 | 4974 | 1 | 436689 | 4914 | 4933 | 3 | 28 |
| 5807 | 5826 | 1 | 387916 | 5763 | 5782 | 1 | 31 |
| 5809 | 5826 | 1 | 437527 | 5765 | 5782 | 1 | 33 |
| 5809 | 5828 | 1 | 444591 | 5765 | 5784 | 1 | 32 |
| 101088 | 101105 | 2 | 437441 | 4340 | 4357 | 2 | 35 |

The gapmers of Table 3 are complementary with the rhesus monkey huntingtin genomic sequence (the complement of GENBANK Accession No. NW_001109716.1 truncated at nucleotides 698000 to 866000, designated herein as SEQ ID NO: 4). 'Rhesus monkey target start site' indicates the 5'-most nucleotide to which the gapmer is targeted in the rhesus monkey gene sequence. 'Rhesus monkey target stop site' indicates the 3'-most nucleotide to which the gapmer is targeted in the rhesus monkey gene sequence. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the rhesus monkey gene sequence.

TABLE 3

Complementarity of antisense oligonucleotides having phosphorothioate linkages with rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mismatches | SEQ ID NO. |
|---|---|---|---|---|---|---|---|
| 4511 | 4530 | 1 | 436665 | 98182 | 98201 | 0 | 6 |
| 4599 | 4618 | 1 | 419627 | 101353 | 101372 | 1 | 8 |
| 4609 | 4628 | 1 | 436671 | 102256 | 102275 | 3 | 12 |
| 4610 | 4629 | 1 | 444608 | 102257 | 102276 | 2 | 13 |
| 4617 | 4636 | 1 | 444615 | 102264 | 102283 | 0 | 14 |
| 4622 | 4639 | 1 | 437168 | 102269 | 102286 | 0 | 15 |
| 4679 | 4698 | 1 | 419630 | 102326 | 102345 | 0 | 16 |
| 4733 | 4752 | 1 | 419636 | 102380 | 102399 | 0 | 17 |
| 4813 | 4832 | 1 | 444618 | 105030 | 105049 | 0 | 18 |
| 4814 | 4833 | 1 | 419637 | 105031 | 105050 | 0 | 19 |
| 4823 | 4842 | 1 | 444627 | 105040 | 105059 | 0 | 20 |
| 4860 | 4877 | 1 | 437507 | 105077 | 105094 | 1 | 21 |
| 4862 | 4881 | 1 | 388241 | 105079 | 105098 | 1 | 22 |
| 4868 | 4887 | 1 | 436684 | 105085 | 105104 | 0 | 23 |
| 4925 | 4944 | 1 | 419640 | 106844 | 106863 | 0 | 24 |
| 4928 | 4947 | 1 | 419641 | 106847 | 106866 | 0 | 25 |
| 4931 | 4950 | 1 | 419642 | 106850 | 106869 | 0 | 26 |
| 4931 | 4948 | 1 | 437442 | 106850 | 106867 | 0 | 27 |
| 4955 | 4974 | 1 | 436689 | 106874 | 106893 | 0 | 28 |
| 4960 | 4977 | 1 | 437175 | 106879 | 106896 | 0 | 29 |
| 5801 | 5820 | 1 | 444584 | 125331 | 125350 | 0 | 30 |
| 5807 | 5826 | 1 | 387916 | 125337 | 125356 | 0 | 31 |
| 5809 | 5826 | 1 | 437527 | 125339 | 125356 | 0 | 33 |
| 5809 | 5828 | 1 | 444591 | 125339 | 125358 | 0 | 32 |
| 101088 | 101105 | 2 | 437441 | 97904 | 97921 | 0 | 35 |
| 115066 | 115085 | 2 | 436754 | 110518 | 110537 | 0 | 36 |

The gapmers of Table 4 are complementary with rat huntingtin mRNA (GENBANK Accession No. NM_024357.2, designated herein as SEQ ID NO: 5). 'Rat target start site' indicates the 5'-most nucleotide to which the gapmer is targeted in the rat mRNA. 'Rat target stop site' indicates the 3'-most nucleotide to which the gapmer is targeted in the rat mRNA. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the rat mRNA sequence.

TABLE 4

Complementarity of antisense oligonucleotides having phosphorothioate linkages with rat mRNA (SEQ ID NO: 5)

| Human Start Site | Human Stop Site | Human Target SEQ ID NO. | ISIS No. | Rat Start Site | Rat Stop Site | No. of mismatches | SEQ ID NO. |
|---|---|---|---|---|---|---|---|
| 4384 | 4403 | 1 | 436665 | 4343 | 4362 | 1 | 6 |
| 4511 | 4530 | 1 | 436668 | 4470 | 4489 | 1 | 7 |
| 4599 | 4618 | 1 | 419627 | 4558 | 4577 | 0 | 8 |
| 4605 | 4624 | 1 | 419628 | 4564 | 4583 | 0 | 9 |
| 4607 | 4626 | 1 | 444607 | 4566 | 4585 | 0 | 10 |
| 4608 | 4627 | 1 | 419629 | 4567 | 4586 | 0 | 11 |
| 4608 | 4627 | 1 | 444578 | 4567 | 4586 | 0 | 11 |
| 4609 | 4628 | 1 | 436671 | 4568 | 4587 | 0 | 12 |
| 4610 | 4629 | 1 | 444608 | 4569 | 4588 | 0 | 13 |
| 4617 | 4636 | 1 | 444615 | 4576 | 4595 | 1 | 14 |
| 4622 | 4639 | 1 | 437168 | 4581 | 4598 | 2 | 15 |
| 4679 | 4698 | 1 | 419630 | 4638 | 4657 | 0 | 16 |
| 4733 | 4752 | 1 | 419636 | 4692 | 4711 | 0 | 17 |
| 4813 | 4832 | 1 | 444618 | 4772 | 4791 | 0 | 18 |
| 4814 | 4833 | 1 | 419637 | 4773 | 4792 | 0 | 19 |
| 4823 | 4842 | 1 | 444627 | 4782 | 4801 | 1 | 20 |
| 4925 | 4944 | 1 | 419640 | 4884 | 4903 | 1 | 24 |
| 4928 | 4947 | 1 | 419641 | 4887 | 4906 | 1 | 25 |
| 4931 | 4950 | 1 | 419642 | 4890 | 4909 | 1 | 26 |
| 4931 | 4948 | 1 | 437442 | 4890 | 4907 | 1 | 27 |
| 4955 | 4974 | 1 | 436689 | 4914 | 4933 | 3 | 28 |
| 5801 | 5820 | 1 | 444584 | 5757 | 5776 | 3 | 30 |
| 5807 | 5826 | 1 | 387916 | 5763 | 5782 | 0 | 31 |
| 5809 | 5826 | 1 | 437527 | 5765 | 5782 | 0 | 33 |
| 5809 | 5828 | 1 | 444591 | 5765 | 5784 | 0 | 32 |
| 101088 | 101105 | 2 | 437441 | 4340 | 4357 | 2 | 35 |

Gapmers with Mixed Phosphorothioate and Phosphodiester Internucleoside Linkages

The chimeric antisense oligonucleotides in Table 5 were designed as 5-10-5 MOE gapmers. The 5-10-5 gapmers have twenty linked nucleosides, wherein the central gap segment has ten 2'-deoxynucleotides and is flanked on both sides (in the 5' and 3' directions) by wings having five nucleosides each. Each nucleoside in the 5' wing segment and each nucleoside in the 3' wing segment has a 2'-MOE modification. The internucleoside linkages within the central gap segment, the linkages connecting the gap segment to the 5' or 3' wing segment, and the linkages for the 5'-most and 3'-most nucleosides of each wing segments are all phosphorothioate (P=S) linkages; the internucleoside linkages connecting the rest of the nucleosides of both the 5' and 3' wing segments are phosphodiester linkages; i.e. the gapmer has a mixed backbone. All cytosines throughout each gapmer are 5-methylcytosines. Each gapmer in Table 5 is targeted to the human mRNA sequence (GENBANK Accession No. NM_002111.6, designated herein as SEQ ID NO: 1). 'Start site' indicates the 5'-most nucleotide to which the gapmer is targeted in the human mRNA. 'Stop site' indicates the 3'-most nucleotide to which the gapmer is targeted in the human mRNA.

TABLE 5

Chimeric antisense oligonucleotides with phosphorothioate and phosphate internucleoside linkages targeting human huntingtin mRNA (SEQ ID NO: 1)

| Start Site | Stop Site | Target SEQ ID NO. | ISIS No. | Sequence (5' to 3') | Motif | SEQ ID NO. |
|---|---|---|---|---|---|---|
| 4607 | 4626 | 1 | 444658 | GCCTCTGATTCCCTGAACTG | 5-10-5 | 10 |
| 4608 | 4627 | 1 | 444659 | TGCCTCTGATTCCCTGAACT | 5-10-5 | 11 |

TABLE 5-continued

Chimeric antisense oligonucleotides with phosphorothioate and phosphate internucleoside linkages targeting human huntingtin mRNA (SEQ ID NO: 1)

| Start Site | Stop Site | Target SEQ ID NO. | ISIS No. | Sequence (5' to 3') | Motif | SEQ ID NO. |
|---|---|---|---|---|---|---|
| 4609 | 4628 | 1 | 444660 | TTGCCTCTGATTCCCTGAAC | 5-10-5 | 12 |
| 4610 | 4629 | 1 | 444661 | ATTGCCTCTGATTCCCTGAA | 5-10-5 | 13 |
| 4813 | 4832 | 1 | 444663 | CTGCATCAGCTTTATTTGTT | 5-10-5 | 18 |
| 4862 | 4881 | 1 | 443139 | CTCAGTAACATTGACACCAC | 5-10-5 | 22 |
| 5809 | 5828 | 1 | 444652 | TTTCTCTATTGCACATTCCA | 5-10-5 | 32 |
| 4928 | 4947 | 1 | 451541 | TTCTCCTTGTGGCACTGCTG | 5-10-5 | 25 |

The complementarity of the gapmers in Table 5 with mouse, rhesus monkey and rat huntingtin gene sequences are further described in Tables 6, 7, and 8.

The gapmers of Table 6 are complementary with mouse huntingtin mRNA (GENBANK Accession No. NM_010414.1; SEQ ID NO: 3). 'Mouse target start site' indicates the 5'-most nucleotide to which the gapmer is targeted in the mouse mRNA. 'Mouse target stop site' indicates the 3'-most nucleotide to which the gapmer is targeted in the mouse mRNA. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the mouse mRNA sequence.

TABLE 6

Complementarity of antisense oligonucleotides having mixed phosphorothioate and phosphate linkages with murine mRNA (SEQ ID NO: 3)

| Human Start Site | Human Stop Site | Human Target SEQ ID NO. | ISIS No. | Mouse Start Site | Mouse Stop Site | No. of mismatches | SEQ ID NO. |
|---|---|---|---|---|---|---|---|
| 4607 | 4626 | 1 | 444658 | 4566 | 4585 | 0 | 10 |
| 4608 | 4627 | 1 | 444659 | 4567 | 4586 | 0 | 11 |
| 4609 | 4628 | 1 | 444660 | 4568 | 4587 | 0 | 12 |
| 4610 | 4629 | 1 | 444661 | 4569 | 4588 | 0 | 13 |
| 4813 | 4832 | 1 | 444663 | 4772 | 4791 | 0 | 18 |
| 5809 | 5828 | 1 | 444652 | 5765 | 5784 | 1 | 32 |

The gapmers of Table 7 are complementary with the rhesus monkey huntingtin genomic sequence (the complement of GENBANK Accession No. NW_001109716.1 truncated at nucleotides 698000 to 866000; SEQ ID NO: 4). 'Rhesus monkey target start site' indicates the 5'-most nucleotide to which the gapmer is targeted in the rhesus monkey gene sequence. 'Rhesus monkey target stop site' indicates the 3'-most nucleotide to which the gapmer is targeted in the rhesus monkey gene sequence. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the rhesus monkey gene sequence.

TABLE 7

Complementarity of antisense oligonucleotides having mixed phosphorothioate and phosphate linkages with rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mismatches | SEQ ID NO. |
|---|---|---|---|---|---|---|---|
| 4609 | 4628 | 1 | 444660 | 102256 | 102275 | 3 | 12 |
| 4610 | 4629 | 1 | 444661 | 102257 | 102276 | 2 | 13 |
| 4813 | 4832 | 1 | 444663 | 105030 | 105049 | 0 | 18 |
| 4862 | 4881 | 1 | 443139 | 105079 | 105098 | 1 | 22 |
| 5809 | 5828 | 1 | 444652 | 125339 | 125358 | 0 | 32 |

The gapmers of Table 8 are complementary with rat huntingtin mRNA (GENBANK Accession No. NM_024357.2; SEQ ID NO: 5). 'Rat target start site' indicates the 5'-most nucleotide to which the gapmer is targeted in the rat mRNA. 'Rat target stop site' indicates the 3'-most nucleotide to which the gapmer is targeted in the rat mRNA. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the rat mRNA sequence.

CTCCGTCCGGTAGACATGCT, designated herein as SEQ ID NO: 37; reverse sequence GGAAATCAGAACCCT-CAAAATGG, designated herein as SEQ ID NO: 38; probe sequence TGAGCACTGTTCAACTGTGGATATCGG-GAX, designated herein as SEQ ID NO: 39) was used to measure mRNA levels. Huntingtin mRNA levels were adjusted according to total RNA content, as measured by RIBOGREEN®. Results are presented in Table 9 as percent inhibition of huntingtin mRNA, relative to untreated control cells and demonstrate antisense oligonucleotide-mediated dose-dependent reduction of huntingtin mRNA levels.

The half maximal inhibitory concentration ($IC_{50}$) of each oligonucleotide is also presented in Table 9 and was calculated by plotting the concentrations of oligonucleotides used versus the percent inhibition of huntingtin mRNA expression achieved at each concentration, and noting the concentration of oligonucleotide at which 50% inhibition of huntingtin mRNA expression was achieved compared to the control. The $IC_{50}$ is expressed in μM.

TABLE 8

Complementarity of antisense oligonucleotides having mixed phosphorothioate and phosphate linkages with rat mRNA (SEQ ID NO: 5)

| Human Start Site | Human Stop Site | Human Target SEQ ID NO. | ISIS No. | Rat Start Site | Rat Stop Site | No. of mismatches | SEQ ID NO. |
|---|---|---|---|---|---|---|---|
| 4607 | 4626 | 1 | 444658 | 4566 | 4585 | 0 | 10 |
| 4608 | 4627 | 1 | 444659 | 4567 | 4586 | 0 | 11 |
| 4609 | 4628 | 1 | 444660 | 4568 | 4587 | 0 | 12 |
| 4610 | 4629 | 1 | 444661 | 4569 | 4588 | 0 | 13 |
| 4813 | 4832 | 1 | 444663 | 4772 | 4791 | 0 | 18 |
| 5809 | 5828 | 1 | 444652 | 5765 | 5784 | 0 | 32 |

Example 2: Dose-Dependent Antisense Inhibition of Human Huntingtin mRNA In Vitro About seventeen hundred newly designed antisense compounds of various lengths, motifs and backbone composition were tested for their effect on human huntingtin mRNA in vitro in several cell types. These compounds were compared to about two hundred and fifty previously designed compounds including the compound ISIS 387916 which was previously determined to be a compound of considerable potency in vivo. As shown in this example, ISIS 419640, ISIS 419641, ISIS 419642, ISIS 436665, ISIS 436671, ISIS 436689, ISIS 437507, ISIS 443139, ISIS 444591, ISIS 444661, ISIS 437527, ISIS 444584, and ISIS 444652 and previously designed ISIS 388241 were found to have similar or better potency than the benchmark compound ISIS 387916 in vitro.

A. GM04281 Fibroblasts

Cultured GM04281 fibroblasts at a density of 25,000 cells per well were transfected using electroporation with 500 nM, 1000 nM, 2000 nM, 4000 nM, or 8000 nM of antisense oligonucleotide. After a treatment period of approximately 16 hours, RNA was isolated from the cells and huntingtin mRNA levels were measured by quantitative real-time PCR. Human primer probe set RTS2617 (forward sequence

TABLE 9

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 33 | 73 | 90 | 96 | 97 | 1.00 |
| 388241 | 44 | 70 | 82 | 95 | 97 | 0.61 |
| 419641 | 26 | 32 | 71 | 90 | 93 | 1.06 |
| 436665 | 56 | 67 | 87 | 95 | 96 | 0.32 |
| 436671 | 12 | 35 | 68 | 82 | 91 | 1.55 |
| 436689 | 10 | 34 | 61 | 80 | 91 | 1.89 |

ISIS 387916, ISIS 388241, and ISIS 437507 were further tested for their effect on human huntingtin mRNA in vitro. Cultured GM04281 fibroblasts were tested in a similar procedure, as described above. The results are presented in Table 10 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 10 expressed in μM.

TABLE 10

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 56 | 84 | 94 | 98 | 99 | 0.34 |
| 388241 | 58 | 75 | 94 | 98 | 99 | 0.23 |
| 437507 | 61 | 74 | 85 | 93 | 93 | 0.22 |

ISIS 387916, ISIS 388241, and ISIS 437507 were further tested for their effect on human huntingtin mRNA in vitro. Cultured GM04281 fibroblasts were tested in a similar procedure as described above. The results are presented in Table 11 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 11 expressed in μM.

TABLE 11

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 40 | 61 | 85 | 94 | 97 | 0.70 |
| 388241 | 51 | 72 | 86 | 94 | 98 | 0.41 |
| 437507 | 30 | 55 | 71 | 79 | 82 | 1.07 |

ISIS 387916, ISIS 388241, ISIS 419641, and ISIS 436754 were further tested for their effect on human huntingtin mRNA in vitro. Cultured GM04281 fibroblasts were tested in a similar procedure as described above. The results are presented in Table 12 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 12 expressed in μM.

TABLE 12

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 58 | 75 | 93 | 98 | 98 | 0.22 |
| 388241 | 40 | 68 | 85 | 95 | 98 | 0.73 |
| 419641 | 37 | 58 | 86 | 92 | 95 | 0.80 |
| 436754 | 44 | 62 | 63 | 84 | 93 | 0.59 |

ISIS 387916, ISIS 388241, and ISIS 437507 were further tested for their effect on human huntingtin mRNA in vitro. Cultured GM04281 fibroblasts at a density of 25,000 cells per well were transfected using electroporation with 250 nM, 500 nM, 1000 nM, 2000 nM, 4000 nM or 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 13 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 13 expressed in μM.

TABLE 13

Dose dependent reduction of huntingtin mRNA in GM04281 fibroblasts

| ISIS No. | 250 nM | 500 nM | 1000 Nm | 2000 nM | 4000 nM | 8000 nM | $IC_{50}$ (μM) |
|---|---|---|---|---|---|---|---|
| 387916 | 10 | 9 | 61 | 85 | 97 | 99 | 0.79 |
| 388241 | 0 | 18 | 42 | 90 | 98 | 99 | 1.08 |
| 437507 | 1 | 0 | 32 | 71 | 92 | 98 | 1.30 |

ISIS 387916, ISIS 388241, ISIS 419628, ISIS 419629, ISIS 419637, ISIS 436684, ISIS 443139, ISIS 444584, ISIS 444615, ISIS 444627, ISIS 444652, ISIS 444658, ISIS 444659, ISIS 444660, and ISIS 444661 were further tested for their effect on human huntingtin mRNA in vitro. Cultured GM04281 fibroblasts at a density of 25,000 cells per well were transfected using electroporation with 156.25 nM, 312.5 nM, 625 nM, 1250 nM, or 2500 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 14 as percent inhibition of huntingtin mRNA, relative to untreated control cells, and demonstrate antisense oligonucleotide-mediated dose-dependent reduction of huntingtin mRNA levels. The data presented is the average of two experiments. The $IC_{50}$ of each antisense oligonucleotide is also presented in Table 14 expressed in μM.

TABLE 14

Dose dependent reduction of huntingtin mRNA in GM04281 fibroblasts

| ISIS No | 156.25 nM | 312.5 Nm | 625 nM | 1250 nM | 2500 nM | $IC_{50}$ (μM) |
|---|---|---|---|---|---|---|
| 387916 | 19 | 22 | 44 | 62 | 85 | 0.73 |
| 388241 | 3 | 13 | 24 | 42 | 71 | 1.42 |
| 419628 | 56 | 45 | 59 | 71 | 83 | 0.20 |
| 419629 | 42 | 38 | 67 | 70 | 89 | 0.33 |
| 419637 | 24 | 17 | 32 | 61 | 77 | 0.91 |
| 436684 | 15 | 28 | 55 | 73 | 85 | 0.59 |
| 443139 | 13 | 45 | 50 | 64 | 81 | 0.61 |
| 444584 | 0 | 0 | 25 | 50 | 74 | 1.28 |
| 444615 | 36 | 35 | 37 | 38 | 70 | 0.12 |
| 444627 | 40 | 38 | 48 | 73 | 87 | 0.43 |
| 444652 | 15 | 28 | 55 | 73 | 85 | 0.59 |
| 444658 | 50 | 54 | 75 | 84 | 96 | 0.18 |
| 444659 | 47 | 61 | 69 | 79 | 93 | 0.18 |
| 444660 | 41 | 61 | 65 | 84 | 95 | 0.22 |
| 444661 | 47 | 59 | 72 | 84 | 96 | 0.19 |

ISIS 387916, ISIS 436671, ISIS 444661, ISIS 419641, and ISIS 436665 were further tested for their effect on human huntingtin mRNA in vitro. Cultured GM04281 fibroblasts at a density of 25,000 cells per well were transfected using electroporation with 13.6719 nM, 27.3438 nM, 54.6875 nM, 109.375 nM, 218.75 nM, 437.5 nM, 875 nM, 1750 nM, 3500 nM, or 7000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 15 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15 expressed in μM.

TABLE 15

Dose dependent reduction of huntingtin mRNA in GM04281 fibroblasts

| ISIS No. | 13.6719 nM | 27.3438 nM | 54.6875 nM | 109.375 nM | 218.75 nM | 437.5 nM | 875 nM | 1750 nM | 3500 nM | 7000 nM | $IC_{50}$ (μM) |
|---|---|---|---|---|---|---|---|---|---|---|---|
| 387916 | 0 | 31 | 14 | 43 | 44 | 68 | 86 | 89 | 97 | 97 | 0.31 |
| 436671 | 0 | 0 | 21 | 31 | 54 | 73 | 77 | 83 | 88 | 97 | 0.31 |
| 444661 | 0 | 10 | 25 | 53 | 66 | 73 | 87 | 96 | 99 | 99 | 0.16 |
| 419641 | 5 | 23 | 33 | 48 | 44 | 75 | 79 | 90 | 94 | 98 | 0.17 |
| 436665 | 26 | 37 | 47 | 44 | 65 | 83 | 89 | 94 | 98 | 98 | 0.07 |

ISIS 387916, ISIS 388241, ISIS 437168, and ISIS 437175 were further tested for their effect on human huntingtin mRNA in vitro. Cultured GM04281 fibroblasts at a density of 25,000 cells per well were transfected using electroporation with 250 nM, 500 nM, 1000 nM, 2000 nM, 4000 nM, and 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 15.1 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.1 expressed in μM.

TABLE 15.1

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 22 | 63 | 70 | 83 | 95 | 96 | 0.62 |
| 388241 | 17 | 45 | 65 | 87 | 96 | 97 | 0.56 |
| 437175 | 47 | 31 | 56 | 60 | 79 | 91 | 1.19 |
| 437168 | 32 | 46 | 64 | 81 | 89 | 95 | 0.59 |

ISIS 387916, ISIS 388241, ISIS 437441, and ISIS 437442 were further tested for their effect on human huntingtin mRNA in vitro. Cultured GM04281 fibroblasts were tested in a similar procedure as described above. The results are presented in Table 15.2 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.2 expressed in μM.

TABLE 15.2

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 26 | 47 | 58 | 79 | 91 | 95 | 0.65 |
| 388241 | 30 | 52 | 60 | 81 | 94 | 97 | 0.55 |
| 437441 | 25 | 37 | 56 | 69 | 86 | 47 | 0.81 |
| 437442 | 39 | 43 | 47 | 70 | 85 | 50 | 0.59 |

ISIS 387916, ISIS 388241, ISIS 437175, and ISIS 437527 were further tested for their effect on human huntingtin mRNA in vitro. Cultured GM04281 fibroblasts were tested in a similar procedure as described above. The results are presented in Table 15.3 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.3 expressed in μM.

TABLE 15.3

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 40 | 45 | 47 | 76 | 92 | 96 | 0.50 |
| 388241 | 40 | 37 | 50 | 90 | 96 | 97 | 0.80 |
| 437175 | 48 | 55 | 55 | 63 | 80 | 93 | 0.37 |
| 437527 | 33 | 52 | 61 | 80 | 86 | 95 | 0.52 |

B. A549 Cells

Some of the antisense oligonucleotides described in Example 1 were tested for their effect on human huntingtin mRNA in vitro. Cultured A549 cells at a density of 4,000 cells per well were transfected using lipofectin transfection reagent with 7.4074 nM, 22.222 nM, 66.667 nM, or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 16 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 16 expressed in nM.

TABLE 16

Dose dependent reduction of huntingtin mRNA in A549 cells

| ISIS No. | 7.4074 nM | 22.222 nM | 66.667 nM | 200.00 nM | IC$_{50}$ (nM) |
|---|---|---|---|---|---|
| 387916 | 12 | 37 | 76 | 92 | 33 |
| 419640 | 21 | 45 | 73 | 93 | 27 |
| 419641 | 34 | 60 | 83 | 96 | 15 |
| 419642 | 30 | 58 | 85 | 95 | 16 |

ISIS 387916, ISIS 388241, and ISIS 437507 were further tested for their effect on human huntingtin mRNA in vitro. Cultured A549 cells at a density of 20,000 cells per well were transfected using electroporation with 250 nM, 500 nM, 1000 nM, 2000 nM, 4000 nM or 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 17 expressed as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 17 expressed in μM.

TABLE 17

Dose dependent reduction of huntingtin mRNA in A549 cells

| ISIS No. | 250 nM | 500 nM | 1000 nM | 2000 nM | 4000 nM | 8000 nM | IC$_{50}$ (μM) |
|---|---|---|---|---|---|---|---|
| 387916 | 15 | 17 | 25 | 36 | 52 | 75 | 3.09 |
| 388241 | 12 | 22 | 38 | 58 | 77 | 91 | 1.43 |
| 437507 | 25 | 28 | 38 | 57 | 58 | 76 | 1.84 |

C. LLC-MK2 Cells

Some of the antisense oligonucleotides described in Example 1 and targeted to a human huntingtin nucleic acid were tested for their effect on rhesus monkey huntingtin mRNA in vitro. Cultured LLC-MK2 cells at a density of 25,000 cells per well were transfected using electroporation with 625 nM, 1250 nM, 2500 nM, 5000 nM, 10,000 nM, or 20,000 nM of antisense oligonucleotide. After a treatment period of approximately 16 hours, RNA was isolated from the cells and huntingtin mRNA levels were measured by quantitative real-time PCR. Human primer probe set RTS2686 (forward sequence GTCTGAGCCTCTCTCGGTCAA, designated herein as SEQ ID NO: 40; reverse sequence AAGGGATGCTGGGCTCTGT, designated herein as SEQ ID NO: 41; probe sequence AGCAAAGCTTGGTGTCTTGGCACTGTTAGTX, designated herein as SEQ ID NO: 42) was used to measure mRNA levels. Huntingtin mRNA levels were adjusted according to total RNA content, as measured by RIBOGREEN®. Results are presented in Table 18 as percent inhibition of huntingtin mRNA, relative to untreated control cells and demonstrate antisense oligonucleotide-mediated dose-dependent reduction of huntingtin mRNA levels. The IC$_{50}$ of each antisense oligonucleotide is also presented in Table 18 expressed in μM.

TABLE 18

Dose dependent reduction of huntingtin mRNA in LLC-MK2 cells

| ISIS No. | 625 nM | 1250 nM | 2500 nM | 5000 nM | 10000 nM | 20000 nM | IC$_{50}$ (μM) |
|---|---|---|---|---|---|---|---|
| 388241 | 21 | 12 | 35 | 46 | 46 | 94 | 4.1 |
| 444591 | 37 | 46 | 51 | 52 | 82 | 96 | 1.9 |
| 419641 | 32 | 52 | 69 | 87 | 94 | 97 | 1.2 |
| 444661 | 45 | 59 | 66 | 85 | 91 | 95 | 0.8 |
| 419642 | 6 | 3 | 56 | 81 | 91 | 98 | 2.9 |
| 436665 | 40 | 43 | 70 | 73 | 84 | 89 | 1.2 |
| 436671 | 31 | 51 | 68 | 82 | 90 | 97 | 1.2 |
| 436689 | 24 | 37 | 59 | 74 | 89 | 98 | 1.9 |
| 437507 | 21 | 15 | 11 | 33 | 55 | 92 | 6.4 |
| 443139 | 31 | 36 | 37 | 56 | 76 | 97 | 2.6 |

ISIS 387916, ISIS 388241, ISIS 436684, ISIS 437168, ISIS 437175, ISIS 437441, ISIS 437507, ISIS 437527, ISIS 444578, ISIS 444584, ISIS 444591, and ISIS 444607 were further tested for their effect on rhesus monkey huntingtin mRNA in vitro. Cultured LLC-MK2 cells were tested in a similar procedure as described above. The results are presented in Table 19 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 19 expressed in μM.

TABLE 19

Dose dependent reduction of huntingtin mRNA in LLC-MK2 cells

| ISIS No. | 625.0 nM | 1250.0 nM | 2500.0 nM | 5000.0 nM | 10000.0 nM | 20000.0 nM | IC$_{50}$ |
|---|---|---|---|---|---|---|---|
| 387916 | 23 | 42 | 57 | 81 | 88 | 96 | 1.95 |
| 388241 | 6 | 12 | 37 | 43 | 62 | 84 | 5.32 |
| 437168 | 72 | 47 | 60 | 78 | 83 | 92 | 1.43 |
| 437175 | 27 | 48 | 36 | 56 | 68 | 78 | 3.58 |
| 437441 | 29 | 34 | 50 | 67 | 56 | 85 | 2.43 |
| 437507 | 18 | 29 | 18 | 33 | 45 | 66 | 6.12 |
| 437527 | 36 | 36 | 48 | 57 | 81 | 90 | 2.71 |
| 436684 | 0 | 12 | 24 | 29 | 36 | 49 | n.d. |
| 444578 | 34 | 40 | 65 | 74 | 82 | 87 | 1.70 |
| 444584 | 28 | 38 | 68 | 75 | 90 | 94 | 1.69 |
| 444591 | 25 | 45 | 55 | 74 | 85 | 94 | 1.84 |
| 444607 | 41 | 54 | 76 | 87 | 92 | 94 | 0.96 | n.d. = IC$_{50}$ could not be measured for that compound

ISIS 387916, ISIS 388241, ISIS 444608, ISIS 444615, ISIS 444618, ISIS 444627, ISIS 444652, ISIS 444658, ISIS 444659, ISIS 444660, and ISIS 444661 were further tested for their effect on rhesus monkey huntingtin mRNA in vitro. Cultured LLC-MK2 cells were tested in a similar procedure as described above. The results are presented in Table 20 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 20 expressed in μM.

TABLE 20

Dose dependent reduction of huntingtin mRNA in LLC-MK2 cells

| ISIS No | 625.0 nM | 1250.0 nM | 2500.0 nM | 5000.0 nM | 10000.0 nM | 20000.0 nM | IC50 |
|---|---|---|---|---|---|---|---|
| 387916 | 35 | 44 | 68 | 74 | 90 | 96 | 1.35 |
| 388241 | 23 | 37 | 54 | 56 | 68 | 89 | 2.64 |

TABLE 20-continued

Dose dependent reduction of huntingtin mRNA in LLC-MK2 cells

| ISIS No | 625.0 nM | 1250.0 nM | 2500.0 nM | 5000.0 nM | 10000.0 nM | 20000.0 nM | IC50 |
|---|---|---|---|---|---|---|---|
| 444608 | 43 | 50 | 64 | 83 | 90 | 95 | 1.07 |
| 444615 | 29 | 45 | 55 | 76 | 90 | 97 | 1.67 |
| 444618 | 30 | 34 | 57 | 73 | 89 | 95 | 1.66 |
| 444627 | 35 | 56 | 76 | 90 | 97 | 98 | 1.00 |
| 444652 | 32 | 55 | 66 | 55 | 92 | 98 | 1.23 |
| 444658 | 50 | 62 | 80 | 90 | 95 | 97 | 0.55 |
| 444659 | 31 | 56 | 68 | 86 | 95 | 97 | 1.17 |
| 444660 | 38 | 49 | 62 | 86 | 89 | 96 | 1.26 |
| 444661 | 41 | 50 | 75 | 68 | 95 | 97 | 0.95 |

ISIS 387916, ISIS 419627, ISIS 419628, ISIS 419629, ISIS 419630, ISIS 419636, ISIS 419637, ISIS 419640, ISIS 419641, and ISIS 419642 were further tested for their effect on rhesus monkey huntingtin mRNA in vitro. Cultured LLC-MK2 cells at a density of 3,000 cells per well were transfected using lipofectin transfection reagent with 6.25 nM, 12.5 nM, 25 nM, 50 nM, 100 nM, or 200 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 21 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 21 expressed in nM.

TABLE 21

Dose dependent reduction of huntingtin mRNA in LLC-MK2 cells

| ISIS No. | 6.25 nM | 12.5 nM | 25.0 nM | 50.0 nM | 100.0 nM | 200.0 nM | $IC_{50}$ |
|---|---|---|---|---|---|---|---|
| 387916 | 1 | 37 | 37 | 53 | 84 | 90 | 35 |
| 419627 | 0 | 9 | 18 | 45 | 58 | 72 | 75 |
| 419628 | 9 | 30 | 49 | 63 | 73 | 77 | 31 |
| 419629 | 9 | 16 | 40 | 56 | 80 | 85 | 36 |
| 419630 | 17 | 8 | 43 | 58 | 71 | 81 | 40 |
| 419636 | 23 | 25 | 38 | 55 | 72 | 78 | 37 |
| 419637 | 10 | 35 | 31 | 62 | 78 | 76 | 33 |
| 419640 | 3 | 28 | 39 | 59 | 74 | 87 | 36 |
| 419641 | 11 | 34 | 51 | 65 | 85 | 87 | 26 |
| 419642 | 25 | 30 | 49 | 65 | 85 | 88 | 24 |

ISIS 387916, ISIS 419641, and ISIS 436689 were further tested for their effect on rhesus monkey huntingtin mRNA in vitro. Cultured LLC-MK2 cells at a density of 3,000 cells per well were transfected using LipofectAMINE2000 transfection reagent with 6.25 nM, 12.5 nM, 25 nM, 50 nM, 100 nM, or 200 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 22 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 22 expressed in nM.

TABLE 22

Dose dependent reduction of huntingtin mRNA in LLC-MK2 cells

| ISIS No | 6.25 nM | 12.5 nM | 25 nM | 50 nM | 100 nM | 200 nM | $IC_{50}$ (nM) |
|---|---|---|---|---|---|---|---|
| 387916 | 0 | 50 | 31 | 68 | 83 | 90 | 47 |
| 419641 | 28 | 23 | 28 | 51 | 65 | 81 | 74 |
| 436689 | 16 | 30 | 29 | 48 | 67 | 83 | 69 |

ISIS 387916, ISIS 388241, ISIS 436665, ISIS 436671, and ISIS 436689 were further tested for their effect on rhesus monkey huntingtin mRNA in vitro. Cultured LLC-MK2 cells at a density of 3,000 cells per well were transfected using lipofectin transfection reagent with 4.6875 nM, 9.375 nM, 18.75 nM, 37.5 nM, 75 nM, or 150 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 23 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 23 expressed in nM.

TABLE 23

Dose dependent reduction of huntingtin mRNA in LLC-MK2 cells

| ISIS No. | 4.6875 nM | 9.375 nM | 18.75 nM | 37.5 nM | 75.0 nM | 150.0 nM | $IC_{50}$ (nM) |
|---|---|---|---|---|---|---|---|
| 387916 | 7 | 6 | 38 | 59 | 82 | 91 | 32 |
| 388241 | 0 | 0 | 5 | 35 | 62 | 81 | 60 |
| 436665 | 7 | 0 | 36 | 59 | 64 | 69 | 37 |
| 436671 | 21 | 7 | 35 | 59 | 80 | 86 | 31 |
| 436689 | 38 | 45 | 45 | 59 | 76 | 86 | 15 |

D. BACHD Transgenic Mouse Hepatocyes

Some of the antisense oligonucleotides described in Example 1 and targeted to a human huntingtin nucleic acid were tested for their effect on human huntingtin mRNA in vitro. Cultured BACHD mouse hepatocytes at a density of 10,000 cells per well were transfected using cytofectin transfection reagent with 7.4074 nM, 22.222 nM, 66.667 nM, or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 24 as percent inhibition of huntingtin mRNA, relative to untreated control cells, and demonstrate antisense oligonucleotide-mediated dose-dependent reduction of huntingtin mRNA levels. The data presented is the average of two experiments. The $IC_{50}$ of each antisense oligonucleotide is also presented in Table 24 expressed in nM.

TABLE 24

Dose dependent reduction of huntingtin mRNA
in BACHD transgenic murine hepatocytes

| ISIS No. | 7.4074 nM | 22.222 nM | 66.667 nM | 200.00 nM | IC$_{50}$ (nM) |
|---|---|---|---|---|---|
| 387916 | 8 | 19 | 58 | 89 | 40 |
| 419640 | 15 | 30 | 64 | 93 | 33 |
| 419641 | 20 | 35 | 73 | 97 | 31 |
| 419642 | 3 | 29 | 70 | 96 | 43 |

ISIS 387916, ISIS 388241, and ISIS 419641 were further tested for their effect on human huntingtin mRNA in vitro. Cultured BACHD mouse hepatocytes at a density of 10,000 cells per well were transfected using cytofectin transfection reagent with 12.5 nM, 25 nM, 50 nM, 100 nM or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 25 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 25 expressed in nM.

TABLE 25

Dose dependent reduction of huntingtin mRNA
in BACHD transgenic murine hepatocytes

| ISIS No. | 12.5 nM | 25 nM | 50 Nm | 100 nM | 200 nM | IC$_{50}$ (nM) |
|---|---|---|---|---|---|---|
| 387916 | 0 | 37 | 51 | 78 | 91 | 51 |
| 388241 | 0 | 10 | 45 | 70 | 92 | 68 |
| 419641 | 17 | 38 | 70 | 88 | 96 | 34 |

ISIS 387916, ISIS 388241, ISIS 419641, ISIS 436665, ISIS 436671, and ISIS 436689 were further tested for their effect on human huntingtin mRNA in vitro. Cultured BACHD mouse hepatocytes were tested in an identical manner as described above. The results are presented in Table 26 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 26 expressed in nM.

TABLE 26

Dose dependent reduction of huntingtin mRNA
in BACHD transgenic murine hepatocytes

| ISIS No. | 12.5 nM | 25 nM | 50 nM | 100 nM | 200 nM | IC$_{50}$ (nM) |
|---|---|---|---|---|---|---|
| 387916 | 19 | 48 | 64 | 86 | 93 | 32 |
| 388241 | 20 | 34 | 54 | 81 | 93 | 38 |
| 419641 | 38 | 54 | 70 | 85 | 95 | 21 |
| 436665 | 32 | 40 | 67 | 84 | 93 | 29 |
| 436671 | 32 | 42 | 58 | 78 | 91 | 32 |
| 436689 | 35 | 44 | 70 | 88 | 96 | 25 |

ISIS 387916, ISIS 419640, ISIS 419641, and ISIS 419642 were further tested for their effect on mouse huntingtin mRNA in vitro. Cultured BACHD mouse hepatocytes at a density of 20,000 cells per well were transfected using cytofectin transfection reagent with 6.667 nM, 20 nM, 60 nM, or 180 nM of antisense oligonucleotide. After a treatment period of approximately 16 hours, RNA was isolated from the cells and huntingtin mRNA levels were measured by quantitative real-time PCR. Murine primer probe set RTS2633 (forward sequence CAGAGCTGGT-CAACCGTATCC, designated herein as SEQ ID NO: 43; reverse sequence GGCTTAAACAGGGAGCCAAAA, designated herein as SEQ ID NO: 44; probe sequence ACTT-CATGATGAGCTCGGAGTTCAACX, designated herein as SEQ ID NO: 45) was used to measure mRNA levels. Huntingtin mRNA levels were adjusted according to total RNA content, as measured by RIBOGREEN®. Results are presented in Table 27 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 27 expressed in nM.

TABLE 27

Dose dependent reduction of huntingtin mRNA
in BACHD transgenic murine hepatocytes

| ISIS No. | 6.667 nM | 20 nM | 60 nM | 180 nM | IC$_{50}$ (nM) |
|---|---|---|---|---|---|
| 387916 | 15 | 15 | 68 | 94 | 37 |
| 419640 | 4 | 39 | 73 | 94 | 32 |
| 419641 | 16 | 45 | 81 | 96 | 24 |
| 419642 | 23 | 39 | 75 | 93 | 25 |

Example 3: Systemic Administration of Antisense Oligonucleotides Against Huntingtin mRNA in BACHD Mice Of the about seventeen hundred newly designed antisense compounds, sixty six compounds were selected based on in vitro potency compared to ISIS 387916 for testing in systemic tolerability screens.

BACHD mice were treated with ISIS oligonucleotides and evaluated for changes in the levels of various metabolic markers as well as inhibition of huntingtin mRNA in the liver. Antisense oligonucleotides which caused adverse changes in body weight, organ weight or in the levels of metabolic markers were deemed unsuitable for utilization in further studies.

Study 1.
Treatment

Nineteen groups of four BACHD mice each were injected intraperitoneally with 12.5 mg/kg of ISIS 387916, ISIS 388241, ISIS 419629, ISIS 419637, ISIS 436684, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 28 and 29 and were calculated as percent inhibition of human and murine huntingtin expression levels respectively, relative to the PBS control. All the antisense oligonucleotides effect significant inhibition of human huntingtin mRNA levels. ISIS 388241 has more than three mismatches with the murine huntingtin mRNA (SEQ ID NO: 3) and therefore did not show significant inhibition of murine mRNA levels compared to the control.

TABLE 28

Percent inhibition of human huntingtin mRNA in BACHD mice

| ISIS No. | % inhibition |
|---|---|
| 387916 | 82 |
| 388241 | 52 |
| 419629 | 80 |
| 419637 | 83 |
| 436684 | 55 |
| 444578 | 70 |
| 444584 | 62 |
| 444591 | 54 |
| 444607 | 76 |
| 444608 | 61 |
| 444615 | 89 |
| 444618 | 91 |
| 444627 | 92 |
| 444652 | 79 |
| 444658 | 62 |
| 444659 | 74 |
| 444660 | 66 |
| 444661 | 72 |
| 444663 | 77 |

TABLE 29

Percent inhibition of murine huntingtin mRNA in BACHD mice

| ISIS No. | % inhibition |
|---|---|
| 387916 | 77 |
| 419629 | 75 |
| 419637 | 87 |
| 436684 | 32 |
| 444578 | 64 |
| 444584 | 20 |
| 444591 | 32 |
| 444607 | 76 |
| 444608 | 66 |
| 444615 | 60 |
| 444618 | 88 |
| 444627 | 58 |
| 444652 | 66 |
| 444658 | 53 |
| 444659 | 62 |
| 444660 | 47 |
| 444661 | 67 |
| 444663 | 60 |

Organ Weight Measurements

Liver, spleen and kidney weights were measured at the end of the study, and are presented in Table 30 as a percent of the saline control normalized to body weight.

TABLE 30

Percent change in organ weight of BACHD mice after antisense oligonucleotide treatment

| ISIS No. | Liver | Spleen | Kidney |
|---|---|---|---|
| 387916 | −5 | −13 | +6 |
| 388241 | −1 | +14 | −5 |
| 419629 | +5 | +13 | −12 |
| 419637 | −6 | −17 | −25 |
| 436684 | −2 | −3 | +6 |
| 444578 | +11 | +18 | +1 |
| 444584 | +8 | +54 | +1 |
| 444591 | +4 | −4 | −3 |
| 444607 | +3 | +22 | −8 |
| 444608 | +6 | +18 | −3 |
| 444615 | +6 | +1 | +3 |
| 444618 | +11 | +0 | −2 |
| 444627 | +3 | −14 | +14 |
| 444652 | −11 | −4 | −18 |
| 444658 | −1 | 0 | −16 |
| 444659 | +1 | +15 | −2 |
| 444660 | −5 | +4 | −6 |
| 444661 | −1 | +7 | −1 |
| 444663 | +7 | +10 | +8 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 31.

TABLE 31

Effect of antisense oligonucleotide treatment on markers of liver function

|  | ALT | AST |
|---|---|---|
| PBS | 40 | 69 |
| 387916 | 69 | 84 |
| 388241 | 42 | 76 |
| 419629 | 51 | 71 |
| 419637 | 59 | 86 |
| 436684 | 60 | 87 |
| 444578 | 62 | 93 |
| 444584 | 48 | 76 |
| 444591 | 39 | 53 |
| 444607 | 51 | 111 |
| 444608 | 48 | 75 |
| 444615 | 74 | 95 |
| 444618 | 687 | 908 |
| 444627 | 105 | 127 |
| 444652 | 54 | 64 |
| 444658 | 46 | 59 |
| 444659 | 90 | 138 |
| 444660 | 34 | 64 |
| 444661 | 49 | 99 |
| 444663 | 90 | 164 |

Study 2

Treatment

Fourteen groups of four BACHD mice each were injected intraperitoneally with 12.5 mg/kg or 50 mg/kg of ISIS 419581, ISIS 419602, ISIS 419628, ISIS 419629, ISIS 419640, ISIS 419641, or ISIS 419642 twice a week for 2 weeks. A group of four BACHD mice was injected intraperitoneally with 12.5 mg/kg of ISIS 387916 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 32 and 33 and were calculated as percent inhibition of human and murine huntingtin expression levels respectively, relative to the PBS control.

TABLE 32

Percent inhibition of human huntingtin mRNA in BACHD mice

| ISIS No. | Dose (mg/kg) | % inhibition |
|---|---|---|
| 387916 | 12.5 | 71 |
| 419581 | 12.5 | 54 |
|  | 50 | 68 |
| 419602 | 12.5 | 72 |
|  | 50 | 77 |
| 419628 | 12.5 | 65 |
|  | 50 | 76 |
| 419629 | 12.5 | 87 |
|  | 50 | 93 |
| 419640 | 12.5 | 69 |
|  | 50 | 79 |
| 419641 | 12.5 | 61 |
|  | 50 | 80 |
| 419642 | 12.5 | 76 |
|  | 50 | 83 |

TABLE 33

Percent inhibition of murine huntingtin mRNA in BACHD mice

| ISIS No. | Dose (mg/kg) | % inhibition |
|---|---|---|
| 387916 | 12.5 | 70 |
| 419581 | 12.5 | 42 |
|  | 50 | 86 |
| 419602 | 12.5 | 77 |
|  | 50 | 85 |
| 419628 | 12.5 | 67 |
|  | 50 | 86 |
| 419629 | 12.5 | 90 |
|  | 50 | 93 |
| 419640 | 12.5 | 63 |
|  | 50 | 84 |
| 419641 | 12.5 | 52 |
|  | 50 | 81 |
| 419642 | 12.5 | 56 |
|  | 50 | 83 |

Organ Weight Measurements

Liver, spleen and kidney weights were measured at the end of the study, and are presented in Table 34 as a percent of the saline control normalized to body weight.

TABLE 34

Percent change in organ weight of BACHD mice after antisense oligonucleotide treatment

| ISIS No. | Dose (mg/kg) | Liver | Spleen | Kidney |
|---|---|---|---|---|
| 387916 | 12.5 | −9 | 3 | −4 |
| 419581 | 12.5 | −2 | −6 | −1 |
|  | 50 | 14 | −1 | −11 |
| 419602 | 12.5 | 10 | 1 | −2 |
|  | 50 | 28 | 9 | −3 |
| 419628 | 12.5 | −2 | −7 | −2 |
|  | 50 | −3 | 7 | −9 |
| 419629 | 12.5 | −7 | −5 | −10 |
|  | 50 | 16 | 0 | −8 |
| 419640 | 12.5 | −5 | −2 | −8 |
|  | 50 | 1 | −20 | −4 |
| 419641 | 12.5 | −7 | −10 | −11 |
|  | 50 | −2 | −13 | −9 |
| 419642 | 12.5 | −11 | −21 | −19 |
|  | 50 | −1 | −8 | −9 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of ALT and AST are expressed in IU/L and the results are presented in Table 35.

TABLE 35

Effect of antisense oligonucleotide treatment on markers of liver function

| | Dose (mg/kg) | ALT | AST |
|---|---|---|---|
| PBS |  | 44 | 80 |
| 387916 | 12.5 | 44 | 75 |
| 419581 | 12.5 | 56 | 101 |
|  | 50 | 390 | 281 |
| 419602 | 12.5 | 86 | 108 |
|  | 50 | 240 | 229 |
| 419628 | 12.5 | 52 | 110 |
|  | 50 | 51 | 73 |
| 419629 | 12.5 | 104 | 118 |
|  | 50 | 1262 | 1150 |
| 419640 | 12.5 | 36 | 65 |
|  | 50 | 38 | 55 |
| 419641 | 12.5 | 56 | 103 |
|  | 50 | 57 | 172 |
| 419642 | 12.5 | 40 | 64 |
|  | 50 | 47 | 101 |

Study 3

Treatment

Eighteen groups of four BACHD mice each were injected intraperitoneally with 12.5 mg/kg or 50 mg/kg of ISIS 388250, ISIS 388251, ISIS 388263, ISIS 388264, ISIS 419641, ISIS 436645, ISIS 436649, ISIS 436668, or ISIS 436689 twice a week for 2 weeks. A group of four BACHD mice was injected intraperitoneally with 12.5 mg/kg of ISIS 388241 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 36 and 37 and were calculated as percent inhibition of human and murine huntingtin expression levels respectively, relative to the PBS control. All the antisense oligonucleotides effect significant inhibition of human huntingtin mRNA levels. ISIS 388241, ISIS 388250, ISIS 388251, ISIS 388263, ISIS 388264, and ISIS 436645 have more than three mismatches with the murine huntingtin mRNA (SEQ ID NO: 3) and therefore did not show significant inhibition of murine mRNA levels compared to the control. ISIS 436649 and ISIS 436689 have three mismatches with the murine huntingtin mRNA (SEQ ID NO: 3) and therefore did not show significant inhibition of murine mRNA levels compared to the control.

TABLE 36

Percent inhibition of human huntingtin mRNA in BACHD mice

| ISIS No. | Dose (mg/kg) | % inhibition |
|---|---|---|
| 388241 | 12.5 | 32 |
| 388250 | 12.5 | 21 |
|  | 50 | 45 |
| 388251 | 12.5 | 30 |
|  | 50 | 34 |
| 388263 | 12.5 | 29 |
|  | 50 | 35 |
| 388264 | 12.5 | 35 |
|  | 50 | 42 |
| 419641 | 12.5 | 71 |
|  | 50 | 73 |
| 436645 | 12.5 | 43 |
|  | 50 | 48 |
| 436649 | 12.5 | 40 |
|  | 50 | 38 |
| 436668 | 12.5 | 45 |
|  | 50 | 69 |
| 436689 | 12.5 | 62 |
|  | 50 | 78 |

TABLE 37

Percent inhibition of murine huntingtin mRNA in BACHD mice

| ISIS No. | Dose (mg/kg) | % inhibition |
|---|---|---|
| 419641 | 12.5 | 68 |
|  | 50 | 77 |
| 436668 | 12.5 | 41 |
|  | 50 | 62 |

Organ Weight Measurements

Liver, spleen and kidney weights were measured at the end of the study, and are presented in Table 38 as a percent of the saline control normalized to body weight. Mice treated with ISIS 388263 and ISIS 436645 suffered increases in liver weight at the 50 mg/kg dose compared to the PBS control.

TABLE 38

Percent change in organ weight of BACHD mice after antisense oligonucleotide treatment

| ISIS No. | Dose (mg/kg) | Liver | Spleen | Kidney |
|---|---|---|---|---|
| 388241 | 12.5 | 1 | 6 | 9 |
| 388250 | 12.5 | 2 | 1 | −2 |
|  | 50 | 1 | 30 | 3 |
| 388251 | 12.5 | 4 | −8 | 1 |
|  | 50 | 19 | 19 | 2 |
| 388263 | 12.5 | 4 | 8 | 9 |
|  | 50 | 23 | 52 | 1 |
| 388264 | 12.5 | 2 | −2 | 3 |
|  | 50 | 12 | 9 | 6 |
| 419641 | 12.5 | −1 | −9 | 3 |
|  | 50 | 2 | −4 | 3 |
| 436645 | 12.5 | 8 | 6 | 5 |
|  | 50 | 26 | 25 | 9 |

TABLE 38-continued

Percent change in organ weight of BACHD mice after antisense oligonucleotide treatment

| ISIS No. | Dose (mg/kg) | Liver | Spleen | Kidney |
|---|---|---|---|---|
| 436649 | 12.5 | 1 | 0 | 6 |
|  | 50 | 0 | 1 | 3 |
| 436668 | 12.5 | 1 | 5 | 10 |
|  | 50 | −2 | 3 | 11 |
| 436689 | 12.5 | −3 | −5 | 4 |
|  | 50 | 6 | 11 | 5 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 39.

TABLE 39

Effect of antisense oligonucleotide treatment on markers of liver function

| | Dose (mg/kg) | ALT | AST |
|---|---|---|---|
| PBS |  | 43 | 76 |
| 388241 | 12.5 | 43 | 88 |
| 388250 | 12.5 | 37 | 55 |
|  | 50 | 44 | 89 |
| 388251 | 12.5 | 42 | 98 |
|  | 50 | 67 | 91 |
| 388263 | 12.5 | 51 | 90 |
|  | 50 | 55 | 93 |
| 388264 | 12.5 | 31 | 59 |
|  | 50 | 65 | 90 |
| 419641 | 12.5 | 39 | 70 |
|  | 50 | 42 | 83 |
| 436645 | 12.5 | 43 | 82 |
|  | 50 | 179 | 143 |
| 436649 | 12.5 | 35 | 47 |
|  | 50 | 38 | 76 |
| 436668 | 12.5 | 36 | 73 |
|  | 50 | 28 | 57 |
| 436689 | 12.5 | 31 | 52 |
|  | 50 | 49 | 164 |

Study 4
Treatment

Eighteen groups of four BACHD mice each were injected intraperitoneally with 12.5 mg/kg or 50 mg/kg of ISIS 388241, ISIS 437123, ISIS 437132, ISIS 437140, ISIS 437442, ISIS 437446, ISIS 437477, ISIS 437478, or ISIS 437490 twice a week for 2 weeks. A group of four BACHD mice was injected intraperitoneally with 12.5 mg/kg of ISIS 387916 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 40 and 41 and were calculated as percent inhibition of human and murine huntingtin expression levels respectively, relative to the PBS control. ISIS 388241 and ISIS 437490 have more than three mismatches with the murine huntingtin mRNA (SEQ ID NO: 3) and therefore did not show significant inhibition of murine mRNA levels compared to the control. ISIS 437132 has three mismatches with the murine huntingtin mRNA (SEQ ID NO: 3) and therefore did not show significant inhibition of murine mRNA levels compared to the control. ISIS 437123 and ISIS 437140 have two mismatches with the murine huntingtin mRNA (SEQ ID NO: 3) and do not show significant inhibition of murine mRNA levels compared to the control.

TABLE 40

Percent inhibition of human huntingtin mRNA in BACHD mice

| ISIS No. | Dose (mg/kg) | % inhibition |
|---|---|---|
| 387916 | 12.5 | 51 |
| 388241 | 12.5 | 47 |
|  | 50 | 67 |
| 437123 | 12.5 | 0 |
|  | 50 | 21 |
| 437132 | 12.5 | 31 |
|  | 50 | 33 |
| 437140 | 12.5 | 7 |
|  | 50 | 32 |
| 437442 | 12.5 | 42 |
|  | 50 | 85 |
| 437446 | 12.5 | 39 |
|  | 50 | 70 |
| 437477 | 12.5 | 52 |
|  | 50 | 75 |
| 437478 | 12.5 | 54 |
|  | 50 | 78 |
| 437490 | 12.5 | 42 |
|  | 50 | 44 |

TABLE 41

Percent inhibition of murine huntingtin mRNA in BACHD mice

| ISIS No. | Dose (mg/kg) | % inhibition |
|---|---|---|
| 387916 | 12.5 | 48 |
| 437442 | 12.5 | 27 |
|  | 50 | 76 |
| 437446 | 12.5 | 38 |
|  | 50 | 71 |
| 437477 | 12.5 | 63 |
|  | 50 | 87 |
| 437478 | 12.5 | 60 |
|  | 50 | 89 |

Organ Weight Measurements

Liver, spleen and kidney weights were measured at the end of the study, and are presented in Table 42 as a percent of the saline control normalized to body weight.

TABLE 42

Percent change in organ weight of BACHD mice after antisense oligonucleotide treatment

| ISIS No. | Dose (mg/kg) | Liver | Spleen | Kidney |
|---|---|---|---|---|
| 387916 | 12.5 | 1 | 6 | 12 |
| 388241 | 12.5 | −3 | 16 | −2 |
|  | 50 | −6 | 10 | 0 |
| 437123 | 12.5 | −4 | 0 | 4 |
|  | 50 | 4 | 0 | −4 |
| 437132 | 12.5 | −2 | −3 | −5 |
|  | 50 | 2 | −6 | −2 |

TABLE 42-continued

Percent change in organ weight of BACHD mice after antisense oligonucleotide treatment

| ISIS No. | Dose (mg/kg) | Liver | Spleen | Kidney |
|---|---|---|---|---|
| 437140 | 12.5 | −4 | 11 | −3 |
|  | 50 | 4 | 5 | −5 |
| 437442 | 12.5 | −10 | 9 | 3 |
|  | 50 | −3 | −20 | −10 |
| 437446 | 12.5 | −6 | 7 | 2 |
|  | 50 | −4 | 1 | −1 |
| 437477 | 12.5 | 1 | −2 | 0 |
|  | 50 | 25 | −9 | −6 |
| 437478 | 12.5 | −7 | −4 | −9 |
|  | 50 | 22 | 4 | 3 |
| 437490 | 12.5 | −5 | 0 | −5 |
|  | 50 | −7 | 3 | −9 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 43.

TABLE 43

Effect of antisense oligonucleotide treatment on markers of liver function

|  | Dose (mg/kg) | ALT | AST |
|---|---|---|---|
| PBS |  | 32 | 58 |
| 387916 | 12.5 | 40 | 122 |
| 388241 | 12.5 | 39 | 93 |
|  | 50 | 28 | 62 |
| 437123 | 12.5 | 38 | 88 |
|  | 50 | 34 | 66 |
| 437132 | 12.5 | 34 | 52 |
|  | 50 | 30 | 52 |
| 437140 | 12.5 | 30 | 62 |
|  | 50 | 40 | 63 |
| 437442 | 12.5 | 40 | 106 |
|  | 50 | 63 | 119 |
| 437446 | 12.5 | 35 | 119 |
|  | 50 | 35 | 89 |
| 437477 | 12.5 | 39 | 68 |
|  | 50 | 52 | 162 |
| 437478 | 12.5 | 37 | 53 |
|  | 50 | 55 | 71 |
| 437490 | 12.5 | 48 | 71 |
|  | 50 | 34 | 59 |

Study 5

Treatment

Eleven groups of four BACHD mice each were injected intraperitoneally with 12.5 mg/kg of ISIS 388241, ISIS 419640, ISIS 419641, ISIS 419642, ISIS 436665, ISIS 436671, ISIS 436689, ISIS 437507, ISIS 443139, ISIS 444591, or ISIS 444661 twice a week for 2 weeks. A control group of four mice was injected intraperitoneally with phosphate buffered saline (PBS) twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 44 and 45 and were calculated as percent inhibition of human and murine huntingtin expression levels respectively, relative to the PBS control. All the antisense oligonucleotides effect significant inhibition of human huntingtin mRNA levels. ISIS 388241, ISIS 437507, and ISIS 443139 have more than three mismatches with the murine huntingtin mRNA (SEQ ID NO: 3) and therefore do not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 44

Percent inhibition of human huntingtin mRNA in BACHD mice

| ISIS No. | % inhibition |
|---|---|
| 388241 | 53 |
| 419640 | 34 |
| 419641 | 63 |
| 419642 | 55 |
| 436665 | 63 |
| 436671 | 66 |
| 436689 | 57 |
| 437507 | 54 |
| 443139 | 39 |
| 444591 | 48 |
| 444661 | 50 |

TABLE 45

Percent inhibition of murine huntingtin mRNA in BACHD mice

| ISIS No. | % inhibition |
|---|---|
| 419640 | 24 |
| 419641 | 51 |
| 419642 | 34 |
| 436665 | 49 |
| 436671 | 63 |
| 444591 | 41 |
| 444661 | 46 |

Body Weight and Organ Weight Measurements

The body weights of the mice were measured at the onset of the study and subsequently twice a week. The body weights of the mice are presented in Table 46 and are expressed as a percent change over the weights taken at the start of the study. The results indicate that treatment with these oligonucleotides did not cause any adverse change in body weight of the mice throughout the study.

TABLE 46

Percent change in body weight of BACHD mice after antisense oligonucleotide treatment

|  | day 4 | day 7 | day 10 | day 12 |
|---|---|---|---|---|
| PBS | −3 | 0 | +2 | +1 |
| ISIS 388241 | −2 | −1 | −1 | +1 |
| ISIS 419640 | +1 | 0 | +3 | +4 |
| ISIS 419641 | +1 | +1 | +2 | 0 |
| ISIS 419642 | −3 | −2 | +1 | −5 |
| ISIS 436665 | +1 | +4 | +5 | +1 |
| ISIS 436671 | +1 | +2 | +5 | +4 |
| ISIS 436689 | +1 | +3 | 0 | −1 |
| ISIS 437507 | −1 | −2 | +2 | −2 |
| ISIS 443139 | −2 | +6 | +4 | +1 |
| ISIS 444591 | −1 | +1 | +2 | 0 |
| ISIS 444661 | +1 | +3 | +2 | 0 |

Liver, spleen and kidney weights were measured at the end of the study, and are presented in Table 47 as a percent of the saline control normalized to body weight.

TABLE 47

Percent change in organ weight of BACHD mice after antisense oligonucleotide treatment

| ISIS No. | Liver | Spleen | Kidney |
|---|---|---|---|
| 388241 | +2 | +13 | −7 |
| 419640 | −2 | +12 | −12 |
| 419641 | +4 | +3 | −13 |
| 419642 | +5 | +19 | −8 |
| 436665 | −3 | +3 | −13 |
| 436671 | 0 | +1 | −18 |
| 436689 | −6 | −10 | −12 |
| 437507 | −5 | −5 | −14 |
| 443139 | −2 | −9 | −13 |
| 444591 | −2 | −10 | −12 |
| 444661 | 0 | −16 | −12 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of ALT and AST are expressed in IU/L. Plasma levels of bilirubin and albumin were also measured using the same clinical chemistry analyzer and expressed in g/dL. The results are presented in Table 48.

TABLE 48

Effect of antisense oligonucleotide treatment on markers of liver function

|  | ALT | AST | Bilirubin | Albumin |
|---|---|---|---|---|
| PBS | 42.5 | 86.5 | 0.2 | 3.1 |
| ISIS 388241 | 39.3 | 54.5 | 0.3 | 3.0 |
| ISIS 419640 | 36.8 | 85.8 | 0.2 | 2.9 |
| ISIS 419641 | 50.0 | 71.8 | 0.2 | 3.0 |
| ISIS 419642 | 42.8 | 77.0 | 0.1 | 3.0 |
| ISIS 436665 | 51.5 | 123.0 | 0.2 | 3.0 |
| ISIS 436671 | 52.0 | 71.0 | 0.1 | 3.0 |
| ISIS 436689 | 38.3 | 75.3 | 0.2 | 3.1 |
| ISIS 437507 | 37.0 | 77.5 | 0.1 | 3.0 |
| ISIS 443139 | 41.3 | 124.8 | 0.2 | 3.0 |
| ISIS 444591 | 46.5 | 61.3 | 0.2 | 3.0 |
| ISIS 444661 | 67.5 | 109.8 | 0.2 | 3.1 |

Measurement of Kidney Function

To evaluate the impact of ISIS oligonucleotides on the kidney function of mice described above, plasma concentrations of blood urea nitrogen (BUN) and creatinine were measured using an automated clinical chemistry analyzer (Hitachi Olympus AU400e, Melville, N.Y.). Results are presented in Table 49 expressed in mg/dL.

TABLE 49

Effect of antisense oligonucleotide treatment on markers of kidney function

| | BUN | Creatinine |
|---|---|---|
| PBS | 24.0 | 0.17 |
| ISIS 388241 | 22.6 | 0.17 |
| ISIS 419640 | 21.4 | 0.16 |
| ISIS 419641 | 19.9 | 0.16 |
| ISIS 419642 | 23.6 | 0.18 |
| ISIS 436665 | 20.2 | 0.17 |
| ISIS 436671 | 22.6 | 0.17 |
| ISIS 436689 | 19.2 | 0.18 |
| ISIS 437507 | 19.9 | 0.16 |
| ISIS 443139 | 23.3 | 0.16 |
| ISIS 444591 | 23.5 | 0.18 |
| ISIS 444661 | 25.4 | 0.18 |

Measurement of Other Metabolic Parameters

To evaluate the impact of ISIS oligonucleotides on other metabolic functions in mice described above, plasma concentrations of glucose, cholesterol and triglycerides were measured using an automated clinical chemistry analyzer (Hitachi Olympus AU400e, Melville, N.Y.). Results are presented in Table 50 expressed in mg/dL and demonstrate that treatment with these oligonucleotides did not cause any adverse changes in the levels of these metabolic markers between the control and treatment groups.

TABLE 50

Effect of antisense oligonucleotide treatment on metabolic markers

| | Glucose | Cholesterol | Triglycerides |
|---|---|---|---|
| PBS | 198 | 142 | 225 |
| ISIS 388241 | 197 | 133 | 185 |
| ISIS 419640 | 198 | 132 | 189 |
| ISIS 419641 | 188 | 140 | 219 |
| ISIS 419642 | 184 | 128 | 192 |
| ISIS 436665 | 199 | 134 | 152 |
| ISIS 436671 | 196 | 148 | 174 |
| ISIS 436689 | 194 | 132 | 174 |
| ISIS 437507 | 198 | 139 | 155 |
| ISIS 443139 | 178 | 122 | 239 |
| ISIS 444591 | 202 | 145 | 263 |
| ISIS 444661 | 180 | 140 | 247 |

Example 4: Bolus Administration of Antisense Oligonucleotides Against Huntingtin mRNA to the Striatum of BACHD Mice BACHD mice were treated with ISIS oligonucleotides via bolus administration to a defined mouse brain area, the striatum, for the purpose of screening the activity of the oligonucleotides in brain tissue against human and mouse huntingtin mRNA expression.

Treatment and Surgery

Groups of four BACHD mice each were administered with ISIS 388241, ISIS 419628, ISIS 419637, ISIS 419640, ISIS 419641, ISIS 419642, ISIS 436665, ISIS 436671, ISIS 436684, ISIS 436689, ISIS 436754, ISIS 437168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661 or ISIS 444663 delivered as a single bolus injection at 3 µg, 10 µg or 25 µg concentrations into the striatum.

A control group of 4 BACHD mice were similarly treated with PBS. ISIS 388241 was administered in seven groups of 4 mice each and the results presented are the average of the data derived from the 28 mice. ISIS 419628 was administered in 2 groups of 4 BACHD mice each and the results presented are the average of the data derived from the 8 mice. Seven days after the bolus administration, the mice were euthanized using isoflurane and the organs were removed. The animals were decapitated and the brain was removed for dissection of the striatal tissue.

RNA Analysis

RNA was extracted from striatal tissue for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. The results for human huntingtin mRNA levels are presented in Table 51 and are expressed as percent inhibition compared to the PBS control group. All the antisense oligonucleotides effect dose-dependent inhibition of human huntingtin mRNA levels. The results for murine huntingtin mRNA levels are presented in Table 52 and are expressed as percent inhibition compared to the PBS control group.

The effective doses ($ED_{50}$) of each oligonucleotide for human huntingtin mRNA and mouse huntingtin mRNA were calculated by plotting the concentrations of oligonucleotides used versus the percent inhibition of huntingtin mRNA expression levels of either species and noting the concentrations at which 50% inhibition of huntingtin mRNA expression was achieved for each species compared to the corresponding controls. The $ED_{50}$ (µg) for each antisense oligonucleotide is also presented in Tables 51 and 52 for human and murine huntingtin mRNA respectively.

ISIS 388241, ISIS 436684, ISIS 436754, ISIS 437175, ISIS 437507, ISIS 443139, and ISIS 444584 are each mismatched by 8 base pairs or more with murine huntingtin mRNA (SEQ ID NO: 3) and therefore do not show significant inhibition of murine mRNA levels compared to the control. ISIS 437168 and ISIS 437441 have 2 mismatches each with the murine huntingtin mRNA (SEQ ID NO: 3) and do not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 51

Percent inhibition of human huntingtin mRNA levels in vivo and $ED_{50}$ of the antisense oligonucleotides

| ISIS No. | 3 mg | 10 mg | 25 mg | $ED_{50}$ |
|---|---|---|---|---|
| 388241 | 33 | 55 | 68 | 7.4 |
| 419628 | 49 | 58 | 83 | 5.1 |
| 419637 | 40 | 62 | 79 | 6.1 |
| 419640 | 52 | 64 | 77 | 4.8 |
| 419641 | 71 | 77 | 89 | 2.2 |
| 419642 | 67 | 70 | 83 | 3.0 |
| 436665 | 52 | 71 | 60 | 5.8 |
| 436671 | 68 | 80 | 84 | 2.4 |
| 436684 | 2 | 18 | 37 | 36.9 |
| 436689 | 27 | 63 | 81 | 7.0 |
| 436754 | 31 | 54 | 61 | 10.5 |
| 437168 | 2 | 49 | 60 | 15.2 |
| 437175 | 0 | 53 | 64 | 12.9 |
| 437441 | 3 | 32 | 38 | 35.3 |
| 437442 | 38 | 50 | 56 | 11.9 |
| 437507 | 38 | 59 | 79 | 6.6 |
| 437527 | 37 | 47 | 59 | 11.9 |

TABLE 51-continued

Percent inhibition of human huntingtin mRNA levels
in vivo and ED$_{50}$ of the antisense oligonucleotides

| ISIS No. | 3 mg | 10 mg | 25 mg | ED$_{50}$ |
|---|---|---|---|---|
| 443139 | 39 | 61 | 70 | 6.7 |
| 444578 | 51 | 66 | 75 | 4.6 |
| 444584 | 30 | 63 | 71 | 7.8 |
| 444591 | 60 | 54 | 70 | 5.6 |
| 444607 | 57 | 69 | 75 | 3.2 |
| 444608 | 67 | 68 | 82 | 3.1 |
| 444615 | 47 | 55 | 91 | 5.2 |
| 444618 | 57 | 64 | 83 | 4.0 |
| 444627 | 47 | 70 | 61 | 5.0 |
| 444652 | 36 | 62 | 66 | 7.8 |
| 444658 | 60 | 66 | 79 | 3.6 |
| 444659 | 61 | 67 | 84 | 3.4 |
| 444660 | 55 | 62 | 66 | 4.2 |
| 444661 | 48 | 57 | 70 | 6.4 |
| 444663 | 42 | 60 | 80 | 5.5 |

TABLE 52

Percent inhibition of murine huntingtin mRNA levels
in vivo and ED$_{50}$ of the antisense oligonucleotides

| ISIS No. | 3 mg | 10 mg | 25 mg | ED$_{50}$ |
|---|---|---|---|---|
| 419628 | 50 | 55 | 83 | 5.1 |
| 419637 | 63 | 79 | 86 | 2.6 |
| 419640 | 51 | 60 | 86 | 4.9 |
| 419641 | 65 | 80 | 87 | 2.7 |
| 419642 | 69 | 73 | 88 | 2.5 |
| 436665 | 68 | 82 | 66 | 2.7 |
| 436671 | 75 | 87 | 90 | 2 |
| 437442 | 30 | 53 | 82 | 9 |
| 437527 | 67 | 73 | 90 | 2.7 |
| 444578 | 50 | 65 | 74 | 4.9 |
| 444591 | 69 | 69 | 81 | 2.8 |
| 444607 | 57 | 70 | 75 | 3.8 |
| 444608 | 70 | 72 | 90 | 2.5 |
| 444615 | 30 | 37 | 88 | 9.5 |
| 444618 | 66 | 71 | 90 | 2.8 |
| 444627 | 41 | 60 | 57 | 8.8 |
| 444652 | 47 | 62 | 66 | 4.7 |
| 444658 | 60 | 62 | 85 | 3.9 |
| 444659 | 54 | 62 | 85 | 4.2 |
| 444660 | 42 | 48 | 64 | 9.5 |
| 444661 | 49 | 57 | 74 | 5.9 |
| 444663 | 42 | 65 | 84 | 5.1 |

The ten compounds marked with an asterisk had an improved ED$_{50}$ over ISIS 388241.

Example 5: Assay for Neurotoxic Effects of Bolus Administration of Antisense Oligonucleotides in the Striatal Tissue of Rats About 30 compounds were selected as having high tolerability and high potency. Compounds were then tested by CNS bolus injection in rat to further assess neurotoxicity.

Sprague-Dawley rats each were treated with ISIS oligonucleotides via bolus administration to a defined brain area, the striatum, for the purpose of screening for the induction of the microglial marker AIF1 as a measure of CNS toxicity.

Treatment and Surgery

Groups of four Sprague-Dawley rats were administered with ISIS 387916, ISIS 388241, ISIS 419627, ISIS 419628, ISIS 419629, ISIS 419630, ISIS 419636, ISIS 419637, ISIS 419640, ISIS 419641, ISIS 419642, ISIS 436665, ISIS 436668, ISIS 4196671, ISIS 436684, ISIS 436689, ISIS 436754, ISIS 443168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663 delivered as a single bolus injection at 50 µg concentration into the striatum.

A control group of 4 rats were similarly treated with PBS. A group of 4 rats were similarly treated with ISIS 104838, an antisense oligonucleotide against TNF-α, as a negative control group. ISIS 387916 was administered in four groups of 4 rats each and the results presented are an average of the data derived from the 16 rats. ISIS 419628 was administered in two groups of 4 rats each and the results presented are the average of the data from the 8 rats. ISIS 419629, ISIS 444584 and ISIS 444618, which had toxic indicators in the systemic administration study (Example 3) were also tested in this study. Seven days after bolus administration, the rats were euthanized using isoflurane and the organs were removed. The animals were decapitated and the brain was removed for dissection of the striatal tissue.

RNA Analysis of AIF1 Expression Levels

RNA was extracted from striatal tissue for real-time PCR analysis of AIF1 mRNA levels. Rat AIF1 levels were measured using the rat primer probe set rAif1_LTS00219 (forward sequence AGGAGAAAAACAAAGAACACCAGAA, designated herein as SEQ ID NO: 46; reverse sequence CAATT-AGGGCAACTCAGAAATAGCT, designated herein as SEQ ID NO: 47; probe sequence CCAACTGGTCCCCCAGCCAAGAX, designated herein as SEQ ID NO: 48). Results were calculated as the percentage of AIF1 expression over that of the PBS control and are presented in Table 53. ISIS 419629, ISIS 444584, and ISIS 444618, which had toxic indicators in the systemic administration study (in Example 3), also had toxic indicators in this study (greater than 300% above saline control). Later studies showed that ISIS 444584 is neurotolerable and exhibits negligible toxic indicators (see Example 16 and 17).

TABLE 53

Percent expression of AIF1 mRNA levels
in vivo as a measure of neurotoxicity

| ISIS No. | % expression |
|---|---|
| 104838 | 111 |
| 387916 | 870 |
| 388241 | 236 |
| 419627 | 168 |
| 419628 | 497 |
| 419629 | 247 |
| 419630 | 227 |
| 419636 | 464 |
| 419637 | 275 |
| 419640 | 305 |
| 419641 | 206 |
| 419642 | 173 |
| 436665 | 217 |
| 436668 | 447 |
| 436671 | 239 |
| 436684 | 700 |
| 436689 | 149 |
| 436754 | 125 |
| 437168 | 130 |
| 437175 | 131 |
| 437441 | 158 |
| 437442 | 157 |
| 437507 | 133 |
| 437527 | 184 |
| 443139 | 143 |
| 444578 | 352 |
| 444584 | 317 |

TABLE 53-continued

Percent expression of AIF1 mRNA levels
in vivo as a measure of neurotoxicity

| ISIS No. | % expression |
|---|---|
| 444591 | 194 |
| 444607 | 362 |
| 444608 | 476 |
| 444615 | 645 |
| 444618 | 547 |
| 444627 | 377 |
| 444652 | 336 |
| 444658 | 364 |
| 444659 | 319 |
| 444660 | 411 |
| 444661 | 249 |
| 444663 | 448 |

RNA Analysis of Huntingtin Expression Levels

RNA was extracted from striatal tissue for real-time PCR analysis of huntingtin mRNA levels. Rat huntingtin mRNA levels were measured using the rat primer probe set rHt-t_LTS00343 (forward sequence CAGAGCTGGT-GAACCGTATCC, designated herein as SEQ ID NO: 49; reverse sequence GGCTTAAGCAGGGAGCCAAAA, designated herein as SEQ ID NO: 50; probe sequence ACTT-CATGATGAGCTCGGAGTTCAACX, designated herein as SEQ ID NO: 51). Results were calculated as the percentage reduction of huntingtin expression over that of the PBS control and are presented in Table 54. ISIS 388241, ISIS 436684, ISIS 436754, ISIS 437175, ISIS 437507, and ISIS 443139 are each mismatched by 6 base pairs or more with the rat gene sequence (SEQ ID NO: 5) and therefore do not show significant inhibition of rat mRNA levels compared to the control. ISIS 419640, ISIS 419641, ISIS 419642, ISIS 436665, ISIS 436668, ISIS 437442, ISIS 444615, and ISIS 444627 have 1 mismatch each with the rat gene sequence (SEQ ID NO: 5) and do not show significant inhibition of rat mRNA levels compared to the control. ISIS 437168 and ISIS 437441 have 2 mismatches each with the rat gene sequence (SEQ ID NO: 5) and do not show significant inhibition of rat mRNA levels compared to the control. ISIS 436689 and ISIS 444584 have 3 mismatches each with the rat gene sequence (SEQ ID NO: 5) and do not show significant inhibition of rat mRNA levels compared to the control.

TABLE 54

Percent reduction of rat huntingtin mRNA levels in rats

| ISIS No. | % reduction |
|---|---|
| 387916 | 70 |
| 419627 | 67 |
| 419628 | 57 |
| 419629 | 85 |
| 419630 | 11 |
| 419636 | 53 |
| 419637 | 84 |
| 436671 | 77 |
| 437527 | 86 |
| 444578 | 72 |
| 444591 | 35 |
| 444607 | 57 |
| 444608 | 68 |
| 444618 | 56 |
| 444652 | 75 |
| 444658 | 61 |
| 444659 | 55 |
| 444660 | 63 |
| 444661 | 52 |
| 444663 | 59 |

Example 6: Intracerebroventricular Administration of Antisense Oligonucleotides Against Huntingtin mRNA-Tolerability Study in BACHD Mice Selected compounds were compared with previously designed compound ISIS 388241 by ICV administration in BACHD mice.

Selected compounds plus the benchmark 388241 were selected based on in vitro and systemic potency and systemic tolerability as well as CNS potency and tolerability.

BACHD mice were treated with ISIS oligonucleotides via intracerebroventricular (ICV) administration to a defined mouse brain area, the right lateral ventricle, for the purpose of evaluating the tolerability of ICV dosing in mice.

Treatment and Surgery

Groups of five BACHD mice each were administered ISIS 388241, ISIS 437507, ISIS 443139, ISIS 419640, ISIS 419641, ISIS 419642, ISIS 444591, ISIS 436665, ISIS 436671, ISIS 444661, or ISIS 436689 at 150 µg/day delivered ICV with Alzet 2002 pumps at the rate of 12 µL/day for 2 weeks. A control group of 4 BACHD mice were similarly treated with PBS. The mice were surgically implanted with the pumps in the following manner: Mice were individually anaesthetized with 3% isoflurane for pump implantation. After two weeks, the mice were anesthetized again and the pump was surgically removed. The animals were then allowed to recover for two more weeks before being euthanized.

The body weights of the mice were taken weekly during the treatment and recovery periods. After 4 weeks, the mice were euthanized using isoflurane and decapitated. The brain was removed for tissue acquisition from the anterior and posterior sections.

RNA Analysis

RNA was extracted from the right hemisphere of the anterior cortex and the posterior cerebellar section of the cannulation site for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. Results were calculated as percent inhibition of human and murine huntingtin mRNA expression compared to the control and are presented in Tables 56 and 57 respectively. All the antisense oligonucleotides effect significant inhibition of human huntingtin mRNA levels. ISIS 388241, ISIS 437507, and ISIS 443139 are each mismatched by 8 base pairs or more with the murine huntingtin mRNA (SEQ ID NO: 3) and therefore do not show significant inhibition of murine mRNA levels compared to the control. ISIS 444591 has 1 mismatch with the murine huntingtin mRNA (SEQ ID NO: 3) and does not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 56

Percent reduction of human huntingtin mRNA levels in BACHD mice via ICV administration of antisense oligonucleotides

| ISIS No. | Number of mice | Anterior cortex | Posterior cortex |
|---|---|---|---|
| 388241 | 3 | 82 | 70 |
| 419640 | 1 | 60 | 46 |
| 419641 | 2 | 75 | 66 |
| 419642 | 3 | 29 | 42 |
| 436665 | 5 | 62 | 38 |
| 436671 | 3 | 69 | 77 |
| 436689 | 3 | 49 | 40 |
| 437507 | 3 | 77 | 66 |
| 443139 | 5 | 93 | 90 |
| 444591 | 5 | 79 | 78 |

TABLE 57

Percent reduction of murine huntingtin mRNA levels in BACHD mice via ICV administration of antisense oligonucleotides

| ISIS No. | Number of mice | Anterior cortex | Posterior cortex |
|---|---|---|---|
| 419640 | 1 | 22 | 34 |
| 419641 | 2 | 40 | 26 |
| 419642 | 3 | 63 | 71 |
| 436665 | 5 | 72 | 56 |
| 436671 | 3 | 80 | 71 |

Body Weight Measurement

The body weights of the mice were measured at the onset of the study and subsequently once a week. The body weights of the mice are presented in Table 58 and are expressed as a percent change over the weights taken at the start of the study. The body weights were considered a measure of the tolerability of the mice to the ICV administration of antisense oligonucleotide. 'n.d.' means that there was no data available for that time period.

TABLE 58

Percent change in body weight of BACHD mice during antisense oligonucleotide treatment

| | week 1 | week 2 | week 3 | week 4 |
|---|---|---|---|---|
| PBS | −1 | +2 | +6 | +6 |
| ISIS 388241 | +3 | +11 | +15 | +7 |
| ISIS 437507 | +21 | +10 | +13 | −4 |
| ISIS 443139 | +10 | +10 | +16 | +12 |
| ISIS 419640 | +21 | +11 | −10 | +9 |
| ISIS 419641 | +24 | +3 | −5 | −12 |
| ISIS 419642 | +45 | +39 | +12 | +1 |
| ISIS 444591 | +18 | +38 | +27 | +17 |
| ISIS 436665 | +34 | +43 | +23 | +9 |
| ISIS 436671 | +19 | +17 | +11 | 0 |
| ISIS 444661 | +19 | −10 | −21 | n.d. |
| ISIS 436689 | +49 | +40 | +2 | −17 |

Survival of the Mice

The survival of the mice was assessed throughout the entire study period. Table 59 below shows the survival pattern in the groups of mice treated with ISIS oligonucleotides as well as the control.

TABLE 59

Number of survivals during antisense oligonucleotide treatment

| | week 1 | week 2 | week 3 | week 4 |
|---|---|---|---|---|
| PBS | 5 | 5 | 5 | 5 |
| ISIS 388241 | 4 | 3 | 3 | 3 |
| ISIS 437507 | 5 | 5 | 4 | 4 |
| ISIS 443139 | 5 | 5 | 5 | 5 |
| ISIS 419640 | 5 | 5 | 4 | 1 |
| ISIS 419641 | 5 | 5 | 4 | 2 |
| ISIS 419642 | 5 | 5 | 4 | 2 |
| ISIS 444591 | 5 | 5 | 5 | 5 |
| ISIS 436665 | 5 | 5 | 5 | 5 |
| ISIS 436671 | 4 | 4 | 3 | 3 |
| ISIS 444661 | 5 | 5 | 1 | 0 |
| ISIS 436689 | 4 | 4 | 4 | 3 |

Example 7: Intracerebroventricular Administration of Antisense Oligonucleotides Against Huntingtin in C57/BL6 Mice Wild-type C57/BL6 mice were treated with ISIS oligonucleotides via intracerebroventricular (ICV) administration to a defined mouse brain area, the right lateral ventricle, for the purpose of evaluating the potency of the oligonucleotides against mouse huntingtin in these mice.

Treatment and Surgery

Groups of ten C57/BL6 mice each were administered ISIS 408737 (5' TCCTAGTGTTACATTACCGC3' (SEQ ID NO: 52), start site 5263 of SEQ ID NO: 3) at 50 µg/day delivered ICV with Alzet 2002 pumps at the rate of 0.5 µL/day for 7 days or 14 days. A control group of six C57/BL6 mice were similarly treated with PBS. The mice were surgically implanted with the pumps in the following manner: Briefly, Alzet osmotic pumps (Model 2002) were assembled according to manufacturer's instructions. Pumps were filled with a solution containing the antisense oligonucleotide and incubated overnight at 37° C., 24 hours prior to implantation. Animals were anesthetized with 3% isofluorane and placed in a stereotactic frame. After sterilizing the surgical site, a midline incision was made over the skull, and a subcutaneous pocket was created over the back, in which a pre-filled osmotic pump was implanted. A small burr hole was made through the skull above the right lateral ventricle. A cannula, connected to the osmotic pump via a plastic catheter, was then placed in the ventricle and glued in place using Loctite adhesive. The incision was closed with sutures. Antisense oligonucleotide or PBS was infused for 7 or 14 days, after which animals were euthanized according to a humane protocol approved by the Institutional Animal Care and Use Committee. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with S1 being most rostral and S5 most caudal.

RNA and Protein Analysis

Total RNA was extracted from mouse brain and spinal cord with RNeasy Protect Mini Kit (Qiagen, Mississauga, ON, Canada) for real-time PCR analysis of huntingtin mRNA levels using an RNeasy Mini prep kit (Qiagen). Q-PCR reactions were conducted and analyzed on an ABI Prism 7700 Sequence Detector (Applied Biosystems). Mouse huntingtin mRNA levels were measured using the murine primer probe set ABI #Mm01213820 ml (Applied Biosystems) and normalized to peptidylprolyl isomerase A mRNA levels. Protein lysates were prepared from mouse brain slabs as described previously (Li S. H. and Li X. J., *Methods in Molecular Biology* (2008), 217:1940-6029). Lysates were run on 3-8% tris-acetate gel and transferred using the iBlot dry blotting system (Invitrogen). Blots were probed with anti-beta tubulin (Chemicon) and monoclonal MAB2166 antibody (Millipore) that reacts specifically with murine huntingtin protein. Immunoblots were quantified using Odyssey V3.0 software.

The results are presented in Table 60 as percent reduction compared to the PBS control and demonstrate significant inhibition of huntingtin mRNA and protein levels by the antisense oligonucleotide both at day 7 and day 14.

TABLE 60

Percent inhibition of murine huntingtin mRNA in C57/BL6 mice

|  | day 7 | day 14 |
|---|---|---|
| mRNA | 66 | 68 |
| protein | 21 | 49 |

Example 8: Intracerebroventricular Administration of Antisense Oligonucleotides Against Huntingtin mRNA in Cynomologous Monkeys Cynomologous monkeys were treated with ISIS oligonucleotides via intracerebroventricular (ICV) administration to a defined brain area, the lateral ventricles, for the purpose of screening the activity of the oligonucleotides in brain tissue against huntingtin mRNA expression.

Treatment and Surgery

Two groups of 3 cynomologous monkeys each were administered either 0.635 mg/ml (1.5 mg/day) or 1.67 mg/ml (4 mg/day) of ISIS 436689 delivered ICV with individual ambulatory pumps (Pegasus Vario) at the rate of 0.05 ml/hr for 4 weeks. A control group of 2 cynomologous monkeys were administered with PBS in a similar manner. The groups were administered ISIS 436689 bilaterally. One animal was administered ISIS 436689 at the 4 mg/day dose unilaterally to the right ventricle.

Animals were allowed 10 days to recover from surgery prior to infusion being performed. During the post surgery recovery period, the animals were maintained on PBS ICV infusion at a flow rate of 0.05 mL/h using one ambulatory infusion pump per ventricle. At the end of the recovery period, each cannula was connected to an individual ambulatory pump (Pegasus Vario) placed within a primate jacket (Lomir, PJ-02NB). The pumps remained connected until completion of the infusion period. After 4 weeks administration, the animals were euthanized and the brain, liver and kidney were harvested.

RNA Analysis of Htt mRNA

RNA was extracted from the anterior caudate, posterior caudate, temporal cortex, parietal cortex, hypothalamus, mid-brain, hippocampus, and spinal cords, as well as the liver and kidney for real-time PCR analysis of huntingtin mRNA levels. Huntingtin mRNA levels were measured using the human primer probe set RTS2617 and normalized to monkey cyclophilin A levels. Results were calculated as percent inhibition of huntingtin mRNA expression compared to the PBS control and are presented in Table 61. ISIS 436689 effected significant inhibition of human huntingtin mRNA levels in the CNS.

TABLE 61

Percent reduction of huntingtin mRNA levels in cynomologous monkeys via ICV administration of antisense oligonucleotides

| | Dose (mg/day) | | | |
|---|---|---|---|---|
| Tissue | 1.5 (bilateral) | 4 (bilateral) | 4 (right unilateral) | 4 (left unilateral) |
| Anterior caudate | 59 | 49 | 85 | 12 |
| Posterior caudate | 52 | 81 | 63 | 0 |
| Temporal cortex | 10 | 34 | 41 | 31 |
| Parietal cortex | 22 | 38 | 46 | 24 |
| Hypothalamus | 59 | 71 | 35 | 100 |
| Mid-brain | 32 | 38 | 2 | 0 |
| Hippocampus | 18 | 18 | 28 | 10 |
| Cervical cord | 58 | 65 | n.d. | n.d. |
| Thoracic cord | 50 | 67 | n.d. | n.d. |
| Lumbar cord | 49 | 62 | n.d. | n.d. |
| Liver | 0 | 13 | n.d. | n.d. |
| Kidney | 0 | 13 | n.d. | n.d. | n.d. = no data

Example 9: Measurement of Half-Life of ISIS 387898 in the Striatum of C57/BL6 Mice Via Single Bolus Administration C57/BL6 mice were administered ISIS 387898 as a single bolus to the striatum for the purpose of measuring half-life and duration of action of the antisense oligonucleotide against huntingtin mRNA expression in that tissue.

Treatment

Forty C57/BL6 mice were treated with ISIS 387898 (5' CTCGACTAAAGCAGGATTTC3' (SEQ ID NO: 53); start position 4042 of SEQ ID NO: 1 and start position 4001 of SEQ ID NO: 3) delivered as a single bolus of 50 µg in a procedure similar to that described in Example 5. Eight control C57/BL6 mice were treated with PBS in a similar procedure. Groups of 4 mice each were euthanized at various time points and striatal tissue extracted in a procedure similar to that described in Example 5.

RNA Analysis

RNA was extracted from striatal tissue for real-time PCR analysis of huntingtin mRNA levels. Mouse normal huntingtin mRNA levels were measured using the murine primer probe set RTS2633. The results are presented in Table 62 and are expressed as percent inhibition compared to the PBS control group at day 7. The inhibitory effect of ISIS 387898 was observed to be prolonged for at least 91 days.

TABLE 62

Effect of ISIS 387898 as a single bolus administration on murine huntingtin mRNA expression at various time points in C57/BL6 striatum

| Treatment | Days after dosing | % inhibition |
|---|---|---|
| ISIS 387898 | 1 | 66 |
| | 7 | 74 |
| | 14 | 68 |
| | 21 | 77 |
| | 28 | 75 |
| | 50 | 63 |
| | 73 | 55 |
| | 91 | 48 |
| PBS | 50 | 5 |

Analysis of Antisense Oligonucleotide Concentration in the Brain:

Brain tissues were minced, weighed, homogenized, and extracted using a phenol/chloroform liquid-liquid extraction method. This was followed by solid phase extraction of the supernatant on a phenyl-bonded column before capillary gel eletrophoresis electrokinetic injection. A P/ACE MDQ capillary electrophoresis instrument (Beckman Coulter, Fullerton, Calif.) was used for gel-filled capillary electrophoretic analysis. Oligonucleotide peaks were detected by UV absorbance at 260 nm.

Figure 2:
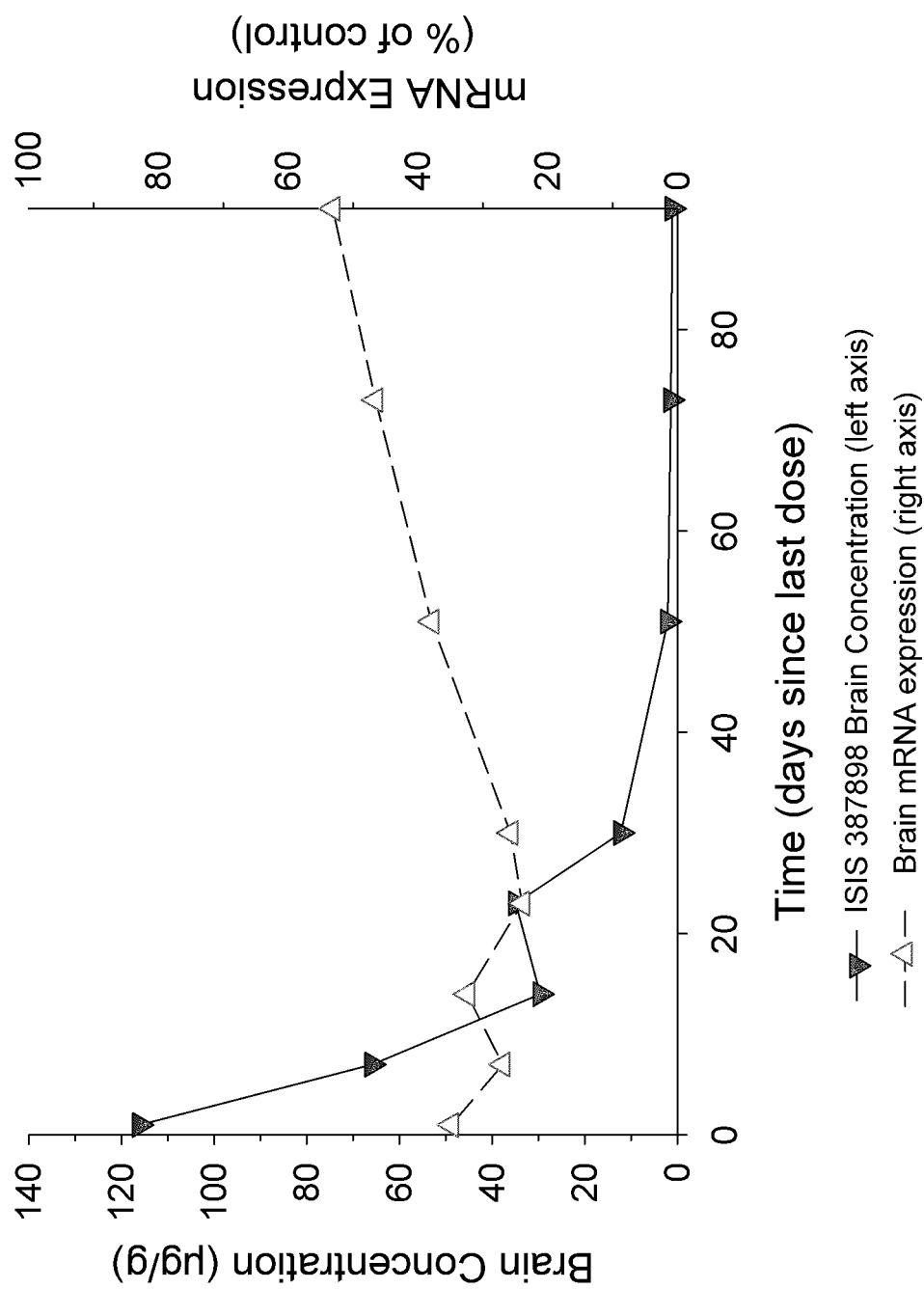

The concentration of ISIS 387898 in the brain (µg/g) was plotted against the expression of human huntingtin as a percentage of the PBS control (Table 63 and FIG. 1). The concentration of ISIS 387898 which achieves 50% inhibition of huntingtin mRNA expression ($EC_{50}$) was calculated. The $EC_{50}$ was determined to be 0.45 µg/g. The time-dependent concentration of ISIS 387898 in the brain tissue and corresponding percentage huntingtin mRNA expression was also plotted (Table 64 and FIG. 2) and the half-life of the oligonucleotide was calculated as 21 days.

TABLE 63

Concentration of ISIS 387898 in brain tissue and its effect on htt mRNA expression as a percentage of the control

| concentration (µg/g) | % mRNA expression |
| --- | --- |
| 0 | 105.0 |
| 25 | 28.8 |
| 50 | 28.2 |
| 75 | 27.9 |
| 100 | 27.8 |
| 125 | 27.8 |

TABLE 64

Time-dependent concentration of ISIS 387898 in brain tissue and its effect on htt mRNA expression as a percentage of the control

| Time (day) | Conc (µg/g) | mRNA % expression |
| --- | --- | --- |
| 1 | 116 | 35 |
| 7 | 65.7 | 27 |
| 14 | 30 | 32 |
| 23 | 34.9 | 24 |
| 30 | 12.2 | 26 |
| 51 | 2.1 | 38 |
| 73 | 1.4 | 47 |
| 92 | 1.1 | 53 |

Example 10: Measurement of Half-Life of ISIS 387898 in the Lateral Ventricles of BACHD Mice Via ICV Administration BACHD mice were administered ISIS 387898 by ICV to the lateral ventricles of the brain for the purpose of measuring half-life and duration of action of the antisense oligonucleotide against huntingtin mRNA expression in that tissue.

Treatment

Twenty eight BACHD mice were treated with ISIS 387898 delivered by ICV administration at 75 µg/day for 2 weeks in a procedure similar to that described in Example 9. Twenty eight control BACHD mice were treated with PBS in a procedure similar to that described in Example 9. Groups of 4 mice each from both the treatment and control groups were euthanized at biweekly time points and anterior cortical tissue extracted in a procedure similar to that described in Example 9.

RNA Analysis

RNA was extracted from the right hemisphere, both anterior and posterior to the cannulation site for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. Human mutant huntingtin mRNA expression levels are presented in Table 65 and are expressed as percent inhibition compared to the average of that measured in the PBS control groups. Murine normal huntingtin mRNA expression levels are presented in Table 66 and are expressed as percent inhibition compared to the average of that measured in the PBS control groups. The inhibitory effect of ISIS 387898 was observed to be prolonged for 91 days.

TABLE 65

Effect of ISIS 387898 administered ICV on human huntingtin mRNA expression at various time points

| Treatment | Days after dosage | anterior | posterior |
| --- | --- | --- | --- |
| ISIS 387898 | 14 | 74 | 65 |
|  | 28 | 67 | 61 |
|  | 42 | 70 | 61 |
|  | 56 | 57 | 52 |
|  | 70 | 57 | 43 |
|  | 91 | 41 | 61 |
|  | 127 | 28 | 16 |
| PBS | 14 | 0 | 0 |
|  | 28 | 0 | 0 |
|  | 42 | 1 | 0 |
|  | 56 | 9 | 10 |
|  | 70 | 13 | 10 |
|  | 91 | 13 | 25 |
|  | 127 | 11 | 0 |

TABLE 66

Effect of ISIS 387898 administered ICV on murine huntingtin mRNA expression at various time points

| Treatment | Days after dosage | anterior | posterior |
| --- | --- | --- | --- |
| ISIS 387898 | 14 | 85 | 81 |
|  | 28 | 81 | 69 |
|  | 42 | 86 | 79 |
|  | 56 | 74 | 69 |
|  | 70 | 73 | 58 |
|  | 91 | 39 | 63 |
|  | 127 | 39 | 0 |
| PBS | 14 | 0 | 0 |
|  | 28 | 0 | 0 |
|  | 42 | 0 | 0 |
|  | 56 | 17 | 14 |
|  | 70 | 5 | 24 |
|  | 91 | 9 | 17 |
|  | 127 | 32 | 0 |

Figure 3:
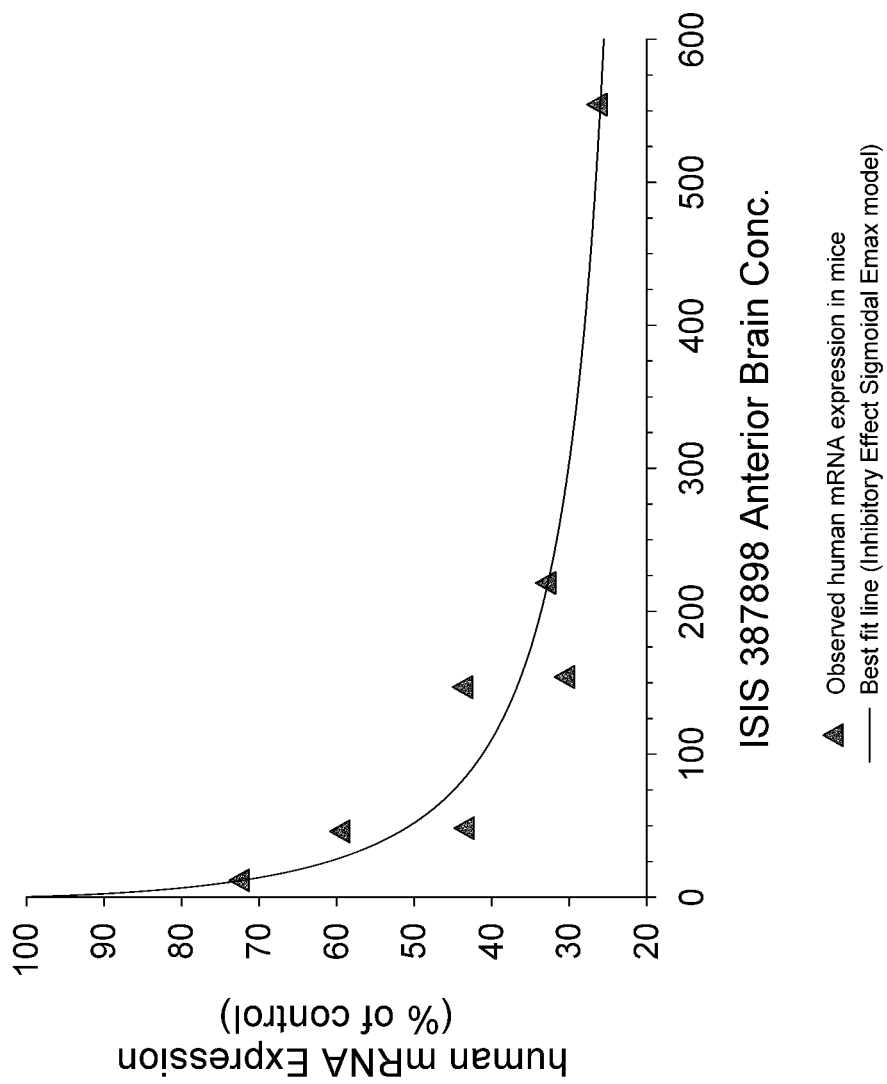
Figure 4:
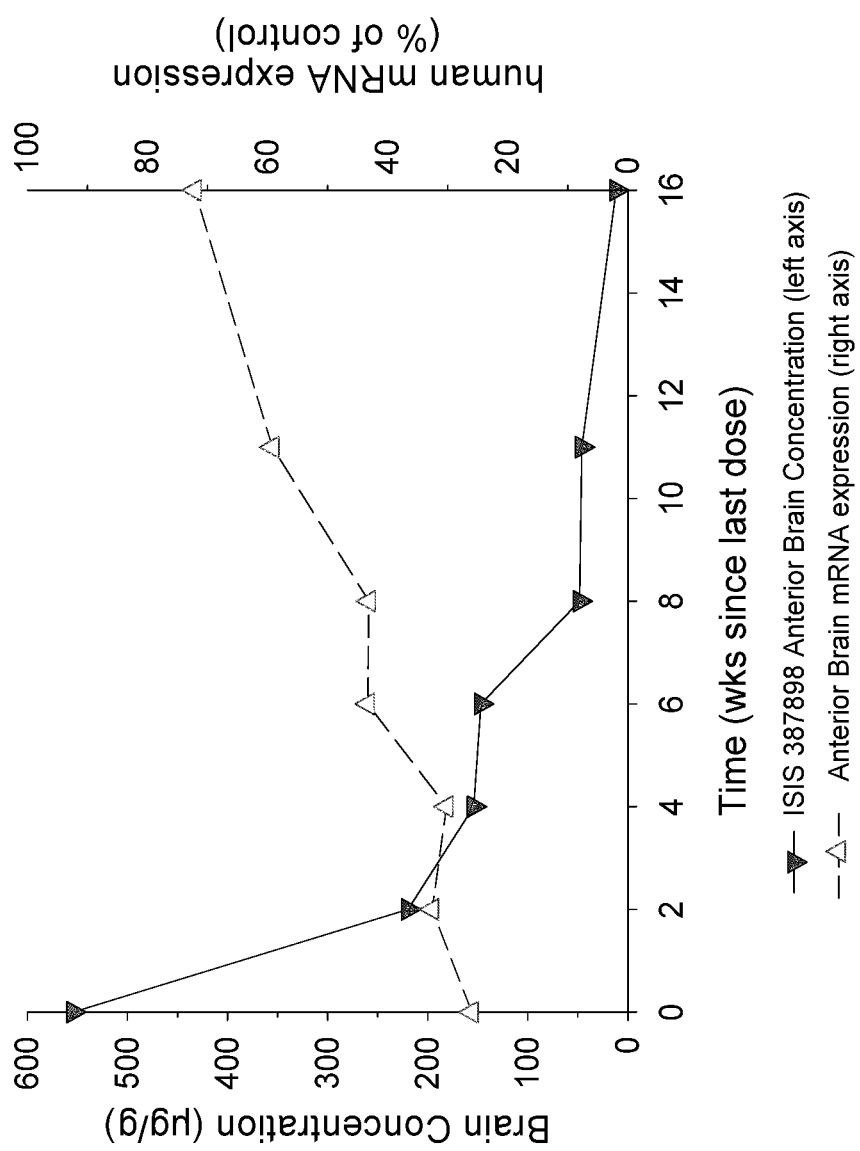

Analysis of Antisense Oligonucleotide Concentration in the Brain:

Brain tissue was processed in a procedure similar to that described in Example 9. The concentration of ISIS 387898 in the anterior cortex of the brain (µg/g) was plotted against the inhibition of human huntingtin as a percentage of the PBS control (Table 67 and FIG. 3), and the $EC_{50}$ was calculated to be 26.4 µg/g. The time-dependent concentration of ISIS 387898 in the brain tissue was also plotted (Table 68 and FIG. 4) and the half-life of the oligonucleotide was calculated as 21 days.

TABLE 67

Concentration of ISIS 387898 in brain tissue and its effect on htt mRNA expression as a percentage of the control

| Concentration (µg/g) | % mRNA expression |
|---|---|
| 0 | 105 |
| 10 | 90.7 |
| 100 | 19.3 |
| 200 | 14.3 |
| 300 | 13.2 |
| 400 | 12.7 |
| 500 | 12.5 |
| 600 | 12.4 |

TABLE 68

Time-dependent concentration of ISIS 387898 in brain tissue and its effect on htt mRNA expression as a percentage of the control

| Days after last dose | Conc (mg/g) | % mRNA expression |
|---|---|---|
| 14 | 554.3 | 12 |
| 28 | 219.8 | 15 |
| 42 | 154 | 13 |
| 56 | 146.9 | 32 |
| 70 | 48.3 | 28 |
| 91 | 46.1 | 66 |
| 127 | 11.8 | 90 |

Example 11: Measurement of Half-Life of ISIS 388241 and ISIS 443139 in the Lateral Ventricles of BACHD Mice Via ICV Administration BACHD mice were administered ISIS 388241 or ISIS 443139 by ICV to the lateral ventricles of the brain for the purpose of measuring half-life and duration of action of the antisense oligonucleotide against huntingtin mRNA expression in that tissue.
Treatment Twenty BACHD mice were treated with ISIS 38241 delivered by ICV administration at 50 µg/day for 2 weeks in a procedure similar to that described in Example 9. Twenty BACHD mice were treated with ISIS 443139 delivered by ICV administration at 50 µg/day for 2 weeks in a procedure similar to that described in Example 9. Twenty control BACHD mice were treated with PBS in a procedure similar to that described in Example 9. Groups of 4 mice each from both the treatment groups and control group were euthanized at biweekly time points and tissue extracted in a procedure similar to that described in Example 9.
RNA Analysis RNA was extracted from the right hemisphere, both anterior and posterior to the cannulation site for real-time PCR analysis of huntingtin mRNA levels. Human mutant huntingtin mRNA levels were measured using the human primer probe set RTS2617. The results are presented in Table 69 and are expressed as percent inhibition compared to the average of that measured in the PBS control groups. The inhibitory effects of both ISIS 388241 and ISIS 443139 were observed to be prolonged for at least 16 weeks.

Both ISIS 388241 and its mixed backbone equivalent, ISIS 443139, have more than 3 mismatches with murine huntingtin mRNA (SEQ ID NO: 5) and therefore did not show significant inhibition of murine mRNA levels compared to the control.

TABLE 69

Effect of ISIS 388241 and ISIS 443139 administered ICV on human huntingtin mRNA expression at various time points

| Treatment | Weeks after dosage | anterior | posterior |
|---|---|---|---|
| ISIS 388241 | 0 | 63 | 64 |
| | 4 | 79 | 56 |
| | 8 | 67 | 51 |
| | 12 | 76 | 68 |
| | 16 | 35 | 34 |
| ISIS 443139 | 0 | 35 | 55 |
| | 4 | 20 | 62 |
| | 8 | 61 | 59 |
| | 12 | 67 | 53 |
| | 16 | 46 | 37 |
| PBS | 0 | 15 | 10 |
| | 4 | 0 | 2 |
| | 8 | 5 | 0 |
| | 12 | 32 | 4 |
| | 16 | 6 | 2 |

Figure 5:
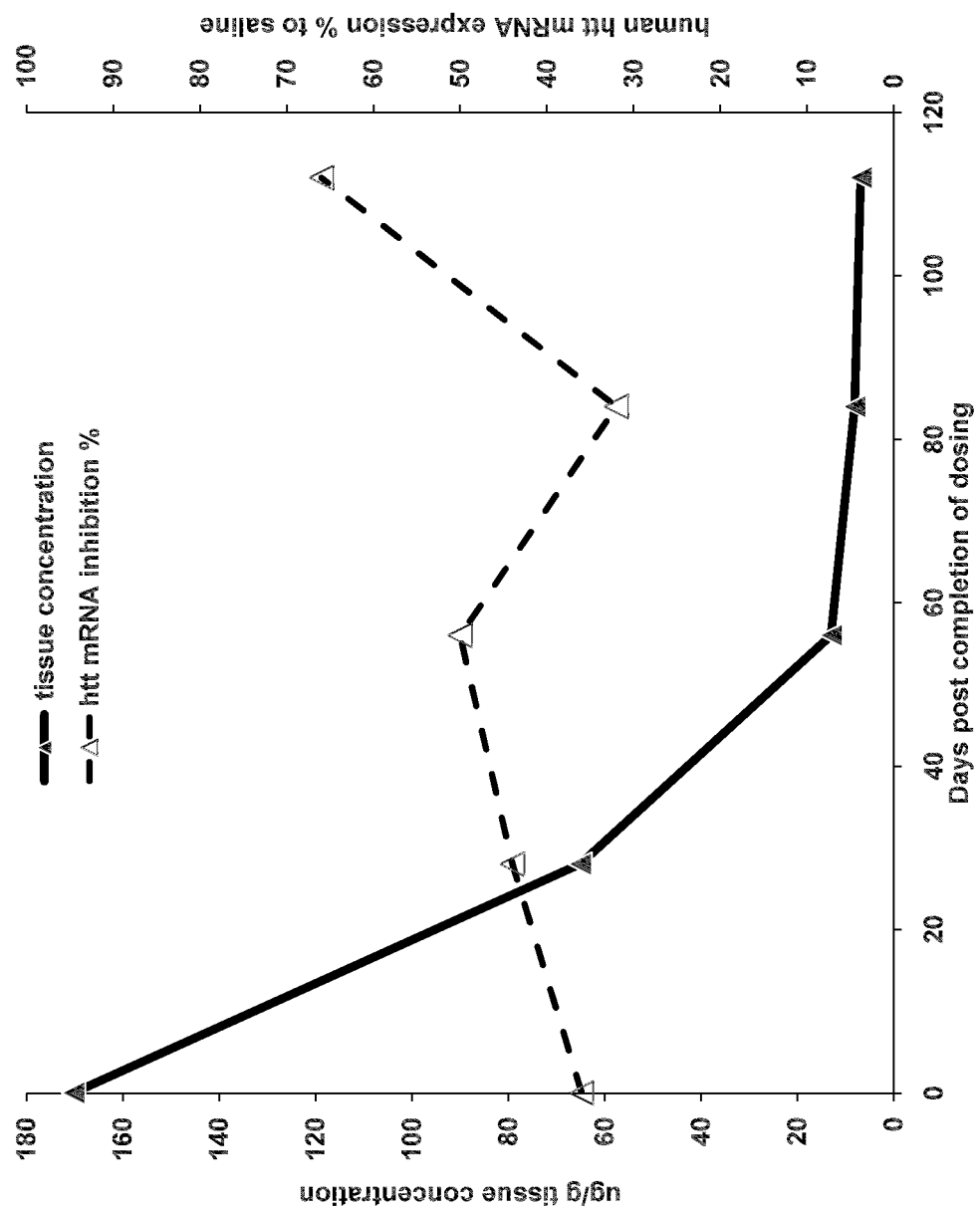
Figure 6:
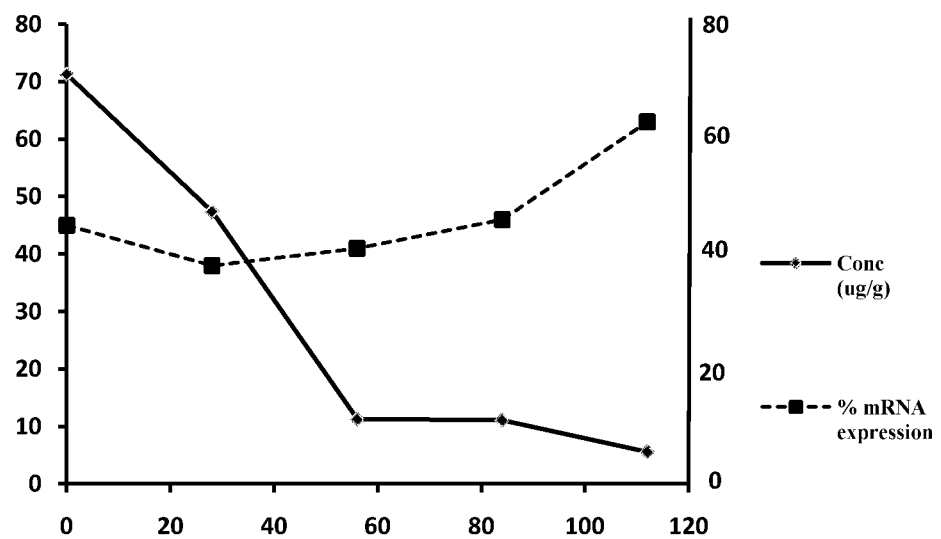

Analysis of Antisense Oligonucleotide Concentration in the Brain:

Brain tissue was processed in a procedure similar to that described in Example 9. The time-dependent concentration of ISIS 388241 in the posterior brain tissue was plotted (Table 70 and FIG. 5) and the half-life of the oligonucleotide was calculated as 20 days. The time-dependent concentration of ISIS 443139 in the posterior brain tissue was plotted (Table 71 and FIG. 6) and the half-life of the oligonucleotide was calculated as 20 days.

TABLE 70

Concentration of ISIS 384241 in brain tissue and its effect on htt mRNA expression as a percentage of the control

| Days after last dose | Conc (ug/g) | % mRNA expression |
|---|---|---|
| 0 | 170.3 | 36 |
| 28 | 65.2 | 43 |
| 56 | 13 | 49 |
| 84 | 8.2 | 32 |
| 112 | 6.9 | 66 |

TABLE 71

Concentration of ISIS 443139 in brain tissue and its effect on htt mRNA expression as a percentage of the control

| Days after last dose | Conc (ug/g) | % mRNA expression |
|---|---|---|
| 0 | 71.3 | 45 |
| 28 | 47.4 | 38 |
| 56 | 11.3 | 41 |
| 84 | 11.1 | 46 |
| 112 | 5.6 | 63 |

Example 12: Effect of Antisense Inhibition of Mutant Human Huntingtin on the Motor Performance of BACHD Mice BACHD mice were treated with ISIS oligonucleotides via intracerebroventricular (ICV) administration for the purpose of evaluating the effect of the oligonucleotides against huntingtin mRNA expression on their motor performance via the rotarod assay.

Treatment

The accelerating rotarod assay was performed on the Ugo Basile rotarod. Animals were placed on the rotarod at a speed of 2 RPM, the rotarod accelerated to 40 RPM over 5 minutes. The duration to fall was recorded. Duration to fall is defined by the animal either falling from the rotarod, or stopping their run, hanging on to the rotarod and rotating on it. Six month old BACHD mice and their non-transgenic littermates were trained to run on the rotarod for one week prior to treatment. This consisted of three consecutive trials of 5 minutes each, with a 20 minute rest period between trials. A group of 15 BACHD mice were then treated with ISIS 388241 at 50 µg/day delivered ICV with Alzet 2002 pumps at the rate of 12 µL/day for 2 weeks. The mice were surgically implanted with the pumps in a similar procedure as that described in Example 6. A control group of 14 BACHD mice were treated with PBS in a similar manner. A control group of 9 non-transgenic littermates were treated with PBS in a similar manner.

Rotarod Performance Assay

Figure 7:
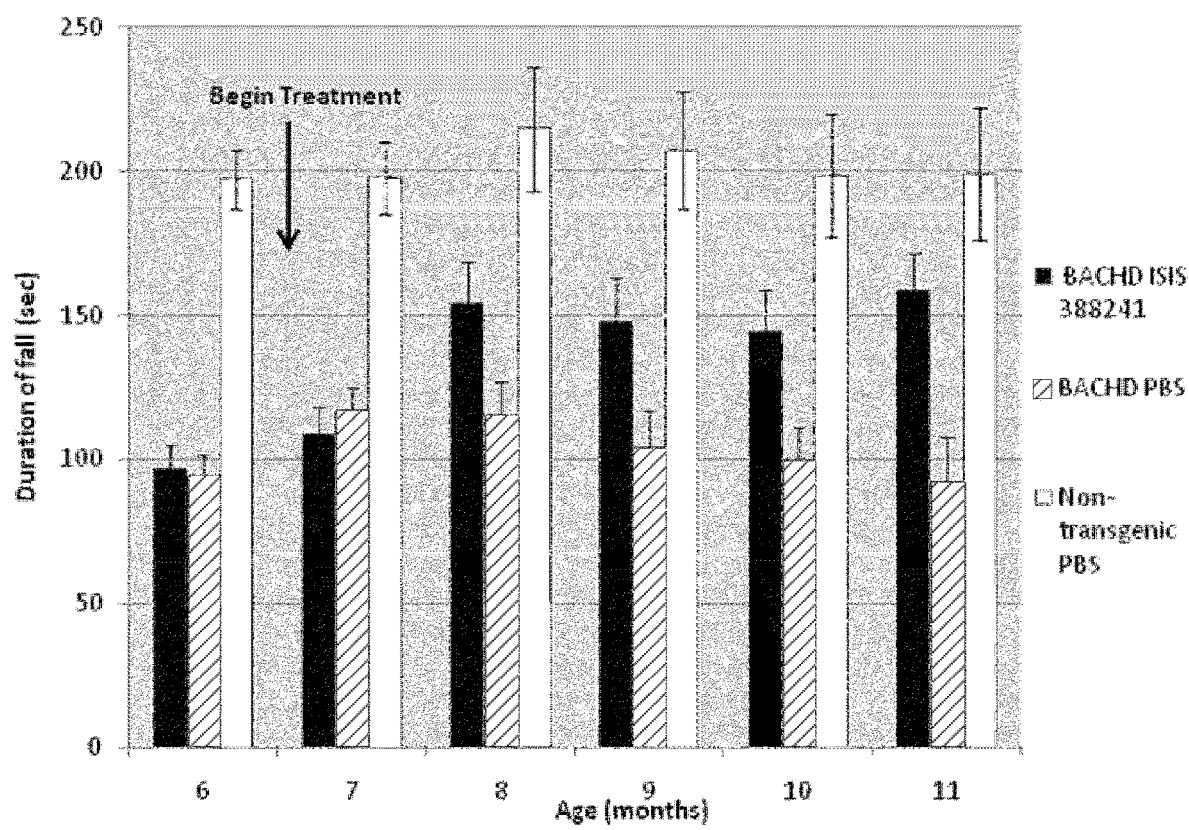

At the end of the treatment period, the pumps were removed and two weeks later, the first post-treatment rotarod assay was conducted. Rotarod behavior was analyzed monthly till the mice were 11 months of age. Each month, the animals were placed on the rotarod for three trial runs a day for 2 days. The results are presented in FIG. 7, as well as in Table 72 expressed as duration to fall in seconds. Baseline values at 6 months age were taken before the treatment and the time points given are the age of the mice at which the assay was conducted. The data indicates that treatment of BACHD mice with ISIS 388241 increased the duration to fall compared to that observed in untreated BACHD mice.

TABLE 72

Effect of antisense inhibition of mutant huntingtin mRNA on duration to fall (sec)

|  | 6 months | 7 month | 8 months | 9 months | 10 months | 11 months |
|---|---|---|---|---|---|---|
| ISIS 388241 | 97 | 108 | 154 | 148 | 144 | 159 |
| PBS control | 94 | 117 | 115 | 104 | 99 | 92 |
| Non-transgenic control | 197 | 198 | 215 | 207 | 198 | 199 |

Example 13: Effect of Antisense Inhibition of Mutant Human Huntingtin and Wild Type Murine Huntingtin mRNA on the Motor Performance of BACHD Mice BACHD mice were treated with ISIS oligonucleotides via intracerebroventricular (ICV) administration for the purpose of evaluating the effect of the oligonucleotides against huntingtin mRNA expression on their motor performance via the rotarod assay.

Treatment

The accelerating rotarod assay was performed on the Ugo Basile rotarod. Animals were placed on the rotarod at a speed of 2 RPM, the rotarod accelerated to 40 RPM over 5 minutes. The duration to fall was recorded. Duration to fall is defined by the animal either falling from the rotarod, or stopping their run, hanging on to the rotarod and rotating on it. Two month old BACHD mice and their non-transgenic littermates were trained to run on the rotarod for one week prior to treatment. This consisted of three consecutive trials of 5 minutes each, with a 20 minute rest period between trials. Groups of 17-21 BACHD mice each were then treated with ISIS 388241 at 50 µg/day, ISIS 408737 at 75 µg/day, or ISIS 387898 at 75 µg/day, delivered ICV with Alzet 2002 pumps at the rate of 0.5 µL/hour for 2 weeks. The mice were surgically implanted with the pumps in a similar procedure as that described in Example 6. A control group of 20 BACHD mice were treated with PBS in a similar manner. Groups of non-transgenic control mice were also similarly treated with ISIS oligonucleotides or PBS in a similar manner.

Rotarod Performance Assay

At the end of the treatment period, the pumps were removed and two weeks later, the first post-treatment rotarod assay was conducted. Rotarod behavior was analyzed monthly till the mice were 10 months of age. Each month, the animals were placed on the rotarod for 3-5 trial runs a day for 3 consecutive days. The results are presented in Table 73 expressed as duration to fall in seconds. Baseline values at 2 months age were taken before the treatment and the time points given are the age of the mice at which the assay was conducted. ISIS 387898 (designated in the table as Human-mouse ASO) is cross-reactive for both mouse and human huntingtin mRNA and therefore would inhibit both human mutant huntingtin mRNA and wild-type murine huntingtin mRNA in the mice. ISIS 388241 (designated in the table as Human ASO) specifically targets human huntingtin mRNA and is mismatched by 8 base pairs with murine huntingtin mRNA. Therefore, ISIS 388241 would specifically inhibit only human mutant huntingtin mRNA and not wild-type murine huntingtin mRNA in the mice. ISIS 408737 (designated in the table as Mouse ASO) specifically targets murine huntingtin mRNA and is mismatched by 7 base pairs with human huntingtin mRNA. Therefore, ISIS 408737 would specifically inhibit only wild-type murine huntingtin mRNA and not human mutant huntingtin mRNA in the mice. 'Tg' indicates the BACHD mice and 'Non-Tg' indicates the non-transgenic control mice.

The results of the study indicate that inhibition of human mutant huntingtin mRNA by ISIS 388241 (Tg-Human ASO) significantly improved the performance of the mice in the rotarod assay compared to the control (Tg-PBS). The results also indicate that treatment of mice with ISIS 387898 (Tg-Human-mouse ASO), which targets both mutant and wild-type huntingtin mRNA in the mice, did not cause any deleterious effects on the motor performance of the mice and, in fact, also significantly improved rotarod performance compared to the control (Tg-PBS). The mice treated with ISIS 408737 (Tg-Mouse ASO) did not show improved rotarod performance compared to the PBS control, as expected, since the oligonucleotide does not target the mutant huntingtin mRNA. The non-transgenic controls were utilized as positive controls in this assay.

TABLE 73

Effect of antisense inhibition of huntingtin mRNA on duration to fall (sec)

| | 2 months | 3 months | 4 months | 5 months | 6 months | 7 months | 8 months | 9 months | 10 months |
|---|---|---|---|---|---|---|---|---|---|
| Tg-Human ASO | 146 | 167 | 190 | 192 | 190 | 188 | 181 | 191 | 191 |
| Tg-mouse ASO | 151 | 142 | 152 | 143 | 139 | 144 | 139 | 123 | 130 |
| Tg-Human-mouse ASO | 149 | 187 | 203 | 199 | 196 | 194 | 189 | 194 | 171 |
| Tg-PBS | 152 | 164 | 169 | 160 | 159 | 155 | 148 | 135 | 136 |
| Non-Tg-Human ASO | 212 | 223 | 234 | 236 | 247 | 248 | 245 | 247 | 235 |
| Non-Tg-Mouse ASO | 201 | 212 | 215 | 213 | 231 | 243 | 244 | 250 | 247 |
| Non-Tg-Human-mouse ASO | 220 | 240 | 239 | 224 | 243 | 244 | 246 | 229 | 235 |
| Non-Tg-PBS | 193 | 220 | 228 | 227 | 228 | 216 | 220 | 208 | 208 |

Example 14: Effect of Antisense Inhibition of Huntingtin mRNA on the Brain Mass of R6/2 Mice R6/2 mice were treated with ISIS oligonucleotides via intracerebroventricular (ICV) administration for the purpose of evaluating the effect of the oligonucleotides against huntingtin mRNA expression on brain weight and volume.

Treatment

R6/2 mice were housed in groups of up to 5 per cage (mixed genotypes, single sex), All mice were housed in shoe-box cages with sterile wood bedding covering the ground that were changed as frequently as needed to provide the animals with dry bedding. This basic environment was enriched with the addition of play tunnels, shredded nestlet, and plastic bones for all mice; i.e. an environmentally-enriched cage containing a Mouse Tunnel, (amber color, certified, transparent, BioSery Product #K3323), a Petite Green Gumabone (BioSery Product #K3214) and a nestlet (Hockley et al., Ann Neurol. 2002, 51: 235-242). Food and water were available ad libitum to the mice in their home cages.

A group of ten six month old R6/2 mice was administered 50 µg/day of ISIS 388817 delivered ICV with Alzet 1004 pumps at the rate of 0.12 µl/hr for 4 weeks. A group of two non-transgenic littermates was administered 50 µg/day of ISIS 388817 delivered in a similar manner. A control group of five R6/2 mice was administered 50 µg/day of ISIS 141923 delivered in a similar manner. A control group of nine R6/2 mice was administered PBS delivered in a similar manner. A group of eight non-transgenic littermates was administered PBS delivered in a similar manner. A group of four untreated eight-week old pre-symptomatic R6/2 were also included in the study.

Brain Weight Measurement

Figure 8:
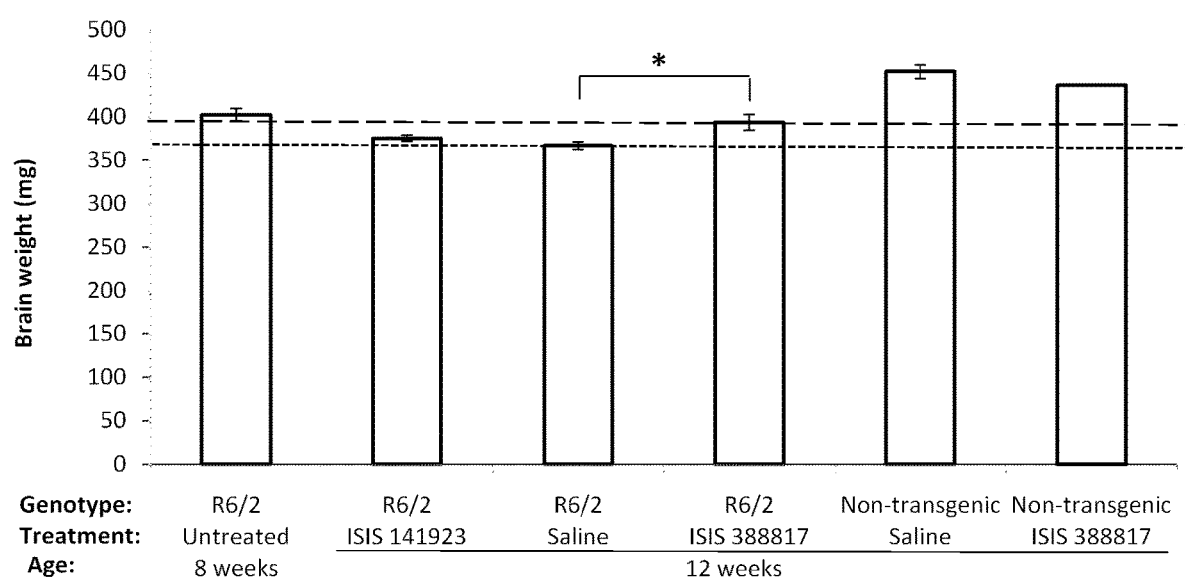

Animals were anaesthetized with isofluorane and then subjected to transcardial perfusion with ice-cold Sorenson's phosphate buffer (SPB), and fixed with 4% paraformaldyhyde in SPB. Brains were removed, and trimmed with coronal cuts immediately rostral to the forebrain (removing the olfactory bulbs) and immediately caudal to the cerebellum (removing the spinal cord). The remaining brain was weighed in mg. The results are presented in FIG. 8 and Table 74 and demonstrate the increase in brain weight in R6/2 mice treated with ISIS 388817 compared to the PBS control

TABLE 74

Effect of antisense inhibition of mutant huntingtin mRNA on brain weight (mg)

| Mouse model | Treatment | Brain weight |
|---|---|---|
| R6/2 | PBS | 367 |
| | ISIS 141923 | 375 |
| | ISIS 388817 | 394 |
| R6/2 (8 weeks old) | None | 402 |
| Non-transgenic | ISIS 141923 | 452 |
| | ISIS 388817 | 436 |

Example 15: Effect of Antisense Inhibition of Huntingtin mRNA on Anxiety Performance of YAC128 Mice YAC128 mice were treated with ISIS oligonucleotides via intracerebroventricular (ICV) administration for the purpose of evaluating the effect of the oligonucleotides against huntingtin mRNA expression on anxiety in these mice as measured by their performance in the open field and elevated plus maze assays.

Treatment

A group of seven five-month old YAC128 mice was administered 50 µg/day of ISIS 388241 delivered ICV with Alzet 1004 pumps at the rate of 0.5 µl/hr for 14 days. A control group of four YAC128 mice were similarly treated with PBS. A control group of eight non-transgenic FVB/NJ littermates were included in the study and did not receive any treatment. The mice were surgically implanted with the pumps in the following manner: Briefly, Alzet osmotic pumps (Model 2002) were assembled according to manufacturer's instructions. Pumps were filled with a solution containing the antisense oligonucleotide and incubated overnight at 37° C., 24 hours prior to implantation. Animals were anesthetized with 3% isofluorane and placed in a stereotactic frame. After sterilizing the surgical site, a midline incision was made over the skull, and a subcutaneous pocket was created over the back, in which a pre-filled osmotic pump was implanted. A small burr hole was made through the skull above the right lateral ventricle. A cannula, connected to the osmotic pump via a plastic catheter, was then placed in the ventricle and glued in place using Loctite adhesive. The incision was closed with sutures. Antisense oligonucleotide or PBS was infused for 14 days, after which the pumps were removed. The animals were allowed to recover for 2 weeks after which behavioral analysis was done and the mice were finally euthanized according to a humane protocol approved by the Institutional Animal Care and Use Committee. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with S1 being most rostral and S5 most caudal.

Open Field Assay

Figure 9:
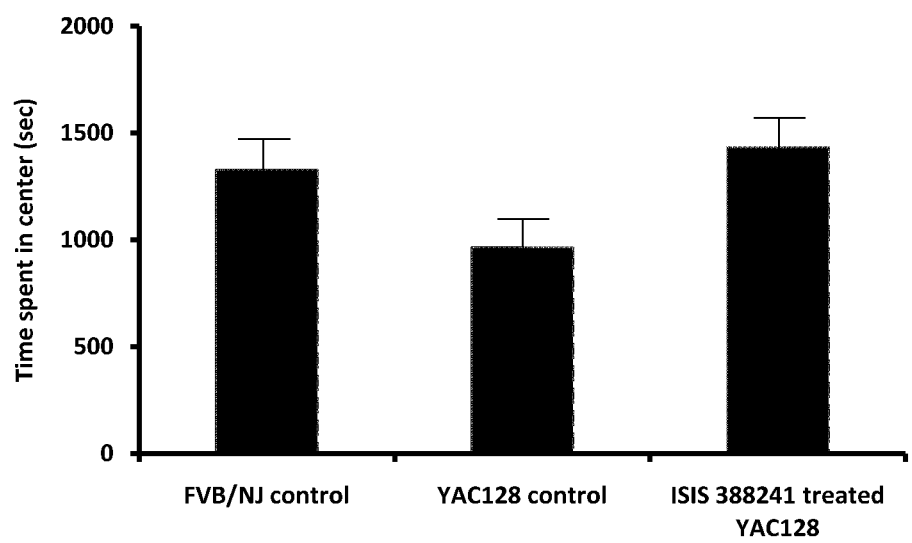

Mice were placed in an open field arena (Med Associates) that uses photobeam breaks to measure horizontal and vertical movement over a 30 min test session. Data was analyzed using Activity Monitor software to examine total ambulatory movement within the arena and movement within the center of the arena as a measure of anxiety. YAC128 control mice were expected to spend less time at the centre of the arena compared to their non-transgenic, less anxiety-prone FVB/NJ littermates. The results are presented in FIG. 9 and Table 75 and indicate that treatment of YAC128 mice with antisense oligonucleotide decreased anxiety in these mice, according to the parameters of the open field assay.

TABLE 75

Effect of antisense inhibition of mutant htt mRNA on open field performance of YAC128 mice

| Mice model | Time in center (sec) |
| --- | --- |
| FVB control | 1326 |
| YAC128 control | 964 |
| ISIS 388241 treated YAC128 | 1433 |

Elevated Plus Maze Assay

Figure 10:
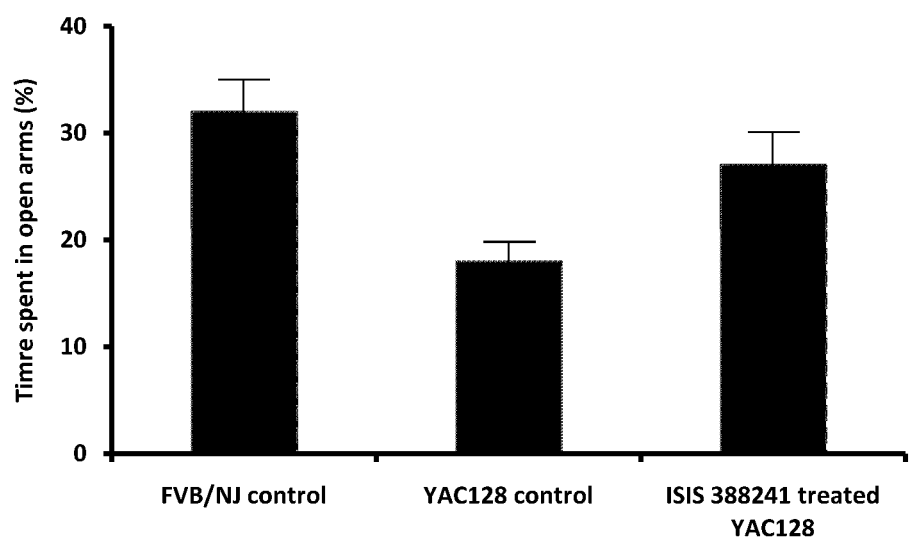

The apparatus consisted of two open arms and two closed arms each measuring 65×6.25 cm and elevated 50 cm above the ground. Mice were placed in the center of the apparatus and their location was recorded over a 5 minute test session. YAC128 control mice were expected to spend less time at the open arms of the apparatus compared to their non-transgenic, less anxiety-prone FVB/NJ littermates. The results are presented in FIG. 10 and Table 76 and indicate that treatment of YAC128 mice with antisense oligonucleotide decreased anxiety in these mice, according to the parameters of the elevated plus maze assay.

TABLE 76

Effect of antisense inhibition of mutant htt mRNA on elevated plus maze performance of YAC128 mice

| Mice model | % time in open arms |
| --- | --- |
| FVB control | 32 |
| YAC128 control | 18 |
| ISIS 388241 treated YAC128 | 27 |

RNA and Protein Analysis

Total RNA was extracted from mouse brain and spinal cord with RNeasy Protect Mini Kit (Qiagen, Mississauga, ON, Canada) for real-time PCR analysis of huntingtin mRNA levels using an RNeasy Mini prep kit (Qiagen). Q-PCR reactions were conducted and analyzed on an ABI Prism 7700 Sequence Detector (Applied Biosystems). Human huntingtin mRNA levels were measured using the human primer probe set RTS2686 and normalized to peptidylprolyl isomerase A mRNA levels.

Protein lysates were prepared from mouse brain slabs as described previously (Li S. H. and Li X. J., *Methods in Molecular Biology* (2008), 217:1940-6029). Lysates were run on 3-8% tris-acetate gel and transferred using the iBlot dry blotting system (Invitrogen). Blots were probed with anti-beta tubulin (Chemicon) and mouse monoclonal EM48 antibody that reacts specifically with human huntingtin protein (Millipore). Immunoblots were quantified using Odyssey V3.0 software.

The results are presented in Table 77 as percent reduction compared to the PBS control and demonstrate significant inhibition of huntingtin mRNA and protein levels by the antisense oligonucleotide.

TABLE 77

Percent inhibition of huntingtin mRNA in YAC128 mice

| | % inhibition |
| --- | --- |
| mRNA | 85 |
| protein | 86 |

Example 16: Intracerebroventricular Administration of Antisense Oligonucleotides Against Huntingtin in C57/BL6 Mice C57/BL6 mice were treated with ISIS oligonucleotides via intracerebroventricular (ICV) administration to the right lateral ventricle, for the purpose of evaluating the tolerability of the oligonucleotides in these mice.

Treatment and Surgery

Groups of five C57/BL6 mice each were administered ISIS 387916, ISIS 437527, ISIS 444578, ISIS 444584, ISIS 444607, ISIS 444608, ISIS 444627, ISIS 444652, ISIS 444659, ISIS 444660, or ISIS 444661 at 150 µg/day delivered ICV with Alzet 2002 pumps at the rate of 0.5 µL/day for 2 weeks. A control group of six C57/BL6 mice were similarly treated with PBS. The procedure for implanting the pumps and oligonucleotide administration is described in Example 6.

The animals were allowed to recover for two weeks before being euthanized using isoflurane. Brain and spinal cord tissue were harvested and snap frozen in liquid nitrogen. Prior to freezing, brain tissue was cut transversely into five sections (51, S2, S3, S4, and S5) using a mouse brain matrix. Sections 1 to 5 were approximately 2 mm apart from each other with 51 being the most rostral and S5 the most caudal.

RNA Analysis

Total RNA was extracted from anterior and posterior cortices of the brain for real-time PCR analysis of huntingtin mRNA levels using an RNeasy Mini prep kit (Qiagen). RT-PCR reactions were conducted on an ABI Prism 7700 Sequence Detector (Applied Biosystems). Mouse huntingtin mRNA levels were measured using a murine primer probe set RTS2633 and normalized to cyclophilin mRNA levels. The results are presented in Table 78 as percent reduction compared to the PBS control. ISIS 387916, ISIS 437527, ISIS 444627, and ISIS 444652 all have one mismatch with the murine huntingtin mRNA (SEQ ID NO: 3) and therefore did not show significant inhibition of murine mRNA levels compared to the control.

The microglial marker, AIF1 was also measured by RT-PCR analysis using murine primer probe set mAIF1_LTS00328 (forward sequence TGGTCCCCCAGC-CAAGA, designated herein as SEQ ID NO: 54; reverse sequence CCCACCGTGTGACATCCA, designated herein as SEQ ID NO: 55; probe sequence AGC-TATCTCCGAGCTGCCCTGATTGG, designated herein as SEQ ID NO: 56). The results are presented in Table 79 and indicate that the tested ISIS oligonucleotides did not induce an inflammatory response.

TABLE 78

Percent inhibition of murine huntingtin mRNA compared to the control in C57/BL6 mice

| ISIS No | anterior | posterior |
|---|---|---|
| 387916 | 72 | 74 |
| 437527 | 59 | 62 |
| 444578 | 69 | 69 |
| 444584 | 0 | 9 |
| 444607 | 59 | 79 |
| 444608 | 41 | 66 |
| 444627 | 41 | 45 |
| 444652 | 61 | 64 |
| 444660 | 35 | 33 |
| 444661 | 72 | 69 |

TABLE 79

Percent increase in AIF1 mRNA expression compared to the control in C57/BL6 mice

| ISIS No | anterior | posterior |
|---|---|---|
| 387916 | 159 | 67 |
| 437527 | 102 | 77 |
| 444578 | 22 | 7 |
| 444584 | 33 | 37 |
| 444607 | 34 | 58 |
| 444608 | 29 | 1 |
| 444627 | 46 | 22 |
| 444652 | 59 | 50 |
| 444660 | −3 | 11 |
| 444661 | 67 | 62 |

Body Weight Measurements

Body weights were measured at regular intervals throughout the study period, and are presented in Table 80. These weights were utilized as an indicator of tolerability. Mice treated with ISIS 437527, ISIS 444584, and ISIS 444652 had consistent body weight throughout the study period and were deemed the most tolerable of all the ISIS oligonucleotides included in the study. 'n/a' indicates no data for that group of mice.

Example 17: Assay for Neurotoxic Effects of Bolus Administration of Antisense Oligonucleotides in the Striatal Tissue of Rats Sprague-Dawley rats were treated with ISIS oligonucleotides via bolus administration to the striatum, for the purpose of screening for the induction of the microglial marker AIF1 as a measure of CNS toxicity.

Treatment and Surgery

Groups of four Sprague-Dawley rats were administered ISIS 388241, ISIS 443139, ISIS 436671, ISIS 437527, ISIS 444584, ISIS 444591, or ISIS 444652 delivered as a single bolus at a concentration of 25 µg, 50 µg, 75 µg, or 100 µg.

A group of 4 rats were similarly treated with ISIS 387916, delivered as a single bolus at 10 µg, 25 µg, 50 µg, or 75 µg concentrations. A control group of 4 rats were similarly treated with PBS. Seven days after bolus administration, the rats were euthanized using isoflurane and the organs were removed. The animals were decapitated and the brain was removed for dissection of the striatal tissue. A pair of fine curved forceps was placed straight down into the brain just anterior to the hippocampus to make a transverse incision in the cortex and underlying tissues by blunt dissection. The tips of another pair of fine curved forceps were placed straight down along the midsaggital sinus midway between the hippocampus and the olfactory bulb to make a longitudinal incision, cutting the corpus callosum by blunt dissection. The first pair of forceps was then used to reflect back the resultant corner of cortex exposing the striatum and internal capsule, and then to dissect the internal capsule away from the striatum. The second set of forceps was placed such that the curved ends were on either side of the striatum and pressed down to isolate the tissue. The first set of forceps was used to pinch off the posterior end of the striatum and to remove the striatum from the brain.

RNA Analysis of AIF1 Expression Levels

RNA was extracted from striatal tissue for real-time PCR analysis of AIF1 mRNA levels. Rat AIF1 levels were measured using the rat primer probe set rAif1_LTS00219. Results were calculated as the percentage of AIF1 expression over that of the PBS control and are presented in Table 81. The results indicate that ISIS 388241, ISIS 443139, ISIS 436671, ISIS 444591, ISIS 437527, ISIS 444584, and ISIS 444652 were well tolerated in rat brain.

TABLE 80

Body weights of C57/BL6 mice after antisense oligonucleotide treatment

| | Day 0 | Day 4 | Day 8 | Day 12 | Day 16 | Day 19 | Day 23 | Day 26 | Day 28 |
|---|---|---|---|---|---|---|---|---|---|
| PBS | 105 | 108 | 111 | 114 | 111 | 111 | 113 | 114 | 112 |
| ISIS 387916 | 107 | 108 | 106 | 111 | 106 | 104 | 101 | 101 | 97 |
| ISIS 437527 | 105 | 116 | 116 | 120 | 111 | 112 | 112 | 108 | 108 |
| ISIS 444578 | 105 | 116 | 112 | 115 | 103 | 98 | 83 | 81 | 87 |
| ISIS 444584 | 105 | 117 | 115 | 111 | 105 | 105 | 103 | 104 | 102 |
| ISIS 444607 | 105 | 115 | 112 | 110 | 101 | 98 | 106 | 109 | 106 |
| ISIS 444608 | 102 | 111 | 112 | 112 | 97 | 91 | 78 | 75 | 87 |
| ISIS 444627 | 105 | 116 | 124 | 126 | 105 | 104 | 93 | 94 | 91 |
| ISIS 444652 | 106 | 122 | 124 | 126 | 119 | 113 | 111 | 111 | 108 |
| ISIS 444659 | 105 | 118 | 123 | 116 | 92 | 89 | 68 | n/a | n/a |
| ISIS 444660 | 104 | 115 | 120 | 118 | 103 | 93 | 89 | 84 | 90 |
| ISIS 444661 | 107 | 125 | 120 | 106 | 76 | 86 | 89 | 86 | 91 |

TABLE 81

Percent expression of AIF1 mRNA levels in vivo as a measure of neurotoxicity

| ISIS No | Dose (µg) | % increase |
|---|---|---|
| 387916 | 10 | 145 |
| | 25 | 157 |
| | 50 | 247 |
| | 75 | 316 |
| 388241 | 25 | 29 |
| | 50 | 12 |
| | 75 | 30 |
| | 100 | 41 |
| 436671 | 25 | 37 |
| | 50 | 2 |
| | 75 | 13 |
| | 100 | 50 |
| 443139 | 25 | 0 |
| | 50 | 7 |
| | 75 | 167 |
| | 100 | 26 |
| 444591 | 25 | 18 |
| | 50 | 80 |
| | 75 | 50 |
| | 100 | 207 |
| 437527 | 25 | 98 |
| | 50 | 45 |
| | 75 | 23 |
| | 100 | 126 |
| 444584 | 25 | −1 |
| | 50 | 10 |
| | 75 | 35 |
| | 100 | 31 |
| 444652 | 25 | 17 |
| | 50 | 46 |
| | 75 | 39 |
| | 100 | 48 |

RNA Analysis of Huntingtin Expression Levels

RNA was extracted from striatal tissue for real-time PCR analysis of huntingtin mRNA levels. Rat huntingtin mRNA levels were measured using the rat primer probe set rHt-t_LTS00343. Results were calculated as the percentage reduction of huntingtin expression over that of the PBS control and are presented in Table 82. ISIS 388241 and ISIS 443139 are each mismatched by 6 base pairs or more with the rat gene sequence (SEQ ID NO: 5) and therefore do not show significant inhibition of rat mRNA levels compared to the control. ISIS 444584 has 3 mismatches with the rat gene sequence (SEQ ID NO: 5) and therefore does not show significant inhibition of rat mRNA levels compared to the control.

TABLE 82

Percent reduction of rat huntingtin mRNA levels in rats

| ISIS No | Dose (µg) | % inhibition |
|---|---|---|
| 387916 | 10 | 6 |
| | 25 | 39 |
| | 50 | 55 |
| | 75 | 60 |
| 388241 | 25 | 8 |
| | 50 | 23 |
| | 75 | 27 |
| | 100 | 19 |
| 436671 | 25 | 52 |
| | 50 | 57 |
| | 75 | 57 |
| | 100 | 70 |
| 443139 | 25 | 35 |
| | 50 | 29 |
| | 75 | 28 |
| | 100 | 27 |
| 444591 | 25 | 26 |
| | 50 | 57 |
| | 75 | 68 |
| | 100 | 69 |
| 437527 | 25 | 40 |
| | 50 | 55 |
| | 75 | 60 |
| | 100 | 74 |
| 444584 | 25 | 43 |
| | 50 | 38 |
| | 75 | 38 |
| | 100 | 41 |
| 444652 | 25 | 49 |
| | 50 | 70 |
| | 75 | 55 |
| | 100 | 59 |

Example 18: Dose-Dependent Antisense Inhibition of Huntingtin mRNA in Cynomolgous Primary Hepatocytes ISIS 437527, ISIS 444584, and ISIS 444652 were tested in cynomolgous primary hepatocytes at various doses. The benchmark oligonucleotides, ISIS 387916 and ISIS 388241 were also included for comparison. Cells were plated at a density of 35,000 cells per well and transfected using electroporation with 39.0625 nM, 78.125 nM, 156.25 nM, 312.5 nM, 625 nM, 1,250 nM, 2,500 nM, 5,000 nM, 10,000 nM, and 20,000 nM concentrations of each antisense oligonucleotide. After approximately 16 hours, RNA was isolated from the cells and huntingtin mRNA transcript levels were measured by quantitative real-time PCR using primer probe set RTS2686. Huntingtin mRNA transcript levels were normalized to total RNA content, as measured by RIBOGREEN®. Results are presented in Table 83 as percent inhibition of huntingtin, relative to untreated control cells. Control oligonucleotide, ISIS 141923 was included in this assay and did not demonstrate inhibition of huntingtin mRNA, as expected.

ISIS 437527, ISIS 444584, and ISIS 444652 had lower $IC_{50}$ values than the benchmark oligonucleotide, ISIS 388241. ISIS 437527 and ISIS 444652 had as low or lower $IC_{50}$ values than the benchmark oligonucleotide, ISIS 387916.

TABLE 83

Dose-dependent antisense inhibition of huntingtin mRNA in cynomolgous primary hepatocytes

| | ISIS 387916 | ISIS 388241 | ISIS 437527 | ISIS 444584 | ISIS 444652 | ISIS 141923 |
|---|---|---|---|---|---|---|
| 39.0625 nM | 0 | 6 | 0 | 0 | 0 | 0 |
| 78.125 nM | 17 | 4 | 19 | 0 | 16 | 0 |
| 156.25 nM | 6 | 0 | 27 | 11 | 12 | 3 |
| 312.5 nM | 19 | 0 | 23 | 16 | 35 | 0 |
| 625.0 nM | 31 | 0 | 37 | 30 | 50 | 0 |
| 1250.0 nM | 45 | 0 | 28 | 23 | 52 | 0 |
| 2500.0 nM | 62 | 4 | 33 | 47 | 74 | 0 |
| 5000.0 nM | 78 | 54 | 55 | 42 | 86 | 0 |

TABLE 83-continued

Dose-dependent antisense inhibition of huntingtin
mRNA in cynomolgous primary hepatocytes

|  | ISIS 387916 | ISIS 388241 | ISIS 437527 | ISIS 444584 | ISIS 444652 | ISIS 141923 |
|---|---|---|---|---|---|---|
| 10000.0 nM | 82 | 80 | 68 | 77 | 91 | 0 |
| 20000.0 nM | 84 | 75 | 70 | 69 | 92 | 0 |
| IC$_{50}$ (μM) | 1.4 | 5.4 | 2.0 | 4.0 | 0.8 | >20 |

Example 19: Measurement of Half-Life of ISIS Oligonucleotides in BACHD Mice Via Single Intrastriatal Bolus Administration BACHD mice were administered ISIS oligonucleotides as a single bolus to the striatum for the purpose of measuring the duration of action of the antisense oligonucleotides against huntingtin mRNA expression, or its half-life, in that tissue.

Treatment and Surgery

Groups of 25 BACD mice each were treated with ISIS 388241, ISIS 436689, ISIS 436671, or ISIS 444591, delivered as a single bolus of 40 μg in a procedure similar to that described in Example 4. A control group of 25 BACHD mice were treated with PBS in a similar procedure. At various time points, 5 mice from each group were euthanized and striatal tissue was extracted. A pair of fine curved forceps was placed straight down into the brain just anterior to the hippocampus to make a transverse incision in the cortex and underlying tissues by blunt dissection. The tips of another pair of fine curved forceps were placed straight down along the midsaggital sinus midway between the hippocampus and the olfactory bulb to make a longitudinal incision, cutting the corpus callosum by blunt dissection. The first pair of forceps was then used to reflect back the resultant corner of cortex exposing the striatum and internal capsule, and then to dissect the internal capsule away from the striatum. The second set of forceps was placed such that the curved ends were on either side of the striatum and pressed down to isolate the tissue. The first set of forceps was used to pinch off the posterior end of the striatum and to remove the striatum from the brain.

RNA Analysis

RNA was extracted from anterior and posterior sections of the striatal tissue for real-time PCR analysis of huntingtin mRNA levels. Human mutant huntingtin mRNA levels were measured using RTS2617. Mouse normal huntingtin mRNA levels were measured using the murine primer probe set RTS2633. The results are presented in Tables 84 and 85 and are expressed as percent inhibition compared to the average of the PBS control group at week 1, week 10, and week 20. The half-life of the ISIS oligonucleotides in the anterior section of the brain was calculated from the inhibition data and is presented in Table 86.

TABLE 84

Percent inhibition of human huntingtin
mRNA expression at various time points

| ISIS No | Time (weeks) | Posterior | Anterior |
|---|---|---|---|
| 388241 | 1 | 72 | 91 |
|  | 5 | 65 | 86 |
|  | 10 | 52 | 73 |
|  | 15 | 26 | 56 |
|  | 20 | 14 | 53 |
| 436671 | 1 | 82 | 92 |
|  | 5 | 78 | 89 |
|  | 10 | 68 | 82 |
|  | 15 | 61 | 77 |
|  | 20 | 30 | 77 |
| 444591 | 1 | 60 | 85 |
|  | 5 | 58 | 76 |
|  | 10 | 48 | 60 |
|  | 15 | 27 | 43 |
|  | 20 | 27 | 36 |
| 436689 | 1 | 72 | 83 |
|  | 5 | 72 | 87 |
|  | 10 | 60 | 74 |
|  | 15 | 50 | 74 |
|  | 20 | 44 | 59 |

TABLE 85

Percent inhibition of mouse huntingtin
mRNA expression at various time points

| ISIS No | Time (weeks) | Posterior | Anterior |
|---|---|---|---|
| 388241 | 1 | 1 | 12 |
|  | 5 | 22 | 36 |
|  | 10 | 17 | 14 |
|  | 15 | 7 | 18 |
|  | 20 | 9 | 38 |
| 436671 | 1 | 84 | 96 |
|  | 5 | 77 | 80 |
|  | 10 | 64 | 86 |
|  | 15 | 51 | 78 |
|  | 20 | 19 | 75 |
| 444591 | 1 | 74 | 95 |
|  | 5 | 70 | 90 |
|  | 10 | 57 | 67 |
|  | 15 | 34 | 47 |
|  | 20 | 33 | 38 |
| 436689 | 1 | 40 | 32 |
|  | 5 | 47 | 40 |
|  | 10 | 35 | 18 |
|  | 15 | 34 | 22 |
|  | 20 | 36 | 5 |

TABLE 86

Half-life of ISIS oligonucleotides in the anterior section of
the brain in BACHD mice after intrastriatal bolus injection

| ISIS No | Half-life (days) |
|---|---|
| 436671 | 46.6 |
| 436689 | 39.4 |
| 444591 | 24.3 |
| 388241 | 25.8 |

Body Weight Measurements

Body weights were measured at regular intervals, and are presented in Table 87 as a percent of the weight of the mice at the start of the study. These weights were utilized as an indicator of tolerability. There were no adverse changes in body weight in any of the mice treated with ISIS oligonucleotides.

TABLE 87

Percent change in body weight of BACHD mice after antisense oligonucleotide treatment

|  | Week 5 | Week 10 | Week 15 | Week 20 |
|---|---|---|---|---|
| PBS | 8 | 19 | 26 | 28 |
| ISIS 388241 | 9 | 22 | 29 | 26 |
| ISIS 436671 | 5 | 19 | 35 | 38 |
| ISIS 444591 | 7 | 21 | 30 | 43 |
| ISIS 436689 | 3 | 18 | 31 | 38 |

Example 20: Effect of Intrathecal Administration of ISIS 437527 in Sprague Dawley Rats Sprague Dawley rats were dosed with ISIS 437527 by intrathecal (IT) administration either as a single dose, repeated doses, or continuous infusion.

Treatment and Surgery

Rats were anesthetized with isoflurane and a 28-gauge polyurethane catheter was placed into the IT lumbar space of each rat. The proximal end of the catheter was attached to a dosing pedestal that was extended through the skin for animals in groups receiving bolus injections. The catheter for animals in the group receiving continuous infusion was attached to an ALZET pump (Model 2ML1) which was placed in a subcutaneous pocket on the dorsal aspect of each animal. Post-surgically the animals received a single intramuscular dose of ceftiofur sodium (5 mg/kg) and butorphanol tartrate (0.05 mg/kg). The rats receiving continuous infusion began receiving the oligonucleotide dose immediately. The animals that would receive bolus injections were allowed a surgical recovery period of at least five days after which the patency of the catheter was evaluated.

A group of 5 Sprague Dawley rats was administered a single bolus injection of 350 µg of ISIS 437527 delivered intrathecally. Another group of 5 Sprague Dawley rats was administered bolus injections of 120 µg of ISIS 437527 delivered intrathecally three times over the course of 1 week. Another group of 5 Sprague Dawley rats was administered bolus injections of 350 µg of ISIS 437527 delivered intrathecally three times over the course of 1 week. Another group of 5 Sprague Dawley rats was administered 50 µg/day of ISIS 437527 delivered by continuous infusion at a rate of 0.01 mL/hr for 7 days. A control group of 5 Sprague Dawley rats was administered bolus injections of PBS delivered intrathecally three times over the course of 1 week. Each group was given a recovery period of 7 days, after which the rats were euthanized. The brain and spinal cord from all groups were harvested and analyzed.

RNA Analysis of Huntingtin Expression Levels

RNA was extracted from the frontal cortex, temporal cortex, and the cervical cord for real-time PCR analysis of huntingtin mRNA levels. Rat huntingtin mRNA levels were measured using the primer probe set rHtt_LTS00343 normalized to Cyclophilin levels. The results are presented in Table 88 and are expressed as percent inhibition compared to the average of the PBS control groups.

TABLE 88

Percent inhibition of huntingtin mRNA expression in Sprague Dawley rats

| Tissue | Dose schedule | Dose | % inhibition |
|---|---|---|---|
| Frontal Cortex | IT Infusion | 50 µg/day | 11 |
|  | Single IT Bolus | 350 µg | 28 |
|  | Repeated IT Bolus | 120 µg × 3 | 21 |
|  | Repeated IT Bolus | 350 µg × 3 | 0 |
| Temporal Cortex | IT Infusion | 50 µg /day | 0 |
|  | Single IT Bolus | 350 µg | 34 |
|  | Repeated IT Bolus | 120 µg × 3 | 44 |
|  | Repeated IT Bolus | 350 µg × 3 | 48 |
| Cervical Cord | IT Infusion | 50 µg /day | 22 |
|  | Single IT Bolus | 350 µg | 45 |
|  | Repeated IT Bolus | 120 µg × 3 | 58 |
|  | Repeated IT Bolus | 350 µg × 3 | 46 |

RNA Analysis of AIF1 Expression Levels

RNA was extracted from frontal cortex, temporal cortex, and the cervical cord for real-time PCR analysis of AIF1 mRNA levels. Rat AIF1 levels were measured using the rat primer probe set rAif1_LTS00219. Results were calculated as the percentage of AIF1 expression over that of the PBS control and are presented in Table 89. The results indicate that repeated IT bolus administrations lead to inflammation at the cervical cord tissues. Continuous IT administration and single IT bolus administrations were well tolerated in the rats.

TABLE 89

Percent expression of AIF1 mRNA levels in Sprague Dawley rats as a measure of neurotoxicity

| Tissue | Dose schedule | Dose | % inhibition |
|---|---|---|---|
| Frontal Cortex | IT Infusion | 50 µg/day | −36 |
|  | Single IT Bolus | 350 µg | −4 |
|  | Repeated IT Bolus | 120 µg × 3 | 41 |
|  | Repeated IT Bolus | 350 µg × 3 | −7 |
| Temporal Cortex | IT Infusion | 50 µg /day | 15 |
|  | Single IT Bolus | 350 µg | 22 |
|  | Repeated IT Bolus | 120 µg × 3 | 25 |
|  | Repeated IT Bolus | 350 µg × 3 | 76 |
| Cervical Cord | IT Infusion | 50 µg /day | 108 |
|  | Single IT Bolus | 350 µg | 72 |
|  | Repeated IT Bolus | 120 µg × 3 | 473 |
|  | Repeated IT Bolus | 350 µg × 3 | 268 |

Example 21: Measurement of Half-Life of ISIS 436689 in the CNS Tissues of Cynomolgous Monkeys Via Intrathecal Administration Cynomolgous monkeys were administered ISIS 436689 intrathecally (IT) for the purpose of measuring the half-life and duration of action of the antisense oligonucleotide against huntingtin mRNA expression in various CNS tissues.

Treatment

The study was conducted at Northern Biomedical Research, MI. Prior to the start of the treatment, the monkeys were kept in quarantine for a 4-week time period, during which standard panels of serum chemistry and hematology, examination of fecal samples for ova and parasites, and a tuberculosis test, were conducted to screen out abnormal or ailing monkeys. The monkeys were implanted with intrathecal lumbar catheters using polyurethane catheters connected to a subcutaneous titanium access port (P.A.S. PORT® Elite Plastic/Titanium portal with Ultra lock connector). For continuous infusion using an external pump, the animals were anesthetized to attach the dosing apparatus to the port. The animals were pretreated with atropine sulfate by subcutaneous injection at a dose of 0.04 mg/kg. Approximately 15 minutes later, an intramuscular dose of 8 mg/kg of ketamine HCl was administered to induce sedation. The animals were masked to a surgical plane of anesthesia, intubated and maintained on approximately 1 L/min of oxygen and 2% halothane or isoflurane. The animals received a single intramuscular dose of 5 mg/kg ceftiofur sodium antibiotic. An incision was made near the port for placement of the modified needle support. The modified needle was placed in the port and secured with sutures. Upon recovery from surgery, a jacket was placed on the animal.

Fifteen male cynomolgus monkeys were administered 4 mg/day of ISIS 436689 at a concentration of 1.67 mg/mL and at a flow rate of 2.4 mL/day for 21 days. A control group of 3 cynomolgus monkeys was administered with PBS in a similar manner for the same time period. Groups of 3 monkeys each were allowed recovery periods of 1 day, 2 weeks, 4 weeks, or 8 weeks, after which they were euthanized. During the study period, the monkeys were observed daily for signs of illness or distress.

All animals were sedated with an intramuscular injection of 8.0 mg/kg of ketamine HCl, maintained on a halothane or isoflurane/oxygen mixture, and provided with an intravenous bolus of heparin Na at 200 IU/kg. The animals were perfused via the left cardiac ventricle with 0.001% sodium nitrite in saline.

At the time of sacrifice, the brain was cut in a brain matrix at 3 mm coronal slice thickness. Several brain structures were sampled using a 4 mm biopsy punch. One 4 mm diameter sample from each structure was placed in 2 mL screw capped tubes containing 1.0 mL of RN Alater RNA stabilization solution (Qiagen, CA), incubated for 1 hour at ambient temperature and then frozen. Adjacent 6 mm diameter samples were placed in 2 mL screw capped tubes and frozen for pharmacokinetic analysis.

The spinal cord was sectioned into cervical, thoracic and lumbar sections, and approximately 3 mm thick sections of each area of the spinal cord were taken for RNA and pharmacokinetic analysis. These samples were processed in a manner similar to those of the brain samples.

Samples of the liver were harvested for RNA and pharmacokinetic analyses. These samples were processed in a manner similar to those of the brain and spinal cord described above.

RNA Analysis

RNA was extracted from the lumbar spinal cord, thoracic spinal cord, cervical spinal cord, frontal cortex, occipital cortex, cerebellar cortex, caudate tissue, hippocampus, middle brain, and pons for real-time PCR analysis of huntingtin mRNA levels with primer probe set RTS2617. The results measured in the various sections of the spinal cord are presented in Table 90 and are expressed as percent inhibition compared to that measured in the PBS control group at 8 weeks. The results measured in the various sections of the brain are presented in Table 91 and are expressed as percent inhibition compared to that measured in the PBS control group at 8 weeks.

TABLE 90

Effect of ISIS 436689 administered IT on huntingtin mRNA expression in the spinal cord at various time points

| Recovery period | Lumbar spinal cord | Thoracic spinal cord | Cervical spinal cord |
| --- | --- | --- | --- |
| 1 Day | 36 | 66 | 65 |
| 2 Weeks | 56 | 55 | 54 |
| 4 Weeks | 0 | 63 | 65 |
| 8 Weeks | 48 | 48 | 44 |

TABLE 91

Effect of ISIS 436689 administered IT on huntingtin mRNA expression in various brain tissues at various time points

| Recovery period | Frontal cortex | Occipital cortex | Cerebellar cortex | Caudate | Hippocampus | Middle brain | Pons |
| --- | --- | --- | --- | --- | --- | --- | --- |
| 1 Day | 53 | 37 | 8 | 21 | 19 | 24 | 22 |
| 2 Weeks | 42 | 28 | 16 | 3 | 28 | 0 | 32 |
| 4 Weeks | 47 | 32 | 25 | 7 | 22 | 2 | 43 |
| 8 Weeks | 33 | 34 | 11 | 17 | 27 | 5 | 22 |

Oligonucleotide Concentration Measurement by ELISA

Tissues (20 mg) were minced, weighed, and homogenized prior to liquid/liquid extraction using phenol/chloroform. The supernatant was removed, lyophilized, and reconstituted in human EDTA plasma (1 mL) before being analyzed using a hybridization ELISA procedure.

ISIS 436689 was detected in the tissues by hybridization to a labeled complementary cutting probe (digoxigenin at the 5' end and a C18 spacer and BioTEG at the 3' end). The complex was then captured on a neutravidin-coated plate and S1 nuclease was added to digest the unhybridized cutting probes. Since ISIS 436689 protected the cutting probe from digestion, the undigested cutting probe was used as a measure of the oligonucleotide concentration. The undigested cutting probe was detected using an anti-digoxigenin antibody conjugated to alkaline phosphatase followed by fluorogenic substrate readout. Oligonucleotide concentrations were measured in the cervical, thoracic, and lumbar sections of the spinal cord and in the liver on days 7, 20, 34, and 62 of the recovery period, and are presented in Table 92. The half-life of ISIS 436689 in these tissues was calculated from this data, and is presented in Table 93. The data indicates that the oligonucleotide was mainly concentrated in the CNS with negligible concentrations in the systemic tissues.

TABLE 92

Concentrations (μg/g tissue) of ISIS 436689 administered IT on huntingtin mRNA expression in various tissues at various time points

| Organ | Day 7 | Day 20 | Day 34 | Day 62 |
|---|---|---|---|---|
| Cervical cord | 118.9 | 78.7 | 79.8 | 42.8 |
| Thoracic cord | 503.5 | 215.8 | 101.6 | 61.4 |
| Lumbar cord | 557.1 | 409.5 | 143.3 | 49.5 |
| Liver | 33.6 | 10.3 | 2.0 | 0.2 |

TABLE 93

Half-life of ISIS 436689 administered IT on huntingtin mRNA expression in various tissues

| Organ | Half-life |
|---|---|
| Cervical cord | 4.0 |
| Thoracic cord | 15.1 |
| Lumbar cord | 18.7 |
| Liver | 7.6 |

The invention claimed is:

1. A single-stranded modified oligonucleotide consisting of 20 linked nucleosides and having:
- a gap segment consisting of ten linked deoxynucleosides;
- a 5' wing segment consisting of five linked nucleosides; and
- a 3' wing segment consisting of five linked nucleosides;
- wherein the gap segment is positioned between the 5' wing segment and the 3' wing segment;
- wherein each nucleoside of each wing segment comprises a 2'O-methoxyethyl sugar; and
- wherein the nucleobase sequence of the oligonucleotide consists of the sequence recited in SEQ ID NO: 36, or a pharmaceutically acceptable salt thereof.

2. The single-stranded modified oligonucleotide of claim 1, wherein at least one nucleoside comprises a modified nucleobase.

3. The single-stranded modified oligonucleotide of claim 2, wherein the modified nucleobase is a 5-methylcytosine.

4. The single-stranded modified oligonucleotide of claim 1, wherein each cytosine is a 5-methylcytosine.

5. The single-stranded modified oligonucleotide of claim 1, wherein at least one internucleoside linkage is a modified internucleoside linkage.

6. The single-stranded modified oligonucleotide of claim 1, wherein each internucleoside linkage is a phosphorothioate internucleoside linkage.

7. The single-stranded modified oligonucleotide of claim 4, wherein at least one internucleoside linkage is a modified internucleoside linkage.

8. The single-stranded modified oligonucleotide of claim 4, wherein each internucleoside linkage is a phosphorothioate internucleoside linkage.

9. A composition comprising the single-stranded modified oligonucleotide or pharmaceutically acceptable salt thereof of claim 1 and at least one pharmaceutically acceptable carrier or diluent.

10. A composition comprising the single-stranded modified oligonucleotide or pharmaceutically acceptable salt thereof of claim 4 and at least one pharmaceutically acceptable carrier or diluent.

11. A composition comprising the single-stranded modified oligonucleotide or pharmaceutically acceptable salt thereof of claim 6 and at least one pharmaceutically acceptable carrier or diluent.

12. A composition comprising the single-stranded modified oligonucleotide or pharmaceutically acceptable salt thereof of claim 8 and at least one pharmaceutically acceptable carrier or diluent.

13. The single-stranded modified oligonucleotide of claim 1, which is capable of inhibiting huntingtin expression.

14. The single-stranded modified oligonucleotide of claim 4, which is capable of inhibiting huntingtin expression.

15. The single-stranded modified oligonucleotide of claim 6, which is capable of inhibiting huntingtin expression.

16. The single-stranded modified oligonucleotide of claim 8, which is capable of inhibiting huntingtin expression.

* * * * *

SEQUENCE LISTING

<160> NUMBER OF SEQ ID NOS: 56

<210> SEQ ID NO 1
<211> LENGTH: 13481
<212> TYPE: DNA
<213> ORGANISM: Homo sapiens

<400> SEQUENCE: 1

```
gctgccggga cgggtccaag atggacggcc gctcaggttc tgcttttacc tgcggcccag      60
agccccattc attgccccgg tgctgagcgg cgccgcgagt cggcccgagg cctccgggga     120
ctgccgtgcc gggcgggaga ccgccatggc gaccctggaa aagctgatga aggccttcga     180
gtccctcaag tccttccagc agcagcagca gcagcagcag cagcagcagc agcagcagca     240
gcagcagcag cagcagcagc aacagccgcc accgccgccg ccgccgccgc cgcctcctca     300
gcttcctcag ccgccgccgc aggcacagcc gctgctgcct cagccgcagc cgccccccgcc     360 gccgccccg ccgccacccg gccggctgt ggctgaggag ccgctgcacc gaccaaagaa     420
agaactttca gctaccaaga agaccgtgt gaatcattgt ctgacaatat gtgaaaacat     480
agtggcacag tctgtcagaa attctccaga atttcagaaa cttctgggca tcgctatgga     540
actttttctg ctgtgcagtg atgacgcaga gtcagatgtc aggatggtgg ctgacgaatg     600
cctcaacaaa gttatcaaag ctttgatgga ttctaatctt ccaaggttac agctcgagct     660
ctataaggaa attaaaaaga atggtgcccc tcggagtttg cgtgctgccc tgtgggaggtt     720 tgctgagctg gctcacctgg ttcggcctca gaaatgcagg ccttacctgg tgaaccttct     780
gccgtgcctg actcgaacaa gcaagagacc cgaagaatca gtccaggaga ccttggctgc     840
agctgttccc aaaattatgg cttcttttgg caattttgca aatgacaatg aaattaaggt     900
tttgttaaag gccttcatag cgaacctgaa gtcaagctcc ccaccattc ggcggacagc     960 ggctggatca gcagtgagca tctgccagca ctcaagaagg acacaatatt tctatagttg    1020
gctactaaat gtgctcttag gcttactcgt tcctgtcgag gatgaacact ccactctgct    1080
gattcttggc gtgctgctca ccctgaggta tttggtgccc ttgctgcagc agcaggtcaa    1140
ggacacaagc ctgaaaggca gcttcggagt gacaaggaaa gaaatggaag tctctccttc    1200
tgcagagcag cttgtccagg tttatgaact gacgttacat catacacagc accaagacca    1260
caatgttgtg accggagccc tggagctgtt gcagcagctc ttcagaacgc ctccacccga    1320
gcttctgcaa accctgaccg cagtcggggg cattgggcag ctcaccgctg ctaaggagga    1380
gtctggtggc cgaagccgta gtgggagtat tgtggaactt atagctggag ggggttcctc    1440
atgcagccct gtcctttcaa gaaaacaaaa aggcaaagtg ctcttaggag aagaagagc    1500 cttggaggat gactctgaat cgagatcgga tgtcagcagc tctgccttaa cagcctcagt    1560
gaaggatgag atcagtggag agctggctgc ttcttcaggg gtttccactc cagggtcagc    1620
```

-continued

```
aggtcatgac atcatcacag aacagccacg gtcacagcac acactgcagg cggactcagt    1680
ggatctggcc agctgtgact tgacaagctc tgccactgat ggggatgagg aggatatctt    1740
gagccacagc tccagccagg tcagcgccgt cccatctgac cctgccatgg acctgaatga    1800
tgggacccag gcctcgtcgc ccatcagcga cagctcccag accaccaccg aagggcctga    1860
ttcagctgtt accccttcag acagttctga aattgtgtta gacggtaccg acaaccagta    1920
tttgggcctg cagattggac agccccagga tgaagatgag gaagccacag gtattcttcc    1980
tgatgaagcc tcggaggcct tcaggaactc ttccatggcc cttcaacagg cacatttatt    2040
gaaaaacatg agtcactgca ggcagccttc tgacagcagt gttgataaat ttgtgttgag    2100
agatgaagct actgaaccgg gtgatcaaga aaacaagcct tgccgcatca aggtgacat    2160 tggacagtcc actgatgatg actctgcacc tcttgtccat tgtgtccgcc ttttatctgc    2220 ttcgttttg ctaacagggg gaaaaaatgt gctggttccg acagggatg tgagggtcag    2280 cgtgaaggcc ctggccctca gctgtgtggg agcagctgtg ccctccacc cggaatcttt    2340 cttcagcaaa ctctataaag ttcctcttga caccacggaa taccctgagg aacagtatgt    2400
ctcagacatc ttgaactaca tcgatcatgg agacccacag gttcgaggag ccactgccat    2460
tctctgtggg accctcatct gctccatcct cagcaggtcc cgcttccacg tgggagattg    2520
gatgggcacc attagaaccc tcacaggaaa tacattttct ttggcggatt gcattccttt    2580
gctgcggaaa acactgaagg atgagtcttc tgttacttgc aagttagctt gtacagctgt    2640
gaggaactgt gtcatgagtc tctgcagcag cagctacagt gagttaggac tgcagctgat    2700
catcgatgtg ctgactctga ggaacagttc ctattggctg gtgaggacag agcttctgga    2760
aacccttgca gagattgact tcaggctggt gagcttttg gaggcaaaag cagaaaactt    2820
acacagaggg gctcatcatt atacagggct tttaaaactg caagaacgag tgctcaataa    2880
tgttgtcatc catttgcttg gagatgaaga ccccagggtg cgacatgttg ccgcagcatc    2940
actaattagg cttgtcccaa agctgttta taaatgtgac caaggacaag ctgatccagt    3000
agtggccgtg gcaagagatc aaagcagtgt ttacctgaaa cttctcatgc atgagacgca    3060
gcctccatct catttctccg tcagcacaat aaccagaata tatagaggct ataacctact    3120
accaagcata acagacgtca ctatggaaaa taaccttttca agagttattg cagcagtttc    3180
tcatgaacta atcacatcaa ccaccagagc actcacattt ggatgctgtg aagctttgtg    3240
tcttctttcc actgccttcc cagtttgcat ttggagttta ggttggcact gtggagtgcc    3300
tccactgagt gcctcagatg agtctaggaa gagctgtacc gttgggatgg ccacaatgat    3360 tctgacccctg ctctcgtcag cttggttccc attggatctc tcagcccatc aagatgcttt    3420
gattttggcc ggaaacttgc ttgcagccag tgctcccaaa tctctgagaa gttcatgggc    3480
ctctgaagaa gaagccaacc cagcagccac caagcaagag gaggtctggc cagccctggg    3540
ggaccgggcc ctggtgccca tggtggagca gctcttctct cacctgctga aggtgattaa    3600
catttgtgcc cacgtcctgg atgacgtggc tcctggaccc gcaataaagg cagccttgcc    3660
ttctctaaca acccccctt ctctaagtcc catccgacga aggggaagg agaaagaacc    3720 aggagaacaa gcatcgtgtac cgttgagtcc caagaaaggc agtgaggcca gtgcagcttc    3780
tagacaatct gatacctcag gtcctgttac aacaagtaaa tcctcatcac tggggagttt    3840
ctatcatctt ccttcatacc tcaaaactgca tgatgtcctg aaagctacac acgctaacta    3900
caaggtcacg ctggatcttc agaacagcac ggaaaagttt ggagggtttc tccgctcagc    3960
cttggatgtt ctttctcaga tactagagct ggccacactg caggacattg ggaagtgtgt    4020
```

```
tgaagagatc ctaggatacc tgaaatcctg ctttagtcga gaaccaatga tggcaactgt    4080
ttgtgttcaa caattgttga agactctctt tggcacaaac ttggcctccc agtttgatgg    4140
cttatcttcc aacccagca agtcacaagg ccgagcacag cgccttggct cctccagtgt    4200
gaggccaggc ttgtaccact actgcttcat ggccccgtac acccacttca cccaggccct    4260
cgctgacgcc agcctgagga acatggtgca ggcggagcag gagaacgaca cctcgggatg    4320
gtttgatgtc ctccagaaag tgtctaccca gttgaagaca aacctcacga gtgtcacaaa    4380
gaaccgtgca gataagaatg ctattcataa tcacattcgt ttgtttgaac ctcttgttat    4440
aaaagcttta aaacagtaca cgactacaac atgtgtgcag ttacagaagc aggttttaga    4500
tttgctggcg cagctggttc agttacgggt taattactgt cttctggatt cagatcaggt    4560
gtttattggc tttgtattga aacagtttga atacattgaa gtgggccagt tcagggaatc    4620
agaggcaatc attccaaaca tcttttcctt cttggtatta ctatcttatg aacgctatca    4680
ttcaaaacag atcattggaa ttcctaaaat cattcagctc tgtgatggca tcatggccag    4740
tggaaggaag gctgtgacac atgccatacc ggctctgcag cccatagtcc acgacctctt    4800
tgtattaaga ggaacaaata aagctgatgc aggaaaagag cttgaaaccc aaaaagaggt    4860
ggtggtgtca atgttactga gactcatcca gtaccatcag gtgttggaga tgttcattct    4920
tgtcctgcag cagtgccaca aggagaatga agacaagtgg aagcgactgt ctcgacagat    4980
agctgacatc atcctcccaa tgttagccaa acagcagatg cacattgact ctcatgaagc    5040
ccttggagtg ttaaatacat tatttgagat tttggcccct tcctccctcc gtccggtaga    5100
catgctttta cggagtatgt tcgtcactcc aaacacaatg gcgtccgtga gcactgttca    5160
actgtggata tcgggaattc tggccatttt gagggttctg atttcccagt caactgaaga    5220
tattgttctt tctcgtattc aggagctctc cttctctccg tatttaatct cctgtacagt    5280
aattaatagg ttaagagatg gggacagtac ttcaacgcta aagaacaca gtgaagggaa    5340 acaaataaag aatttgccag aagaaacatt ttcaaggttt ctattacaac tggttggtat    5400
tcttttagaa gacattgtta caaaacagct gaaggtggaa atgagtgagc agcaacatac    5460
tttctattgc caggaactag gcacactgct aatgtgtctg atccacatct tcaagtctgg    5520
aatgttccgg agaatcacag cagctgccac taggctgttc cgcagtgatg gctgtggcgg    5580
cagtttctac accctggaca gcttgaactt gcgggctcgt tccatgatca ccacccaccc    5640
ggccctggtg ctgctctggt gtcagatact gctgcttgtc aaccacaccg actaccgctg    5700
gtgggcagaa gtgcagcaga ccccgaaaag acacagtctg tccagcacaa agttacttag    5760
tccccagatg tctggagaag aggaggattc tgacttggca gccaaacttg gaatgtgcaa    5820
tagagaaata gtacgaagag gggctctcat tctcttctgt gattatgtct gtcagaacct    5880
ccatgactcc gagcacttaa cgtggctcat tgtaaatcac attcaagatc tgatcagcct    5940
ttcccacgag cctccagtac aggacttcat cagtgccgtt catcggaact ctgctgccag    6000
cggcctgttc atccaggcaa ttcagtctcg ttgtgaaaac ctttcaactc caaccatgct    6060
gaagaaaact cttcagtgct tggagggat ccatctcagc cagtcgggag ctgtgctcac    6120
gctgtatgtg gacaggcttc tgtgcacccc tttccgtgtg ctggctcgca tggtcgacat    6180
ccttgcttgt cgccgggtag aaatgcttct ggctgcaaat ttacagagca gcatggccca    6240
gttgccaatg gaagaactca acagaatcca ggaataccct cagagcagcg ggctcgctca    6300
gagacaccaa aggctctatt ccctgctgga caggtttcgt ctctccacca tgcaagactc    6360
```

```
acttagtccc tctcctccag tctcttccca cccgctggac ggggatgggc acgtgtcact   6420
ggaaacagtg agtccggaca aagactggta cgttcatctt gtcaaatccc agtgttggac   6480
caggtcagat tctgcactgc tggaaggtgc agagctggtg aatcggattc ctgctgaaga   6540
tatgaatgcc ttcatgatga actcggagtt caacctaagc ctgctagctc catgcttaag   6600
cctagggatg agtgaaattt ctggtggcca gaagagtgcc ctttttgaag cagcccgtga   6660
ggtgactctg gcccgtgtga gcggcaccgt gcagcagctc cctgctgtcc atcatgtctt   6720
ccagcccgag ctgcctgcag agccggcggc ctactggagc aagttgaatg atctgtttgg   6780
ggatgctgca ctgtatcagt ccctgcccac tctggcccgg ccctggcac agtacctggt    6840
ggtggtctcc aaactgccca gtcatttgca ccttcctcct gagaaagaga aggacattgt   6900
gaaattcgtg gtggcaaccc ttgaggccct gtcctggcat ttgatccatg agcagatccc   6960
gctgagtctg gatctccagg cagggctgga ctgctgctgc ctggccctgc agctgcctgg   7020
cctctggagc gtggtctcct ccacagagtt tgtgacccac gcctgctccc tcatctactg   7080
tgtgcacttc atcctggagg ccgttgcagt gcagcctgga gcagcagcttc ttagtccaga  7140
aagaaggaca ataccccaa aagccatcag cgaggaggag gaggaagtag atccaaacac    7200
acagaatcct aagtatatca ctgcagcctg tgagatggtg gcagaaatgg tggagtctct   7260
gcagtcggtg ttggccttgg gtcataaaag gaatagcggc gtgccggcgt ttctcacgcc   7320
attgctaagg aacatcatca tcagcctggc ccgcctgccc cttgtcaaca gctacacacg   7380
tgtgccccca ctggtgtgga agcttggatg gtcacccaaa ccgggagggg attttggcac   7440
agcattccct gagatccccg tggagttcct ccaggaaaag gaagtcttta aggagttcat   7500
ctaccgcatc aacacactag gctggaccag tcgtactcag tttgaagaaa cttgggccac   7560
cctccttggt gtcctggtga cgcagccct cgtgatggag caggaggaga gcccaccaga    7620
agaagacaca gagaggaccc agatcaacgt cctggccgtg caggccatca cctcactggt   7680
gctcagtgca atgactgtgc ctgtggccgg caacccagct gtaagctgct ggagcagca    7740
gccccggaac aagcctctga aagctctcga caccaggttt gggaggaagc tgagcattat   7800
cagagggatt gtggagcaag agattcaagc aatggtttca aagagagaga atattgccac   7860
ccatcattta tatcaggcat gggatcctgt cccttctctg tctccggcta ctacaggtgc   7920
cctcatcagc cacgagaagc tgctgctaca gatcaacccc gagcgggagc tggggagcat   7980
gagctacaaa ctcggccagg tgtccataca ctccgtgtgg ctggggaaca gcatcacacc   8040
cctgagggag gaggaatggg acgaggaaga ggaggaggag gccgacgccc ctgcaccttc   8100
gtcaccaccc acgtctccag tcaactccag gaaacaccgg gctggagttg acatccactc   8160
ctgttcgcag tttttgcttg agttgtacag ccgctggatc ctgccgtcca gctcagccag   8220
gaggaccccg gccatcctga tcagtgaggt ggtcagatcc cttctagtgg tctcagactt   8280
gttcaccgag cgcaaccagt ttgagctgat gtatgtgacg ctgacagaac tgcgaagggt   8340
gcacccttca gaagacgaga tcctcgctca gtacctggtg cctgccacct gcaaggcagc   8400
tgccgtcctt gggatggaca aggccgtggc ggagcctgtc agccgcctgc tggagagcac   8460
gctcaggagc agccacctgc ccagcagggt tggagcccctg cacggcgtcc tctatgtgct   8520
ggagtgcgac ctgctggacg acactgccaa gcagctcatc ccggtcatca gcgactatct   8580
cctctccaac ctgaaaggga tcgcccactg cgtgaacatt cacagccagc agcacgtact   8640
ggtcatgtgt gccactgcgt tttacctcat tgagaactat cctctggacg tagggccgga   8700
attttcagca tcaataatac agatgtgtgg ggtgatgctg tctggaagtg aggagtccac   8760
```

```
cccctccatc atttaccact gtgccctcag aggcctggag cgcctcctgc tctctgagca    8820
gctctcccgc ctggatgcag aatcgctggt caagctgagt gtggacagag tgaacgtgca    8880
cagcccgcac cgggccatgg cggctctggg cctgatgctc acctgcatgt acacaggaaa    8940
ggagaaagtc agtccgggta gaacttcaga ccctaatcct gcagccccg acagcgagtc     9000
agtgattgtt gctatggagc gggtatctgt tcttttgat aggatcagga aaggcttcc      9060
ttgtgaagcc agagtggtgg ccaggatcct gccccagttt ctagacgact tcttcccacc    9120
ccaggacatc atgaacaaag tcatcggaga gtttctgtcc aaccagcagc catacccca     9180
gttcatggcc accgtggtgt ataaggtgtt tcagactctg cacagcaccg gcagtcgtc     9240
catggtccgg gactgggtca tgctgtccct ctccaacttc acgcagaggg ccccggtcgc    9300
catggccacg tggagcctct cctgcttctt tgtcagcgcg tccaccagcc cgtgggtcgc    9360
ggcgatcctc ccacatgtca tcagcaggat gggcaagctg gagcaggtgg acgtgaacct    9420
tttctgcctg gtcgccacag acttctacag acaccagata gaggaggagc tcgaccgcag    9480
ggccttccag tctgtgcttg aggtggttgc agccccagga agcccatatc accggctgct    9540
gacttgttta cgaaatgtcc acaaggtcac cacctgctga gcgccatggt gggagagact    9600
gtgaggcggc agctggggcc ggagcctttg gaagtctgcg cccttgtgcc ctgcctccac    9660
cgagccagct tggtccctat ggcttccgc acatgccgcg ggcggccagg caacgtgcgt     9720
gtctctgcca tgtggcagaa gtgctctttg tggcagtggc caggcaggga gtgtctgcag    9780
tcctggtggg gctgagcctg aggccttcca gaaagcagga gcagctgtgc tgcaccccat    9840
gtgggtgacc aggtcctttc tcctgatagt cacctgctgg ttgttgccag gttgcagctg    9900
ctcttgcatc tgggccagaa gtcctccctc ctgcaggctg gctgttggcc cctctgctgt    9960
cctgcagtag aaggtgccgt gagcaggctt tgggaacact ggcctgggtc tccctggtgg   10020
ggtgtgcatg ccacgccccg tgtctggatg cacagatgcc atggcctgtg ctgggccagt   10080
ggctgggggt gctagacacc cggcaccatt ctcccttctc tcttttcttc tcaggattta   10140
aaatttaatt atatcagtaa agagattaat tttaacgtaa ctctttctat gcccgtgtaa   10200
agtatgtgaa tcgcaaggcc tgtgctgcat gcgacagcgt ccggggtggt ggacagggcc   10260
cccggccacg ctccctctcc tgtagccact ggcatagccc tcctgagcac ccgctgacat   10320
ttccgttgta catgttcctg tttatgcatt cacaaggtga ctgggatgta gagaggcgtt   10380
agtgggcagg tggccacagc aggactgagg acaggccccc attatcctag gggtgcgctc   10440
acctgcagcc cctcctcctc gggcacagac gactgtcgtt ctccacccac cagtcaggga   10500
cagcagcctc cctgtcactc agctgagaag gccagccctc cctggctgtg agcagcctcc   10560
actgtgtcca gagacatggg cctcccactc ctgttccttg ctagccctgg ggtggcgtct   10620
gcctaggagc tggctggcag gtgttgggac ctgctgctcc atggatgcat gccctaagag   10680
tgtcactgag ctgtgttttg tctgagcctc tctcggtcaa cagcaaagct tggtgtcttg   10740
gcactgttag tgacagagcc cagcatccct tctgccccg ttccagctga catcttgcac    10800
ggtgacccct tttagtcagg agagtgcaga tctgtgctca tcggagactg ccccacggcc   10860
ctgtcagagc cgccactcct atccccaggc caggtccctg gaccagcctc ctgtttgcag   10920
gcccagagga gccaagtcat taaaatggaa gtggattctg gatggccggg ctgctgctga   10980
tgtaggagct ggatttggga gctctgcttg ccgactggct gtgagacgag gcaggggctc   11040
tgcttcctca gccctagagg cgagccaggc aaggttggcg actgtcatgt ggcttggttt   11100
```

```
ggtcatgccc gtcgatgttt tgggtattga atgtggtaag tggaggaaat gttggaactc    11160
tgtgcaggtg ctgccttgag accccccaagc ttccacctgt ccctctccta tgtggcagct    11220
ggggagcagc tgagatgtgg acttgtatgc tgcccacata cgtgaggggg agctgaaagg    11280
gagcccctcc tctgagcagc ctctgccagg cctgtatgag gcttttccca ccagctccca    11340
acagaggcct cccccagcca ggaccacctc gtcctcgtgg cggggcagca ggagcggtag    11400
aaaggggtcc gatgtttgag gaggcccttta agggaagcta ctgaattata acacgtaaga    11460
aaatcaccat tccgtattgg ttgggggctc ctgtttctca tcctagcttt ttcctggaaa    11520
gcccgctaga aggtttggga acgaggggaa agttctcaga actgttggct gctccccacc    11580
cgcctcccgc ctcccccgca ggttatgtca gcagctctga cacagcagta tcacaggcca    11640
gatgttgttc ctggctagat gtttacattt gtaagaaata acactgtgaa tgtaaaacag    11700
agccattccc ttggaatgca tatcgctggg ctcaacatag agtttgtctt cctcttgttt    11760
acgacgtgat ctaaaccagt ccttagcaag gggctcagaa caccccgctc tggcagtagg    11820
tgtcccccac ccccaaagac ctgcctgtgt gctccggaga tgaatatgag ctcattagta    11880
aaaatgactt cacccacgca tatacataaa gtatccatgc atgtgcatat agacacatct    11940
ataattttac acacacacct ctcaagacgg agatgcatgg cctctaagag tgcccgtgtc    12000
ggttcttcct ggaagttgac tttccttaga cccgccaggt caagttagcc gcgtgacgga    12060
catccaggcg tgggacgtgg tcagggcagg gctcattcat tgcccactag gatcccactg    12120
gcgaagatgg tctccatatc agctctctgc agaagggagg aagactttat catgttccta    12180
aaaatctgtg gcaagcaccc atcgtattat ccaaatttttg ttgcaaatgt gattaatttg    12240
gttgtcaagt tttgggggtg ggctgtgggg agattgcttt tgttttcctg ctggtaatat    12300
cgggaaagat tttaatgaaa ccagggtaga attgtttggc aatgcactga agcgtgtttc    12360
tttcccaaaa tgtgcctccc ttccgctgcg ggcccagctg agtctatgta ggtgatgttt    12420
ccagctgcca agtgctcttt gttactgtcc accctcattt ctgccagcgc atgtgtcctt    12480
tcaaggggaa aatgtgaagc tgaacccccct ccagacaccc agaatgtagc atctgagaag    12540
gccctgtgcc ctaaaggaca ccctcgcccc ccatcttcat ggaggggtc atttcagagc    12600 cctcggagcc aatgaacagc tcctcctctt ggagctgaga tgagccccac gtggagctcg    12660
ggacggatag tagacagcaa taactcggtg tgtggccgcc tggcaggtgg aacttcctcc    12720
cgttgcgggg tggagtgagg ttagttctgt gtgtctggtg ggtggagtca ggcttctctt    12780
gctacctgtg agcatccttc ccagcagaca tcctcatcgg gctttgtccc tcccccgctt    12840
cctccctctg cggggaggac ccgggaccac agctgctggc cagggtagac ttggagctgt    12900
cctccagagg ggtcacgtgt aggagtgaga agaaggaaga tcttgagagc tgctgaggga    12960
ccttggagag ctcaggatgg ctcagacgag gacactcgct tgccgggcct gggcctcctg    13020
ggaaggaggg agctgctcag aatgccgcat gacaactgaa ggcaacctgg aaggttcagg    13080
ggccgctctt cccccatgtg cctgtcacgc tctggtgcag tcaaaggaac gccttcccct    13140
cagttgtttc taagagcaga gtctcccgct gcaatctggg tggtaactgc cagccttgga    13200
ggatcgtggc caacgtggac ctgcctacgg agggtgggct ctgacccaag tggggcctcc    13260
ttgtccaggt ctcactgctt tgcaccgtgg tcagagggac tgtcagctga gcttgagctc    13320
ccctggagcc agcagggctg tgatgggcga gtcccggagc cccacccaga cctgaatgct    13380
tctgagagca aagggaagga ctgacgagag atgtatattt aatttttttaa ctgctgcaaa    13440 cattgtacat ccaaattaaa ggaaaaaaat ggaaaccatc a                         13481
```

<210> SEQ ID NO 2
<211> LENGTH: 172001
<212> TYPE: DNA
<213> ORGANISM: Homo sapiens

<400> SEQUENCE: 2

```
cctgcagggg cctctccagc tcactggggg tggggtgggg gtcacacttg gggtcctcag      60
gtcgtgccga ccacgcgcat tctctgcgct ctgcgcagga gctcgcccac cctctccccg     120
tgcagagagc cccgcagctg ctccccgca gggctgtccg ggtgagtatg gctctggcca      180
cgggccagtg tggcgggagg gcaaacccca aggccacctc ggctcagagt ccacggccgg     240
ctgtcgcccc gctccaggcg tcggcggggg atcctttccg catgggcctg cgcccgcgct     300
cggcgccccc tccacggccc cgcccgtcc atgggccccgt ccttcatggg cgagcccctc    360
catggccctg cccctccgcg ccccacccct ccctcgcccc acctctcacc ttcctgcccc     420
gcccccagcc tccccaaccc tcaccggcca gtcccctccc ctatcccgtc cgcccctcag     480
ccgccccgcc cctcagccgg cctgcctaat gtcccccgtcc ccagcatcgc cccgccccgc    540
ccccgtctcg ccccgcccct caggcggcct ccctgctgtg ccccgccccg gcctcgccac     600
gccccctacct caccacgccc cccgcatcgc cacgccccc gcatcgccac gcctcccctta    660
ccatgcagtc ccgccccgtc ccttcctcgt cccgcctcgc cgcgacactt cacacacagc     720
ttcgcctcac cccattacag tctcaccacg ccccgtcccc tctccgttga gccccgcgcc     780
ttcgcccggg tggggcgctg cgctgtcagc ggccttgctg tgtgaggcag aacctgcggg     840
ggcaggggcg ggctggttcc ctggccagcc attggcagag tccgcaggct agggctgtca     900
atcatgctgg ccggcgtggc cccgcctccg ccggcgcggc cccgcctccg ccggcgcagc     960
gtctgggacg caaggcgccg tgggggctgc cgggacgggt ccaagatgga cggccgctca   1020
ggttctgctt ttacctgcgg cccagagccc cattcattgc cccggtgctg agcggcgccg   1080
cgagtcggcc cgaggcctcc ggggactgcc gtgccgggcg ggagaccgcc atggcgaccc   1140
tggaaaagct gatgaaggcc ttcgagtccc tcaagtcctt ccagcagcag cagcagcagc   1200
agcagcagca gcagcagcag cagcagcagc agcagcagca acagccgcca ccgccgccgc   1260
cgccgccgcc gcctcctcag cttcctcagc cgccgccgca ggcacagccg ctgctgcctc   1320
agccgcagcc gccccgccg ccgccccgc cgccaccccgg cccggctgtg gctgaggagc   1380
cgctgcaccg accgtgagtt tgggcccgct gcagctccct gtcccggcgg gtcccaggct   1440
acggcgggga tggcggtaac cctgcagcct gcgggccggc gacacgaacc cccggccccg   1500
cagagacaga gtgacccagc aacccagagc ccatgaggga cacccgcccc ctcctggggc   1560
gaggccttcc cccacttcag cccgctccc tcacttgggt cttcccttgt cctctcgcga   1620
ggggaggcag agccttgttg gggcctgtcc tgaattcacc gaggggagtc acggcctcag   1680
ccctctcgcc cttcgcagga tgcgaagagt tggggcgaga acttgtttct ttttatttgc   1740
gagaaaccag ggcgggggtt cttttaactg cgttgtgaag agaacttgga ggagccgaga   1800
tttgctcagt gccacttccc tcttctagtc tgagagggaa gagggctggg ggcgcgggac   1860
acttcgagag gaggcgggt ttggagctgg agagatgtgg gggcagtgga tgacataatg   1920
cttttaggac gcctcggcgg gagtggcggg gcagggggg ggcggggagt gagggcgcgt   1980
ccaatgggag atttctttt ctagtggcac ttaaaacagc ctgagatttg aggctcttcc   2040
tacattgtca ggacatttca tttagttcat gatcacggtg gtagtaacac gatttttaagc  2100
```

```
accacctaag agatctgctc atctaagcct aagttggtct gcaggcgttt gaatgagttg    2160
tggttgccaa gtaaagtggt gaacttacgt ggtgattaat gaaattatct taaatattag    2220
gaagagttga ttgaagtttt ttgcctatgt gtgttgggaa taaaaccaac acgttgctga    2280
tggggaggtt aattgccgag ggatgaatga ggtgtacatt ttaccagtat tccagtcagg    2340
cttgccagaa tacgggggt  ccgcagactc cgtgggcatc tcagatgtgc cagtgaaagg    2400
gtttctgttt gcttcattgc tgacagcttg ttacttttg  gaagctaggg gtttctgttg    2460
cttgttcttg gggagaattt ttgaaacagg aaaagagaga ccattaaaac atctagcgga    2520
accccaggac tttccctgga agtctgtgtg tcgagtgtac agtaggagtt aggaagtact    2580
ctggtgcagt tcaggccttt ctcttacctc tcagtattct atttccgatc tggatgtgtc    2640
ccagatggca tttggtaaga atatctctgt taagactgat taattttag  taatatttct    2700 tgttctttgt ttctgttatg atccttgtct cgtcttcaaa gtttaattag aaaatgattc    2760
ggagagcagt gttagcttat ttgttggaat aaaatttagg aataaattat tctaaaggat    2820
ggaaaaactt tttggatatt tggagaaatt ttaaaacaat ttggcttatc tcttcagtaa    2880
gtaatttctc atccagaaat ttactgtagt gcttttctag gaggtaggtg tcataaaagt    2940
tcacacattg catgtatctt gtgtaaacac taaacagggc tcctgatggg aaggaagacc    3000
tttctgctgg gctgcttcag acacttgatc attctaaaaa tatgccttct ctttcttatg    3060
ctgatttgac agaacctgca tttgcttatc ttcaaaatat gggtatcaag aaatttcctt    3120
tgctgccttg acaaggaga  tagattttgt ttcattactt taaggtaata tatgattacc    3180
ttatttaaaa aatttaatca ggactggcaa ggtggcttac acctttaatc cgagcacttt    3240
gggaggccta ggtggacgaa tcacctgagg tcaggagttt gagaccagcc tggctaacat    3300
ggtgaaaccc tgtctctact aaaaatacaa aaattagctg gtcatggtgg cacgtgcctg    3360
taatccaagc tacctgggag gctgaggcag gaaaatcgct tgaacccggg aggcagagtc    3420
tgcagtgagt tgagatcacg ccactgcact ccagcctggg tgacagagcg agactctatc    3480
tcaaaaaaaa tttttttaa  tgtattattt ttgcataagt aatacattga catgatacaa    3540
attctgtaat tacaaaaggg caataattaa aatatcttcc ttccacccct ttcctctgag    3600
tacctaactt tgtccccaag aacaagcact atttcagttc ctcatgtatc ctgccagata    3660
taacctgttc atattgtaag atagatttaa aatgctctaa aaacaaaagt agtttagaat    3720
aatatatatc tatatatttt ttgagatgta gtctcacatt gtcacccagg ctggagtgca    3780
gtgatacaat ctcggctcac tgcagtctct gcctcccagg ttcaaatgct tctcctgcct    3840
cagccttctg agtagctggg attacaggcg cccaccacca tgtccagcta ttttttgtat    3900
ttttagtaga gatgggggttt caccatgttg gccaggctgg tcttgaactc ctgaccttgt    3960
gatctgtcca cctcggcctc ccaaagtgct gggattacag gtgtgagcca ccatgcctgg    4020
ctagaataat aactttttaaa ggttcttagc atgctctgaa atcaactgca ttaggtttat    4080 ttatagttttt atagttattt taaataaaat gcatatttgt catatttctc tgtatttgc     4140 tgttgagaaa ggaggtattc actaattttg agtaacaaac actgctcaca agtttggat     4200 tttggcagtt ctgttcacgt gcttcagcca aaaaatcctc ttctcaaagt aagattgatg    4260
aaagcaattt agaaagtatc tgttctgttt ttatggctct tgctctttgg tgtggaactg    4320
tggtgtcacg ccatgcatgg gcctcagttt atgagtgttt gtgctctgct cagcatacag    4380
gatgcaggag ttccttatgg ggctggctgc aggctcagca aatctagcat gcttgggagg    4440
gtcctcacag taattaggag gcaattaata cttgcttctg gcagtttctt attctccttc    4500
```

```
agattcctat ctggtgtttc cctgacttta ttcattcatc agtaaatatt tactaaacat    4560
gtactatgtg cctggcactg ttataggtgc agggctcagc agtgagcaga caaagctctg    4620
ccctcgtgaa gctttcattc taatgaagga catagacagt aagcaagata gataagtaaa    4680
atatacagta cgttaatacg tggaggaact tcaaagcagg gaaggggata gggaaatgtc    4740
agggttaatc gagtgttaac ttattttat ttttaaaaaa attgttaagg ctttccagc     4800 aaacccaga aagcctgcta gacaaattcc aaaagagctg tagcactaag tgttgacatt    4860
tttattttat tttgttttgt tttgttttt ttgagacagt tcttgctcta tcagccaggc    4920
tggagtgcac tagtgtgatc ttggctcact gcaacctctg cctcttgggt tcaagtgatt    4980
ctcatgcctc agcctcctgt ttagctggga ttatagacat gcactgccat gcctgggtaa    5040 ttttttttt ttcccccgag acggagtctt gctctgtcgc ccaggctgga gtgcagtggc    5100
gcgatctcag ctcactgcaa gctccgcttc ccgagttcac gccattctcc tgcctcagtc    5160
tcccaagtag ctgggactac aggcgcctgc caccacgtcc agctaatttt tttgtatttt    5220
taatagagac ggggtttcac cgtgttagcc aggatgatct tgatctcctg acctcgtcat    5280
ccgccgacct tgtgatccgc ccacctcggc ctcccaaagt gctgggatta caggcatgag    5340
ccactgtgcc cggccacgcc tgggtaattt ttgtatttttt agtagagatg gggttttgcc    5400
atgatgagca ggctggtctc gaactcccgg cctcatgtga tctgcctgcc ttggcctccc    5460
aaagtgctag gattacaggc atgagccacc atacctggcc agtgttgata ttttaaatac    5520
ggtgttcagg gaaggtccac tgagaagaca gcttttttt tttttttttt tggggttggg    5580
gggcaaggtc ttgctctta acccaggctg gaatgcagta tcactatcgt agctcacttc    5640
agccttgaac tcctgggctc aagtgatcct cccacctcaa cctcacaatg tgttgggact    5700
ataggtgtga gccatcacac ctggccagat gatggctttt gagtaaagac ctcaagcgag    5760
ttaagagtct agtgtaaggg tgtatgaagt agtggtattc cagatggggg gaacaggtcc    5820
aaaatcttcc tgtttcagga atagcaagga tgtcatttta gttgggtgaa ttgagtgagg    5880
gggacatttg tagtaagaag taaggtccaa gaggtcaagg gagtgccata tcagaccaat    5940
actacttgcc ttgtagatgg aataaagata ttggcattta tgtgagtgag atgggatgtc    6000
actggaggat tagagcagag gagtagcatg atctgaattt caatcttaag tgaactctgg    6060
ctgacaacag agtgaagggg aacaccggca aaagcagaaa ccagttagga agccactgca    6120
gtgctcagat aagcatggtg ggttctgtca gggtaccggc tgtcggctgt gggcagtgtg    6180
aggaatgact gactggattt tgaatgcgga accaactgca cttgttgaac tctgctaagt    6240
ataacaattt agcagtagct tgcgttatca ggtttgtatt cagctgcaag taacagaaaa    6300
tcctgctgca atagcttaaa ctggtaacaa gcaagagctt atcagaagac aaaaataagt    6360
ctggggaaat tcaacaataa gttaaggaac ccaggctctt tctttttttt ttttttgaaa    6420
cggagtttcg ctcttgtcac ccgggctgga gtgcaatgat gtgatctcag ctcactaaaa    6480
cctctacctc ctgggttcaa gtgattcttc tgcctcagcc tcccaagtaa ctgggattac    6540
aggcgtatac caccatgccc agctaatttt tgtgtttta gtagagatgg ggtttcacca    6600
tgttggccag gctggtctcg aacttctgac ctcaggtgat ccactcgcct cagcctgcca    6660
aagtgctggg attacaggtt tgggccactg cacccggtca gaacccaggc tctttcttat    6720
acttaccttg caaaccttg ttctcatttt ttccctttgt attttattg ttgaattgta    6780 atagttcttt atatattctg gatactggat tcttatcaga tagatgattt gtaaaaactc    6840
```

```
tcccttcctt tggattgtct ttttactttc ttgatagtgt cttttgaagt gtaaaagttt    6900
ttaattttga tgaagtcgag tttatctatt ttgtctttgg ttgctgtgct tcaagtgtca    6960
tatctaagaa atcattgtct aatccaaagt caaaaaggtt tactcctatg ttttcttcta    7020
agaattttag agttttacat ttaagtctga tccattttga gttaattttt atatatggtt    7080
caggtagaag tccaacttta ttcttttcca tgtggttatt cagttgtccc agcactgttt    7140
gttgaagaga ctattctttc cccatggaat tatcttagta cccttgttga aaattaatcg    7200
tccttaattg tataaattta tttctagact gtcagttcta cctgttggtc tttatgtcga    7260
tcctgtgcca gtaccataca gtcttgatta ctgaagtttg tgtcacagtt taaattcatg    7320
aaatgtgagt tctccaactt tgttcctttt caagattgat ttggccatgc tgggtccctt    7380
gcatttccgt acgaattgta ggatcagctt gtcagtttca acaaagaagc caagtaggat    7440
tctgagaggg attgtgttga atctgtagat caacttgggg agtattcgca tcttaacaat    7500
attgtcttcc acctatgaac atgggcaaac tttgtgtaaa tggtcagatt gtaagtattt    7560
cgggctgtgt gggcacagtg tctctgtcac agctacgcgg ctctgccatt gtagcatgaa    7620
agtagccata agcaatatgt atgagtgtct gtgttccaat agaattttat taatgacaag    7680
gaagtttgaa tttcatataa ttttcacctg tcatgagata gtatttgatt attttggtca    7740
accatttaaa aatgtaaaaa catttcttag cttgtgaact agccaaaaat atgcaggtta    7800
tagttttccc actcctaggt taaaatatga taggaccaca tttggaaagc atttcttttt    7860
tttttttttt ttttttttt gagacggagt ttcactcttg ttgcccaggc tggagtgcag    7920
tggcgcgatc tcggctcact gcaacctctg cctcccaggt tcaagacatt ctcctgcacg    7980
gcctccctag tagctgggat tacaggcatg cgccaccaca cccagctaat tttgtatttt    8040
tagtagagac ggggtttctc catgttggtc aggctggtct tgaactcctg acctcaggtg    8100
atccacccgc ctcagcctcc caaagtgctg ggattacagg gtgtgagcca ccacaccctg    8160
ctggaaagca tttctttttt ggctgttttt gttttttttt taaactagtt ttgaaaatta    8220
taaaagttac acatatacat tataaaaata tcttcaagca gcacagatga aaaacaaagc    8280
ccttcttgca agtctgtcat cttttgtcta acttcctaaga acaaaagtgt tcttgtgtc    8340 ttcttcccag atttttaatat gcatatacaa gcatttaaat gtgtcatttt ttgtttgctt    8400
gactgagatc acattacata tgtatttttt tacttaacaa tgtgtcatag atattgttcc    8460
atagcagtac ctgtaattct tattaattgc tatgtaatat tttagaattt cttttttaaaa    8520 gaggactttt ggagatgtaa aggcaaaggt ctcacatttt tgtggctgta gaatgtgctg    8580
gtgacatatt ctctctacct tgagaagtcc ccatccccat cacctccatt tcctgtaaat    8640
aagtcaacca cttgataaac tacctttgaa tggatccaca ctcaaaacat ttagtcttat    8700
tcagacaaca aggaggaaaa ataaaatacc ttataaagca ctgtttaata ttgtattaaa    8760
ttggatcaat ttgggggcta gaatgtatgt tagagacatg atatgtccat aggtccttgc    8820
tatcacagtg aggtctcagg gacagtcgtt tggtatcatt tgggatctca taagcagact    8880
ctctctgctt gacctgacaa atcagagtct gtgttttaac aggttcagtg agtgacttac    8940
atgcacattg gagtttggga agctccactg taggtgctta gaccttacct ttgttgttgc    9000
taataacaat gcaagcattt gggaggaaga cctgtgttgc tcatatgtgt ccaggtgtag    9060
ctgaggtggc cttgcttatc tgctgtaggg ccgttgagca tttctgtagc tgtgatgagt    9120
gagctgaggt gagcctgcgg agagctccca gccattggta gtgggactcg cttagatgaa    9180
ctggaaggac ccttcatct gagcagccac tatggagaaa aacaaccgaa tgaggggaga    9240
```

```
gacaatgtgc aattttattt agggcacaaa ggagagctgt ggttagaagg tgacatttga   9300
gtggaaaggg ggcaagccat gtgtatagcg ggagaagaga ggtccaggca gagttaacag   9360
aaggcagaaa tgcttccat gtttgagaac cagtaaggag gccagtggct gaagtaaggt   9420
gaagggcaga ataaggatg aggctgcgag agatgagagg ttagagacga gcgtcttgtg   9480
caccaagata agcttgtgtg gtcaaaacaa gtagtttaat ttatgttttt aaaagatcat   9540
tttggctggg cacaatggtt catgcctgta ataccagtag tttgagacgg tgtggtggga   9600
ggattgcctg aggccagacg accagcatag ccaacatagc agcacctata aggtctctac   9660
aaaaaacttt aaaaaattag ctgggcatag tggtgtgtgc ctgtagtccc agctactcag   9720
gaggctgagg aggctggagg attgcttgag tccaggagtt tgaggctgca gtgagctatg   9780
attatgccac tacactacaa cctgggcaag agagtgagac cctgtctcta aatatacaca   9840
cacacacaca cacacacaca cacacacaca cacacacaca cacacacaca catatatatg   9900
tatatatatg catttagatg aaaagatcac tttgacaata ccacatgctg gtgaggattt   9960
agaaaaacta ggtcacttat tgctggtggg aatataatat agtacggcca ctctggaaaa  10020
cagtttggca gtttgtcata aaactgaaca taccgttagt atacagccca gcagcaacta  10080
caatcctggg cattaatcct agagaaatga aaccttaatg ttcacataaa aacctatact  10140
caagtatgca tagcagcttt acccataata tctaagaact ggaatcagct cagatgtcct  10200
tcaacaggtg aatggttaaa ctactcagta ataaaaagga atgagctact gatagcatgc  10260
aacagtttag gtgaagttat gctaatgaaa aaagccaatc ccaaaaggtt atacatactg  10320
tatgattcta tgttttttg caatggcaca gttttaggga tggagaatag attagtggtt  10380 gcctgggtt agagatgggg tagtagagta ggttagtggt ggcagaggag agaaaagaga  10440
gggaggtgaa tgtggttata aaaggacaac acagggaat acttgtaatg gaaatgctt  10500 gtcttttt tttttttttt tttttggcg acagagtctt gctctgttgc ccaggctgga  10560
gtgcagtggc atgatctttt ctcactgcaa cctctgcctc ctgggttcaa gtgatacttg  10620
tgtctcagtc tcccatgttc agagtgaaac aaaccagagg taatgttcat ccaaataatc  10680
caacacacat gacattaaaa catcaagatc aggtcggacg tggtggctca tgcctgtaat  10740
cccagcactt tgggaggcc aaggtgggca gatcacttga ggtcaggagt tcgagaccag  10800
ccgggccaac atgatgaaac ccatcttga ctaaaaatac aaaaattagc cgggcatggt  10860
ggtgtgcacc tgtagtccca gctacttggg aggctgaggc aagagaactg cttgaacccg  10920
aggggcagag gttgcagtga gctgagagtg cgccattgca cttcagcctg tgtgacagag  10980
taagactcca tctccaaaaa aaaaaaacca agatcaatta aaatacagca ttactgggcc  11040
gggtgtggtg gctcacacct gtaatcccag cactttggga ggccgagatg gcagatcac  11100 gaggtcagga gatccagacc atcccggcta acacggtgaa accccgtctc tactaaaaaa  11160
tacaaaaaat tagccgggta tagtggtggg tgcctgtagt cccagctact ggggaggctg  11220
aagcaggaga atggtgtgaa cccgggaggc agagctggca gtgagctgag atcgcgccac  11280
tgcactccag cctgggcgac agagcaagac tccgtctcgg gggaaaaaaa aaaataaata  11340
aatagaatgc tgtagtgtcc ttgagtttac atgcccctcc ttacgcttgt gtgcccgtgc  11400
agattgcttg attacacaat tagaggaggc tggcggagga ttgttttaat ttttttttt  11460 ttgagacagt ctggctctgt tccccaggct agagtgcaat ggcgcaatct tggtgcactg  11520
caacctctgc ctcctgggtt caagcagttc ttctgccgca gcctcccgag tagctgggat  11580
```

```
tataggcgcc cgccaccacg cccaactatt ttttgtattt ttagtagagc agcgtttcac   11640
catgctggcc aggctggtct cgaactcctg acctcagatg atctgctgcc ccagcctccc   11700
aaagtgctgg gattacaggc gtgagccaca cctggccgtt tgttttaatt ttgaaggtga   11760
agtgaaagtg actacattta ccaaaagtga ttgaaaagcc aggactgttc ttaccctgtt   11820
tttccagttc ttgctcagag caaggtggtt tcttttttcac ttaatcacca tacttacttt   11880
tcatgtagaa caagtcagtt tgagttatca gttcatcatc ttaactaaat tccatggggg   11940
aaggaattag ttttagtttc ttaaacttcc aggtttgctt attggacaaa atgagatagc   12000
aaggcagtgt ttttaagtta gattttttat ttctttggta atacaatttt ctcagaaact   12060
tagtagtctt ttagtttagt tgttttagt tggtcctatg ttttggatca cccctctcta   12120
ctttattttg atagtgccaa ctgtgaagac atctgaagcc ataggtttgg atgggaagga   12180 ggcatctta gcctgatcat cttcgccagg ctgtttatct ccttttgctt ggctgagaag   12240
tcttaatagg aggcttattc ccagctattt ggggacatag aagcagttag ccattgctta   12300
tattttactg aggtctgtgt ggtatgttga ttgtagtcag ttaacgattt tgagaactga   12360
aggcagcctg gtatatatag agtaggtatt agactgtgtt tcttctaatt gaatttccca   12420
tctcttgtaa tctatgccat catcttctgt actgctgaga aagaaagaaa gtttctaatc   12480
aaactatacc actggttgta agatgcagtt tggctttagt gatgttaaca catgattcaa   12540
acgtgaaatt gattgagtat tggtgaaata cagaggagat ttaaagccag aagacctggg   12600
tttaaatgct ggctgtatga cttcatatct gtgtgatctt gggcatgtca tggttggcac   12660
ttcaatttct tctctctata atgggggaag tgaggccagt catggtggct catacctata   12720
atcccagtgc tttgggaggc caagatggga agatcgcttg aggccaggag tttgagcaat   12780
tgggcaacat cgtgaggccc cgtctctaca aaatattttg aaaaaattag ccaggcccag   12840
tggtgcgtgc ctgtggtccg cgccactcag gaggctgaga cgggaggatc ctttcagcct   12900
aggagtttaa ggctaaagtg agccatgatt gtgctatcgt actccagcct gggcagcaga   12960
gcaagatcct gactctaaaa aaaagtaaaa taaagtaaaa tgggggaaat gaactgcttt   13020
agtaacatca tctgtttttt ctgtgagcag cgtagcttga cagccattgg tgaactcgtg   13080
ccctgtgctt ccctgtccag atccccattc tgcccgcaac atggagtata acggtttatt   13140
catagtagtc gagaaacact cactgaatga atgaatgagg tgtagaacta agtggagtgg   13200
gtaattcaac acatattaat ttccttcttt tttttatttt tagaaagaaa gaactttcag   13260
ctaccaagaa agaccgtgtg aatcattgtc tgacaatatg tgaaaacata gtggcacagt   13320
ctgtcaggta attgcacttt gaactgtcta gagaaaataa gaactttgta tatttttcagt   13380 cttaatgggc tagaatattc tttgtgtccc agctatttta aatggattca gaaatccatt   13440
taagatgaag aaggacccctt tcccatatt tctggctata tacaaggata tccagacact   13500
gaaatgaata atgttccctt tttgtaatct tttatgcaaa aattaaaacc attatggtaa   13560
ttgaacaaca tgtttatgtt tagttaacac ccttagcaac tatagttatt ttaaaaccat   13620
ctatggtttg atattttgc atttgttgca atagtaggaa cagcacaaga cagttcagtt   13680
tgtctctctt atttgctttt tcttggcagt ttgctgtcct attgtacctc tgctcctagc   13740
agtggctgga gcccactcct ctgtgcttcg ggattagtgg ggatcgtggg gcattgactg   13800
taggtcagct ttccttgctt gatctttctc actgggatga actagcagca ccttcttttg   13860
tagctgcttt gcttttgact atctttctga ccgttgttcc tagtagctgt agatggtaaa   13920
tatatttagg cctgtttcca atggctcagt aggagacata ttcacctatg atatctgaat   13980
```

```
tctgttaccc acatgggcat gcgtgaaata gttgccttgc cttactttcc cttggaataa   14040
ataattcatg ttattctcct ggtagaagct agaaaaagcc tttatagtca gtcagaaaaa   14100
aattttttaga caaataatct tgattttagt actgacaaaa acgtgtggtg attcttttt   14160
taatttttt ttgagacgga gtttcactct tgttgcccag gctggagtgc aatggcgtga   14220
tctcggctca ctgcaacctc tgcctcctgg gttcaagtga ttctcctgcc tcagcctccc   14280
aagtagctgg agttacaggc atgtgctact gtgcccagct aattttgtat ttttagtaga   14340
gatgttggtc aggctgatct cgaactccca accttaggtg atctgcccgc ctcagcctcc   14400
caaagtgctg ggattacagg cgtgagccag gcgcccggt gattcatttg ttttttcaaa   14460
aaatttcctc ttggccattg cttttcactt ttgtttttt tttttttttg agacggagtc   14520
acgatctgtc acccaggctg gagtgcagtg gcatgatctt ggcttactgc aagctctgcc   14580
tcccaggttc acgccattct cctgcttcag cctggcgagt agctgggact acaggtgctc   14640
gccaccacac ccggctaatt ttttgtattt ttagtagaga tggggttca ccgtggtctt   14700
gatctcctga cctcatgacc cgctcaactc agcctcccaa agtgctggga ttacaggcgt   14760
gagccaccgc gcccggccct ctcttgtctt tttattgtgg taaatgcac ataaaattga   14820
ctgtcttaac cattttagg ggtacagttc agtatatata ttcgtaatgt tgtacagcca   14880
tcactgccat ctacttcata agttttctt ctgtcaaaac tgaacatctg tcttcattaa   14940
actccctatc atccattctt tcctgtagtc cctttctact ttctgtctgt atgagtgtaa   15000
ctgctctgga gacctcatgt aagtggattc ctacaggatt tgtgttttt ttttggtgat   15060
ctgcttattt ttaatgcctc tgtgcatttg tattatatac tttcaaagtg atttcacaaa   15120
accgtttcat tttaggttaa ctcatttctg ttgtttgtga aatactgtgt atgattctgt   15180
tctgtttctg tctaatttgt ggaaatgttg tgggaagaaa atgaaataac aaatgagcat   15240
atgtcctgaa aataaaaata taaaaattct aagttagcat gctattgtag aatacaacgc   15300
tatgataaaa gtaggaaaaa aaaaggtttg aattctatct ctgctacctg tgtaagctgg   15360
gtgactttag ataagctgta acgtgtttga gccttactgg ctcattttg aaatgtaatc   15420
cctagttaca cagttcttgt gggatcagat ggtacatgtg aaacactgtg aaaaagcaac   15480
tgcatagata tgttcattag ccacctgagc gggaagcgta tcccattgcg atgcccatca   15540
tccaaagcta tatgttatct ttactttttt tttttgaga cagagtcttg ctctgttgcc   15600
caggctagag tgcagtggtg caatctcagc tcactgcaag ctccacctcc cgggttcacg   15660
ctattctcct gccccagcct cccaagtagc tgggactaca gcacccgcc accatgcctg   15720
gctaaattt tgtatttta gtagagatgg ggtttcaccg tgttagccag gatggtcttg   15780
atctcctgac ctcgtgatcc gcccgcctcg gcctcccaaa gtgctgggat tacaggcgtg   15840
agccactgcc cctggccatc tttactttt ttgtgaaatg actttaaata cttggcaaac   15900
atttggtcat tgttcatctg atctccacca tccaggtctc agagaacata atttctctct   15960
gaaagcttat tgacccagga aataagatct ctttcaatct gagtgcgtca ggctttattc   16020
ttgtcatttt gtcttttgat aattttcaaa tggaattcat ggaatgttgg cttatattca   16080
tatattagta aagtatgttg agacatctta agattgattt gtggttctat atgccatatt   16140
aaatcaaaat aatagctgtt aatggttttc acattagtct gtctcttgtt tttatggagt   16200
aatgctgaga gttcattatg cttgttctac agaagagcat gttaaaagga gttttttggag   16260
tcagagaggt tattcttggt ttcataggat acactctata cttttttaggg atttcagagt   16320
```

```
atatagctga aggtgatatt ttatgtaaat atgttttatg gaaacttatt gctcatcgct  16380
gtttcctgtt aactctccta aaatataatt aaacttttgg aacttttta tagcttttgt    16440 gctagactaa tttttgtctc taatgaggtt atataaatgg cagcttctga cgttttcaat  16500
gtaggaagtc atttaaaact tcatgtatat tgtgaaaatg tagtctgctt taagctctct  16560
aaagtggtct aagttactgg ttcctaagta tggatgagca tcaaaatcat ctggaaaatt  16620
tgttaaaaat acagtaatga aggcacctca ctgtccttt tcccaaacat acttctgcat   16680
tctgtttgag taggtaggga ctacacattt ttcacaagta tcctcttggg aatacccagg  16740
aatgcttact tgagcaacct cttactaata tgtaccttga taaggtggct aggtaaacat  16800
aaatatacaa aaatccatag atctcccata tattagcata aatcagctag aaaatataac  16860
gtttaaagat ctagttcaca gtagcaccaa tatatcgaac tctaaggaat cgataaatat  16920
gcaaaaactt tataaaaact tctgttaatg tttctgaaag atataggtga ccactttcta  16980
gataggaaga ttttatatta ctaagttgaa ttttctctaa attaacacag aaatttaaaa  17040
taatcttgat caaaattcta gtagaggtat ttttgaactt gttcactgca agaataaata  17100
cataattgca aagaatatct caaaatcatc accaggcctg gtgtggtggc ccatgcctgt  17160
aatcccagca ctttgggagg ctgaggcagg cagatcacct gaggtcaaga gtttgagacc  17220
agctggacca gtgcggtgaa acactgcctc tactaaaaat acaaaaatta gctgggtgtg  17280
gtggtgcatg cctgtagtcc cagctacttg ggaggctgag gcaggagaat tgcttgaacc  17340
caggaggtac aggttgcggt gagcctagat cgcaccactg cattccagcc tgggcgacaa  17400
gagcaaaatt ctgtctcaag aaaaaagaga aaaagaaaa agaaatcaac actaatatgg   17460
tgagacttaa tgtatgtgac attaaaatag tgattggatg ttaaaacagg tatagaacag  17520
aaagaagagt gtatgtgtgt atctgtatga atttatgatg ggtgtaacat atatgtatta  17580
gggaaatgag ggaaatgata catttctctg actttgggag aacattatat ctctacctca  17640
tattgcaaac aaacataaag ttcagattaa ttacctaaat gtgaaaaaat gaaataattt  17700 cttaaaaaa tgtaatctta gtttgaggaa ggttaacatt ataaggaaa aaactgtttt    17760 gagtggaata tagttcaata tgtcaaaatc caccttcaac aaaattgaaa gtaaattgaa  17820
cttggggaaa gtattgacag catatagatc aaaggttact agcctgtgta aagagcagtt  17880
ataaatatcg ttaagaaaaa cactgtcgac ctgtcggcac cttgttctcc gactcccagc  17940
ctccagaact gtgacgagta agtgcttatt gtttaaacca cccagtctgt atgtggtatt  18000
ttgttataga aactcaagct gattaggaca ctagtaatca gtagactgaa actgaaacaa  18060
aaataagaac ctttttacc tgtcaaattg gcaaacatta agaatattca gattttttgtc  18120 agaggtgata caaccttcta agaaggcaat ttgggaaaat ataaagcttt agattattat  18180
atgtctgacc tagcagtttt acctctaggg tgcttacccc taggaaagtg tgtaatgata  18240
ttggtgcagt gcccttcatc ccattagaaa attaaaaata accttaatgg cctaccacta  18300 aaagggggatt gaaaatttaa gatatattta tttatgtgtt tattgagatg gagtcttgca  18360
ctgtccgcct gggccagagt gcaatggtgc gatctcggct cactgcaacc tctgcttccc  18420
gggttcatgt gattctcctg cctcagcctc ctgagtagct gggattacag gctcacacca  18480
ccgcacccgg ctaatttttt gtattttag tagagatggg gtttcactgt gttggccaga   18540
ctggtctcga actcctgacc tcatgatccg cgccctcgg cctcccagtg ttgggattac    18600
aggtgtgagc cactgcgcct ggccagatac atttatacaa gagaatgtta gttaacattc  18660
atagatattt atattttgtt tactttttat taaaaaaatt ttttttagag acaggatctt  18720
```

```
actctgtcac ccaggcagga tgcagttgca caatcatagc ccactgcagc ctgaactcct   18780
gggcttaagt gatccttctg cctcagcctt ttgagtacct gggggacttt aggcagtgct   18840
actatacctg gctaattttt aaatgtttta tagatgagat cttgctgtat tgcccaggct   18900
ggtctagaat tcctgggccc aagtgatcct cccaccttgg cctcccaaag cgctgagatt   18960
acaggcatga gccaccactt ctgaccaata gatatttata tttgtgactg gaaaatatat   19020
taacaatgtg ttaaaaaatt cagttaaaaa ataatgaaag atttttgctt ctggctaaga   19080
tagaataaca aggacagcat ttatcttctt gccttgaaat agttgaaaac ggaagaaata   19140
tatgtaacag tggttttcaa gttattgggc atcaggcaaa aagaatagt tatcccagga   19200 aaatgaatgt ggagagccct acaatttcct tacattactg cctggtcatg caagaggaa   19260 aaactgagag gagactgagg ctgagccagt ggtttgctgg gttgaggagg cagagctggg   19320
agtgcagaga tgcaaggtgg tgagagccca tatggaagaa taccagggaa gagagctgca   19380
gagggagctc cggagacctg caccctgccc tctcagtacc ctgtcatgtg tgtagctgag   19440
tactgacgag cacttgcttg tgcggaaatg acccagggct ggaggtagag ccacctgaaa   19500
ggattagaag gaacagttgc tgaaagtcac acagggccag gaagaatttc taatcacacc   19560
agttggagtg gaaaacctca gctctcatag agcaggtagg gtactcagaa gggtttgccc   19620
acctagcccc agactaagtt tcgttactct gaccctacct aatattaaaa agagattaat   19680
taaattgttc gcaacaaaaa taatatattt cagtgtttgt aacacgtaga agtgaattgt   19740
atgacaatag cataaaggct ggaagagcag aaattgacat gtatttgcgc tgggcagaat   19800
aatgctcccc tctttcccca aaagatatca agtcctaatc cctggagcct gtaaatatta   19860
ctttatatgg aaaattgttt tatgatgtga ttaaattcag gatcttgaga tgaggggggct   19920 atcttggatg atctgggtag gcactaaatg caatcacata tatataaaaa ggaggcagag   19980
ggagatttta cacacagaga gaaggccctg tgaagatgga acagaaagat ttgaaggtgc   20040
tggccttgaa aattggagtg atgaagctat aagccaagga atgcagcagc caccaaagct   20100
ggaagaggca cggagcagtt ctcatttaga gcctactcca gagggaatgt ggtgctgcca   20160
attccttttt tttttttttt tttaagatat catttacccc tttaagttgg ttttttttt   20220 tttttttttt ttttagtatt tattgatcat tcttgggtgt ttcttggaga gggggatttg   20280
gcagggtcat aggacaatag tggagggaag gtcagcagat aaacatgtaa acaaggtct   20340 ctggttttcc taggcagagg gccctgccac gttctgcagt gtttgtgtcc ctgggtactt   20400
gagattaggg agtggtgatg actcttaacg agtatgctgc cttcaagcat ctgtttaaca   20460
aagcacatct tgcaccgccc ttaatccatt taaccttag tggacacagc acatgtttca   20520
gagagcacgg ggttggggt aaggttatag attaacagca tcccaaggca gaagaatttt   20580
tcttagtaca gaacaaaatg gagtgtccta tgtctacttc tttctacgca gacacagtaa   20640
caatctgatc tctctttctt ttcccacatt tcctcctttt ctattcgaca aaactgccac   20700
cgtcatcatg gactgttctc aatgagctat tgggtacacc tcccagatgg ggtggcggcc   20760
gggcagaggg gctcctcact tcccagatgg ggcggccggg cagaggcgcc ccccaacctc   20820
ccagacgggg cggcggctgg gcgggggctg ccccccacct cccggacggg gcgggtggcc   20880
gggcgggggc tgcccaccac ctcccggacg gggcggctgg ccgggcgggg gctgccccc   20940 acctcccgga cggggcgggt ggccgggcgg ggctgcccc ccacctcccg gacggggcgg   21000
ctggccgggc gggggctgcc ccccacctcc cggacggagc ggctgccggg cggagggggct   21060
```

```
cctcacttcc cggacggggc ggctgctggg cggaggggct cctcacttct cagacgggc    21120
ggctggtcag agacgctcct cacctcccag acggggtggc agtggggcag agacattctt    21180
aagttcccag acggagtcac ggccgggcag aggtgctctt cacatctcag acggggcggc    21240
ggggcagagg tgctccccac ttcccagacg atgggcggcc gggcagagat gctcctcact    21300
tcctagatgg gatgacagcc gggaagaggc gctcctcact tcccagactg gcagccagg    21360
cagaggggct cctcacatcc cagacgatgg gcggccaggc agaaacgctc ctcacttcct    21420
agacggggtg gcggctgggc agaggccgca atcttggcac tttgggaggc caaggcaggc    21480
ggctgggagg tgaaggttgt agtgacccga gatcacgcca ctgcactcca gcctgggcaa    21540
cactgagcac tgagtgagcg agactccgtc tgcaatcccg gcacctcggg aggccgaggc    21600
tggcagatca cttgcagtca ggagctggag accagcccgg ccaacacggc gaaacccgt    21660
ctccaccaaa aaacacgaaa accagtcaga catggcggtg cgtgcctgca atcccaggca    21720
cttggcaggc tgaggcagga gaatcaggta gggaggttgc agtgagtaga gatggtggca    21780
gtacagtcca gccttggctc ggcatcagag ggagactgtg cgagggcgag ggcgagggcg    21840
agggaattcc ttaatttcag tttagtgata ctaattttgg actctggcct ctaaaactgt    21900
gaaagaaaaa attttttgtt tgtttgtttc ttttaagcca catagtttgt ggtaatttgt    21960
tacagcagct gcaggaaact aatttatgct gcatgtgaaa tggtgtaata aggtagattg    22020
tgatgaagat acatagtata aacaattaag caacaactaa aagcacaaca aggaattata    22080
gctaatgaac caaaaaagga gattagaata ataaaatgg tgaatcccaa agaagccaga    22140
aatagggaa gaggcaaata aaggaaagaa agagcttgat ggtagatttc aacctaacta    22200
tgtcaaaaag gacattacat gtaaaaggca gcgattttc agattgaatg gaaaagtaag    22260
actcggtata tgctgctgcc tgcaagaaac acattctaaa tataaaggca aaaataacct    22320
acaggtaaca gaacggaaag aagttcactg tgcttacaag aattagatgc aagctagact    22380
ggttctgtta atatcagaca aagtggattt caaagcaaag gctcttgccc aggatgagat    22440
ggtcatttca taatgatgaa ggggattcgt tcatcagcct ggcatagcaa gctgaaatgt    22500
ttatgcaccg gactacagag ctaaaataca tgaagcaaag cctgacagaa ctacaagtag    22560
aaacagacaa atccacagtg atagagattt cagtagccgc tctcaatgat ttgtagaaca    22620
cgtagccata atatctggat ctagaacact tgaccaacac tgtcccctgt gcaacctcat    22680
tggcatttac aggacactcc acccagcacc agcagaagag acactctctc aagtgctcac    22740
agaatgtttg ccaagataga gcagatgctg ggccataaaa caagtctcta aattaaaagc    22800
attcaaatta ttcagagtat gttttctgac ctcagtatca ttaagttgga atatattata    22860
ggaagataac ctggaaaagc ctcagatatg tggaaaaacc catttccaca tggcccatgg    22920
gtcagaagtg aagtcaaaag ggaaatttga aagtcttttg gattgactga tataaaaaca    22980
atagatttct aaacttgtgg ggtgctgtta cagcatagta aatggaaatt tctagcatta    23040
aatgcctgtt ttaggaaaga aagatttcaa atcaatgacc tcagcttcta cctttggaaa    23100
cttgaaaatg acaagcaaat ggaatccaga gttaccagaa gggccaggta cggtggctta    23160
tgcctgcagt tctgccactt tgggaggccg aggcaggtgg attgtttgag actggcagtt    23220
gaagaccagc ctgggcagcc tagggagacc ccatatctac aaaaaacaaa aaattagcc    23280
aggtgtggtg gcatgtgcct gtagtcccag ctaaccagga gtctaaggtg ggaggattgc    23340
ttgagtctgg gaggttgagg ctgcagtgaa ctgtgattgt gccactgtgt tccatcctgg    23400
gcaacagaat gagaccctgt ctcaaaaaca aaaacagtta ctagaagaat ggacatcata    23460
```

```
aagataggag cagaagtcag taaaatagaa aacaaaaata cataggaaat caataaaacc   23520
aaaagctggt tcatcaagaa catcaataaa ttggtaaagc tgataggaaa aacagtgaag   23580
tcacaaatta gcaatatcag gaatgaggga gatgacagta gtatagatta tatagatatt   23640
aaaaggactg tatgaggcag gtgtggtggt tcacgcctgt aatcccagca ccttgggagg   23700
ccgaggtgga cagatcacct gaggtcagga gtttgggacc agcctggcca acatggtgaa   23760
actctgtctc tactaaaaat acaaaaatta gttggtcgtg gtgctgtgtg cctgtaatcc   23820
cagctacttg ggaggctgag gcaggagaat tgcttgaacc tgggaggcgg aggttgcagt   23880
gagctgagat tgtgccgttg cactccagcc tgggtgacag agcaagactc catctcaaaa   23940
caaataaata aataaaaagg actatatggt aatattatga acaactttat gccaataaat   24000
ttgacaactt atagatgaaa tgatgagtt ccttgaaaga cacagaaact attaaagctc    24060
tctcaagaag atatagataa gctgattagc cctatatcta ttttattgaa tttaaatgta   24120
aaaatcaata tttagttact ggaaaacttt taagtgtggt tggaaatggt atacgaactt   24180
tttcaactga attttatgaa gtctaatcac aggtaaaggt tttctgatga aaatttagtg   24240
tctgaattga gatatactgt aaaaaatgtt atatatctta attatttctt cacattaatt   24300
acatgttgaa ataatacttt gggtgtattg ggttaaatta aatattatga aaatcttgcc   24360
tgttttcttt ttacttttga tgcgtcagct aggaaaatata aaagtgtagc tcacattctg   24420
tttctgttga cagtactgct ttggagcaca gtgtttgaat gatctatcat ttcaaagacc   24480
tttcctcagt tcgttattca tggctgtctg tattccacat agataaggtc tgaaatactg   24540
ctaagtggca tgttttgttt tatgctttta aagtttgtt gatcattact gatgtggact    24600
tttggtgcct cttaggctca ttgctatctt ccaaccattg tttgcaattt ttacctagag   24660
ataaagagaa agagacattt ggtttcagag tagttagatt gggatcatga aagagcaacc   24720
tcattttgat gcttcaaaaa tagcacatcc cccgtattac tgggatttgc tattcttggg   24780
attacttcaa gaacatcctt gtgttactgg tttggatgct tctgaatgct gtgaagtcag   24840
tttcatgtac atggctcatc agtttagctc tctcttggct ttgtttagac agttggagca   24900
tgatggccta aacagcttct ttcaattaaa cattttaaaa tagtttacaa atagtaaaca   24960
aactccagtt tttgtgactc tttgtctcgc acaacaaaaa cacaatctga ccatgatcat   25020
ctggcatctt agggtgaaat atggttatac tttggcccat accgaaagca agattaaaaa   25080
ggggcaggag agatagactg ctgaactgat tttcaaggtt ccaagaatat tgtaggttaa   25140
gagtaaaagt aaacttttgg tagaaagcag tgggttgtct aggattgaag tatctgaagt   25200
ttttaaacga aaatttaaaa agaaaaatga gaattgcctt acaagtacaa tctcttcttt   25260
tttaaaaaat aaactttatt ttgaaatagt tttagattta tagaaaaaaa ttagataggg   25320
taggaagttt tcatataccc tacatccagt taccccagtt attatcatcc taatttagtg   25380
tgagacattt tcatgtttaa tgaatcaata ttgatatgct attaacttaa gtccagactt   25440
tattcagatt ttcttaattt ctatgtaatg tcctttttct gttccagaat tccatgcagg   25500
acaccggata cctcattaca tttcattgtc atgtcacctt aggctcctct tgacagtttc   25560
tcttcttttt ttgcttagaa attctccaga atttcagaaa cttctgggca tcgctatgga   25620 acttttctg ctgtgcagtg atgacgcaga gtcagatgtc aggatggtgg ctgacgaatg    25680
cctcaacaaa gttatcaaag taagaaccgt gtggatgatg ttctcctcag agctatcatt   25740
gttgtaggct gagagaagaa gcgatcattg agtgttcttc tgttttgagt ccctgaggat   25800
```

```
gtctgcactt ttttcctttc tgatgtatgg tttggaggtg ctctgttgta tggtttggag     25860
gtgctctgtt gtatggtttg gaggtgctct attgtatggt ttggaggtgc tctgttgtat     25920
ggtttggagg tgctcttgta tggtttggag gtgctcttgt atggtttgga ggtgctctgt     25980
tgtatggttt ggaggtggtc ttgtatggtt tgcaggtgct ctattgcatg gtttgcaggt     26040
gctctattgt atggtttgga agtgctcttg tatggtttgg aggtgctctt gtatggtttg     26100
gagatgctct attgtatggt ttgcaggtgc tctattgtat ggtttggaag tgctcttgta     26160
tggtttggag gtgctcttgt atggtttgga ggtgctctgt tgtatggttt ggaggtgctc     26220
tgttgtatgg tttggaggtg ctcttgtatg gtttggaggt gctctattgt atggtttgga     26280
gatgctctgg tatctgcctg cattgcttgc cacacctgcc cggtcagaag gcgctatgtt     26340
gacaattgtg cctgcacggt gcctaggtca atgaagggaa ccgatggtag ccactggatg     26400
ctcctgggaa aatgtcacta caggcaccag agaagccaga gctatgccca aatttctatg     26460
agtctcagtt ttcttaacca taaaatggga tcaatgtttt tgtggcatgt gtatgagtgt     26520
gtgtctgtgt atgtgtgagg attaaattgt gtatgtgtga ggactaattg ccactactgg     26580
atcctcaaag tggtaagaag tgttcttatt aataatgaca tccttacact cttacccagc     26640
aagattgatg ggtgtggcac tgcttctctt tttccatcac atggtttcca tggtatcctt     26700
ttgcccaggg aatctttgct ttgtggctag cactttgttg tttggctaat cacgctttct     26760
gtggtcagga cgctggcttc tctggagcca tgggattcta gctccctgtc ttgtccctag     26820
agtggtcact gtcttctctc tccgcttgca attcctgctt tgctcgcatc tcacttatgc     26880
agtgacgtat atcagtttca ccttgttctc cgtgcctgct gatcattggc accacttgca     26940
tggtgccatt tagggcctgc ttccagttaa gcttgcttct ccacaggcct aaatatcctt     27000
gcttgcttct tttattctca ctggcaggac cagggcggtc tgtctttgca tgagacaggg     27060
tctcgctcag tcacccaggc tggagtgcag tggctgatca cggctcattg cagccttgag     27120
ctaccgggct caagctatcc tcctggcttg gcccttgag tagctgggac tacaggcgtg     27180
caccaccatg cccagctaat ttttaaaatt atttgtagag atgggatctc gccaggttgc     27240
ccaggctggt cttgaacgcc tgggctcaag tgatcctccc tccttggttt cccaaagtgc     27300
tgggatcaca ggtgtgagcc actgtgcctg gcccttgatg tttcagttct tgatatttga     27360
tcctcagagt cagaaaatct aaaaagaggg ctatcccagg ttgccttggt tcatggcaaa     27420
tgggacgtta agagggcaga gagaatatga acagaaactg ttctaatatt ggtcatttaa     27480
tgtgtaagta ttgttctttt ttaaacctcc ttcattttt ttccaggaat tgctggacac     27540
agtggcttgg tgtgtgtctg aggactgtag gccatggccc taggttgtgg ttttaggtct     27600
caggtgctct tcctggctgt ctccttgctt ctttcccatg tcctcttctt tgtttccagc     27660
catttctccc ttatgcttaa gtttggtgca gcagggtttg gctgctctca gattcctgct     27720
tcctcagatg ctgtagttgt caggcccagc gggctggcag cgggatcagg atctggctag     27780
gtttgctctc actgtggcag agtagggga ggcgtgggag agcacgtgtg accccaggcc     27840
agctgtaggg agcataggca tggtcacgta gccttcaggt cctagacttt gtcttctcat     27900
gagtatggct gtgtgtgtat ggtgaaaact aggttctact tagcccaaga aaatgggcac     27960
attttgcatg tggtttctgt agagaaatgc actgggtatc tgacatagcc tggcagcatg     28020
cctccctcag gtaggttagt ctcaggcggt gaagcacgtg tgtccagcaa gaacttcata     28080
tgtggcataa agtctccgtt ctgtgaggtg ctggcaaatc accaccaccg tcaagaggct     28140
gaagtgattt ttgtctaggg aggcaggaaa ggcttcctgg agtcagcagc cagtaggtga     28200
```

```
aagagtagat tggagacctt cttaatcatc accgcctctt gtctcaaggg gtgccaggaa   28260
gctgtggagg ctgaacccat cttatgctgc cagagagtgg gacaccatga gggtcaggtc   28320
aaggggttgt accttgtttg gtagagaatt aggggctctt gaagactttg gatgtggtca   28380
ggggagtgta tcatttagga agagtgaccc ggtgaggacg tggggtagag gaggacaggt   28440
gggagggagt ccaggtggga gtgagtagac ccagcaggag tgcagggcct cgagccagga   28500
tggtggcagg gctgtgagga gaggcagcca cctgtgtgtc tgcggaagca ggggcaagag   28560
ggaagaggcc agcagcgtgc tgccatcacc cagcgactgg cgtagattgt gagagaccat   28620
tccctgctct taggaggggc tgagttttag ttttctcttg ttatacaata agcttggtat   28680
ttgtttacaa aacatttgta aagctaaatc aaggtttgat aaggcttcta gttttatttta  28740 agaagtaatg ttgaaataaa tgtttgtcca attcgctttg ctcatttaag gactttcagt   28800
acaaactgca acaacaggat taggatttaa acgtttctga gatgttttta ctcctcagaa   28860
tttcccagaa tgtgatctgg ttttgatttt caagcttgct gacccaatag gttaacccac   28920
aagttttacg aagaccatct cagtccactt acatcaactg cccatgccac ggttaaagag   28980
atcatcgact gatgtttggc acagcttcct ccctcttggg tgggcaagca tttggaagag   29040
aaggctccta tgggtgagag tggggcacca aagtcttccc tgtcccatcc cctagcttga   29100
gaagcccttc tctaatgtgg actttgtgcc gttagcatcg ttactagctt gaagttgacc   29160
atctggacgt actttctggt ttagcctcac aagtgagcaa ggagggttga gagatgtgct   29220
gtgaggaatg tggggcccca gctggcagca ggctctgggt caggggggca gggaccacgg   29280
gcatacctga cagtgaggag gggccacacc tgcagaaaag gatgcaggac tccgccttgg   29340
gaagtgttct aggccagagc gagggtctgt ggtttataag tacacccaca gtgctcggga   29400
ccctgcagat gtccagggtg ccgtctgagc ccgtatcatc caacagaatg ttctgctagt   29460
gaagattaaa gatttactcc aggggcttta ggatttatta tatatatata aatcctatat   29520
atataatttt ttttttttt tttttgaga tggagtttcg ctcttgttgc ccaggctgga   29580
gtgcaatggc gtgatcttgg ctcactgcaa cctccgcctc ccgggttcaa actattctcc   29640
tgcctcagcc tctcgagtag ctgggattac aggcgcccac caccacaccc ggctaatttt   29700
tgtatttttt agtagagacg gagtttctcc atgttggtca ggctggtctt gaactcctga   29760
cctcaggtga tctgcccgcc ttggcctccc aaagtgctgg gattacaggc atgagccacc   29820
ccacctggcc aggatttatt gtatttgaac catctaccat tttaattttg atgttatgta   29880
gtatttgatg ataatgaaag ttaaattgtt tttctttcca ttttctgtt taagtgaatg    29940 acctgtatct agtttattca gtaacttcct gcatatattt gtttctttca ttcttaatga   30000
atatattctt aatttagttg ctattatgtt ttgctttgcc ccaaaattga aatcttagtt   30060
tccttttagc tcgttttaga actagtgatg ggatgtgtct tccataaatc tcttgtgatt   30120
tgttgtaggc tttgatggat tctaatcttc caaggttaca gctcgagctc tataaggaaa   30180
ttaaaaaggt gggccttgct tttcttttt aaaaatgttt taaattttaa atttttatag    30240
gtacacgtat tttgtaggta catgtaaatg tatatattta tggggtacat gagatatttt   30300
gatacaggta tacaatacat aataatcaca ccatggaaag ttggatatcc atgccctcaa   30360
gcatttatcc tttgtgttac aaacaatcca gttacatgct ttacttattt tattttattt   30420
ttgagacaga gtcttgcttt cacccatgct agagtacagt ggcatgacct tggctcactg   30480
caacctccgc ctcccgggtt caaccgaact ttgggctggt ctcgaactcc tgacctcagg   30540
```

```
tgatccgccc gcctcggcct cccaaagtgt tgggattaca ggcgtgagcc actgtgccgg    30600
gcctgattgt acatttaaa ataactaaaa cagtcagggc acagtggctc atgcctgtaa    30660
tcccagcatt ttgggaggct gaggcaggtg atcacctgag atcaggagtt cgagaccagc    30720
ctggccaaca tggagaaacc ctgtctctac taaaaataca aaaattagcc aagtgtggtg    30780
gcgggcgcct gtaatcctgg ctactcggga ggctgaggta ggggaatcgc ttgaacctgg    30840
gggtggaggt tgcagtgagc cgagatcacg ccactgcatt ccagcctgag cgacagagtg    30900
agactttgtc tcaaaaaata aaatgaaat aaaattgggc cgggtgtggt ggctcacacc    30960
ttagtcccag cactttggga acctgaggca ggtggatgct tgagaccagg agtttgagac    31020
cagcatgggc aacatggcaa aacgctgtct gtacagaaat tagctgggtg tggtggtgca    31080
caactatagt ctcagctact gggagattg aggtgggagg attaattgag cctggaaggt    31140
tgaatctata ggtagctgag attgtgccac tgcccttcag cctgggcgac caagtgagac    31200
cctgtctcaa aagaaaaaca aaaaacaaa aacaaacca ctattatcga ctatatatta    31260
ttgtctatga tccctctgct gtgctgtcga ataccaggtc ttgggcccct attccatca    31320 ctgagcaaac ttcactctgt taagcagcag gtgtgggatt tcatcgttat tcagtaattc    31380
acaatgttaa aggaaatgc tgtttggtag acgattgctt tacttttctt caaaaggtta    31440
ctctttatta gatgagatga gaattaaaaa tggtaactta ctttatatct ttataattga    31500
agcccactag accttaaagt agttaccaga tgttttatgc atttaaatgg ccttttctct    31560
aaaattagaa agtaacaagg aaagaaaatg cttcgtttct atgcaaccct cttggtgact    31620
agtatgtgac tcttaatgca accctcattg caccccctca gaatggtgcc cctcggagtt    31680
tgcgtgctgc cctgtggagg tttgctgagc tggctcacct ggttcggcct cagaaatgca    31740
ggtaagttgt acactctgga tgttggtttt tgtcgggggc cagctgctac tgatccttta    31800
tgtctcagct cagatgtcat ttcaaaagtc tgctctgccc tctccaaatt gcagtcgacc    31860 ttgcccgtt tatgtttccc tcatagcact aatccatgtc agaaattgtc acgtacagtc    31920
tatctgtgtg cttgtttatt ttctatccca cccttccgca agagacttat gggatgtgtg    31980
ccccaggaca gcagggtct tactgtctta tgctctgttg cagcccagca gcgataacag    32040
tgtctgcaca tagtacttgc ttaaaagata cttgccaaat tgttgaaggt tgaggtacca    32100 attttcattat tgctgactat aggagttata gcaaaatatc catttgtctg ttacatgagt    32160 taaaatatg gttgttgcac tgtgaatagt ttggtttagt caaaacagtt gtatcttaac    32220
ggattgagaa acaaaagcag gaccactttt catcagctcc ctccttctcc ttaaccagca    32280
atacatgctg atgctgatat cccatagacc ctcagctcca tcctgagtca ctgggaatgt    32340
ggtctaaacc ctcactatta atatgaactg agtttcaata agaatcttat atgggtcggg    32400
catagtggct cataccttg atcccagcac ttcaggaggc caaggcaggt ggattgcttg    32460
acccagacta ggcaacatgg tgaaacgccg cctctacaaa aaatacaaaa cttagccagg    32520
catggtggtg cgtgcctgtg gtcacagcca ctcgagaggc tgaggtggga ggatcacttg    32580
agcctgggag gtggaggtcg tgttgagcca agatcgcacc actgcactcc agcctgggca    32640
acagagtgag acctgtctca aaaaaaccaa aatccagaaa agaacttata tggctgcaga    32700
ggtataatca ctaaggaaat ttccttttgt ataatctttt ttcttttact atcatttaaa    32760
aaaatgtgtt atatttctga agcaacacat ccaggttctg cacatagcag ccaaagtgac    32820
cttaaagaat ataactgggt cttgtcattc ccttatttaa actcttgtac ccatttccca    32880
gtgccgttta gatagagatt ccagactcgt caatggctct gtcacctcag acaccctgca    32940
```

```
ttgactcatt agtctgatta gagtcaggtt tttcttcctc ctgatggttt tttttttcccc    33000 cttagttctc agcggaacag tcacttcctt agggaggttt ccccagccac cctctgaggc    33060
cgtgcttgtt gccagactct gccactagag ggcagggctg caccactcct ggcacctcgc    33120
acccggcctg ccctgtcact ctgtgtgttg ggtgaattcc tgtgatctgt gactcactgc    33180
tctgtgtcct acacattcgg ctttctcttct ctccccacaa ccccattttta taattctcct   33240 ttttcaggaa agctttattc ccatttaaaa attttgttt ttaaaatggt attttcttac     33300
acttattttc taattaaaaa tgagtgtttt aagaagtatt atgatttact gcaaataatt    33360
tttaaaccca gccttttaga tcctctgtga tcataagaga aatgaaggat gtctcccaac    33420
acttgagctt catccacatt tcatcctcct gttctttcag ctgagttttc cccatcccat    33480
tagggactgt tggaatataa aactggcttt tccctaacag ggaatgaatt gcttctgttt    33540
ctcctgaagg agagctggaa gaatgacttg cgttcttttg catacacagg ccttacctgg    33600
tgaaccttct gccgtgcctg actcgaacaa gcaagagacc cgaagaatca gtccaggaga    33660
ccttggctgc agctgttccc aaaattatgg cttcttttgg caattttgca aatgacaatg    33720
aaattaaggt atgattgttg cctcaggtca caaacatgcg agtgatgctg tgagtgagtc    33780
tgtggagggt gagggcttct gaacagggag tcctgtggga gtgcttcttg gggtatgttg    33840
tatgtcgtaa tttagactac catcatttgt gttattttg aggcacctaa ggacttcttt      33900
ccacttctca tttcttactg tggggtgaag agttgaattg ggagatggtt tctagatgca    33960
aattgaaaag gcattttccc agagcagatt tgttttcggc gtactagagt gactctttaa    34020
cctagctgcg ggaagatgac tgtgccaaga ctgcaggtag gagaaagctc actgacgagg    34080
ccttgtgggg ctgaacgtcc tgcagctatc agagcctgtt ggcttcctgt tgtgcattcc    34140
aacaaatcat cttcaaaccc actttagtgt tttgtttata atgtccagaa atagtgaccc    34200
tgtcacatgc tctacagatt acaggattct tagcctcttc cttttttggta ggtcagtcct    34260 gggtttgagc ccaagtgacc ctcctgggag gtgatgatac acactgggta gagtggaatc    34320
agatggactt ggattagaat tctgtcctct ttactagtta ttttcctcta ggcaaactgc    34380
ccaacagctc taagctattt ccttcgtatt ctgaaaaata agccttaatg ggacccatat    34440
agggcaactc tgagagtaaa ataaaggaat atgtgttaga gtgtagcata gtcacccacg    34500
ggaagggctt agatgttagc tgctactgct cttattagct gaatgatttg gaataaactg    34560
ttagcctctc tcatgttttt tctcttgagc ttcgaagttt tcttgttaat actaaggaga    34620
tattcaaact agtcatgggg ttttggaatg acgaagggag atgatgaatc taagaatttt    34680
agtgtaatat ttcttcatgc tcagtaaatg gtagtttctg ctgctgttat tttattacc     34740 atctctttgg aatgggagta ggtgctcctt tgtggtcaga ggctgtgaga gctccacagc    34800
gccagtttgc ccatctgtac actggggtct gttgaaggca gtcccctctg tgatatctct    34860
ggctgtcaga gctcagatga tagatggtat ttttgtactc ttagttctca tcattttcat    34920
gatttcgatc accatttgag tatgatgatg ctaacacttt gttgaacgta gaatccgtta    34980
attacttcct tcctgaacct ttggcattaa aaaaaatcta ttctgctacc tctctgctca    35040
tttatggtta ttcaaatttta ttatcaagag cctggtacag tggcttgtgc ctataattgt    35100
agctacttgg gaggctgagg taggaggatt gcttgaggcc aggagtttga gaccagcctg    35160
ggcaagatag tgagacccta tctctaaaaa aactgaaaaa aaattagctg gacatgatgg    35220
catgtgcctg tggtcctagc tactcaggag gctgagacag gaggctcggt tgagcccagg    35280
```

```
agttggagtt cgaggctaca ctgagctgtg attgtgccac cacactccag catgggtggt    35340
aaaacaagat gccatttctt aaaaaaaaaa aatatatata tatatattat caatgaaatt    35400
cagtagtacc aacaggatta taaacaaaga tagtagttcc cttcctactt tttctcttaa    35460
tccttgtgtc tcacaggcaa acataactct tagtatttct tccaatattt actttcatgt    35520
ttctttcttt ctttctttt ttttctttga gatggagttt tgctcttgtt gccaaggctg     35580
gagtgcaatg acgcaatctt ggctcaccac aacctctgtc tcccgggttc aagcgattct    35640
cctgcctcag cctcctagta gctgggatta caggcatgca tcaccacgct cggctaattt    35700 tgtacttta gtagagatgg ggtttctccg ggttggtcag gctggtctcg aactcctgac     35760
ctcaggtgat cctcccacct cagcctccca aagtgctggg attacaggcg tgagccactg    35820
cgcccagcaa cttccacatt tctaaataac atgcttctac tgctattttt tttttcaatt    35880
ttagacattt ttttactttc actatagttc tatcagaatt cagtgtgtac gttattatgc    35940
ctaagtaaat agtcatggtt gcttacgtat tatatttctt tgattgtgtt tcttatttga    36000
tgagaaagct gtgttttttg ctctgggttg aaactggaga gaggacctgg ggaggaggag    36060
gaggacagat gaagttggtg actgtacctt catggccata gctgggttct cagcacccgg    36120
ggatctgctg atcacctact cataggccag gccctatcg aagttctagg tgacccagtg      36180
ctggggacgg gggggccacc tgcaaggtct aatcatggag gtgggggcta cagtgttggc    36240
ttgtgctggg gccagcatcc ttaggaaggc atcttggagg tggaggagac agccgccac     36300 ttcttgattg gggccttcag cagcaccagc ttcttgggca ggctggtgct ggctttcatc    36360
accatgtcgt gttcaatctt cttccagatc ctgacttcta ggttcagctt tcctcagacc    36420
ctggttcctt tcagaggcca ttgctgctgc cttgctcttt gctggcttgt gccttgatta    36480
tatgtctttg tacaactttt tgttttcctg gagttaatct tcacatctgt tttcttggag    36540
ttaatcgtta cctctatatc gcttgcttat tattctttgg ccttttttgtc ttctcacacc    36600 ttccaacttc tttgtaatat gtgttagta caattttca tgacaggtag tttactgaat      36660 cagttttttcc ccagtgtggt catccaactt gagttatcca gctctctgcc ccagtctggg    36720
caggttgatc ttcaggtctg tagtacactt gtatcctagg acttctcttt gccattagcc    36780
tggaatttcc tttgcagttc tcccgttgga tgcccagttc ctagatgcca tatgttttc     36840 tatcgtctag tagcttcctg agagaagatg aatgggaggg aaattgtatg aggttttgca    36900
ttcataaaaa tgccatttt ttttcctgtac acttggctgg gtatggtgtt ctggggtaga     36960
aatcattttc cctcagaaat gcaaagtctt tgccctgttg tcttaaaatc tccaacgtga    37020
cccgattcct taacctatga atgtactttt ctttggaagc tttccatttt tggggaggtg    37080
aagtgctagg tacttagtag gccttttaat ttggaaactt acatcccttc agttctggga    37140
aaattttctt aacatttctc tgagaagttc ttgccttta ttttctgtgt tctctcctga     37200
aattggttag ttggatgttg gtcctcctag attgactcac atcttacctt tttcttttct    37260
ttttctggta ctttttagat atccatctca aactcttcta ttcattgtta tgttttaac     37320 ttctttcttt tctttgtctc ttgatggggt cttgccctgt tgcccaggtt gtggtgcagt    37380
ggtgcgatca tagctcactg cagcctcaaa ttcctgggct caagcagctg ttctgcctca    37440
ccctcccaag tagttgggac tacaggtatg caccaccacg tccagctatt ttctttactt    37500 ttttttttt tttttgaga tggagtccta ctctgtcgcc caggctagag tgcggtggtg       37560
ggattttggc tcacttaagc ctctgcctcc caggttcaag cagttctcct gcctcagcct    37620
ctcaagtagc tgggattaca ggtgtgcacc accatgcccg gctaattttt gtattttag     37680
```

```
tagagccaga gtttcaccat gttggccagg ctggtctcga acgcctgacc tcaggtgatc   37740
cgcctgcctt ggcctccgaa agtgccggga ttacaggcgt gagcccatca ttagatcttt   37800
aaataccagt atctataagt cttttcctct tgagtcagct agtatccctg aaggaaatt    37860 actcattttc ctgcttggag ctataagct tggctatgtt tatcctgcaa ccggggactg    37920
gaagggaggg gactgacagt gttgctggtc agggtgccct cttactttt gttttctgtg    37980 tgcatctcac gtctgtcctc agcctatgta aacacctctt gagattatcc ctctcaatct   38040
ttgccggagg tgggggaggg gctgcttcct gggctgcctt ggattggagg gaagacctca   38100
ggtgagtggg tgggaatttg cccaaggagc catgagacca gccactattt cacccctctcc  38160 atccctccac tttcagatgt atgtggcgcc tccaaagccc gagctcttct tggcgtctgt   38220
ggcttcaata agcttgcttt tgctggtat ccctcctacc ctccctgtc cccagcaaag     38280 cttgcatttg aacttcttcc tacgggctaa caaatcagtc agttatgtag ctcttgttac   38340
tttttagctt ccgaagtttt gttgacaccc gtagtctgct aatgtccctg ttctgttctt   38400
tctgttcgtg taaatatatg ctttatacaa cttctttaca tgattttgt ggggtttctg    38460 ggtagcagag cttcacaagt tcaatccagc gtgttggatt agaaatctcc caccctctgg   38520
tttattctta ttctcaaaat tacctgccaa acactgatac tcccttgttt ttccttttcc   38580
tgacaggaaa tgtacatacc atacaggaca gaaatcatta gtgtatccct tggtgaataa   38640
ccacaaagtg aacttaaccc ttgtaaccgc cacccaggtc aagacagaat attaccaagc   38700
actcagaagc ctctcccta ttccccgtc actgctcctg ccttcctccc caaggtcatg     38760
actgctggct tctaattcca gagtctgttt ttaaattctg tgtacataga ccatggatta   38820 agtgttctt ttgtctggtt tattttggtc gacattaagt tcatgagagt cttctatatt    38880
atcgtgtgta ttagtattcc tgtagtttta ggagcttcat agcattccat tgtagggata   38940
taccacagtt tattcattgt attatcactg ggttgtttct agttcttggc tattgcgagc   39000
agtgctactg tgaccactct taggtgtgtc ttttggagta catgtgcagg tttccatctt   39060
gcacagctag aggtggagtt gttgggtgat agggtgtgtg catctcagct gcagtagaaa   39120
ctgccaaata gctttccttg agtgcttgta ccagctcacc cttttgccac tgtgtatggg   39180
gattccagga gctctggtcc tcgctagcac ttggaattgc tgatgctttt actcttagcc   39240
ttcctgatgg gtgttttctg gaatcacatt atgattttaa tttccattcc ttaaagtacc   39300
cttggctctg aagtttaatg attcatgcat ctcttcccctt ttgaagtact cttacaggta  39360
tgttgtgcat gtgttgaaaa gtggcactat ctattctaaa atacagtatg cctcctctgt   39420
gtttgaacag ttgtagcgtg gccttggggc ctcctgttag ctggcttgga aagggattc    39480 ttgggattgt agagattaga cctgaggagg cccccttggag ctctctgact aaatttatt   39540 ctttattatt ccaaactatt taagctcacc gtgtgctgac tcatcataat aatgagtagc   39600
tctcattgtg cttgtctatt tggactcata caatgatttt ttttttttct ttgagacaga   39660
gtcttgctct gttgcctagg ctggagtgca gtggcacaat ctcggctcac tgcagcctcc   39720
acctcccagg ttcaagtgat tcttgtgcct cagcttctca gtagctgag actgcaggtg    39780 cgtaccacca tgcctggcta atgtttgtat ttttagtaga gacgggggttt caccatgttg  39840 gccaggttgg tctcaaactc ctgaccctcaa gtgatctgcc ttcttcagcc tcccaaagtg  39900
ctgggattac aggtgtgagc cactgagctt ggccaaagta gtttttttaag atgttagtat  39960 cttttcttgc agctaaaaaa gtttgtcaga gatgattcta ctttgttctc caggtgtttt   40020
```

| | |
|---|---|
| ctcagggaga aattggaggc agtaagccac tgggggagtc ctgtggctgg ggggtgggt | 40080 |
| agtcctgtgg ctccttgtca gggagtcctg tggctggcaa ggagagaagt cctgtggctg | 40140 |
| ggttgggagg gagtcctgtg gctggggtct catcctgtgc ctaacagtgt ccagaggtgc | 40200 |
| cgagaccagc tcagtcgggg agaccctaac ccagcagcgc tagaggaatt aaagacacac | 40260 |
| acacagaaat atagaggtgt gaagtgggaa atcagggtc tcacagcctt tagagctgag | 40320 |
| agccctgaac agagatttac ccacatattt attaatagca aaccagtcat tagcattgtt | 40380 |
| tctatagatg ttaaattaac taaaagtatc ccttatggga aacgagggga tgggccgaat | 40440 |
| taaaagaaga ggttgggcta gttaaccgca gcaggagcat gtccttaagg cacagatcgc | 40500 |
| tcatgctatt gtttgtggct taagaatgcc tttaagcggt tttccaccct gggtgggcca | 40560 |
| ggtgttcctt gccctcattc ctgtcaaccc acaaccttcc agtgtgggca ttagggccat | 40620 |
| tatgaacatg ttacagtgct tcagagattt tgtttatggc cagttttggg gccagtttat | 40680 |
| ggccagattt tgggggcct gctcccaata cagaggtctc gtgtaaattc cctgggaggc | 40740 |
| gataagcctc tgagaaacag actatgctaa ccacgccatg aaagagaaac ttatttataa | 40800 |
| atcagatgcc agttactagt ttactgctta tttgcccagg cgtagctctg acagagtccc | 40860 |
| cgactcatag tgcttgctca gtgcatgctg aacaatgatt ggaatcaagt catggctcag | 40920 |
| agcatagttt tgaataatgg gaaatggatg ttcttaagta acatagtcac caagataatg | 40980 |
| cgactagctg ggtcacccct tttcaatttt aggatatttt tatcaagatt taaatggcca | 41040 |
| tcattagagt tatagcactt tctcctttgg attgtcctag aggcccatga gaaagtattc | 41100 |
| cctaatttct taggagaaca gtttgtgggt agtatgcggt catgtccagt taaattgcag | 41160 |
| atatttccga tcgaagatgt tccagtcctg agaacttcgt gacattagca ggacttctac | 41220 |
| aagccatctc ttagggtggg gcatttactg cagttggcta gtactctttt ctccttaact | 41280 |
| ttgtcatttg ttgattttt tttaactgtc cccaaatact gtgggcagag tgtatctaga | 41340 |
| attgaggcct ccaccattgc ggagaggaca tggatgctga gcagtcccct gagtgaaggt | 41400 |
| tataaagaag caaatagact acacatgtct gtaaactgct cttgagtgtc ccaaatttgg | 41460 |
| ggtacttcag ttcagctgta ggaaaagcct caaactgttt atactttgca agaattggaa | 41520 |
| acttctaatt cacgttaagt tttatgtaat acatgataag cttcatagga gcttcatctt | 41580 |
| ttatctactt ggacttttgc ttccgtaggt tttgttaaag gccttcatag cgaacctgaa | 41640 |
| gtcaagctcc cccaccattc ggcggacagc ggctggatca gcagtgagca tctgccagca | 41700 |
| ctcaagaagg acacaatatt tctatagttg gctactaaat gtgctcttag gtaaggtgga | 41760 |
| ggcatatgag tggaagagtc tccagcatgt actcaagata gacctttgaa ataaataaaa | 41820 |
| ccagatgatc cctcagcttc tagaccaggc tatttggcac tggttgattg aatgtgaact | 41880 |
| gcactgggc tgctgtgagc ccgcatgggt ctctgtgacc ctgcagatgc agccgtgccc | 41940 |
| agggactggg cagtgggtgt gggctggtgt gagccctgtc tgccacccag ggcctggccc | 42000 |
| tctgtctgtg tcggccatga ctatggtgag tcttgtaggc ttgagactgt gcctcgggtt | 42060 |
| cctgcgggtt ctctgtaggt cagttgacag tttctcctgt tgtttgggta actgtggaaa | 42120 |
| cgaacactgg caagtgctga agcgagcatg tggacgtgcg atatgaaata acgacctggc | 42180 |
| tttcaaaggc agtgaggctc tctggaaagg accttgctga gctagggatg tgggtgtgta | 42240 |
| gccattccca gtgggcctca tggcgtactc gttcatgatc atgtttgtgc catcttgatc | 42300 |
| tctcaggatc tcttcttttt taacagatta agccgggaat ctccaaacag tgagtcagat | 42360 |
| gttaagatgt cttgcttcca cccccacagg cttactcgtt cctgtcgagg atgaacactc | 42420 |

```
cactctgctg attcttggcg tgctgctcac cctgaggtat ttggtgccct tgctgcagca    42480
gcaggtcaag gacacaagcc tgaaaggcag cttcggagtg acaaggaaag aaatggaagt    42540
ctctccttct gcagagcagc ttgtccaggt aggagcacag ggtttactct aggccctgca    42600
tgtgaatgac tgacattcaa agaaccgatt aatttggaag agaagcggca gaaccgagag    42660
ttagaggtgt ggactctgga gctgcgctgc tcgtttccaa ccctaggtgc tgacctctag    42720
ctgtcttccc tctgtatgtc cctgtcaccg tgagtcaaat gcgggtgatg cctcctcagg    42780
tgccgtgtta cctaagcctc tcagagacca ctgctaccct gtttctaaaa ccagaggtca    42840
cgatatgtgt tcatccaccc agtaaatact gattgagcac ccactgtgtg ctaggctctg    42900 ggatagggc tgggtataca atggtgagta tttcagctgc agcttctgcc ccgtggaggc    42960
tgtggcctag cacactggtc taggcacggt ggtatatgct cactcaagga gatagggacg    43020
tggtcgtttg gggtgtcgga acaaaatgtc ggaacttctc tttccaatgc agagaaacct    43080
tgcagtaatt ctaatgtact gtgattggca gttgacttca gttctttgta gcacgcttac    43140
tcaggttatt tcactaacta tgtaaccatg cagcctcatt ttaagcaatt ggattttttg    43200
aactttactt aaaatgttat gtcagggttt ttattgtgct taatgtgtgc catttagcta    43260
agttttgtag gatacgaaat tgtaagtggc ttaaaatgat tcttaataga atcatgaatt    43320
gaagataatg ctaataattt aagcactgag ttaggtagtg tttgtaaaat gcttagaatg    43380
cttcctggca catgttaagg ccatgtaagt gctgcgtgtt gataaacagc tgagcaaaag    43440
tggactctta agaaagtatt ggggctgaga gttctgttcc aaccagctgc cctttggtta    43500
tttttcagaa taaaagcaga gtctcatggg atatgacatt tatatttcct tcacaaaaaa    43560
cactgctgag tgttttgttg agtaaaaagg gtgtagccat ggtaataata catttaaaat    43620
atagtttatt tcatctttac cttgccttgt ttttttttta agctagcttt ttattgagaa    43680
ttccacacat acaaaagtat caactcatga ccagttatat ttcatttata atcctacttc    43740 tcccttttt tattatttga aagcaaaccc caattatcct cttatttcat ctataagtat    43800
ttcagtatct ctatagatga ggactcttct ttatttttaa aactttattt ttaaaatgat    43860
ggtcagatgc agtgttcatg cctgtaatcc cagaactttg ggaggccaag ctgggcggat    43920
cacttgaacc tgggagtttg agaccagccc gggaaacatg gcgaaacccc atgtcttaaa    43980 gaaaaaatc agccaagtgt ggtgatgcat gcctgtagtc ccagctactt gggaggctga    44040
gatgggaggg tcacatgagc ctggaagatc aaggctgcag tgatccatga ttgtaccact    44100
gcactccatc ctgggtgatg gagcaagatt ctgtctcaaa aaaacaaaac tgcaaaacaa    44160
cgtcacaaaa cagtgccatt gttagacctg aaaatattaa acatttccta catcaaatac    44220
ccaccaactc attatcaatt tttctctcta ctctttgga atcagcatct aaataaaatt    44280
ggtcgataag gattgtaaat ctctttgatg aactggttcc cctccatccc agtttttttc    44340
ccttagagtt catttattga gaaaccagat tgtttgtctt ctaagttttc ctgtggtctg    44400
atatactgct tccatctcca ctgtgtaaat taacacccttt ttctcttctc tgtatttcct    44460
gtaaatcaat aattggagga aaagccttgt cagatttagt gtatatttta tatctgagtc    44520
cagtatttct tatataatat tttaagataa gtgtactctt ttaaaagta ttgaaactat    44580 atgctcaatt ttttttaact gatgctttta agaaggctgc ttgatcataa aagtttagag    44640
atcattggtc tgatgggaaa agcaaataat tactaaaccg tttagcaagg ttgaggtgca    44700
catggtgggg cctggagaag ttcagtcatg agccgtcact tatgggcacg tggaatctga    44760
```

```
cccggcacag agttgggaga agacaggagc tttatagaca gaaaatgtgg tctttgctaa   44820
gtcccaggag tgaaagggtg agacagtgct cacagcacac gagtgtgggt gcgtagacag   44880
agcaagggtg ggtcctgaaa aggcctgcag gctttctcat agattagcaa gagtgctggt   44940
tacggaggtt tctaacattt gtgaacagat cgaaactgtg ttaaattggg attgcagtaa   45000
tcctggaagg acagggatag agggtgaagg ggaaaaaagg gtatggatgt gagacttaat   45060
tgctgatttt cttaagacct ttctccaaag taaataaatg atgtggcaca tttttgaact   45120
ggcaaattct aaactctaga tatgattatc tctataacat atcttactcc atcttctttt   45180
gactaaaaac tgttcttaat taaattacca tgagacgttc aattcagcaa atgtagtttg   45240
gctaaccata tttaattaga atttaatata atcctaggcc tggccaaact attaagcaag   45300
tgtgggcaaa atattgataa ttttagatat gcaggaactt agtttgcttt ccatgtgtgc   45360
ttttcgaaaa aggaataaat tgaaaaatag aggaagccct gaaatccaag aagcaaactc   45420
tctcacctag gcatgcagta aaagcaattc taggatgatt gctgtttggc gcgtagttcg   45480
tattagaaac cattcttctt gaataaatag tatgtttaag aagctgggca gagggaaggc   45540
atatgcatat attatcaaca aggagggaga aaaaggcaat tagtaaccat ccataggagg   45600
gtcagcaaga tttataaagg aaatttgtga tccaagtatg aagcaaaata aggtgcagaa   45660
taaattttaa gcaagtaata gattagagta agagaaccca tttgaccatt aaccttggga   45720
cattctcttt caaatgacat ggagtagtac tgaaatcttt cttctttct gagtctaggt   45780 tattgtgact ggactcagaa agaaatattt cattattgca gtgaataaca tttgtgaaca   45840
ttattgttca taaattatgc agtgaataac atttatgaac acgtgatgtg taagatacat   45900
actgtttatt tttagttaag ttttttggct caacttctag gcagagaaca ttaaatgtaa   45960
atagtgttac ctaggagcat gtaaatggaa atctccatag tatgaaagca gtgctgttgc   46020
taacagaatt taggaggggg cagatgaggt gaaggaaatg tgggtgctga tttccttatt   46080
acattgagag gagccaggag attctttgtt caaaatggat ggcttaagaa gtcaaagtat   46140
aagctgatta cgtagagcag gtacccaaaa atgttttgtg taaggggcca gatagtaaat   46200
attttcagtc ttgcaggcca tcccaagtct gtggcagcta ctcaacacta cctttgtagc   46260
atgaaagcag ccacaggcag cccataaatg tggctctgtt ccggtgaaac tttaggtaca   46320
aaagcaggtg caggccagac ctgacctgtg cactgtggtt tgctgacctg ggattcaggg   46380
gtatagaagt taccatcaga agagctaaaa gtgagacttt ttactttata ctcttctaca   46440
ctgtctgatt ttgaaaaaaa gaaacatgta ttttataata ttaaagatag ggttggcaaa   46500
tagcaaataa aaatacagaa taccagtgaa atttgaactt cagatacatt atgagtaatt   46560
ttatggtgta agtatattcc aaatcatgtg ggacatactt acactacaaa attatttgtt   46620
gtttgtttac agtttaaatt tgagtgcctt gtattttatc tggcaactgt aattaaaggg   46680
aaaaagaata aattcattat gttcatataa tgtgatatag caggggtccc caaccccccag   46740 gctgcagagt ggtactggtc catgggtccc caaccccccag gctgcagagc ggtattggtc   46800
catggcctgt taggaaccag gctgcccagc aggaagtgag cagcaggtga gctggcattc   46860
ccacctgagc accgcctcct gtcagatcag tggcagcatt agattcccat aggagtgcaa   46920
accctattgt gaactgcaca tgtgaggggt ctaggttgtg cgctccttat gagaatctaa   46980
tgcctgatga tctgaggtgg aacagtctcg tcttgaaacc atcccctggc cctgtggaaa   47040
aattgtctcc catgaaacca gtctctggtg ccagaaaggt tgggtagcac tgtgatatag   47100
tattaaaagt gctaataaat atggcatact gcctttaaaa tgtctggtag ctctttctca   47160
```

```
gtggcactca taatagtgtt ttttgatttt taaatgtgtg tcaagctgac tctcccctcc   47220
gtgtatgctg ggctttattt tcccttcct  agtcaccagt tttgggaaat agagatcttc   47280
attctcatgc tgctcctcta gtgcaagtgc tccatttatt tttaaggaat taatataaca   47340
aaaaatcatg ggaatttaga aaacaacatg gaagctaatg atcacattgg tggaagtgat   47400
agggaaatat ttaggggag  aagttaaggt ataaactttg tcaatgaagt cctattaaaa   47460
acaacaaaaa agtgaagctt aggatgcatt ttataaactc tgaccagaac acctgtgttt   47520
ctctgtttct aggtttatga actgacgtta catcatacac agcaccaaga ccacaatgtt   47580
gtgaccggag ccctggagct gttgcagcag ctcttcagaa cgcctccacc cgagcttctg   47640
caaaccctga ccgcagtcgg gggcattggg cagctcaccg ctgctaagga ggagtctggt   47700
ggccgaagcc gtagtgggag tattgtggaa cttataggca agttattagc aaggtctact   47760
cttacaatta actttgcagt aatactagtt acactctatt gattatgggc ctgccctgtg   47820
ctaagcagtc tgcattccat cttccttgcc aaaacttata atacaaattt catctttatt   47880
ttataaatag gggagttggg ctgggtgtgg tggctcacgc ctgtaatttc agcactttgg   47940
aaggatcgct tcagcccagg agtttgagac aacctggcca agtgagaccc tgtctctaca   48000
aaaaaaaaaa aaaaaaaaaa attagctggg catggtggca catgcctgta gtcccagctg   48060 cttttggaggc tgaggtggta ggattgctta agcccaagag gttgaggctg cagtgaatct   48120
tgatggcagc tgcactgagc ctggtgacag agcaagatgc tgtctcaaaa taaatttaaa   48180
aataaaataa gagaattaaa gtttagcagg ttgggtggca aaatgaggcc acacatttaa   48240
agcccctcct cctgattctt ttctctgcct tggctgcctc ctgtggcatt ttaggtgctg   48300
agaaatgaaa acagtaggga aaatagttcc aggatcctca tgttaatttg ccagaaatgg   48360
catcttcaag tcgtcagagg gatctgagag ttccttcctg gcctgacttg agaaaatccg   48420
tctgtcccca gctctgcgtc tgcctccact gcccagtcac ctcctctcca tgctcttggg   48480
gctgggccct accccaccat gcagtgctgc cctggagcag tgagcttggt gggtcctgtc   48540
tggcatgaga gctgccttg  ggagctggat cccagcctct accactgggt ctggtgccta   48600
gcaggctatg gataaacttc tgctgactcc ggcctctcct aagccactgc aacgtggtcg   48660
gtgtagtgca cagtgtgtgt gcagcgtggc cttactcaca gcctccacat tagagagaat   48720
ctgactgaag tcttactgct gcctcgtgtg aacataaatg tttgccagaa ccatgagcag   48780
gaaatgttaa tctgccttgt ttcctgtcct ttacacggaa gaattttttt ctgtatggaa   48840
tgcgtgcctt acaataatg  agtggaaata cccatcgcta atgaaaagtt atacttgact   48900
gttagtcagc taaataatct gagatttcta atacttttaa tttggctttt acaatgcaat   48960
ttatcttagc ttttttgatt tcttaggtca tatctttaga actatatatt tgaatgttaa   49020
tgtaattttc atattgaaat taaaatgttg aactgcgatg ttaagtgttt cctgtggaaa   49080
aacgttcaca ttttctctag ttttaaagtt gaatcaagct gtttgaagat ttcacatttt   49140
cttctagatt ttatcagctt gttactttat ctgtcacttt ctgtgatttg cagctggagg   49200
gggttcctca tgcagccctg tccttttcaag aaaacaaaaa ggtgattatt tcagaaatca   49260
gagtcttgtg ttgaatctta ctgattttct tgtatttctg taatgtaatg tatcttgtat   49320 ttccttgtaat actgtattgg actctgtgta tatctcttct cagatgagtg attatatgtg   49380
tgaatgttgc tggaatctga taaccaggcc tgaatagttt tgtagggtgg ctttttaaaaa  49440 ttactttcat atcagaattg ctttgtcata aattttgaac gcatcataaa tttctaatgt   49500
```

```
tcggggtcag cagactttttt ttgtaaaggg acagagtgta aacatcttag ctttatgggc   49560
catatggtct cttttgcaac attcagctct gccctgtgac aggaatgcag ttgtaaagac   49620
atgagctact ggccagctat gttccagtag aactttactt acagaaacag acaggctgta   49680
gtttgccaat acctgcctta gggaatgtgt tgttatattt tgtgagttac cttctcagta   49740
aattttattt agtattagtc aggaatatta ttaagtagct tcttttccag cctggtcaac   49800
atagtgagac ccggtctcta ccaaaacaaa acaaaacaaa aaaacagcca cgcatgtggc   49860
atgtgcctgt agcctcagct gctgctcagg gggctgaggc aagaggattg tttgagccca   49920
ggagtttgag gtcacagtga gctgtagtca tgccactgca ctccagccta ggcaacagaa   49980
tgagaccttg tgtcttaaaa aaaaaaagtt tcctttgttg ggttatttta atttggacct   50040
ggttatcatt tttcagccat atttaacttt gtacatatca gaatgttctg ataaaactta   50100
acttttatta aagtgtttgt gatataatct gctagttttg gtacacatta tcttttgcaa   50160
tgccagttat tttctttttcc agtgtgggtt tgcataggaa aagaattgct gtcactttct   50220
attttgaaat cttaaaagac tgatcctttt tgtgtcatg atttgagtat ttaattgaga    50280
gcctaatgcc taatattatt tgcagtatta aatgggatct taacaggaat agcattctag   50340
ccttcattga attaagtaaa catttcttaa gagaacttgg aatctataat atttgcgtca   50400
tcatagtatg agatacttaa tcaagtttga gattttagtg aaacattgtt tagaagccaa   50460
aaggattcta ggaaaaatta atgtctatat tcttgaatta ggagagattt tgggacgtgt   50520
gactaagtta cgctgacact tgtttgtttc ttagtcgctt tttccagtgg cggtgagaac   50580
gaagatgact gattcacatt gctcagatga gtttatcctc ttctggctgg acatgggat    50640 atatcctgtc tcttttaagc ctttttggta tttttccccc attgagagct gtgtcttcaa   50700
actcttctgt tatagctgga aaatcctttt taagtgaaat ctgcccaaat tataagacag   50760
atgaaggtag agttgtgttg gatataggat tagggtgaaa gtagtggggg tgtcctggag   50820
cctctcttct ggtggcagcc tagctcttgt gcctttgagg aaattaccct ggggacggct   50880
ctgtggaaca tatttgcaaa ccactgattt ggaagataga gatggctttt gttaagatct   50940
gaattcacct ttttggcatt ttatttgatt tctcaaggta aagaacttat tttgtaataa   51000
agtttcctat tatttagtag ataggccaag ttgctgtgtt aattccatgt agattttggg   51060
tttcctttgc tcattttttc actcttaatc tcacatcatt gtaagtttat ggaagttatc   51120
atacttctga ctttttcttt gaagagcaga aattagaaat tcccaataat tattttgata   51180
gtgtcattta atgacactca catgtgatgt agccacaaag atttaatgag ttcagtttta   51240
aatcatatta agactgttgg tttcatttgt tctcattaat gtaattctga agatgaacaa   51300
taaaatgtat ttttagaact ttcaaatgaa atattatttc atccttccag atcatataat   51360
gcttaagttc tgattgttaa tcataaagtc tagaaaatta aagataata aaatgaaagt    51420 gactttaggg tattagagtt ttattataaa ttctggtgtg tcattggagc tatgacatga   51480
atatttcaaa ggccaatagc attggatctt tacagttata acttaccatt tttaagttta   51540
agtagtaata tagattattt aataatcaaa atcaataaat attaattatt aaaatgtttt   51600
gtggtatagt ttgagaatca ttgcttttaa ctttttccat ataggtttat tgactttaat   51660
agcattctaa acataacatc tctacattct ttgtgtttaa tactgtggag gtataaaaat   51720
acttatatat gatgataaac tatattagag taaattaaat attcttatga gtttcatttt   51780
agagtgcatt tacttaattt tgaagtcctt attttttagca aactaaaagg aatgttggta   51840
cattatttac taggcaaagt gctcttagga gaagaagaag ccttggagga tgactctgaa   51900
```

```
tcgagatcgg atgtcagcag ctctgcctta acaggtagtt ctcactagtt agccgctggt    51960
gtggaccttc actgtctgcc ttccaccccct tgcccttcct gctcgtcccc ctgcacctgg    52020
tggacagcac gactgggggc agcagtggag ccaggttgct taaatggggc atattcgggc    52080 ttctttata atacttactc tgaagcttgt gtgtctgtgg tgtttgcatc atatatttgt    52140
tgttttccat ggtttaggct gttttaaaat taggtttatg gcttgagcat agggctttgt    52200
gagtagggga tggcaggtcg aaacatctca tgagttggat gggttatgct gggggttggg    52260
aaatgggatg aaaaattatg ggatgaaaaa ttgcctatgg atagtttaac ttgaaagaat    52320
ctgcctttgt ttacagatag ttatctttt tcttttttga gatagagtct cacactgtca    52380
cccagtgcag atacccagtg tcactggagt gcagtggtgt gctcttggtg cactgcagcc    52440
tccgccttct gggttccagc gattctcctg cctcagcctc ccaagtagct gggactacag    52500
gtgcccgcca ccacgcttgg ctaattttg tattttttg tggagacggg ttttgccat    52560 gttggtcagg ctggtcttga actcctgacc tcaagtgatc tgcctgcctc agcctcccac    52620
agtgccggga ttacaggagt gagccactgt gcccggccag ttacagatac ttatctaatg    52680
aaattctctg tgtactttat aaaagatgag gattaactga aggtactaat aactggatta    52740
tatgagggtg gttttggttg tataatccta tctaaaagaa tattttagct ataactgaaa    52800
gtaagactta aatatttaga gaggaaaatc tgaataattc tagtagtaat tatttattta    52860
caaaataaaa atagattttt ttttgattac acaaattaaa caacaataaa acatcacagc    52920
aatccggata ctataaagct cacatgctta ccgacccaac tgcccccagga gtgaccactg    52980 ccaacagctt catgtcgacc tttttgccat aatttttata tagccttttt tgtttttaaa    53040
tggtaattta gaaagtcaac taggaaaatg tgttacaggt ttatcttcca ggagaatagg    53100
actggagtcg agatcttgaa tgtggcttgg aagaaggcaa gcccaccca gagagatgag    53160 ttgacagttg tttctgacca ctgcttgctt agagggcctg cgtgtctgtg accgcctagc    53220
tttgcgcccc tgactaggct gccccttaat tacaaatgtc tttatatatt gctccagcta    53280
aggcttggag tagtcggtta agaacttgaa cttcggtttt tgcagtgaaa cagcatttga    53340
gaatatcacc ttctgataag ccttatttta taaggtgggt actgtagtgg gaggcagtgt    53400
gagagatgct tgaaggatgc actgctgtcc tgcatttcag catcttcagg atgctgtgca    53460
gctgaaacat ttgataacgg tggaactgtt cgttattttg caagcctgtg attccctatt    53520
gaatgttttc tctcgccatt tgacaaatga gtgtttctct gtcttcagcc tcagtgaagg    53580
atgagatcag tggagagctg gctgcttctt caggggtttc cactccaggg tcagcaggtc    53640
atgacatcat cacagaacag ccacggtcac agcacacact gcaggcggac tcagtggatc    53700
tggccagctg tgacttgaca agctctgcca ctgatgggga tgaggaggat atcttgagcc    53760
acagctccag ccaggtcagc gccgtcccat ctgaccctgc catggacctg aatgatggga    53820
cccaggcctc gtcgcccatc agcgacagct cccagaccac caccgaaggg cctgattcag    53880
ctgttacccc ttcagacagt tctgaaattg taagtgggca gaggggcctg acatcttttt    53940 tttattttt tatttgagac agagtctcac tccatagtgc agtggaggcc gggcacaggg    54000
gctcatgcct gtaatcccag cactttggga gactgaggca ggcggatcac ttgaggtcag    54060
gagttcgaga ccagcctggc caacatggtg aaaccctgtc tctactaaaa atacaaaaat    54120
tagttgggcg tggtggcaca tgtctgtagt cccagctgtt agggaggctg aggcaggaga    54180
attgcttgag cctgggaggc agaggttgca atgagccgag atcgtgacac tgcactccag    54240
```

```
cccgggcaac agagcaagac tccatttcaa aaaaaataaa aaaataaagt gcagtggctc    54300
gttctcagcc cactgcaact tctgcctccc aggctcgagc gattctcccg cctcagcctc    54360
ctgagtaggt gggattacag gtgggcacca ccacactcag ctaatgtttg tattttcagt    54420
agagacaggg tttcaccatg ttggccaggc tggtctcaaa ctcctgacct tagatgatcc    54480
acccaccttg gcctcctaaa gtattgggat tatagttgtg agccaccatg cccggccctg    54540
ccacctgcca tcttttgagt tcttccctgg agacctagac ctgaaccctc ctgcttgttc    54600
tcttgttatc taataccccct attgacagcg cagcttagat cattaatgga gagcttgacc    54660
tcatctgata ccttcactga aggaaacaac ttagtgtctt ttgtgttgaa cactgaggta    54720
aaaaattgga atagttgatt atatgaactc tgctaaaatt gagtgcattt tacattttt     54780 aaggccttgt tgggccctgg ttaaataatt attttttaaaa atccttaagg agcctattat    54840
aaacagatct gtggtcttaa tgaaatgtga ttaatactgt gcattatttt aagaactttt    54900
gacttttcaa aaaacttta caacatttcc catttgatag cggcataggt ttaagcactt     54960
ctcatctcta agttagtgga caaaaaaccc tcatggatag tctaataatg tttgctacaa    55020
gtccatgttg agttttatac tccattttat tttcagtttt aaaaactgtg gttaaatatg    55080
tgtaacataa aatttatgtt cttaaccatt ttttgcgtat acagttcgct ggtattaaat    55140
acatttaaat aatgtcatgg aatcattgct accacccatc tctgtaacct tttgatcatg    55200
taacactgaa gctctgttcc cattgaactc tattcctcct ttcccgccaa gtccctggca    55260
accacgattc ttcttttctgt cttctgaatt tgactacttt gggttctcat atactttagg    55320
agtcacacag tatttgtttt acttagcata atgtccccaa agctcatgca tgttgtagcc    55380
tatgttagaa cttcctaatg tttcaggcca aatactattc cattgtatgg ataggccaca    55440
ttttgctttt ccattcctct gtccatggac acttgtattg cttcatgttt tagccattgt    55500
gaatcatgct gttatgaacg tgggtgtaca gatagctcct ggagactctg ctttccattt    55560
ttttggctaa atacccagaa atggagttgc ttttacattc caattttaat ttaaaacatt    55620
catatcattg agtgttttac ttaatagtat agtagttaac aaacttaata aaatagtatt    55680
ttggtaataa tttgctggta gtccattgtt cagttttttt aggtaaatta cacaggacat    55740
ttcaagtgga catgaaacat cttgtgatgt ggaatcatgc cccaagctga tggctaaaca    55800
tatgaaatac cataccctaa atttagtaga tttagtcttt gcaatttagg agataacctg    55860
ttatattgtt aggttttgt cgaaaagctt tgtcctcata tttccaactt gctgtaaaat     55920
ttgtttgtga agacaaatat ttttgtatgg gttttttctt tttcatatta aaagaaatg     55980 tccacattgg aattttttg gagttttag agctaataga gcttttcata atgtagtggg      56040
aatgagtgat cagtaagctc ttagcagttt ccatgcgtgc atttctgtgc cttgaaataa    56100
atgacagatg agtacatttg tgttctgtgt gtaaaatgtg ctctttcctc attgcacttc    56160
catgttggag ggcttgtctc ttggtgatca cacttcaaaa ttctcacagc cccccttgaa    56220
ccgtttaggt gttagacggt accgacaacc agtatttggg cctgcagatt ggacagcccc    56280
aggatgaaga tgaggaagcc acaggtattc ttcctgatga agcctcggag gccttcagga    56340
actcttccat gggtatgtgg actacaggtg atgcgctaca aagtggtttg tattcagacc    56400
tggacatctt aattatatct tgcttccaa gaagaagtcc tttgatactg ttttctgagt     56460
tctgaatagc tgatgaaaat gaccaattga ggaataatca tacttttct tgatctaaat     56520 cttatacttt tgagttatct tagcataaat gtataattgt attttaagtg gaaatttgtc    56580
acttaatctt gatttctctg ttttaaagc ccttcaacag gcacatttat tgaaaaacat     56640
```

```
gagtcactgc aggcagcctt ctgacagcag tgttgataaa tttgtgttga gagatgaagc    56700
tactgaaccg ggtgatcaag aaaacaaggt gagggacata ggcttgagac gacttggtgt    56760
ttctgagctt gtgtgaggat ttaaaatcgc cctggctact gtctacttta ttgctttccc    56820
atccctgggc ctttaaattt cccctttaaa taccagctct tcccaggcct gttgttttct    56880
gcctttccag gtactaccca cagccttgag aattgcctga gttctgcctc ctttgagagt    56940
gtgccccaga caaatctatt ctgtactgaa tgtttccttg tctgatttct tggatcattc    57000
atttgatggt tgcgtatggc ctgcaacgtt tcttgttttg gttctactga actgttctaa    57060
aagtctctct tcatattatc tttttacatg taaatgtaac tgtcttcact tttaattcct    57120
caaggacaag gaatagcgtt tcacagttcg tcccatcaat cagaattata gcctttggca    57180
tctccctatc taccaggccc acttcctctt agatttgggc ttccccaggc tgttgccttt    57240
ccccaagtag cttctgcttg tcctgtagaa gacctttcat gctttgcttc tgcagcagcc    57300
gttcctgaat gccagtgtc aactgccttc ttaccacgcc caccctccct gcatgctgca    57360
tttatcccct gccacagccc tgtgaccctg tgtcctgctg cctctgactt gtctgtttct    57420
gcttggccat ggtctctgtg aggtcaggtg tgcatatggg cacaaaccag ggcatctctt    57480
tatccccagc acctggctta agtgctgctc tggaactatc tgttgaatga actaatgcat    57540
gaatgtattg ttgagtatga gacaaacaag tgtcattgtc tcctttctag ccttgccgca    57600
tcaaaggtga cattggacag tccactgatg atgactctgc acctcttgtc cattgtgtcc    57660 gcctttatc tgcttcgttt ttgctaacag ggggaaaaaa tggtgagtac aaaagggat    57720 gtgcacagtt gaaggaaata actaggtttc agaggtcagc ttggtggcct gttttttgcct    57780 tgcgtgcagc agaggaagta gaatctgagg atgagtttgg ttttcactag ccgagggggag    57840 ggaggaaatg atgggagcag gtaggttatt gggtctggtt ttgttcattt gaaaacaatc    57900
tgttgtttga ggctgaaggt ggcttgggtg atttcttggc agtgctggtt ccggacaggg    57960
atgtgagggt cagcgtgaag gccctggccc tcagctgtgt gggagcagct gtggccctcc    58020
acccggaatc tttcttcagc aaactctata aagttcctct tgacaccacg gaataccctg    58080
gtatgttaaa agttcacatc ttattttctc agatttaatc attattgtaa aaactatttc    58140
agtattgact attttagttt tagagcagta agtgttttga gttcatttgg gatatttgac    58200
ctgcgttgta gctcttcaga aaacacatga atagtgaagt tctttgtttc atgggttccc    58260
tttagatgaa acccatagag gagaaaagta gaaacctcag cacgtaagag ccaacatata    58320
tacacatcgg atttaaacct aaagcacaaa ttgtgcctgg tcgcagtggc gctgagtcgc    58380
actcagccag gccaggcatt cacactcagg gtgagtggga accaggactg gctgaggcag    58440
cagtggaccc aagtctccat cgcgcccatg cttactatgg agccttctcg ttctctcttt    58500
ttctttgggt gagagggtac acttgtgttt ttgaatttat atgaggtaag tgtgtaatag    58560
ggttttttct aatctttttt aagtggaatc tggaatttta atcagattta ttatctgaca    58620
acctagaatt ataatccaga aagtctgtgg tattgaggac atattggcaa tatgatgaat    58680
ctctaattct taaatcctga aactttttt tttttaatca cttagggtta ttatagtgaa    58740
gtcatttctg aatttggatc ttctcttcac acctctttt ctctttcctg agaattaagc    58800
ttttgtttcg agttagaaag ttgatagtag ggaattgttc catggctgag caatttatct    58860
ccacagagga acagtatgtc tcagacatct tgaactacat cgatcatgga gacccacagg    58920
ttcgaggagc cactgccatt ctctgtggga ccctcatctg ctccatcctc agcaggtccc    58980
```

```
gcttccacgt gggagattgg atgggcacca ttagaaccct cacaggtaac ggccagtttt    59040
tcagctgtgt tttttctagt tatgcttact aaggtttaag tttagatgat gatgtttgtt    59100
gcttgttctt ctggttagga aatacatttt ctttggcgga ttgcattcct ttgctgcgga    59160
aaacactgaa ggatgagtct tctgttactt gcaagttagc ttgtacagct gtgagggtga    59220
gcataatctt ctgtggaacc atttcttcac ttagtggaca ttttatcatt gctacaatta    59280
aaattggagc ttaataggaa atatttccat gcactctaaa gctgtaacca gtaatacccca   59340
ccatgtatcc atctctcagc tttagaaaga aaacgttgcc agtaaagtta atgcttcata    59400
aacttcagtt taagttctaa ttctcagaat atttgtttga aatagacctc ttcctaaagg    59460
atatatttag aaataaccta tcattaagtg taaagtctgt tgaatatgct gggcacggtg    59520
actcacacct gtaatctgac cactttggga ggccaaggtg gaaggattgc ttgagcccag    59580
gagttcaaga ctatgggcaa catagttgac cctgtcccta cagaaaatta aaaaaaaaa    59640
aaaaaaagt agctgggtat ggtggtgcat acctgtagtc tcagctactc gggaagctga     59700
ggtggagggg ggattgcttg agccccagag atcaaggctg cagtaaggcg tggttacacc    59760
actgccctct agcctgggca acagagtgag actgtctcaa aataatagt aataataatc     59820
agttgaatta aaaaaaaaaa aaaaaaaacc actgtgctag gcccatagta tggtaagagt    59880
taaagtgagc cttagggatt atttactcaa cctctgtttc tgtataaagt ggaataggct    59940
caattcttta agtgatagca tgttgaacct ttccatacca actggctcat aagtcacaac    60000
tggccagtca acaagagtaa aaattaactg gtaaaaatca agcaaaaaa cctacaattg     60060
tcaaatttgt gggataactc cccctttttaa aatgtcatgc ctgacagtaa tttctctcta   60120
gtttccaggt tttcagtcag ttgtgtcttt tttgagcaga aggaagcatg ctaagagctc    60180
aatcttgtgg ctagctgggg gtctttgtgt cagccatgca tgtgatggtg ccctggggt     60240
cttggggctg caggggaggg gtacagcagt aggggcctgt tctgttctct cgtgctgtgg    60300
agtacatagt gacatagtgg ggtggtcctt ggtgtaggtc ccttgttcct accccctgggt   60360
ctgagattta tttagaagtg gtgttggggc tgtgcggcag gcccctctgt aactgatcaa    60420
tgtttgtgaa gttgctgttt gagagttgaa accatgacat aagcagaaat ggaaggaaga    60480
aagaaccagt tatgtgaaag ggacacattt acttttaagc ttgtatttac tgagataaag    60540
tattcttaat caatgttctt gagaggtgtg ggaaaaatgc aacatcctgg ttgcagttaa    60600
acccagaaca ttgtgtgttg aagagtgacg ttctcaaac cgtcaagacg cgggtactga     60660
gtgggactaa cctgctgtcc tcttgccttg gaccttgtgt tccagaactg tgtcatgagt    60720
ctctgcagca gcagctacag tgagttagga ctgcagctga tcatcgatgt gctgactctg    60780
aggaacagtt cctattggct ggtgaggaca gagcttctgg aaacccttgc agagattgac    60840
ttcaggtaag tgagtcacat ccattagatt tcatgaacta agctcaattg aaagttctgg    60900
gatcacttga tgcaaggaat gatgttatca agtaccctgt ccatcagaaa tccgagtggt    60960
ttaggtagat gacagtgatt ttctcctccc agtggctttt tgctgaactt tgccctatgc    61020
ttggaatttt atttatttt attatttatt tagagacaag atcttgctct gtcgcccagg    61080
cttgaatgca gtagcacaat catagctcac tgaagctttg aactctagga ctcaagtggt    61140
cctcctgcct cagcctcccg attagctagg agaataggtg tgtgccgtca cactggctaa    61200
tattttttgt agaaatgggg tcttgctatg ttgcccaggc tggtctcaaa ctcctgggct    61260
tgattgatcc tccatcttgg cctcccaaag tgctgggatt acaggcatga gccactgtgc    61320
ctggcctaga attttaaaat ataagtagaa gagtagattt tttttttttgg tagtcctcgt    61380
```

```
catttaagta ttctggatag tgggaataaa agagcttaga attttcatc tttgtcttaa    61440 acttttaaaa aaatgtagct tatattaatt ctgcttgttt aaaaagaata tactcttcat    61500
tatactgaac ctaggtaaga cagctggttt atattttgtt gcaattaaaa aacgtgagct    61560
gtggttgcag tgagccaaga ttgtggccat tgcacttcag cctggcaaca gagtgagact    61620
tggcctcaaa aaaaaaaaaa taacatgagc tgtgttggca ctttcatttt ctaagagtag    61680
ttttggctgg agaagttttc tttcagtact ttcttttaga agggaaattt cctttataa     61740 tttagggttt gttttttttt tttccaagcc accttttata gagcccttgt gggttatttc    61800
atttaatcct tagaatgttt ataaatctgg gcttgttctc ggctccaccc acagataggg    61860
acgctgagcg tgcatgagtg ggcagcaaga tagcaggtta tggagggccc agctcacccc    61920
ttctgtggct tgagccaatt ttatagggca cttacagagt cttttgaaat agtatttatt    61980
ttgaagaaaa agaaaaacag tttactgagt actgtcttat tgagtctgga attgtgagag    62040
gaatgccacc tctatttatt taaagccatt ggcctttttt gttgttttga gtaagtgctg    62100
cccaaggtcc ttccagggca cctggatgag cctgctctgg agcaagctgg cggtaagtgt    62160
ttactgagta actaaatgat ttcattgtta aatgtgctct tttgttaggc tggtgagctt    62220
tttggaggca aaagcagaaa acttacacag aggggctcat cattatacag gggtaagcgg    62280 tttattttg tgagatgctg ttttaccttc aagaaggtga aagtgaggct ttccttgtgg    62340
aatttctcta aatgcattcg tcatgttta gatgtttatt tcacagttta tatcatgaaa    62400
gttataatct tgtcatatgg atttaagtct agtaatgttg agttcttcct cactagcttt    62460
ccaaaatatc ttacctaaaa tttagtcaaa tacaagatta tgtttatttt tattatcctt    62520
ctctctaaag cttttaaaac tgcaagaacg agtgctcaat aatgttgtca tccatttgct    62580
tggagatgaa gaccccaggg tgcgacatgt tgccgcagca tcactaatta ggtatttacc    62640 aatatttat ctcttttcct tttttggttg aagtactaaa agatacgaga atggaaagag    62700
agggaagaat tcaaaggatg tagagcagta ttcctgaatc tgagctcatt tcagccattc    62760
tattcttaaa ctataatgaa aaaaaaatcc aaaaaagtct aaaattataa ttaaaaaaac    62820
aacaaaatac taactgtcca ttgtaaaaag taatgcactt tcattgtaaa aattttggac    62880
tatagagaat agtactaaga agaaaaaaaa aatcaccttc aattctgctg ccacctggag    62940
gtaatcactg ttaatatttt gctatatact ctatgagttt cttgttcaaa atcaggtcaa    63000
aattacatgc aattttgtaa tctgacaatt tccacttaat attttattag cattttcctg    63060
ttatgaaaca gtaattttag ttatgggtcg ttgttttgct atgcggttgg gataaaattt    63120
tatatacttt ttttggcaat tacttattat acataaatgt ttgtgtatag ttttctttt     63180 ctgagaattc ctggaagttg agttaccagg cccggctttg aatttttttt tttattttt    63240 ttttgagaca gagtcctgct ctattgtcca ggtgctatct cggctcactg caacctctgt    63300
ctccctggtt caagcgattc tcctgcctca gcctcccgag tagctgggat tacaggggca    63360
caccaccacg cccaattaat ttttgtattt ttagtagaga cagggtttca cgatattggc    63420
caggctggtc tcgaacttct gacccgtga  tccacctgca ttggcctccc aaagtgctgg    63480
gattacaggc gtgagccatg cgcctggcc aggcttaaa ttaaaacaa atcttctaat      63540 agctttatgg aggttataat ttacatttct tgaaatgtac tcactttgag tgtatagtaa    63600
actccaattt tatcacattt ctgtcacccc aaatgtatcc ttgtgcccat ttgctgtaac    63660
ctccggttcc tgccccaact cctaggcagc cactcatcta ttttctgtcc cttaagattt    63720
```

```
gtgttttcgc caggcgctca tgcctgtaat cccagcactt tgggaggccg aggttggtgg    63780
atcacttgag gtcaggagtt cgagaccagc ctggccaaca tggtgaaacc ttgtctctac    63840
taaaaataca aaaattagtc ggatgtggtg gcacacgcct gtaatcccag ctactcggga    63900
ggctgaggca ggagaatcac ttgaacctgg gaggcggagg ttgcagtgag cagagatcgc    63960
gccactgcct tccaacctgg gcaacagaga gagactgtct caaaacaaac aaagatttgt    64020
attttctgga cattttatag tactggggtc atagtataga tggacttttg catttggctt    64080
cttttactta attgtgagat tggttcttgt tgtagcatgt atcagtagtt tgttcatttt    64140
tattggcgaa agtattctat tatatgaata ataccatatt ttatctatcc atcagatgga    64200
tattatagag ttcatgtttt ggctaattta tgaattatgg tactgtgaac atttgcctgc    64260
aagattttgt gtagacatgt cttcatttct cttgagtaga tcacctagaa gtggattttt    64320
aaataatttt ggtacttact gtgaaactgc tcttcaaaaa cataccattg ttccttcctt    64380
ccttccttcc ttccttcctt ccttctttcc ttcctccctt cctccctccc ttccctactt    64440
ccctctccct ttccctttcc cttccccttt tcccttcccc ttcccgcctg cctgcctgcc    64500
tgccttcctt ccttccttcc ttcgtttctt tctacatata cacattttt taaatttcaa    64560 tggttttgg ggtacaagtg gttttggtt acatggctga attttggtta catggtgaag    64620
tctgagattt tagtacacct gtcacccgag tagtgtacct tgtacccaat atgtagtttt    64680
ttgtccctca ccttccagcc ttccgccttg tgagtctcca atgtccatta taccacactg    64740
tatgcccttg cgtacccaca gctcagctcc cacttctgag aacatatagc agaaacatgc    64800
caaagtatac tcccactacc agaatgtgat tgtgcctgat tcttctcacc agtacaaata    64860
tttcaaaaaa agttaaatat gtatcagttt tttgggcaga agttgatact tctctttatt    64920 tatttattttt ttttgagata gggtctcatt ctatgatgcc caggctggag tgtggtggtg    64980
cgatctcggc tcactgcagt ctctgcctcc caggttcaag tgattcccac gtcagcctcc    65040
caggaagctg gaattacagg cgagggccac cactgccagc taattttgt atttttggt     65100 agagatgggg tttcaccatg ttggccagac tggtctcaag ctcctgacct caagtgatcc    65160
acctgccttg gccttccaaa gtgctgggat tacaggcgtg agctaccaca cccggctgat    65220
atttcttttt aaaataactt accttctttt gaaagtaata catgtttaat gaacagaatt    65280
taaggaaaat ataaaaaaac gaaataatct ttgtaatcaa actactgaaa agaaaaccaa    65340
agttacattt tggtgcatat tcttttcat tttcatcatt gtaatttgca tttctttgat    65400
tacttgtgag acactccttt catttactta ataggtttat atgacttgcc tattcagaga    65460
ttttgcagct ttaccatttt ctgcaaatga tagcaacttc tttttgtttg tttgtttgtg    65520
gagacagagt ctcgctctgt cactcaggca ggaatgcagt ggtggaatct tggctcattg    65580
caactattgc ctcctggggtt caagcgattt tcctgcctca gcctcccaag tagctgggat    65640
tacaggagtg tgccaccatg cccggctaat ttttgtatct ttagtagaga tgggggtttg    65700
ccatgttggc cgggctgatc ttgaactcct ggcctcaagc ggtccccctg tctcggcctc    65760
ccaaagtgct gggattacag gcgtgagcac cgtacccagc cagtagttac ttcttatatt    65820
ctagaaaaaa ttctactcat gatcaagtct ccatgaggaa agagacttta attgaagatc    65880
atggggcttg cagaccaata tgataaaata gttcattgtt tctaaaagta ttactgagtg    65940
ttgatggcag atatgaaccc ttttgttttt gtaggaaaat gttacccgta ttctccattt    66000
gaattcagtt tagatttgtt aggaatcgca gcttaagctt tgccatctgg gagtgtttgg    66060
gacagttttg cagacaaaat tgcaaaagtg cctaaggaat gcagctggca ttcagacctg    66120
```

```
ctctgtgctc agtactctgt ggacagacac tgttcagcac ttgttgatca gaaggtttag   66180
aaagagaact ttcaaagttg gtttttaatt aaagcattta atagtgtaaa tagaaaggga   66240
ttaaatttta tgacagacaa aagaaagtac agcacccagc tgggcgtggg ggctcacgcc   66300
tgtaatccag cactatgggg ggctgaggtg ggtggatcac gaggtcagga gttcaagagt   66360
tcaagaacag cctggccaag gtgatgaaac cctgtctcta ctaaaactac aaaaattagc   66420
cgggcgcggt ggcaggcgcc tgtaatccca gctactcagg aggctgaggc aggagaatca   66480
cttgaacctg gacggcagag gttgcagtga gccaagattg caccattgta ctccggcctg   66540
ggccacagag tgcattctg tctcaaaaaa aaaaaaaaaa gaaaaaaaga aagtacagca   66600
cccagttatg tccgagtggg tgcatgagag tgaccctgag attggagaca acgctgtcac   66660
gtgcttgaag aacgccacct gagaaagggg gcgagaagtg gtgtccgctg gtaaccagag   66720
gtgttggctt agccatctgc agggaggagg gtggtctatc acaggtgagt ttcatctact   66780
ttcttaagca aattaacctt acttttgtgt taggcttgtc ccaaagctgt tttataaatg   66840
tgaccaagga caagctgatc cagtagtggc cgtggcaaga gatcaaagca gtgtttacct   66900
gaaacttctc atgcatgaga cgcagcctcc atctcatttc tccgtcagca caataaccag   66960
gtatgctgac ccagtggcat cttcacattg tcgggaaaat gccctttcct gatgcctttc   67020
tttaggcttt aattgaaaac attttatttt ctagaaaaaa gcttcagctc aggatgtttg   67080
agtgtaggtc agtcctttga taggatatta tcattttgag gattgaccac accacctctg   67140
tatttaagct ctgccacaat cactcagctg tgacactgta aatctcttaa tagtttatta   67200
cattccatgt gctgacagtt gtattttgt ttgtgacact tacgtattat ctgttaaaac   67260 atttcactt tagttgtgtt acctttaaag aggattgtat tctatcatgc ctgttgattt   67320
tttggtgagc gggctattaa agtcagtgtt atttagggtt atccactagt tcagtgattt   67380
gcgagattat cattcacatt tattgtggag cttttgaata tcgtgtcaaa tggcccacata   67440 tatcccattc ttatctgctt cttaggtgag tgggacacag tgctttaatg aagctataat   67500
cttcagaatt ctagcttgca gagaagattg cagaagtgat aagacttgtg cttttttaatt   67560 ttgtctttta aatgttattt taaaaattgg ctttatatga tactcttttt ttctgctgag   67620
taacagtgtt ttacaaaact tggactaaat gacttctaag cttaaatgat cacttgatgc   67680
tttttttctg aattaggaac tcagcttatc aaatatcaaa gtcataattc ctgaataaat   67740
aacgtctttt ttcatgtaaa gactgcttta aaaacacat ggaaggctgg gtgcggtggc   67800
tcacgcctgt aatcctaaca ctttgggagg cccaggtggg caggtcgctt gagctcaggg   67860
gttcaagacc acccagggca acatggcaaa acccacctct actcaaatac aaaaaattag   67920
ccaggcgtgg tggcgggccc ctgtaatccc agctactcgg gaggctgagg gatgagaatc   67980
acttgagccc cggaggcaga ggttgcagtg agccaagatt gtgccattgc actcccagct   68040
tgggctacag agtgagactc tgtctcaaaa aaagacacac acacaaacaa aaaaacatg   68100 gagacatttt tttggccacc ttaatatttc ccctcagata atttcctttg tttaaactca   68160
gaactggcat tttctctctt ggagaagatt caggacaaat actcctttaa gataagtaga   68220
agcagtgaaa gaggatttga ttatcaggaa tttgataagc ttagaataaa ttgttgcttc   68280
ttaatgtcat ttcagaagat gaatatttat taatagatgc caactgagat atcattaaaa   68340
ttgattacta actactactt ggaaaagtct cccagttcca aacttcagca ggcctcttga   68400
caattcagct gtggtcaatt gggtcttgcg tgatagatac aatgaccaat tgtgcagcag   68460
```

```
agtgtgctgc ttagctgcct attctgttag cattcatgtg ttaacttaaa atcataatct   68520
ccttagtttt gttgagtgtc tccgtggaca agacactgtg agggatacaa aatcagattg   68580
gctttattca aaccactggg gtattataat tcatttataa tttattttat tttttgcctt   68640
ttttccatgt gttctaaagg aattagagtt tgtatataac tataatgggg gatagaaatt   68700
gacatgtgcc atgaagggaa tgcaaaaaag tgccgtggga gatgagaagt ggagaaagga   68760
atttcttttt tcttggaagc aggaataact tcatgaagca tgtatttcaa cttaaacaga   68820
tagtaggcaa cgctgtaagg ggagtatggc tgcagcaaaa gtgttcgggg cagactggga   68880
ggaagggagg gaataaaattc agccattgtt atggaataat gatcaaaatt tattttcagc   68940
ccgtttcact taaaagttga gactgcttaa cttttttttaa tctttaatct taaacttttta  69000
aatgccattt gatctttaaa aatatatgtt ttaatagtgt attttaagtc tctatatttt   69060
tgttattaga atatatagag gctataaacct actaccaagc ataacagacg tcactatgga  69120
aaataaccctt tcaagagtta ttgcagcagt ttctcatgaa ctaatcacat caaccaccag  69180
agcactcaca gtaagtctct ttcttgatcg gtccttactga cattgtaata gttttttggta 69240
gcttgtatgg ccagttagtt gtatggtcat cttacggtga ggtgcttgtc ttacagctct   69300
tacttatcca tgaggcttgc taagaaattg tgcttctgtg aaaagaatct cagcttactc   69360
caggaatgta aatgactatg ttttttctga ttattaaagt aatacacgcc caaaataaaa   69420
aaattcagcc aatttaggaa gacacaacaa ttaaaataag ccaggcatgg tggctcatgc   69480
ctgtaatccc agcactttgg gaggccaagg ttgggggctc acttgaggtc aggagtcgga   69540
taccagcctg gccaacgtgg tgaaaccccca tctctactaa aaatacaaaa attagctggg  69600
cgtggtggcg ggcgcctgta atcccagcta ctcaggaggc tgaggcagga gaatcgcttg   69660
aacctgggag gtagaggttg cagtgagctg aggtcaagcc actgcactcc agcctgtgca   69720
atagagcgag actctgtctc aaaaaaaaaa aaaaaaaaag aaaagaaaaaa agtaaactac  69780
tgtcacctgc attggtaatg tatcagaagt ttaaaatgtc tagattataa ttaactcagt   69840
gacctggtaa tatatactaa gggaaaaata tttataattt acattttttac atttttatttt 69900
tttttaatttt attattttttt ttttgagaca gagttttgct cttgttgccc aggctggagt  69960
gcaatggcat gatctcagct caccacaacc tccacctccc gggttcaagc aattctcctg   70020
cctcagcctc ctgagtagct gggattacag gcatgcacca ccatgcccgg ctaattttgt   70080
attttagta gagacagggt ttctccatgt tggtcaggct ggtctcaaac tcccaacctc    70140
aggtgatccg ccctcctcga ccccccaaag tgctgggatt acaggtgtga gccaccatgc   70200
ctggccttac attttttataa taagaattta tgttgctgac attagaaaag aaccataata  70260
tccaagaatc caagaataat taaattatgt acatatgcta gtatatagtg tgatgctttg   70320
gagaatttt aacaatatgg agatgtataa tctggattgt aatattgagt gaaaaaggc     70380
agaatacaaa cctggtgggg gtatagtcgg atttcagtta agaaaaataa tatttacata   70440
tatacatttc tcacactggc agataatcac caagataaat tttgggattg tggatgattt   70500
ttttcttctt tatatttttc agatattctc aaattttcta aaatgagcaa gtataacttt   70560
tgttatcaga aaaaaataat atacaaaagt aatgttaatt tgctggtgac caggttaaac   70620
ctttttattt ttatttttttg agatggaatc tcactctgtt gcccaggcta gagcacagtg   70680
gcatgatctt ggctcactgc agcctccgct tcctgggttc aaatgattct ctggccccag   70740
cctcctgagt ggctggaatt acaggcgtgt ggcaccacac ctggctaatt tttgtatttt   70800
tagtagaggt agggtttcac caggttggtc aggctggtct cgaactcctg acctcgtgat   70860
```

```
ccacccacct cggcctccca aagtgctggg attacaggcg tgagctactg cgcccagcca    70920
gacctttta  ttttatttga caaaagaaat acttccatgt tatagaagac taaatattgt    70980
ttgggctgtc tgcagtatgg tcttcccttg atttgttcaa aatatcgtaa actttgctta    71040
tttattttta ttgtggccga ctgtgtcggg cactgttgta ggcttgggat ggaaaaacag    71100
gattcctgcc cttagggttt ctgcaggctg gtcagggaga cgatgtggta agctggagct    71160
cagctcctaa ggatgtgcag gggcagttga gaggcggaag ggtgggagat cattccaggg    71220
tgtgggcagc acaggaacct ctcttcattg ggatataatt gccattctga taacacgtgt    71280
ttgaggtgtc taaagtagga agttgtacca tggtgggaca gatatcctgt ggttatcata    71340
cacagatctc agtttcttc  tcattgtttg tacttttat  aaagggtaac aggagatata    71400
attcaataaa cctttgtggt gtttgggtgt gattttattg tttctttctt ctcagtttgg    71460
atgctgtgaa gctttgtgtc ttctttccac tgccttccca gtttgcattt ggagtttagg    71520
ttggcactgt gggtatgtat tttcctcagt atatattaat agttgctac  aacagtatga    71580
cataaacata gttattagga tgccctttt  cttctttt   aagtctttta tcaatttggc    71640
ttttggaaa  aatatctgat ggaatacttg tttctgctat attagctgtg tgagactagt    71700
gacaggagct gtgggaaatg aatgccaaat gttcttaggc attgatggga atttcagggt    71760
gtggtcttca agttcattta agggaatttt catatgctgg caaaaggctt ttctcattag    71820
cttgactctt tccaaaatta tttgctgtga attagaagtt taggaacctt ttttcactta    71880
attgtgacct agcatacgaa atggtgatga tttaggaact actgttcttg tattaacagc    71940
ttttatttaa aaatgatttt cctccagtag atggccctac tagcatctgg gaaataattt    72000
caagtcttct ccagcattca ggaataggct ttcattttgt gtatcaatta ctgagaatga    72060
ttttggtgac tcacatcaca tttgagaagt aaacctgcag atttcttgtg tgtgtcagca    72120
aatgaccaac tgatatttgc ttgaagtgga ttacattatc tgctctagaa tgattgcttt    72180
cccaccttcc tcacatacag actgagcagc tacggtttct aatcataggt ctggcactag    72240
acttcacttc tgggcaactt tggcattgga gtaaaatgta ttaatttaaa gaaagttaaa    72300
aatccgttca agtaaacata cagttctaat acttttaca  atttaaaata tagatttaaa    72360
tgataaaata aaaagaaaa  tatgggtaga caccataatc ctcgtttctg catctgttca    72420
caaggggttg atatttatga gttctattct ccatatccat tctatgttct cttaatgctc    72480
agtcagcacc tcaggtggtt ggagttcaat gcttggtagt ttgacttaca ctgtcttttc    72540
tagggattg  agccctgggt agtcctgctt atttgaggtt gcaatttgtc tttcaataac    72600
tttactaca  agatatggcg tgttaaagga taccattggg gaaccaacat aataatatca    72660
ggaaaactaa ccacgtcaga cctgccccat tgtgtatcaa gtacactatt tttccatagt    72720
aataaagagt tcaccccagc caattctctt ttattttgtg cctgtttact caatggcatt    72780
aacatgccca aatgtctggg tagctgtctc atctccagtt cagcagaacc attgtcatat    72840
gccctagtaa aagcattcct tcattggaca cttaggcccc aatactttca ttcagatcta    72900
ctacctgatt tcatttctca aatgattttt atggagctct gatttatagg aaagatgtta    72960
gttgattaaa aataaaacaa tttctgagct ggtataaaat gtattgtgac atgccttcct    73020
cttggaattg caagagaaag gaagactgtt gtttgcttaa aaattgtcta taatttgact    73080
ttgcaaatgt ctgcttccag agtgcctcca ctgagtgcct cagatgagtc taggaagagc    73140
tgtaccgttg ggatggccac aatgattctg accctgctct cgtcagcttg gttcccattg    73200
```

-continued

```
gatctctcag cccatcaaga tgctttgatt ttggccggaa acttgcttgc aggtactggt    73260
actgagttga acagggact ccaggacttg gattttgatt tccttagggg aatgggggt     73320 ggtgagcata tgaggggaaa atactataag gtcattgcca gtgatggctt gtcccttag    73380 tcaaatttca gatgttacct atatgcataa acacatgcag ttggcagctg ttctgtgctg    73440
agtattttaa agtagcctct tcccaatata gcccctcagt taactacaag taaactcatt    73500
ttgaatttca ttttaatggg caccatatgc cagtactccc tcgggcactg ggatgttaag    73560
aaagtataat gtatggactt cattctcaag ttagttttag attagagggg gatacacgta    73620
aacaaaagtg cagtggtcac acagagtggc cctaatcact ctccttgggc agatttatgg    73680
gctggtagga aagagcacaa cacggagagg gtgtagcacc ttggcgatga taatggagga    73740
tgtggccagc aaggaagacg gagtccattg aaattgattt tgggagaagt tgccaatctc    73800
catgaaagaa ttggggcctg tgctatttgc ttcagggggc tataggagag tttcgtgaaa    73860
gggactaaaa gatgagtatt ttaataagat cattcatcca acttgaacat gggctggagg    73920
agaaggtagg gagactcagg agattaatgt tgatgctaag gcaagataat ggctttggga    73980
ctgtagggaa gacactgatt gtaagagaat gaaggaggca gaattgccag gcctggttca    74040
ccaactgaac ttcggttgtg aagacaaaga aacctgggat gacttcacat cctgggcagg    74100
tgtgtggtgg tgacagtcat ggaaattggg aacacagatt tgtgcgggaa acatcagttt    74160
cagtttgagt ttggcttatc agttgaatat caggcacaga tgtctggcca actctcaaca    74220
tagggtctta aatgacttca gttccccaag caatttgtcc ttcccatgct attggggtgg    74280
agaggtaatg tctgtgccca tatcacagcc agtgctccca aatctctgag aagttcatgg    74340
gcctctgaag aagaagccaa cccagcagcc accaagcaag aggaggtctg gccagccctg    74400
ggggaccggg ccctggtgcc catggtggag cagctcttct ctcacctgct gaaggtgatt    74460
aacatttgtg cccacgtcct ggatgacgtg gctcctggac ccgcaataaa ggtaatgtcc    74520
cacttgggtg ctggattcat acagccttaa tgactatggg tttccagact accttttgttt    74580 agtaatctgt cccttcttta ttctcttttt gctttaaatg aacaaaattg ctcagattgt    74640
gacactaaat ttaacatcaa aatgtgacca tgtggatggg tgcagtggct cgtgcctgtt    74700
attccagcac tttgggagac tgaggcaagt ggatcacttg aggccaagag ttcgagacca    74760
gcctgggcaa catcacgaaa ccccctctct actaaaaata caaaaaatta gatgggttgg    74820
gccgggcgtg gtggctcaag cctgtaatcc cagcactttg ggaggccgag gtgggcggat    74880
cacgaggtca agagatcaag accatcctgg ctaacacagt gaaacccgt ctctactaaa     74940 aatacaaaaa aattatctga gcatggtggc gggcgcctgt agtcccagct gctcgggagg    75000
ctgaggcagg agaatggcgt gaatccggga ggcggagctt gcagtgagcc gagatcgtgc    75060
cactgcactc cagcctgggt gacagagcga gactccgtct caaaaaaaaa attagatggg    75120
catggtggtg cgtgcctgta atcccagcta cttgggaggc tgaggcaaga gagttgcttg    75180
aacctgggag gcggagttg cagtaagcct tgattgtgcc gctgcactcc agcctgggtg     75240
acagagtcag actctttcca aaagaagaaa aaaatgtgac catgtgtttt atagctcttt    75300
tagtatcatc agtcactgtt atccctaaga gggaaatacc tagctttagt tttaggtttc    75360
cagcattagc caagaaagct cagaattgat gttcctggcc aagtacctca ttgctgtctc    75420
cttaaatctt ggttaatggc tactgtcctg gctagcatag ttatggagca tttccatggt    75480
tgtagaatgt tctgccaatc tcagggacag ttttgctttt ctgtgaagca ataaaatcaa    75540
cttcaaaaca aatgttaact atttgtacaa tggatttaag atagaccagt tcacatactt    75600
```

```
tttttttttt ttttttttga gatggagttt cattcttgtt gcctgggctg gagtgcaatg   75660
gtgtgatctc agctcactgc aacttctgcc tcctgggttc aaacgattct tctgcctcag   75720
cctctcgagg cagattacag ctgggattac aggcatgcac caccacaccc agctaatttt   75780
tttgtagttt tagtagagac ggggtttcac catgttggtc aggttggtct caaactcctg   75840
acctgaagtg atctatccgc ttcggcctcc caaagtgttg ggattacggg catgagccac   75900
cacgcccagc ctaagataga ccagttcact tactgtttat atctgattac tctctctttg   75960
ccttgtcttc tacctttaaa aatctcccta ctaacttccc attctccttt agctgccatc   76020
agtcttctcc cttctctgca aacatctctg gagagtccca gcctcagccc acagagcttc   76080
ccactgctct gaggtggacc ttgtttgcaa ggcttctttg gctctcttgg cctggaccct   76140
gtctactact tcagccatcc ttccttaacc cctgctggtg gtttctgttg ccacactcca   76200
tagcagcgtt tcccgcccag atcatgtctt tacatctctg ggcactgctc tggtcctgcc   76260
tgcctttccc tctttgtatc ctgcaggctg ctacccccat cttgagtgtc tcttcagtt   76320 ggctttcaga gggcctcctg ggtgttccct tacccacttg ccactcccca gtcactgggt   76380
tcagtccttc ctgcccacca gcacatgctt tctaggctct gtcctaggcc gtcttctctc   76440
tttgtagtct ctgggccagt gctgttctag agagtggcag aattttctat aaccatggca   76500
gtgctccata gctatgccag gcaagacagt agccactaaa cacatatagc tgttgagccc   76560
ttgaaatgca gctagtgtga ctgaagaact gaaccccgat tcggtttaat tttcattaaa   76620
tttaaattta aataacctta tgtgggtagt ggctccagta ttgggcaggg cagcctgaga   76680 gtcgggggctg ttctcctgtc ttcagtgtct agatgaggga cctcagagga cctgtctctg   76740
gagctgcagt tcaatgtagc cagctgcccc gtgacactta catatagctg atttgtggat   76800
atgtcagaca cggtgtgatg agctcagctt tctgtcctcc tccccacatc tgccctgcc    76860 ccatttaccc cactttgtgt cttatcaagc tagaaacagg tcaccacaag tcttcatttc   76920
cactcaccaa gtcttttgtt tcccctacta aatattttgc gagaagaaag tgtgtacctt   76980
tgtattcaca tacatgtaca tgcacatata catgcacata tgcagggggtc cccaacctct   77040 gttaaaaacc ggactgcagg ccgtgcgtgg tggctcacgc ctgtaattcc agaactttgg   77100
gaggccgaga ccagtgcatc acaaggtcag gagatcgaga ccattccggc tcacacggtg   77160 aaacccccgtc tctactaaaa atacaaaaaa aaattagccg ggtgtggtgg cgggcgccca   77220
tagtcccagc tacctgggag gctgatgcag gagaacggcg tgaacctggg aggcggagct   77280
tgcagtgagc cgagattgtg ccattgcact ccagcctggg cgacagagcg agactctgtc   77340
tcaaaaacaa acaaaacaa aaaaaaaaa aaccaggctg cacaggaaga agtgagcaag   77400
cattaccatc tgagctctat ctcctctcag gccagtggtg gcattagatt ctcataggag   77460
cgtgtatgag ttcgttctca cacttctgta aagacatacc tgagacatat aaagaaaaga   77520
ggtttaattg gctcacagtt ctgcaggctg tacaggcttc tgtttctggg aaggcctcag   77580
gaaacttgca gtcatggcag aaggtgaagg ggaagtaggc acatcttcac atggcccaca   77640
ggaaaaagag agaaggagag agagagagag acagagagag agagagaaaa agaaagattg   77700
agagggagag aggagggaga aaggagagtg cctgtagggg gagttgctac acaaaggagc   77760
accaggggga tggtgctcaa ccattagaaa ctaccccccat gatccaatca cctcccacca   77820
ggccccacct ccgacactgg agattacaat tcagcatgag atttgggtgg ggacacagag   77880
ccaaaccata tcagagcatg aaccctattg tgaactgcac atttgaggga tctaggttgc   77940
```

```
atgctcctta tgagaatcta atgcctgatg atgatttgag gtggaacagt tcatcccga    78000 aaccatcccc cgccaaccct ggtttgtgga aaaattgtct tccacagaac cggtccctgg    78060
tgccaaaaag tttggggacc tctgcacata tgcatgcacc tgtacatgga cacataatac    78120
atgtacatat gcatacttta tattctctgc cacttctggt ccagactgat atactatctc    78180
atttggatta ctgcactagc cttttgtttt ggaaacagca tttttaaaa aatttaattt     78240 aattttttg agatagggtg tcattctgtt gcccagcttg gagtgcagtg tcatgatcat     78300
agctcactgc ggcctcgatc tcccaggctc aagtgatcct tctgcctcag ccttctcagt    78360
agttgggact acaggcatac ccaccatgcc cagctaattt tttgattttt tttttttttt    78420
gagacagagt ctcagcctgt cgcccaggct ggagtgggtt ggcgcgatct cagctcactg    78480
caacttctgc ctcccaggtt caagtgattc tcctgcctca gcctcccgag tagttgggat    78540
tacaggcgcc tgccaccaca cccagctaac tttttgtatt tttagtagag acggggtttc    78600
accatgttgg ccaggctggt ctcgaacttg tgacctcgtg attagcccgc ctcggcctcc    78660
caaagtgctg ggattacagg cgtgagctac cgctcccagc caggaaacag cattcttgag    78720
ataattcata taattcaccc atttaaagta tataattcat tctctttagt atgcccacag    78780
agttgtacag ccatcaccag aatcagtttt agaacccata aaggaactct gtactcttta    78840
cccaaaacct ccatgcctcc agctgcaggc agccactaac ctgccttctg tctctgtgac    78900
tctacgtctt ctggacatta ctgtggatgg gctcatacag tcagtgagct tgtgactggt    78960
gccttctacc aagcagggtt ttcagtgtag cagcctctct gtttttcttt tttttttaaa    79020
ttgtgacgga acttctgcct cccggggttca agcgattctc ctgcctcagc ctcccgagtg    79080
gctgggacta caggcccatg tcaccatgcc tggctaattt tttttttttt tttttttagt    79140
agagatgggt ttcaacatgt tagccagggt ggtctcgatc tcctgacttc atgatccgcc    79200
tgcctcggcc tcccaaagtg ctgggattac aggcgtgagc caccatgccc ggctaacctt    79260
tcatttactg tctgcatttc ttccctgatg ccttccagtc catgcacccg attgtagcca    79320
ttcatcctat tatggtttaa ggtgactgtc ttagtcagca tgggttgcca taacaaaata    79380
ccatagcctg ggtggcttca acaacagaat ttacttctca cacttctgga ggttgggaag    79440
tccaagatcc aggactttcg ccttgccctc atgtggtgag ggggtgagga agctctgtgg    79500
ggcctcttat atatggatgc taatctcatt catgagggt ctgccctcat gacccagtca     79560
cctcccaaag gccccacctc ctaataccat caccctggta attaagtttc agtgtataaa    79620
tttgggggac tatagacatt gaaaccataa caagcacttt tctaagatca gggagtgagt    79680
aagtagcaga gctaggacct caattccaca tgtcagtcat cttgccttca ctctgctcca    79740
tgatggctgc ctcctagagc attgggagtc tcgatgttct atatgctctc atgtgttgtg    79800
tattggagat agttgaggct ttatgaatac atctggattt gttgacttct agctttgctg    79860
gtaaccagct gtgaccttga ataagttact tcatctctga gcctgtttcc tctttagaa    79920 acaggagttt aaaatgctgc tttgggttgg gcacggtggc tcatgcctgt aattccagca    79980
ctttgggagg ctgagatggg aggatcactg gagcttggag ttcgagacca gcctgggcat    80040
catagtgtga atcctgtct cctcaagaaa ttaaaaaatt agctgggtga tgtggcgtgt     80100
gcctgtggtc ccatctactc tggaggctga ggtgggagga ttgcttgagc ccaggaggtt    80160
gaggctacaa tgaaatatga ttgcacccca tcctgggtga cgagtgagac cctgtctcaa    80220
aaaagaaaaa aaaatgctg ctttgtaccc ctttcatgtc atggcgtcat ggccaacata     80280
gaatgccctg gttgtttgct gttggagggc atgggcctgg gggctccctg agggctcctt    80340
```

```
ccatcttcaa ctcattctct gtgcacctgt taggaagttg tgggccagtc cctaccatgt    80400
atcattgtgt gggtaaaagt aaataaaatg tgtacagtgt ctgaactgta catatcaggg    80460
tccaagaaca aaatgagtga catgggttag ctcttttaa taaatggtaa aaccaaatat     80520
tctaattttc agttttgtta tacttccatc acatgttttt gttttttgt ttttgtttt     80580 tgttttcta ttttaggcag ccttgccttc tctaacaaac ccccttctc taagtcccat      80640 ccgacgaaag gggaaggaga aagaaccagg agaacaagca tctgtaccgt tgagtcccaa    80700
gaaaggcagt gaggccagtg caggtaggaa acagcgtggg aagggaggg acatgagtgc     80760 agcatctgtc atgtagaaac ataggattta agtaacttgg tgttttagag aaataaatat    80820
aatacacatc agtaaagtga gagaaagttt ctccaggtgc ggttcaagat attagaaact    80880
aatgactgat gtacacagac cacctttgg tctgaagcat ttctaagtgc cactggctga    80940
catgcagccc ctacagcctc caggcttcca gccctagcat ggagcatcac tctcctatgc    81000
ttccctggtt gcaggtgatg gctggagagg cctcctgatt ttcagtaagg gaagtggtgt    81060
agatgcttag gaatagatgt agtgagtgaa aaaactgatt ctgatatgtc aaaaattctg    81120
attggaaatg gaatatttac atttggaaga gctaaaggcg agagaaagtg gggataaagt    81180
catctgagtt ggaggagctt aaaccattca caagtttgga ggaccttttt ttacccatga    81240
aaaggtcaga acagaagggg ctaggattta ggtgtgactg cagtttattg aattcccatc    81300
catactgctc tcggtgggca gtggcagggg caggagagga gcctggcaaa gcatgaagtg    81360
actgctgctg cctctgctat ctgggacgcc tggccacctg tctgtacagt ctccctccag    81420
acccattctc acgctgtctc ttggcaccca ggggccagtg atggttctcc catttgtttt    81480
gtgtatatag catttatatc aaggctattt atttatttat ttattttatt tatttatttt    81540
tttgagacag agtctcactc tgtcacccag gctggagtgc agtggtgcaa tctcggctca    81600
gtgcaagctc tgcctcctgg gttcaagcaa ttctcctgcc tcagcctcct gagtagctgg    81660
gactacaggt gtgcaccacc acacctggct aattttttgt attttttatt agtggagacg    81720
gggtttcacc ttgttggcca ggatggtctt gatctcctga cctcgtgatc cgtccacctc    81780
agcctctcaa agtgctggga ttacaggcat gagtcactgt acccggccta tttatttatt    81840
tttaattgac aaaattgtat atatctgtaa tatacaacat gatgtttgaa atatgtgtac    81900
attggccagg cgtggtggct cacacctttt atcccagcac tttgggaggc tgaggtgggc    81960
ggattacgag gtcggggggtt aaggccaaa ctggccagca tggtgaagag gtgcccctac    82020
taaaaatacc ccaaaaaaaa aaaaaaaaa aaaaagccgg gcatggtggc tcgcgccagt     82080
cgtcccagct acttgggagg ctgaggcagg agaattgctt gaatctggca ggtggaggtt    82140
gcagtgagct gagttcatgc cactgcactc tagcctgggc gatagagcga gactccgtct    82200
caaaaaaaaa aaaaaagaa gaaatacata tgcattgtgg aatggctaat taacctgtgc     82260
atcacctcac gtatcattgt tttgtggtga gaacacttaa aatctactct ttcagtgatt    82320
ttcttgcata tggtacattg ctattaactg cagtcaccat gctatacagt agatctcttg    82380
aactcattcc tcctgtctat aaatgaaatt ttgtatcctt gaccaacaca ttcaaggttt    82440
tttttgagat ggagtcttct tcacccaggc tggagtacca tggcacgatc tcatctcact    82500
gcaacctccg cctcccaggt tcaagcaatt ctcctgcctc agcctcctga gtagctggga   82560
ttacaggcac atgctactgc acctggctaa ttttttgtatt tttagtagaa gtggagtttc    82620
accatgttgg ccaggctggt ctcgaactcc tgacctcaag tgatccgcct gccttggcct    82680
```

```
gccaaagtgc tgggattaca ggtgtgagcc actgcacccg gcctcaagcg tttttaaaaga   82740 tgctctttc taaggattga ctgtagtaca ggaggaagat tgacctgttg aaaagcctca    82800
gcctttacaa gtgtaaaatt atcagtatat tactatcatc tttctgatga attaaataaa   82860
ctaaggactc caagtcaaaa gtcttcaaac tgaagtagaa tagttgtata tagtgcttgg   82920
cactttaata tttagtatcg gtttaatgat aatgtttgtg cctttgccgt cttttaaaaca  82980 tttttacatc atccctgttt gattacttgg tgtgctcatg aagttgttgg ccactaagga   83040
atcttaggct cagagaggtt ctggaattgg ccagtggtcc ttgaatcagc tgctcctatg   83100
attctctaac tgatttctca caaagcaaac aagcaatcat aacaaaacaa ctgtgcacac   83160
tgctcttctt attttgttat ttaaaaagta cttaggctct acttatgttt gttagtcaat   83220
ttctcattac ttctagttaa tcaaaaggtc agaggaaata cttgaatatt ttcatactag   83280
aatactttaa aaaatcatga tttccagtaa tctctttaaa acttggcaag ttattttgat   83340 ctaaagttt atcttttgtg tgcatatttt taaagcttct agacaatctg atacctcagg   83400
tcctgttaca acaagtaaat cctcatcact ggggagtttc tatcatcttc cttcatacct   83460
caaactgcat gatgtcctga aagctacaca cgctaactac aaggtatggg cctctgcatc   83520
ttttaaaaat atatatgcac acatacttac gtctaatgga tagttgatgt ttttcttatg   83580
atttgtagga tgtataagcc ctttgagata tgagttacat ttagtttttt caagtttgtt   83640
tgtctttcag ctttgtttat gatagcttct atcatacagg tgttttggat tttcatattg   83700
tttgtactca cagctaagat tgattacagt gacagagcta ggatgtgcag ccaggttata   83760
gggggaagtg gccctggtgg agtctggagg gatccgtgta caggcttcct tccctcccgt   83820
gaggctcaca caaaaataca gcaacatgct ggtcctgcag gtaccctctg cctaacatga   83880
gccacaattc cagactcaca gaagaaaagc aggtgttcgg cataaaccat gtgtttcaaa   83940
tagtctgggc atggtgagcc acttgttatc agctaggaa agtttatgtc agcgtaagaa    84000
actgttcacc agatacccc aagagccagc ctttctgtct agggatgttt tagttttta     84060 gttcattttt tttttaact ttaaaatttt ctgttcatct gcaatttgtt agatatgaag    84120
tatgtgtcta atttaattt tgtttttggt tgtccccaat aatgtttaca gaagaatttt   84180
tctgcactaa ttggcttgag ttacttacat tctcatagtt ctctagtttc agtagtttca   84240
tttattattt tgttatatca atctatctgt ctgctcatct attagaagca tccttgtttt   84300
ttttttttct tttttagaca gagtcttgct ctgtcccag gttggagtgc agtggtgcaa    84360
ccatgcctcc ctgcagtctc agggctcaag tgatcctccc acctcagctc ctgagtacct   84420
gggactaccg gcatgtgcca ccacacccag ctaattttta cattttttgt agagacaggg   84480
tctccctaag ttgcctgggc tggtctcaag ctcctggctt aagtaatcct ccctccttgg   84540
cctcccaaag tgctgggatt acaggtgtga gcaactgcac ccggctacaa gtatacttct   84600
taattattgt agcttaatgg tatttatgag gggatcagtt cccctgttgt tctttagaat   84660
tttctggata ttccttcttta ttgattttgg gatgtgaaca atagaatcaa cttctacttg  84720
tagattgatt tagggagaac ttataccctca gatgttaagt caccctgtcc agaatgtggg   84780
atgctttcct atttgttcag aactttttaa attacctcag aagcacatga atttaaagg    84840 attttaaaaa aaacttaaag attatttcac atagctcttg cacatttctt gataaatgaa   84900
tcctcaggta ttcctctgtt tttgttacta atagttactt cttatgggtt ttttttcccc   84960
tgaaaatcat ttatcaaacg tatgtggctt attttctgaa ggatgtttga taattttgga   85020
agatatgaaa gtcttcatat tttacaaggt ttgaggtctc tttaagctgc atggttctca   85080
```

```
tgtcagctcc caaagcagaa gacggcatgt tgaaaaatgc cgtagagaag atacttcttt    85140
tccacctgtt ttcaactcat atcatcttga atttcagggc acctttccat gctcctagtg    85200
cttgctatct gtttattatt ttccttcctg aatacoctga actccagcat gttctgctgt    85260
aattctggcc tccctggcat cttggactcc tgtttccttt gctctgtcat ccccgcggtc    85320
agctcctgct gcgcagcttc tcagctgaag tgcgtttgga gtgcctggcg tgtcttgctg    85380
gatctttgag tattgcctct ggtttccttg gttccttctg ctgagttgct cagcgtctcc    85440
actccccatt tcttgtgtgg cccttcctgc actcctctga ttccttttgt cttccctggt    85500
ttcttgcttt ggtttcgagt ctccacagaa cttttgcagc tcttctgaag acctggaagc    85560 ttttcatct taattctcat ctcatgacct cttttccctt ctttgagagc tagaacttcc     85620
catggtgaac ttctctttcc agaattccat gccttctttt ccctcccact tacctgttgt    85680
ccaggagagg tcagattgct gtgcatattg gaggagaacc ctttcttccc tgggctcttc    85740
atctcacatg acatcaccac atcacctcgt tccttggacc ctcagtggtg tcactgctgg    85800
attttctttt cctttggctg gccttagggc acacccaggt tgactagcgt agtcatggta    85860
tttagatcca ctcacatttt cagtttctgt gtctgtctct tgcctgcttc tgacttcgcc    85920
cagagaaagc ttctctttca caagggttct tagatttatg ttcactgagc accttctttt    85980
ctgaggcagt gttttaccaa tatttatttt cctagtcagt ctcgccttac ctttcttgtt    86040
atgcatgtct ttggtcctga cccattctct gagtctgtaa aatagaattg ctgtataatt    86100
taattacatg aaatccttta gaatcttaac acatcttaca cctgatttaa tattttattg    86160
tatccaaatt gaaccaaccc tatgtgaatt tgacagtgat ttctcccagg gatcctagtg    86220
tataaggaat aggacttagt attttctatt ttttgatata ccacatacca gatactgatt    86280
atgatggaca tttaaccctt ttttctcatt atgaaagaaa gttaggaatt atttcttcca    86340
gtagcgccag tgtaacctga aagcctttga aagagtagtt tttgtatagc tatctgaaag    86400
gaatttcttt ccaaaatatt tttccagtgc tgacaacaaa cacgcagaca caccctgcaa    86460
ggtgagtgta cggcgccgca cagtggaggc atctgctgca gccgtcgatg tttgtgtctt    86520
tggttgtaca ttatgagatc gtgacagggc cagtaaccgt gtgttctctc cttcaccttc    86580
ccaaggtcac gctggatctt cagaacagca cggaaaagtt tggagggttt ctccgctcag    86640
ccttggatgt tctttctcag atactagagc tggccacact gcaggacatt gggaaggttt    86700
gtgtcttgtt ttttctcctt gggttgtggc tggcacactt gatgtgcgtc ttctgggctg    86760
agttcatcta ggatggagcc tggttctcca gggtgcctcc gggagactcc tccctgcccc    86820
acgtgcttgc gtcacaggac ccaagtctga ctctgcctta gccatgaagt ttaggggggaa   86880 gtttctattt gtattctatt tttgtctgtt atcatgtatt agcttagacc cagtttagtt    86940
tggaaaatca gtgggtttca aaatgtgttt gtagagtcct ttatttctta acttgaccott   87000 ttcaagtgga aagggcaaa acagacgggt aaggggcgg gcgggaggt gtgacttgct      87060 cttttgtgcc tgaggaagta acagagctgg ggttgacagt catattctct gacacagata    87120
gtctctgact tatctcacag aaagtcagcg gcagagcctg agttaaaagt ctcgtagatt    87180 ttcttttttct ttttttggt ggctaatttc agttttattt atatttgttt attttatttat   87240 tatactttaa gttctgggtt acatgtgcag aatgtgcagt tttgttacat aggtatacac    87300
gtgccatgat ggtttgctgc acccatcaac ccatcaccta cattaggtat ttctcctaat    87360
gttatccctc ccccagtccc ctcactcccc atgggcccog gtgtgtgatg ttctcctccc    87420
```

```
tgtgcccatg tgttctcatt gttcaatttc cacttgtgag tgagaacatg cggtgtttgg    87480
ttttctgatc ttgtgatagt ttgctgagaa tgatggtttc cagcatcatc catgtgcctg    87540
caaaggacat gaactcatcc ttttttatgg ctgtatagta ttccatggtg tatatgtgcc    87600
acattttctt aatccagtct atcattgatg acattcgggt tggttccaa gtctttgcta    87660 ttgtgactag tgccacaata aacatacatg tgcatgtgtc tttatcgtag aatgatttat    87720
aatcctttgg gtatatgccc agtaatggga ttgctgggtc aaatggtatt tctagttcta    87780
gacctttgag gaatcgccag actgtcttcc acaatagttg aactaattta cactcccacc    87840
aacagtgtaa aagtgttcct attttttccac aacctctcca gcatctgttg tttcgtgact    87900
ttttaacgat cgccatccta actggcgtga gatggtatct cattgtgatt ttgatctgca    87960
tttctctaat gaccagtggt gatgagcatt ttttcgtatg tctgttggct gcataaatgt    88020 cttctttgc gaagtgtctg ttcatatcct ttgtccattt tttgatgggg ttgtttgctt    88080 tttttcgta aatttgttta agttctttgt agattctgga tgttaatctt ttgtcagatg    88140
ggtagattgc aaaaatttta tcccattctg taggttgcct gttcactctg atgatagttt    88200
cttttgctat gcagaagctc tttagtttaa ttagatcccg tttgtcaatt ttggcttttg    88260
ttgccattgc ttttggtgtt ttagacatga agtcttgcc tatgcctatg tcctgaatgt    88320
tatggcccag gttttcttct aggatttta tggtcctagg tcttatgttt aagtctttga    88380
tccatcttga gttgatttt tgtaaggta taaggaaggg gtccagtttc agttttctgc    88440
atgtggctag ccagttttcc caacaccatt tattaaatag ggaatctttt ccccattgct    88500
tatgtgtgtc aggtttgtca aagatcagat gattgtagat gtgtggtggt atttctgagg    88560
cctctgttct gttccattgg tctatatatc tgttttggta ccagtaccat gcagttttgg    88620
ttactgtagt gttgtagtat agtttgaagt caggtagtgt gatgcctcca gctttgttct    88680
tctagcccag gattgtcttg gctatgcagg ctctttttg gttccatatg aagtttaaaa    88740
tagttttttc caattctgtg aagaaagtca gtgatagctt gatgggggga tagcattgaa    88800
tctataaatt actttgggca gcaaggccat tttcacgata ttgattcgtc ctatccatga    88860
acatggaatg ttttttctatt tgtttgtgtc ctctcttatt tccttgagca gtggttttgta    88920 gttctccttg aagaggtcct tcacatccct tgtaagttgt cttcctaggt gtttcattcc    88980
cttagtagca tttgtgaatg ggagttcact catgatttgg ctctctgttt gtctgttatt    89040
ggtgtatagg aatgcttgtg atttttgcac attgattttg tatcctgaga ctttgctgaa    89100
gttgctaatc agcttaagga gattttgagc tgaaccaata gggttttcta aatatacaat    89160
catgtcatct gcaaacaggg acagttttac ttcctctctt cctatttgaa tacccttat    89220 tgctttctct tgcctgattg cgctggccag aacttccaat actatgttga ataggagtgg    89280
tgagagaggg catccttgtc ttgtgccggt tttcgaaggg aatgcttcca gttttgccc    89340 attcagtatg atattagctg tgggtttgtc ataaatagct cttactatgt tgagatacg    89400 tccatcgata cctagtttat tgagagtttt tagcatgaaa ggctgttgaa ttttgtcaaa    89460
ggccttttct gcatctgttg agataatcat atggttttg ttgttggttc tgtttatgtg    89520
atggattacg tttattgatt tgcgtatgtt gaaccagcct tgcattccag ggatgaagct    89580
gacttgattg tggtggataa gcttttgat gtgctgctgg attcagtttg ccagtatttt    89640
attgaggatt ttcacatcga tgttcatcag ggatattggc ctaaaattct cttttttgt    89700 tgtgtctctg ccaggctttg gtatcaggat gatgctggcc tcataaaatg agttagggag    89760
gattctctct ttttctattg attggaatag tttcagaagg aatggtacca tctcctcttt    89820
```

```
gtacctctgg tagaattcgg ctgtgaatcc atcctggact ttttttggtt agtaggctat    89880
taactattgc ctcaagttta gaacctgtta tcagtctatt cagagattca gcttttttct    89940
ggtttagtct tgggagggtg tatgtgtcca ggaatttatc catttcttct agattttcta    90000
gtttatttgg gtagagatgt ttatagtatt ctctgatggt agtttgtatt ctgtgggat     90060 cggtggtgat atcccctta tcgttttat tgagtctatt tgattcttct ctcttttctt      90120
ctttattagt cttgctagcg gtctacctat tttattgatc ttttcaaaaa accagcacct    90180
ggattcattg atttttttg gagggttttt tttcgtgtct ctatctcctt cagttctgct     90240
ctgatcttag ttatttttg tcttctgcta gcttttgaat ttgtttgctc ttgcttttct     90300
agttctttta attgtgatgt tagggtgtta attttagatc ttttctgctt tctcttgtgg    90360
gcatttagtg ctataaattt ccctctacac actgctttaa atgtgtccca gagattctgg    90420
tatgttgtgt cttcgttctc attggtttcc aagaaaattt ttatttctgc cttcatttcg    90480
ttatttaccc agtagtcatt caagagcagg ttgttcagtt tccatgtagt tgtgtggttt    90540
tgagtgagat tctcaatcct gagttctaat ttgattgcac tgtggtctga cagacagttt    90600
gttgtgattt ctgttctttt acatttgctg aggagtgttt tacttccaac tatgtggtca    90660
gttttagaat aagtgcaatg tggtgctgag aagaatgtat gttctgttga tttggggtgc    90720
agagttctgt agatgtctat taggtccgct tggtccagtg ctgagttcaa gtcctggata    90780
tccttgttaa ttttctggct cattgatctg cctaatattg acagtggggt gttaaagtct    90840
cccactatta ccgggtggga gtctctttgt aggtctctaa gaacttgctt catgaatctg    90900
ggtgctcctg tattgggggc gtgtatattt aggatagtta gctcttcttg ttgaattgat    90960 cccttacca ttatgtaatg gccttctttg tctcctttga actttgttga tttaaagtct     91020
gttttatcag agactaggat tgcaatccct gcttttttt tgctttccat ttgcttgtta     91080
gatcttcctc catcccttta ttttgagcca atgagtgtct ttgcatgtga gatgggtctc    91140
ctgaatacag cacaccaatg ggtcttgact ctttatccaa tttgccagtc tgtgtctttt    91200
aattggggca tttagcccat ttacatttaa ggttaatatt gctatgtgtg aatttgatcc    91260
tgtcattatg atcctagttg gttatttgc ccgttaactg atgcagtttc ttcatagcgt      91320
cagtagtctt tacaatttgg catgtttttg cagtggctgg tactggttgt tccttttcat    91380
gtttagtgct tccttcagga gctcttgtaa ggcaggcctg gtggtgacaa aatctctgca    91440
tttgcttgtc tgtaaaggat tttatttctc gttcacttat gaagcttagt ttggctggat    91500
atgaaattct gggttgaaaa tactttttt aaagaatgtt gaatattggc tcccactctt     91560
ttctggcttg taggatttct gcagagagat ctgctgttag tctgatgggc ttccctttgt    91620
gggtaacccg acctttctct ctggctgccc tttccttcat ttcaatcttg gtggatctga    91680
tgattatgtg tcttggggtt gctcttctcg aggagtatct tgtggtgtt ctctgtattt      91740 cctgaattga atgttggtc tgccttgcta ggttggggaa gttctcctgg ataatatcct      91800
gaagagtgtt ttctaacttg gttctattct ccccatcact ttcaggtaca ccaatcaaac    91860
gtagatttgg tcttttcaca tagtcccata tttcttggag gcttggttca tttcttttca    91920 ctctttttc tctaatcttg tcttctcgct ttatttcatt aatttgatct tcaatcactg      91980
atatcctttc ttctgcttga ttgaatcggc tgtcgaagct tgtgtatact tcacaaaatt    92040
ctcgttctgt ggttttttagc tccatcaggt catttaagct cttctctaca ctggttattc    92100
tagccattag tctaacattt ttttcaaggt ttttagcttc cttgtgatgg gttagaacat    92160
```

```
gctcctttag ctcggagaag tttgttatta ccgacttct gaagcctact tctgtcaatt    92220
catcaaactc attctccatc cagttttgtt cccttgctgg tgaggagttg tgatcctttg    92280
gaggagaaga ggtgttctgg tttttggaat tttcagcctt tctgctatgg tttctcccca    92340
tcattgtggt tttatctacc tttggtcttt gatgttggtg acctacggat ggggttttgg    92400
tgtgggtgtc cttttttgttg atgttgatgc tattcctttc tgtttgttag ttttccttct    92460
aacagacagg cccctcagct gcaggtctgt tggagtttgc tggaggtcca ctccaggccc    92520
tgtttgcctg ggcatcacca gcagaggctg cagaacagca aatattgctg cctgatcctt    92580
cctctggaaa catcgtccca gagcacgaag gtgtctgcct gtatgaggtg tttgttggcc    92640
cctactggga ggtgtctccc agtcaggcta catgggggtc agggaccac ttgaggcagt    92700 ctgttcatta tcggagcttg aatgccgtac cgggagaacc actgctctct tcagagctgt    92760
caggcacgta tgtttaaatc tggagaagct gtctgctgcc ttttgttcag atgtgccctt    92820
cccccagagg tggaatctag agaggcagta ggccttgctg agctgcagtg ggctctgccc    92880
agttcgagct tccctgctgc tttgtttaca ctgtgagcat agaaccacct actctagcct    92940
cagcagtggt ggacacccct ccccagcca agctcctgca tcccaggtcg atttcagagt    93000
gctgcgctag cagtgagcaa ggccccatgg gcgtgggacc cgctgagcca ggcacaggag    93060
agaatctcct ggtctgctgg ttgtgaagac tgtgggaaaa gtgcagtatt tgggcaggag    93120
tgtactgctc cttcaggtac agtcactcat ggcttccttt ggcttggaaa gggaagtccc    93180 ccgaccctt gtgcttccca ggtgaggcaa caccccgccc tgcttcggct gccctccgt    93240 gggctgcacc cactgtccag caagtcccag tgagatgaac taggtacctc agttggaaat    93300
gcagaaatca cctgtcttct gtgtcgatct cactgggagc tgtagactgg agctgttcct    93360
attcggccat tttggaagca tcccttgttt tttgaggtgg agtcttgctc tgtcgcccag    93420
gctgacgtgc atcggcacaa tctcggccca ctgcaacctt gcctcctgg tttcaagcga    93480 ttctcctacc tcagcctccg gagtagctgg gattacaggc acctgccacc atgcctggct    93540
aattttttgt attttttagtg gagatggggt ttcaccacat tggccaggct agtctcgaac    93600
tcctgacctt gtgatccacc cacctcagcc tcctagagtg ctgggatcac aggtgtcagc    93660
caccacgccc agccatattt tcagatctcc ctctctttgc cctaaaccac tgtgcttaat    93720
aagtagtttt tagtggccag cagtctccat gtataacaca ttttagcaaa atggaaaata    93780
ctatatgttt taaatttgaa cgtgagatta tactgaaata aaaatcatct aactgggatt    93840 cttaaatag taagatttc ttttttgtat gtgggttttt ttttaacctt attattatga    93900
ctgtcatata tagaaatggc tgttttcag ttacagtcag tgaatgtatc aaatgctgcc    93960
ttatccaaat aataaagta aattattaat aagtcacaat ttaatgaaga ttgatgttag    94020
ttgatcttta tattcttgaa atcagccata tggttgtgtg tgtatgtata tatttttaaa    94080
ggtacataaa gataataagc tcatctctga aaattttac atttggcata agaataactg    94140
gataattaag catcttattc tctggcctgt gtctttacag ttaaaggtag atttactcac    94200
ctctcctttt ttgttttctct aagttcatct ttttgctgt ttcaagacag aggcccattt    94260
tagctttctc gcatatcctt ttgtttgtac tttgaaagcc tcacctgctt aattgttgag    94320
tttttatccg tggtctttta gagggggata tgtagggtag aagctttcac aggttcttgt    94380
ttgcacttgg ccctgactg ttttgaggaa tctccctcac tgactcacag catggcaagg    94440
tttcagatct ctttctgcca cacagcagtt ctgaggcagc tggaaagata tccagatgct    94500
tagattgtca ggccaggctt gagatataca aactattgag ccttatctgt gaccttgctt    94560
```

```
aggtgaaggc atcagagccc ctgcaccaac atgcataggc ctctgcatgt gtgcgggget    94620 gggtgttgag gtctgagcac aagtgtagct ggagaggtga gcttgatgtg gcgacgggta    94680
tgagcaggtt ttcttcagac ttctgtgagt ttacctagtt ccaggattta aaggcacaga    94740
gactttagaa ttaaaataga atcattttct ttttctaaat agcaacacta ggaataaaaa    94800
ataataattc cacattcttg acaggtaatg ttttttcttg tcttctaatc cttatttatt    94860
ccatactcat ttttatacat aattgaaatg tattatgcat tggatttttc ttttgcatta    94920
tattatagac gatttttcat gtaactcctt actgttccat tttatatgtt ttgtctggtt    94980
taagacttta tctgcaaacc gggaaactgt ctctacaaaa agaaaaacaa aaatagttgg    95040
ccgcagtggc atgcgtctgt ggtcccagct actcggggct gaggtgggag gattgcttga    95100
gccttgggag gttgaggctg caaagagcca tgatcatgcc attgcactcc agcatgggtg    95160
acagacttta tactgtctgt tttgggtgat ttgataatga tatgccctga tgtagttttt    95220
ttatatcttg tgtttcttgt gcctgggttt attgaggttg ggtctgtggc ttcatagtat    95280
ttttaaagtt tggaaaattt taggccattc tttctttctt tctttctttt tttttttttt    95340
gagacagtgt ctcgctctgt cgcctgcgtt ggagtgcagt gacactatct tggctcactg    95400
caagctctgc ctcctgggtt cacgccattc tcctgcctca gcctcctgag tagctgggac    95460
tacaggcgcc tgccaccacg cctggctaat ttttgtatt tttagtagag acgaggtttc      95520
actgtgttag ccaggatggt ctcaatctcc tgacctcgtg atctgcccgc ctgggcctcc    95580
caaagtgctg ggattacagg cgtgagccac tgcacccagc taggccatta tttcttcaaa    95640
gatttttttt ctgccctgcc tcctcctttt tttccctctc ttaaagggc tgtgatttcc      95700 tgaatgattg cttagtgttg tcccatagct tactgatgct cttttcagtg tttgattgtt    95760
ttatgtgttt tctgttttgt atagtttcta ttattgtgtt ttcaagttct ctgatctttt    95820
cttctacagt gtctactctg ttgttaatct gttaatctgt tgttaatcct gtccagcgta    95880
tttttttttt tgttttttgaa acagtctcac tctgttgccc aggctggagt ttagtggtgc     95940
gatatcagct cactgcaacc tccacctccc aggctcaagc aattcttctg cctcagcctc    96000
ccgagtagct gggactatag gcacgtgcca ccacacctgg ctaatttgtg tattttttatt    96060 agagatgggg tttcaccatg ttggccaaac tggccttgaa ctcctgacct caggtgattc    96120
atccgcctcg gtctcccaaa gtgttgggat tataggcatg agccaccgtg tctgcccct      96180 gttcagtgta tatcactaat tttgttttta tctctagaag tttgatttag gtcttttaaa    96240
aatgtctccc tgtgtttctg tttagctttg tgaacacaat tgtaataact gttttaatat    96300
ccttctctgc tagttctaag atcttctaat aacttcccag ttcttggtgt ttctcattgg    96360
ttgattgata ctcctcgttt tgggttgtat tttcctgcct ctttgtatgg ctgccaattt    96420
tttattggat gcccaacctt gtgaatttta ctttgttgga tgctatatat ttttgtgttc    96480
ccatagatct tcttgagctt tgttctgagg ttagttgagt tacatataga tggtttactc    96540
ttttgggtct tgctttataa tttgtcagat gggttggagc agtgcttagt ttaggactaa    96600 ttttttttt ggactaatta ttcctcttta ggaataatta ggtaccatgc ttaggaggca       96660
agaccatcct gagtactcta cctaatgaac cagaaagttt gggttttcca gtccgcctgc    96720
tgagaacagt gacttttctag ccctgtgtga gcgctgagct ctgctccttc taatcctttc    96780
caatgcttct ttccctggcc tcagggagtt ttctcacaca catatctctg ctgagtactc    96840
gagagggacc ttccccagat ctccagagct ctctctgtct tgttttctct tctctggtgc    96900
```

```
tctgtcttat gaactgtggc tgtcttggtc tccttagatt ctcagcacct cttcaattca    96960
gagggttgcc tgtccctcct ccttgtgcca cagcctagga actctctcaa agcagcgagt    97020
tggggcagcc atagggctga cttagtctct cgtctcccag ggatcactgt ccttcattgc    97080
tcatgtccag tgtcttgagg actctgggtt ttgtctgttt tgttttttgg tttgctttgg    97140
ttgtctcagg caggagggta aacccagtcc ctcaccctca ttgtgctcag tagtggaagt    97200
ctcactctat tacattagat attagtattt gtagcagagc cctggttccc tggtacttgg    97260
ggagctcttg aaaggccaga aacagcatgc tttctcacct tttccagggc ttcagtttct    97320
ggtgcacatc aagcattcca tacacatttg ttaaagtcct ttgttagaca agtagtgatt    97380
cacaggttct atttgtaatt ttttcagtta acatgtattg ggtatctgct gggagctagt    97440
aaaaacaaaa agtggtgtgt gacaaattca attctgacaa gaacaaccct aaacacttag    97500
aatatacttt gagcatatca gaattttaaa aatgtgtggc ccttgagtat ttgaaaccaa    97560
caagaatcta ttgcttatta gtagaggata ttttgttaaa caagtggaga gagaggcatt    97620
ttcagtctaa ttggtgttgg cttttagcag ctgatggaaa ccagttcgtg attagccagg    97680
cagtggtgaa acaggctgtg cattctgaat gcctaggtat ctaggcattc agaatggtgg    97740
cgctcttttga gttagcatct tcttctttct tgattctttt tttttttttt ttgagatgga    97800
ctttcgctct tgttgcccag gtaacaactc cagtgcaatg gcgccatctc ggctcactgt    97860
aacctctgcc tccctggttc aagcgattct cctgcctcag cctctcaagt agctgggatt    97920
acaggtgtgc gccaccacgc ctggctaatt ttgtattttt ggtagagatg gggtttcact    97980
atattggtca ggctggtctt gaactcctga cctcaagtga tgcacctgcc tcgatctccc    98040
aaaatgctgg gattacaggc gtgagccacc actcccagcc ccttcttgat tcttgaaaag    98100
gacattgggt gctgtacatc tcgttataga tgttgataaa aatgcttgtg agaagagtaa    98160
cattaaggta gttatttggt cattttttgca gattatttta agacaattct aggactgatt    98220
tgtggtaaat cacacattgc tgtatcatag ttgtgttcac tgaacatatt cagggggctct    98280
acagatgcag ggctcttagc tgctttgcac acttctgaat tcctgccctg cgaacaggac    98340
tggataccta atagacaaca ggtacttgat aacagtttat tgaattaatg agtgaatgaa    98400
cagatacata aatgcatgaa agaatggttg taatgtatat aacttggatt tcaagacttt    98460
ttactgactg ttcaaaataa gaaattgaaa actttcctct gattttcctc tactatttac    98520
acaatttaaa tggaagttat cttgtacctt caatttctgt ctaggattcg tacaataacg    98580
ggtcatctct gagtcgctta atgtctcact tgtctttcta cagtgtgttg aagagatcct    98640
aggataccotg aaatcctgct ttagtcgaga accaatgatg gcaactgttt gtgttcaaca    98700
agtaagagct tcattctttt cctcttctgt taagacgttc gggtatgaca gcaaaacgct    98760
gctactcctt aagaggcagg cgctgttggc ataatcagct gggaggattg tggggtccag    98820
cgcagcactt tttggctcag tccatgattg agccaagagg ccatccttcc cttcactccc    98880
caggaggacg aggtctgtca ctgtggaggg cagaggacac cagaagctcc tctgcaacct    98940
cgctagttaa cttccagtcc ctcggagttt ctgtttagaa tgctcaatct catttagaat    99000
tgcaaggaaa cccaaaacgc ctatttaagg tacaaacagc acttcataca atatctcatg    99060
aggtattaat agtgattcac aggaagaatt tcacgctgtg agtctttgct aacatatcca    99120
gttatttaca gatggatttg atatttgtgt gggagattct taaaagtgtt gttcacgcca    99180
cattgttgat gcctcatttt tttcactgta gttgttgaag actctctttg gcacaaactt    99240
ggcctcccag tttgatggct tatcttccaa ccccagcaag tcacaaggcc gagcacagcg    99300
```

```
ccttggctcc tccagtgtga ggccaggctt gtaccactac tgcttcatgg ccccgtacac    99360
ccacttcacc caggccctcg ctgacgccag cctgaggaac atggtgcagg cggagcagga    99420
gaacgacacc tcggggtaac agttgtggca agaatgctgt cgttggtgga agcacgaaag    99480
agcaagcagg aaatactttg taaaagaata aaaacgaaaa atgttagcga acatcttcta    99540
atagtctgct gtattcagag aactctagga gatatatatg gttgatgcaa agatgattta    99600
aggcatagcc cggccttcca agaagtgtgt ggccagtgag tgagatgggc ttgggactta    99660
cacatctcag aggtgggggt agaggaggag gaacactgag tgggctgaga agcagccagc    99720
tctcattgcc aaagtgtgtc agcaaaccag aatgcagttc ataatgtccc cacccattca    99780
aagcacagga cctgtagagt ggtgtggcat gtgttggtgg cacttttcag gcctgtaaca    99840
aggatgaaag aacagcttca tagcagcaca gtagtgctgg tgttcagagg tgtgtgaagg    99900
ccatagaagc atcttggata tattaccttg tgttttgtca gctttatgac tagaagtctc    99960
ttttcactta aatttgtttt ttttttttttt gagacggagt cttgctctgt cgcccaggct   100020
ggagtgcagt ggtgcaatct cagctcactg caagctctgc atcctgggtt catgccattc   100080
tcctgcctca gcctcccgag tagctgggac tacaggcgcc tgccatcacg cctggctaac   100140 tttttttttgt attttagta gagacggggt ttcaccatgt tagccaggat ggtctcgatc    100200
tcctgacctc gtgatctgcc cgtcccggcc tcccaaagtg ctgggattac aggcgtgagc   100260
caccgcgccc ggcctctttt cacttaaatt tatgtttgtg tttttaatgc ctagtataca   100320
ggacttctta aattgcctta agtatgaaca ggtatttgag ttgctaatct gtatagtagc   100380
aataatagaa tcccttgttt ttccttttat aaatttagcg attaaatagc tacaattaaa   100440
acactagagt caggagtcaa ggaaaatacc catgttccag gctgtatgtt agtgatgtac   100500
ttactatata ttggagtttc aggagtaagt ctgtttcaat gctttctgta accatttggg   100560
gtattaataa gcatgtgagt gtgtgcatgt ttgggttaat ttcatatatg tttcttagaa   100620
gggatatcat tgatgtaaat attttaaagg cttgtcctcc aaaaaaatca tgtaatttct   100680
tctaaattac tgatctttta aatgaccttc acctttctct caaatctcac ttaagactgg   100740
gctgagtagt cagtttcctg tagcagaaaa aagctcagac ttgagtagcc ttctgcgagt   100800
gaggagactt gatggctgtc aggcagctgt aaactctaaa tagagtgtca ttatctgaag   100860
agggcgatgc tgccacactg agtggccttt caagttgttt ctcaatctga cacgttctga   100920
tcgtgtgaat gtgaaattgg tttgagcagg agtatatctg agtgcagagg agattattta   100980
aagatattct cattctctgc ttcccttttta ttcccatttg gcagatggtt tgatgtcctc   101040
cagaaagtgt ctacccagtt gaagacaaac ctcacgagtg tcacaaagaa ccgtgcagat   101100
aaggtaaatg gtgccgtttg tggcatgtga actcaggcgt gtcagtgcta gagaggaaac   101160
tggagctgag actttccagg tattttgctt gaagctttta gttgaaggct tacttatgga   101220
ttctttcttt ctttttttct ttttttataga atgctattca taatcacatt cgtttgtttg   101280
aacctcttgt tataaaagct ttaaaacagt acacgactac aacatgtgtg cagttacaga   101340
agcaggtttt agatttgctg gcgcagctgg ttcagttacg ggttaattac tgtcttctgg   101400
attcagatca ggtttgtcac ttttatcttt catccatcat acctgttcct aatttagtac   101460
aaattaccct aaaagacact gaaatctact ttaaagaaat gtggtctgca tgtttccctc   101520
atcagttgct gctgcttatc ttttcatgc acctagctgg tgcagaaggc ctggggcata   101580
gccagcctca gcaagtcagc atccttgccc cagctccctg gactcaaggc taacctgggg   101640
```

```
ttggctgtta gggatttcca aaggtttgtc ccatccactt gcctcccctc caaaataagt   101700
ttgaatttaa attgtgagat acaattaaga tttattgttt ggggaacatt tttgcaaaat   101760
ctagagttag tttaaacaga ttatcaatta ttaccataat tgatcatctg cagtttcaag   101820
ctatctaaca ggttcactta cctctttaaa aaggaatgga atttagcagg acagtaactg   101880
agacccgtgc tcctggagtc catgtgggag ctgtgtggct ctgcacaagc atttgcacgc   101940
ttcccctctt gactgcatta ccttcctcct atagttgctg tgggcaccag attctggcta   102000
gtcctgtccc ttcatgatgc acattttcct caagattcgt cccagttaaa tcactgcaga   102060
tgaaactgcc ttttcatcgt caaaatttaa ctgtcatttt tgagccgtga tcttgggcta   102120
ctttcttatg tggggtagga atatttgtga gttagaaata ttacacttct ctatttcctt   102180
ctagacgtaa atctgttaat cctgtcagca ctgttactca cctgaaaggg tctgtttccc   102240
taggagaact gagggcactc ggtcaacact gattttccac agtgggtatt ggggtggtat   102300
ctgcttgttt tttttgttgt tgttgtttgt tttttttgt tttttttttg agatggagtc   102360
tcgctctgtc acccaggctg gagtgcaggg gtgcgatctc ggctcactgc cagctccgcc   102420
tcagaggttc acgccattct cctgcctcag cctcccgagt agctgggact acaggcaccc   102480
accactacgc caggctaatt ttttgtattt ttagtagaga cgaggtttca ctgtgttagc   102540
caggatggtc tccatctcct gacctcgtga tctgcccgcc tcggcctccc aaagtgctgg   102600
gatgacaggc gtgagccacc gcgcccggcc tggggtctgc ttttaatgaa ggaggcatca   102660
aggggtgggc tttgcgttgg cctgatgctt tcatctttct ttcacaaaac ctgtccgaag   102720
aaaatccgtc taaatgggcc attgctctcc tcaggaaata gtcattggga acttcttttc   102780
ctttcctttg acactaggag gctgactggg gagaagccct ggtctatggc tgtgggcagc   102840
aggggctgag aggagcaggc tctcagggg gcacgggtac cccaagggaa gccagagccc   102900
tgatttgttc cattctagta agaacaaaga ctgctctggt ttcatgtttg ttctgattgc   102960 cttttcatcaa ccggtcccct ttctcccagt tcttaagatt cagtacagtg acagttttat   103020
gaacaagaat agaacactag aacagacaaa ccattgaact ctatgctgat aaagatttat   103080
tgagctcctg ctgtatgttt gcattctgcc cagaggctct gagaaaacca ggccatatgc   103140
tccatgcttt atccatggaa gctccccgtc aggttgggaa agctgacagc tgcagggaat   103200
acagtgtgac acaaaactgg ctcccatgca gcccttacgt gtcgcctctc agatggttgg   103260
gggacgaagg tcgactcctt tgggtatctt attactaaac cagtttcagg gaatctgtgc   103320
caccctatct gccattaacg tgaacagatg agtccccaag gtgtaatttt gggtattgtc   103380
tgatgtctct tggaatttat tatttgtttt tccaatgaga tttcacctca gggtatagta   103440
aagttgttga ggggattcct ggatgtgttc tgcaattatc taggctgatt tcagaataga   103500
gttatgctta tagtcaaatt tatcagctgt caagaatttt atttaaaatt tatgcagata   103560
agcaggagga aaagaagcct ggttttaca ttttaatcct attattgatg tgaaattta   103620 ttttccttcc tgtaggtgtt tattggcttt gtattgaaac agtttgaata cattgaagtg   103680
ggccagttca ggtaatagca ttttattatt ttagatttt tcttcttct tgtgtactta   103740 catgtaattt aggttattaa gtgaatgttt aaactactgt taggcatttt tgctgttttc   103800
tttaaatgga aatctgacta acatactgtg catttttgct tctcttaaaa attaatgtat   103860
atctcaagac ttgtttggaa gtagttatgt atctgaaaat tccatatgtt gtcagtattc   103920
attgcacatt tcaaagcatt taattgtgtt gacagatggg gaatgaaat cttgtggtgg   103980 agcactagtt tttaaatctt cttagagaaa gcagttttat ataatgttgt ctttagtaat   104040
```

```
tattatgcat ttgtattctc tgcagctttt tcttgctaga tgttgaggtt ttaatacttc   104100
ttgctagtcc attacaggtt tataattatt aaaagttaaa attcttttag tacctaaaat   104160
gcttaataaa cattgtaatt aggaaaattt agtgcagaag gaaagtgttc ccagattccc   104220
tggggtctgg aaacatagtg tttattctaa ttacatgaca cctccactgt gttttggggc   104280
aagttactgt ttctcttttg agtttcaatt tcttcaagag caaagaggca gaggagagct   104340
aggaagatcg tagctgctgt gcccctgtgc cgtcgggtgc cttctacctg ctgcctccga   104400
acctttacac atgtccctgc tctgcgcgag ggcacagatg ggatgcactg tggcaggggt   104460
ggggttagag tagatcacgg acacctgtta gcttgatgtg tgcttgctgt caaggttgaa   104520
tcatgaatta ttttatgttg cttatattga tatgtatctt aattttaaaa gaaaggtcta   104580
aatgdatgtt tttgttttta gggaatcaga ggcaatcatt ccaaacatct ttttcttctt   104640
ggtattacta tcttatgaac gctatcattc aaaacagatc attggaattc ctaaaatcat   104700
tcagctctgt gatggcatca tggccagtgg aaggaaggct gtgacacatg gtaacgggac   104760
acacctttca ctgtcgtctt cggtgtcgtg atgtgcttgg cagtgttcgt tttcatatac   104820
ccactttgaa cgttgtcagt ggcagccatg tgcttctcag gctctgcatg tgtgtctgtg   104880
tatgtgaagg tactggttag agacgtttca aaagagaaga gagcatattc tttactctca   104940
gcaatttgta atcttctcag ggaaaaaaat tcaagaaaca gtaagataac ctaaggtaca   105000
gatagattct gaatataaag ttcctgttca ttcacatgaa acgctaaaag ttcttcactt   105060
gatcttagcc aaaaggccaa gaagcgatgc aacactaaaa attcttaaat cgaacttgcc   105120
gtgaattaaa ttttgatctc tcatccagtg gtattggaga tatagtttga cttgggttca   105180
gggctttctg ttttgcctga tgattttgct ggagcttaaa taaggaaccc aggagatggc   105240
cagctgtgca agcccccagc ctgtggaagg agctagtgtg gttttatgaa tgagttgcaa   105300
atctttcttt gagcttttg aactgatctt ccagcattgc cctattgacc cctccctgac   105360
tcctttgctg gaatctgtag gcttttgaac tttgacaggg acacatccta agacccttgc   105420
aaactcccag atgtgagaat ggcactacta cttagagtct tttcgactca gcgtgtgtgc   105480
agaagagcat caaccgggct gtgttgcgag gcagggcctt ggctgacctc tcagtgttta   105540
catagctaag ccagttagtg tttgccacgg cctcacaagg gcttcagatt cacacagcca   105600
aagtatagat tattaaaggc ataggtgttt ggtttcctgg acttggaggg tctttggaca   105660
gaaaatcagt aggcaaccac acccagtact ttgtgctggg aagcttggtc atctgtgaga   105720
gggtcagaga gtatacccat gcgtgcatgc caccgaaggg tcagtgagta ttcctgtgtg   105780
tgcatgtctc agggccggag agagtatgtg tcactgagag gtcagagtgt ttgtgtgtgt   105840
gtcaaagagg gttgcattgt gcccttcact gaggggtcag agggtgcctc gcgtgtgtgt   105900
gtgtgtacgt gtgtgtgtgt cactgagggg tcagagtgtg cctgtgtgtg tgcttgtgtg   105960
tgcgtacatg tcactgaggg gtcagagtgt gcctctgtgt gtgtgctcat gtgtgtgcat   106020
acgtgtcact gaggggtcag agtgtgcctc tgtgtgtgct catttgtgag cgtatgtgtc   106080
actgaggggg tcagagtgtg cctctgtgtg tgtgctcatg tgtgagcgta tgtgtcactg   106140 aggggtcag agtgtgcctc tgtgtgtgtg ctcatgtgtg agcgtatgtg tcactgaggg   106200
gtcagtgttc ctatgtgctc atgacattga gggtcagagt gtgcctgtgt gccaatgaaa   106260
ggcatttctt atatttttt atatgtggtc atagtagacc agttaattta ttttgactcc   106320
tgtgttagac caaaataaga cttgggggaa agtcccttat ctatctaatg acagagtgag   106380
```

```
tttacttaaa aaagcataat aatccagtgg ctttgactaa atgtattatg tggaagtctt 106440
tattgtcttt tcagatgaat caagtagatt attcttgaga ccaggaatgt tgctgttttg 106500
gttatttgga aagttttatc attttcaaat tgacttttga atttgagtca ccttttttca 106560
gaagtggtgt taaattatag gagccctagg ttttttttct ttttttagaa gtcatcacaa 106620
aatgatcagt gttcagagga agagcttgac cttccacat ggtataatga ttgataaccct 106680 taattcatct cttaccataa accaagtatg tgtaagggtt ttctttattt cttgaaagca 106740
ttttgtagat gttgagagca gttttccaaa tgtaatttcc atgaaatgcc tgataagggt 106800
acccttttgt ccccacagcc ataccggctc tgcagcccat agtccacgac ctctttgtat 106860
taagaggaac aaataaagct gatgcaggaa aagagcttga aacccaaaaa gaggtggtgg 106920
tgtcaatgtt actgagactc atccagtacc atcaggtaag aggaatgtat gttggaactg 106980
tcgtggatac tttattgacc cgtgcagatg aaggaagtg ccatgtggta acgctcactg 107040
ttaactgtgt tactttgaac caggtttggg ctttctgggg cctgggtaga tgccggtgca 107100
gggggatggg gagggaggcg ggggtgggg gggtgtggtg gagttgggga ggtgcagtgg 107160
caggaggtgt tgttggtgtg tatccttttt tttttttga gatggagtct ctctccgtcg 107220
cccaggctga gtgtggtgg cacgatcttg gctcattgca agctccacct cccgggttta 107280
agcaattctc ctgcctccac ctcccgagta gctgggatta caggcatgca ccaccatgcc 107340
cagcaaattt ttttttttgt attttttagta gagatggggt ttcaccatga tggccaagct 107400
gtttcgaact cctgacctca agtgatcctc ctgccttggc ctcccaaagt gctaggatta 107460
caggcgtgag ccaccatgcc cagcctggtg tttatcttta aagtgggcac agccacagga 107520
gttcacctga ctcctggtct gagagtcacg agatcgttca agatagtgag gccctctttt 107580
ccaaaacgag gaccaaaaat caattgacag tgttggtcaa gatggtagaa accttaaaat 107640
gatagaaatc tcaactctga aataaaaact ttatttgtat atttatttac cactatttg 107700 acatagggct aaggtctttt tctttgagct gatttctggt tttgttttct taaagtggca 107760
taagaattca aagacatttt gaggaaggct gagtgcagaa atctctcttt ttaaatgact 107820
tctcctttct tttaacttgc actgttgtct agccctcact tattttgtca attcttttta 107880
gctgtttgtc tttgaatctt cataaagcca tagcttttct cataagaagc agcactttct 107940
ttgttcattc atattttaat gaaccccctgt agtatttaat taaatactta atgcctaatt 108000
aaatcacata attgcaatgc aaaagtacat gtatcataaa gaggtctgaa aatgagcaac 108060
tggcaagcag gtggtggcag gcagagctgc ttgggtgggt gggtgtcatg gagaggagtt 108120
catcagccac atgttcagtg agctctggat atgtctgttt agaaatgatc actaataaac 108180
ttgtgctcaa ccatgtatac ctctgggaag caggtgctct tcagtagatt gcctctgcag 108240
agaacacaga attgaagtga atgtccacaa aggcaatgag ccacctgcag aatagtttag 108300
tcaaggctgt gtttgaagtt tgccaaagat taatatacat ttgatttta tgttgtgcct 108360 tttctctgat tgtgaaatat tacaaattct atacaaataa caatgatggc aaatcctcct 108420
gagcaaagtg tgcaccttgt atgtgcccta gaggaacttg tgtttcgttc tgattcccct 108480
acatttctca tgtcatagag tggggttgc attagtgtcc ccctgtcctc gctgggatca 108540
catctgtttg gatcctagag tcttccagct gaactgggac aagtataaca gacggacacg 108600 tagggggtgga aaggcgtctc ttggcagcag actttctaat tgtgcacgct cttataggtg 108660
ttggagatgt tcattcttgt cctgcagcag tgccacaagg agaatgaaga caagtggaag 108720
cgactgtctc gacagatagc tgacatcatc ctcccaatgt tagccaaaca gcaggtttgt 108780
```

```
ccccgcagcc ttggcttgtt gttgcatagt gatggtagct taaggtcctt gtgaaaggtg 108840
ggtggctgga atcagctctt ccttcagtcc taatctgtgc cttgatagca gttctccgtg 108900
ctagtcatgg gacagctgac ttcatttctt ctcacaatgc catctcaggt tggtattgcc 108960
cacctacttt acagggggga tcccacagct ccgagaggtt atggaggtga tcaggcagca 109020
cacagcttta gagtgctggg gtgagggcgg gccaaggcta actctaaagc ccgaacccctt 109080
acctcctaca ctgcctcctg cattctggtc aacccagtgt tttatttggt ggttagattt 109140
ttgttttttgt taccttactg cttgtaattt agcagttttc cttttccttttc ccttcctttc 109200
ctttccgaca gggtctcact ctgtcaccca ggctagagtg cagtcgtgta atctcactgc 109260
aacaacctct gcctcccagg ttcaaccaat tctcccacct cagcctcctg agtagcaagg 109320
accacaggtg tgcaccacta cgcctggcta gttttttgta ttttttagtag atgtgaggtc 109380
tcgctgtgtt gcccaggctg gtttttaaact cctgggcgca agtgatccac caaccttggc 109440
ctgccaaagt gctggcatta caggtgtgag ccacctcgcc tggcctattc atcactaatc 109500
agaatttcta tgatcaaatg acatgaatca ttgtttccac aactgcagtg gaaggaaatg 109560
gcctggcagt gccagtttca gaagcagcct gcccccagtc aggcacaggc cactgtgccc 109620
ccagtgtagc agcacctctg tagctcacag agaagggtgg tggggacctc cttgaggcag 109680
ctctgccaga aaatctcatg agctgcctgg cacagcttga ggttgccttt taagtggact 109740
cagcaaatac atgtttgttc atcttgatta tacacaataa caactactc tgtatagtac 109800
gagtagtccg tggttttttgg catttgattt aaacttagag gcatgtgata ttgatgttac 109860
tgccttcatg actgcacccc cattctgatt tcataatgga atgttatctt gagaccagtt 109920
agacaacagg acagggatct tggcttctgg tgagattgac agcagttta gtgtggtcag 109980
ggtctccctg cctacagatg gttttagaat ggtgccctgg aagctttatc ccattctttt 110040
ctgtgcgtaa tctgagtaga gtggagatcg aaggcctgaa tacatagtaa atacctgact 110100
taatatctgc cgcaatggaa attgtgtgat acaacattta tgaaacgctt agtgcagcac 110160
ctgccaggta gctcaccaca ggtgcatgtt gcattcagaa gtagtgctag atactatcct 110220
gttactggca gtgcatacat cagtgatcaa agcagattaa agaaagaccc cctgccttct 110280
tggagtgaag attttgttgg gatgcgggta aggggacaga caatagaaaa gcaagtgagt 110340
gaagtctata ccatggcggc tgatcaggaa caccgtacag aagaatccag gagggaagag 110400
agttaggtgg tgtctgcggt gggagtggca ttgttcagct ggtgatgaga agaagctttg 110460
gtgatctggt gacatttgag tgaatttgca gaaaggaaag atacaagcct aggagatacc 110520
tggggaagga acattccagg cagagcaaat agcagtgcaa aggccctggc ggggggcgga 110580
catgctgtta gggtacaagc aatgagggtg gaggagtggg gcagccatgg ggagggaagg 110640
gagtgaggcc tggtggggtg aggccagtgt ggaggagcct tgagagggtt tgcgctgatg 110700
tggtgtaggt tttagcagga tcattcttat tcctgagttg agaatagcct tgaggggag 110760
gtgagggcag agcagggcca cccatgtgag acccggcact ggagtggaat ggcccaagtc 110820
agcatccctt ggcagcatga aagcaaaacc agcaaggttt gctggtggct tagatgtggc 110880
atgtgagaga gagcagggct ttgggggtga tttcaggggtg aggacagggt ggctgtgac 110940
aaggtagggc agacattggg ggcagcagga ggtcagagcc tgtctggatg tagcagttga 111000
gaccccatag gtgcctaatg aggtgaggcc agcatcaggt gtatgagcct ggagttgtcg 111060
agagactgtg gggcagggggg tcagcatctg agatgtccac tcacagtgga cccagactgg 111120
```

-continued

```
ctggagagga ggaggagctt gaataccgag cctgctgagt cccagctcca aggtcaggta 111180
ggtgagggga gccagtgctg gggcaggggg agtaggcagg tgtggggttc ctaaagccaa 111240
gattttttt aaggcatttt gtgcaggagg gcgacatctg ctgtcagcac cttgggaact 111300
tggcccaggt ttggcagcac cgagggcact gatgagtgct tttggaggag caaagggagc 111360
caaaccctaa tgggaatgtg ttcctgaaag gacaggagag agacttggga aaaggtttta 111420
cttgaagagg gaacggagaa atagggcagt agccagagga ggagaggagt cggcaatggg 111480
ttaagttggc agaaatgaag gcctgtttac gcactgaggg cagaagcaac agggaggatc 111540
agttcatgac acaggagaca caaatcgccg ttgtggtgtt cacagacatg ggttaggatt 111600
ggctgcatgg atgacagagc actgtgggtt ctcccagagt tgctggggag gaggcagagt 111660
tggtgagcac aggcgagggt ccaggatgca ggaatcctgg agctcaagtc agttgttccc 111720
ttgttgtaag atgtggccag tgttgtgagc ttcacatctg tgccttgaaa aacaccacat 111780
ctgtttgcag agttgtttac tatgtataca cactcagtag aaacaaaaat tggaaacagt 111840
cagtgcccac catcaataag taatggttga acacactgtg gtataagctt agactatttt 111900
agcttgggct attttgcatg attaaaaatg ttctggccag gtgtggtggc tcatgcctgt 111960
aatcccagca ctttgggagg ccaaggcagg cagattgctt gagctcagga gtttgagacc 112020
agcctgggca acatggtgaa accctgtctc tactagaaat acaaaaagta gctgggtgtg 112080
gtggtgtgcg cctgtagtcc tggctaactc aggaggctga ggtgggagga tcacttgagc 112140
ccattcgtgc gccactgcac tcctggggca cagagtgaga ctctgttaga aagagagaga 112200
gagaaagaag agagagggag ggaggaagga aggaaggaaa taaatggaag aaatggaagg 112260
gaggaagggg agggaggaag gaagaaagga agttcagcca gttgccttgg gagttctcca 112320
ttgcactggg ttaagtgaga agagcagaga cgtttatgat ttttcaaaac aactaaaaca 112380
aaacctctgt gggtgagggg gcaaggatat ggctatagga acatgggca gattaagaaa 112440
gggatataca cacaccactt agcatttgtt acaactgttg tgggagggat ggagtgcaga 112500
aaaagaaaaa aaaagtgca caccatccca tgtatgtgta tacaaaggga cgcttggaag 112560
actggtcccc aaaatgttgg taatgattgt gtcagggtgc tgcagtgcta gttgattttt 112620
tttcacactt ttgtatattt gagtctttta cagaaagcat ttattattta tgtaataaaa 112680
atctaaatga caagatttct gttatgggaa aaatgtagct atacagtgtt gttgtaaaaa 112740
tgtttgcttg gttcaccact gaacttaaaa tgcttttaaa tgagggaagg tgacgatgag 112800
atgattatga tgatttgccc ttgagttaca tagctggtgt acaggaagct gtcgtttctt 112860
ttggcttacg tagaaatgtt tgtggtgtct aattccacag atgcacattg actctcatga 112920
agcccttgga gtgttaaata cattatttga gattttggcc ccttcctccc tccgtccggt 112980
agacatgctt ttacggagta tgttcgtcac tccaaacaca atggtgagtc tctcgcctgg 113040
ctcagcagat gaatctggac ggcttgttca ggctctgatt actgggacca cccccagaat 113100
gtctgagtca gtcagtttgg gtagggcttc ttgagagttt gcttttttt ttttttttt 113160
ttttggtgtg ggggtggtgc ggaacagagt ctcactctgt cgcccaggct ggagtacagt 113220
gtcatgatct cggctcactg caagctctgc cttccagctt cacaccattc tcctgcctca 113280
gcctcccgag ttgctgggac tacaagcgcc caccaccacg cccggctaat ttttttgtat 113340
ttttagtaga gatggggttt caccgtgtta gccaggatgg tcttgatctc ctgacctcgt 113400
gacccgccca tctcagcctc ccaaagtgct gggattacag gcgtgagcca ccgcacccgg 113460
ccttttttatt ttttttggag atggagcctt gctctgtcac ccaggctgga gtacagtggc 113520
```

```
gctacctcga ctcactgcaa cctccgcctc ccgggttcaa gcaattttcc tgcctcagcc 113580
tcccgagtag ctgggactac aggtgcgtgc cactgtgccc ggctaatttt ttgtattttt 113640
agtagagacg gggtttcact gtgttagcca ggatggtcgc gatctcctga ccttgtgatc 113700
cgcccgcctc ggcctcccaa agtgttggga ttacaggtgg ctctcgcacc aagccaagag 113760
tttgcatttt tagcaaattc ccaggtgaaa ctaatgcctg cttttctggg agcacacttt 113820
gggactcagt gatagagagg tttattggta ggatagtaaa ataggagtta ttttctttca 113880
caaaattggc aattggggga aatttaatct tcctttttc ttcagctgtg acttatgtat 113940
tatgtttatt ttaggcgtcc gtgagcactg ttcaactgtg gatatcggga attctggcca 114000
ttttgagggt tctgatttcc cagtcaactg aagatattgt tctttctcgt attcaggagc 114060
tctccttctc tccgtattta atctcctgta cagtaattaa taggttaaga gatgggaca 114120 gtacttcaac gctagaagaa cacagtgaag ggaaacaaat aaagaatttg ccagaagaaa 114180
cattttcaag gtatgctttc tatctgagcc tataactaac ccatgccttt tgggaagtca 114240
cgtgatgttt cacagtcagt aagtctggaa taatacctgg tcttgcttca cttctgagtt 114300
gggtaaagaa gtctgtatca gtgtaatttt ctaatccgtc ctgcattatc tatggctctt 114360
ggttcatacc tgtcttgaag ttctgtcatg ttctgtctct tgtcctcagt agagatgcta 114420
cagcagtggc tcgcctcagg cagggcaggg cagtggggtg gctgtcctgg gggcaggcag 114480
taggggcacg ctgacgtcag ggaagttgaa acccaagaga agccagtaaa agtgagtctc 114540
agattgtcac catgtgctgg cagttttaca cgctgtcagt aataaaagtc ttctccctgc 114600
agggcagcct gcctccaata aatacgtgta gtatcaaatc ctgtcttccc tcataaattg 114660
tttggaagct ccccaaggac agtgatgagg cactcgtaag tgcttgctgc ctagatgggt 114720
ccctctccac ctttgctaga ttctgagcat tcactgagtt agagctgctt ctgcaaatgt 114780
gctgcttctg ctaagtggct gtgacttcat gcagccttca cttggtttgt catcagtgga 114840
gatgccctgt gttgtcgaag gagataagcc cagtaagcct gctgggcacc ttttggtttg 114900
caggttcagc aggcagccca tggctttccc tgtgtcgcat tgaagcagct ggctaaaatt 114960
gatgatacat taaattcctg tgacagatga tcagcttgta tttgtgtaat ggtgtacagt 115020
tcacaaagct taaaaaaatg ctacctgcca tttcatcctc agtgaggaag gtgatacaca 115080
gagagaccaa gtgactgtgt ccacggcgac ggcgctctgc atttcacttt agcggttaat 115140
gtactctacc tatatttta ctttatattt accatatatc ttttcatgta tacttggcgt 115200
aagtgcttta tagtagtcac ctaattcact gtcatctttt ttgtttcttg gaaggtttct 115260
attacaactg gttggtattc ttttagaaga cattgttaca aaacagctga aggtggaaat 115320
gagtgagcag caacatactt tctattgcca ggaactaggc acactgctaa tgtgtctgat 115380
ccacatcttc aagtctggta ggtgaatcac attagtcttc ctggagtgtc tcgttcccca 115440
ttctgcacta tacactctca gagtgtagga gctgtgctgc ccggtagaaa ctctgccttg 115500
cccagtgtgc cagttgaaaa tatttgttgc tgtaagagta cacctgatac catgtgaccc 115560
agcagttcca ctcttgggta tatacccaaa agaatggaaa gcagggtggt gaaaagatat 115620
ttgcatgcca gcattcatag cagcattatt cacgatagct aaaatgtgga accaactgaa 115680
gtgtccctcg atggatgaat ggataagcaa aatctggtgt atatttacag tggaatatta 115740
ttcagcctta aaaaaggac attctgacac atgctacaac atgggtgacc cttaaggaca 115800
ttatgctaaa tgaaataagc cagtcacaaa aggacaaata ctatgtgatt ccacttacat 115860
```

```
gagggacctg gagtagttaa ttcatagata tagaaagtag aatggtggtt gccaggggct   115920
gcaggggagg ggagttattt ttacaagatg aagagagtta ttctagaaat gaatggtggt   115980
gatggttgta taacattatg aatgtactta atgctactga actgtacagt taaaaatagt   116040
taagaggacc aggtgtcatg gctcatgcct gaaatccaag cactttgaga ggccaaggca   116100
ggaggattgc ttgagccaag gagtttgaga ccagcctcag caacatggta ggaccccatc   116160
tgtacaaaca aactagccgg ggatagtggt gtgcatgtgg tcccagctac tcaggagact   116220
gaggctggag gatcgcttga gcccaggagg ttaagtctct agtgagatgt gttcatgcca   116280
ctgcactcca gcctcggcta tagagtaaga ccctgcctca aaaaaacaaa acaaaacaag   116340
acaagagcca aaaatggtta agatgggcca atcacagtgg cttatgcctg taatcccaac   116400
actttgggag gtcaaggtaa aaggatcact tgaagccagg agcttgggac cagcctgagc   116460
aacatatcga gacccctatc tctacaaaga aaatcaaaaa ctagctagat atggtgggca   116520
catgcctgta gtcccagcta cttgggaggc tgaggtggga ggatctcttg agctcaggag   116580
ttcgaggctg cagggagcta ttattgcact ccagcctggg ctacagaatg ataccctgcc   116640
tcttattaaa aaaaaatcca aaaaaaaaaa aaagtaaacc tgagagcttc ctcctcctgt   116700
gttaaatttg gaggccaaga tgttttttgtt acttttacaa atgatcaagg acggtgaagg   116760
ttgggcatgg tagctcacac ctgaaatccc agcactttgg gaggctgagg cggggtgatc   116820
gcttgagctt gagaccagcc tggacaacat agcaagagac cccatctcca caaaaataaa   116880
aaaataaaaa aaaatagcca ggagtagtgg catgagcctg agcccaggag gtcaagctgt   116940
agtgagccat gatcatgcca ctgcactcca gcctgggcga gatcgagacc atgtctctag   117000
agaaagaaaa tgacaaggac agtgaaccca agaaagtcat aagatgccag ctgtgcagca   117060
agcatggaaa gcagccagtc caaattagga cagtgtgttt tccaagaaga acgatcgttt   117120
gtaatgagaa tgctttgctt taaataaatg actaaatagc tagaagccta gttctagggg   117180
ataggcacgt ctttcttctc tcaagaaaat agaaaggcaa ttctaatttc tagtaacagc   117240
aaacagcatt aagtcatggt ccaaatatga ggcaaaccaa aatgtggctt gattgttcag   117300
cagttgatct gttggaagcc cttgatatta aaaaggttct cctttaagcg gcttaggagt   117360
cacgatcaaa gacctataga aagagatgcc atccttctag gatccttggc tctcttggga   117420
actagattca gatagtcata atgtaaatac tgcttgagct ttctttcttt ctttctttct   117480
ttctttttt ttttgagaca gagtttcact cttgttgccc atcctggagt gcaatggtgc   117540
catctcggct caccgcaacc tctgcctccc aggttcaagc aattctcctg cctcagcctc   117600
ccgagtagct gggattacgg gcatgcacca ccacgcctgg ctaatttttt gtatttttag   117660
tagagacagg gtttctccat gttgaggctg gtctcgaact cctgacctca ggtgatccac   117720
ccgcctcggc ctcccaaagt gctgggatta caggtgtgag ccaccgcacc cggcccgagc   117780
tttcattttt gaaatcaatg tatgactgaa acactgaaga cttactgact taattatggt   117840
ttcagaacag aatgaaaatg tcttcggttc tgatgaatat aaaaggaaaa ctaaccaagt   117900
taatttggca agtagatggt agagatagag gtggggagtg aagggggaac taaaatcttc   117960
acctagcatt gttgggatta tatggttaca tcatctgaag ttgacagacc aaaatataga   118020
ggcttcagag gtctccaaat agaactaaac atgtaattca gattgttagg aggtagtata   118080
aatgagctaa atctcatctt tattacggta gagttaatgg gtgatgtcta aagttgtctg   118140
aagtctataa atcatgacaa attatgatgt ggtgattgta ttcaacagtc tttcagttgc   118200
agggataaaa ccccagttta aactagagta agagaaagaa tgtgttggtt taagctcctg   118260
```

```
gaaagtgcag gcaagggtag ttggtaggac tgcatctagt gttgtaattc tgtggtctgc   118320
attgtatatt tatgcatctc agctctgctt tcttcttttc atttatataa ttttaaaatt   118380
ttattttaaa gatagggtct cactttgtcg cctaggctga agtgcagtgg catgaagtgc   118440
agtgcgaggc tcactctagc ctcgaactcc tgggctctag agttcttcct gcctcagcct   118500
tctaagtagc tgagacaata ggcatgtacc aacatgcctg gataggtttt aaaattttt   118560 tgtagaaatg gaagtcttgc tgtgttgccc aggcgggtct ttaactctta gcttcaggcg   118620
atcctcctgc ctctgcctcc caaaatgctg aggttatagg tgtcacccac cacgcccagt   118680
ctcatctctg cttcctgtgt tagttttgtt ctctggtggg ctgttttcac atgaccgaag   118740
atgacctcta gcaggctgtg ttctcagccc ctcaagtagg cctatgtgat tggccttgca   118800 tgagtaaatat gggtgaccat aaacccctga atgctctggt ccacatgggc caaatggag   118860 actggacagc attccattga tgaggaggtg gggctggtct ccgggagtaa gggagaggag   118920
cacatgcagt aactgatggt ctgctgcaag ggatagcagc acagcagtta gaattttgga   118980
ggtaactacc agaactgaaa acagaaatga taacaagtag ttgccttaaa aagggatggg   119040
agcagggtgc ttttgtgatc aaagctcctt tctcttactg gatttttgta cacatttgc    119100 atacatatct tagagtaaaa gatagcattt tcagccttgg tccatttgag gatactcttg   119160
gcgtggcccg cctccatgct agcaggctct ggttgtgcca agttcagttg agcatcctgg   119220
ctcttgcctg cacggaactt ccagtcagtg cgtcagtatc acaagtcttg atatttccta   119280
tgaagaagaa cagtagtgca gtgacagacg aaatgggtgg gcaggcagag gcaggatttc   119340
tgagggagag aagtagctag cttttttgcag agaagagttc cggcacccaa gagagcagct   119400
gagagtacag gcaggcaggc aggatgccgg tagggcccgg ccgcacggcg ccacagaatc   119460
ctggagaaag gggcctcttc atggcctctg cattcagctg ctgtcaccct ccgcacaggc   119520
catggccaaa atttaatttt catagtggac tctagttttt gagccttact tgctattatt   119580 gaaataatt tcttgtttct ttttaaagat cttcggatta tgcttcactg accactgtaa    119640
taagtttaaa gttgagaaaa tatggcttgt taatgaatga taggtcaatt ttagtatgtt   119700
ggtcatttta atattttgcc accagttggt ttggatttga tgccaggagg agacagcctc   119760
atttctaagg actagtcttg cctttgtggg ataagggtgg tgtgttctgt gtccttctac   119820
atgtccgagc gatctctgtg cagctcaaat gtggtcactg tcttattgcg ctgatttcct   119880
ctccttccat ctcacaattg aggcaaaata ttgttactgt tgaagtgttg tccaatagga   119940
cttccagcag agacaggatg tctgcactgt ctaatttagt tgcctttagc cacatgtggt   120000
gttctgtacc tgaaatgtgg ctggtctgat tggatagctt aatttataat tttatttaat   120060
tttaattaac ttaaatttaa acagctctgt gtggatagtg gctcctgtat gagacagtgc   120120
aggtctgttg agaagcagct ttactggtgg gagtggaggg cttggagagg gcacgtgggt   120180
ttcctgctgt tatctttga ccttatttaa tctgcccaac atttgcaagt aagttgtgtg     120240
tgtgtgtata tataaatgtg tgtttctgtc ttcttgtttc ctttgactgc atttatttga   120300
aagacactag gtggcagaat tactgtattt gattggtttc aagataagag ttgaaataat   120360
tcatctcgtg ttttttatata agtaaggtgt gtttagcatg taaaattggt aatatgtatt   120420
cacgtactgc ttaaacaaag gctatgaatt ccacccataa accgaaaatg aagacctta     120480 aatttgtcca tttcaggcgt gggtacttct taaataatac ctggttcagg aactagtcag   120540
aatggcaccc ttgacttttt gtttcctgct tttcctcttg ttgggagagg agggtattca   120600
```

```
tcccaaagtg gtttgcctat ttcacattcc atctaggata agcagaatag ccaagaaaga    120660
tagctgtcct cctgtttaca acatttgggg taaccagcat ccctctcttt tggtccaaga    120720
tagactggtt tagaaacaga tgatggcacc agaggcccag gaggtggaaa catcagcttt    120780
gtttgttgtc catgtggctg aattagagct gtctggcctt gtagcctcaa cacggccttc    120840
cagctttgct caccgtgatt ttcaaggaca catcttgtgc tcttccctgc ctgccatcca    120900
gactataccc agtcagggtg gcaggagctg ctgcccctcc ctccctgagt cctggtcgtg    120960
ggtggtggag atgtgccatg acgctcacgg aggcatgctc accccttcct ctgtggcaga    121020
ggggatggct gcacgacagc tcttccctgt cctttccaaa gcgtctgtgg ttccactttt    121080
tggggcaaag caggaatact ggaagagaga gaaagtggtc ctttctatag taataaagtt    121140
gacattgatt caagttcatg cttggggaaa ggacagggct actaacaatt ataatgctgg    121200
gagcaatgga attttctcat gggtatgtgg taggtttaat tttaattatc ccagttaatt    121260
cttagaactg ctctgtgaag tatttcccgc tttgtgctta agttctaaaa gatcctgtgc    121320
caaaaccaag aatgaaaacc caagcattct ttcttgccca tcgatctttc tctcatcagg    121380
ccacttcttg ggttgatagt ggtgagtgta gccgctgcca cttcagaat acccaccatg     121440
ggccccagtc actgtgtggc gtggagaaga gatggttctc tctgtgtcat agctgaacaa    121500
gcccagccca gagaggtttc tgccctagga gctctcgatg gtggaattgg gatgcgatcc    121560
cacatcctgc ctgttttgaa aacagcattc tttatttcca attcctgctt ccattgttcc    121620
ttttaatatt tctttgttta gctcacaaaa acacggcttg cggagctgct gcgtgcagct    121680
gtagctgttt ctctgggtgc agcctgcatc cgccttcctg cccgcctcct ttcctgcact    121740
gccatcgtgg tctccgggca cttggtccct ttctcttccc ctgagtccct ttggctcccc    121800
tgtgccaccc ttgtgatcca caggctctgc cttctttctg tctcagactg ctgctcatca    121860
ctactcggga ccctaggaag ggaggttcca ccgagaagca tcttctcatc tcagccacgt    121920
tctcagtgcc actgttgtct tgttaggta atggtagcta ctgtaacaaa taaaccaaca     121980
tttccatggc ttcacaccag agaaggttgt ttcttggttt tatgacaatg tattgagggt    122040
gttcttggtt cacggatggt tttcctccat gtgggaattc ggggacccag gctcctttcc    122100
ttcttttggt tctgttctcc aggccttcac atcctctgtg tctggttggg gacaaggaga    122160
gggaaggtaa agaaggcttt gtggccttgg ataagtgaca ggcatgcctt tgctggtgtt    122220
ctctcgtggt gacaggtcac agccccaccc tgtaaaaggg gactgagaga cgtcgtcctg    122280
ctgcttccca gcagcagcac tgtggtctct gatgtgtttt ctgtgaggat aaaaacaggt    122340
gattccagga tgaggaaagt cagggaaacc cttggaagga ggggaccagg cgggtgtcac    122400
catgggatta gtggtggctt cagaatgagc tgcagcgagt gccatgcctt ctaaagcttt    122460
tgctattctg atatgcccac accatgccca gcaggtgtct gccttgctct ccgcagagag    122520
agtgatgaat ccttctcatg agcctctgtc cagttgttcc tccctccacc tggaagggac    122580
cctgggttcc tcataacatc ccagcggaac aggggacctt ctatcctgtc cccaagttca    122640
tcctcatcct cctgccggct tcctggcccc tcttatgtct gcttcctgac gccacatcct    122700
tctggattct ctggaattga attttgcctt tgatgcttat ttaaaaatat ccattgcagg    122760
ccaggtgtgg tggctcacac ctgtaatcct gtgcactttg ggaagccaag gtgggcagat    122820
tgcttgagcc caggagtttg agattagcct gagcaacatg ttgaaatcct gtttctatag    122880
aaaatacaaa aattagctgg gcatggtggc gcacacctat actcccagct actcaggaac    122940
ctgagacagg aggatcaatt gagccccgga ggccaaagct acagtgggct gtgatcgtgc    123000
```

```
cactgtactc cagtctggtc aaacagagtg agacctgtc tgaaaaaaa aaaaaatcc    123060
attgcatact tcaccgtagc gaaacatgta tgtcttacct ttcctttcct gcctgtagct  123120
gctcttttac acttaacagc cacactaagc cagccttaaa tgaaaaacaa accagcactt  123180
cctgtgccct cctgcttcct tcatgagggg tccctccctc tgtgtacact ccattctcat  123240
tgcccatggt ggtttgtttc cctcttgttt ctcaagccat ggcagcctgc ctcttgccct  123300
ctttactaaa aaggcctttg cagaggctgc ctgtgttctt tctttctagg tctctctcat  123360
cctaggccct ccagcttgat tctgtggagc tgccctcttg tcactcagta gcttgtgggg  123420
tcttctctgt ctagccactt aattgattgt gttcctcgag ttgctgtcca tggtctctcg  123480
ttactgtttt ctctgtgttt ctgcctctct ccttggcctt ggtaggtcca tccccttgt   123540
gaccttggct gttgctctca tggacaactt tctcttgctg gtccttgtag tcctggcatc  123600
cagcttctcg acacgggact tgtcctgcca gtacctcaga cttgcactta aaattgaact  123660
agcaccactg tcactctcca gggcctcttc ttgttaatta gatcattagg gatgttcaga  123720
atcccagcat catagtatgt tcctcctccc gctaccccag gaaccctaac cttacctcct  123780
cctctctatc tactaggagg tggccctcag agtccgtctc atcttccacc tgaacttccc  123840
taataggctc cagcagctgc caccccgggg gctgagtact tcctccatgc cttgtgcagt  123900
gctgagccct ttacctgggt tctcctgttt gctccttatt acagccctgc gaacagatac  123960
tgctcttaat tccatcttac acctaaggaa gctgaggccc caggtaaggt gcatccaagg  124020
tcacccaggt agtagacagt agagccacga tctgaaccag gcagtctgat tcagagcctg  124080
tgttgacact cagccaccta gaacacagct tggattgtgg gtttctatta cctgttcaaa  124140
acccctacat cccgggtctg tccctgcacg tgctctgtgg cctggctgca tcttccttga  124200
aggcagtgca tgcctcttca ctcagggggc ccatgcagga acagagggcc ccacagaagg  124260
atgaggccag tgcagaatgg gctggagggg acaatgctga ccaggaagca agtgtagaga  124320
aatcccagga aacctggagg agccagagac aaggcattag aactcctcgt cgtgacctgg  124380
tctgcattct ctgagtgtgc tgcttctgtt agctcgcttc cttggtctca ggttatagtt  124440
taaggcattg tggagcccta aaaagcctgt actctgtttt tacctgtttt aggacccttt   124500
cactttgggg atgtgttgat tttttttttt tttttttttt tttttttgag atagagtctc   124560
gctccattgc ccaggctaga gtgcagtggc acgatcttgg ccactgctgc ccctgcctcc   124620
tgggttcaag caattcttgt gctcccgcct cccaaatacc tgggattaca ggcacccgcc   124680
accacactcg gccaattttt gtattttag tggagacagg ttttaccat gttggtcagg     124740
ctggtctcga actcctgacc tcaagtgatc tgcccacctt ggcctcccaa agtgctgtga   124800
ttataggcgt gagccaccac acccggcctg aaatttaaat cagaaataaa attttgatcc   124860
caacagtgat gccaggcagc ccagatctgg gggagagggt ggccttggcc agctgggcct   124920
ttctctgttt cccaagtctt gctgcctctc cctgctgggc tttgcagcct gtgcatgtct   124980
ctgtgccttt gaccttgttt atccaaagga gaggatagaa tgaagtcatg attcctggag   125040
ccctgagaag gatgctgtgg agaaatttgc cggtagaatc tagctgagtg tgttgctgag   125100
gtgccagcat tgtgtgtggg gaggctgacc gcttggcctg cctaggccca ggatgctcca   125160
tggccgggca cagaggccac ttggctgtca ggtgtcagga gcctgcagag ggcacacaga   125220
gcctggaccg caggggggtc ctgctttctc acctggcctc cttcagcatt tctgtccctc   125280
agtccttagc aagcccagga gctgttgagt ttggcaggtg ccgagtgctg ttcctgcctg   125340
```

```
tgtagctgtg gctcagtcct gtgggggccc cgctgtggcc cgagtgcagt gattcgaggc   125400
gctgagtgtt ccctgactcc ttctccagga gctgtgttca gactttcgca gctcttggct   125460
tggagctcct ggagggcttg gcattgccga ccaatgtgga ggtcgacagt gagagaggag   125520
gaatgctagc tttcttgacc agtccattaa ataagtggga tattggccag gcacggcggc   125580
tcacgcctta atcccagcac tttgggaggc tgaggcgggt ggatcacgag ctcaggagtt   125640
caagaccagc ctggccaaca tggtgaaacc ccctctatac taaaaataca aatattagct   125700
gggcgtggtg gcaggcgcct gtaatcctag ctacttggga ggctgaggca ggagaacagc   125760
ttgaaaccgg aaggtggagt ttgcagtgag ccaagattgc gccactgcac tccaacctgg   125820
gcaacaagag caaaactcta tctcaaaaaa aaaaaaaaa gtaggatatc tgtttctgct   125880
tagaaaaatc agaattttct aaatgccagg tgttctgaat acgtaagtat gggagacgac   125940
tcagcctgtt tcatttttat gtaaaatctt cgcgtagcca tgtggcactg gaccgagatg   126000
aaagcaaaga catttctcct taactttgtt tctaggaatg ttccggagaa tcacagcagc   126060
tgccactagg ctgttccgca gtgatggctg tggcggcagt ttctacaccc tggacagctt   126120
gaacttgcgg gctcgttcca tgatcaccac ccacccggcc ctggtgctgc tctggtgtca   126180
gatactgctg cttgtcaacc acaccgacta ccgctggtgg gcagaagtgc agcagacccc   126240
gaagtaggtt cataatgccc cacagcccag ggcgccagcc cagcaccctg tcctgagact   126300
cccagtaacc tgagctttgg ccaccgttaa agcatttttca ttttccattt tttgtgaggg   126360
cttgtgaaat ttctgctgca tattaatatt cctttcatgg acagcatatt attgggacaa   126420
acatgcggtc cagctaaagg cattcaaaat agcagttgct ttctaaatgc gattttcttt   126480
ggcaggttct ttgacaccat tgcatcttgt gggatatgct tgtcatgctc tgtggctcct   126540
actaagttct agtccttaaa ttggttccat agccagacat gttgcaatgt cttaacctca   126600
ttataaagta aatgtggttc tggttatcct tagataatga agtaacagtg tagcaaattt   126660
caaaacctct tggaaatgtt attttaccat tcaaaaaggc ttactaaggt tctcgttatg   126720
ggtggccctc ttttttgcaaa aggttttcag gcttaagctc catttctagg tgctccaaca   126780
ctccattatt tgtatatgta tggaaataaa agctgtgacc accccaacc ctggccccg   126840 cccagctgaa tcctcagcac agtatttctg gaaggctcaa gatcccacgc tggggaaaag   126900
aagttctgga gacaaaagag ggcaggtgct gccgtgcctc tctgctcagt atggatactg   126960
gaccttgtgc tgccagggct cccagtaggg ccagttcatg gcactcagct ggaaagtcca   127020
ctgttgggag gcattcttaa ccatccactc tgtgccgtat gtagtggggt ctggtcattc   127080
tgttggagga gacagaccag tgacgacatt tgaaatgctt ggtggatgtc ttaggcctgt   127140
tacgatgact gagcactgtg ggggcaggag acagaaagtc agtgtctcct agttctgtgc   127200
tgctttaacg tgcatagaaa tcagctgcgg attcagcaga tcactccttt tctgacagat   127260
gggcctgctt actctgatgt tatatcagaa agctctgaat ctgggaattg tgtccctga   127320 attggagtaa cagaaatgct tagatgatga gtgtttaaaa gaaataaacc aaaggtaaat   127380
ttagtttgga attcagcaag cgtcttcatt cagccctctg agggcaaact acagcttttt   127440
gtaaatgtag gtaaattctg tgactgtttc gtgacccccct ctgatccagt tttcctttat   127500
aaccttctgt attgttcctt ctattatcct gaaataacat taatagatta ggctgggcgt   127560
ggtggctcat gcctataatc ccagcacctt gggaagccaa ggcgggcaga tcacctgagg   127620
ccaggacttc gagaccagcc tggccaacat gatgaaatgc tgtctctact gaaaataaca   127680
aaaattagcc gagcatggtg acaggtgcct gtagtccctg ctactcagaa ggctgaggcg   127740
```

```
ggagaatcgc ttgaacctag gaggaaaagg ttgcagtgag ctgagatcgc gccactgcac   127800
tctagcctgg gtgacagagt gagactccat ctcaaaaaaa aaaaaaaaaa aaaaaaatta   127860
atggatcaat ggattttaa cctaataatt aaatttcaaa aaatatcgtt ctttaatggt    127920
aatgtaaagg taaaattaag ataatatgta acaagcatgt gagtgtctaa ggtgtccccg   127980
tggtggaagg aaaaaataaa tccccataag tgtccaagat gcccatagag agcagagctg   128040
ttctggttta aacccctgct cttagcactg tgtttttcca gctgtgggtg gtggggatg    128100 agtatctttt tatttccatg agatgagaaa aatgaattac tagaagtgtg aaatacaaaa   128160
cacagctgct cttttttag ccatagactc agcagccata aaattgctgt atccagttgc    128220
agaaattcct gctgcttact cttgaccctc tctcggtttg tgtgcatctc ctctcaggct   128280
ggctcccaga tgggagctgg ctccaggcga cactgggtgc tctgctccag gaggtcctta   128340
tgtgggtcct gccctagcct agcccctctc ttatggactc tgtcactgtg ggtttatgat   128400
tcactctcaa tctgtcttac ctcttggtga actgttagag tcctgcctat actttggcgc   128460
ttgtgggtgt gttgtggtac acatgatgtg ttggtcactt cccagctcat cttgttctga   128520
gtcaccctag atttgggaca ttcattcgcc accagtaccg gcggtgtat ggcctgagat     128580 ttgggggggc ttgtgctgct acaaattggg gctgaatttg agttgacagt ggaccttctt   128640
tatgtctact gctcatattt gaattgcaaa tactgcctct tctctttcag aggctcatta   128700
ccctatagct gtattattgc aaagtgcaca attacagctt gagtgtaagt cacactgcgc   128760
tggcaggacg gcccactgag aaagggcacg tttcctgttc gttagttttc acattgacac   128820
ataatttaca atacagtaaa atgtactttt ctatcaactg tagtcagtaa cagcccccct   128880
ccccaaacca catcaagata tagaggagtg ctgtcacttc aaacagttcc ctcttcctct   128940
gccacatcct gcccctcccc aggtctaacc accaatccgt gctctgtccc tctgttcagc   129000
ccattgcaga aggccataga aatagaatct ataggctagg tgtggtggct catgcctgta   129060
atcccagtat tttgagaggc tgaagtggga ggatgacttg aggctgggag ttcaagacta   129120
gcctgggctg cctagcaaga ccccatctcc agaaaaaaaa aatttaaaaa ttacaatcac   129180
gtccctgtag ttcagctgct tgggaggctg aggcaggagg atcacttgag ctcaggagtt   129240
agaggttaca gtgagctatg atcgtgccac tgtgctccag cctaggtgac acagcaagac   129300
gttgtctctg gggaaaaaag aaagaaacgg aaccacgcgg tgtgcagcct tctgagtctg   129360
gcccctttcg gtgagcagtg tctaaagttc tgtcgcgtgt tgcccacgcg tcggtggctc   129420
gctccttgca actgctgagc attgtatggc taggctgtag tttgtttca cttcaccagt     129480 tgggaaacag agaaaaggca cttttttaaaa agtttaaatc tgtagaattt tggttttttac 129540 cagttctctt ctaaatcctg agggattaca ggaaaagttg ttgtatttca gaatattctt   129600
agcttgatgt gacctctgtc cccgttaagg ccctttgccg caatgggaag gacgtcgctc   129660
ggtcagaccc tgaaggtcag agggggcagtt tgggagtgtg tcaacatttt aactgtatgg   129720
actagagcca agagtctcaa ggtttataat tcccacgtat tcaaaagaa aaaacaata    129780 aagtgagaag tcagtgtaga gtgaaataac ctgtgttagt ggggaagaag tgttttaaa    129840 caggatttcc ataacgtata acatcaacat gtttagagtg gtgatgttc attgggaaac    129900 gaacagtaaa acatgaaagc agggaggttt tcattctggc agttggcaac tttcacggca   129960
gatggagaat ttcaaaagca attgctcaat tatcaaacat agccagtgtg agttctgaaa   130020
taaaggtgct gattgaatgt gcagctttat ggtggatttt gctattcagg caagcatttt   130080
```

```
aattttctgc ctgttaaatt ctgttttctt tagtttttca tatgtggttt attgtagctt 130140
aggaatagat aactgagagt atatattaca catacaacat tctgatatgg caatatttaa 130200
aacaacttgt ctgttttaga actagaatta aacataatca tcttcagtat tttgcaaata 130260
agctcactgc catccagaaa cattgtcaat gcatctgttg ctccttctag aagacacagt 130320
ctgtccagca caaagttact tagtccccag atgtctggag aagaggagga ttctgacttg 130380
gcagccaaac ttggaatgtg caatagagaa atagtacgaa gaggggctct cattctcttc 130440
tgtgattatg tcgtaagttt gaaatgcctg taaacggggt tgagggaggt ggggaccagg 130500
agaacatcct gtgtagatga cacttgcatg gaccctctgg aacccagacc gcccggtgtc 130560
ctgccaagct ccatcgaaac taaatctaga atgaatgttt acttctgctg tgacatataa 130620
ttggagacca ggcctggcct tccagtcact ggattctaag ttggactgtg agagttttg 130680 cagctgactc atttatcaaa tgcccggcta ttggctcacg cctacatgat gctgggtatg 130740
tttgttaatt tgagggaagc aatggaataa taataactaa tgatttaaaa aacaaagtaa 130800
gtgcattgac tgtagtgggg ttctgatttt aaattttttt aaaaattaat accaggagca 130860
gtggcttatg cctaaattcc agcaactcga gaggctgagg taggaagatc acttgagccc 130920
aggagtttga gacaagcctg gctatggtg tgagacaccc atctctaaaa aaataaaaaa 130980
taaaaaatta tccaagtgtg gtggctcgtg cctgtaatca cagctctttg agaagctgag 131040
ggcggaggat ggcttgagcc tgggagttcg agaccagcct ggcaacacag agaaaccctg 131100
cctctaccaa aaaagaaag agaggaagaa agaaaaatta gcctggcgtg gtggtgcatg 131160
cctgtggtcc cagccacctg agagactgag aagggaggat tgcttgagcc cagaagtttg 131220
aggctgcagt gagctgtgac tgtgtcactg cactccggcc tgggtgacaa ggcgagaccc 131280
ctgctctaaa ataattttt taagttaatt tgtagaaaag gtgttagatg ttctttgtca 131340
cattttatga tggattcctg tttaaatgcc gttctcttta agaaaaaaa aataacttgt 131400 gggagttttt aaccataaaa ctagcatcac atatttacca tggagaattt acaaaaaaac 131460
aaataaacgg aggaaaataa aacctcctgt aatcatacta ctcagagata acttgctgtt 131520
agattttggt ctagatttaa tacttttttct atatttatat taaaaatatt taaaacatat 131580
gcatttcttt gtcacaaaca tggtatctta tagatactac tgtcacatag caaaacagtg 131640
ttaaatattc tgaatcagaa aaggaagccg actctccaac tgaaagaggt gttatcctag 131700 agacttttt tggtgatgac aatttattaa tagtcacttt ttgctttact ttctctattg 131760
aagtagtttt tctattttgt tctactttta aggataataa aatttataat gctgtttttc 131820
acagaaatat aagaaaaag atactaattt tataagttaa taaagtttga tcatcccaaa 131880
tccaaaaatc tgaaatccaa aatgctccaa attctgaagc ttttttgagtg ctgacattat 131940 gttcaaagga aatgttcatt ggaaggtttc agattttcgg atttagggag ctcaacaaat 132000
aagtataatg cacatatttc aaaacctgaa aaaaatccta aattcagaat acttctgatc 132060
ccaaacattt cagataaggg ttattcaacc tgtactgtca gatgatccca aatgaaaaat 132120
attaatcgtt aaccaaatat caaggaattg atcacatttt acagtttctg cctaggatta 132180
tgaatcaaga tgaaaaggct ctgcatgttt aaaaatatat attttatttt tcttataaat 132240
cttaaatatc tacacttaag atttatttga tatgtgggat ccattcatat tttggattca 132300
acagttctgt caaaactgtg gcagtgatag gggattcttt ttttcccact gaactatcac 132360
aaaattggaa aaagagtaat tggagaaccc cactggctta gccggcccga agcccgggag 132420
agggcaggca gtgctgtgga tggggtcatc ccagcgcaac gctgcccctg ctacctgcgg 132480
```

```
atctcgctga ggcctgcctt tgtcctttga cccttggcca tttgttagtg tctctgagag 132540
ctggactgct gtaccctact tccccagggg gcctaacttc acacagcctc tgccgcagtg 132600
cgtggttgga ggtgacggcc ttggtaaatc gagtttccta cctcctcaat tatttgtgct 132660
catacactgt atattttag tgaggttat atttgggatg tgttttctcc ttcttaccct 132720
ttctggcctt tctatggcat taatacctgg tctcttcttg tgtacttgaa aatgaatctc 132780
tcatcatatt tttccttagt gtcagaacct ccatgactcc gagcacttaa cgtggctcat 132840
tgtaaatcac attcaagatc tgatcagcct ttcccacgag cctccagtac aggacttcat 132900
cagtgccgtt catcggaact ctgctgccag cggcctgttc atccaggcaa ttcagtctcg 132960
ttgtgaaaac ctttcaactg tacgtcttca tcctgccgac tattgccagt tgcagttttc 133020
cctgccttaa aaatggagta ttgaaatttt taactttaat ttctgatttg caaaatagtc 133080
atcttttgtt cttttccttc ttgctgttag ccaaccatgc tgaagaaaac tcttcagtgc 133140
ttggagggga tccatctcag ccagtcggga gctgtgctca cgctgtatgt ggacaggctt 133200
ctgtgcaccc ctttccgtgt gctggctcgc atggtcgaca tccttgcttg tcgccgggta 133260
gaaatgcttc tggctgcaaa tttacaggta ttgggaagag aaaccctgat attgatttat 133320
attgaaaatt tagcaggcca agcaaaacag gtggctggct ttttcctccg taagtatggt 133380
cttgacatgg tcaccgatag aaacatgaaa acatctgcaa acttgccgtt actcgtgtgt 133440
ccgatctgac tgtttcttgt attttttttct agtctgccct tactaggatg aactgtacac 133500
atcagttcat cctttttaaa tgagcatgag gttattttgg gttgttaggt gttacaaaca 133560
cactaatgtg tttttgtcta ttagagcagc atggcccagt tgccaatgga agaactcaac 133620
agaatccagg aataccttca gagcagcggg ctcgctcaga ggtaatgctg gaaacacagg 133680
tcgtccttgt gttaggacaa cccaggatat aaaggatata gatttgtacg ggaataaatt 133740
cacaggacaa gaaatcgatg tgccttatag gtgggtttac tgcagaagtg ccataataga 133800
accttcctac ttttaaaaca accagatctc actttctaaa gagtaaagga tgaccggcag 133860
gatcacgtct gtgacgtgag tggaggcagt ttgcactcct ggtggctgtt tgagaggtag 133920
catttagaat gcctgtattc actgtcctgt gatgagtggg aaaataggtt atcaggttta 133980
tcttagcaaa atcaaagcat gtcatctaat tgctaaacaa gagttggcaa atctgagaga 134040
cattactcaa tccttggcat gcaggactta catctgcatc ctgttgccat tttatgtctt 134100
caaagcattt aatcatttag ttgtgtttgc aaagtctttg agaagccttt gtcagaaatc 134160
cctacatctc ctatgtgagt gtatttccat gactgcagaa taagttaaac ttttacccttt 134220 ttccttccct tgcggggcgg ggtgggggc agggattgtg tgtgtgagag ggagagagag 134280
acagcagaga aggagaatat aattatcatg ctgtgtactt tgagctgaaa ctgcaaaaaa 134340
ggaaaaacac acaaaaatta ttatgctttt cagtctttag agtaccttgt ctattatgct 134400
tttcagtctt tagagtacct tgttgatggt gtttttaaat gggattgggc acaattaggt 134460
ggacagtttg ggatgatttt tcagtctgta gggccaagct cttttgtaat ttgcattatg 134520
aagttgtcac tctcatagca gatggcggga gataaactat tattactttt tgaccctaga 134580
cttagtcttc agtccagatg agggagatta aaagattata aatatcttgt gccagatgag 134640
gtgattttat tttgaaatga ccatgaattc ctatcagttg tcttactggg atatttgata 134700
gtggaatttg tgcatttgag tcttagatga tctgttttac atttattaag aaagccttta 134760
ttagctttta tactgtgtat tgcctgttgc agtgtttgag tataaatgaa atttctggaa 134820
```

```
aatattaatg gagtacaaac tgtgatactt aaaagtaaac tagggcctgc atttgtatca   134880
tgacctgttt gagtattgat gagaagatag ctgtgaagaa aaaggtttaa acaagtgtat   134940
tttcctttaa gaagccacta atagtgcatc tccttagagt gtatatttct agaatcctag   135000
tgtgcagagt ttagactaag actaaaaaaa aaaaaaaaca aattatactg taatttcatt   135060
tttatttgta ttttagacac caaaggctct attccctgct ggacaggttt cgtctctcca   135120
ccatgcaaga ctcacttagt ccctctcctc cagtctcttc ccacccgctg acggggatg    135180 ggcacgtgtc actggaaaca gtgagtccgg acaaagtaag tgtccagcgt gtctgcatgg   135240
gaggcacagg gcgctgagtg cctctgtcac ctgtggcaga tacagagagt gcagaggagg   135300
tgccgtggac ccaaggagtt ctggcgctcg gctcggctca gtgaagctgt ggttagagac   135360 gtgggggggcc atcaaggtct gagggagcca agcagtgctg atgtgggacc cttttggtag  135420
gagtgtgggg tgagtagtta gtgggtgaat caaggaatag tcggccgtgg cctgcaggcc   135480
cctgactgca caggccttca agcacatgtc aatgccgtta gcctccctcc atctcctcat   135540
accttctggc cacctgtgag ttgcactgcc actgccagcc attctggtat gttgtcagca   135600
cctccactgc tcatacctca tggttaggga ccacctggag ccttggtaga gccttggtag   135660
agccttggta ctctactttc ctggacaaag ttcagcttat gaatatgaat ttagatttca   135720
aaaaccagca gcccaagtat aagaaagcga aggttcagtc ctgccttctt aggctctatt   135780
cgctaagcac ctgccctgcc ctggttgctg gggagagatg agtaaagcag acaacccagg   135840
agaggatggc aaaggggccg ctaacccctta gtggtttagc tatatttgga aggcctattg   135900
gaagttcacc aggtgaaggg ggaggctgtg agggtgccca ggcaggtaac agaagtccaa   135960 agggggaaaac ctgtggtgtg gtgagccgta tagccacagc ctgccggccg gcagccctct  136020
cagcctagtg cggtgttccc aagcactggc ctaggcctgt agctccaggg atgtgaagtc    136080
cccttgaacg ccgcccatca tgttcccctt atccattttt ttcttcccag gactggtacg   136140
ttcatcttgt caaatcccag tgttggacca ggtcagattc tgcactgctg gaaggtgcag   136200
agctggtgaa tcggattcct gctgaagata tgaatgcctt catgatgaac tcggtacggg   136260
gggagcagtg gaggcaagga atcctcagct ttcttgtga cttccaagtg ggatttgtct    136320
catcatcatg tgacccactt gttgacaaca catgttgggg actccagtct gggcagggac   136380
gggatgtcgg agagactcca ctctgaatgg ggccgggaag tggggaggac tccatttcag   136440
atggggtcgg gacatggggg ttatgctgat cgagacagaa aagcacattg tttcagccac   136500
attagaatcc acgagggtgt tgttttgaaa tccagctggc cccaaggctg ggtgtatggt   136560
ttgggatgag aactatctgg cctccactgg aggaacaaac acaggatgtt atcatctaag   136620
ctccatggcc aagacagaat ggaagtcaag gttgcgtatt tgccgtagac ttcaacacag   136680
tgtcgtaatg cgtgacgtca ataacttgtt tctagtgtct tggaagttga tctttagtcg   136740
taaaagagac ccttggatgc agcgagattt cctctactca cacctctgtt agatgtagtg   136800
aggttcttca cccccccaacc ccagatgtca gagggcaccc tgcgcagagc taggaggcca  136860
tgcaaagcct tggtgtccct gtccctcacc cgtgggcagg tcctgtgagc agtggggggg   136920
ccacctcttg ggtatggtgc agccatggcc caagcagggc ttcttctcag acctactagg   136980
acgggagaaa cctcctggtg ctttagccct gcgttgatat gcagcaaatg ggagggaagt   137040
gggcacctgg gaggacaaat gcctgtagag gccgggagtg acggcaggtg ttcatgaaaa   137100
gagaccttgt ggggagggca acacaacagt gtgttctgat gtactgaaga gctcaactga   137160
aaacaacagg agaattagcc caaaatccat ttactaaaat tgtttatctt tttttttttt   137220
```

```
tttgagacaa agtctcgctg ttgtccccca ggctggagtg caatggcgct atcttggctc   137280
actgcaacct ccgcctcctg ggttcatacg attctcctgc ctcagcctcc caaatagctg   137340
gtattaacag gcatgcacca ccacgcccgg ctaattttg tatttttagt agagacggga    137400
tttcaccatg ttggccaggc tggtctcaaa ctcctgacct caggtgatcc gcccacctcg   137460
gcctcccaaa gtgctgggat tataggcctg agccaccacg cccggcctaa aattgtttat   137520
cttaagattc atgcagtgaa agctaactta ctgagtgata aatttgctta gtgatctgtt   137580
tattaggttt tccaaatttg ctaattgggc tttgaacagc tgtaaaagtt ctgactgtaa   137640
aagaaagctt caacttttgg cattcatgat gcttttctga gtattaaact aagatagatg   137700
ttttacctga aggatcggcc accaatcttt aaatggctaa acaaagggt tgctaaaaca    137760
taatccaaat tgacataaga aataccattt ttccaaccaa aattttggca ttcatatggc   137820
tacttttacg tatttcagct gcatttgaac atcttttca aactttaggg tggttggtgt    137880
atcactgagg tcttggatga cactttagct ttgattttgt ttttatgaat taaaattgtc   137940
ataccaaaat ttttatttca agcaaatcca agagcataaa aaattaaaat attacttaaa   138000
atactaagag agaacagata tatttttac taagcatatg ttgaatgaaa ttgttcaaat    138060
atttataaca ggcatagagt agaattttct taaaaatatt tttgatggta taccaatttg   138120
tattttctca gaaacatttg ccttattctt ttttctgttg tgttttcctt acctgattga   138180
aagctcataa tctgttgtta ttgtttgtta acctttaatg ctctgatttc aggagttcaa   138240
cctaagcctg ctagctccat gcttaagcct agggatgagt gaaatttctg gtggccagaa   138300
gagtgccctt tttgaagcag cccgtgaggt gactctggcc cgtgtgagcg gcaccgtgca   138360
gcagctccct gctgtccatc atgtcttcca gcccgagctg cctgcagagc cggcggccta   138420
ctggagcaag ttgaatgatc tgtttggtaa ttaaaattaa aatttatctt attttaaaa    138480
agcattccag ggccagtata gtactttgca ccaagtaaat gtacaataaa ggcagtggat   138540
ctaatacatt gaaagcgttt acagaggtag ctaaagagca gcacgggtgt cctcggctca   138600
gaatttcttc ctgtgtgttt gccactttgc cattcattga catggtcatg gacatagggc   138660
tctaagccct tgaggaaggc tgggccagac ctcaggggag atgcagcccc aaaccacgtg   138720
cagtcctgtg gacggatgtg tagatgtgcc actgaggaac aatgtcttga gctttcatca   138780
gattctcaga gaattgcttg actgcctttc gaagttgatg catctgtgct cacgtttgca   138840
cccacccacg aggtccttct gtttcagggg atgctgcact gtatcagtcc ctgcccactc   138900
tggcccgggc cctggcacag tacctggtgg tggtctccaa actgcccagt catttgcacc   138960
ttcctcctga gaaagagaag gacattgtga aattcgtggt ggcaacccct gaggtaagag   139020
gcagctcgga agctcagtgt tgctgtgggg aggggcatg gggctgacac tgaagagggt    139080
aaagcagttt tatttgaaaa gcaagatctc tgaccagtcc agtcactttt ccatctcagc   139140
ctggcagtaa gtcttgtcac cgtcaagtta ttgtagccat ccttcaccct cacctcgcca   139200
ctcctcatgg tggcctgtga ggtcagccag gtccccttct catctgcacc taccatgtta   139260
ggtggatcct aattttagag acatgaaaaa taatcatctg gaagtacttt atgtcttaag   139320
ttggcctgga catgtcagcc aaggaatact tacttggttt gtgttagtgc ttgtaattcg   139380
cccccagaat gtgtacacgt tctggatgca ttaaagtctg gcctgtatcc ttaaagggcc   139440
atcgctgtgc tgcctgccct cagcaaggac acactttgca gacccacaga ggctccgcct   139500
ccacctcaca ccaaagaaag ggaggagtcc aaagggcatc agtgccatta ctcacaaaat   139560
```

```
gataaataca cccttattct gaaccacgtg gagtcatatg gtttgtgatc cctgtccttc   139620
aggtttcagc ttagtgggga agtgggaaag tcagcgtgtg atcacagcac agggtgattg   139680
ctgctgatta tattatgtgc ctgctgtatg caggatgaaa tactttatat gcgtcatctt   139740
atttgactct cacaaccccc tgtgagatag gctctgttac tcccatttga caggtgagga   139800
aagcaaggct tagagaattt cagtgacttg cccaggtcct ctgagctagg aagtagccat   139860
tctggcattt gaacccaagg cctgctatcc ctagaaccca cgctctcaaa ttcaacctat   139920
gacagaggca agccctggtg ctgtgggagc cccaaggaag agcctctggc ctggtggcca   139980
cgtagcccag gagagatttc tacaggagcc cacagcgctg aaggagagag aggcagcaga   140040
gtaaggggggc tttgtggcag agaggggact ggcactttgg ggaataggtg ggtcaggact   140100
gaatgtaatg gagccatgtc agagctgtcc ttctggaagg gcaagggcac ctggacgcgc   140160
tgcccctcag tgctttggac ggttccacaa ctgtgattca cacggcttcc ccaaacgaag   140220
gtacacgagt gggcattctg tgactcggta cttcccttta ggccctgtcc tggcatttga   140280
tccatgagca gatcccgctg agtctggatc tccaggcagg gctggactgc tgctgcctgg   140340
ccctgcagct gcctggcctc tggagcgtgg tctcctccac agagtttgtg acccacgcct   140400
gctccctcat ctactgtgtg cacttcatcc tggaggccgg tgagtccccg tccatgaacg   140460
gtgggttcct atcatagttc ctgtctgctt caccatgttt ttattttgtg ctgcctgttt   140520
gccaggtact aagctaggaa ttggggatgg agagtagt aaaatatgca tcaggaaggg   140580
ctgggcccca tctcttactc tccaatatat tggagtctac actggaattt aactggaatt   140640
tgctttttta gtcattttat ttagattttg aagtttcagc tttcatcaaa atacctcta   140700
aactttatgt ctctgtgatc tttggtctta gctgttttat gtatttagtc ttatatgatc   140760
ataagattaa taacattaca ttcagaagat tatttgtttt ctgtcagagt taaaatgttt   140820
gtttttatac tgcattgtaa tattaacgta ctgtaaaata aaagtggctt gttctttttca   140880
aggaacagta tcctcaacaa gggtcattag ccacaatttt taaaaaattg gacgtcatag   140940
tttacatgtt agagggcgtt ttgaagcttt gtatttttaa attaaatgtt atagagtgat   141000
gttttcatgt ttcataattg ttttcatctg tgcatttgta gccaacttga aaacaaagat   141060
ccagggatta ctacttaaaa gccagacttc ttggaggtta tagtgatgat tttgatagta   141120
tcttgagccg tctcataata acctcagggt gagagatggc caacaggaga cagtcgaggg   141180
acttagaaat ctgaatgaaa tctgaagttc aaatcttcag acatatacca ctaaccaaga   141240
gattggtacc tcagtctagt attgtctgtt tgtctaaaat tggttctaag gaatctaggc   141300
tagtctgtct atcccttttca acttttgtga ggctgcacaa atgtaaatg ttgaataaaa   141360
agcactgatg gaagtgtgta gaaattcttc tctttgttct gttgtaattt tagttgcagt   141420
gcagcctgga gagcagcttc ttagtccaga aagaaggaca aatacccccaa aagccatcag   141480
cgaggaggag gaggaagtag atccaaacac acagagtaag tctcaggacc cattttttc   141540
ttacatgttg ttcctccagg acttaaaaat cattcacaga gacgtgcacc gcggtgagtg   141600
tggactcctg gaagcgcacc gtagctccgc tgtgtcctgc tgctcctccc tagctgtcag   141660
ggaggctgta gtccattgct ttgccagctc ttttgtttcc gagtgaacac cttatccgta   141720
cacatgcggc tgtctctgac cctacagacc agctgggatg ccactgggggg agcgctccct   141780
tcccccccgca cttcccacac tctgcagtta ttctgagatc cttgagggca gggaacaggt   141840
ttgtcttctt tgtgttctca gaaattaatg ctcggcctct ggtcagcaag caacaacctt   141900
ttgttgagtg ataatgaata aataaatgtt tcccacatga gtattcagta acctcagtgt   141960
```

```
caggttcagc catctgtttt ggtggatatt taaaagaaaa ttccgctttt cctacagaaa 142020
aaaaaaaaaa tccaaatccc agtgatttaa gccagttata gacttagaca tatactacgg 142080
cttttcatgc actttcctcc caattctaga gtaggtattt tactaggaaa atggtggcag 142140
tgcctgttgg gaggaagatt ctttggccaa gtgtcttttg ttcttgccag ggcccctagg 142200
ctgctggggt gcttcagctt ctttagccca gtgtctggtg gggaatggcc cctgttgcct 142260
gtcccacaga ggtgggggtg cctcacctgg agcctgtcca cacattttac acagcacgct 142320
tacctggagc atcaggcatc ttttccatgc tctgtggctc aggaaacacg ccttttcaat 142380
catgagtgca ccagtgcttt tgggcttttt ctccccgctt ttgtgcaatc ctggttgtgg 142440
atggagtttt cctgtcttta gtcttctgca tagtactttt ctcttctggt tcccggttca 142500
aggttttgta attagagaat gacccagaag caatggcatt ttaatgcaca gccaaggact 142560
tctctgaatt tgtatctcaa acctctgtgg gtccttcagg cttcagtttg tgatttcatg 142620
atttcttgtt gctacctaag gaatatgaaa acacccacct ccctactctg catcttccag 142680
ccgagtggca cctcaggctg tggatcctgt gcttctgtgg tgaggataag aatagtgcca 142740
accgtgtgga ttgaaatcaa tcagttaatc cctccatgta aagcacctgg aacggatgac 142800
agtcttgtta tgaatactca acaaatgcta tcatgatttt tagttagatt tccattgctt 142860
taaaacagtt gagacatctt ggcggtttga gttagagcaa cgggccctga agtgggttct 142920
gtttgggtga agatgattat gcttattccc catggccctc tttaggcaag agtgggaagc 142980
tttctttgtt ttttttaatca cctcgatagg acgttacttc ttaaaggtca tccaataaat 143040
attaataggc cgggcgcggt ggctcacgcc tgtaatccca gcactttggg aggccgaggc 143100
gggcggatca cgaggtcagg agatcgagac catcccagct aaaacggtga accccgtctc 143160 tactaaaaa tacaaaaaat tagccgggcg tagtggcggg cgcctgtagt cccagctact 143220
tgggaggctg aggcaggaga atggcgtgaa cccgggaggc ggagcttgca gtgagccgag 143280
atcccgccac tgcactccag cctgggcgac agagcaagac tccgtctcaa aaaaaaaaaa 143340
aaatattaat aaagccaact cgttagcgtg gggcttaatt gcttaagtcc aatgagaagt 143400
ccttctctat cctaggaagt tgcccaaact gtagaatctc gtggcctgtg ggtaatagcc 143460
acgtaataca cactcactgc ctcaacaaat catattttag taggtatgat attctagact 143520
caagacacca ttctgtggat cttcccaagg gtgtgaagtg tccacagcgt ctgccttggg 143580
agtttccatg cccaccagaa ccatgcccca agccctcaa gcactctgac ctaggaaagc 143640
cagtgaagca aggatgacaa catggccctt tgatactagc tgagggacag acacaggtcc 143700
tgggagacca gagaaagacg aggggcagag gaggtgtcct aaaggaagtc tgaggctgag 143760
gagccacagg atggcttcca gctgtcacag gctgctgctg gccttatcac agagagtggg 143820
ccagagggct gggaaccaag gccagagctc aggttcagga ccattccagc aatcccagca 143880
gaaaatgggg agaattgtat ggtataggcg gatatgaagg tagaatctgc aggccttcag 143940
tggccaactc agagtctaag tggattccac agttacagct tgagcagctg ttgtaggtc 144000 atgctttcta cactgggcat ataggatgtg ttttttaaaa agtcctctct taaccgttgc 144060
ttgtttagat cctaagtata tcactgcagc ctgtgagatg gtggcagaaa tggtggagtc 144120
tctgcagtcg gtgttggcct tgggtcataa aaggaatagc ggcgtgccgg cgtttctcac 144180
gccattgcta aggaacatca tcatcagcct ggcccgcctg cccttgtca acagctacac 144240 acgtgtgccc ccactggtga gtctgctcgt tccttgcaga agaccaagta cggtgaaagg 144300
```

```
caccggtagg ccctgggctg ggcacacgtg agagggcggg acagaatccc cgcagcccag   144360
aggctgcctg ctgtggttct ggtgcccact gtggttctgg tgccaggctg ctttcctcag   144420
gcaccacgtg tggaggtcgc tagtagaaat actgggtttt ctaaaatgaa ctgaggccct   144480
acatccctaa gagattagtg ttagacctga ttctagagca actagaccac tttgcttaat   144540
agcagaccag aaaccacacc ccctcgagtg agtgagattt cctttggag ataattcatg    144600
tttttctaca cagttttgca gttgtcttca gaattggttt aaagtaggtg ttattgccaa   144660
gcgcagtagc tcatgcctgt aatcccagca ctttgggaag ccaaggtggg cggatcactt   144720
gaggtcagga tttcgagacc agcctggcca acatggtgaa accccatctc tactaaaaat   144780
ataaaaatta gccaggtgtg gtggtgtacg cctgtaatcc cagctactca ggagactgag   144840
acaggagaat cgcttgaacc caggaggcga aggttgcagt aagccgagat cgcgccactg   144900
cactctagcc tgggcaacag agcaagactc cgtctcaaaa aaaaaaagg taggtgttat    144960
tgatcagaac ccttgtttca gataacatga ggagcttagc ttgaggagag tgagggttga   145020
tggaggggga ctgacttctg cccagtgaaa tggcatcatc tcccaccagc ccgctgaaat   145080
aagatgatgg ggcctgttcc ttagggcctg cagcatcctc aggcaggaaa gaaaggccga   145140
cctggcaggg tgtgagccag caggtgtagg tcagggagaa tggagccagg tcccaggaa    145200
gaggcttgtg gctgcctgag aagggtgcgt gcctgcctgt gtgtgtgtgt gcacgtgtgt   145260
gtatgtatgc tggagagtct agggaggctt gctccaagga cgcagtattg tttgatcctg   145320
agagataagg attctgccgc agggaatgaa ggtattccag atggcgggct tattccgaag   145380
aagaggccag tgcctggcgg tgctggaagc agttgcagaa cagggagttg taggcttttcc  145440
tgggaagaga gcagcagggg tgctggagaa gcaggccaca cttgctgcat ggggttgctc   145500
tcggccccac tcttggtgca cagcgagtca ctgtgggttc attagcatct ggttatgaga   145560
cagtaactgc tccttttggag gggctcgtgg agaccatgca ggagggcacg gtcttgaggt   145620
catgccgtcc agagcacacc tgaggatagg ccaggacggg ctgcacgctg taggtaaaat   145680
tcctccagca agctcttcac tggcattgag gagttccctg agtgcggtca tctggaaggc   145740
agctgtaaca ggcactgcag tctctcccctg ggtgggtacc agagaggagc ataggggagc  145800
ataccgatt taaagagagg gcttttcctgt ggtgaggtaa gagattagct ggtcattatc    145860
atagagcccc ctctgccttt gtgcagatgg gctgtgggaa tcctgggggtt ccgtgggtc   145920
ctttgtcacc tcactgaagg catgtaagct gagctggcca gaccgtgagc tgatcctgcc   145980
acttgaacag catcaagcct gcctctggat tcttctgtgc atggcacttg tctgagcacc   146040
tcacgcacag agaactggac ttcagagttt acagaaataa gctgtatggt tcattttcat   146100
gcctgcttgc caataaacat atctgagctg aacctcattg aacgcctgcc tttattctag   146160
cacagcacct gctgtttgtg ggcgaggggt gctgtctcta actcctgcct gcttctccca   146220
gcactccctg agtggggtgt gccagcagcc tcaggatgag gacaggaagt gggagggcag   146280
agcagatttg ggagggccac ttgatgggga aggaagtccc aggaagcagt tggagctgtt   146340
ttctggggga gaaggtgcca gctctgggac agtgttgggg tagtgaggag ggagcccagt   146400
ggagagaagt cgggcttcct gcttcctcac agtatgtctg tcctgactca actcggatga   146460
tgtcacttcc tttcatcttt ctcaggtgtg gaagcttgga tggtcaccca aaccgggagg   146520
ggattttggc acagcattcc ctgagatccc cgtggagttc ctccaggaaa aggaagtctt   146580
taaggagttc atctaccgca tcaacacact aggtactctt gggcctctc cttcaggtca    146640
ccattgtcgg acatctaccg ggaggaaatc cagagccccc agtactggga tcttctcatt   146700
```

```
tgactccaga aaagatttaa gcatgataat aatacaaacc tatgtgaata cattttgcag   146760
tgttggcaaa actccttta tactgagaaa atagatccca gttcctgtgt tttgtggctt    146820
gaatcccagc tttgtgtatt ccgggcttgt ttgaagtcag gaaaggttca tgtgtagtgg   146880
acaacgtgag accaaattct gccttagatt ttgcatttag gctaaacagt ggcagcactt   146940
gtctcagaat gttttcttgt gttcaccagt ctgatcctgt tgtgtctcag tggtccattt   147000
tctcatatgg gaacaagcag acgggagcag atggagtcag gtttcttggc actcgccttc   147060
cccagagcct agaggcagca tggggagaaa gcaggcttgg ggctcagaca gtcctggtct   147120
gcttccagcc ctcctacctg agcagcgcag ggcaagtccg tctaacctct agagaccctc   147180
agttttgtca tatgtaaaat gggggtcgtg tctatttcat agaattgttg cagatttaga   147240
aattacattt ctaaacaaat gttacccctt atttctaaat aagtgtctaa atgaataagt   147300
caccactttt gcccctattt gatggcaaga ggtgtgatct tgtggtggga ctgtaatcag   147360
tcagttctca gtgactgtgc cctgctgtgg tgtttcctgg aatgttcctg tcttgtccta   147420
gaaagtctgg caggggcacc ctgactccac tgtccagtcc tctccccagt ccctcgggct   147480
tctgcagatt tgaggcttgt ttggatccca gaaggttgtg gcaggagaca ccttgcctct   147540
actttcccct ttataattca atgtccaaag agagccctga gcaggtacct cacgccagct   147600
gcctcacgga gctcctcctc ttcctggctg tgaggatcgg tatcagtggc ctcctgctct   147660 ctccccttg cctaacacga gcacctttgc ttacttgggt gcccttgctc ttgaactgcc    147720
catcggacgt gcgtgaccca agactgtgcc gcagtccttg ccttgtctgt gctcattttc   147780
tttgttcatt tttttccctg taacgtaaat tgttatattt gtctgtatct gtgtctgaat   147840
cagtcctgca cgctctcctt ctctctgtct cttgttcttt ctttacccg tttatcacgg     147900 ggaccccgat gtccattgct ctagttctcc tgtcctaagc accccatccc gtctctctgg   147960
ccttaccaca agtggcgtgg ctgcctcaga catcatgatg gggacatgaa gcacagctgt   148020
cagaaacaac tgttcgttag atacactcga atgcagctca tcaatagga tggagggtct     148080 gtcggatgta ttttcactga atccccgttc ctaccttgat acactctttt taatctattc   148140
ttctagacag gtcagaggaa ccattacttt gactttaaa ttttagcag ctttattgag      148200 gtagaattca catactacag atttcaccca ctctaagcgg acagcttggt ggccattagt   148260
tttatccaca gagttgtgca gccagctgca cagtctcagg gctggactcc agggaagatt   148320
ttagcccatt tagtgagtgg ggcagaagtg gccctggccc tgcacgaggt tgcctgcatg   148380
ggcgtccctg ccctgtccct gtgtctgctc cactgggggt tgaccaggct gccagggccg   148440
acttgggcct gtgccacctg cctctcatgt gtctcggaca gtgcagccga tgtctatact   148500
tcggtttcct caatgatgaa atggagggga tagtgttccc cgcatcatag aactgtgtga   148560
ggtttaaggg actcactgcc cttggcgtgg agccttctcc aggggccgtg ctgtgtcggc   148620
gtagctgtca gctctccgtt acaggcttga gaagggttga cactctctca tgtaacattt   148680
atatttctag gctggaccag tcgtactcag tttgaagaaa cttgggccac cctccttggt   148740
gtcctggtga cgcagcccct cgtgatggag caggaggaga gcccaccaga agtaaggcca   148800 cacccctgtgc tggttggcac atgggcagtt atggccgctt gcaggccttt ggtggggaat   148860
aaaataaggc agcaagctgg tgttctttt ttctcttacc ttatttttga aagagtagct     148920
gaatggtgtc ttgactgata ttccagagca gggacaaagc ctgctgaggt ctggggctg    148980 cgattaccaa tggctggaat gcattttatt acggtgcatt ccatgttaag gatcaatacg   149040
```

```
attgtgccct ttctggaaaa tatctttag tttatcaata ttcagaggag tgtaggttga    149100
attaaaatga aaaggcactt tataaaggcc atgagtagta cctggtttca tttttctaat    149160
gtcttgcaga gatttatca ggcttcttga agtgttcacg tacattacgc taacacgata    149220
ttaataataa ctgtgctctg gtacagcgga gccagcagaa tgggaagttg tggaatgcag    149280
gcccttgatt ctgatagaag gtgtggtttg aactcacaga aatgacagtt tggagggtag    149340
acatatgtca caagtcatca agattgtctt taaattcatg catagaagct aacagggtgt    149400
cataagcaag gcctgtaaaa tgtatgaggg aattcaaaga taatttatta aaaagtaatt    149460
catgtttgga gttttgtgcc caaaggagtc cttgatttga aaaatgggct tttgcccatc    149520
agattgtttc agggcccgtg tgtgcggagg ccctgccttg tgccccgtga gctcagcctg    149580
acagaaatcc tttggtagca cttaaggctc ctcttcctcc cattgaggca gggaagactc    149640
tgggttctgc aggcagaggt ggttgtgggt gtcttgctgc tcttgttgac atgtgggctc    149700
tccttccagg aagacacaga gaggacccag atcaacgtcc tggccgtgca ggccatcacc    149760
tcactggtgc tcagtgcaat gactgtgcct gtggccggca acccagctgt aagctgcttg    149820
gagcagcagc cccggaacaa gcctctgaaa gctctcgaca ccaggtttgc ttgagttccc    149880
acgtgtctct gggacatagc aggtgctggg acagtgggt tccccgctga agcgtccagc    149940
agcttcaacc aggccgtttt ccttcattgc tagaattgaa acaccgtccc gtgtggcctg    150000
tgcaggagat gcagacccaa aggtggcctc ctggtcagtg agaagctgga acgtgacag    150060 gaactgacgt ggggttattg agcatttagg ggaagacgtt agcagagcag aatgagcag    150120 gcaactagta gaacacccac ttaagggctc acggacaggt gctcacttag gaagtgagtt    150180
tcatttggta ttacaccagg ttcctttagg caaagcggag ggaaagttct ggtgtttttc    150240
acttgtaaga ttttgaagga aacaaaacac tctttacctt ttttctaaaa tgtaggtttg    150300
ggaggaagct gagcattatc agagggattg tggagcaaga gattcaagca atggtttcaa    150360
agagagagaa tattgccacc catcatttat atcaggcatg ggatcctgtc ccttctctgt    150420
ctccggctac tacaggtacc tgagggaaag ggtgcggggg agcggttgta cttgggctag    150480
aatgagagaa gactggcatg ctcaccacac cagtgatgcg ggaagacctg agtgtggtct    150540
gagttggagg ctgtggtgct aaatacgctg cccctttcat aagcaggagt cttagtcagg    150600
cccagggagg aagtaaaatc tggaaatgaa tgagaagcat tctctcctgc cagtcaagaa    150660
atgagaagcg aaagaattct cacgggctgt aagaccagca ggatttaaaa gttgaattag    150720
ttgcttatgt taagaactca accaagttca tctacacaag ctgaatctcc agcttttcct    150780
aagaaaccat gtgtggcagt ggctgcaggg cagggcacag ctgggcctga gcaccccgct    150840
ccctgcacct ctcccctccc tgggcccctgc ctgtcactgc ccactctccc accaagcctt    150900
ccggttgtgt gcctgcccta tcacaggcat cggagcttgt cacctggttt aaaagaagag    150960
agttgtgtgg ggatttggga tgcacgtttt tcactcaaaa gtattttagc gtagagctct    151020
gtgattccgt agctatttag gagtttaagc accttgaagg ctttaattgc agaaagttct    151080
atgtggacgt gcaatgtgtt atacgcagtg tctatgagac tcaaatgttt attagggcgt    151140
tgaagtaaac tgagcacttg gagggccatg gatccagcct tcaaggagct cataagtcag    151200
gaggacccag gagcaatgac ctgtcataga aggcagaaaa gaggggcaca gaggtgggtg    151260
ggaggcatac acaggcagct cctggagctc caagggagc aagtgcttcc agggaagggg    151320
gcgtggaggc ccctttggag gaggcaagtt gatctgggt ctggcagagg gttagctggg    151380
gacatttagc gggaggctgg tgcccgggaa ttgggggat gcccagcaga aagacatgag    151440
```

```
gaggctggcc tggggcgtgg gggggtgtga aaggttaagt gggggcatta tcctgctccc    151500
gctcctgccg gctgtatctg gtcagcctgg gcaccgaggt ggggttctgg aaggcactgt    151560
tcaccaaaat gcttatctgg gtcccccaga gagcttgcct gcctggactg tcggctcgcc    151620
tgcaactgct gactcctaag cttttgcagc tcagcccaca accagttcct attcacagag    151680
gtgggagctg aggggtgaca agtgactgct gcagtcttat ttgtcataga gaaaaagtga    151740
cagagtccag cttgcccact ggccctgcca gcttaactgg ttataaagtg acaaatcccc    151800
aagacccaca gggctctgca caacctgggc cctcctgcca gtggcggcga gggcaggtgg    151860
ctcacgctg ggtgcctgtc tgggcaggag ctgggctggt atggggtggg cctgcggccc    151920
tgccccctg tgcagatcaa gactcagggt gctggtgttc acaggtgccc tcatcagcca    151980
cgagaagctg ctgctacaga tcaacccga gcgggagctg gggagcatga gctacaaact    152040
cggccaggtc agtctcgcgc ccccgccgcc tggcctctgt ccgtttctgt cctcagactt    152100
tggcgcttga cacacccagg agaaaagctc agtgcacttt ttaaatgaaa ggaagttttc    152160
cttttttta aaaaaaaatt taatgttcat tgttttatc tgttttattc ctaggtcccg    152220
caagcagagg aagcattagt tttgttttta tttatgttct gtattccaga aagtagttaa    152280
gagacctcac atgtagcgat agagatgtgt gtaagagaca gtgagagggc gtgacttgga    152340
cttaagcaag gaccgtgaga cacaaaaagg ggggtgagga cagagtggag tcagctgaaa    152400
tgctcaggag gaagtagacg ccatgaaggg ccatggtatg ggggccgca ggcgtggccg    152460
tgagtgtccc tggggccagc tcttgggggg ctccctgagt gtccctgtcc ctgtggccag    152520
ttctgggtgg gagccccgtg tgcaggcaga cagctcggcc acttcctagc aggtcacatt    152580
ggtctgtgct tctgtttcct cctcagataa gtgaagggat tcaagggtct gggtgtggtg    152640
gctaacacct gtaatctata acattttagg aggctgaggc aggaggctta cctgagctca    152700
ggaggttgag gctgcagtga gccatgattg caccactgca ctccagcctg gcaacagac    152760
cagtactctg tcccttaaaa aaaaatgtaa acagaaacgt agggccattt gcatatgatg    152820
gcacatggcg tggagcccta caggtgtatg ctgggcgggg cccggctgtg ctggccgact    152880
tgcacctttc cctccacccc ggtgctgtgt ctttcgctca ccgggttcct gatttagtga    152940
aagcagttgt gcaggacagt tctctttgta gcttttgttt ctgtggaaat gggtcagaat    153000
atggtgttta gaaacactta tgagctctga gagtttcctc ttctgagttc ctggcctgca    153060
gccttcacag cagaaaccct gtgatgtcac aagcctgttt ctgttccctg ctctctgcct    153120
gtactgtcct gttttgtgcc tgccggtttc agtgacagga agcagggagc tactggacca    153180
gcctgtattt ttctagacat agttggaaaa agaagtccca ctcttctgtc ctttcacctt    153240
tgacagatgt ttccacccca agataagtga aaatgaccaa taggatgcac tgtatttttc    153300
atgaaagtgt ttctgaaggg caggctgaga gtgagaggcc tggggctcac tgggtgcctc    153360
tggccttgtc ctgggcccag ggacactggt ctgtgcccga ggtattccct atcccccaa    153420
ccccgctgca tttggccaca tccttcaatg tttgcgttgt gtccagcgtc cgcaaaccaa    153480
ctgtcatggg atcatactgg ggctgaagta cggtcccacc cctgccctgt ctggggctga    153540
agtacagtgc caccctgcc ctgtctgggg ctgaaggaca gtgccacccc tgccctgtct    153600
ggggctgaag tacagtgcca ccctgccct gtctggggct gaaggacagt gccaccctt    153660
ccctgtctgg ggctgaagga cagtgccacc cctgccctgt ctggggctga aggacagtgc    153720
cacccctgcc ctgtctgggg ctgaaggaca gtgccacccc tgccctgtct ggggctgaag    153780
```

```
gacagtgcca cccctgccct gtctggggct gaaggacagt gccacccctg ccctgtctgg    153840
ggctgaagga cagtgccacc cctgccctgt ctggggctga aggacagtgc cacccctgcc    153900
ctgtctgggg ctgaaggaca gtgccacccc tgccctgtct ggggctgaag gacagtgcca    153960
cccctgccct gtctggggct gaaggacagt gccacccctg ccctgtctgg ggctgaagga    154020
cagtgccacc cctgccctgt ctggggctga aggacagtgc cacccctgcc ctgtctgggg    154080
ctgaaggaca gtgccacccc tgccctgtct gggatgttta gccctagat gccactggac     154140 tgagccgcta cttgcttttg ggaagaggg gtggggtta ggggtctggg cgaggggagt      154200 gcagggctc ctccttggcc tgagagctgt tcatacagac tcctcgccca ctccctgcag     154260
ggtgctgggt cccagggggg aaatggccct tggtgccaag aacgtgagtt ggggctagtg    154320
ccagtgatga tggagaacag ctttttatgg gcacacagcc cacagcactg tgccaagtgc    154380
tcgaggcttc ccgagaacca ggcagaaagg aggacagtcg aggtgtgctg actgcgtggt    154440
ggctgcgtga tctagagcgc gggtcacaaa ggcgcgaggg agctctggcc ttgggtttac    154500
cgcaatgact gccagtgcgg gagactggaa aaggaatctc acgtattggt tccgtgtttt    154560
ggggactcca ttcagatgtc acttaggagt gaaagcatcc cttcgtagag cctctttctg    154620 tgtcacccte ctcagctgct cctggggttg actggcccct gattcatgcc tttagcatgt    154680
gctggagctt cccagcagct gtccagcccc tgccccaccc tctctgtggg ctcccttgcc    154740
cgtaacctgg ggtgtctgaa cgacccttgc taagggcag actgttagac ggtaggcatg    154800
tgctgagtcc cagtggccac acccacccac caggagcctg gcactgtggc cgcagcactg    154860
agcagtgccc cgtttctgtg gcaggtgtcc atacactccg tgtggctggg aacagcatc    154920 acacccctga gggaggagga atgggacgag gaagaggagg aggaggccga cgcccctgca    154980
ccttcgtcac cacccacgtc tccagtcaac tccaggtttt ccaatggcct ttttcttttt    155040
aacagaaatt tgaaatttct tatcagtcat ttgatttgtt tgaggtgctt cttgaaatga    155100
gcctctcatc tcatgtactt ggaaaatacc catctcgcat attccacagg aaacaccggg    155160
ctggagttga catccactcc tgttcgcagt ttttgcttga gttgtacagc cgctggatcc    155220
tgccgtccag ctcagccagg aggacccegg ccatcctgat cagtgaggtg gtcagatccg    155280
taagtgagcc ttcccattcc cctcacacct gcacgtgcca cacgcaccac acacgccaca    155340
caccccacac acacacaccg cccacacaca tgccacttgc acacacaccc ctcatgcatg    155400
caacacacac acaggccaca cgcaccatag acaccacaca cacatgccac atgcacacac    155460
atacacggca tgcaccatac acacaacaca cacagcacac atgccacaca cacacgccac    155520
accacatgca ccacacacat gccacatgca cacacactcc acatgcatgc accacacaca    155580
cacacacaca ccacacacac cacatgcacc acaccacaca ggttacatgc acacaacaca    155640
cacatgccac gtgcacacac cccacacacc acatgtatgt gccacacaca gcacacaacc    155700
acacacatgc accacacaca tgccacatgt gcatgcacca gacacatggc acacactaca    155760
cacacgccac gtgcacacac cccacacaca tgtacgcacc acacacatgc cacacacaca    155820
tgcaccacac acatgccaca tgtacacaca tgtatataca caccccacac cacacacaca    155880
ccacttgcac accacgcaca caccacacat gcgcacacac acaccacata cgccacatgt    155940
acacaccata cacacaccat acatgcacca cgtgtaccac gcacccacac agacacagca    156000
cacgcataca ccacacacac acgcacacat gcgtcccgca cagtaatgtc tcttgggtgt    156060
aagaacacga cttgccagta gtagcgttct ggatgcgttg cctggattct aacagcgcga    156120 ttctccccctt gccctcctgg ttttccacat ctccagcttc tagtggtctc agacttgttc    156180
```

```
accgagcgca accagtttga gctgatgtat gtgacgctga cagaactgcg aagggtgcac  156240
ccttcagaag acgagatcct cgctcagtac ctggtgcctg ccacctgcaa ggcagctgcc  156300
gtccttggga tggtaagtga caggtggcac agaggtttct gtgctgaagc cacggggcc   156360 catctgcctt gggacctggt gttggccaga ggtgccgggt gcggctgcct ccttccaaga  156420
gttgacccga accggactcc acggcccacg tgagctgcag tgcttctcag atggaggggg  156480
ttcagcgacg gtcagtgcca ttcacaggtc actgtgatgt gggttgtggc ggccaagcca  156540
tggtttgggg tcccgtatcc ctgggcttat gacatcattg tagtagccca tccccacaga  156600
accacggtgt gtggtggcgc tgaggcatcg tagatggtgg aaatgctact ggcttcccca  156660
tgctctgccc tgaggcctga ctgcctcact ccccttctca gttatgttcc aggccccccg  156720
agcttcctgg ctggacagct tctctcctgg gggccgtttt gtcacagtga ccctgtgttt  156780
ctagtcccaa atctgggtgc tatagtctct ttttagcgtg gtggttgtct tagtcttttt  156840
tggctgctac cacaagttac cttagactgg gtaatttata aacagtggaa atttacttct  156900
caccgttctg ggggctggaa gttttcatgg tcaaggtgcc agcagatttg gtgtgtgatg  156960
agggctgctc tctgcttcat agatggcatc ttctggctgg gtcctcacgg tggaaggagt  157020
gaacaagctc cctcaggcct tttagaaggg ccccaatcca caagggctct cccatcatga  157080
cctcatcacc tcccaaggcc ccaccttctt gtactgtggc actgcaaatt aggtgtcagt  157140
gtaggagttt caggagggat agaaacattc agaccatccc agcggtcaag tgttcatcct  157200
cttgagttcc tccttattct gcttctggtt tatcaggatt cagccagtgc agcatggtac  157260
ctgtattctg tggcacatca ccacatggta tttgccaagt atccatcacc tgcacacgtg  157320
aaatcattgc ccgtgggtcc cgacatctgg cgaagcatat tcaaggatgg cagaactgtc  157380
agagctggca cctctggttc cttgtcatgt ggcattacct agtaatccat tttatgatag  157440
caatggaaac tcatttcttc aacaaacacc tgagtgctg ccgtgtgcca gccgtctggg  157500
gcccttggtg agaatggcat ggtggtgccc atcagggcct gcctagcccg tgctctggac  157560
gggctcctgt gtgtcaggaa cgacaatgct gtcatgacgg tgaatgattt tttttttgc   157620 catcactcca gccgctaaca tttgcggagc tcttcctccc gcaccccac ctgacaaggc   157680 caagggtgac cttggcccca ccctaggcgg ccaaggtcag aggttagctg gcttgtctgg  157740
gtcacacaaa atgcagcaga ggttgaggtg agcacatgtc cgtgacctgg agcctgactc  157800
cctctctgcg agtcttgact gctcttgcct agactctgtc ctccccgagc caaacgcca   157860 gtcatcttcc cttgtgggtg tccttcagcc tggtgccatg ctggtgactc agcagccgtc  157920
cagggagtgg aaacaattga gtgtgtgggt tccctgtgtg ggcatctctc ttcacggcga  157980
acaccctctg ggtgttgccc acacgatgtc aaagcggctc ttggaagggg tccttctcct  158040
ttgtgggaag tttcagctgc tgggctaact tgaattgtaa ctgtggtttt gtgctcaggc  158100
ccagatcccc ctaggcaagt gttgtgccat cagtaatcaa atgagaaata atcattttga  158160
aaagcagatc ctaaggcagg atggtcatgg acactcactc ccagctcttt gtgcactcat  158220
gctttctgga agatggccat cctctgtgaa ggttttcagc gcgtcatgct tggtacccac  158280
gtatccagag catgtcgttt tgaggtattt gcccaccgtt gtgaaatccg tgccaccga   158340 gagcaggtcc tgatgtgggg ctttcagaag tgggacctgg ggccgtacgc agtccttagg  158400
gaggggccgt gtggcgttgt gcgtgtgagg ggatagcaca gggtgaggtg ggggcccaag  158460
aaggaagtga cccacaaaga acagcctcct cttttggtcc ttgttcctgg gatggctggg  158520
```

```
agtggcttct gtgtcgtccg gccatttccc ctgcggagag gctcctacca ctgccgagaa    158580
cctcatcatt ccacaaaaac aagaggccgc ctggccatcc agcgctccat gggaattctg    158640
tgtccccata gtcttgggct gaaggagggt gacattcctt gctgacttct gcagggtct     158700
cctcactgtt aaagagcaga ttgaaagtga agaacgtggg ctaagtgttt aggtcgatat    158760
ttaaccctgc taggttttgg atactaagtg aaattgaggc cattttggtt gaagttgaca    158820
gaaaccacta tcagggatcc ccaagactac cccaggcttt tctagaaaga ctctcagcta    158880
agatgtgtta tggtaaaagc acacaaaaca aaatcagcaa agaaaattag caagggcaga    158940
ggcccatggg gcgatgtccc gaggacacca ggcttgagct tccagaatcc tctcccagcg    159000
gggtcgtgca ggacgcactt aactccccgc acagtgagcc gtgacagcgc gtgtgcagtg    159060
tcgtcgccag gaaagcacac tagagactcg gtgccagggt ttttactggg gctgggcac     159120
atgggcaccc tctgcctgcc tcgtgcccag actctggact cccggaggga aggcaagttc    159180
tcagcaccaa ccctggtgcc cacacaagca gctgagcaca gggagcccct cctcagtgag    159240
gatggtgggc accgtcccaa caccagccag gggccagcct tgcacacagg cctctcagga    159300
tggtctccgg cctgctgtgt agtctcttct gcacacaagc gtgagggcag cgcccccgcc    159360
tcggctgtgg ggaggagcca ctgggacgtg agctctggtg gcatgcagca gcttttgtct    159420
gtgtgtgcct aggacaaggc cgtggcggag cctgtcagcc gcctgctgga gagcacgctc    159480
aggagcagcc acctgcccag cagggttgga gccctgcacg cgtcctcta  tgtgctggag    159540
tgcgacctgc tggacgacac tgccaagcag ctcatcccgg tcatcagcga ctatctcctc    159600
tccaacctga aagggatcgc ccagtgagtg ggagcctggc tggggctggg gcggggtct     159660
cagaatgagc tgtgaaggaa gcagcatcac cctctccaag tgcccaggct cctggccaga    159720
tggcaggcca ggtatcagtg ggaacccagg tgggtgccat ggctgaggtc agtgagacgc    159780
aagagcacag gtgcgtccta gaggcttcct cgggcacctc cagcgagctg gagctctcgc    159840
ctctgctgct gtctcatgtg gcgcttagca cactctccca cgtgcccatt cctgactctg    159900
ctctcgaggc catcggctct cattctctgc tcccagaacc ctgttattac ccaggctagc    159960
ctcctctctg caccttcccc gccctggccc agtacctccc tcttgtttcc actgtgattc    160020
cgacctcacc ttatcttaaa gctgctggac ggcaggttct gtacacacgt gtccttgaca    160080
aagcacggct ggtgccgcaa cccctcagcg agcaagtcaa gctcttcaca gcgatgtctt    160140
acaagcgcag agggctctgt gacaccctgg tctcaccgcc actcttccaa agtcgcagag    160200
gctttagcag agatgggccc agcctctctg agtcataggc ttctgcacac gggagctgtc    160260
tttagaggga gggtggaatt tcatcagcca cccacatggg ggagttgagg gcaagaatta    160320
ggagcaaaga tgggaagggg tctgggagga atggccagtg atccccttg acaagtgggc     160380
aggaaacggg ggctaggtca aagttgagtg gaagacctgg agggagacgg gaaggtctct    160440
gtaggcacag ttcagacagg agggaggtgt gagccagggc acatgccggt ggccgtctgg    160500
caggatttgg gacatgctgg agcagggaca gcggctcatc aggggccatt gccctcatcc    160560
aggccagagt gtcacaagcc cgtggggagg cccttctcgc ctgtcatcct tgctgggcag    160620
tgggtgctgt gctagcagga caggcggacg gctggcaact gtctctgcat ccctggagcc    160680
tggcataggg ccaagtcaca cggggcacag gcctgcaaat caggcacata tgttggtgca    160740
gtgacgtgat tttgggggc agccccagaa caggccccag acacaggcca aagccctgcc     160800
tgtgctggtg tgttggcctg ttctatggct cttgctgtgg gcatgaggga ctcagggaag    160860
gagagttgag gtggtccagg agttgcgttt gggatgcaga gagcttgtgg catccaggta    160920
```

-continued

```
gaaatggtgc gtggggctga cctcagcacc atgggcagag gggccgtgtc acgtgcctcc   160980
gaggtggagg tgggaccacg tggtgacaga tatacgcatc actgggcacg ttttgtggg    161040
tgttgggggg catcgtattg gctcctctgt tcacagtggc cactcattca gtccctggct   161100
accaggtcct cactgtgcca tggggaaggc cggcgctgtc gggggatcac agaaggcagc   161160
acgtcatgat ggcatgtgcc atgaaggaaa agcacagggc actcaggaag tagaggggac   161220
tggcctgggg tgtgggaatc tagggcctcg ttgagggaca gagagaggaa gtgtgtggtg   161280
gccagcatgg aggtggccac aggggaggct gagttaggcc gagagggcag ggcgttgggg   161340
aggtagacgg gctcagccac tcagggagtg gtcaagcaga ggctgaaggg tcaggccagg   161400
ttgcaggggc ctgggggagc cactcagggt aggcgctccc gggagcccgc ctggcccata   161460
gctctacact cccgcgtggg gccggacatg ctgtgaagcc ctctccacgt tggatggggg   161520
tggctgagcc tggatgctgt ctcccgtttt cagctgcgtg aacattcaca gccagcagca   161580
cgtactggtc atgtgtgcca ctgcgtttta cctcattgag aactatcctc tggacgtagg   161640
gccggaattt tcagcatcaa taatacaggt gagtgggccc tggctgtctt cctctgcaca   161700
cggggagtgg gcttcccttc tcttttcctt gcaggatcat accagtgggc cagttttgac   161760
ttggtcggga ggaggcatga acacctgaga ctgtgcagcg attctttgac acagaggcct   161820
ttctccctgt gcagatgtgt ggggtgatgc tgtctggaag tgaggagtcc accccctcca   161880
tcatttacca ctgtgccctc agaggcctgg agcgcctcct gctctctgag cagctctccc   161940
gcctggatgc agaatcgctg gtcaagctga gtgtggacag agtgaacgtg cacagcccgc   162000
accgggccat ggcggctctg ggcctgatgc tcacctgcat gtacacaggt gagcatgtac   162060
acggtgccca taaggccagc ccaagtcctg ttcaagggag gcaggagcat gctcactcaa   162120
gggacctcga ctaggtgccc tctgatttca cacttctggt gttgccccaa gccggcccca   162180
tcaccttgca agaaaggctc tggagccccc agggctggag tacctggtca gggttgaccg   162240
tccctgtggt cactcatccc atgtggctga gctgggctgg gtcctgggca agcaagggc    162300
tgatatcacc tgcttcaga tctccaggga ctcactggac ccctgtgtac aaagcactgt    162360
ctacagagcc tattggggttg tatagaggta accttcgtac tgaacacttt tgttacagga   162420
aaggagaaag tcagtccggg tagaacttca gaccctaatc ctgcagcccc cgacagcgag   162480
tcagtgattg ttgctatgga gcgggtatct gttcttttg ataggtaaga agcgaagccc    162540
catccctcag ccgttagctt ccctagaact ttggcctgaa gctgtgcttt tgtgtgtgtc   162600
tgctgatccc ctggcgctgt tgctggagtc ctgccagta ttccccacca cagcctgacc    162660
atgggctgcc ttggctcagg gttccactgg cgagctggtg gtccttggac cccagcactc   162720
aggtgtagcg ttgaccagtt ccaaggttgt cccagtgcct gcccatctct cctgagggct   162780
cagggacagt acctggcagt tgggggtgtg gcagggggca ggaatgacca gcctctggga   162840
gggtggggca gaagcctgta cagtgaggag gagctggctc agcctggctg cctatcgtga   162900
gagggggagcc cacggggctg tgggagggg ccgtggtgc ctgtgagcag ggtgaggagc     162960
agcggcagga ggatgaaggt ggaacccaca catgcatctt tgagacccgt gtggtcagtg   163020
gcttctgccc cccaccaccc cccactgctg tgcgtgcata gaattggctt ccctcacctg   163080
ctctggaagt gggttaggag cttggtaggg cttttctca aggacaaggg ccctgatttt    163140
gctctcaggc ctcagtcctg gcgacatggt ggatctggag ccttgttgca ctgccttgcc   163200
tgtgctctcc aatcagggtg gccagtgggg agccatttgg cttttctcaa gagcatactc   163260
```

```
aggtggacct tgctccactg tttgaccaga tgaggcattc tgaacagcca agcctgtgct   163320
ggtctgtttt catgttgatt ttttttttc ttttcttttt gagatggagt ttttcccttg    163380
tcacccaggc tggagtgcaa tggtgtgatc tcggctcact gcaacctccg cctcccgggt   163440
tcaagtgatt ctcctgcctc agcctccta gtagctggga ttacaggcac acaccaccat    163500
gcccagctaa ttttgtgtt tttagtagag acggggtttc accgtgttgg ctgggctggt    163560
ctcgaactcc tgaactcaag tgatccaccc tccttggcct cccaaagtgc tgggattgca   163620
ggcgtgagcc actgcgcccg gcccccatgt cgatttttaa atgcacctct gcatcgttct   163680
tcagtcccca tatgctcact gagcaccact gcgactggca gacgggcaca gggaggcgcc   163740
acgaccagtc ctggccttca aggggcttgt ggtctagtgg gcccaatgct aggtggcgag   163800
tgctccaaag agtgtggtgc acgccttccg cttgaccgct ctccagacgc cacagggagg   163860
cacctcgcag ctgaccacag atttctctct gtggagcagt gtcttcagag cggctgccat   163920
gccactgctg ggcgagggtc tgcgggcggg tagagccagg agcacctgtg aggaagtgca   163980
ctgccatttt cgtagctgct tcccgtgtgt ctcagttaca cacggctggc atgtgtgcac   164040
tgatgagacg ggaacgtgat ggttgctttt cagcactgaa agggatactg ctcaggggc    164100 gtgtttcagg atctggttag ggaagaagca gcgagagcac agatgggggcc ctgtgtgta   164160 acaagaaaaa agtcctggtt gacaacagtg ccacgaagcg ttagaacaca tagggatgtt   164220
tgtggagcat ttgcatgtgg aaagcagcaa aaacataatg ggaacgggtt cttttgttat   164280
gatttttaaa aatctctttt gtaacatcct tcccgctgcg ccgtttctgc atattccttt    164340
atgtagcttt caaactcctc ttaggagttc tggtccctac agggcgtggg agcccaggct   164400
ttacgtagct ttcaaactcc tcttaggagt tctggtccct acagggtgtg ggagcccagg   164460
gcctgtgccg agcagcctgc ctccacgagc tagacagagg aagggctggg gttttgcctt   164520
tttagtctca aaattcgtac tccagttgct taggctctga cttttcccac ttggaaagtc   164580
cctcacggcc gagggtccct cccagccctg atttcacatc ggcattttcc ccagtattag   164640
agccaaggcc ctccgcgggc aggtggggca gctgtgggag ctggtgccag tctctgacct   164700
gcgtccctcc tcccaggatc aggaaaggct ttccttgtga agccagagtg gtggccagga   164760
tcctgcccca gtttctagac gacttcttcc cacccagga catcatgaac aaagtcatcg    164820
gagagtttct gtccaaccag cagccatacc cccagttcat ggccaccgtg gtgtataagg   164880
tgaggttgca tgtgggatgg ggatggagtg ggaaagcctg gaggtggagt tgcctccgac    164940
ttcccagcag attcgccagc agagcccagc tcctccgctt taaagcagca atgcctctgg   165000 ccccacccc acccccgcca cccaggcgca gcaggtgctt cccgtccccc cagccctgac     165060
actcaggcac ctgcttgctc cttgcaggtg tttcagactc tgcacagcac cgggcagtcg   165120
tccatggtcc gggactgggt catgctgtcc ctctccaact tcacgcagag gccccggtc    165180 gccatggcca cgtggagcct ctcctgcttc tttgtcagcg cgtccaccag cccgtgggtc    165240
gcggcgatgt atcctctctg gtccctggt gctggccccg tttcccttgt caacaccgag     165300
gctcatgttt catgataagg ttttgaaacc taacctttgc aaaaacccca cagatgccag   165360
ggtgacaggc cctcagcccc aggaagtaa atgctgaca ggggtacaga aaggagcacg      165420
tccagacatt tgctgaccag ggcctctcag aggggccggt gtatggcagg agggtcgcag   165480
ctgaggggcc tttctgtgga gggcctggg gaggggagcg agggtgggcg gtggtctctg     165540
cagacgtccc gcccactcgc gggctctgtg tggctgggct tctcctgaca ctgcttctca   165600
ttagctttgg tcattgtgcc tcgatcgccc tctcggggaa aggcttaagt aaagatccag   165660
```

```
ttcccacccc cagatgctgg ctgccaggag tttcccttc cacagccctt ccccaagaca   165720
gaccacaaga gcctccaagc agcacagttg tcctggtgct gacagcacag ccttgcccgg   165780
cgtgcctggc acggctctgc cctcactgca ttggagcagg gctagtggag gccagcggaa   165840
gcaccggcca ccagcgctgc acaggagcca ggccaggtga gtgctgccga gtgggtgccc   165900
tgcctgcagg gcatccagcc agccaagggt tgcaggaatg gaggtggagg cgctgatgca   165960
gctggaggca tccaggtggc ccttccgggg ctctgctcgc tctccaggct ccctggaccc   166020
ctttgtagac tgtttcagga gaggaactcc caggtgagga cagggaggca gcattcccct   166080
catttgccgg ccttttttcct taactcctgc accagcctcc cacatgtcat cagcaggatg   166140
ggcaagctgg agcaggtgga cgtgaacctt ttctgcctgg tcgccacaga cttctacaga   166200
caccagatag aggaggagct cgaccgcagg gccttccagt ctgtgcttga ggtggttgca   166260
gccccaggaa gcccatatca ccggctgctg acttgtttac gaaatgtcca caaggtcacc   166320
acctgctgag cgccatggtg ggagagactg tgaggcggca gctggggccg gagcctttgg   166380
aagtctgcgc ccttgtgccc tgcctccacc gagccagctt ggtccctatg ggcttccgca   166440
catgccgcgg gcgccaggc aacgtgcgtg tctctgccat gtggcagaag tgctctttgt   166500
ggcagtggcc aggcagggag tgtctgcagt cctggtgggg ctgagcctga ggccttccag   166560
aaagcaggag cagctgtgct gcaccccatg tgggtgacca ggtcctttct cctgatagtc   166620
acctgctggt tgttgccagg ttgcagctgc tcttgcatct gggccagaag tcctccctcc   166680
tgcaggctgg ctgttggccc ctctgctgtc ctgcagtaga aggtgccgtg agcaggcttt   166740
gggaacactg gcctgggtct ccctggtggg gtgtgcatgc cacgcccgt gtctggatgc   166800 acagatgcca tggcctgtgc tgggccagtg gctgggggtg ctagacaccc ggccaccattc   166860 tcccttctct cttttcttct caggatttaa aatttaatta tatcagtaaa gagattaatt   166920
ttaacgtaac tctttctatg cccgtgtaaa gtatgtgaat cgcaaggcct gtgctgcatg   166980
cgacagcgtc cggggtggtg gacagggccc ccggccacgc tccctctcct gtagccactg   167040
gcatagccct cctgagcacc cgctgacatt tccgttgtac atgttcctgt ttatgcattc   167100
acaaggtgac tgggatgtag agaggcgtta gtgggcaggg ggccacagca ggactgagga   167160
caggccccca ttatcctagg ggtgcgctca cctgcagccc ctcctcctcg gcacagacg   167220 actgtcgttc tccaccccacc agtcagggac agcagcctcc ctgtcactca gctgagaagg   167280 ccagcccctcc ctggctgtga gcagcctcca ctgtgtccag agacatgggc ctcccactcc   167340
tgttccttgc tagccctggg gtggcgtctg cctaggagct ggctggcagg tgttgggacc   167400
tgctgctcca tggatgcatg ccctaagagt gtcactgagc tgtgttttgt ctgagcctct   167460
ctcggtcaac agcaaagctt ggtgtcttgg cactgttagt gacagagccc agcatccctt   167520
ctgcccccgt tccagctgac atcttgcacg gtgacccctt ttagtcagga gagtgcagat   167580
ctgtgctcat cggagactgc cccacggccc tgtcagagcc gccactccta tcccaggcc   167640 aggtccctgg accagcctcc tgtttgcagg cccagaggag ccaagtcatt aaaatggaag   167700
tggattctgg atggccgggc tgctgctgat gtaggagctg gatttgggag ctctgcttgc   167760
cgactggctg tgagacgagg cagggctct gcttcctcag ccctagaggc gagccaggca   167820
aggttggcga ctgtcatgtg gcttggtttg gtcatgcccg tcgatgtttt gggtattgaa   167880
tgtggtaagt ggaggaaatg ttggaactct gtgcaggtgc tgccttgaga cccccaagct   167940
tccacctgtc cctctcctat gtggcagctg gggagcagct gagatgtgga cttgtatgct   168000
```

```
gcccacatac gtgaggggga gctgaaaggg agccctcct ctgagcagcc tctgccaggc   168060
ctgtatgagg cttttcccac cagctcccaa cagaggcctc cccagccag gaccacctcg   168120 tcctcgtggc ggggcagcag gagcggtaga aaggggtccg atgtttgagg aggcccttaa   168180
gggaagctac tgaattataa cacgtaagaa aatcaccatt ccgtattggt tgggggctcc   168240
tgtttctcat cctagctttt tcctggaaag cccgctagaa ggtttgggaa cgaggggaaa   168300
gttctcagaa ctgttggctg ctccccaccc gcctcccgcc tccccgcag gttatgtcag   168360 cagctctgag acagcagtat cacaggccag atgttgttcc tggctagatg tttacatttg   168420
taagaaataa cactgtgaat gtaaaacaga gccattccct tggaatgcat atcgctgggc   168480
tcaacataga gtttgtcttc ctcttgttta cgacgtgatc taaaccagtc cttagcaagg   168540
ggctcagaac accccgctct ggcagtaggt gtccccacc cccaaagacc tgcctgtgtg   168600
ctccggagat gaatatgagc tcattagtaa aaatgacttc acccacgcat atacataaag   168660
tatccatgca tgtgcatata gacacatcta aattttaca cacacacctc tcaagacgga   168720
gatgcatggc ctctaagagt gcccgtgtcg gttcttcctg gaagttgact ttccttagac   168780
ccgccaggtc aagttagccg cgtgacggac atccaggcgt gggacgtggt cagggcaggg   168840
ctcattcatt gcccactagg atcccactgg cgaagatggt ctccatatca gctctctgca   168900
gaagggagga agactttatc atgttcctaa aaatctgtgg caagcaccca tcgtattatc   168960
caaattttgt tgcaaatgtg attaatttgg ttgtcaagtt ttgggggtgg gctgtgggga   169020
gattgctttt gttttcctgc tggtaatatc gggaaagatt ttaatgaaac cagggtagaa   169080
ttgtttggca atgcactgaa gcgtgtttct ttcccaaaat gtgcctccct tccgctgcgg   169140
gcccagctga gtctatgtag gtgatgtttc cagctgccaa gtgctctttg ttactgtcca   169200
ccctcatttc tgccagcgca tgtgtccttt caaggggaaa atgtgaagct gaacccctc   169260 cagacaccca gaatgtagca tctgagaagg ccctgtgccc taaaggacac ccctcgcccc   169320
catcttcatg gaggggtca tttcagagcc ctcggagcca atgaacagct cctcctcttg   169380
gagctgagat gagccccacg tggagctcgg gacggatagt agacagcaat aactcggtgt   169440
gtggccgcct ggcaggtgga acttcctccc gttgcgggt ggagtgaggt tagttctgtg   169500
tgtctggtgg gtggagtcag gcttctcttg ctacctgtga gcatccttcc cagcagacat   169560
cctcatcggg ctttgtccct ccccgcttc ctccctctgc ggggaggacc cgggaccaca   169620
gctgctggcc agggtagact tggagctgtc ctccagaggg gtcacgtgta ggagtgagaa   169680
gaaggaagat cttgagagct gctgagggac cttggagagc tcaggatggc tcagacgagg   169740
acactcgctt gccgggcctg ggcctcctgg aaggaggga gctgctcaga atgccgcatg   169800
acaactgaag gcaacctgga aggttcaggg gccgctcttc ccccatgtgc ctgtcacgct   169860
ctggtgcagt caaaggaacg ccttcccctc agttgtttct aagagcagag tctccgctg   169920 caatctgggg ggtaactgcc agccttggag gatcgtggcc aacgtggacc tgcctacgga   169980
gggtgggctc tgacccaagt ggggcctcct tgtccaggtc tcactgcttt gcaccgtggt   170040
cagagggact gtcagctgag cttgagctcc cctggagcca gcaggctgt gatgggcgag   170100 tcccggagcc ccacccagac ctgaatgctt ctgagagcaa aggaaggac tgacgagaga   170160 tgtatattta attttttaac tgctgcaaac attgtacatc caaattaaag gaaaaaatg   170220 gaaaccatca gttgttgctg tgtgaggctt gctttgcttc atgagaacct agaccttgct   170280
gagctggagt cttaggaagc agtctcctaa gtgcttctcc agcaggggca gaaactgtcc   170340
caccagctaa catctggcat tatggagggt ccccaggca gctgccagca gggacaggcc   170400
```

```
ccgtgttttc tgtagccagg gatgaggaag tggccccagg gcatgggcct ggctgggtgc    170460
ttctgcaagg gccttcccaa accacagtac aggtggtctt cctgccctgc agatgggagc    170520
tgtgggagct gctggagctg ctggagcctt catggtcaag tgacatcata agcttatatg    170580
acatacacaa gcctcaggac ttggcccatg gcactgaagc aggtcatcag gcccagcaca    170640
gagactagag ctgtgttctc acagggccca ccacccttcc acctccttgg ccattgacac    170700
ctgcgtccct ggcccagctg ctcccaggta accccaaag cagctggcac atcccacctc     170760
tggtgtggcc ggggctgctg tgtgtccgca gggcctgccc cgtctattct agcttgtttg    170820
tcctgtctga accagcgcct actccaagaa gcctctgctc agcccagcgg ggatgcttct    170880
aagctccgga cgagcctctc ggaagccttg gtgattggtg gtgtagtcat cttgggatgc    170940
agatgtctta ccaacctgca agaacaaaaa ccctgtggct tcctctggtg cagggtattt    171000
agtcaatgtt tgctgaggtc ccgtctggtt ctggctaatt ggcagggtc gtccacccat     171060
tctttccctg ctctgctgtc tgtgccagga gagacggggg ccagtcggcc aaggggccag    171120
ctcctgctgc ctgctcctct tgggcacgtg cgggggcccc ctttctctga gcagggatag    171180
ggatcagtct gccggaggga tgtggtggac aggcctaaag catttggggc ggggcatgcc    171240
acttgagctc cctaaatctg tctcctcata ggtgacaccg ctccagggcc ccccagtggc    171300
ctctcctttc agagctacct aaattctggt cacttcagag aaatggagca ccccttctc     171360
cctggtccag gtgtggacag cctggcacac tgagcacacc tggcatggct ggtaatttca    171420
gaaagaagag gggccggggt ccagtgggaa gcagcggtga accctcgtg agtgggcttt     171480
gcagtccctc cccatgccac ggcagagctg ccctcaacac agccttcctc ttcctcatcg    171540
gagagcacac cctgtcccct tgccgagctg tgccctgtgc cttcggtggt atttgatttt    171600
ggctgctact ggctttgttg ggatctggaa gtcgcttccc ctgcgtggtg cgtggagcac    171660
tgtaagtcag atgagggaag tagccagggt gaggtgagta ccgggtggag ccgccactga    171720
agggactggg tagggggggcc ttgcctctac atgatgtgac acagccaacc gaggacagag    171780
gaagccccgt tcctggggt gtgggtgca cccctcaggg aagcctgcag tggggcctga     171840
ggaaaggcat cctccgcgag cccacgagtc tggtccatga gcaccgtgac agtgtctgtg    171900
ggtagaggtg gacccggcct tgtgtcatca ccaggacctc ttttgggaaa ccatgtggac    171960
atcgcttgcg ggtcccccag gctctgcagc cccagcagcc t                        172001
```

<210> SEQ ID NO 3
<211> LENGTH: 10081
<212> TYPE: DNA
<213> ORGANISM: Mus musculus

<400> SEQUENCE: 3

```
gcactcgccg cgagggttgc cgggacgggc ccaagatggc tgagcgcctt ggttccgctt     60
ctgcctgccg cgcagagccc cattcattgc cttgctgcta agtggcgccg cgtagtgcca    120
gtaggctcca agtcttcagg gtctgtccca tcgggcagga agccgtcatg gcaaccctgg    180
aaaagctgat gaaggctttc gagtcgctca agtcgtttca gcagcaacag cagcagcagc    240
caccgccgca ggcgccgccg ccaccgccgc cgccgcctcc gcctcaaccc ctcagccgc     300
cgcctcaggg gcagccgccg ccgccaccac cgccgctgcc aggtccggca gaggaaccgc    360
tgcaccgacc aaagaaggaa ctctcagcca ccaagaaaga ccgtgtgaat cattgtctaa    420
caatatgtga aaacattgtg gcacagtctc tcagaaattc tccagaattt cagaaactct    480
```

-continued

```
tgggcatcgc tatggaactg tttctgctgt gcagtgacga tgcggagtca gatgtcagaa    540
tggtggctga tgagtgcctc aacaaagtca tcaaagcttt gatggattct aatcttccaa    600
ggctacagtt agaactctat aaggaaatta aaaagaatgg tgctcctcga agtttgcgtg    660
ctgccctgtg gaggtttgct gagctggctc acctggttcg acctcagaag tgcaggcctt    720
acctggtgaa tcttcttcca tgcctgaccc gaacaagcaa agaccggag gaatcagttc    780 aggagaccct ggctgcagct gttcctaaaa ttatggcttc ttttggcaat ttcgcaaatg    840
acaatgaaat taaggttctg ttgaaagctt tcatagcaaa tctgaagtca agctctccca    900
ccgtgcggcg gacagcagcc ggctcagccg tgagcatctg ccaacattct aggaggacac    960
agtacttcta caactggctc cttaatgtcc tcctaggtct gctggttccc atggaagaag    1020
agcactccac tctcctgatc ctcggtgtgt tgctcacatt gaggtgtcta gtgcccttgc    1080
tccagcagca ggtcaaggac acaagtctaa aaggcagctt tggggtgaca cggaaagaaa    1140
tggaagtctc tccttctaca gagcagcttg tccaggttta tgaactgact ttgcatcata    1200
ctcagcacca agaccacaat gtggtgacag ggcactggag gctcctgcag cagctcttcc    1260
gtacccctcc acctgaactc ctgcaagcac tgaccacacc aggagggctt gggcagctca    1320
ctctggttca agaagaggcc cggggccgag gccgcagcgg gagcatcgtg gagcttttag    1380 ctggagggg ttcctcgtgc agccctgtcc tctcaagaaa gcagaaaggc aaagtgctct    1440
taggagagga gaagccttg gaagatgact cggagtccag gtcagatgtc agcagctcag    1500
cctttgcagc ctctgtgaag agtgagattg gtggagagct cgctgcttct tcaggtgttt    1560
ccactcctgg ttctgttggt cacgacatca tcactgagca gcctagatcc cagcacacac    1620
ttcaagcaga ctctgtggat ttgtccggct gtgacctgac cagtgctgct actgatgggg    1680
atgaggagga catcttgagc cacagctcca gccagttcag tgctgtccca tccgaccctg    1740
ccatggacct gaatgatggg acccaggcct cctcacccat cagtgacagt tctcagacca    1800
ccactgaagg acctgattca gctgtgactc cttcggacag ttctgaaatt gtgttagatg    1860
gtgccgatag ccagtatta ggcatgcaga taggacagcc acaggaggac gatgaggagg    1920
gagctgcagg tgttctttct ggtgaagtct cagatgtttt cagaaactct tctctggccc    1980
ttcaacaggc acacttgttg aaagaatgg gccatagcag gcagccttcc gacagcagta    2040
tagataagta tgtaacaaga gatgaggttg ctgaagccag tgatccagaa agcaagcctt    2100
gccgaatcaa aggtgacata ggacagccta atgatgatga ttctgctcct ctggtacatt    2160
gtgtccgtct tttatctgct tccttttgt taactggtga aaagaaagca ctggttccag    2220
acagagacgt gagagtcagt gtgaaggccc tggccctcag ctgcattggt gcggctgtgg    2280
cccttcatcc agagtcgttc ttcagcagac tgtacaaagt acctcttaat accacggaaa    2340
gtactgagga acagtatgtt tctgacatct tgaactacat cgatcatgga gacccacagg    2400
tccgaggagc tactgccatt ctctgtggga cccttgtcta ctccatcctc agtaggtccc    2460
gtctccgtgt tggtgactgg ctgggcaaca tcagaaccct gacaggaaat acattttctc    2520
tggtggactg cattcctta ctgcagaaaa cgttgaagga tgaatcttct gttacttgca    2580
agttggcttg tacagctgtg aggcactgtg tcctgagtct ttgcagcagc agctacagtg    2640
acttgggatt acaactgctt attgatatgc tgcctctgaa gacagctcc tactggctgg    2700 tgaggaccga actgctggac actctgcag agattgactt caggctcgtg agttttttgg    2760
aggcaaaagc agaaagttta caccgagggg ctcatcatta tacagggttt ctaaaactac    2820
aagaacgagt actcaataat gtggtcattt atttgcttgg agatgaagac cccagggttc    2880
```

```
gacatgttgc tgcaacatca ttaacaaggc ttgtcccaaa gctgttttac aagtgtgacc    2940
aaggacaagc tgatccagtt gtggctgtag cgagggatca gagcagtgtc tacctgaagc    3000
tcctcatgca tgagacccag ccaccatcac acttttctgt cagcaccatc accagaatct    3060
atagaggcta tagcttactg ccaagtataa cagatgtcac catggaaaac aatctctcaa    3120
gagttgttgc cgcagtttct catgaactca ttacgtcaac aacacgggca ctcacatttg    3180
gatgctgtga agccttgtgt cttctctcag cagccttttcc agtttgcact tggagtttag    3240
gatggcactg tggagtgccc ccactgagtg cctctgatga gtccaggaag agctgcactg    3300
ttgggatggc ctccatgatt ctcaccttgc tttcatcagc ttggttccca ctggatctct    3360
cagcccatca ggatgccttg attttggctg gaaacttgct agcagcgagt gcccccaagt    3420
ctctgagaag ttcatggacc tctgaagaag aagccaactc agcagccacc agacaggagg    3480
aaatctggcc tgctctgggg gatcggactc tagtgcccctt ggtggagcag cttttctccc    3540
acctgctgaa ggtgatcaat atctgtgctc atgtcttgga cgatgtgact cctggaccag    3600
caatcaaggc agccttgcct tctctaacaa accccccttc tctaagtcct attcgacgga    3660
aagggaagga gaaagaacct ggagaacaag cttctactcc aatgagtccc aagaaagttg    3720
gtgaggccag tgcagcctct cgacaatcag acacctcagg acctgtcaca gcaagtaaat    3780
catcctcact ggggagtttc taccatctcc cctcctacct caaactgcat gatgtcctga    3840
aagccactca cgccaactat aaggtcacct tagatcttca aacagcact gaaaagtttg    3900
gggggttcct gcgctctgcc ttggacgtcc tttctcagat tctagagctg gcgacactgc    3960
aggacattgg aaagtgtgtt gaagaggtcc ttggatacct gaaatcctgc tttagtcgag    4020
aaccaatgat ggcaactgtc tgtgtgcagc agctattgaa gactctcttt gggacaaact    4080
tagcctcaca gtttgatggc ttatcttcca accccagcaa gtctcagtgc cgagctcagc    4140
gccttggctc ttcaagtgtg aggcccggct tatatcacta ctgcttcatg gcaccataca    4200
cgcacttcac acaggccttg gctgacgcaa gcctgaggaa catggtgcag gcggagcagg    4260
agcgtgatgc ctcggggtgg tttgatgtac tccagaaagt gtctgcccaa ttgaagacga    4320
acctaacaag cgtcacaaag aaccgtgcag ataagaatgc tattcataat cacattaggt    4380
tatttgagcc tcttgttata aaagcattga agcagtacac cacgacaaca tctgtacaat    4440
tgcagaagca ggttttggat ttgctggcac agctggttca gctacgggtc aattactgtc    4500
tactggattc agaccaggtg ttcatcgggt ttgtgctgaa gcagtttgag tacattgaag    4560
tgggccagtt cagggaatca gaggcaatta ttccaaatat attttcttc ctggtattac    4620
tgtcttatga gcgctaccat tcaaaacaga tcattggaat tcctaaaatc atccagctgt    4680
gtgatggcat catggccagt ggaaggaagg ccgttacaca tgctatacct gctctgcagc    4740
ccattgtcca tgacctcttt gtgttacgag gaacaaataa agctgatgca gggaaagagc    4800
ttgagacaca gaaggaggtg gtggtctcca tgctgttacg actcatccag taccatcagg    4860
tgctggagat gttcatcctt gtcctgcagc agtgccacaa ggagaatgag gacaagtgga    4920
aacggctctc tcggcaggtc gcagacatca tcctgcccat gttggccaag cagcagatgc    4980
atattgactc tcatgaagcc cttggagtgt taaataccct tgtttgagatt ttggctcctt    5040
cctccctacg tcctgtggac atgcttttgc ggagtatgtt catcactcca agcacaatgg    5100
catctgtaag cactgtgcag ctgtggatat ctggaatcct cgccattctg agggttctca    5160
tttcccagtc aaccgaggac attgttcttt gtcgtattca ggagctctcc ttctctccac    5220
```

```
acttgctctc ctgtccagtg attaacaggt taaggggtgg aggcggtaat gtaacactag    5280
gagaatgcag cgaagggaaa caaaagagtt tgccagaaga tacattctca aggtttcttt    5340
tacagctggt tggtattctt ctagaagaca tcgttacaaa acagctcaaa gtggacatga    5400
gtgaacagca gcatacgttc tactgccaag agctaggcac actgctcatg tgtctgatcc    5460
acatattcaa atctggaatg ttccggagaa tcacagcagc tgccactaga ctcttcacca    5520
gtgatggctg tgaaggcagc ttctatactc tagagagcct gaatgcacgg gtccgatcca    5580
tggtgcccac gcacccagcc ctggtactgc tctggtgtca gatcctactt ctcatcaacc    5640
acactgacca ccggtggtgg gcagaggtgc agcagacacc caagagacac agtctgtcct    5700
gcacgaagtc acttaacccc cagaagtctg gcgaagagga ggattctggc tcggcagctc    5760
agctgggaat gtgcaataga gaaatagtgc gaagaggggc ccttattctc ttctgtgatt    5820
atgtctgtca gaatctccat gactcagaac acttaacatg gctcattgtg aatcacattc    5880
aagatctgat cagcttgtct catgagcctc cagtacaaga ctttattagt gccattcatc    5940
gtaattctgc agctagtggt ctttttatcc aggcaattca gtctcgctgt gaaaatcttt    6000
caacgccaac cactctgaag aaaacacttc agtgcttgga aggcatccat ctcagccagt    6060
ctggtgctgt gctcacacta tatgtggaca ggctcctggg cacccccttc cgtgcgctgg    6120
ctcgcatggt cgacaccctg gcctgtcgcc gggtagaaat gcttttggct gcaaatttac    6180
agagcagcat ggcccagttg ccagaggagg aactaaacag aatccaagaa cacctccaga    6240
acagtgggct tgcacaaaga caccaaaggc tctattcact gctggacaga ttccgactct    6300
ctactgtgca ggactcactt agccccttgc ccccagtcac ttcccaccca ctggatgggg    6360
atgggcacac atctctggaa acagtgagtc cagacaaaga ctggtacctc cagcttgtca    6420
gatcccagtg ttggaccaga tcagattctg cactgctgga aggtgcagag ctggtcaacc    6480
gtatccctgc tgaagatatg aatgacttca tgatgagctc ggagttcaac ctaagccttt    6540
tggctcccctg tttaagcctt ggcatgagcg agattgctaa tggccaaaag agtcccctct    6600
ttgaagcagc ccgtggggtg attctgaacc gggtgaccag tgttgttcag cagcttcctg    6660
ctgtccatca agtcttccag cccttcctgc ctatagagcc cacggcctac tggaacaagt    6720
tgaatgatct gcttggtgat accacatcat accagtctct gaccatactt gcccgtgccc    6780
tggcacagta cctggtggtg ctctccaaag tgcctgctca tttgcacctt cctcctgaga    6840
aggagggga cacggtgaag tttgtggtaa tgacagttga ggccctgtca tggcatttga    6900
tccatgagca gatcccactg agtctggacc tccaagccgg gctagactgc tgctgcctgg    6960
cactacaggt gcctggcctc tgggggtgc tgtcctcccc agagtacgtg actcatgcct    7020
gctccctcat ccattgtgtg cgattcatcc tggaagccat tgcagtacaa cctggagacc    7080
agcttctcgg tcctgaaagc aggtcacata ctccaagagc tgtcagaaag gaggaagtag    7140
actcagatat acaaaacctc agtcatgtca cttcggcctg cgagatggtg gcagacatgg    7200
tggaatccct gcagtcagtg ctggccttgg gccacaagag gaacagcacc ctgccttcat    7260
ttctcacagc tgtgctgaag aacattgtta tcagtctggc ccgactcccc ctagttaaca    7320
gctatactcg tgtgcctcct ctggtatgga aactcgggtg gtcacccaag cctggagggg    7380
attttggcac agtgtttcct gagatccctg tagagttcct ccaggagaag gagatcctca    7440
aggagttcat ctaccgcatc aacacccctag ggtggaccaa tcgtacccag ttcgaagaaa    7500
cttgggccac cctccttggt gtcctggtga ctcagcccct ggtgatggaa caggaagaga    7560
gcccaccaga ggaagacaca gaaagaaccc agatccatgt cctggctgtg caggccatca    7620
```

```
cctctctagt gctcagtgca atgaccgtgc ctgtggctgg caatccagct gtaagctgct    7680
tggagcaaca gccccggaac aagccactga aggctctcga taccagattt ggaagaaagc    7740
tgagcatgat cagagggatt gtagaacaag aaatccaaga gatggtttcc cagagagaga    7800
atactgccac tcaccattct caccaggcgt gggatcctgt cccttctctg ttaccagcta    7860
ctacaggtgc tcttatcagc catgacaagc tgctgctgca gatcaaccca gagcgggagc    7920
caggcaacat gagctacaag ctgggccagg tgtccataca ctccgtgtgg ctgggaaata    7980
acatcacacc cctgagagag gaggaatggg atgaggaaga agaggaagaa agtgatgtcc    8040
ctgcaccaac gtcaccacct gtgtctccag tcaattccag aaaacaccgt gccggggttg    8100
atattcactc ctgttcgcag tttctgcttg aattgtacag ccgatggatc ctgccatcca    8160
gtgcagccag aaggaccccc gtcatcctga tcagtgaagt ggttcgatct cttcttgtag    8220
tgtcagactt attcaccgaa cgtacccagt ttgaaatgat gtatctgacg ctgacagaac    8280
tacggagagt gcacccttca gaagatgaga tcctcattca gtacctggtg cctgccacct    8340
gtaaggcagc tgctgtcctt ggaatggaca aaactgtggc agagccagtc agccgcctac    8400
tggagagcac actgaggagc agccacctgc ccagccagat cggagccctg cacggcatcc    8460
tctatgtgtt ggagtgtgac ctcttggatg acactgcaaa gcagctcatt ccagttgtta    8520
gtgactatct gctgtccaac ctcaaaggaa tagcccactg cgtgaacatt cacagccagc    8580
agcatgtgct ggtaatgtgt gccactgctt tctacctgat ggaaaactac cctctggatg    8640
tgggaccaga attttcagca tctgtgatac agatgtgtgg agtaatgctg tctggaagtg    8700
aggagtccac cccctccatc atttaccact gtgccctccg gggtctggag cggctcctgc    8760
tgtctgagca gctatctcgg ctagacacag agtccttggt caagctaagt gtggacagag    8820
tgaatgtaca aagcccacac agggccatgg cagccctagg cctgatgctc acctgcatgt    8880
acacaggaaa ggaaaaagcc agtccaggca gagcttctga ccccagccct gctacacctg    8940
acagcgagtc tgtgattgta gctatggagc gagtgtctgt tctctttgat aggatccgca    9000
agggatttcc ctgtgaagcc agggttgtgg caaggatcct gcctcagttc ctagatgact    9060
tctttccacc tcaagatgtc atgaacaaag tcattggaga gttcctgtcc aatcagcagc    9120
catacccaca gttcatggcc actgtagttt acaaggtttt tcagactctg cacagtgctg    9180
ggcagtcatc catggtccgg gactgggtca tgctgtccct gtccaacttc acacaaagaa    9240
ctccagttgc catggccatg tggagcctct cctgcttcct tgttagcgca tctaccagcc    9300
catgggtttc tgcgatcctt ccacatgtca tcagcaggat gggcaaactg gaacaggtgg    9360
atgtgaacct tttctgcctg gttgccacag acttctacag acaccagata gaggaggaat    9420
tcgaccgcag ggctttccag tctgtgtttg aggtggtggc tgcaccagga agtccatacc    9480
acaggctgct tgcttgtttg caaaatgttc acaaggtcac cacctgctga gtagtgcctg    9540
tgggacaaaa ggctgaaaga aggcagctgc tgggcctga gcctccagga gcctgctcca    9600
agcttctgct ggggctgcct tggccgtgca ggcttccact tgtgtcaagt ggacagccag    9660
gcaatggcag gagtgctttg caatgagggc tatgcaggga acatgcacta tgttggggtt    9720
gagcctgagt cctgggtcct ggcctcgctg cagctggtga cagtgctagg ttgaccaggt    9780 gtttgtctttt tcctagtgt tccctggcc atagtcgcca ggttgcagct gccctggtat    9840
gtggatcaga agtcctagct cttgccagat ggttctgagc ccgcctgctc cactgggctg    9900
gagagctccc tcccacattt acccagtagg catacctgcc acaccagtgt ctggacacaa    9960
```

```
aatgaatggt gtgtggggct gggaactggg gctgccaggt gtccagcacc attttccttt    10020
ctgtgttttc ttctcaggag ttaaaattta attatatcag taaagagatt aattttaatg    10080
t                                                                    10081
```

<210> SEQ ID NO 4
<211> LENGTH: 168002
<212> TYPE: DNA
<213> ORGANISM: Macaca mulatta
<220> FEATURE:
<221> NAME/KEY: misc_feature
<222> LOCATION: (8794)..(8848)
<223> OTHER INFORMATION: n is a, c, g, or t
<220> FEATURE:
<221> NAME/KEY: misc_feature
<222> LOCATION: (11952)..(12155)
<223> OTHER INFORMATION: n is a, c, g, or t
<220> FEATURE:
<221> NAME/KEY: misc_feature
<222> LOCATION: (13733)..(14137)
<223> OTHER INFORMATION: n is a, c, g, or t
<220> FEATURE:
<221> NAME/KEY: misc_feature
<222> LOCATION: (17299)..(17497)
<223> OTHER INFORMATION: n is a, c, g, or t
<220> FEATURE:
<221> NAME/KEY: misc_feature
<222> LOCATION: (18993)..(19355)
<223> OTHER INFORMATION: n is a, c, g, or t
<220> FEATURE:
<221> NAME/KEY: misc_feature
<222> LOCATION: (30628)..(32144)
<223> OTHER INFORMATION: n is a, c, g, or t
<220> FEATURE:
<221> NAME/KEY: misc_feature
<222> LOCATION: (37234)..(37641)
<223> OTHER INFORMATION: n is a, c, g, or t
<220> FEATURE:
<221> NAME/KEY: misc_feature
<222> LOCATION: (56357)..(56602)
<223> OTHER INFORMATION: n is a, c, g, or t
<220> FEATURE:
<221> NAME/KEY: misc_feature
<222> LOCATION: (66208)..(66275)
<223> OTHER INFORMATION: n is a, c, g, or t
<220> FEATURE:
<221> NAME/KEY: misc_feature
<222> LOCATION: (72472)..(72756)
<223> OTHER INFORMATION: n is a, c, g, or t
<220> FEATURE:
<221> NAME/KEY: misc_feature
<222> LOCATION: (82608)..(83314)
<223> OTHER INFORMATION: n is a, c, g, or t
<220> FEATURE:
<221> NAME/KEY: misc_feature
<222> LOCATION: (108856)..(108875)
<223> OTHER INFORMATION: n is a, c, g, or t
<220> FEATURE:
<221> NAME/KEY: misc_feature
<222> LOCATION: (131686)..(132275)
<223> OTHER INFORMATION: n is a, c, g, or t
<220> FEATURE:
<221> NAME/KEY: misc_feature
<222> LOCATION: (143992)..(145163)
<223> OTHER INFORMATION: n is a, c, g, or t
<220> FEATURE:
<221> NAME/KEY: misc_feature
<222> LOCATION: (147895)..(148388)
<223> OTHER INFORMATION: n is a, c, g, or t

<400> SEQUENCE: 4

```
atacaggcgt gagccaccgc acccagctgg aacttaatttt ttttaaagat cgtgttgctc     60
tatcgcccaa gctggagtgc agtggtgcaa ccatagctca cttgcagcca caaattcctg    120 gttttcaggtg atcctcctac atcagcctcc caagaactgg gaactaacgg ctgtttctct    180
```

```
gctgtccttc tcaagagaag ggagggagac aatgctgggt ttcccttttgg gacaggctct    240 gagacaaggt ggaggtgctg cttgtggcca cagagcaggg gactctgggt tgcaggtgtg    300
gcctggcttg agtaggcttt agtgggcttc tctctgcctg caccaccccc gggctgggtg    360
gttgtctctg aggccaaccc tactccctaa tgggcaggct ggacagctgc cctctctgtt    420
tgcccctcta ccacccaaaa ggcgggaggc tctggagacc aggaccctgc ctgcgccggc    480
ctgtgcccca ggcgtgaggg ggtgcccacc agatctctgc tgagctgagg ctgaatggca    540
ccccttgggg gtcctgccag gtcagagcag ggtgctttcc catacagaaa cgcccccagg    600
tcgggactca ttcctgtggg aggcgtcttg tggccacaac tgcttctcgc tgcactaatc    660
acagtgcctc tgtgggcagc gggcgctgac catccgggcc tgcctcagac cctctcctcc    720
cttccggggc gctgcgctgg gaccgatggg gggcgccagg cctgtgggca ccgccctgca    780
ggggccgctc cagctcactg ggggtgggg aggtcacac ttggggtctt cagatggcgc    840
cgaccacgcg caatctctgc gctctgcgca ggggctcgcc caccctctcc ccgtgcagcg    900
agtccccagc aggctccccg cagggctgtc caggtgagcc tggctctggc cgcgggccag    960
tgtggcgggg gggcaagccc cgaggccacc tcggctcaga gcccacggcc ggctctcgcc   1020
cagctccaga cgtctgcgag ggttccattc cgcttgggcc ggcgccccgc gcgccgcgcc   1080
ctggccccgc ccctccctca tcccgccccc tctgcacccc accctccct ggccccgccc   1140 tccgcgcccc acctctcatc ttcccgcccc gccccagcc acgcccctca cggtcagccc   1200
cctcccctat ccgccccgcc tctcatcgtc tcgcctcgct ccgcccctca gccgtcccgc   1260
ccctcagccg ccctgcctaa tgtccccgcc cccagcctcg ccccgctccg ccccagcctc   1320
gccccgcccc gcccctcagg cgccctgcct gctgtgcccc gccccagcct cgccacgccc   1380
ctcgttacca tgtagtcccg ccccgtccct tccgcgtccc gcctcgcccc taccccttca   1440
cagcttcgcc ccacccattt acagtcttgc cacgccccgt ccctgtccg ttgagccctg   1500 ctccttcgcc caggtgggc gctgcgctgt cagaggcttt ggtggctctg tgaggcagaa   1560
catgcgggcg cagggactgg ctggctcccct ggccagtcat tggcagagtc cgcaggctag   1620
ggctgtcaat catgctggcc ggcgtggccc cgcctccgcc ggcgcagcgt cttgagacgc   1680
aaggcgccgc gggggctgcc gggacgggtc caagatggac ggccgcttcg gttccgcttt   1740
tacccgcggc ccagagcccc attcattgcc ccggtgctga gcggcgctgc gagtcggccc   1800
gaggcctccg gggactgcct agccgggcgg gagaccgcca tggcgaccct ggaaaagctg   1860
atgaaggcct tcgagtctct caagtccttc agcagcagc agcagcagca gcagcaacag   1920
ccgccgccgc cgccgccgcc gcctcctcct cctcctcagc ttcctcagcc gccgcaggca   1980
cagccgatgc tgcctcagcc gcagccgccc cgccgccgc ccccgccacc acccggcccg   2040
gctgtggctg aggagccgct gcaccgaccg tgagtttggg cccgctgcag ctccctgtcc   2100
cggcgggtcc cagcctacgg cggggatggc ggaatcctgc agcctgcggg ccggcgacac   2160
gaaccccccc ggccccgcag cgacagagtg acccagcaac ccagagccaa tgagggacac   2220 ccgcccccctc ctgcggcgag accttccccc acttcagccc cggtcccgca cttgggtctt   2280
gtcctcccgc gaggggaggc agaacctcgt tgggacctgt cctgaattca cggaggggag   2340
tcacggcctc agccctctcg ccctttccag ggtgcgaaga gttggggcga aaacttgttt   2400 cttttttattt gcgagaaact agggcggggg tttaactgtg ttctgaagag aacttggaag   2460
agccgagatt tgctcagggc cacttccctc atctagtcag agagggaaga gggctggggg   2520
```

```
cgcgggacac ctcgagagga ggcggggttt ggagctagag agatgtgggg gcagtggatg    2580
acataatgct tttaggacgc ctcggcggga gtggctggag tggggggcgg ggagtgaggg    2640
cgcgtccaat gggagattta ttttccaagt ggcatttaaa acagcctgag atttgaggct    2700
cttcctacat tctcagggca tttcatttag ttcatgatcg cggtggtagt aacacgattt    2760
taagcaccac ctaagagacc tgctcatcta agcgcaagtt agtgtgcagg catttgaatg    2820
agttgtggtc gccaaataag tggtgaactt acgtggtatt aataaaatta tcttaaatat    2880
taggaagagt tgattgaagt ttattgcctg tttgtgttgg gaataaaact aacacgttgc    2940
tgagggggag gttaattgcc gagggatgaa tgaggtatac attttaccag tattgcagtc    3000
aggcttgcca gaatatggga ggtctgcaga ctccgtggac atctcatgtg ccagtgaaag    3060
ggtttctgtt cgcctcattg ctgacagctt gttactttt ggaagctaga ggtctctgtt    3120
gcttgttctt ggggagaatt tttgaaacag aaaagagac cattaaaaca tctagcggaa    3180
ccccaggacg tgggagtgtg tgctgagtgt ttagcaggat ttaggaagta ctccgctgca    3240
gttcaggcct ttctcttacc tctcagtgtt ctatttccga tctggacgtg tatcagatgg    3300
catttgataa gaatatctct attaagactg attaattttt agtaatattt cttgttcttt    3360
gtttctgtta tgatccttgc cttgtcttga agtttaatt agaagaggag gatttggaga    3420
gcagtgttag cttatttgtt agagtaaaat ttaggaataa attcttctaa aggatggaaa    3480 aacttttgg atatttagag aaattttaa acaatttggc ttatctcttc agtaagtaat    3540
ttctcatcct tccagaaatt taatgtagtg cctttctagg aggtaggtgt catagaagtt    3600
cacacattgc atgtatcttg tgtaaacact aaactgggct cctgatggga aggaagacct    3660
ttctgctggg ctgcttcaga cacttgatca ttctgaaaat atgccgtctc tttcctgtgc    3720
tgatttgata gaacctgcgt ttgcttatct tcaaaatatg ggtatcaaga aatttccttt    3780
gctgccttta caaggagat agattttgtt tcattacttt attttaaggt aatatatgat    3840
taccttattt taaaaattta atcaggcctg gcaaggtggc tcatgccttt aatccgagca    3900
ctttgggagg cttaggcgga tgaatcacct gaggtcagga gttcgagacc agtctggcta    3960
acatggtgaa accccatctc tactaaaagt acaaaaatta gttggtcatg gtggcacgtg    4020
cctgtaatgc cagctacctg ggaggctgag gcaggaaaat cgctggaacc cgggaggcag    4080
aggctgcagt gagctgagac tgcgccactg cactccagcc tgggtgacag agcgagactc    4140 tgtctcaaa aaaaaaaaa ttattatttt tgcataagta atacattaac atgacacaaa    4200
ttccgtaatt acaaaagagc aatacttaaa atatcttcct tccacccctt tcatctgagt    4260
acctaacttt gtccccaaga acaagcacta ttacagttcc tcctgtatcc tgccagatat    4320
aatctatgca tattgtaaga tagatttaaa atgctgtaaa aataaaagta gtttacagta    4380
ataatttttt ttctttattt tttttgagat gtagtctcac attgtcaccc aggctggagt    4440
gcggtggtat gatcttggct cactgcaacc tccacctccc aggttcaaac gattctcctg    4500
cctcagcctc cagagtagct gggattacag gtgctcacca ccatgtccag ctgattttg    4560 tatttttagt agagatgggg tttcaccatg ttggccaggc tggtcttgaa ctcctgacct    4620
cggaatccat ccacctcggc ctcccaaagt gctgggtta caggtgtgag ccactgcccc    4680
tggctagaat aataactttt aaaggttctt agcattctct gaaatcaact gcattaggtt    4740
tatttatagt tattttaaat aaaatgcata tttgtcatat ttgtatgtat tttgctgttg    4800
agaaaggagg tattcgctaa ttttgagtaa caaacactgc tcacaaagtt tggatttgg    4860 catttctgtt catgtgcttc agccaaaaaa tcctcttctc aaagtaagat tgactaaagc    4920
```

```
aatttagaaa gtatctgttt ttatggctct tgctcttttg tgtggaactg tggtgtcatg      4980
ccatgcatgg gcctcagtct aagtatgagc gtatgtgctc tgctcagcat acaggatgtg      5040
ggagttccgt gtggggctgg ccacagtctc agcaaatcta gcatgcttgg gagggtcctc      5100
acagtaatta ggaggcaact gatacttgct tctggcaatt ccttattctc cttcagattc      5160
ctatccggtg tttccctgac tttattcatt catcagtaaa tatttactaa acatgtacta      5220
tgtacctagc actgttctag atgcagggct cagcagtgag cagacaaagc tgtgccctca      5280
tgaagctttc attctaatga aggacataga caataagcaa gatagataag taaaatatac      5340
agtatgttaa taagtggagg aatgtcaaag cagggaaggg gataggaaa tgtcaggggtt       5400 aatcaattgt taacttattt ttattaaaaa aaattttttt taagggcttt ccagcaaaac      5460
ccagaaagcc tgctggacaa cttccaaaaa aactgtagca ctaagtgttg acatttttat      5520
tttattttat tttattttgt tttgttttgt ttttgaggc agtcttgctt tgtcagccag       5580
gctgcagtgc actggtgtga tcttagctca ctgcaacctc tgcctgttgg gttcaagcga      5640
ttcttatgcc tcagcctcct gattagctgg gattatagac atgcaccgtc ccgcctgggt      5700 aattttttt ttttcccct gagacagagt cttgctctgt cgcccaggct ggagtgcagt        5760
ggcacaatct ggctcactg caagctccgc ctcccaggtt catgccattc tcctgcctca       5820
gcctcccagg tagctgggac tacaggcgcc tgccaccacg cccagctaat ttttgtatt      5880 tttagtagag atggggtttc actgtgtcag ccaggatggt cttgatctcc tcacctcgta      5940
gtccgccccc cttggcctcc caaagtgctg ggattacagg cgtgagccac cgcgcccggc      6000
ctgtaatttt tttttttttt ttttgagaca gagtcttgct ttgttgctag gctggactgc      6060
agtggtgtga tcttggcaca ctgcaacctc tgcctcccgg gttcaagcga ttctcctgcc      6120
tcagcttccc gagtagctgg gactacaggc acgtgccatc acgcttggct acttttgta      6180 tatttagtag aaacggggtt tcaccatgtt agctgagatg atctcgatct cttgacctcg      6240
tgatccgccc gcctcggcct cccagagtgc tgggattaca ggtgtgagcc actgtgcctg      6300
accacgcctg ggtaattttt gtatttttag tagagacggg atttcaccac gatggccaga      6360
ctggtctcga actcccagcc tcatgtgatc tgcctgccta ggcctcccaa agtgctagga      6420
ttacaggcat gagccaccat gactggccag tgttgatatt ttaaataggg tgttcaggga      6480
aggtccactg aggtgacagc tgttttttg ggggagtgg tgggacaggg ccttgctctt        6540
taacccaggc tggaatacag catcacaatc gtagcttact gcagccttga actcctaggc      6600
tcaagtgatc ttcccacctt gacctcacaa cgtgttggga ctgtaggtgt gagtcaccat      6660
gcctggccag atgatggctt tgagtaaaga cctcaggcga gttaagagtc tagcgtaaag      6720
gtgtatggag taggggtatt ccagatagggg ggaacaggtc caaagtcttc ctgtttgagg     6780
aatagcaagg gtgccatttt agttgggtga attgagtgag ggcgacattt gtagtaagag      6840
gtaaagtcca agaggtcaag ggagtgccat atcagaccaa tactacttgc cttgtagatg      6900
gaataaagat attggcattt atgtgagtga gatgggatgt cactggagga ttagaggaga      6960
ggagtagcat gatctgaatt tcattcttaa gtgaactctg gctgacaaca gagtgaaggg      7020
gaacatggac aaaagcagaa accagttagg aagccactgc agtgctcaga taagcgtggt      7080
gggttctgtc agggtaccgg ctgtgggcag tgtgaggaat gactggattt tgaatgcaga      7140
agcaactgta cttgttgaac tctgctaagt ataactattt agcagtagct ggcattatca      7200
gttaggtttg tattcagctg caagtaacag aaaattctgc tgcaatagct taaactggta      7260
```

```
acaagaaaga gcttatcaga agacaaaaat aagtctgttt ggggaaattc aacaataagt      7320
taaggaaccc aggctctttc ttttttttt tgaaatggag ttttgctctt gtcacccagg       7380
ccggagtgca atgatgcgat cttggctcac tataacctcc gcctcctagg ttccagtgat      7440
tcttctgcct cagccttcca ggtatctggg attagaggcg cacgcacacc accatgccca      7500
gctaattttt gtattttag taggcacggg gtttcatcat gttggccagg ctggtctcga       7560
actcctgacc ttaggtgatc aacccgcctc agcctgccaa agtgctgaga ttacaggtgt      7620
gagccactgc actcggtcag aacccaggct cttttttaca cttagcttgc aaaccctgt       7680 tctcattctt ttcccttgt attttattg tcgaattgta acagttcttt gtgtattctg        7740
gatactggat tcttatcaga tagatgattt gtgaaaacat tctctcttcc tttggattgt      7800
cttttacttt tcttgatcat gtcttttgaa gtgtgaaagt ttttaatttt gatgaagtct      7860
agtttatcta gtttgtcctt ggttgctatg ctttgagtgt catatctaag aaatcattgt      7920
ctaatccaaa gtcaaaaagg tttacccgta tgttttcttc taagaattt agagttttac       7980 atttaggtct gatccatttt gagttaattt ttatatgtgg ttcaggtaga agtccaactt      8040
cattcttttg catgtggtta ttcagttgtc ccagcacagt ttgttgaaga gactgtactt      8100
tccccatgga attgtcttag catccttgtt gaaaattcat tgtccttgat tgtatagatt     8160
tatttcttga ctctcagttc tacctattgg tctttatgtt gatcctgtgc cagtaccata     8220
cagtcttgat tactgaagtt tgtgtcacaa tttaaattca tgaaatgtga ttctccaac      8280 tttgttcttt ctcaagattg atttggccat gctgggtccc ttgcatttcc atatggattg     8340
taggatcaac ttgtcagttt ctacaaagaa gccaaggagg attctgagag ggattgtgtt     8400
gaatctgtag atcaacttgg ggagtattac catcttaaca gtattgtctt ccatctctga     8460
actgggcaaa ctttgtgtaa atggtcagat ttaggtattt caggctgtgt gggcacaatg     8520
tctctgtcac agctactcag ctctgccatt gtagcgtgaa atagccataa gcaatatgta     8580
tgagtgtctg tgttccagta taattttatt aatgacaagg aaatttgaat ttcgtgtaat     8640
tttcacctgt catgaaatat tatttggttt ttttggtcaa tcatttaaaa atgtaaaaac     8700
ttttcttagc ttttgaactg gccaaacata tgcaggttat aatttttccca ctcctagatt    8760 aaaatatgat aggaccacct ttgaaaagca tgtnnnnnnn nnnnnnnnnn nnnnnnnnn      8820 nnnnnnnnnn nnnnnnnnnn nnnnnnnnaa cactttggga ggccgagcca ggtggatcac     8880
ttgaggccag gagttcgaga ccagcctaac caacatggtg aaaccccatc tctactaaaa     8940
ataaaaaaat tagctggggg tggtggtggg tgtagggtcc agcccatgg ggcttagcgg      9000 gtgttctccc cgtgcgggga gacgagagat cttaagaaat aaagacacgg ccgggcgcgg     9060
tggctcacgc ctgtaatccc agcactttgg gaggccgagg cgggcggatc acaaggtcag     9120
gagatcgaga ccacggtgaa accccgtctt tactaaaaat acaaaaaatt agcggggcgc     9180
ggttgtgggc gcctgtagtc ccagctactc gggaggctga ggcaggagaa tggcgtgaac     9240
ccgggaggag gagcttgcag tgagccgaga tcgcgccact gcactccaga cggggcgaca     9300
gagcgagact cctgtctcaa aaaaaaaaa aaaaaaaaa agaaaagcat gttttttttt       9360
ttttgagatg gagtttcgct tttgttgccc aggctggagt gcagtggcgc gatctcgggt     9420
caccacaacc tctgcctccc aggttcaagc gattctcctg cctcagcctc ccttgtagct     9480
gggattacag gcatgtgcca ccatgcccgg ctaattttgt atttttagta gagacggggt     9540
ttctccaggt tggtcaggct ggtctcgaac tcctgacctc aggtgatctg cctgcctcgg     9600
cctcccgaag tgctgggatt acaggcgtga gccactctgc ccagccagaa agcatttctt     9660
```

```
ttttggctgt ttttttgttg tttttttttaa ttaactagtt ttgaaaatta tagaagttac   9720
acatatatgt tataaaaaca tctccaagca gcacagaaga tgaaaacaa agcccttctt    9780 gcaagtctgt catctttgtc taacttccta agaacaaaag tatttcttgt gtcttcttcc   9840
cagattttaa tatgcatata caagcattta aatatgtcat tttttgttgg cttgactgag   9900
atcacattac atacgtattt ttttacttaa caatttgagt acaatgtgtc atggaaattg   9960
ttccatagca gtatctgtaa ttcttattaa ttgctgtgta atattgtaga atttctttt   10020 aaaagaggac ttttggagat gtaaaggcaa aggtctccca ttattctggc tgtacaacgt  10080
tctggtgaca tattctctct accctgagag gtccccatac ccatcacctc catttcctgt  10140
aaataagtca accacttggt aaactacctt tgaatggatc cacactcaaa acatttagtc  10200
ttattcagac aacaaggagg aaaaataaaa taccttataa agcactgttt catatgtatt  10260
aaattggatc aatttgcgtg ctagaatgta tgttagagac atgatatgcc cataggtcct  10320
tgctatcacg gtgaggtctc agggacagca gtttggtatc atttggtatc tcataagcag  10380
actctgtctg cctgacttaa caaatcagag tctgcgtttt aacaggttca gtgagtgact  10440
tacatgcaca ttggagtttg ggaagctcca ctataggtgc ttagacctta cctttgttgt  10500
tgctaataac aatgcaagca tttgggagga agacctgtgt tgctcgtatg tgtccaggtg  10560
tagctgaggt ggccttgctt gtctgctgta gggccattga gcatttgcgt agctgtgatg  10620
aatgagctga ggtgagcctg cggagagctc ccagccattg gtagtgggac ttgcttagat  10680
gaactagaag gacctgagca tccactttgg ggaaaaacaa ccgaatgaag ggagaggcaa  10740
catgcagttt tatttagggt acgaaggaga gctgtggtta aaggtgaca tttgagtgga   10800 aagggggcaa cccatgtgtg gagcgggaga agagcggtcc aggcagagtt aacagaaggc  10860
agaaatgctt tccatctttg aaaactagga aggatgccag tggctgaagt aagatgaagg  10920
acagaaatag gggatgaggc ttcgagagat gagaggttag agacgagggt cttgtgcacc  10980
aagataagct tgtgtggtca aaacaagtag tttcgttttt gttttttaaaa gatcactttg  11040 gctgggtgca atggttcatg cctgtaatac cagtactttg agaggctgtg gtgggaggat  11100
tgcctgaagc caggggacca gcgtagccaa catagcagca cctataaggt ctctacaaaa  11160
aacttttaaa aagtagctgg gtgtagtggt gtgtgcctgt agtcccagcc acccaggagg  11220
ctgaggaggc tggaggggttg cttgagtcca gcagtttgag gctgcagcga gcaatgattg  11280
tgccactgca ctacagcctg ggcatgagag tgagaccctg tctctaaata tatgtgtata  11340
tataaaagaa aagatcactt tgacaacacc acatgctggt gaggatttag aaaaactagg  11400
tcacttattg ctggtgggaa tataatatag tacggccact ctggaaaaca gtttggcagt  11460
ttctcataaa actgaatgta caattagtat acaacccagc aactcctgca atcctgcgca  11520
ttaatcctag agaaatgaag ccttcatgtt cacataaaaa cctatactca agcgtgcata  11580
gcagctttac ccataatatc taagaactgg aatcagctca gatgtccttc tgcaggtgaa  11640 tggttaaaact actcagtaat aaaaaggaat gatctactga tagcatgcaa cagtgtaggt  11700
gaagttatgc taatgaaaaa agccaatccc aaaaggttac atattatatg attctatgta  11760
tataacgttt tggcagtgac acagttttag ggatggagaa tagattagtg gttgcctggg  11820
gttagagatg gggttgtaga gtaggttagg ggtggcagag gagagaaaag agagggaggc  11880
gagtgtggtt ataaaaggac aacacagggg gatacttgta acagaaatgc tttgtctttt  11940 ttttttttt tnnnnnnnn nnnnnnnnnn nnnnnnnnnn nnnnnnnnnn nnnnnnnnnn  12000
```

```
nnnnnnnnnn nnnnnnnnnn nnnnnnnnnn nnnnnnnnnn nnnnnnnnnn nnnnnnnnnn    12060
nnnnnnnnnn nnnnnnnnnn nnnnnnnnnn nnnnnnnnnn nnnnnnnnnn nnnnnnnnnn    12120
nnnnnnnnnn nnnnnnnnnn nnnnnnnnnn nnnnngctca ctgcagcctc tgcctctggg    12180
gttcaagcga ttcttctgcc tcagcctcct gagtagctgg gactacaggt gcacgccacc    12240
atgcccggct aattttttgta ttttttagtag agacagggtt tcatcatgtt ggccaggctg   12300
gtcttgatct cctcacctca tgatccgccc acctcgccca cctcggcctc ccagagtgct    12360
gggattacag gcttgagcca ccgcgtccgg cctattttat ttttttttgag acagagtctc   12420
actctgtatc ccagactgga gtacagtggc gcgatcttgg ctcactgcag cctctgcctc    12480
tggggttcaa gcgattctcc tgcctcagcc tcctgagtag ctgggactac aggtgcacgc    12540
caccatgccc ggctaatttt tgtattttta gtagagacgg ggtttcacca tgttggccag    12600
ggtggtcttg atctcctcac ctcatgatcc gcccacctcg gcctcccaaa gtgctgggat    12660
tacaggatt tttgtgtttt tcgtagagac agggtttcat tatgatggcc aggttggttt     12720
tgaactcctg acctcctgtg atctgctggc ctcgcctccc aaagtgttgg gattatagac    12780
gttgagccac tgcactcggc caaggaaaga gatgctttgt cttgagtgtg gtgtgtata     12840
gaaattgtat agaactaagg ctgggcacgg tggctcactc ctgtaatccc agcattttgg    12900
gagaacgagg tgggcagatc gtgagttcag gagattgaga ccatcctggc taacatggtg   12960
aaaccctgtc cctgctaaaa ataccaaaaa ttggccgggc gtggtggctc acgcctataa    13020
tcccagcact ttgggaggct gaggcgggtg gatcacgagg tcaggagatc gagaccatcc    13080
tggctaacac agtgaaaccc tgtctctact aaaaatacaa aagcaaaatt agccgggcgt    13140
ggtggcgggc gcctgtagtc ccagctactt gggaggctga gacaggagaa tggcgtgaac   13200
ctgggaggtg gaggttgcag tgagctgaga tcgcgccact gcactccagc ctgggcaaca   13260
gagtgagact ctgtctcaaa aaaaaaaaa aaaagaaat tgtatagaac taaatacaca     13320
aatgaacaac aataaaactt gaaactctaa gtaagatcac tggattgtat cagtgtcaat   13380
attctggttg tgataatgta gtatattaaa tagttttgca aagtgttacc attggggaaa   13440
actggataaa gggcacactg gatctctgtt atttcttaca actgcacgtg aaccaataat   13500
tatcttaaaa aaacttcaat tcaaaaaagt ctgccctgat ccagttggga ggctactgaa   13560
gtaatcaaag ctagacatgc tggtgtcttg tgactggtag cagtggtgat ggtaagtggt   13620
cagattctgg atctcttgga gaaagatctg acaagatttg cagattcttt aaaaaaaatg   13680
agattaggct gggcacggtg gctcacgctt gggaggctga ggagggcgga tcnnnnnnnn    13740
nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnnnnnn nnnnnnnnnn nnnnnnnnnn nnnnnnnnnn nnnnnnnnnn nnnnnnnnnn    14040
nnnnnnnnnn nnnnnnnnnn nnnnnnnnnn nnnnnnnnnn nnnnnnnnnn nnnnnnnnnn    14100
nnnnnnnnnn nnnnnnnnnn nnnnnnnnnn nnnnnnnttg ataatttata aaatgtgatt    14160
atagaatgct gtagtgtcct tgagtttaca tgcccttcct tacacttgtg tgcctgtgca    14220
gatgccttga tttcacaatt agaggaggct gactgagatt tgtttaattt ttttttttt    14280
tgaggcagag tcttgttatg tccccaggc tagagtacag tagcgcaatc ttggtgcact    14340
gcaacatccg cctcctgggt tcaagcaatt cttctgcctc agcctcccga gtgcctggga   14400
```

```
taacaggtgc cagccccccac gcccagctat ttttttgtatt tttagtagag acgggatttc   14460
accatgttga ctgggctggt ctcaaactcc tgacctcaga tatctgccgc cccagcctcc   14520
caaagtgctg ggattacagg cgtagccaca cctggccgtt tgttttaatt tttaaggtga   14580
cgttaaagtg actgcattta ccaaaagtgg ttgagaagcc aggactgttc ttatcctgtt   14640
tttccagttc ttgctcagag caaggtggtt tattttttcac ttaattacca tacttacttt   14700
tcatgtagaa caagtcagtt tgagttatca gttcatcatc taactaaatt ccatggggga   14760
aggaatagtt ttagtttctt aaacttccaa ggttgcttat tggacaaaat gagatagcaa   14820
ggcggtgttt ttaagttaga tttttttattt ctttggtaat ataattttct caaaaactta   14880
gtagtctttt agtttagttg tttttagttg gtcctatgtt ttgcatcccc cctctctact   14940
tttattttga tagtgccaat tgcgaagaca tctgaagcca taggtttggg tgggaaggcg   15000
gcacctttag cctgattatc tttgccaggc tgtttatctc cttttgcttg gctgagaagt   15060
cttaatagga ggcttattcc cagctacttg gggacataga agcggttagc tattgttcat   15120
gttttactga ggtctgtgtg gtatgttgac tgcagtcagt tactggtttt gagaattgaa   15180
ggcagcctgg tatatagagt aggtattata ttgtgtttct ttgaattgaa tttcctatct   15240
cttgtaatct ttgccatcat cttctgtgaa agaaaaaaag tttctatcaa actataccat   15300
tggttgtaag atgcagttcg gctttagtga tgctaacaca tgatccaaac gtgaaactga   15360
gtattggtga aatacagagg agatttaaag ccagaagacc tgggtttaaa tgctggctct   15420
atgacttcaa atctgtgtgt tcttgggcac gtcatggttg gcacttcaat ttcttctctc   15480
tgtaatgggg gaaatgaggc cagtcatggt ggctcatacc tatgatccca gcactttggg   15540
ggccaagatg ggaagatcgc ttgaggccag gaggttgagc aattgggcaa catagtgagg   15600
ccccgtctct acaaaacatt taaaaaaaat tagccaggcc cagtggtgca tgcctgtggt   15660
ccccaccact caggaggctg agatggggagg atcctttcag cccaggagtt taaggctaaa   15720
gtgagccatg attgtgctac tgtactctag cctgggcagt agagcaagat cctgactcta   15780
aaaaaaagta aaatgaaata aaatggggga aatgaactgc tttagtaaca tcatctgttt   15840
tttctgtgag cagtgtagct tgaaagccat tggtgaactc atgcactgtg cttccctgtc   15900
cagatcccca ttctgccccc agcatggagt ataacagttt attagtagta gtcgagaaac   15960
cctcattgaa tgaatgaatg agatgtagaa gtaagtggag tgggtaattg aacacatatt   16020
catttccttt tcttttttct tattttttaga aagaaagaac tttcagctac caagaaagac   16080
cgtgtgaatc attgtctgac aatatgtgaa aacatagtgg cacagtctgt caggtaattg   16140
cactttgaac tgtctagaga aaataagaac tttgtatatt ttcagtctta atgggctaga   16200
atattctgtg tcccagttat tttaaatgga ttcaaaaatc cttgaagaag gacccttttc   16260
ccatatttct ggctatatac aaggatatcc agacactaaa atgaataatg ttccctttttc   16320 gtaatctttt atgcaaaaat taaaaccatt atggtaattg aacaacatgt ttatgtttag   16380
ttaacaccct tagcaactat agttatttta aaatcctgtg tggtttgata tttttgcgtt   16440
tattgtaaca gtgggaacag cacaaggcgg tccactttgt ctctctcatt ttgcagtttg   16500
ctgtcctgtt gtgctggtgc tcctagcagt ggctggagcc cacttctctg tgctttggga   16560
ttagtggggt catggggcat tgactggagg tcagctttcc ttgcttgatc tttctcactg   16620
gggtgaacta gcagcacctt cttttgtagc tgctttgctt ttggctatct ttctgaccgt   16680
tgttcctagc agctgtagat ggtaaatatg tttaggcctg tttccaatgg ctgagtagga   16740
```

```
gacatatgca cctatgatat ctgaattctg ttacccagat gggcgtgtgt gaaatagtta   16800
ccttgcttta ctttcccttg gaataaataa ttcatgttat tctcctggta gaagctagaa   16860
aaagctcttt atagtcagtc agaaaaaaat ttttagacaa ataatcttga ttttagtact   16920
gacaaaaatg tgtggtgatt cttttttta gtttttttg agatggagtt tcactcttgt     16980
tgcccaggct ggagtgcaat ggtgcgatct cggctcactg caacctccgc ctcctgggtt   17040
caagcgattc tcctgcctta gtcctgag tagctgggt tacaggcatg tgccaccacg      17100
cccagctaat tttgtatttt tagtagagac agggtttctc catgttggtc aggctgatct   17160
caaactccca acctcaggtg atccgcccgc ctcagcctct caaagtgctg ggattacagg   17220
cgtgagccat ggcacctggt gattcatttg ttttttaaa aatttcctct tggccattgc    17280
ttttcactgt tttcttttnn nnnnnnnnn nnnnnnnnn nnnnnnnnnn nnnnnnnnnn    17340
nnnnnnnnnn nnnnnnnnnn nnnnnnnnnn nnnnnnnnnn nnnnnnnnnn nnnnnnnnnn   17400
nnnnnnnnnn nnnnnnnnnn nnnnnnnnnn nnnnnnnnnn nnnnnnnnnn nnnnnnnnnn   17460
nnnnnnnnnn nnnnnnnnnn nnnnnnnnnn nnnnnntgt agaaatattg tgggaagaaa    17520
atgaaataac aaatgagcat gtgtcctgaa aataaaaata taaaaattct aagttagcat   17580
gctattgtag aatacaacac tatgataaaa gtagggaaaa aaagtttga attccacgtc    17640
tgctgcctgt gtaagctggg tgactttaga taagctttaa cgtgtttgag ccttactggc   17700
tcatgtttga agtgtaatcc ctcgttacac agttcttgtg ggatcagacg atgcatgtga   17760
aacactgtga agaagtaact gcgatagatg tgttcattag ccgcctgaac gggaagcaca   17820
tcccattgcg atgcccatca tccaaagcta tatgttatct ttacttttt tgttttttg    17880
agacagagtc tcactctgtc gcccagactg gagtgcagtg gcgccatctc ggctcactgc   17940
agtttctgcc tcctgggttc acgccattct cctgcctcag cctcccaagt agctgggact   18000
acaggtgccc gccaccacac ctggccaaat ttttgtattt ttagtagaga cagggtttca   18060
ctgtgttagc caggatggtc tcgatctcct gacctcgtga tccgcccacc tcagcctctc   18120
aaagtgctgg gattacaggc gtgagacact gtgcccagcc atcttcactt tcttgtgaa    18180
atgatgactc taaatgtttg gcaaacattt ggtgattgtt catctgattt ccactatcca   18240
ggtctcagag aatataattt atctctgaaa gcttattgac ccaggaaaca agatctcttc   18300
caatctgagt acatcaggct ttattcttgt cattttgtct tttgagaatt ttcaaatgga   18360
attcatggaa tgttggctca tattcacata ttagtaaagt acgctgagac atcttaagat   18420
tgatttgtgg ttctatttgc catattaaat caaaataata actgttaatg gttttctttt   18480
ttttttttt ttttttgag acggagtctt gctctgtcgc ccaggccgga gtgcagtggc    18540
ccgatctcag ctcactgcaa gctccgcctc ccgggtttat gccattctcc tcctcagcc    18600
tcccgagtag ctgggactac aggcgcccgc tacctcgccc agctagtttt tttgtatttt   18660
ttttagtaga cgggggttt cgccgtgtt agccaggatg gtctcgatct cctgagctcg    18720
tgatccgccc gtctcggcct cccaaagtgc tgggattgag ccaccgcgcc cggcctgtta   18780
atggttttca cattagtctg tctcttgttt ttatggagta atgctgagag ttcattatgc   18840
ttcttgttct acagaagagc atgttaaaag gattttttgg gatcagagag gttatccatg   18900
gtttcatagg atactctgta ctttgcaggg atttcagggt atatagccaa aggtgatatt   18960
ttatataaat atgttttatg gaaacttact gannnnnnnn nnnnnnnnnn nnnnnnnnnn   19020
nnnnnnnnnn nnnnnnnnnn nnnnnnnnnn nnnnnnnnnn nnnnnnnnnn nnnnnnnnnn   19080
nnnnnnnnnn nnnnnnnnnn nnnnnnnnnn nnnnnnnnnn nnnnnnnnnn nnnnnnnnnn   19140
```

```
nnnnnnnnnn nnnnnnnnnn nnnnnnnnnn nnnnnnnnnn nnnnnnnnnn nnnnnnnnnn    19200
nnnnnnnnnn nnnnnnnnnn nnnnnnnnnn nnnnnnnnnn nnnnnnnnnn nnnnnnnnnn    19260
nnnnnnnnnn nnnnnnnnnn nnnnnnnnnn nnnnnnnnnn nnnnnnnnnn nnnnnnnnnn    19320
nnnnnnnnnn nnnnnnnnnn nnnnnnnnnn nnnnncctgt agtcccagct actcagaagg    19380
ctgaggcagg agaatagcgt gaacccggga ggcagagctt gcagtgagcc gagatcgccc    19440
cactgcactc cagcctaggt gacagagtga gactctgtct caaaaaaaaa aaaaaacaaa    19500
aaaacaaaaa aaccaaaacc ttatgtatat tgtgaaaatg tagtctgctt taagctctct    19560
aaagaggtct aagttactgg ttcctaagta tggatgagca tcaaaatcat ctggaaaatt    19620
tgttaaaaat acaataatga aggtacctca ctgtccttt tcccaaacac acttctgcat    19680
tctgtttgag taggtagggc ctacacattt ttcacaagta ttctcttggg aatacccagg    19740
aatgctcact tgagcaacct cttactaata ccatatactt tgataaagtg gctaggtaaa    19800
aataaatata taaaaatcca tcaatctccc atatattagc ataaatcagc tagaaaacag    19860
taatgtttaa agatctagtt cacagtagca ctgaagtatt gaattccaag aaattgataa    19920
gaaatatgca gaaactttat aaaaacttct gttaatgttt ctgaaagata taggtgacca    19980
ctttctagac aggaagattt tatatcatta agttgacttt tctctaaatt aacacagaaa    20040
tttaaaataa tcttgattaa aattctagta gaggtatttt tgaacttgtt cactgtaaga    20100
ataaatacat aactgcaaag aatatcttaa aatcatcact aggcccggtg tggtggccca    20160
cgcctgtaat cccagcactt ttggaggcca aggcaagcgg atcacctgag gtcaggagtt    20220
tgagcccagc ctgaccaatg tggtgaaacc ctgtctctac taaaaataca aaaattagct    20280
gggtgtggtg gtgcatgcct gtagtcccag ctacttggga ggctgaggca ggagaatcgc    20340
ttgaatccag gaggtggagg ttgtggtaag cctagatggc accactgcac cactgcctgg    20400
gtgacgagca aaattgtgtc tcaaaaaaaa aaaaaaaaa gaaaaaaaga aaagaaatc     20460 aacgctaata tggtgagact tgatatatgt gacattaaaa tagtgattgg acattagaac    20520
aggtatagaa cagaaagaag agtgtgtgta tctgtgtgga tttatgatgg gtgtagcata    20580
ttgtattagt agggaaatga gggaaatgat atatttcttt gactttggga caacattata    20640
tctctacctc atattgcaaa caagcataaa attctgatta attacctaaa tgtgaaaaaa    20700
tgaaatactt tcttcaaaaa atgtaatctt agtttgagga agactaacat tatgaaggaa    20760
aaacctgttt tgactggaat atagttcaat atgtcaaaat ccaccttcaa caaaattgaa    20820
agtaaattga acttggggaa agtattgata gcatgtagat caaaggttac tagcctgtgt    20880
aaagagcaat tataaatcat taagaaaaga ctgtcaaccc gtcggcacct tgttctccga    20940
ctcccagcct ccagaactgt gacgagtaag tgcctgttgt ttaaaacacc tagtctatat    21000
gtactatttt gttatagcaa ctcaagctga ttaggaccct agtaatcagt agactgagac    21060
taaaacaaaa ataagaacct ttttacctg tcaagttggc aaacattaag aatatgcaga    21120
tttttgtcag aggtgataca acctttaaga aggcaatttg ggaaaacata aagctttaga    21180
ttattaatgt gtctgatcta gggcacttac cctaggaaag tgtgtaatga tattggtgca    21240
ctgctgttca tcccattaga aaataaaaat aaccttaata gcttaccact aaaaggggga    21300
ttgaaaaatt aagatacatt tatttattta tttattgaga cagagtcttg cactgttgcc    21360
tgggccggaa tgcaatggtg cgatctcagc tcactgctac ctccgcctcc tgggttcaca    21420
tgattctcct gcctcagcct cccgagtagc tgggaataca ggctcacacc tccacaccca    21480
```

```
gctaattttt tgtatttta gtagagatgg ggtttcactg tgttgaccag actggtctcg    21540
aactcctgac cttgtgatcc atccccctcg gcctcccaaa gtgtcaggat tagaggcgtg    21600
agccattgta cctggccaga tacatttata caagagagtg ttagttaaca ttcatagatt    21660 tttttttct tgtttacttt ttattaaaaa aattttttt tagagacagg gtcttactct    21720
gtcacccagg ctgaatgcag ttgcacaatc gtagcccact gcagcctgaa ctcctgggcg    21780
gaagtgatcc ttctgcctca gcctttgag tacctggggg actttaggca gtgctgctat    21840
atatacctgg ctaagtttta aatgttttat agatgggatc ttgctatgtt gcccaggctg    21900
gtctagaatt cctgggccca agcaatcctc ccaccttggc ctcccaaagc actgagatta    21960
caggcattga gccaccactt ctgatcaata gatatttata tttgtgactg gaaaatatat    22020
taacaatgtg ttaaaaaatt cagttaaaaa ataatgaaag attttgctt ctagctaaga    22080 tagaataaca aggacagcat ttatcttctt gccttgaaat agttgaaaat ggataaaata    22140
tatgtaacag tggttttcaa gttattgggc attaggcaaa gaagagtagt tatcacagga    22200
aaattaatgt ggagagccct acaatttcct tacattgctg cctggccatg gcaagaggaa    22260
aaactgaaag gaaactgagg ctgagccagt ggtttgctgg gttgaggagg cagagctggg    22320
agtccagaga tgcaaggtgg ctagagcccg tatggaaaaa taccagggaa gagagctgca    22380
gagggagctc cggagaactg cacagtaccc tctcatgtgt gtagctgagt attgatgagc    22440
acatgctggt gaggaaatga cccagggctg caggtagaac cacttaaaag gattagaagg    22500
aacaattgct gcaactcaca cagggccagg aagaatttct ttttttttt tttttttt     22560 gtattttag tagagatggg gtttcaccat gttagccagg atggtctcga tctcctgacc    22620
tcgtgatccg cccgtctcgg cctcccaaag tgctgggatt acaggcttga gccaccgcgc    22680
ccggccaaag ggccaggaag aatttctaat cacacaagtc ggagtggaaa acctcggctc    22740
tcatagagca gcaggtagag tactcagaag ggtttgcctg cctagcccca gactaagttt    22800
cgttactctg accccgccta atattaaaaa aagattaatt aaattaattg tttgcaacaa    22860
aagtaatata tttcagtgtt tataacgtgt agaagtgaat tgtatgacaa tagcataaag    22920
gctggaagag cagaaattga catgtatttg tgctggacag aataatgttc ccctcttttc    22980
ccaaaagata tcgagtccta atccctggaa cctgtaaatg ttactttata aggaaaatgg    23040
tttcatggtg tgattaaatt caggatcttg agatgagggg gctgtcttgg atgatttggg    23100
taggcactaa atgcaatcac atgtgtatgc aaaggaggca gagggagatt ttacatacac    23160
agagaaggcc atgtgaagat agaacagaaa gatttgaagg tgctggcctt gaaaattgga    23220
gtgatgaagc tataagccaa ggaatgcagt agccaccaaa gctggaagag gtaggagcaa    23280
ttctccttca gagcctactc cagagggaac gtggtgctgc cagttcctta atttcagctc    23340
agtgatacta attttggact ctggtctctg aaactgtgaa agaataaatt tttttgttt    23400 gtttgtttaa gccacacagt ttgtggtaat ttgttacagc agctgcagga aactaattta    23460
tgctgcatgt gaaatggcat aatatcatta agatagattg tgataaaggt acatagtata    23520
aacaattaag caacaactaa agcacaaca aggagttata gctaatgaac caaaaaagga    23580
gattagaatc ataaaaatag tgaatcccaa agaagccaga aataggggaa gaggcaaata    23640
aaggaaagaa agagcttgat ggtagattta aacctagtta tgtcaaaaag gacattaaat    23700
gtaaaagata ttttcggat tgaatggaaa agtaagaccc agtatatgct gctgcctgca    23760
agaaacatat tctaaatgta aaggcaaaaa tagcctacaa gtaacagaac agaaagaagt    23820
tcaccgtgct tacaagaatt agatgcaagc tagactggtt ctgttaatat cagacaaagt    23880
```

```
ggatttcaga gcaaaggcta ttgcctagga tgagatggtc gtttcataat aacgaagggg    23940
attcgttcat cagccgcaca taacaaactg aaatatttat gcacctgact acggagctaa    24000
aatacacgaa gcaaagccta acaactacga gtagacacag gcaaatccac agtgagagag    24060
atttcagtgg cttctctcag tgatttgtag aacacgtagc cataatatct ggatctagaa    24120
cagttgaaca acactgtccc tatgcaacct gattggcttt tacaggacac tccacccggc    24180
accagcagaa gagacactct ctcaagtgct cacagaatgt ctgccaagat agagcagatg    24240
ctgggccata aaacaagtct ctaaattaaa cgcattcaaa ttattcagag tacgttttcc    24300
gacctcagta tcattaagtt ggaatatatt ataggaagat aacctggaaa agcctcagat    24360
atgtggaaaa actcatttct aagtggccca tgggtcagaa gtgaagtcaa aagggaaaac    24420
tgaaaatctt ttggattgac tgatatgaaa acaatagatg tctatacttg tggggtgctg    24480
ttacagtata gtaaagggaa atttctagca ttaaatgcct gttttagtaa agaaagattt    24540
caaatcaatg acctcagctt ctaccttggg aaacttgaaa atgacaagca aatggaatcc    24600
agagttacca gaaaggccag gtacagtggc tcatgcctgc aattctgcca ctttgggagg    24660
ccaaggcagg cggattgttt gagactggca gttcaagacc agcctgggca gcataggagg    24720
actccatatc tacaaaaaac acagaaaatt agccaggtgt ggtggcatgt gcctgtagtc    24780
ccagctaacc aggagtctaa ggtgggagga ttgcttgagc ctgggaggtt gaggctgcag    24840
tgaactgtga ttgtgccact gcgctccacc ctgggcaaca gaatgagacc ctgtctcaaa    24900
aacaaaaaca gttactagaa gaatggacat catagagata agagcagaag tcagtaaaat    24960
agaaaacaaa aatacataga aaatcaataa aaccaaaagc tagttcatca agaacatcaa    25020
taaattggtg agactaatag gaaaaaaagt gaagtcacat attatcaata tcaggaatga    25080
gggagatgac agtagtatag attatataga tattaaaagg gctatatgag gcaggtgcgg    25140
tggctcacgc ctgtaatccc agcactttgg aaggccgagg tggacagatc acctgaggtc    25200
aggagtttga gaccagcctg cccaacatgg tgaaactccg tctctactaa aaatacaaaa    25260
attagctggt catggtgcca tgcgcctgta gtcccagcta ctcgggaggc tgaggcagga    25320
gaattgcttg aacctgagag gcagaggttg cagtgagctg agatggcgcc attgtgctcc    25380
agcctgggtg acagagtgag actccgtctc aaaaaataat aataataaaa aggactatat    25440
gggaatatta tgaacaactt tatgccaata aatttgataa cttatagatt aaatggataa    25500
gttccttgaa agacacacaa actattaaag ctctctcaag aagaaataga taaactgatt    25560
agccctatat ctattttatt aaatttaaat gtaaaaatca atatttagtt actgaaaaac    25620
ttttaagtgt ggttggaaat ggtatatgaa cttttttcaac tgaattttat gaaggctaat    25680
cacaggtaaa ggttttctga tgaaaattta gtgtctgaat tgagatgtgc tgtaaaaaat    25740
gttgttatgt atcttaatca tttcttcaca ttaattacat gttgaaataa tactttgggt    25800
gtattgggtt aaatgaaata ttatgaaaat cttgcctgtt ttcttttttac ttttgatgtg    25860 tcacctggga aataaaaaag tgtgacttac attctgtttc tgttgacagt actgctttgg    25920
agtgcagtgt tggaatgatc tagcatttcg aagaccttc ctcccttcgt tattcagggc    25980
tgtattccac atagataagt ctgaaatact gctaagtggc acgttttgtt ttgtgctttt    26040
gtaagtttgt tgatcgttac tgatgtggac ctttggtgcc tcttaggctc atggctatct    26100
tccaaccatt gtttgcaatt tttacctaga gataaagaga aaagagatt tggtttcaga    26160 gtaagttaga ttgagatcat gaaagagcaa tctcatttg atgcttcaaa aatagcacat    26220
```

```
ccccgtatt actgggattt gctattcttg ggcttacttc aagaacatcc ttgtgttgct   26280
ggtttggatg cttccgaatg ctgtgaagtc agtttcatgg acgtggctca tcagtttagc   26340
tctcttggct ttgtttaggc agttggagca tgatagcctg aacagcttct ctcaattaaa   26400
catttacaaa tcgtttacga atagtaaaca aactccaggt tttgtgactc tttgatagtt   26460
catctagcac aacaaaaaca caatgtgacc atgatcacct ggcatcttag ggtgaaatac   26520
tttggcccag actgaaagca aaattaaaaa ggggcaagag agatatactg ctgaactgat   26580
tttcaaggtt ccaagaatat cataggttaa gagtaaaagt aaacttttga cagagagcag   26640
cgggttttct gggattgaag tatctgaagt tttcaaacga aaatttaaaa agaaaaaatg   26700
agaattgcct tataagtaca atctcttctt ttttaaaaaa taaactttat tttggaatag   26760
ttttaggttt atcgaaaaaa attagggtag agagttttca tatccctac atccggttac    26820 cccagttatt atcttaatta agtgtgagac attttcatgt ttaatgaatc agtatcgata   26880
tgctgttaac taaagtgcag actttattaa gattttctta atttctatgt aatgtccttt   26940
ttctgttcca gaattccgtg caggacaccg gatacctcat tacatttcat tgtcatgtca   27000
ccttaggctc ctcttgacag tttctcttct tttttgctta gaaattctcc agaatttcag   27060
aaacttctgg gcatcgctat ggaactttt ctgctgtgca gtgatgacgc agagtcggat    27120
gtcagaatgg tggctgatga atgcctcaac aaagttatca agtaagagc cgtgtggatg    27180 gtgttctcag aaatgtcatt ggtgtaggct aagagaagca gccatcgttg agtgttcttc   27240
tgtttggagc ccctgaggat gtctgcactt ttttcctttc tggtgtgtgg tttggaggtg   27300
ctctggtatc tgcccgcatt gcttgccaca cctgcctggt cagaaggaac tgtgttgacc   27360
cttgtgcctg catggtgcct aggtcaatga agggaaccaa tggtgaccac tggatgctcc   27420
tgggaaaatg tcactacagg taccagagaa gccagagcta tgcccacatt ttttttttt    27480 ttttttttgag acggagtctc actctgtcgc ccaggctgga gtgcagtggc gcgatctcag   27540
ctcactgcaa gctccgcctc ctgggttcac gccattctcc tgcctcagcc tcccgagcag   27600
gtgggactac aggcacctgc caccgcgccc ggttaatttt ttgtattttt agtagagaca   27660
gggtttcact atggtctcga tctcctgacc tcgtgatccg cccgcctcag cctcccaaag   27720
tgctgggatt acaggcgtga gccaccgcgc ccggcgctat gcccacattt ctatgagtct   27780
cagttttctt aactataaaa tgggatcaaa gttttgtgg catgcgtatg agtgtgtgtc    27840
tgtgtgagga ttaaatgcac taattgccac taccggatcc tcaaagtggt aagaagtatt   27900
cttattaatc atgacatcct cacactctta tgcagcaaga ttgatgggtg tggcactgct   27960
tctctttttc catcacatgg attccatgct atcctttgc ccagggaatc tttcctttgt    28020
ggccagcact ttgttgtttg gctcatcacg ctttctgtgg gcaggacgct ggcttctctg   28080
gagtcttggg attctagctc cctctcttgt ccctagagtg gtcactgtct tctctctctg   28140
cttgcaattc ttgctttgct cgcatctcac tcatgcggtg acctgtatca gtttcacctt   28200
gttctccgtg cctgctggtc gttggcacca cttgcctgtg gatggcatcc catagcgtat   28260
ttagggcctg cttccccagt taagcttgct tttccacagg cctgaatatc cttgcttgct   28320
tctgttattc ccactggcag gaccacggcg gtctttttg gatgagacag ggtcttgctc    28380
agtcacccag gctggagtgc agtggctgat cacggctcac tgcagccttg agctactggg   28440
ctcaagctat catcctggcc tggcttcttg agtagctggg actacaggcg tgcaccacca   28500
tgcccagcta attttaaaaa ttatttgtag atatgggatc tcgccaggtt gcccaggctg   28560
gtcttgaaca cctgggctca agtaatcctc cctccttggt ttcacaaagt gccgggatca   28620
```

```
caggtgtgag ccactgtgcc tggcccttga tgtttcagtt cttgatattt gatcctcaga    28680
gtcagaaagt ctaaaagag gactatccca ggttgccttg gttcacggca aatgggacgt     28740
taagagggca gagaaaacaa tatgaccaga aacgcttcta atattggtca tttaacgtgt    28800
aagtattgtt ctttttttaaa cctccttcat cttttttctag ggattgctgg acacagtggc  28860
ttggtgtgtc tgagggctgt aggccatggc cctgggttgt ggttttaggt ctcaggtgct    28920
cttcctggtt gtctccttgc ttcttttccca tttcctcttc tttgtttcca gccatttctc   28980
cctttttgctt aagtttggtg cagcaggggtt tggctgctct cagattgctg cttcctcaga  29040
tgatgcagtt gccaggccca gtgggctggc agtgggatca ggatctgact aggtttgctc    29100
tcactgtggc agaggagggg caggcgtggg agagcacgtg tgaccccagg ccaggtgtag    29160
ggagcccagg catggtcact tagccttcag gtcctagact ttgtcttctc atgagtgtgg    29220
ctgtgtgtgt atggtgagaa ccaggttcta cgtagcccaa gaaaatgtag agaaatgcac   29280
tgggtatctg acatagcctg gcagcacgcc tccctcaagt aggttagtct caggcggtga   29340
agcatgtatg tccagcaaga acttcatatg tggcataaag tctccgttct gtgcggcact   29400
gacaaatcac caccgtcagg aggctgaagt aatttctgtc tagggaggca gggaaggctt   29460
cctggagaca gtagccaata ggtgaaaggg tagattggag accttcttaa tcatcaccgc   29520
ctcttggttc gaggggtgcc aggaagctgt ggaggctgag aggaggggga acccatctta   29580
tgctgccaga gagtgggaca ccctgagggt caggtcaagg ggttgtacct tgttgggtgg   29640
agaattaggg gctcttgaag acttttgatg tggtcagggg agtgtatcat ttaggaagag   29700
tgacctggta aggacgtggg atagaggagg acagaggtgg gagggagtct aggtgggagt   29760
gagtgggccc agcaggagtg cagggcctcg agccaggatg gtggcagggc tgtgaggaga   29820
ggcagccacc tgtgtgtctg cggaagcagg ggcaagagag aagaggccag cggcgcgccg   29880
ccatcaccca gcaactggcg tagattgtga gagcccattc cctgctttta ggaggggccg   29940
agttttagtt ttctcttata aaataaactt ggtatttgtt tacaaaacat ttgtaaagct   30000
aaatcaaggt ttgataaggc ttctagtttt atttaagaag taatgtttaa ataaatgtcc   30060
aattcgcttt gcttatttaa ggactttcag tacaaacttc aacaacagga tcaggattta  30120
aacatttctg agatgttatt accccctcaga atttcccaga acgtgatctg gttttgattt   30180
tcaagcttgc tgacccagta ggttaaccca caaattttac taagatacac ctcagtccat   30240
ttatatcgac tgcccatgtc acggtcaaag agatcatcga ctgatgtttg gcacagcttc   30300
ctccctcttg ggtgggcaag catttggaag agaaggctcc catgggtgag agtggggcac   30360
cagagtcttc cccgtcctgt cccctggctt gagaaaccct tctctaatgt ggactttgtg   30420
ccgttagcat cgttactggc ttgaagttga ccatgtggac ataatttctg gtttagcctc    30480
acaagtgagc aaggagggtt gagagatgtg ctgtgaggaa catggggccc ccgctggccg   30540
tgggctctgg gtcagggggg caggggacca tgggcatacc tgacagtgag gaggggccac   30600
acctgcagaa agcatgcggg actcggcnnn nnnnnnnnn nnnnnnnnnn nnnnnnnnnn    30660
nnnnnnnnnn nnnnnnnnnn nnnnnnnnnn nnnnnnnnnn nnnnnnnnnn nnnnnnnnnn   30720
nnnnnnnnnn nnnnnnnnnn nnnnnnnnnn nnnnnnnnnn nnnnnnnnnn nnnnnnnnnn   30780
nnnnnnnnnn nnnnnnnnnn nnnnnnnnnn nnnnnnnnnn nnnnnnnnnn nnnnnnnnnn   30840
nnnnnnnnnn nnnnnnnnnn nnnnnnnnnn nnnnnnnnnn nnnnnnnnnn nnnnnnnnnn   30900
nnnnnnnnnn nnnnnnnnnn nnnnnnnnnn nnnnnnnnnn nnnnnnnnnn nnnnnnnnnn   30960
```

```
nnnnnnnnnn nnnnnnnnnn nnnnnnnnnn nnnnnnnnnn nnnnnnnnnn nnnnnnnnnn   31020
nnnnnnnnnn nnnnnnnnnn nnnnnnnnnn nnnnnnnnnn nnnnnnnnnn nnnnnnnnnn   31080
nnnnnnnnnn nnnnnnnnnn nnnnnnnnnn nnnnnnnnnn nnnnnnnnnn nnnnnnnnnn   31140
nnnnnnnnnn nnnnnnnnnn nnnnnnnnnn nnnnnnnnnn nnnnnnnnnn nnnnnnnnnn   31200
nnnnnnnnnn nnnnnnnnnn nnnnnnnnnn nnnnnnnnnn nnnnnnnnnn nnnnnnnnnn   31260
nnnnnnnnnn nnnnnnnnnn nnnnnnnnnn nnnnnnnnnn nnnnnnnnnn nnnnnnnnnn   31320
nnnnnnnnnn nnnnnnnnnn nnnnnnnnnn nnnnnnnnnn nnnnnnnnnn nnnnnnnnnn   31380
nnnnnnnnnn nnnnnnnnnn nnnnnnnnnn nnnnnnnnnn nnnnnnnnnn nnnnnnnnnn   31440
nnnnnnnnnn nnnnnnnnnn nnnnnnnnnn nnnnnnnnnn nnnnnnnnnn nnnnnnnnnn   31500
nnnnnnnnnn nnnnnnnnnn nnnnnnnnnn nnnnnnnnnn nnnnnnnnnn nnnnnnnnnn   31560
nnnnnnnnnn nnnnnnnnnn nnnnnnnnnn nnnnnnnnnn nnnnnnnnnn nnnnnnnnnn   31620
nnnnnnnnnn nnnnnnnnnn nnnnnnnnnn nnnnnnnnnn nnnnnnnnnn nnnnnnnnnn   31680
nnnnnnnnnn nnnnnnnnnn nnnnnnnnnn nnnnnnnnnn nnnnnnnnnn nnnnnnnnnn   31740
nnnnnnnnnn nnnnnnnnnn nnnnnnnnnn nnnnnnnnnn nnnnnnnnnn nnnnnnnnnn   31800
nnnnnnnnnn nnnnnnnnnn nnnnnnnnnn nnnnnnnnnn nnnnnnnnnn nnnnnnnnnn   31860
nnnnnnnnnn nnnnnnnnnn nnnnnnnnnn nnnnnnnnnn nnnnnnnnnn nnnnnnnnnn   31920
nnnnnnnnnn nnnnnnnnnn nnnnnnnnnn nnnnnnnnnn nnnnnnnnnn nnnnnnnnnn   31980
nnnnnnnnnn nnnnnnnnnn nnnnnnnnnn nnnnnnnnnn nnnnnnnnnn nnnnnnnnnn   32040
nnnnnnnnnn nnnnnnnnnn nnnnnnnnnn nnnnnnnnnn nnnnnnnnnn nnnnnnnnnn   32100
nnnnnnnnnn nnnnnnnnnn nnnnnnnnnn nnnnnnnnnn nnnnggtggg agaatcactt   32160
gaacctgggc ggtggaggtt gccttgagcc gtgatcacgc cactgcactc cagcctgggc   32220
aacaaagtga gacttcgtct caaaaaataa aaataaaaat gaaataaaat cagtccgggt   32280
gtggtggctc gtacctgtag ccccagcact tcaggaagct gaggcaggtg gattgcttga   32340
gaccaggagt ttgagaccag cataggcacc atggcaaaac gctgtctgta cagaaatgag   32400
ctaggtgcgg tggtgcacaa ctatagtccc agttacttgc gaggtggagg tgggaggata   32460
aatggagcct ggaaggttga atctacagtg agctgagatt gtaccactgc ccttcagcct   32520
gggcgagcaa gtaagaccct gtctcaaaaa aaaaaattat tgactatatc ttattgtcta   32580
taatccctcc tctgtgctat tgaataccag gttttgggcc cttatttcca tcactgaaca   32640
aacttcactc tattgagcag catgtgtgga atttcatctt tattcaataa ttaacagcta   32700
ggaggaaatg ctgtttgcta gactattgct ttacttttct tcaaaaggtt actctttatt   32760
agatgagatg ggaattaaaa atggtaactt actttatgtc tttataattg aagcccgcta   32820
gatcttaaag tagttaccag atgttttatg catttaaatg gccttttctc taaaaataga   32880
aagtaacaat gaaagaaaat gcttcgtttc tatgcaaccc tcttggtgac tagtgtgtgt   32940
gactcttaat gtgacactca ttgcaccccc tcagaatggt gccctcgga gtttgcgtgc    33000 tgccctgtgg aggtttgccg agctggctca cctggttcgg cctcagaaat gcaggtaagt   33060
tgtacattct ggatgttgat ttttgttggg ggccagctgc tactgatcct ttatgtctca   33120
gctcagatgt catttcagaa atctgctctg ccccttccaa attgcagtcg accttgccct   33180
gtttatgttt ccgtcatagc actaatccgt gtcagaaagt gtcacgtaca gtctgtgtgc   33240
ttgttcattt tctatcccac cctcccccaa gagacttatg ggatgtgtgc cccaggacag   33300
caggggtctt actgtcttat gctctgttgc agcctaaaca gcagtaacag tgtctgcaca   33360
```

```
tagtacttgc ttaaatgatt cttgccaaat tgttgaaggt tgaggtacca gtttcattat   33420
tgctgactat aggagttaca gcaaaatatc catttgtcta ttacatgagt taaaaatatg   33480
gttgtttcac tatgaatagt tttgtctagt caaaacagtt gtgtcttaac ggattgagaa   33540
acaaaagcag gaccactttt catcagctcc ctcctcctta acctgcagta tacgctgatg   33600
ctgatgtcct gtagaccctc agctccatcc tgagtcactg gaacgtggt ctaaaccctc    33660 attattagta tgaactgagt ttcaataaga atctcacatg ggtcgggtgt agtggctgat   33720
acctgtaacc ccagcacttc aggaggccaa ggcaggtgaa tggcttgatc cagactaggc   33780
aatatggtga aaccccgcct ctacaaaaaa tacaaaaatt agctgggcat ggtggtgcgt   33840
gcctgtaatc acagctactg gagaggctga ggtgggagga tcagttgagc ctgggaggtg   33900
gaggtcgtgt tgagccaaga tcacatcact gcactccagc ctgggcaaca gagtgagacc   33960
tgtctcaaaa aaacaaaaaa caaagaaaca aaaaaaagct tatatgggtg cagaggtata   34020
atcactaagg aaatttcttt ttgtgtagtc ttttttcttt tactgtcatt tcaaaaaatg   34080
tgttatattt ctgaagtaac acatccaggt tctccacata gcagccaaag tgaccttaaa   34140
gaacataatt gggtcttgtc attcccttat ttaaactctt gtgcccgttt cccagtgccg   34200
tttagattga ttccagactg gtaactggct ccgtcacctc agacactctg cattgactca   34260
ttagcctgat cagttcttca gatgagtcag gttttcttc ctcctgatgg tttgtttgtt    34320
ttgtttattc ccctcagttc tcagcaaaac agtcatttcc ttagggaggt ttccctagcc   34380
tccctgtctt tccctgtccc aggagcctgg tggtgtggtc actgccctct gaggccctgc   34440
ttgttgccag gctctgccac tagagggcag ggctgcacca ctcctggcac ctcacacctg   34500
gcctgccctg tcagtgtttg ttgggtgaat tcctgtgatc tgtgactcac tgctctgtgt   34560
cctacacatt ctgcttttct tctcccctca caataccatt tataattctc cttttcagg   34620 aaagctttat ttccattaaa acattttgt ttttaaaatg gtattttctt acactattat    34680
tttctaatta aaaatgagtg ttttggcagg gcgtggtggc tcacccctgt aatcctagca   34740
ctttgggagg cccagatggg cggatcacaa ggtcaggaga tagagaccat cctggctaac   34800
atggtgaaac cccgtctcta ctaaaaatac aaaaaaaaat taggcgagtg tggtggtggg   34860
cgcctgtagt cccagctacg tgggaggctg aagcaggaga atggtgtgaa cccgggaggt   34920
ggagcttgca gtgagccgag atcacgccac tgcactccag cctgggcgac agagcgagac   34980
tccgtctcaa aaaaaataa aaataaaaaa aaaaaataa ataaaaagta aaaaaaaaa      35040 agagtatttt aagaagtatt acgatttact gcaaataatt tttaaaccca gcctttagaa   35100
tcctctgtga tcataagaga aatgaaggat gtctcccgac acttgagctt catccacatt   35160
tcattctctc gttctttcag ctgagctttg cccatcccca ttagggaccg tttggcatat   35220
gaaactggct tttccctaac agggaatgaa ttgcttctat ttctcctgaa ggagagctgg   35280
aggaatgact tgcgttcttt tgcatacaca ggccttacct ggtgaacctt ctgccgtgcc   35340
taagtcgaac aagcaagaga cccgaggaat cagtccagga gaccttggct gcagctgttc   35400
ccaaaattat ggcttctttc ggcaattttg caaatgacaa tgaaattaag gtacgattat   35460
tgcctcagat cacaaacatg tgagtgacgc tgtgagtgag tctgtggagg ttacggctt    35520 ctgagcaggg agtcatgtgg gagcgcttct tagagtatgt tgtatgtcgt aatttagact   35580
accgtcattt gtgttatttt tgaggcacct aaagacttct ttccacttct gatttcttac   35640
tgtggggtga agagttgaat tgggagatgg tttatagatg cacattcaaa aggcatattt   35700
```

```
ccagagcaga ttggttttca gtgtattaga gtgactgttt aacctagctg tggaaagatg   35760
gctgtgccag gactgcaggt aggagaaagc tcactgacga ggccttgtgg gtctgaacat   35820
cctgcagcta tcagggcctg ttggctccct gttgtgcatt ccaacaaacc accttcaaac   35880
ccactttagt gtttgtttat aatgtccaga aatagtgacc ctgtcacatg ctctacagat   35940
tacaggattc ctagcctctt cctttttggt gggtcagtcc tgggtttgag cccaagtggc   36000
cctcttggaa ggtgatgata cacagtgggg agagtggaat cagatggact tggattagaa   36060
ttctgtccgc tttactggtt cttttcctct aggcaaacta tccaacagct ctaagctatt   36120
tccttcgtat tctgaaaact aagccttaat gggacccata tcgggcaatt ctgagagtga   36180
aataaatgaa tatgtgttag cgtgtagcat agtcgcccac aggaagggct tagatgttag   36240
ctgctactgc tcttattagc tgaatgactt ggaataaagt gttagcctct ctcatgtttt   36300
tttctctgag ctttgaagtt ttcttgttaa tactaaggag atattcaaac tagtcatggg   36360
gttttggaat gacgaaggga gatcatgaat ctaaagaatt tagtgtggta attcatcatg   36420
ctcagtaaat ggtagctgct gcttgctgtt attttttatta ccatctcttt ggagtgggag   36480
taggtctcct ttgtggtcag aggctgtgag agctccgcag cgccagtctg cccgtcagta   36540
caccgggctc tgatgaaggc agttccctct gtggtatctc tggctgtcag agctcagatg   36600
atagatggtg tttttgtact ctcagttctc atcattttca tgatttcgat cactatttga   36660
gtatgatgat gctaacactt tgttgaacat agagtccatt aattacttcc ttcctgaacc   36720
ttaggtattt aaaaaaatct attctgctac ctctctgctc atttatgatt attcagattt   36780
attatcaaga gcctggtaca gtggcttgtg cctataattg tagctacatg ggaagctgag   36840
gtaggaggat tgctggaggc caggagtttg agaccagcct gggtaacatg gtgagaccct   36900
atcgctaaaa aatgaaaaaa gttagctggg catgatggca cgtgcctgtg gtcctagcta   36960
ctcaggagac tgaggcagga ggattgcttg agcccaggag ttggagttcg aggctatact   37020
gagctgtgat tgtgccacca cactctggga tgggtggcaa agaagatgc catttcttca   37080
aaacaaaaca aaacaaaaaa aggtattatc ggtgaaattc aatagtacca acaggattat   37140
aaacaaagat agttctcttc ctactttttc tcttaatcct tgtgtctcag aggcaaacat   37200
aactcttagt gtttcttcca atatttactt cgannnnnnn nnnnnnnnnn nnnnnnnnnn   37260
nnnnnnnnnn nnnnnnnnnn nnnnnnnnnn nnnnnnnnnn nnnnnnnnnn nnnnnnnnnn   37320
nnnnnnnnnn nnnnnnnnnn nnnnnnnnnn nnnnnnnnnn nnnnnnnnnn nnnnnnnnnn   37380
nnnnnnnnnn nnnnnnnnnn nnnnnnnnnn nnnnnnnnnn nnnnnnnnnn nnnnnnnnnn   37440
nnnnnnnnnn nnnnnnnnnn nnnnnnnnnn nnnnnnnnnn nnnnnnnnnn nnnnnnnnnn   37500
nnnnnnnnnn nnnnnnnnnn nnnnnnnnnn nnnnnnnnnn nnnnnnnnnn nnnnnnnnnn   37560
nnnnnnnnnn nnnnnnnnnn nnnnnnnnnn nnnnnnnnnn nnnnnnnnnn nnnnnnnnnn   37620
nnnnnnnnnn nnnnnnnnnn nggagtacaa tgacatgatc ttggctcacc acaacctccg   37680
cctcccgggt tcaagcgatt ctcctgcctc aatctcctga gtagctggga ttacaggcac   37740
gcaccaccat gctcggctaa ttttgtattt ttagtagaga cggggtttct ccagattggt   37800
caggctggtc tcaaactcct gacctcaggt tatccaccca cttcagcctc ccaaagtgct   37860
gggattacag gcatgagcca ctgcacccgg caacttccac atttctcagt aacatgcttc   37920
tactgctttt tttttttttt tttttcaat tttagacatt ttttactttc acactataat   37980
tctatcagaa ttcagtatgt acattattat acctaagtaa atagtcatgg ttggttgtgt   38040
attatatttc tttgtatttc ttatttgatg agagagctgt gttttttgct gtgggttgaa   38100
```

```
actgtggaga gaggacatgg ggaggggaag gaagacagat gaagttggtg actgtacctt    38160
cctggccata gctgggttct cagcaccctg ggatctgctg atcacctgct cgtaggccaa    38220
gcccctagcg aagttctagg tgacccagtg ctggggatgg gggggtcacc tgcaaggtct    38280
agtcatggag gtgggggcta cagtgttggc ttgtgctggg gccagcatcc ttaggaatgc    38340
atcttggagg aggaggagac agccacccac ttcttgactg gggccttcag cagtgccagc    38400
ttcttgggca gactggtgct ggctttcatc accacatcgt gttcaatctt cttccagatc    38460
ctgacttcta ggttcacctt tccttagacc ccggttcctt tcagaggctg tcgctctgcc    38520
ttgctctttg ctggcttgtg ccttgattat atgtctttgt acaactttt gttttcctgg     38580 agttaatcct cacatctgtt ttcctagagt gaattgttac ctttatatca cttgcttatt    38640
attctttgac ctttttttct tctcacacct tccaacttct ttgtaaaatg tgtttagtac    38700 aattttcat gacaggtaat ttaccaaatc agttttccc cagtgcagtc atccatcttg       38760
agttacccag ctcgctgccc cagtctgggc ggattgctct tcaggtctgt tgtacacttg    38820
tatcctagga cttctctttg ccatcagcct ggaatttcct ttgcagttct cctgttggat    38880
gcccagttcc tacatgccat atgtttatct ttctatcctc tagtagcttt gtgagagaag    38940
atgaatggga ggtaaattgt ttggagtttt gcattcataa aaatgccatt ttttctcgcg    39000
tacacttggc tgagtatagt gttctggggt agaaatcatt tttcctcaga aatgtgaagt    39060 cttccccgt tgtcttaaag tctccaacat aacccaattc cttaacccat gaatgtgctt      39120
ttctctggaa gctttccatt tttgggagg tgaagtgcta ggtacttagt aggcctttta     39180
ttttttattt ttatttgttt tttgaggcgg agtctcactt tgtcgccgag gctggagtgc    39240
agtggcatga tctcggctca ctacaagctc tgcctcccag gttcacgcca ttctcctgcc    39300
tcagcctcca agtagctggg actacaggcg cacaccacca cgcccggcta gttttttttt    39360
tgtattttta gtggagacgg ggtttcaccg tgttagccag gatggtctcg atctcctgac    39420
ctcgtaatcc gcctgcctcg gcctcccaaa gtgctgggat tacaggcgtg agccaccgcg    39480
cccagccagt aggcctttta atttggaaac ttatatactt cagttctggg aaaattttct    39540
tacatttctc tgataaattc ttgccttta tttttctgtgt tctctccttc tgaaattagt     39600
tagttggatg ttggtcctcc tgggttgact cacatcttac cttttctttt ttctggtact    39660
ttttagatat ccatctcaaa ctcttctatt cagtgttatg ttttaactt cttctttttc      39720 tttgtctctt gatggggtct tgctttgttg cccaggttga ggtgcagtgg tgcaatcata    39780
gctcactgca gcctccaact cctgggctca agcaaccgtt ctgccttagc ctcccaagta    39840
gttgggacta caggtatgca ccaccatgtc cagctatttt ctttactttc tttctttttt    39900 tttttttt ttgagatgga gtgctgctct gttacccagg ctgagtgca gtgatgcgat         39960 tttggctcac ttaagcctct gcctcccagg ttcaagcaat tctcctgcct cagcctccta    40020
agtagctggg attataggtg tgcaccacca cgcccggcta atttttgtat ttttagtaga    40080
gacggggttt cgccatgttg gccaggctgg tctcaaacac ctgacctcag gtgatccacc    40140
tgcctcagcc tcccacagtt ctgggattac aggcgtgagc ccatcattaa atctttaaat    40200
actagtatct gtaagtcttt tcctcttgag tcagccagta tccctggaag gaaattcctc    40260
attttcctgc ttggagacta taagcttggc tgtgtttatc ctgcaaccgg ggactggaag    40320
gggatggaag gggactgaca ctgttgctgg tcagggcgcc ctcttttgt tttctgtatg       40380 catctcacat ctgtcctcag ttatgtaaac acctcttgag attatccctc tcagtctttg    40440
```

```
ctggaggtgg ggaaggggct gcttcctggg ctgccttgga ttggagggga gacctcaggc   40500
gagtgggtgg gaatttgccc aaggagccat gagacaagcc actgttccac cctctccgtc   40560
cctccacttt cagatgtatg tggtgcctcc aaagcccgag tgcttcttgg agttctgtgg   40620
cttgaataag cttgcttttc actggtatcc ctcatacctt ctcccccatc cccagcaaag   40680
cttgcatttg aacttcttcc catgggctaa caaatcagtc agttatgtag cccttgttac   40740
tttttagctt ccgaagtttt gttgacacac gtagtctgct agtgtccctg ttctgttctt   40800
tctgtccgtg tacatttatg ctttatacaa cttctttaca tgattttcgt ggggtttctg   40860
ggtagcagag cttcacatgt tcaatccagc atgttggatt agaagtctcc caccctctgg   40920
tgtattctca ttctcagaat tacctgccaa acaccgatac tcccttgttt ttccttttcc   40980
tgacaggaaa tgtacatacc agacaggaca gaaatcatta gtgtatccct tggtgaataa   41040
ccacaaagtg atcttaccct cgtaaccacc acccaggtca agacagagta ttaccagcac   41100
tcagaagcct caccccatc ctcccatcac tgcttcttcc ttcctcccca aggtcatgac   41160
tgtcctggct tctaatgcca gagtctgttt ttaaattctg tgtacataga ccatatagta   41220
tgtattcttt ttgtctggtt tcttttgctc gacagtaatt tcttaagagt cttctatatt   41280
atcgtgtgta ttagtagttc ctgtagtttt aggagcttca tagcattcca ttgtaggtat   41340
ataccacagt ttattcattg tgttatcact gggttgtttc tagttcttgg ctattgtgag   41400
caatgctact gtgaccactc tcaggtgttt ttttggagc acatgtgcag gtttccatca   41460
tgcgcagcta gaggtggagt tgttgggtga tagggtgtat gcatgtcagc tgcagcagaa   41520
actgccaaat agctttcctg agtgcttgta ccagctcacc ctttggttgc tgcgtatggg   41580
gactccggga gctctggtcc tcgctagcac ttggaattgc tgatgctttt acttttagcc   41640
ttcctgatgg gtattttctg gaatcacatt atgattttaa tttccgttcc ttaaagtacc   41700
cttgactctg aagtttaatg attaatgcat ctcttccttt ttgaagtact ctgaaaggta   41760
tgttgtgcat gtgttgaaaa ctggagctat ctagtctaaa atacagtgta cctcctccct   41820
gtttgaagag ttgtagcatg gcctcgggc ctcctgttag gtgccttgga aagggattc   41880
ttgggattgt agagattaga cctgaggagg cccttggag ctctcagact aaattttgtt   41940
ctttattatt ccaaactatt taagctcacc gtgtgctgac tcatcataat aatgagtagc   42000
tctcattgtg cttgtatatt tggaccaata gaatgatttt tttttttga gacatagtct   42060
tgctctgtca cctaggctgg agtgcaatgg cacaatcttg gctcactgca gcctctgcct   42120
cccaggttca agcgattctt gtgcctcagc ttctcgagta gctgggactg caggtgtgta   42180
ccaccatgcc tggctaatgt ttgtattttt agtagaaacg gggtttcacc atgttggcca   42240
agttggtctc aaactcctga cctcaagtga tctacccgct taagcctccc aaagtgctgg   42300
gattacaggc gtgagccgct gcgcttggcc aaagtagttt tttaagatgt gaatatcttt   42360
tcttgcagct aaaaagttt gtcagagata attctacttt attctccagg tggttttca   42420
gggagaaatt ggaggcagta aaccacgggg ggagtcctgt ggcttggtgg gtgggtgggg   42480
gaggtgtggc tgggtgggg agaagtcctg tggctcgctg ggttggggg agctgtggc   42540
tggggtgggg agaagtctag tggctggggt ggggagaagt cctatggctc ggtgggtggt   42600
ggggagctg tggctggggt ggggagaagt cctgtggctc ggtgggtggt ggggagctg   42660
tggctggggt ggggagaagt cctgtggctc ggtgggtggt ggggagctg tggctggggt   42720
ggggagaagt cctgtggctc ggtgggtggt ggggagctg tggctggggt ggggagaagt   42780
cttgtggctg gggtgggggg cagtcctgtg gctggtgtct catcatgtgc ctaacagtgt   42840
```

-continued

```
ccagaggtct cgtgtaaatt ccctgggagt cgataagcct ctgagaaaca gatgatgcta    42900
accacgctgt ggaagagaaa cttgtttata aatcagatgt ccgttactgg tttactgctt    42960
gtttgcccag gcatagctcc gacagagtcc ccgactcata gtgattgctc agtgcgtgct    43020
gaacaatgat tggaatcaag tcatggctca gagcatagtt ttgaataatg ggaaattgat    43080
gttcttaagt aacatagtca ccaagataat gcaactagat gagtcacccc ttttcaattt    43140
taggatattt ttatcaagat ttaagtggtc atcattagaa ttatagcagt ttctcctttg    43200
gattgttcta gaggcccagt gagaaagtat tccctaattt ctcaggagaa cagttgtggg    43260
tagtgtgctg tcatgtccag ttaaattgca gacgtttccg gttgaagata ttccagtcct    43320
gagaactttg tgacattagc aggactttta caagccatct cttagggtgg ggcattactg    43380
tagttggctg gtactctttt ctccttaact ttgtcatttg ttgatttttt tttttaact    43440 gtccccaaac actgtgggca gacagtatct agaattgagg cctccacccc tgcagagagg    43500
acgtggatgc tgagcagtcc ccgagtgaag attataaaga agcaaataga gtacacgtgt    43560
ctgtgaactg ttcttgagtc tcccaaattc ggggtacttc tgttcagcta taggaaaagc    43620
ctcaaactgt ttatactttg caagaattgg aaacttctaa ttcaagttaa gttttacgga    43680
atgcatggta agcttcatag gagcttcatc ttttatctgc ttggactttt gcttctatag    43740
gttttgttaa aggccttcat agcgaacctg aagtcaagct cccccactat tcggcggaca    43800
gctgctggat cagcagtgag catctgccag cactcaagaa ggacacagta tttctatagc    43860
tggctactaa atgtgctctt aggtaaggtg gaggcataca ggtggaaggg tctccagcat    43920
gtattcatga tagacctttg aaataattaa aatcagatga tccctcagct tctagaccag    43980
gctatttggc actggttgac tgaatgtgaa ctgcattggg actgctgtga gcacgcatgg    44040
gtctctgtga ccctgcagat gcagccatgc ccagggacac ctagctgggc agtgggtgtg    44100
ggctggtgtg agccctgcct gccacccagg gcctggtcct ccgtctgtgc cggccctgac    44160
tacggtgagt ctgtgaggct tgagactgtg ccttgggtcc ctgtgggttc tctgtaggtc    44220
agttgacagt ttctcctgtt gtttgggtaa ctgtggaaat gaacactggc aagtgctgaa    44280
gtgagcactg gacgcgtgat atggaccctg ccaagccagg gatatgggtg tgtagccact    44340
cccagtgggc ctcatggtgt actcgttcac ggtcatgttt gtgccatatt gatctcttgg    44400
gatctcttct tttttaacaa attaagcggg gaatctccaa acagtgagtt ggatgttaag    44460
atatcttgct gctgccccca caggcttact ggttcctgtc gaggaggagc actccaccct    44520
gctgattctt ggcgtgctgc tcaccctgag gtatttggtg cccttgctgc agcagcaggt    44580
caaggataca agcctgaaag gcagcttcgg agtgacacgg aaagaaatgg aggtctctcc    44640
ttctgcagag cagcttgtcc aggtaggagc acagggttta ctctaggcct ggcatgtgaa    44700
caactgacat ttgaagaact gattactttg gaagagaagc ggcagaaccg agggttagag    44760
gtgtggactc tggagctgtg ctgctcggtt ccgaccctag gtgctgacct ctagctgcct    44820
tccttctgta tgccattgtc accgtgagtc agatgcaggt gatgcctctt caggtgccac    44880 tctgttttcta aaaccagagg tcacgatatg tgttcataca cccagtaaat actgattgag    44940
cacccactgt gtgctcgggt ctggggtagg tgctgggggt cctgtggtga atatttccgc    45000
tgcagcctct gccctgtgga gcctgtggcc tggtgcactg gtcgaggcag ggtggtatgc    45060
cccctcaggg aggtggggac gtggtccttc ggggtgtcag aacaaaatgt tggaacttct    45120
ctttccaatg cagagaaacc ctgcagtaat tctaatgtac tgtgattggc agttgacttc    45180
```

```
agttctttgt agcgtgctta ctcaggttat tttcactaac tgtgtaacag tgcagcctca  45240
ttttaagcaa ttgaattttt tgaactttac ttaaaatatt aggtcagggt tttattgtg   45300 cttaacatgt gccatttagc taaattttgt aggatataaa attgtaagtg acttaaaatg  45360
attcttgcat agaatcatga attgaagata atgctaataa tttaagcact gagttaggta  45420
gtgtttgtga agtgcttaga atgcttcctg gcacatgtga aggccatgta agtgctgctt  45480
attgataaac agctgagcaa gagtgaactc taagaaatga atggggctga gagttctatt  45540
ccacccagct gcccttggt tattttacag aataaaagca gagtctcatg ggatatgaca   45600
tttaattata tttccttcac aaaaaacact gctgaatatt ttgtggagta aaaagggtgt  45660
agccatggca ataatacatt taaaatatag tttatttcat ctttaccttac cctgtttttt  45720 tttttaagc tagctttata ttgagaattg catacatgca aaagtatcaa gtcatgacca   45780
gttacatttc atttataatc ctacttctcc cttttttttt ttattatttg gaagcaaacc  45840
acaatcatcc tcttacttca tctataggta tttcagtatc tctatagatg aggactcttt  45900
tttattttta aaacttaatg atggtcaggc gcagtggctc atgcctgtag tcccagaact  45960 tgggaggcc aaggcgggca gatcacttga gcctaggagt ttgagaccaa cctgggaaac   46020
atggtgaaac cccatgtctt taaaaaaaaa aaacaaagtc agccaagtgt ggtgatgcat  46080
gcctgtagtc ccagctactt gggaggctga gatgggagga tcacatgagc ctggaaggtc  46140
gaggctgcag taagccatga ttgtaccact gcactccagc ctggttgatg gagcaagatt  46200
ctgtctcaag aaaacaaaac gaaactccaa acaatgtca caaaacagtg ccattgttag    46260
acctgaaaat attaaacatt tcctacatca atacccact aactcattgt caattttct    46320 ctctactctt ttggaatcag catataaata aaattggttg ataaggattg taaatctctt  46380
tgatcaactg gttctcctcc atccgaattt ttttttccct ttagagttca tttattgaga  46440
aaccagatta tttgtcttct aagttttcct gtggtctgat atactgctta catctccatt  46500
gtgtaaatta acaccttttt ctgttctctg tatttcctgt acatcaataa ttggaggaaa  46560
aacctggtca gatttagtgt atatttata tctgagttca gtatttcgta tataatattt    46620
taaggtaaga gtatactctt ttaaaaagtg ttgagactat atgctcaatt tttttttaaca  46680 gatgcttttg aaaaggctgc ttgatcataa aagtttagag accattggtc tgttgggaga  46740
agcaaataat tacgaaacag tttagcaagg ttaaggtgca catggtaggg cctggagagg  46800
ttcagtcgtg agccgtcact gatgggcacg tggaatctga cccggcacag agagctggga  46860
gaagacagga gctttataga cagaaaacgt ggtctttgcc aagtcccggg agtgaaagag  46920
tgagagaatg ctcacagcac atgagtgtgg gtgcgtagac agagcaacgg tgggtcctga  46980
aaaggcctcc aggctttctc atagattagc aagagtgttg gttatggagg tcagaaggag  47040
gtcgaaactg tgttaaattg ggattgcagt aatcctggaa ggacagagat agagggtgaa  47100
ggggaaaaaa gggtatggat gtgagactta attgctgatt tcttaatac ctttctccaa   47160 agtaaataaa tgatatggca cattttgaa ctagcaaact ctagatatga ttatctgtat   47220
aacatatctt actccatctt cttttgacta ataactgttc ttaattaaat tactgtgaga  47280
tgttcaattc agcaaatgta gtttggctaa ctatatttaa ttagaattta atataatcct  47340
aggcctggcc aaactattaa gcaagtgtgg gcaaaatatt gataatttta gatatgcagg  47400
agctcagttt ctttctatgt gtgctttttg aaaagaaag aaattgaaaa atagaggaag   47460
ccctgaaatc caagaaacaa agtctctcat ctaggcatgc aataaaagca attctaggat  47520
gattgttgtt cggcatgtag tttgttagaa aacattcttc ttgaataaat agtatgccta  47580
```

```
agaaagtggg cagagggaag gcatatgcat atattattaa caaggaggga gaaaaaggca    47640
attagtaacc atccatagga gagccagcaa gatttataaa ggaaatttgt gatccaagta    47700
tgaagcaaaa taagatgcat aataaatttt aagcaagtaa tagattacag taagagaacc    47760
catttgacca ttaattttgg ggcattttct ttcaaatgac atggagtagt aatgaaatat    47820
ttctttcttt ctgagtctag gttattgtga ctggactcag aaagaaagat ttcattattg    47880
cagtgaataa cattttgaa cattattcat aaattatgca gtgaataaca tttatgaaca    47940
catgatacat aagatacata ctgtttattt ttaattaagt ttttcagctc aacttctcgg    48000
cagggaacat taaatgtaaa tagtgttacc tagtagcatg taaatggaaa tctccatagt    48060
atgaaagcag tgctgttgct aacagaattt aggaggcgac agatgaggtg aaggaaatgt    48120
gggtgccgat ttccttatta cattgagagg agccaggaga ttctttgttc aaaatagatg    48180
gcttaagaag tcaaggtata agctgattac ctagagcagg tacccacaaa tgttttgtgt    48240
aaggggccag atagtaaata ttttcagtct tgcaggccat tccaagtctg tggcaactag    48300
gccccactac cttcgtagca cgaaagcagc cacaggcagc ccataaacgt ggctgtgttc    48360
cagtgaaact ttatgtacaa aagcaggtgc gggccagacc tgacctgtgt actgtggttt    48420
gatgacctgg gattcagggg tataggagtt accatcagag gagctgaaag tgagactttt    48480
tactttatac tcttctacac tgtctgattt ttaaaaaag aaacatatgt attttataat    48540
attgaagatg gggttggcaa atagcaaata aaaatacagg atgccagtga aatttgaact    48600
tcagataaat tatgagtaat tttatgatgt aagtatattc caaatcctgt gggacataca    48660
ctacaaaatt atttgttgtt tctttacaat ttaaatttaa ctgggtgccc ttgtctttta    48720
tctggcaact ctaattaaag ggaaaaagaa taaattcatt atgttcatat aatgtgatac    48780 agcagggtc cccagccccc acgctgcgga gcggtattgg tccatggcct gttaggaact    48840
aggctgccca gcaggaggtg agcagcaggt gagctggcat tcccacctga gctccgcctc    48900
ctgtcagatc agtggcagca tttgattctc atagtgcaaa ccctattgtg aacagcacat    48960
gtaagggatc tagattgtgt gctccttatg agagtctact gcctgatgat ctgaggtaga    49020
acagtctcat cttgaaacca tccctggcc ctgtggaaaa attgtctccc atgaaaccag    49080
tctctggtgc cagaaaggtt ggggagcact gtgatatagt attgaaagtg ctgataaatg    49140
tggctactgc ctttaaaatg tctggtagct cttttctcagt ggcactcata atagtgtttt    49200
ttgattttta aatgtgtgtc aagctaactc tcccctcagt gtatgctgga ctttatttc    49260 cctttcctag tcaccagttt tgggaaatag agatcttcat tctcatgctg cttctctagt    49320
ggaagtgctc catttatttt taaggaatga atataacaat gaaaaaatca tgggaattca    49380
gaaaacaaca tggaaggtaa cgatcacatt ggtagaagtg atagggaaat atttagggg    49440 agaaattaag gtgtaaactt tgccaacgaa gtcctgttaa aaaaaaaaa gtgaagctta    49500 ggatgcattt tataaactct gaccagaaca cctgtgtttc tctgtttcta ggtttatgaa    49560
ctgacgttac atcatacaca gcaccaagac cacaatgttg tgaccggagc cctggagctg    49620
ttgcagcagc tcttcagaac gcctccccc gagcttctgc aagccctgac cacagtgggg    49680
ggcattgggc agctcaccgc cgctaaggag gagtctggtg gccgaagccg tagtgggagt    49740
attgtggaac ttataggcaa gttattagta aggtctactc ttacagttaa ctttcagtg    49800 atactagtta ccctctattg atgatggggcc tgccctgtgc taagcagtct gcattgcatc    49860
ttccttgcca aaacttataa tacagatttc atctttattt tataaatagg ggagttgggc    49920
```

```
tgggtgtggt ggctcaggcc tgaaatttca gcactttgga aggatcactt cagcccagga    49980
gtttgagaca gcctggccaa gtgagaccct gtctctccaa aaaaaaaaaa aaaaacaaaa    50040
actgggcatg gcggcacgtg cctgtagtcc cagctgcttt ggaggctgag gtggtaggat    50100
tgcttaagcc caaaaggttg aggctgcagt gagttgtgat ggcagctgca ctgcagcctg    50160
gtgaccgagc aagatgctgt ctcaacaaaa tttaaaaatc aaagaagaga attaaagttt    50220
agaaggttag gtggcaaaat gaggccacac atttaaagcc cctcctcctg attctttctc    50280
taccttgact gcctcctgtg gtggttcagt tgctgagaaa tgaaaacagt agggaaggcc    50340
gggtgcggtg gctcaagcct gtaatcccag cactttggga ggccgagacg gcggatcac    50400
gaggtcagga gatcgagacc atcctggcta acaccgtgaa accccgtctc tactaaaaaa    50460
tacaaaaaac tagccgggcg cgtggcgggc gcctgtagt cccagctact cgggaggctg    50520
aggcaggaga atggcgtaaa cctgggaggc ggagcttgca gtgagctgag atccggccac    50580
tgcactccag ccggggcaac agagcgagac tccgtctcaa aaaataaaa acaaaacaaa    50640
acaaaaaaaa aaaaaaaaag aaaatccatc tgtcccagc tctgcatctg cctccactgc    50700
ccagtctgct cctctccatg cgcttggggc tgggccctgt cccaccatgc agtgctgccc    50760
tggagcagtg agcttagtgg gtcctttctg gcatgagagc tgcctttggg agctggagtg    50820
ggtgggaatc tctgaatccc agcctctacc gctgggtctg gtgcctagca ggctatggat    50880
aagcttttgc tgactctagc ctcccctagg ccactgcagc gtggtcggtg tagtgcactg    50940
cgtgtgcagc atggccttta ctcacagcct ccacattaga gagaatctga ctgaagtctc    51000
gttgctgcct cgtgtgagca taatgtttg ccggaaccat gagcaggaaa tattaatctg    51060
ccttgtttcc tgtcctttac actgaagaat ctttttctgt atgggatgca tgccttacaa    51120
ataatgagtg gaaatactca tcgctaatga aaagttatac ctgattgtta gtctaccaaa    51180
taatctgaga tttctaatac ttttaatttg gcttttaaaa tgcaatttat cttagctttt    51240
ttgacttctt aggtcatatc tttagaacta tgtatttgaa tgttaatgta attttcatat    51300
tgaaattaaa atgttgaact gtgatgttaa gtgcttcctg tggaaataca ttcacatttg    51360
attcaacttt gaatcaagct gtttgaagat tttcacattt cttctagatt ttatcagctt    51420
gttactttat ctgtcacttt ctgtgattta cagctggagg gggttcctca tgcagccctg    51480
tcctttcaag aaaacaaaaa ggtgattatt tcagaaatca gagtcttgtg ttgaatctta    51540
ctgatttcct tgtatttctg taatgtaatg tatcttgtat ttcttgtaat actgtattgg    51600
actctgtgta tgtatatatc ttctcagtgg agtgattgta tgtgtgaatg ttgctggaat    51660
ctgataacaa ggcctgaata gttttatagg gtggctttta acagttactt tcatatcaga    51720
attgctttgt catacatttt gaatgcatca taaatttcta atgttcgggg tcagcagact    51780
ttttctgtaa agggacagag tgcaaacatc ttagctttat gagccatatg gtctcttttg    51840
caaccattca gctctgccct gtggcaggaa tgcagttgca gacaatacac gagctactgg    51900
ccagccatgt tccagtagaa cttttacttac aggaacaggc aggctgtagt ttgcccatac    51960
ctgccttagg gaatgtgttg ttatattta tgaagttaac ttaccttccc agtgaatttt    52020
gtttagcatt agtcaggaat attattaagt agcttctttt ccagcctggg caatgtcatg    52080
agacccggtc tctaccaaaa caagaccaaa caaaaaaaca gccaggcatg gtggcatgtg    52140
cctgtagcct cagctgctgt tctggaggct gaggcaagag gattgtttga gcccaggagt    52200
ttgaggtcac agtgagctgt gatcatgcca ctgcactcca gcctgggcaa cagaatgaga    52260
cctcgtgtcg ttaaaaaaaa caacaaaaaa agtttccttt gttggactgt tttaatttgg    52320
```

```
acctggttat cattttttcag ccatatctaa ctttgtacat atcagaatgt tctgataaag    52380
cttaacttttt attaaagtgt ttctgatagt tttggtacac attatcattt gcaatgccag    52440
ttatttttctt ttccagtggg gatttgcata ggaaaaaaat tgctgtcact ttctatttttg   52500
aaatcttaaa agactgatcc ttttttgtgt catgatttga gtgtttaatt gagagcctaa     52560
tgcctaatat tatttgcagt attgaatggg atcttaacag gaataacatt ctagccttca     52620
ttgaattaag taaacatttc ttgaaagaac ttggaatcta taatatttgg gtcatcacag     52680
tatgagatac ttaatcaaat ttgagatttt agtgaaacat tgttgaaaag ccaaaaagat     52740
tctaggaaaa attcatctct atattcttga attaggagag attttcggac ctgtgactaa     52800
gttactctga cacttgtttg tttcttagtc actcttccca gtggcagtga aaagaagat      52860
gactggttca cattgttgag attagtttat cctcttctgg ctaggacatg ggatatatcc     52920
tgtctctttt aagcccttttt ggtatttttt cccccattta gagctgtgtc ttcaaactgt    52980
tttgttatag ctggaaaatc cttttttttaa gtgaaatctg cccaaattat aagacagatg    53040
aaagtagagt tgtgttggat ataggattag ggtgcaagtg gcggggggtgt cctggagcct    53100
ctcttctgag ggcagcctag cgcttgtgcc tttgaggaaa ttaccctggg gatggtctat     53160
ggaacatatt tgcaaaccac tgatttgaaa gatagagatg gctttttgtta agatctgaat    53220
tcaccttttt ggcattttat ttgatttctc aagggaaaga acttattttttg taataaagtt   53280
tcctttttatt tagtagatag gccaagttgc tgtgttaatt taacctagag tttgggtttc   53340
ctttgctaat ttttttttcacc tttaatgtca catcattgta aatttgtgga agttatactt   53400
ctgacttatt ctttgaagag cagaaattag aaatttccaa taattatttt gatagtgtca    53460
tttaatgaca ttaatatgta atgtagccac aaagatttaa tgagttcagt taagtcatat    53520
taagactgtt ggtttcatttt gtttttcatta atgtaattct gaagatgaac aataaaatgt  53580
atttttagaa ctttcaagtg aaatattatt tcatccttcc agatcatata atgcttgagt    53640
tctgattgtt aatcataaag tcaagaaaat taaaagataa taaaatgaaa gtgactttta   53700
ggtgttagag ttttatgtac aaattctggt gtgtcattgg agctatcaca tgaatatttc    53760
aaaggccaat agcattgggt ctttacagtt aaaacttact attttttaagt ttaagtagta   53820
ctatagatta tttaataatc gaaatcaata aatattaatt attaaaatgt tttgtggtat    53880
actttgagaa tcattgctttt taacttttttc catataggtt tattaacttt aatagcattc  53940
taaacataac atctctacat tctttgtgtt taatactgta gaggtataaa aatacttata    54000
tatgatgata aaccatatta gagtaaatta aatattctta tgagtttcat tttagagtgc    54060
atttacttaa ttttgaaatc cttattttta gcaaactaaa ggaatgttgg tacattatttt   54120
actaggcaaa gtgctcttag gagaagaaga agccttggag gatgactctg aatcgagatc    54180
ggatgtcagc agctctgcct ttgcaggtag ttctcactag ttagccactg atgtggacct    54240
tcactctctg ccgtccaccc catgcccttc ctgcctgtcc ccctgcacct ggtggacagc    54300
acaactgggg gcagcagtgg acccaggttg cttaaatggg ggatatttgg gcttctttca    54360
taatacttac tctgaagctt gtgtgtctgt ggtgtttgca tcatatattt gctgttttct    54420
gtggtttaga ctgttttaaa attaggttta tgctccttga gcatagggct ttgtgagtag    54480
ggatggcacg ttgaaacgtc tcatgagttg gatgggttat gctgggggtt ggaaatggga   54540
tgaaaaattg tgggatgaaa aattgcctat ggatagttta acttgaaaga atctgccttt    54600
gtttacagat agttatcttt tttttttttt tttgagataa agagtctcac tctgtcaccc    54660
```

```
agtgccgata cccaatgtca ctggcatgga gtggtgtgct cttggcgcac tgcagcctcc    54720
gccttctggg ttccagccgt tctcctacct cagcctccca agtagctggg actacaggtg    54780
cccgtcacca cggctggcta agttttgtat tttttgtaga gacgaggttt taccatgttg    54840
accaggctgg tcttgaagtc ctgacttcaa gtgatccgcc tgtctcagcc tcccacagtg    54900
ctgggattac aggcgtgagc cactgtgcct ggccagttac agacagttat ctaatgaaat    54960
tctctgtgta ctttataaaa gataaggatt aacttaaggt actaataact ggattatatg    55020
agggtggttt tggttgtata atcctatcta aaagaatatt ttagctgtaa ctgaaagtaa    55080
gacttaaata tttagggagg aaaatctgaa taattctagt agtaattatt tacaaaataa    55140
aaatagattt tattttttgat tacacaaatt aaacaacaat aaaacatcac agcgatctag    55200
actagtataa aggtcacacg cttaccaacc caaccgcccc aggagtgacc actgccaaca    55260
gcttcgtgtt gaccttttttg ccatgatttc tatatagtct tttttgtttt taaatggtaa    55320 ttaaaaagt caactaggaa aatgtgttag aagtttatct tccaggagaa taataggact    55380
ggagtcgaga tcttgaacgt ggcttggaag aaggcaagcc cacccagag agattacagt    55440 tgttcgggac cactgcttgc ttagaggacc tgcgtgtctg ggaccgccta gttttgtgcc    55500
cctgactagg ctgccccctta attacgaacg tctttataaa ttgccctagc cagggcttgg    55560
agtagttggt taagaacttg aacttcagtt tttgcagtga aacaccgttt gagaatatta    55620
ccttctgata agccttattt tattaagatg ggtactgtag cgagaggcag tgtgagtggt    55680
acatgaggga tgcactgctg tcctgcattt cactgtcttc aggatgctat gcagtgatga    55740
catttggaaa catttcatca aacattccat caaatgaaaa cattggatga cagtggaact    55800
ttgtgttatt ttgcaagcct ttgattccat attgaatgtt ttctctcgcc atttgacaaa    55860
tgagtgtttc tctgtcttca gcctcagtga aggatgatat cagtggagag ctggctactt    55920 cttcagggggt ttccactcca gggtcagcag gtcacgacat catcacggag cagccacggt    55980
cacagcacac gctgcaggcg gactcagtgg atctggccag ctgtgacttg acaagctctg    56040
ccacggatgg ggatgaggag gatatcttga gccacagctc cagccaggtc agcgccgtcc    56100
catctgaccc tgccatggac ctgaatgatg ggacccaggc ctcctcgccc atcagcgaca    56160
gctcccagac caccaccgaa gggcctgatt cagctgtcac cccttcagac agttctgaaa    56220
ttgtaagtgt gcggaggggc ctgccatctt ttatttttta tttgagacag agtctcactc    56280
tatagtgcag tggaggccgg gcacagtggc tcacgcctgt aatcctagca ctttgggagg    56340
ccgaggtggg cagatcnnnn nnnnnnnnnn nnnnnnnnnn nnnnnnnnnn nnnnnnnnnn    56400
nnnnnnnnnn nnnnnnnnnn nnnnnnnnnn nnnnnnnnnn nnnnnnnnnn nnnnnnnnnn    56460
nnnnnnnnnn nnnnnnnnnn nnnnnnnnnn nnnnnnnnnn nnnnnnnnnn nnnnnnnnnn    56520
nnnnnnnnnn nnnnnnnnnn nnnnnnnnnn nnnnnnnnnn nnnnnnnnnn nnnnnnnnnn    56580
nnnnnnnnnn nnnnnnnnnn nnccacccat cttggcctcc taaagtattg ggattatatt    56640
tgtgagctac catgcccaac cctactgtct gccatctttt gagctcttcc ctggagaccc    56700
agacctgaac cctcctgctt gttctcttct tgtctaatac ccctaatgac agcgcagctt    56760
agatcactag tggagagctt gacctcatct gataccttca ctgaagggaa cagcttagtg    56820
tcttttccac tgaacactga ggtaaaaaat tggaatagtt gattatgtga actctgctaa    56880
aattgagtgc attttacatt tttttaaggcc ttttttaggcc ctggttaaat aattattttt    56940
aaaaatcctg aaggagccta ttataaacag atctgtggtc ttaatgaaat gtgattaata    57000
ctgtgcatta ttttaagaac ttttgacttt tcaaaaaact tttacaacat ttcccatttt    57060
```

```
atagcagcat aggtgtaagt acctctcatc cctgagttag tggacaagaa accctcatgg   57120
atagtctaat aacgtttggt acaagtctat gttgttttat actccatttt attttcagtt   57180
ttaaaaactg gttaaatatg tgtaacataa aatctaccett cttaaccatt ttttacgtat   57240
gcagcttgct ggaataaata attaaataat gtcatggaat catcgctcca cccatctgtg   57300
taaccttttg atcatgtgac actgaagctc tgttcccatt gaactctcta ttcctccttc   57360
cccgccaagt ccctggcaac caccattctt ctttctgtct tctgaatttg actactttag   57420
gttctcatat actttagggt cacaccgtat ttgttttagt tagcataacg tccgcaaagc   57480
tcatgcatat tgtagcctgt gttgaacttc ctaatgtttc aggccaaatg ctattccatt   57540
gtatggatag gccacatttt gcttttccat ttctctgtcc atggacactt gtattgcttt   57600
catgctttag ctattgtgaa tcgtgctgtt atgaacatgc gtgtacaaat gtctcctgga   57660
gactctgctt tccattttt tggctaaata cccagaattg gagttgcttt tacattctga   57720
ttttaattta aaacatttat atcattgagt gttttactta atagtataat agttagcaaa   57780
ctaatatttt ggtaataatt tgctggtagt tttagagtcc attgctcagt ttttttaggt   57840
aaattacaca ggacatttca gtggacgtg gaacaacttg tgatatggaa tcatgcccca   57900
agctgatggc taaacatacg aaataccatg ccctaaattt agtagattta gtctttgcaa   57960
tttaggagat aacctgttat attgttaggt ttttgtctaa aagctttgtc ctcatatttc   58020
caacttgctg taaaatttgt tcgtgaagac aaatattttt gtatgggttt tttcttttt    58080 atattaaaaa gaaatgtcca cattggaatt ttttggagt ttttagagct aatagagctt   58140
ttcataatgt agtgggaatg agtgatcagt aagctcttag cagtttccat gcacacattt   58200
ctgtgcattg aaataaatga cagatgagta catttgtgtt ctgtgtgtaa aacgtgctct   58260
ttcttcgttg catttccatg ttggagggct tgtctcttgg tgatcacact tcaaaattct   58320
cacagccccc cttgaaccgt ttaggtgtta gacggtaccg acaaccagta tttgggcctg   58380
cagattggac agccccagga tgaagatgag gaagccacag gtgttcttcc tgacaaagcc   58440
tcggaggcct tcaggaactc ttccatgggg atgtggacca caggtgacgc gctacaaagt   58500
ggtcttgtat tcaggcctgg acatcttaat tatatctttg ctctcaagaa gaaatccttt   58560
gatattgttt tctgagttct gaatagctga tgaaaatgac caattgagga ataatcatac   58620
tttttcttca tctaaatctt acgcttttga gttatcttag cataaatgta taattgtatt   58680
ttaagtggaa atttgtcact taatcttgat ttctctgttt ttaaagccct tcaacaagca   58740
catttattga aaaacatgag tcacagcagg cagccttctg acagcagtgt tgataaattt   58800
gtgttgagag atgaagctac tgaaccgggt gatcaagaaa acaaggtgag ggacataggc   58860
ttgagacaac ttggtgtttc tgagcttgtg tgaggattta aaatcgccct ggctactatc   58920
tactttattg ctttcccatc cctgggcctt taaattccc ctttaaatac cagctcttcc    58980
caggcctgtt gttttccgcc tttcaggtgc tactgacagc gttaagaatt gcctgagttc   59040
tgcctccttt gagagtgtgc cccagagaaa tctattctgt actgagtgtt tccttgtctg   59100
atttcttggg ccattcattt gatggctgcg tatggccttg caccatgttt tggttctatt   59160
gaactgtttt aaaagtctct gtttatatta cctttttaca tgtaaatgta actgtcttca   59220
cttttaattg ctcaagggca aggaatagcg tttcacagtt tctcccagca atcagaatta   59280
cagcctttgg catctccctg tctaccaggc ccagttcgtc ttagctttgg gcttccccag   59340
gctgttacct ttccctgagt agcttctgct tgtcctgtag aagaccactc atgctttgct   59400
```

```
tccagagcag cctttctga atgcctggtg tcaggtgcct tcttactgtg cccaccctcc    59460
ctgcatgctg catttatccc ctgccacagc cctgggaccc tgtgtccagc tgcctctgac    59520
ttgtctgttt ctgcttggtc atggtctctg tgaggtcagg tgtgcatatg agcacagacc    59580
agggcatctc tttatcccca gcacccagtg taagtgctac tctaggacta tttgttgaat    59640
gaactaatgc atgaatgtat tggttgagta tgagacaaac aagtgtcact gtctcctttc    59700
tagccttgcc gcatcaaagg tgacatcgga cagtccactg atgatgattc tgcacctctt    59760
gtccattgtg tccgcctttt atctgcttcg tttttgctaa caggggaaa aaatggtgag    59820
tacaaaaggg gacgtgcaga gttgaaggaa ataactaggt ttcagaggtc aacttggtgc    59880
ccgtttagta ctgtgtgtag cagaggcagt agaatctgag gatgagtttg ttttcacta    59940
gccaagggga agggaggaaa tgatgggagc aggtaggtta ctgggtctgg ttttgttcat    60000
ttgaaaacaa tctgttgttt gaggctgaag gtggcttggg tgatttcttt gcagtgctgg    60060
ttccggaccg ggatgtgagg gtcagcgtga aggccctggc cctcagctgt gtgggagcag    60120
ctgtggctct ccacccagaa tctttcttca gcaaactcta taaagttcct cttgacacca    60180
cagaataccc tggtatgtta aaagttcaca tcttattttc tcagatttaa tcattattgt    60240
aaaaacgatt tcagtattga ctattttagt tttagcgcgg tgttttgagt ttatttggga    60300
tttttttttt tttttgagac ggagtctcac gctgttgccc aggctggagt gcagtggcgc    60360
gatctcggct cactgcaagc tccgcctcct gggttcacgc cattcctg cctcagcctc     60420
ctgagtagct aggactacag gcgcccgcca ctgcgcccgg ctaatttttt gtattttag    60480
tagagatggg gtttcactgt ggtctcgatc tcctgacctt gtgatccgcc cgccttggcc    60540
tcccaaagtg ctgggattac aggcttgagc caccgcaccc ggcctatttg gatatttga    60600
cccgcgttgt agctcttcag aaaacacatg aatagtgaag ttctttgttt catggttct    60660
ctttagatga aatccgtaga ggaaaaaaat agaaacctca gcacgtaaga gccaacttat    60720
atacgcatcg gatttaaacc taaagcacaa attgtgcatg gtcacggtgg cgctgagtca    60780
cactcagcca ggccaggcat tcacactcag ggtgagtggg caccaggact ggctgaggca    60840
gcagtggacc cgtgtctgca ccctgcccat gcttattgtg gagccttctc gctcgctctc    60900
tttctttggg tgagagggta cacttgtgtt tttgaattta tatgaggtaa gggttatat    60960
atagggtttt ttctaatctt tttttaagtg gaatctggaa ttttaatcag atttactatc    61020
tgacagccta gaattataat ccagaaagtc tgtggtattg aggacatatt ggcaatatga    61080
tgaatctgta atccttaaat cctgaaactt ttttttttt ttaatcactt agggttatta    61140
tagtgaagtc atttctgaat ttggatcttc tcttcatacc tctttttctc tttcctgaga    61200
attaagcttt tgttttgagt tagaaagttg atagtaggaa attgttccat ggctgggcaa    61260
tttatctcca cagaggaaca atatgtctca gatatcttga actacatcga tcatggagac    61320
ccacaggttc gaggagccac tgccattctc tgtgggaccc tcatctgctc catcctcagc    61380
aggtcccgct tccacgtggg agattggatg gcgccatta gaaccctgac aggtagtggc    61440
cagttttca gctgtgtttt ttctagatat ccttactaag gtttccgttt ccatgacgat    61500
gtttgtttct gttcttctgt caggaaacac attttctttg gcggattgca ttcctttgct    61560
gcggaaaaca ctgaaggacg agtcttctgt cacttgcaag ctggcctgta cagctgtgag    61620
ggtgagcgcg atctctgtgg agccattgct tcacttagtg ggcatttat cattgctgca    61680
attcaattg gagcttaata ggaaatattt ccatacactc taaagctgta accagtaata    61740
tccaccatgt atccatctct tagctttaga aagaaaacat tgccagtaaa gttaatgctt    61800
```

```
cataaacttc agtttaagtt ttaattctca gaatatttgt ttgaaataga cttcttccta   61860
aaggatatat ttagaaataa cctatcatta catgtaaagt ctgttgaata tgctgggcac   61920
ggtgactcat gcctgtaaac tgagcacttt gggaggccaa ggtggaagga ttgcttgagc   61980
ccaggagttc aagactatgg gcaacatggt tgatcctgtc tctacagaaa attaaaaaga   62040
aaaaaaaaaa ttaactgggc gtggtggtgc atacctgtag tctcagctac tcgggaggct   62100
gaggtggggg gattacttga gccccggaga tgaaggctgc agtgaggcat ggctgcatca   62160
ctgccctcta gcctgggcaa cagagtgaga ctgtctcaaa ataatagta ataataatcc    62220
gttgaattaa aaaaacccc aaaaaccact gtgttaggcc catggtgtag taagagttaa    62280
agtgagcctt agggattatt tactcaacct ctgtgtttgt atgaagtgga atggccccag   62340
ttctttaagt gatagcatgt tgaacctttc cataccagct ggctcgtaag tcacaactgg   62400
ccagtcaaca agagtcaaaa ttaactagta aaaatcaaag caaaaaactt agaattgtcg   62460
aatttgtgcg atacctcccc cttttaaaat gtcatgcctg acagtaattt ttccctagtt   62520
tccaggtttt gtttcagtca attgtgtctg tcttgagcag aaggaagcgt gctaacagct   62580
cagtctcatg gctagctggg ggtctatgtg tcagccatgc atgtgatggt gcccctgggt   62640
gcctgaggct gcagggagg ggtacagcag taggggcctg ttctgttctc ccgtgccttg    62700
gagtacatag tgatatagtg gggtggtcct tggtgtaggt ccctcgttcc taccctgggt   62760
ctgcgattta tttagaagtg gtgttggagc tgtgcggcag gccccttgt aactgatcaa    62820
tgtttgtgaa gttgccgttt gagaattgaa accatgacat aagcagaaat ggaagaaaag   62880
aaccagttat ttgaaaggga cacattcact tttaagcttg tatttactga gataaaatat   62940
ataccatcag tgttcttgag aggtgtggga aaagtgcaac atcctggttg cagttaaacc   63000
cagaacgttg tgtgttgaag actgacagtt ctcaaaccgt caagacgcgg gtactgagtg   63060
ggactaacct gctgccctct tgcctcggac cttgtgttcc agcattgtgt catgagtctc   63120
tgcagcagca gctacagtga gttaggactg cagctgatca tcgatgtgct gactctgagg   63180
aacagttcct attggctggt gaggacagag cttctggaaa cccttgcgga gattgacttc   63240
aggtaagtga gtcacgtcca ttagatttca tgaactaagc tcaattgaaa gtcctggggt   63300
cacttggtat aaggaatgat gttatcaagt accctgccca tcagaaatct gagcggttta   63360
ggtagatgac agtgattttc tcccccagt ggcttttgc tgaacctcgc cctatgcgtg     63420
gattttattt tatttatta tttatttaga gacatgatct tgctctgttg cccaggcttg    63480
gatgcagtag cacagtcata gctcactgta gctttgaact ccaggactcg agtggtcctc   63540
ctgcctcaga ctcccggtta gctaggacaa taggtgtgtg ccatcacact ggctaatatt   63600
ttattttttg tagaaatggg gtcttgctct gttgcccagg ctagtctcat ctcctgagct   63660
caattgatcc tccaatcatg gcctcccaaa gtgctgggat tacaggcatg agccactgtg   63720
cctggcctag aattttaaaa gataaataga agagtagttt ttttttttt tttgatagt    63780
cctagtcatt taagtgttct ggatagtagg aataaaagag cttagaattt ttcatctttg   63840
tcttaaactt tttaaaaaat gtagcttatg ttaattctgc ttgttttaaa agaatatact   63900
catcattata ctgaacctag gtaagacagc tggtttatat tttgttgcaa ttaaaaaatg   63960
tgagctgtgg ttgcagtgag ccaagatcgt ggccattgca cttcagcctg gcgacagagc   64020
gagactccgt ctcaaaaaaa aaacaaacca aaaacgtga gctgtgttgg aactttcatt    64080
ttctaagagt aaagttttgg caggagaagt tttctgtcag tactttattt tagaagggaa   64140
```

```
attttttataa ttcaggtgtt ttgttttttgt tttttgttttt ccccccaagc caccttttat    64200
agagcccttg tgggttattt tatttaatcc ttagaatgtt tataaatctg ggactgttct    64260
cggctccacc cacagatagg ggcgctgagc atgcgtgagt gggcagcaag atagcaggtt    64320
atggagggcc cagctcgccc cttctgtggt ttgagccagt tctgtacggg acttacagag    64380
tgttttgaaa tagtatttat tttgaagaaa aagaaaaaca gtttactgag tgctatctta    64440
ttgagtctgg agttgtgaga ggaatgccac ccctatttgt ttgaagccat cggccttttc    64500
tgttgtcttg agtaagtgct gcccaagggc cttccagggc gcctgactga gcctgctctg    64560
aagcaagctg gcggaaagtg tttactgagt aactaaatga tttcattgtt aaatgtgctc    64620
ttttgttagg ctggtgagct ttttggaggc aaaagcagaa aacttacaca gagggggctca    64680
tcattataca ggggtaagcg gcttattttt gtgagatact gttttacctt aaggaggtga    64740
aagtgaggct ttccttgtgg aatttctcta aatgcattca tcgtatttta gatctgttta    64800
tttcacagtt tatatcatga aagttataat tgtgtcacat ggatttaagt ctagcaatgt    64860
tgagttcttt ctcactagct ttccaaaata tcttacctaa aatttagtca aatacaagat    64920
tatgtttatt tttattatcc ttctctctaa agcttttaaa gctgcaagaa cgagtgctca    64980
ataatgttgt catccatttg cttggggatg aagaccccag ggtgcgacat gttgctgcag    65040
catcattaat taggtatttta ccagtatttt atctcttttta cttttttggt tgaagtacta    65100
aaaggtatga acatggaaag agagggaaga attcaaagga tgtagagcag tattcctgaa    65160
tctgagctca tttcagctat tctgttctta aactatcaag aaaaaaaaat ccaaaaaagt    65220
ctaaaattat aattaaaaaa acaaaatact aaccatccat tgtaaaaagt aatgcatttt    65280
cattgtaaaa atttggacta tagagaatag cactaagaag aaaaaaaatc accttcaatt    65340
ctgctaccac ctggaagtaa tcgctgttaa tattttgctg tatactttttt atgagtttct    65400
tattcaaaat ggggtcaaaa ttacatgcaa ttgtgtaacc taattttcac tgaatatttt    65460
attagcattt ttctgttatg aaacagtaat tttagttatg ggtcattgtt ttactatgtg    65520
attgtgataa aattttacat aaatttttttt tggaaattaa ctattgtaca taaatgtgta    65580
taattttctt tttccgagaa ttcctggaag ttgagttagc agcccaggct ttgaatttttt    65640
tttttttttt gagacagagt cttgttcgtt tgcctaagcg cgatctcggc tcactgcaac    65700
ctccgcctcc caagctattc tcctgcctca gccccccgag tagccgggat tacaggtgca    65760
caccaccaca cccagctaat ttttgtattt ttagtagaga cagggtttca ccagattggc    65820
caggctggtc tcaaactcct gacccccatga tccacctgcc tcggcctccc aaagtgctgg    65880
gattacaggt gtgaaccacc atgcctggcc aggctttgaa tttaaaaaaa attttctaat    65940
agctttatgg cggtataatt tacatttctt gaaacctact cgttttgagt gtatagtaaa    66000
cttcaatttt atcacatttc tatcaccccca aaggtccttg ggcccattgc agtaacctcc    66060
ggttcccgcc cccattccta ggcagccact catctatttt ctgtcccctta agatttgtgt    66120
tttcgtcagg cacggtggct cacgccttta ctcccaccac tttgggaggc cgaggcaggt    66180
ggatcatggg gtcaggagtt tgagaccnnn nnnnnnnnnn nnnnnnnnnn nnnnnnnnnn    66240
nnnnnnnnnn nnnnnnnnnn nnnnnnnnnn nnnnacccct gtctgtacta acaatacaaa    66300
aattagtcag gtgtggtggc gggcatctgt aatcctagct acttgggagg ctgaggcagg    66360
agaatcgctt gaacgtggga ggcgaagttg acagtgagca gagatcgtgc cactgcattc    66420
cagcctgggc agcagagaga gactctgtct gaaaacaaag atttgtattt tctggacatt    66480
ttatagaact ggggtcatag tataaatgga cttttgcatt tggcttcttt cacttaattt    66540
```

```
tgagattggg tcttgtagca tgtatcggta gtttgttcat ttttattggt gagagtatta    66600
tatgaataat accatatttt atctatccat cagatggata ttattgagtt catgttttgg    66660
ccaatttatg aattatggta ctgtgaacat ttgcctacaa gatttgtata ggcatgtttt    66720
catttctctt gagtggataa cctagaagtg gattttttaaa taattttttgg tacttactgt   66780 gaaactgctc ttcagaaaca taccatcgtt tgtcctttct ttcttgtctt tctctttctt    66840
tctttctttc tttctttctt tctttctttc tttctttctt tctttctttc tttctttctt    66900
tctttctaca tagacacatt ttaagaaaaa tttcagtagt ttttggggta caagtggttt    66960
ttggttacat ggctgaattt tggttgcatg gtgaagtctg agattttagt atacttgtca    67020
cccaagtagt gtatcttgta cccaatatgt agttttctgt ccctcacctt cctcccagcc    67080
tcccgccttg tgagtctcca atgtgcatta taccactctg tatgcccttg cgtactcaca    67140
gcccagctcc cacttctgag aacatactgc agaaacatac caaaggatac tcccactgcc    67200
agaatgtgat tgtgcctgat tcttctcacc aataaatatt tcaaaaaaag ttaaatatat    67260
atcagttttt tgggcagaag ttgatacttc tctttatttt ttatttttttt ttgagatagg    67320 gtctcactct atgatgccca gactggagtg cggtggtgcc atctagctta ctgcagtctc    67380
tgcctcccag gttcaagtga ttctcccacc tcagcctccc aagaagctgg aattacaggg    67440
gagagccact actgccagct aatttttgta ttttttggta gagatggggt ttcaccatgt    67500
tggccagact ggtctcaaac tcctgacctc aagtgatcta cctgccttgg ccttccaaag    67560
tgctgggatt acaggcgtga gctaccacac ccggctgata tttcttttta aaataactta    67620 ccttctttg aaagtaatac atgttaaatg aacaaaattt aaggaaaata taaaaagga    67680 aataatctttt ataatgaaac tactgaaaga aaaccaaaat tacattttgg tgcatattct    67740
ttttcgtttt catcattgta atttgcattt ctttgattac ttgtgagaca cacttttcat    67800
ttacttaaag gttcgtatga cttgcctgtt cagaaatttt gcagctttac cattttctgc    67860
aaatgatagc aacttctttt tatttttttta ttttttatttt tatttttatt ttttttttg    67920 agacggagtc tcgctctgtc gcccaggctg gagtgcagtg gctggatctc agctcactgc    67980
aagctccgcc tgctgggttc acgccattct cctgcctcag cctcccgagt agctgggact    68040
acaggcgccg ccacctcgcc cggctagttt ttgtattttt tagtagagac ggggtttcac    68100
cgtgttagcc aggatggtct cgatctcctg acctcgtgat ccaaccgtct cagcctccca    68160
aagtgctggg attacaggct tgagccaccg cgcccggccg caacttcttt ttatttgttt    68220
gtttgtggtg acagagtctc gctctgtcac ccaggctgga gtgcagtggt ggaatcttgg    68280
ctcattgcaa ctattgcctc ctgggttcaa gcgattttcc tgcctcagcc cccaggtag    68340 ctgggattac aggaatgtac caccatgccc ggccaattt tatatcttta gtagagatgg    68400
ggtttcgcca tgttggccag gctggtcttg aactcctggt ctcaagcggt tccctgtct    68460 cggcttccca aagtgctggg attacaggtg tgagccaccc tacccagcca atagttactt    68520
cttatattcc agaaaaaatt gtactcatga tcaagtctcc atgaggaaaa agactttaat    68580
taaagatatt gcagtttgca gaccaatatg ataaaatagt tgattgtttc taaaagtatt    68640
actgagtaat gatggcagat ataagccctt ttgttttttgt aggaaaatgt tacccatgtt    68700
ctgcatttga attcagttta gatttgttag gaatctcagc ttaagctttg ccatctggga    68760
gtgtttggga caatttgtca gacagaattg caaaagtgcc taagggatgc aactggcact    68820
cagacctgct ccttgctcag tactctgtgg acagatgttc agcgcttgtt gatgttgatt    68880
```

```
aaaaggttta gaaagagaac tttcaaagtt ggttttaat taaagcattt aatagtgtga    68940
ataaaaaggg acttaatttt atgacagaca aaagaaagta cagcacctgg cggggcgcgg    69000
gggctcacgc ctgtaatccc agcactttgg gaggctgagg caggtggatc atgaagtcag    69060
gagttcaaga gttcaagacc agcctggcca aggtggtgaa accccgtctc tactaaaact    69120
acaaaaatta gccaggtgcg ttggcaggca cctgtaatcc cgctactcag gaggctgaga    69180
caggagaatc acttgaacct ggatggcaga ggttgcagtg agccaagatt gtgccactgc    69240
actccagcct gggcaacaga gtgagagtct atctcaaaaa aagaaaaaag aaaatacagc    69300
acccagttat gtcagagtgg gtgcatcaga gagtgaccct gagattggag cgatgctgt     69360
cacgtgcttg aagaatgcta cctgagaaag ggggcgagaa gtggtgtttg ctggtaacca    69420
gaggtgttgg cttagccacc tgcagggagg gtggtctatc acaggtgagt ttcatctact    69480
ttcttaagca aatcaacctt acttttgtgt taggcttgtc ccaaagctgt tttataaatg    69540
tgaccaagga caagctgacc cagtagtggc cgtggcaaga gatcaaagca gtgtttacct    69600
gaaacttctc atgcatgaga cgcagcctcc atctcatttc tccgtcagca caataaccag    69660
gtatgctgac ccagtggcgt cctcacattg ttgggaaaat gcccttccct gatgccttc     69720
tttaggcttt aattgaaaac attttatttt ctagaaaaaa gctttagctc aggatgtttg    69780
agtgtaggtc attcctttga taggatattg tcattctgag gattgaccac accacctctg    69840
tatttaagcc ctgccacaat cacacagctg tgacactata aatcttttaa tcgtttatta    69900
catttaatgt gctgacagtt atattttgt gtgtgacact tacgtattat ctgttaaaaa     69960
attttcactt tagttgtgtt acctttaaag aggattgtat tctatcatgc ctgttgattt    70020
gtaggtgagc gggctattaa agtcagtgtt atttagggct atccactagt tctgtgattt    70080
gcaatgactc tccttcacat ttgttgtgga gcttttgaat atagcgtcaa atggccacat    70140
atatcccatg cttacctgat tcttaggtga gtaggacaga gtgctttaat gaagctataa    70200
tcttcagaat tctagcttgc aaaggagatt gcagaaggat aagacttgtg cttttcaatt    70260
ttgtctttta aatgttattt taaaaattgg cttatatga tactctttt ctgctgagta      70320
acggtatttt acagaacttg gactagatga cttctaagct taaatgatca cttgatgctt    70380
tttttctgaa ttaggaactc agcttacaca tttcaaagtc ataattcctg aatacataac    70440
atcttttttt catgtaaaga ctgctttaaa aaacacatgg aaggtcgggc gtggcggctc    70500
acacctgtaa tcctagcact ttgggaggcc caggcgggca ggttgcctga gttcaagagt    70560
tcaagaccac cctggacaac atggcaaaac ctgcctctac taaaacataa aaaattagcc    70620
gggcgtggtg gtgggcacct gtaatcccag ctacttggga agctggggga tgagaatcac    70680
ttgagccctg gaggcagagg ttgcagtgag ccaagatggt gccattgcac tccagcttgg    70740
gctacagagt gagactgtgt ctcaaaaaaa aaaaaaaaa aaaaaaaag ccacaaaaca      70800
acaacaacaa aaacacacgg aaacatttta tttggccacc ttagtatttc cccttcagat    70860
aattcctttg tttaaactca gaactggcat tttctctctt tgaaaagatt caggacaaat    70920
actccttaa gataagcaga aacagtgaaa gagtatttga ttatcaggaa tttgataggc      70980
ttagaataaa ttgttgcttc ttaatgtcat ttcagaagat gaatattaat agatgccaac    71040
tgagatatca ttaaaattgg ttactactac tttgaaaagt ttcccagttc caaacttcag    71100
caggcctctt cacaattcaa cagtgcttaa ttgggacttg tgtgatagat acgattccca    71160
attgtgtagc agagtgtgct gcttagctac ctattctgtt agcattcgtg tgttaactta    71220
aaatcataat ctccttagtt ttgttgagtg tctctgtgga tgagacactg tgagggatac    71280
```

| | |
|---|---|
| aaaatcagat tggctttatt caaaccattg gggtattatt tttatttttt gccttttttc | 71340 |
| catgtgttct aaaggaatta gagtttgaat ataactataa tgggggatag aaatttacat | 71400 |
| gtgccatgaa gggaatgcag aaaagtgcca tgggagctca gaagtggaga aaggaatttt | 71460 |
| ttttcttgga agcaggagta acttcatgaa gcatttattt caacttagag atagtaggca | 71520 |
| atgctgtaag gggagtgtgg ctgcagcgaa agtgtttggg gcagactggg aggaagggag | 71580 |
| ggaataaatt cagccattgt tatggcataa tgatcaaaat ttattttcag cccctctttc | 71640 |
| acttaaaagt tgagactgct taacttcttt taatctttaa tcttaaactt ttaaatgcca | 71700 |
| tttgatcttt aaaaagatat gttttaatag tatattttaa gtctctgtat ttttcttatt | 71760 |
| agaatataca gaggctataa cctactgcca agcataacag atgtcactat ggaaaataac | 71820 |
| ctttcaagag ttattgcagc agtttctcat gaactgatca catcaaccac gagagcactc | 71880 |
| actgtaagtc tctttcttga ttggtcttaa tgaaattata ataattttc gtgacttgta | 71940 |
| tggccagtta gttttatggt catcttatgg tgaggtgctt gtattagagc tcttacttat | 72000 |
| ctgtggggct tgctaagaaa ttgtgtttct gtgaaaagga tcttagctta ctccaggaat | 72060 |
| gtaaataact atttttttct gattattaaa gtaatacatg ccaaaagtta aaaaattcag | 72120 |
| ccaatttagg aagacataaa aatgaaaata agccaggcgt ggtggctcac acctgtaatc | 72180 |
| ccagcacttt gggaagccga ggtgggggc tcacttgatg tcaggagttc gagaccagcc | 72240 |
| tggccaacat ggtgaaaccc atctctactg aaaatacaaa aattagctgg gcatggtggc | 72300 |
| gggcgcctgt aatcccagct actcgggagg ccgaggcagg agaatcactt gaacgtggga | 72360 |
| ggcagagctt gcagtgagcc gagatcgagc cactgcactc cagcctgtgc aacagagcga | 72420 |
| gactttgttt ccaaaaaaaa aaaagagaaa gaaaactact gtcacctgca tnnnnnnnnn | 72480 |
| nnnnnnnnnn nnnnnnnnnn nnnnnnnnnn nnnnnnnnnn nnnnnnnnnn nnnnnnnnnn | 72540 |
| nnnnnnnnnn nnnnnnnnnn nnnnnnnnnn nnnnnnnnnn nnnnnnnnnn nnnnnnnnnn | 72600 |
| nnnnnnnnnn nnnnnnnnnn nnnnnnnnnn nnnnnnnnnn nnnnnnnnnn nnnnnnnnnn | 72660 |
| nnnnnnnnnn nnnnnnnnnn nnnnnnnnnn nnnnnnnnnn nnnnnnnnnn nnnnnnnnnn | 72720 |
| nnnnnnnnnn nnnnnnnnnn nnnnnnnnnn nnnnnntta gtagagatgg ggtttctcca | 72780 |
| tgttggtcag gctggtctca aactcctgac ctcaggtgat ccacccgcct tggtcaccca | 72840 |
| aagtgctggg attacaggcg tgagccacca cacccgtctt tacattttta taataataat | 72900 |
| ttatgttgct gatattagaa aagaaccata atatccaaga attcaagaac aattaaatta | 72960 |
| tgtacatatg ctagtgtata gtgtgatgct ttggagaatt tttaacaatg tggagatata | 73020 |
| taatctgaat tgtagtattg agtgaaaaaa ggcagaatac aaacctagta gggggtatag | 73080 |
| tcggatttca gttaagaaaa ataatattta catatataca ttcctcacat tggcagataa | 73140 |
| tcaccaagat acattttggg attgtggatg attttttgtgt tctttatatt tttcaggtat | 73200 |
| tctcaaattt tctaaaatga gcaagtataa cttttgtcat cagaaaaaat aatatgcaaa | 73260 |
| agtaatgtta atttgttggt gaccaggtta aaccttttta tttttattat tattttttga | 73320 |
| gatagagtct cgctctgttg cccaggctgg aacgcagtgg tgtgatcttg gctcactgca | 73380 |
| gcctctgctt cccgggttca acgattctc cagcccagc ctcctgagtg ctggaatta | 73440 |
| caggtgcagg gcaccacacc tggctaattt ttgtattttt agtagaggtg gggtttcacc | 73500 |
| aggttggtca ggctggcctc gaactcctga cctcgtgatc cacctcctc ggcctcccaa | 73560 |
| agtgctggga ttacaggtgt gagccgctgc acccagccaa accttttat tttatttgac | 73620 |

```
aaaagaaata cttgcatgtt atagaaaact aaatattgtt tgggctgtct gcagtatggt    73680
cttctcttga tttgttcaaa atattgtaaa ctttgatttg ttcaaaatat tgtaaacttt    73740
gcttattttt tttgttcttc ccttgctttg ttcaaaatat tgtaaacttt acttattttt    73800
ttttgttctt cccttggttt gttcaaaata ttgtaaactt tgcttattta tttttattgt    73860
ggctgacatg tgtcagacac tgttgtaggc ctgggatgta aaaacaggat tcctgccctt    73920
acggtctctg gaggctggtc agggagatga tgtggtcagc tggagctccg ctcctaaggt    73980
tgtgcagggg cagttgagag gcggaagggt gggacagcat ttcaaggtgt gggcagcaca    74040
ggagtctctc ttcattggga tataattgcc attccgataa catgtatttg agttgtctaa    74100
agtaggaagt tgtaccatgg tgggacagat atctcatggt tatcatacac agatctcagt    74160
tctcattgtt tgtacttttt ataaagggta aaggagata taattcaata aaccttgtg     74220 gtgtttgggt gtgattttat tgtttctttg ttctatagtt tggatgctgt gaagctttgt    74280
gtcttctttc cactgccttc ccagtttgca tttggagttt aggttggcac tgtgggtatg    74340 tatttttcctc agtatgtatt aatagttgtc tacaacagta taatataaac gtagttatta   74400
ggatgccctt tttctttctt tttaagtctt ttatcagttt ggcttttgca aaaatatctg    74460
atagaatact tgtttctgct gtattagttg tgtgagacta gtgacaggag ctgtgggaat    74520
tgaatgccaa atgttcttag gcattttttgg gaatttgagg gtgtgatctt caagttcatc    74580 tagggggaatt ttcatatgct ggcaaaatac ttttctcatt agcttgattc tttccagaat   74640
tatttgctgc atattagaag tttaggaacc tttttttcact taaatgtgat ctaacatatg   74700
aaatggtgat gatttaggaa ctactgtact tacattaaca gcttttactt aaaaatgatt   74760
ttcccccagt agatgaccct actcacatct gggaaataat ttcaagtctt ctccagcatt   74820
caggaataag ctttcattct gtgtatcaat tactgagaat gattttggtg actcacatca   74880
catttgagaa gtaaacctgt agatttcttg tgtgtgtcag tgaataacca gctgacattt   74940
gcttgaagtg gattacattc tctgctctag aatgattgct ttcccgcctt cctcacatat   75000
agactgagca actatggttt ctagtcatag gtccggcact agacttgact tctgagcaac   75060
tttggcattg gagtaaaatg tattaattta agaaagcta aaaattcatt caagtaaaca    75120
tacagttcta atactttta aagtttaaaa tatagatagg tttaagtgat aaaaaaatat    75180
gagtagacac cataatcctc atttctgtat ctgttcacaa ggggttgata tttatgagtt   75240
ctattctcca tacccattct gtgttctctt aatcctcagt cagcacctca ggtggttggg   75300
attcagttct tggtagtttg acttatactc tcttttctag gggattgagc cctgggtagt   75360
cctccttata tgagattgca atttgtcttc caataacttt tactacaaga tatggggtat   75420
taaaggatgc cattgggaaa ccaagataat attagtatca ggaaaactaa ccacgtcaga   75480
cctgccccat tgggtatcaa gtatactatt tttccatagt aataaagagc tcaccccagc   75540
caattctctt ttattttgga cctgtttatt caatggcatt aagatgccca aatgtctggg   75600
tagctatctc atctccaatt cagcagaacc attgtcatat gccctagtgg aagcattcct   75660
tcattggaca cttaggcccc agtacttta ttcagatcta ctacctgatt tcatttctca    75720 aatgatttttt atggagcttt aatttatagg aaagttgtta gttgattaac agtaaaacag   75780
tttctgagct ggtataaaac atattgtgac acgcttttct cttggaattg caagagaaag   75840
gaagactgtt gtttgcttga aattttttcta taatttgacc ttgcaaatgt ctgcttccag   75900
agtgcctcca ctgagcgcct ccgatgagtc taggaagagc tgtaccgttg ggatggccac    75960
gatgattctg accctgctct cgtcagcttg gttcccattg gatctctcag cccatcaaga   76020
```

```
tgctttgatt ttggccggaa acttgcttgc aggtactgag ttgaagcagg gactccgagg   76080
cttggatttt gatttcctta gggggaatgg gggtggtgag catatgaggg gaaaatacta   76140
aaaggtcatc gccagtgatg gcttgtccct ttagtcaaat ttcagatgtt acctatatgc   76200
acaaacacat gcagctgttc tgtgctgagt attttaaagt ggcctcttcc cagtatggcc   76260
cctcagttaa ctacaaataa actcattttg aatttcatct tagtgggcac catatgccag   76320
tactgcctca ggcactggga tggtaagaaa gtataaagta tggactccat tctcaagttg   76380
gttttagatt agaggggata catgtaaaca gaagtgcagt ggtcacacag agtggccatg   76440
atcactctcc ttgggcagat ttatgggctg ataggaaagg gcacaacagg gagagggtgc   76500
agcaccgtgg cgatgataat ggaggatgtg gccagcaagg aagacgcagt ccattgaaat   76560
tgattttggg agaagttgcc aatctccatg aaagaatcgg gacctgtgtt ctttgcttta   76620
ggaggctata ggagagtttc gtgaaaggga ctaaagatg agtattttaa taagatcatt    76680
cagccaactt gaatgtgggc tggaggagaa ggtagagaga ctcaggagat taatgttgac   76740
gctaaggcaa gagatgggga gtctaaacca agataatggc tttgggattg tagggaagac   76800
actgatcgta agagaatgaa ggaggcagaa ttgccaggcc tgggtcacca actgaacttc   76860
ggttgtgaag accaagaaac ctgggatgac ttcacatcct gggcaggtgt gtggtagtga   76920
cagtcatgga aattgggaac acagatttgt ggggaagaca tcagtttgag tttgagtttg   76980
agtttgagtt tggcttatcc gttgaatatc agacacagat gtctggccaa ctctcaacat   77040
agattagggt cttaaatgac ttcagttccc caagcaattt gtccttccca tactgttggg   77100
ctagagaggt aatatctatg cccatatcac agccagtgct cctaaatctc tgagaagttc   77160
atgggcctct gaagaagaag ccaacccagc agccaccaag caagaggagg tctggccagc   77220
cctgggggac cgggccttgg tgcccatggt ggagcagctc ttctcccacc tgctgaaggt   77280
gatcaacatt tgtgcacatg tcctggacga cgtggctcct ggaccggcaa taaaggtaat   77340
gtcccactta ggtgctggat taatatagcc ttaatgactg tgggtttcca gactatcttt   77400
atttagtaat ctgtctcttc tttattctct tttactttaa atgaacaaaa ttgctcagat   77460
tgtgacacta aatttaacat caaaatgtga ccatgtggcc gggtgcagtg gctcatgcct   77520
gttattccag tactttggga gactgaggtg ggcagatcac ttgaggccaa gagttcaaga   77580
ccagcctggc caacatcaca aaaccccatc tctactaaaa atacaaaaaa attagttggg   77640
cgtggtggca catgcctgta gtcccagcta cttgggaggc tgaggcaaga gaattgcttg   77700
aacctgagag gtggagtttg cagtgaacct tgattgtgcc actgcattcc agcctggatg   77760
acagagtcag gctctgtctc aaaagaaaaa aaaatgtga ccatgtgttt tacagctcct   77820
ttggtatcat cagtcactgt tacccctaag agggaaatac atagctttag ttttaggttt   77880
ccatcattag ccaagaaagc tcagaattgg ttttcctggc taaagtacct cattgctgtc   77940
tccttaaatc ttagttaatg gctactgtcc tggctagcat agttatagag catgtccatg   78000
gttgtagaat gttctgccaa tctcagggac agttttgctt ttctgtgaag caataaaatc   78060
aacttcaaaa caaatgttaa ctgtttgcac aatggattta agatagacca gttcacatac   78120
tttttttttt ttttgagacg gagtttcact cttgttgcct aggctggagt gcaatggtgc   78180
gatctcaggt cactgcaact tctgcctcct gggttcaaac gattctcctg cctcagtctc   78240
tagagtagct gggattacag gcatgcacca ccacacccag ctaattttt tgtatttta    78300 gtagagacgg ggtttcacca tgttggtcag gctggtctca aactcctgac ctaaagtgac   78360
```

-continued

```
ctacccgcct tggcctccca aagcgttgag attacgggca tgagccacca cgcccagcct    78420
aagatagacc agttcactta ctgttatatc tgtttactct ctctttgctg tgtcttctac    78480
ctttaaaaat ctccccacta acttcccatt ctcctttagc tgccatcagt cacttccctt    78540
ctctgcaaac atctctggag agtctcagcc tcagcccaca gagcttccca ctgctctgag    78600
gtggaccttg tttgtaagac ttcttggccc tcttggcctg gaccctgtct actacttcag    78660
ccatccttcc ttaaccatcg ctagtggttt tgttgccac cctccatagc agcgtttccc    78720
ttccagatca tgtctttaca tctctgggca ctgctctggt cctgcctgcc tttccctctc    78780
tgtaccctgc aggccgctgc cgccatcttg agtgtcctct tcacttggct ttcagagggc    78840
ccacagagtt tcccactgct ctgaggtggg ccttgtttgc aatacttctt ggccctcttg    78900
gattactgca ctagccttt gttttggaaa cagcattttt aaaaaattt aattttattt    78960 ttttgagata ggatgtcact ctgttcccca ggctggagtg cagtgtcatg atcgtagctc    79020
gctgtggcct tgatctccca ggctcaagtg atccttctgc ctcagcctcc tcagtagttg    79080
ggagtacagg tgtgcaccac catgcccagc tagtttttg atttttttc ttttttcttt    79140 tttttgaga cagagtctca cactgtcgcc cggactggca caatcttggc tcactgcaac    79200
aacctccacc tcccaggttc aggtgattct cctgcctcag cctcctgagt agttgggatt    79260
acaggcgcct gccaccacaa cttttgtat ttttaggaga cgggggttt caccatgttg    79320 gccagtctgg tctcgaactc ctgatctcgt gattcgccta cctcagcctc ccaaagtgct    79380
gggattacag gcatgagcca ctgctcccag ccaggaaaca gcattcttga gataattcat    79440
ataattcacc catttaaagt atataattca ttctctttag tatgcccaca gagttgtgca    79500
gccatcacca gaatcagttt tagaacccac aaaggaactc tgtacccttc acccaaaacc    79560
ttccatgccc ccagctgcag gcagccactg acctaccttc tgtctctgtg actctgcatc    79620
ttctggacat tactgtggat gggctcatac agtcagtgag cttgtgactg gtgccttcta    79680
ccaagcaggg ttttcagtgc agtagccttt cttctttt tttttttta aattgagacg    79740 gagcttctgc ctcccaggtt caagcgattc tcctgcctca gcctcccaag tagctgggac    79800
tacaggccca tgccaccatg cctggctaat tttttttt ttttgtatt tttagtagag    79860 atggggtttc accatgttag ccaggatggt cttgatctcc tgacctcatg atccgcccac    79920
cttggcctgc caaaatgctg gaattacagg cgtgaaccac cacacctggc taacctctca    79980
tgtactgtct gcggttcttc cctgatgcct tccagtccat gcacccgatt gtagcccctc    80040
atcctattat ggtttaaggt gactgtctta gtcaccatgg gttgccataa caaaatacca    80100
tagcctgggt ggcttcaaca acagaattta cttctcacag ttctagaggt taggaagttc    80160
aagatctagg actttcacct tgccctcaca tggtgagggg gtgagggagc tctctggtgc    80220
ctcttatatg tggacgctaa tctcattcat gagggtctgc cctcatgccc cagtcacctc    80280
tcaaaggccc cacctcctaa taccatcacc ctggtaatta agtttcagtg tatgaatttg    80340
ggggactata gacattgaaa ccataacaag cacttttcta aaagatcagg gagtgagtaa    80400
gtaccagagc taggacctca attccacctc tcggtcatct tgccttcact ctgctccatg    80460
atggctgcct cctagagtga tgggagcctc catgttttat attctctcat gtgttgtgta    80520
ttggagagag ttcagacttt atgaatacat ctggatttgt tgacttctag ctttgctggt    80580
aaccagctgt gaccttgagt aaattacttc atctctgagc ctgttcctc ttttgaaaa    80640 gggagtttaa aatgctgttt tgggttgggc atggtggctc atgcctgtaa ttccagcact    80700
ttgggaggct gagatgggag gatcacttga gcttggagtt cgagaccagc ctgtgcatca    80760
```

```
tagtgtgaga tcctgtctcc tcaagaaatt aaaaaattaa ctgggtgagg taacgtgtgc   80820
ctgtgggccc atctactctg gaggctgagg tgggaggatt acttgagcct gggaggttga   80880
ggctgcagtg aactatgatt gcgccccatc ccgggtggcg agtgagaccc tatctcaaaa   80940
aaaagaaaaa aaaatgctgc tttgcacccc tttctcatgt catggtgtca tggctaacat   81000
cgaatgccct ggttgtttgc tgttggaagg cgtgggccta ggggctccct gaggactcct   81060
tccatcttca attcgttctc tgtgtacctg ttagcaagtt gtgggccagt ccctgccatg   81120
taccattgtg tgggtaaaag taaataaaat gtgtacagtg tctgaactgt acatataggg   81180
gtccaagaac aaaatgaatg acatgggtta gctctttcta ataaatggta aaccaaata    81240 ttctaatttt cagttttgtt atacttccat cacatgtttt tgttttttgt ttttgttttt   81300 ctatttagg cagccttgcc ttctctaaca aaccccccc ctctaagtcc catccgacga     81360 aagggaagg agaaagaacc aggagagcaa gcatctgtac cgttgagtcc caagaaaggc    81420
agtgaggcca gtgcaggtag gaaacagtgt ggggaaggga gggacaggag tgcagcatct   81480
gtcatgtagc aacataggat ttaagtaact tggtgtttta gagaaatata atacacatca   81540
gtaaagtgag agaaggtttc tccaggtgcg gttcaagata ttagaaacta atgactaata   81600
tacacagacc acctttggt ctgaagcatc tctaagtgcc acctgctgac acgcagcccc    81660
tgcagcctcc aggcttccag ccccagcacg gagcctcact ctcctgtgct tccctggttg   81720
cgggtgaggg ctggagaggc ctcctgattt tcagtaaggg aagtggtgta gatgcttagg   81780
aatagatata gtgagtgaaa aaattgattc tgatatgtca aaatttctga ttggaaatgg   81840
aatatttaca tttggaagaa ctaaaggaga gagaaagtgg ggataaagtc atctgagttg   81900
gaggagctta aaccatgcac aagtttggag gaccttttt taacccatga aaaggtcaga    81960
acagaagggg ctaggattta gttgtgactg cagttttcg aattcccatc catactgctc    82020
ttggagggca gtggcagggg caggagagga gcctggcaaa gcatgaagtg actgctgctg   82080
cctctgctat ctgggtcgcc tggctgcctg tctgtacagt ctccctccaa acccattctc   82140
tcgctgtctc ttggtgccca ggggccagtg atggttctcc cgtttgtttt gtgtatatag   82200
catttatatc aagctatt atttatttag agacagagtc ttgctctgtc gcccaggctg     82260
gagtgtagtg gtgcaatctc ggctcattgc aagctccgcc tcccaggttc aagcaattct   82320
cttgcctcag cctcccaagt agctgggact acaggtgtgc accactacac ctggctaatt   82380
ttttgtattt tttttagtag agacagggtt tcaccatgtt ggccaggatg gtcttgatct   82440
cctgaccttg tgatccacca acctcagcct ctcaaagtgc tggaattaca ggcatgagcc   82500
actgcacctg gcctatttat ttatttttaa ttgacaaaat tgtatatgtc tgtagtatac   82560
aacatgatgt ttgaaatatg tatacattgg ccaggcgcag tggctcannn nnnnnnnnn    82620 nnnnnnnnnn nnnnnnnnnn nnnnnnnnnn nnnnnnnnnn nnnnnnnnnn nnnnnnnnnn   82680
nnnnnnnnnn nnnnnnnnnn nnnnnnnnnn nnnnnnnnnn nnnnnnnnnn nnnnnnnnnn   82740
nnnnnnnnnn nnnnnnnnnn nnnnnnnnnn nnnnnnnnnn nnnnnnnnnn nnnnnnnnnn   82800
nnnnnnnnnn nnnnnnnnnn nnnnnnnnnn nnnnnnnnnn nnnnnnnnnn nnnnnnnnnn   82860
nnnnnnnnnn nnnnnnnnnn nnnnnnnnnn nnnnnnnnnn nnnnnnnnnn nnnnnnnnnn   82920
nnnnnnnnnn nnnnnnnnnn nnnnnnnnnn nnnnnnnnnn nnnnnnnnnn nnnnnnnnnn   82980
nnnnnnnnnn nnnnnnnnnn nnnnnnnnnn nnnnnnnnnn nnnnnnnnnn nnnnnnnnnn   83040
nnnnnnnnnn nnnnnnnnnn nnnnnnnnnn nnnnnnnnnn nnnnnnnnnn nnnnnnnnnn   83100
```

| | |
|---|---|
| nnnnnnnnnn nnnnnnnnnn nnnnnnnnnn nnnnnnnnnn nnnnnnnnnn nnnnnnnnnn | 83160 |
| nnnnnnnnnn nnnnnnnnnn nnnnnnnnnn nnnnnnnnnn nnnnnnnnnn nnnnnnnnnn | 83220 |
| nnnnnnnnnn nnnnnnnnnn nnnnnnnnnn nnnnnnnnnn nnnnnnnnnn nnnnnnnnnn | 83280 |
| nnnnnnnnnn nnnnnnnnnn nnnnnnnnnn nnnngcactt taatatttag tatcggttta | 83340 |
| atgataatgt ttgtgccctt actgtcttta aaacatttt acgtcatccc tgtttgatta | 83400 |
| cttggtgtgc tcatgaagtt gttggccact agggaatctt aggctcagag aggttctgga | 83460 |
| attggtcagt ggtccttgaa ttagccgctc ctatgattct ctaactgatt tctcaaaaag | 83520 |
| caaacaagca accacagcaa aacagctgtg cacaccactc ttcttatttt gttattgttt | 83580 |
| tagtacttag gccgtactta tgtttgttag tcagtttctc attacttcta gttaatcaaa | 83640 |
| agatcagagg caatatttga gtattttcat actagaatgc tttaaaaaaa gtcattattg | 83700 |
| gccgggcgcg gtggctcaag cctgtaatcc cagcactttg ggaggccgag acgggtggat | 83760 |
| cacgaggtca ggagatcgag accatcctgg cgaacacggt gaaacccgt ctctactaaa | 83820 |
| aaatacaaaa aactagccgg gcgagatggc gggcgcctgt agtcccagtt acttgggagg | 83880 |
| ctgaggcagg agaatggcgt aaacccggga ggcggagctt gcagtgagct gagatccggc | 83940 |
| cactgcactc cagcccgggc gacagagcga gactccatct caaaaaaaaa aaaaaaaaaa | 84000 |
| aaaaagtcat tatttccagt aatctcttta aaacttggca agttattttg atctaaaagt | 84060 |
| ttatcttttg tgtgcacatt tttaaagctt ctagacaatc tgatacctca ggtcctgtta | 84120 |
| caacaagtaa atcctcatca ctggggagtt tctatcatct tccttcatac ctcaaactgc | 84180 |
| atgatgtcct gaaagctacg cacgctaact acaaggtatg ggcctctgca tcttttgaaa | 84240 |
| atatatatgc ccacatactt atgtctaatg gatcgttgat gttttctta tgatttgtag | 84300 |
| gacgtataag ccctttgaga tatgagttac aattcgtgtt ttcaagtttg tctttcagct | 84360 |
| ttgtttatga tagcatctgt catacaggtg ttttggattt tcatattgtt tgtactcaca | 84420 |
| gctaagattg attacgtgag agagctagga tgtgcagcca ggttattggg ggaagtggcc | 84480 |
| tcggtggagt ctggagggat ctgtgtacag gcttccttcc ctcctgtgag gctcacacaa | 84540 |
| aaatacagca acctgctggt cctgcaggtc ccctctgcct aacatgagcc acaattccag | 84600 |
| actcacagaa gcaggcgttc agcataaacc acgtgtttca aatagtctgg gcgttgtgag | 84660 |
| ccacttgtta tcagctaggg aaagtttta tgtcagtgta aggaactgtt gaccagataa | 84720 |
| ccccaagagc cggcctttct gtctagggat gttttagttt tctagttcat ttttttttt | 84780 |
| ttaactttaa aattttctat tcatctgcaa tttgttagat atgaagtacg catctaattt | 84840 |
| aattttggtt ttggttgtcc ccaatgctgt ttacagaaga attttttgc actaattggc | 84900 |
| ttaagttact tacattctca tagttctcta gtttcatttg ccattttgtt atatcaatct | 84960 |
| atctgtctgc tcatctatta gaagcatcct tttttcctg ttgtagacag tctcgctctg | 85020 |
| tccccaggct ggagtgcagt ggtgcaacca tgcctcactg cagtctcaac ctccagggct | 85080 |
| caagtgatcc tcccacctca gctcctgggt acctgggact acaggcatgt gccaccatag | 85140 |
| ccagctgctt tttacatttt ttgtagagac agggtctccc taagttgcct gggctggtct | 85200 |
| caagttcctg gcttaagtaa tccttcctcc ttggcctccc aaagtgctgg gattacaggc | 85260 |
| gtgagcaact gcacctggct agaagtatac ttcttagtta ttatagcttc atggtattta | 85320 |
| tgatgggatc agttcctg ttcttagaa ttttctggat attcttcttt gttgattttg | 85380 |
| ggatgtgaac aatagaatca acttctactt gtaggttgat ttagggagaa cttataccct | 85440 |
| agatgttaag ttaccctgtc cagaatgtgg gatgctttcc tatttgttca aaacgttta | 85500 |

```
aattacctca gaagcacatg aaatttaaag gattttaaaa aaaactttaa agattatttc   85560
acatagctct tgcacatttc ttggtaaatg aatcctcagg tgttcttctg tttttgttac   85620
taatagatac ttctcatggt tgttttttt tttttttcc tgaaaatcat ttgtcaaact    85680
tatgtggctt cttttctgaa ggatgtttga aattttgga agatataaaa gtcttcatat   85740
tttacaaggt ttggagtctc tttaagctgc gtggttctca cgtcagctcc caaagcagaa   85800
gacggcatgt cgaaaaatgc catagagaag ctacttcttt tccacctgtt ttcagctcat   85860
atcatcttga atttcggggc accttctat gctcctagtg cttgctgtct gtttattatt   85920
ttccttcctg aataccctga actccagcat gttctgctgt aattctggcc tccctggcgt   85980
cttggactcc tgtttccttt gctctgtcat ccccacggtc agctcctgct gcgcagcttc   86040
tcagctgaac tgtttggagt ggctggcggg tcttgctgga tctttgagta ttgcctctgg   86100
tttccttggt tccttctgct gagttgctca gcgtctccac tccccatttc tcgtgtggcc   86160
cttcctgctc tcctctgatt cctttgtct tccctggttt cttgctttgg ttttcagtct    86220
ccgcagaact tttgccactc ttctgaaaac ccggaggctt tttcatctta attctcattt   86280
catgacctct tttccttat ttgagaggta gaccttccca tggtgagctt ctctttccag    86340
aattccatgt cttcttttcc ctcccactta cctgttgtcc aggagaggtc agattgctgt   86400
gcgcattgga gaagaaccct ttcttccctg ggctcttcat ttcacatgac atcaccacat   86460
cacctcatcc cttggaccct cagtggtggc actgctggat ttttctttcc tttggctggc   86520 cttgggggcac acccaggttg accctagctt agtcatggta tttagatcaa ctcacatttt   86580
cagtttctgt gtctgtctct tgcctgcttc tgactttgcc cagagaaagc ttttcacaa    86640 gggttcttag atttacgagc accttctttc ctgaggcagt gttttgcca atatttattt     86700 tcctagtcag tctcgcctta ccttcttgt tatacatgat gtctttggtc ctgacccatt    86760
ctctgagtct gtaaaataga attgctgtat aatttaatta catgaaatcc tttagaatct   86820
taatacatct tacaccaggt gtaacatttt atgatatcca aattgaacaa ccctgtgtga   86880
atttgacagt gatttctccc agggatccta atgtataagg aataggactt tgtattttct   86940
attttttgat ataccacata ccagatactg atcatgatgg acatttaacc cttttttct   87000 cattaggaaa gaaagttagg aattacatct ttcagtagtg ccagtgtgac ctgaaagatg   87060
cctttgaaag agtagttttt gtatagctat ctgaaaggaa tttctttcca agatatttc   87120 ccagtgctga caacaaacac gcagacacgc cctacaaggt caatgtacag cgccgcacag   87180
tggaggcgtc tgccgcagcc gttaatgttt gtatctttgg ttgtacttta cgagatcttg   87240
acggggccag taaccgtgtg ttctctcctt caccttctca aggtcaccttg ggatcttcag  87300 aacagcacgg aaaatttgg agggtttctt cgctcagcct tggacgttct ctctcagatt    87360
ctagagctgg ccacactgca ggacattggg aaggtctgtg tcttgttttg acgtgcgtcc   87420
tctgggctga gttcatctag gatggagtcc ggttctccag ggtgcctccg ggagactcct   87480
ccctgcgcca cggacttgca tcacaggacc cgagtctgac tctgccttag ccatgaagtt   87540 tgggggggaag gttctatttg tattctgttt ttgtctgtta tcacgtatta gcttagaccc   87600
agtttagttt agaaaattgg tgggtttaaa aatgtgttta tagagtcctt tatttcttaa   87660
tttgaccttt tcaagtggaa aggggcaaaa cagacagatg agggggcggg gcgggaggtg   87720
tgacttgctc ttttgtgcct gaggaagtaa cagagctggg gttgacagtt atattctctg   87780
gttttatgtc caggaatttc ccctgccgca cccctagttg atagcgaaaa tgttcaaaac   87840
```

```
tatgagaaag ttagaatgct gtggtaaaca ctctattatg tacacacaac ccagcttctg    87900
cagttgtttg cgtttggcta cgtttccttt ctatgtatat agccatctct ccatttacca    87960
gtacatctta ctttataatg catttttaaaa ggagtgacag atgcctccct ccaccaaatg   88020
tgtgtcttca cgtgaaatac agtatgtctg atgcacttca tttgttctta tgtcttttgaa  88080 tcttttatc tggacatgga cacaaggtta cctagtttta atcgttacat atgttagtgc    88140
ttcttctctg ttattcctca tgttttttccc atgtatctat ttagtgtgcg cagttgtcat  88200 tttttaatggc tatctagtgt cctgctgtgt tgatactcca tcgttccctt agagtaaaac  88260
ttgttgagac ttcagtaatg tcacctgctc agtgagactt tcctggccat cctttcaaaa   88320
cttgcttctc tctgtactct ctttttcctgt tcatttttct ctttgaccca tagcatcgtc   88380
taacagtcaa ccttaaaata aataaataaa taaagacttc agagaaatgt ccaaatacat    88440
ggagtcagtt tgggaatgag aaatgaggat tataatccgg gatgcacggc atgtccggct    88500
gccagtgcct ctggtgaagg aaggggaagg ggaagctgtt attgtcagaa agggagagaa   88560
tcacataggc tccctggaag cagagttcgt tggctccaga ggctgaaagc cagagttgtc    88620
gtcattcact ggtggaattg taggcaccgg gcaggtgttc agttgagagt attttaactg    88680
aattgctgca gtcctccaga atggctagtg ataaatctgg tcatagaaac atgtattcac    88740
gtggaacatg caagccatgc acagcagata tgtaaaggat gtacgggaag ggtttcttct    88800
agggttgttg gaaagtcttt ggaaacagct ctaacctggg gcataaagc atgaacccca     88860 tctcccttttg tgctttccta gtccaatttt gtctgggtct gacaaagtga tttgatccct   88920
gtatctgcaa ctttcacaaa acatactatt tatttatttt acttccttgt cttttcagtg    88980
cctatagcag tgcctggaag attgtggaat ttagtgaaca tttgttgaat gaatagatgt    89040
tcttgttaaa aatgagtttt agtgtctcat ttatcttaca tccacactgt ggtggagcca   89100
tattagccca tttcacgcca taactggaag ctgaaagatg tgacattctt ggggccagat    89160
aagtcagtgg cagagcctga gttaagtctc atagattttc tttttttcttt ttcgtttttg   89220 gtggctagct ttggttttat tttttatttat ttatttattt ttattatact ttaagttctg   89280
ggttacatgt gcagaacgtg cagttttgtt atataggtat acatgtgcca tgatggtttg    89340
ctgcacccat caacctgtca cctacattag gtatttctcc taatgttatc ccttccctag    89400
tcccctcacc ccgatgggcc ccggtatgtg atgttcccct ccctgtgtcc atgtgctctc    89460
attgttcaac tcccacttgt gagtgacaac atgcagtgtt tggttttctg atcttgtgat    89520
agtttgctga gaatgatggt ttctggcttc atccatatcc ctgcaaagga cattaactca   89580
tcctttttta tggctgtata gtattccatg gtgtatatgt gccacatttc ttaatccagt    89640
ctatcatcga tggacatttg ggttggttcc aagtctttgc tgttgggact agtgccacaa   89700
taaacatacg tgtgcatttg tctttattgt agaatgatat aatcctttgg gtatatgccc    89760
agtaatggga ttgctgggtc aaatggtatt tctagttcta gatctttgag gaattgccac    89820
actatcttcc acaatggttg aactaattta cactcccacc aacagtgtaa aagtgttcct    89880 attttttccac aacctctcca gcatctgttg tttcattaat ttttaatgat cgccattcta  89940
gctggtgtga gatggtatct cattgtgatt tgatttgca tttctgtaat gaacagtgac    90000
gatgagcatt tattcatatg tctgttgact gcataagtgt cttcttttga gaagtgtctg   90060
ttcatatcct ttgtccattt ttagatgggg ttgtttgctt ttttttttttt tttgtaaatt  90120 tgtttaagtt ctttgtagat tctggatatt agccctttgt cagatggtta gattgcaaaa   90180
attttctccc attctgtaag ttgcctgttt actctgatga tagtttcttt tgctgtgcag   90240
```

```
aagctcttta gtttaattag atcccatttg tcaattttgg cttttgttgc cattgctttt   90300
ggtgttttag acattaagtc tttgcccatg cctatggcct gaatgttatt gcccaggttt   90360
tcttctagga tttttatagt cctaggtctt atgtttaagt ctttgatcca tcttgagttg   90420
atttttgtat aaggtgtaag gaaggggtcc agtttcagtt ttcagcatgt ggctagccag   90480
ttttcccaac actatttatt aaatagggaa tcttttcccc attgcttatg tgtgtcagat   90540
ttgtcaaaga tcagatgctg gtagatgtgt ggtgttattt ctgaagcctc tgttctgttc   90600
cattggtcta tatatctgtt ttggtaccat gctgttttgg ttactgtagc cttgtagtat   90660
agtttgaagt caggtagcgt gatgcctcca gctttgttct tcttgcccag gattgtcttg   90720
gctatgcagg ctcttttttg gttccatatg aagtttaaag tagttttttc caattctgtg   90780
aagaaagtca gtggtagctt gatggggata gcattgaatc tataaattac tttgggtagt   90840
aaggccattt tcacaatatt ggttcttcct atccatgaac atggaatgtt tttccatttg   90900
tttgtgtcct ctcttatttc cttgagcagt ggtttgtagt tctccttgaa gaggtccttc   90960
acatctctta taagttgtat tcccaggtat tttattctct tagtagcaat tgtgaatggg   91020
agttcactca tgatttggca caatctcagc ccactgcaac ctttgcctcc tgggttcaag   91080
gaattctcct gcctcagcct ccagagcagc tgggattaca ggcacctgcc accatacctg   91140
gctaattttt tgtattttta gtggaaacgg ggttttacca cattggccgg gctagtctcg   91200
aactcctgac ctcgtgatcc acccacctca gcctcccaga gtgctgggat tacaggcttc   91260
agcaactgcg cccagccaga ttttcagatc tccctctctt tgccctaaac cactgtgctt   91320
aataagaatt ctttagtggc cagcagtctc catgtgtaac acattgtagc aaaatggaaa   91380
atattcatg ttttaaattt gagtgtgaga tatactgaaa taaaaatcat ctaaatgaga   91440
ttctttaaat aataagattt tcttttttgt atgtgggttt tttttaaca ttattattat   91500
gactgtcgta tatagaaatg gctgttttca actacagtca gtgaatgtat caaatgctgc   91560
cttatccaaa taataaaagt aaatgattaa caagtcacaa tttagtgaag attgatgtta   91620
gttgatcttt atattcctga attagccaca tggttgtgtg tgtgtatata tgtttagagg   91680
tacatataga taataagctc atctctgaaa attttttcat ttggcataag aataactgga   91740
taattaagca tcttattctc tggcctgtgt ctttacagtt aaaggtagat ttactcacct   91800
ctccttttt gttttttctca gttcatcttt tttgctattt catgacggag gcccatttta   91860
cctttctcgt atatccttt gtttgtactt tggaagcctc acctgcttaa ttgttgagtt   91920
tttaatctgt ggtcttttag aggaggatgt gtagggtaga agctttcaca ggttcttctt   91980
tgcacttggc ccttggctgt tttgaggaat ctccctcact aactcacagc atagcaaggt   92040
ttgagatctc ttctgccaca cagcagttcc caggcagctg gaaagatatg cagatgctca   92100
gattgtcagg ccagccttga gatatacaaa ctactgagcc ttatctgtga ccttgcttag   92160
gtgaaggcat cagagcccct gcaccgacat gtgtaggcct ctggatgtgt gcggggctgg   92220
gtgttgggt ctgagcacaa gtgtagctgg agaggtgagc ttgttgtggt gacgggtatg   92280
agcaagtttt cttcagactt ctgtgagttt acctcgttcc aggatttaaa ggcacagaga   92340
ccttagaatt aaaatagaat catttttcttt ttctaaatag caacactagg aataaaaaat   92400
aataattcca cattctttac aggtaatgtt ttgttttttct tgtcttctaa tccttattta   92460
ttctgtactt attttttatac gtatttgaaa tgtattatgt gttggagttt tcttttttgca   92520
ttatattata cacggttttt catgtaactc cttactgttc catttatat gttttgtctg   92580
```

-continued

```
gtttatttta agactttatc agcaaatcgg gaaaccgtct ctacaaaaac aaaaacaaaa    92640
gcaaaaatag ttggccacag tggcatgcgt ctgtggtccc agctactcgg ggctgaggtg    92700
ggaggattgc ctgagcccgg gaggttgagg ctgcagacaa ccatggtcgt gtcactgcac    92760
tccagcgtgg gtgacagact ttatactgtc tgtttgggt gatttggtaa tgatatgccc     92820
tgatgtagtt ttttatatc ttgtgtttct tgtgcctggg tttattgagc ttgggtctgt     92880
ggcttcatag tatttttaaa gtttggaaaa tttagggca ttatttcccc aaagatttt     92940
ttctgccctg ttccctcct tttttcctc tcttaaaggg gctgtgattt cctgaatgat     93000
tgcttagtgt tgtcccatag cttattgatg ctcttttcag tgttttttgt gttttctgtt    93060
ttctatagtt tctattattg tatttgcaag ttctctaact tttcttctac gatgtctaat    93120
gtgttgttta tctgttaatc tattgttaat cctgtccagt atttttttt ttttttgaa     93180
acagtctcac tctgttgccc atgctggagt ttagtggtac aatctcggct cactgcaacc    93240
tccacctccc aggctcaagc aattgttctg cctcagcctc ccaagtagct gggactacag    93300
gcacgtgcca ccacacctag ctaatttttg tatttttatt agagatgggg tttccccatg    93360
ttggccagac tggccttgaa ctctgatctc aggtgattca tccacctcgg cctcccaaag    93420
tgctgggatt ataggcatga gctaccttga ctggcccctg ttcagtgtat atcactaatt    93480
gtgttttat ctatataagt ttgatttagg tcttttaaaa atttctccct gtgtctctac     93540
ttagctttgt gaacacagtt gtaataactg ttttaatatc tttctctgct agttctaaga    93600
tcttctaata acttcctggt tctcggtgtt tttgattggt ctattgatgc tccttgttgt    93660
ggattgtgct ttcctgcctc tttgcatcgc tgccaatttt tggttggatg cccaacattg    93720
tgaatttac tttgctggat gctagacatt tttgtgttca cagagatctt cttgagtttt     93780
gctctgaggt tagttgagtt acatgtgat ggtttactct tttgggtctt gctttataat     93840
gagtactcta cctaatgaac cagaaagttc gggttttcca gtctgcctgc tgagaacggt    93900
gactgtttct agccctgtgt gagtgcccga gcgccgctcc ctctgatcct ttctgatgct    93960
tccctctgtg gcctcaggga gtttcctcac acacacagtt ctgctgagta ctcgagggt     94020
ccttccccga tctccaaggc tctctctgtc ttgttctctc ttctctggtg ctctgtccta    94080
taaactgtgg ctatcttggt ctccttagat tctcagcacc tcttcaattc agagggttgc    94140
ctgtccctcc tccttgtgcc acagcctagg aactctctta aagaagtgag gtggggcagc    94200
tgtgggctc actttgtctc tcgtctccca gggatcactg tccttcatgg ctgatgtcca     94260
atgtcttaag gactctggat tttgtctgtt ttgttttttg gttggctttg tttgtttcaa    94320
acaggagggt aaacccagtt cctcactctc attgtgctca gtactggaag tctcgctctg    94380
ttatattgga tattagtatt tgtagcagag ccctggttcc ctggtacttg gggagctctt    94440
gaaaggccag aaacagcatg ctttctcacc tttcccaggg cttccgtttc tggtgcacac    94500
aaagcattcc atacacattt gttaaagttc tttgttagac aaatagtgat tcacaggctc    94560
tatttgtaat tttttcagta agcatgtatt agatatctgc tgggagctag tagaaacaaa    94620
aagtgacatg tgacaaattc aattctgaca agaacaacct taaacattta gaatataatt    94680
tgagtaaatc agaattttaa aaatgtgtgg cccttgaata tttgaaacca acaagaatct    94740
attgcttatt agtagaggat attttgttga acaagtggag agagaggcat tttcagtcta    94800
actggtgttg gcttttagca gctgttggaa accggttcat gattagccag gcagtggtga    94860
aacaggctgt gcattctgaa tgcctagatt ggtggcactc ttcgagttag catcttcttc    94920
tttcttcttt tttttgagat ggactttcac tcttgttgcc caggtaacaa ctccagtgca    94980
```

```
atggtgccat ctcggctcac tgcaacctct gcctcccggg ttcaagcgat tctcctgcct   95040
cagcctccca agtagctggg attacaggtg tgcgccacca tgcctgacta attttgtgtt   95100
tttagtagag atggggtttc actatattgg tcagactggt cttgaactcc tgacctcaag   95160
tgatccacct gcctcgacct cccaaaatgc tgggattaca ggtgtgaacc actgctccca   95220
gccccttctt gattcttgta aaggacattg ggtgctgtac accttgttat agatgttgat   95280
aaaaattctt gtgagaatag taacgttaag gtagttgttt ggtcattttt gtctatcagt   95340
ataagataat tctaggactg atttgtggta aatcacacat tgctgtatca tagttgtgtt   95400
cactgaacat attcaggggc tttacagatg cagggctctt agctgctttg cgcacttctg   95460
aattcctgcc ctgagaacag gactggatac ctagtagacg ataggtattt gataacagtt   95520
taatgaatta atgagtgaat gaacagatac gtaggtatgt gaagaatgg ttgtaatgta    95580 tgtaacttgg atttcaagac ttactctgtt caaataagaa atggaaaact ttcctctgat   95640
tttgctctac tatttacact ctttaaatgg aagttatctt gtacctttga tttctgtcta   95700
ggattcgtac aataatgggt catctctgag tcacttacgg tctcactgtt ctttccacag   95760
tgtgttgagg agatcctagg atacctgaaa tcctgcttta gtcgagaacc aatgatggca   95820
actgtttgtg ttcaacaagt aagagcttca ttcttttcct attctgttaa gactttcagg   95880
tatgacgaca aaatgctgct actccttaag cagcaggtgc tggtggcgta atcagctggg   95940
aggattgtgg ggtccagcat agcacttttc ggctcattcc atgattgagc caagaggccg   96000
accttcccgt cattcccag gaggacgagg tctgtcattg tggagagcaa aggacatcag    96060
aagctcccct gcatcctcac tcgttaactt ccagtccctc ggggttttg tttagcgtgc    96120 tcaatctcat ttagaatcgc aaggaaaccc aaaactctta tttaaggtac aaacagcact   96180
tcatacaata tctcgccgag gtaataatag tgattcacag gaagaatttc acattgtgaa   96240
tctttgctaa tgtatccagt tatttacaga tggatttgat atttgtgtgg gagattctta   96300
aagtgttgtt catgccacgt tgtttgtgct tcaattttt cactatagtt gttgaagact    96360
ctctttggga caaacttggc ctcccagttt gacggcttat catccaaccc cagcaagtca   96420
caaggccgag cacagcgcct tggctcctcc agtgtgaggc caggcttgta ccactactgc   96480
ttcatggccc cgtacaccca cttcacccag gccctcgctg acgccagcct gaggaacatg   96540
gtgcaggcgg agcaggagca cgacacctcg gggtaacagt tgtggcaaga atgctgtcgt   96600
tggtggaagc acaaagagc aagcaggaaa tactttgtaa aagaataaaa acgaaaaatg    96660
ttagccaaca tcttctaata gtctgctgta ttcaaagaac tctaggaaat atggttgatg   96720
caaagatgat ttaaggcata gcccggcctt tcaagaagtg tgtggccagt gagtgagatg   96780
ggcttgggac ttacacatct cagaggtggg ggtagaggag gaggaacact gagtgggctg   96840
agaagcagcc agctttcatt gccaaagtgt gtcagcaaac cagaaggcag ttcataatgt   96900
ccccacccgt tcaaagcaca ggccctgtag agtggtgtgg catgtgttgg tggcacttt    96960 caggcctgta acaaggatga agaacagct tcattgcagc acagtagtgc tggtattcag     97020
aggtatatga aggtcatgga agcatcttgg atatgttacc ttgtgttttg tcaactttat   97080
gactagaaat ctcttttac ttaaatttat gtttgtgtct ttaatgcctg gaatacagga    97140
cttcttaaat tgccataagt atcaacaggt atttgagtta ctaatctgta tagtagcaat   97200
aatagaatcc cttgttttc cttttataaa tgtaatgatt aaatagctac aattgaaaca    97260
ctagagtcag gagtcaagga aaatacccat gttccaggct gtatgttagt gatgtactca   97320
```

```
ctgtgtattc cagtttcagg aataagtctg tttcaatgct ttctgtaacc atttggggta   97380
ttaataagca agtgagtgta tgcatgtttg ggttaatttc atatatgtgt cttagaaagg   97440
atatcattga tgtaaatatt ttcaaggctt atcctccaaa aaaatcctgt gatttcttct   97500
aaattactga tcttttaaat gaccttcacc tttctctcaa gtctcactta agactgggct   97560
gagtagtcag tttcctgtag cagtaaaaag ctcagacttg agtagccttc cacaggtgac   97620
gagacttgat ggctgtcagg cagctgtaaa ctgtaaatag agtgtcatta tctcgagagg   97680
gtgatgctgc cacactgagt ggcctttcaa gttgtttctc agtctgacat gttctgatcg   97740
tgtgaatgtg aaattggttt gaacaggagt atatctgagt gcagaggaga ttatttaaag   97800
atattctcat tgtctgcttc ccttctattc ccatttggca gatggtttga tgtcctccag   97860
aaagtgtcta cccagttgaa gacgaacctc acaagtgtca caaagaaccg tgcagataag   97920
gtaaatggtg ccgtttgtgg cgtgtgaact caggcgtgtc agtgctagag atgaaactgg   97980
agctgagact tcccaggtat tttgcttgaa gcttttggtt gaaggctcac ttacggattc   98040
tttctttctt tcttttgttt ttttatagaa tgctattcat aatcacattc gtttgtttga   98100
acctcttgtt ataaaagctt taaaacagta cacgacaaca acatctgtgc agttacagaa   98160
gcaggtttta gatttgctgg cgcagctggt tcagttacgg gttaattact gtcttctgga   98220
ttcagatcag gtttgtcgct tttaatcttt catccatcat acctgtacct aatttagtac   98280 aaattacccct gaaagacact gaaatctact ttaaagaaat gtgaactgtg tttccccacc   98340
ccccatcaat tgctgctgct tatgtttttc atgcacttag ctagtacaag gcccggggca   98400
tagccagcct cagcaagtcg gcatccttgc cccagctccc tggactcaag gctaacctgg   98460
ggttggctgt tagggatttc caaaggtttg tcccatccac tcgcctcccc tccaaaataa   98520
gtttgaattt aaattgtgag atttaattaa gatttattgt ttggggaaca ttttttgcaaa   98580 atctagagag ttagttttaaa tggattatca attatgacta taattgatca tctgcagttt   98640
caggctatct aacaggttag cttacctctt taaaaaggaa tggaatttag ccggacagta   98700
actgagaccc acgctcctgg agtccacgtg ggagccgcgt ggctctgcac aaacaagcat   98760
ttgcactctt cccctcttgg ctgcgttgcc ctcctcctgc agttgctgtg ggcactagat   98820
tctggctagt catgtcccct tcatgatgcac agtttcctca agattcgtgc cagttaaatc   98880
actgcctttt catagtcaaa atttaactgt catctttgac ccatgatctt gggctacttc   98940
cttatgtggg gtaggaatat ttttgagata gaaatattac acttctctgt ttccttctag   99000
acaaaaatct gttaattctg ttagtaccgt gactcatctg aaagggtctg tttccctagg   99060
agaactgagg gcacgtggtc aacactgatt tcccaccatg ggtattgagg tggggtctgc   99120
ttttttttgt tttgtctttt ttttttttgag acggagtctt gctctgtcgc ccaggctgga   99180
gtgcaatagt gccatctcag ctcactgcaa cctccacctc ccgggttcac gccattctcc   99240
tgcctcagcc tcccaagtag ctgggactac aggcacccac cacttcgcct ggcttatttt   99300
ttgtagagac cgggtttcac catgttagcc aggatggtct ctatctcctg acctcatgat   99360
ccacctgcct cggcctccca aagtgctagg attacaggcg tgagccaccg tgcccggcct   99420
ggggtctgct tttaatgaaa gaggcatcta ggggtgggct ttgccttggc ttgatgcttt   99480
gaacctttgt tcacaaaacc tatctgaaga aaatctgtct cagtgggcca ttgctctcct   99540
caggaaacat gcattgggaa cttcttttcg tttcctttga cactaggagg ctgcctgggg   99600
agaagccctg gtctatggct atgggcaagc aggggctgag aggagcaggc tctcagtggg   99660
gcagggtacc ccaagggaag ccagaaccct gatttgttcc attctagtga gaacaaagac   99720
```

```
tacagtctac cttttcttca gaatttccca gttctaactg ggcatggtgg cacacctctg    99780
tagtcctagt tactgaggag gctgaggcgg gaggatcact tgagtccagg agtttgagtc    99840
cagcctgcac aacatggcaa ggcctgtctc taaaataata gtaataatca taatctctag    99900
ttctagccgg gcacagtggc tcatgcctgt aatcccagca ctttgagagg ccgaggcagg    99960
taaatcattt gagctcagga gtttgagaac agcctggcca acatgatgaa accccatctt   100020
tactaaaagt acaaaaatat tagctgggtg tggtggcagg tgcctgtaat cccagttact   100080
tgggaggctg aggcaggaga atcacttgaa cccgggagat ggaggttgca gtcagctgag   100140
attgtgccac tgtcctccag cctgggcgag acagagcgag actgtgtctc aaaataataa   100200
taacaacctg tggttctgac tcgtcatggg taggaactga ttttctcatg tggtagttac   100260
agactatggt ctccttgggc ctgtctttag tagggaaaaa aggcaactcc ccactctaac   100320
ataaaatggg tggacttgaa tgttttatca aattctttct ttagtcgttc tactggagct   100380 tttcttcaa tgtagaatat tctgttgctt tattatattt gtctgcaatc tccatgtgat   100440
atttccatgt tgagggagga cagccttgag gctcccccgt gctgcctgcg gccctgcagg   100500
catgtggaat tcatctttgg cctgtgcttt cttctgggtc ccggtgcccc tgcccgcgag   100560
gctcatgtcc agctgcccct tgtggtggt gtgaggtcat tcctgctgtg agcgctctgg   100620
tttcatgttt gttccgattg cctttcatca gccgatcccc tttctcccag ttcttaagat   100680
tcaatacagt gacagtttta tgaacaagaa tagaactaga acagacaagc cattgaactc   100740
tatgctgata atgatttacc gagcacctgc tgtatgtttg cattccgcgc agaggctctg   100800
agaaagccgg gccatgtgct ccatgcttta tcggtggaag ctcctcatca ggttgggaaa   100860
gctgacagct gcgtagaata ccagtgtgac acaaagctgg ctcccgtgcg gcccttgcgt   100920
gttgcctctc agatggtggg aggaagaagg tcgactcctt tggggatctt actaccaaac   100980
cagtttcagg gaatctgcta ccctgtctgc cattaatggg aacagatgag tccccaaggt   101040
gtacttctgg gtattgtctg atgtcgcttg gaatttatta cttgtttttc caatgaggtt   101100
tcacctcagt gtgtagtaaa gttgttgagg ggattcctgg aggtgttcta cagttatcta   101160
ggctgatttc agaatagagt tatgcttata gtccaattta tcagctgtca agaaattcat   101220
ttaaaatttg tgcagataag caggaggaaa agaaacctgg ttttacgtt ttaatcctat    101280 tattgatgta aaattttact ttccttcccg taggtgttta ttggctttgt attgaaacag   101340
ttcgaataca ttgaagtggg ccagttcagg taatagcatt tgttatttt agagtttttt    101400 ctccttcttg tgtacttaca tgtaatttag gttattaaga tgaatgttta aactactgtt   101460
aggcattttt gctgttttct ttaaatggaa atctgattaa catgctgtgc attttttgctt  101520 ctcttaaaaa ttaatgtata tctcaagact tgtttggaag tagttacata tctgaaaatt   101580
ccatatgttg tcagttttca ttgcacattt caaagcattt aattatgttg acagatggcg   101640
gaatgaaatc ttgtggtgga gcactagttt ttaaatcttc ttagagaaag cagttttat    101700 ataaggttgt ctttagtaat tattatgcac ttgtattctc tgcagctttt ttttgctaga   101760
tgttgaggtt ttaatacttc ttgctagtcc attacaggtt tataatgatt gaaagttaaa   101820
attctttagt acctgaaata cttaataaat actgtagtta ggaaaactta gtgcagaagg   101880
aaagtgttcc cagattccct ggggtctgga agcatagcgt tgttctaat cacgtgacac    101940 ctccactgtg ttttgggca agttacttt tctcttttga gtttcaattt ctacaagagc    102000
aaaggggcag agagagctag ggagattgta gctgctgtgc ctctgtgccg tcaggtgcct   102060
```

```
tctacctgct ccctctgaac ctttacacct gtcccggctc tgcacaaggg cacagatggg   102120
atgcactgtg gcagggatgg gcttagagta gatcactgac acctgttagc ttcatgtgcc   102180
ctcatgaatt attttatgtt gcttatattg atatgtatct taattttaaa agaaaggtct   102240
aaatggatgt ttttgtttct agggaatcag aggcaatcat tccaaacatc ttttttcttct  102300 tggtattact gtcttatgaa cgctatcatt caaaacagat cattggaatt cctaaaatca   102360
ttcagctctg tgatggcatc atggccagtg aaggaaggc tgtgacacac ggtaatggga    102420
cacatctttc actgtcgtct tcagtgtcac gatgtgcttg gcagtgttcg ttttctttt    102480 tttgttgttg ttgttttttt tttttgaga cggagtctcg ctgtgtctcc caggctggag    102540
tgcagtggcg tgatctcggc tcactgcaag ctccgcctcc cgggttcacg ccattctccc   102600
gcctcagcct cccaagtagc tgagactaca ggcgcccgcc accacgcccg ctagttttt    102660 tgtattttta gtagagacgg ggtttcacca tgttagccag gatagtctcg atctcctgac   102720
ctcgtgatcc acccgcctcg gcctcccaaa gtgctgggat tacaggcttg agccaccgcg   102780
cccggccggc agtgttcgtt ttcatacacc cactttcaac tttgtcagtg gcggccgtgt   102840
gcgtctcagg ctctgcatat gtgtctgtgt gtctgtgtat gtgaatgtac tggttagaga   102900
cgtttcaaaa gagaagagag catattcttt actctcagca atttgtaatc ttctcaggga   102960
aaaaaagttc aagaaacagt aagatagcct aaggtacaga tagattctga atataaagtt   103020
cctgttcatt cacacgaaac actaaaagtt cttcacctga tcttagccca aaggccgaga   103080
agcgatgaaa cactaaaaat tcttcagtcg aacttgctgt gaattaaatt ttgatctctc   103140
atccaggtgg tattggagat acagtttgac ttgggttcag ggctttctgt tttgcctgat   103200
gattattttg ctggagctta aataaagaca gggctccagg agatggccag ctgtgcaagc   103260
ccccagcctg tggaaggagc tagcctggtt ttatgaatga gctgtaaatc tttctttgag   103320 cttttgaac tggtcttcca gcattgccct attgacccct ccctgactcc tttgctggaa    103380
tccgtaggct tttgaacttt gacagggaca catcctaaga cccttgcaaa ccccctagatg  103440 tgagaatggc actactacat agagtctttt ccactcagcg tgtgtgcaga agaacatcaa   103500
ccatgctgtg tggcgaggca gggccttggc tgacctctca gtcaaggcct tagctttaca   103560
gagctaagcc agttagtctt tgccatggct tcacaatggc ttcaggttca cactgccaaa   103620
gtatagatta ttaaaggcat aggtgtttgg tttcctgcac ttggagggtc tttggacaga   103680
aaatcagtag gcagccaaag ccagtacttt gcgctgggaa gcttggtcgt ctgtgagagg   103740
gtcagagagg atacccatgt gtgcgcacca ccgaagggtc agtgagtctc agggctctgc   103800
gtgcatgtct cagggctgga gagagtgtgt cactgagagg tcagagtgtt tgtgcgtgtg   103860
tgtcaaagag ggttgcagtg tgcccttcac tgaggggtca gagggtgcct cacgtgtgtg   103920
tatgtgtgtg tgtcactggg tcagtgagtg ttcttgtgtg tgcatgtcac tgagaggtca   103980
gagggtgcct ttgtgtgtgt gtgctcatgt gtgtgtgcgt gtcactgagg ggtcagtgtt   104040
cctgtgtgca catgacattg agggtcagag tgtgcctctg tgtgcgtgtg ctcgtgtgtg   104100
catgcgtgac acctccactg tgttttgggg caagttactt tttctctttc tcttttactt   104160
ggtcatctgt gagagggtca gagaggatat ggtcctgtgt gcgcatgaca ctggggcaga   104220
gtgtgcctct gtgtgtgtgt gtgctcctgt gtgtgtacgt gtcactgagg ggtcagtgtt   104280
cctgtgtgcg cgtgacactg aggggcagag tgtgcctctg tgtgtgtgtg tgtgctcctg   104340
tgtgtgtacg tgtcactgag gggtcagtgt tcctgtgtgc gcgtgacact gaggggcaga   104400
gtgtacccgt gtgccaatga aaggcatttc ttattttttt ttatatgtgg tcacagtaga   104460
```

```
ccaattaatt tattttgact cctgttttag accaaaataa gacctggggg aaagtccctt    104520
atctatctaa tgagagagtg agtttactta aaaaagcata ataatccagt ggctttgact    104580
aaatgtatta cgtggaagtt tttattgtct tttcagatga atcaaataga ttattctcga    104640
gaccaggaat ggtgctgttt tggttatttg ggaagtttta tcattttcaa attgacctt     104700 gaatttgagt caccttttt cagaagtggt gttaaattac aggagcccta ggtttttttt    104760 cctttttag aagccatcac aaaatgatcg gtgttcagag gaaaagcttt gatcttccac    104820
aatggtataa tgattgataa ccttaattca tctcttacca taaaccaagt atgtgtaagg    104880
gttttcttta tttcttgata tcattttgta gatgttgaga gcagttttcc aaatgtaatt    104940
tccatgaaat gcctgatgag ggtacccttt tgtccccaca gccataccgg ctctgcagcc    105000
catagtccat gaccttttg tattaagagg aacaaataaa gctgatgcag gaaaagagct    105060
tgaaacccaa aagaagtgg tggtatcaat gttactgaga ctcatccagt accatcaggt    105120
aagaggaatg tgtgttggaa ctgtcgtgga tactttattg acccgtacag atggaaggaa    105180
gtgccatgtg gtaacactca ctgttaaccg tgctactttg aactaggttt gagctttctg    105240
aggcctgggg agatgctggg gcagcggcgg gtgcagggg aggtgggggc ggggacagg     105300 cgtggtggca ggaggtatca ttggtgttta tccttccttt tttttttttt tttttgagat    105360
ggagtctcac tccgttgccc aggctggagt gcggtggcat gatcttggct cactgtaagc    105420
tccatctccc gggtttaagc gattctcctg cctccacctc ccgagtagct gggattacag    105480
acatgcacca ccatgcccag ctaattttt tttttttttt tttgtatttt tagtagagat    105540
ggggtttcac catgatggcc aagctggttt caaactcctg acctcaagtg atccgcctgc    105600
ctcggcctcc caaagtgctg ggattacagg cgtgagccac cgcgcccggc ctggtgttta    105660
tctttaaagt gggtacagcc acaggggttc acctgactcc tggtctgaga gtcacaagat    105720
cgttcaagat agtgaggccc tcttttccaa aacaaggacc aaaaatcagt tgacagtgtt    105780
ggtcaagatg gtagaaacct aaaatgatag aaatctcaac tctgaaataa aactttatt    105840 tgcatattta tttaccacta ttttgacata gggctaaggt cttttctttt gagctagttt    105900
ctggttttgt tttcttaagg tggcataaga attcaaagac attttgagga aaactgagtg    105960
tagaaatctc tctttttaa tgacttctct tttctttcag cttgtactgt tgtgtagccc    106020
tcgcttattt tgtcaattct ttttagctgt ttgtctttga atcttttatga agccatagct    106080 tttctcataa gaagcagcac tttctttgtt cattcatatt ttaattaact cctgtagtat    106140
ttaaatactt aatgcctaat taaatcacat aattgcaatg caaaagtaca tgtatcataa    106200
agaggtctga aaatgagcaa ctggcaagca ggtggctgca ggcagagctg gctgggtggg    106260
tgggtgtcct ggagaagagc tcatcagctg catgttcagt gagctctgga tatctctgtg    106320
taaaaatgat cactaataaa cttgtgctca actgtgcaca cttccggaaa ggagatgctg    106380
ttcagtagat tgcctctgca gagaacacag aattgaaggg aatttccaca aaggcggtga    106440
gccgcctgca gaatagttta gtcaaggctg tgtttgaatt ttgccaaaga ttaatataca    106500 tttattttt tcatgctgtg ccttttctct gattgtgaaa tattataaat tctatccaaa    106560
taacaatgat ggcaagtcct cctgagcaaa gtgtgcagct tgcatgtgtc ctagaggaac    106620
tcgtgtttcg ttctgattcc cctgcatttc tcatgtcata gagtggggat tgcatccgtg    106680 tcccctgtc ctcgtgggga tcacatctgt ttggatccta gagtcttcaa gctgagctgg    106740
gacaagtgta acagatggac acatgggggt ggaaaggcgc ctctaggcag cagactctct    106800
```

```
aattgtgcac actcttatag gtgttggaga tgttcattct cgtcctgcag cagtgccaca   106860
aggagaatga agacaagtgg aagcgactgt ctcgacagat agctgacatc atcctcccaa   106920
tgttagccaa acagcaggtt tgtccccgca gccttggctc gttgttgcat agtgatggta   106980
gcttaaggtc cttgtgaaag gtgggtggct ggaatcagct cttccttcaa tcctaatctg   107040
tgctttgata gcagttctcc atgctagtca tggggcaact gacttcattt cttctcataa   107100
tgccatctca ggttggtatt gcccacctcc tttacggggg gaactcatga ctcagagagg   107160
ttatggaggc gatcaggcag cacacagctt tagagtgctg gggtgagggc gggccaagtc   107220
tgactctaaa gcccgaaccc ttacctccta tactgcctcc tgcattctgg tcaacgcagt   107280
gttttatttg gtggttacat ttttgttttt gttaccttac tacttgtaat ttagcagttt   107340
tcctttcctt tcctttccct tccttttctt tttccttctt tctttccttt ctgacagggt   107400
ctcgctctgt cactcaggct agagtgcagt cgtgtaatct cactgcaact tccgcctccc   107460
aggttcaagc aattctccca cctcagtctc ccgagtagca aggaccacag gtgtgcacca   107520
ctacacctgg ctagtttttt gtattttag tagaggcgag gtcttgctgt gttgcccagg   107580
ctggttttag actcctgggt gcaagtgatc caccaacctt ggcctcccaa agtgctggca   107640
ttacaggtgt gagccacctc acctggccta ttcatcacta atcagaattt ctatgatcaa   107700
atgacatgaa ttgttgtttc cacaaatgca gtggaaggaa atggcctggc agtaccaatt   107760
ttggaagcaa caggccccca gtcaggcaca ggacactgtg cccccagtgt agcagcatct   107820
ctatctcaca gagaaggtgg tgcgtcctcc tcaaggcagc tccgccagaa aatctcatga   107880
gcggcctggc acggcttgag gttgcctttt aaatggactc agcaaataca tgtttgttca   107940
tcttgattat acacaataaa caactactct gtatagtaca agtagtccgt ggttttttgc   108000
atttgattta aaccagagac atgtgatatt gatggttact gccttcatga ctgcaccccc   108060
atcctgattt cataatagaa tgttatcctg agaccagtta gacaatggaa cagggatctt   108120
ggcttctggt gagactgaca gcagttttag cgtggtcagg gtctccctgc ccacagatgg   108180
tgttagaatg gtgctctgga agctttattc cattatcttc tgtgcataat ctgagtagag   108240
tggagattga aggcctgaat gcatagtaaa tatctgactt aatttctgcc gcaatggaaa   108300
ttgtgcgata aaacatttat gaaatgcgta gcacagcccc ggccaggtag ctcagcacag   108360
gagcctgttg cattcagaag tagtgctaga tactatcctg ttactggcag tacatacatc   108420
agtgatcaga gcagattcaa gaaagacccc ctgccttctt ggagtgaagg ttttgttggg   108480
atggggtgag gggacagaca atagaaaaac cagtgagtga agtctctacc atggcagctg   108540
atcagggacg ctgtacagaa gaatcccgga gggaagagag ttaggtggtt tcggcggcgg   108600
agtggcattg ttcagttggt gatgagaaac gttgtggtga tctggtgaca tttgagtgaa   108660
tttgcagaaa ggaaagatac aagcctagga gatacctggg ggaggagcat tccaagaaga   108720
gcaaacagct gcaaaggccc tgggggaac gtgctgttag ggtaaaagca atggggtgg   108780
aggagtgggg cagctatgcg gagggaaggg agcgaggcct ggtggggtga ggccagcatg   108840
gaggagcctg agaggnnnnn nnnnnnnnn nnnnnctccc aaagtgctgg gattacaggt   108900
gtgagccact gcaccccggc ctgttttttt tagagacgga gtcttgctct gtcgcccagg   108960
ctggagtata gtggtgcgat ctcggctcac tgcagcctcc gcctccggga ttcaagcgat   109020
tctcctgcct cagcctcctg agtagctggg actacaggcg tgtgccactg tgcctggcta   109080
attttttgta gagacggagt ttcaccgtgt tagccaggat ggtctcaatc tcctgacctt   109140
gtgatccgcc cgtctcagcc tcccaaagtt tacaggtgga ttacaggtgg ctcccacacc   109200
```

```
gagccaagag tttgcatttt taacaaattc ccaggtgata ctaatgctgc ttttctggga 109260
ccacactttg agactcagtg atagaaagat ttattggtag gatagtaaaa taggagtaat 109320 ttttttttc cacaaaattg gcaattgggg gaaatttaat cttcctttt tctttagcta 109380 tgacttattt attctgttta ttttaggcat ctgtgagcac tgttcaactg tggatatcag 109440
gaattctggc cattttgagg gttctgattt cccagtcaac tgaagatatt gttctttctc 109500
gtattcagga gctctctttc tctccatatt taatctcctg tccagtaatt aataggctaa 109560
gagatgggga cagtaattca gcactagaag aacacagtga agggaaacaa ataaagaatt 109620
tgccagaaga aacattttca aggtatgctt tctatctgag cctgtaacta acccatgcct 109680
tttgggaagt cacttggtat ttcatgatca gttaagtctg gaataacacc tggtctcgct 109740
tcagttctga gctgggtaaa gaagtctgta tcagtgtaat tttctaatcc atcctggctt 109800
atctgtggct cctgtttcat acctctcttg aggttctgtc atgttctgtc tcttgtcctc 109860
agcagagatg ctacagcagt ggcttgctca ggtaggacag ggcagtgggg tggctgtcct 109920
gggggcaggc agtaggcgtg cattgccttc agggaagtta aacccaaga gaagccacag 109980 aaagtgaatc ttatattctc accatgtgcc ggcagtttta cacgctgtca gtaataaaat 110040
acttctccct gcaaggcaga ctgcctccag taaatacctg tagtatcaaa tcctgtcttc 110100
cctcataaat tgttgggaag ctccctcagg acagtggtca ggcactcgta aatgcttgct 110160
gcctagatgg gtccctctcc acctctgctg gattctgagc attcactgag ttagagctgc 110220
tgctgcaaat gtgctacttc tgcctgagtg gctgtgactt catgcagccg tcatttggtt 110280
tgtcgtcagt gaagatgccc tgtgttgtcg atggagataa gcccagtaag cctgctgggc 110340 accttttgt ttgcgggttc agcaggcagc ccgtggcttt ccctctgttg cattgaagca 110400
gctggctaaa actgatggta cattaaattc ctatgacaga tgatcagctt gtatttgtgt 110460
aatggtgtac agtttacaaa gcttaaaaaa atactacctg ccatttcatc ctcagcgagg 110520
aaggtgatac acagagagga aaagtgactg tatccaaggc gatggtgtta cgcgtttcac 110580
tttaacggtt taatgtactt tacttctatt tttactttat atttaccaca tatattttca 110640
tatatacttg gcataagtgc tttatagtag tcacctaatt cactgtcacc cttttgttt 110700 cttggaaggt ttctattaca actggtgggt attcttttag aagacattgt tacaaaacag 110760
ctgaaggtgg aaatgagtga gcagcaacat actttctatt gccaagaact aggcactctg 110820
ctaatgtgtc tgatccacat cttcaagtct ggtaggtaaa tcacattagt cttcctcgag 110880
tatctcaatt ccccattctg cactgtacgc tcttagagtg taggagctat gctgcccggt 110940
agaaactctg tcttgcccag agtgccagtt gaaaatgttt gttgctataa gagtcagcct 111000
gatccatatg acccagcagt tctactcttg ggtatgtacc caaaagaatg gaacgcaggg 111060
tggtgaaaag atgtttgcat gccagcgttc atagcagcgt tattcacagc agctaaaatg 111120
tggaagcaac tgaagtgtcc attgatggac gaatggataa gcaaaatctg gtgtatactt 111180
agagtggaat attattgaac cttaatattc aataaccta aaggacattc tgacacgtgc 111240
tacaacatgg gtgaccccta aggacattat gctaaatgaa ataagccagt cacaaaagga 111300
caaatactat gtgattcctc ttatatgagg gacctggagt acttaattca tagatacgga 111360
cagtagagtg gtggttgcca ggggctgcgg gggaggggag ttgttttac aagatgaaaa 111420 gagttattct agaaacgaat ggtggggatg gttgtataac agtgtgaatg tatttaatgc 111480
tactgaactc tacagttaaa aatagttaag atgagccagg tgtaatggct catgcctgta 111540
```

```
atccaagcac tttgagaggc caaggcagga ggactgcttg agccaaggag tttgagacca  111600
gcctcagcaa catggcaaga ccccatctgt acaaacagac tagccaggga tagtggtgtg  111660
cctgtggtcc caactactca ggacactgag gctggtggac cgcttgagct caggaggtca  111720
aggctctagt gaagtatgtt catgcctctg cactccagcc tcgactacag agtaagaccc  111780
tgcctcaaaa aaacaaagca agacaagacc caaaaatggt taagacgggc caatcacact  111840
ggcttactcc tgtaatccca acacttcggg gggtcaaggt ggaaggatca cttgaagcca  111900
ggagcttgaa accagcctga gcaacatagt gagacccccta tctctacaaa gaaaataaaa  111960
aactagctag gtatggtagg cacatgcctg tagtcccagc tacttgggag gccgaggcgg  112020
gatgatcgct tgagcttgag accagcctgg aaaacatagg aagagactcc atctccacaa  112080
aaataaaaaa aataaaaaaa ttatccaggg gtagtgacgt gagcctgagc ccaggaggtc  112140
aagctgtagt gagccacgat cgtgccactg cactccaacc tgggcgagag atcgagacca  112200
tgtctctaaa gaaagaaaat tacaaggaca gtgaacccaa gaaagtcagt tgtgcagcaa  112260
gcatagaaag caaccagtcc aaattaggac agtgtgtttt ccaagaagaa cgatcatttg  112320
tcatgagaat gctttgcttt aaataaatga gtaaataggt agaagactag ttctagggga  112380
taggcacgtc tttcttctct caacaagaaa aagaaaggc aattctaatc tctaggaaaa  112440
gcaaatagca ttaagtcatg gtccaaatat gaggcaaacc aaaatatggc ttgattttc  112500
agcagttgat ctgttggaag cccttgatat taaaaaggtt ctcctttaag cagtttaggg  112560
gtcatgatca aagacccata gaaagagatg ccatccttt aggatccttg gctctcttgg  112620
gaactgtatt cacgtagtca taatgtaagt attgcttgag cttcattttt tggaatcaat  112680
atgtgactga acactgaag acttactgac ttaattatgg tttcagaaca gaatgaaaat  112740
gtcttcagtt ctgatgaata taaaaggaaa actaaccaag ttaatttggc aagtagatgg  112800
tagagatggg gtgggaatgg aagggggcact aaaatcctta cctagcattg ttggagttac  112860
atgattacat catctgaagt tgacagacca aaatatagag gcttcaaagg tatccagata  112920
gagctaaaca tgtaactcag attgttagga ggtagtataa atgagccaaa tctcctcttt  112980
attaccgtag agttaatggg taatgtctaa agttgtctga agtctgtaaa tcatgacaaa  113040
ttatgatgtg gtgattgtat tcaacagtct ttcagttgca gggataaaac cccaatttaa  113100
actagagtaa gagaaagaat ttgttggttt gagctcctgg aaagtgcagg caagggtagt  113160
tggtaggact gcatctagtg ttataattct atggtctgca ttgtatattt atgcatatca  113220
gctctgcttt cttctcttaa tttgtatact tttaaaattt tattttaaag atagggtctc  113280
actttgtcgg ctacgctgaa gtgcagtggt gtgaagtgca gtgcgaggct cgctctagcc  113340
tcgaactcct gggctctaga gttcttcctg cctcagcctt ctaaggagct gagacaatag  113400
gcattcacca ccatggctgg ataggtttta aaattctttt gtagaaatgg aggccttgtt  113460
atgttgccca ggctggtctt taactcctag cttcaggcga tcctcctgcc tctgcttccc  113520
aaaatgctga ggttataggt gtgagccacc gcgcccagtc tcatctctgc ttcctgtctt  113580
agcccctcaa gtaggcatgt gattggcctt gcataagtca tatgggtgac cataaccgc  113640
tgaatgctct ggtccacctg gccaaatgtg gagactggac agcattccat tgacgaggag  113700
gtggggcttg tctccgggag taagggagag gagcgcatgc agtaactgat ggtctgctgc  113760
acgggatagc ggcgcatcag ttagaatttt gaaggtaact accagaactg aaaacagaaa  113820
agataacaag tagttgcctt aaaaagggat ggggcaggg gcttttgtga tcagaaactc  113880
cttctcttta ttggattttt gtacacattt tgcggacata cccttagagt aaagataatt  113940
```

```
agcattttca gccttggtcc atttgaggag tggcccgcct ccctgctagc aggctctggg   114000
tctgctaggt tcagttgagc atcctggctc ttgcctgcat ggaacttaca gtcagtgcgt   114060
cagtatcaca agtcttaata tttcctatga aggaaaacaa tagtgcagtg acagacaaaa   114120
tgggtgggcg ggcagaggca ggatttccga gggggagaag tagctagctt tttgcagaga   114180
aatgttccgg cacccgagag agcagctgag agtgcaggca ggcaggaggc gagtggggcc   114240
tggccgcaca gcgtcacaga gtcccagaga aaggggcctc ttcatggcca ctgcattcag   114300
ctgctgtcac cctccacaca agccatggcc aaaatttaat tttgataatg gactctagtt   114360
tttgagcctt acttgctatt attgaaagaa ttttcttgtt tcttttaaa gatcttcaga   114420 ttatgcttca ctgaccactg taataagttt aaagttgaga aaatatgcct tgttaatgaa   114480
tgataggtca attttagtat attggtcatt ttaatatttt gccaccagtt ggtttgaatc   114540
tgatgccagg aggagacagc ctcatttctt ttttttttt tgagacggag tctcgctctg   114600
ccgcccaggc tggagtgcag gggccggatc tcagctcact gcaagctccg cctcccgggt   114660
tcacgccgtt ctcctgcctc agccgcccga gtagatggga ctgcaggtgc ccaccatctc   114720
gcccggctag ttttttgtat ttttcagta gagacggggt ttcaccgtgt tcgccaggat   114780
ggtctcgatc tcctgacctc gtgatgcgcc cgtctcggcc tcccaaagtg ctgggattac   114840
agacttgagc taccgcgccc ggccgagaca gcctcatttc taaggactag tcttgccttt   114900
gtgggataag ggtggtgtgt tctgtgtctt tctacatgtc cgagcgatct ctgcagctca   114960
aaggtgttca ctgtcttatt gtgctgattt cctcttcttc catctcaaaa ttgaggcaaa   115020
atactttcac tattgaagtg ttgtccagta gaacttccag cagagacggg atgtctgcac   115080
tgtctaattt agttgccttt agccacgtgt ggtgttccat acctgaaatg tggctggtct   115140
gattgggtag cttaatttat aattttattt aattttaatt aagtttgaac agctctgtgt   115200
ggatagtggc tcctgtatga aactgcaggt ctgttgagaa gcatctttac tggagagagt   115260
ggagggcttg gaggggcac atgggtttcc tgctgctatc tttgacctta tttaattggc   115320
ccaacatttg caagtaagtt gtctgtgcgt gtatatataa atgtctgttt ctgtcttctt   115380
gtttcgtttg actgcattta tttgaaagac actaggtggc agaattactg tatttggttg   115440
gtttaaagat aagagttgaa gtaatccgtc ttgtgttttt atatcggtaa ggtgtgttta   115500
gcatgtaaaa ttggtaattc gtattcacgt actgcttaaa caaaggctaa gaattccacc   115560
catacactga aaatggagac ctttgaattt gtccatttca ggcattactt cttaaacaat   115620
acctggttca ggaactagtc agaatggcac ccttgacttt tagtttcctg cttttccttt   115680
tgttggggga ggagggtatt tagctcaaag gtgtgtgcct atttcagatt ccatctagga   115740
gaagcagaat agccaagaca gatacctgtc ctcctgttta caacatttgg ggtaaccagc   115800
atccctctcc tttggtccaa gatagacggg tttagaaaca gatgatggta ccagaggccc   115860
cgggggtgga agcatcagct ttgtttgttg tccatgtggc tggattagag ctgtctggct   115920
ttgtagcctc aacacggccg tccagctttg ctcagtatga ttttcaagga cacatcttgt   115980
gcccttccct gcctgccatc cagaccatac ccagtcaggg tggcaggaac tgctgcccct   116040
tcctccctga gtcctggtcg tgggtggtgg agaggtacca tgaccctcac ggaggcctgc   116100
tcacccttcc tctgcggcag aggcgatggc tgcacgacag ctctttccct gtcctttcca   116160
aagcgtccat ggttccactt gatggggcaa agcaggaata ctggaagaga aagtggtcct   116220
ttctatagta ataaagttga cattgattca agttcaccct tggggaaagg acagggccac   116280
```

```
taacaattat aatgctggaa gcagtggaat tttctcatgg gtatatagta ggtttaattt 116340
taattatccc agttaattct tagaacagct ctgtgaagta tttccccctt tctgcttgag 116400
ttctaaaaga tcctatgcca aaaccaagaa tgaaaaccca agcattcttt cttgctcatc 116460
gatctttctc tcatcgggcc acttcttggg ttgttagtgg tgaatgtagc cgctggcaat 116520
tgcagaatac ccaccatggg ccccagtcac tgtgtggcgt ggattagagg tggttctctc 116580
catgtcatag ccgaacaagc ccagcccaga gaggtttctg ccctaggagc tcttgatggt 116640
ggaattggga tgcgatccca catcctgcct gtgttttgaa agcagcattc ttcatttcca 116700
gttcctgctt ccgttgttcc ttttagtatt tctttgttta actcacgaaa tcaggacttg 116760
gggagctgct gcgtgcagct gtagctgttt ctctgggtgc agcctgcatc caccttcctg 116820
cccccctcct tactgccatc gtggtctctg ggcacttggt ccctttctct tcccccgagt 116880
ccctttggct ccctgtgcc acccttgtga tccacaggct ctgccttctt tctgtctgag 116940
actgctgctc atcactaccc gggaccttag aagggaggt tcctccgaga agcatcttct 117000
aatctcagcc acgttctcaa tgccgctgtt ggctttgtta aataatgta gctactgtaa 117060
caaataaacc aacatttcca tggcttcaca ccagagaagg ttgtttcttg gttttatgac 117120
aatgtgttga gggtgtttct ggttcacgga tggttttcct ccatgtggga attcgggac 117180
ccaggctcct ttccttcttt tggttctctt ctctgggcct ccacatcctc tgtgtctagt 117240
tggggacaag gagagggaag gtagagaaga aggctctgtg gccttggaca agtgacatgc 117300
atgcctttgc tggtgttctc tgctggtggt gggtcacagc cccacccgt acgagggac 117360
tgggagacgt cgtcctgctg cctcccagca gcaagcagca ctgtggtctc tgatgtgttt 117420
tctatgagga taaaacagg cgattccagg atgagtaaag tcagggaaac ccttggaagg 117480
aggtgaccag gcaggtgtca ccatgggatt agtggtggct tcagaatgag ccgccaagag 117540
tgcagtgcct tctaaagctt ttgctattct gatatgccca caccatgccc agcaggtgtc 117600
tgccttgctc tccgcagaga gagtgatgaa tccttctcgt gaacctctgt cccgttcttc 117660
ctccctccac ctggaaggga ccctgggttc cttgaaacat cccggtggaa caggggacct 117720
tctgtcctgt ccctaagctc agcctcatcc tcctgccagc ttcccaaccc ctcttatgtc 117780
tgcttcctca cgccacatcc ttctggattc tctggaattg aattttgcct ttgatgctta 117840
tttaaaaata tccattgcag gccaggtatg gtggctcaca cctgtaatcc tgtgcacttt 117900
gggaagccaa ggcgggcaga ttgcttgaac ccaggagtct gagattagcc tgagcaacat 117960
ggtgaaatcc tgtttataga gaatacaaac agggcatggt ggcgcacacc tatactccca 118020
gctagacagg atcgactgag ccctggaggc cctggaggcc gaagctgcag tgggctgtga 118080
tcgtgccact gtattcccgt ctgggcaaca gagtgagacc ctgtctttaa aaaaaaaaa 118140
aaatccattg catacttcac cacagtgaaa cgtgtgtctt atctttcctt tccggcctgt 118200
agctgctctt ttgcacttat agccgcacta agtcaacctt aaattaaaag caaaccagca 118260
cttcctgtgc tcttctgctt ccttcatgag ggtccctccc tctgtgtacg ctccattctc 118320
attgccccgg tggtttgttt ccctcttggt tctcaagctg tggcagcctg cctcttatca 118380
tctttactga aaagtccttt gcagaggctg cctgtgttct ttctttctcg gtccctctca 118440
tcctgggccc cccagcttga tgctgtgggg ctgccctctc ctcactcagt agcttgcagg 118500
gtcttctctg tctagccact taattggttg tgttccccga gttgctgtcc gtggtctctc 118560
gtcactgttt tctctgtgtc tctgcctctc tcctcggcct tggtaggtct ctcccctttg 118620
tgaccctggc tgttgctctc gtggacaact ttctcttgct ggtccgcgta gtcctggcat 118680
```

```
ccagcttctc aacatgggac ttgtcctgcc agtacctcag acttacgctg aaaattgaac  118740
tagcaccact gtcactctcc aggacctctt cttgttaatt aggtcattag ggatgttcga  118800
aatcccagca tcattgtcca ttcctcctcc tgccagccca gggaccctga ccttacctcc  118860
tcctctccat ctaccgggag gtggctctca gagtccgtct catcttccac ccgaacttcc  118920
ctacagactc cccgctgccg ccccaggggc tgagcacttc ctccgtgcct cgtgcagcgc  118980
tgagcccttt acctgggttc tcctgttttgc tccttattgc aacccgtgtgg acagatactg  119040 ctcttaattc catcttaaac ctgaggaagc tgaggcccca ggtaaggtgc atccaaggtc  119100
actcaggtag taaactgtag agccacgatc cgaaccaggc agtctgattc ggagcctgtg  119160
ttgacactca gccacctaga acacagctca gattgtgggt ttctattacg tgttcaaaac  119220
cgccacatcc cgggtctgtc cctgcacgtg ccctgtggcc tggctgcatc ttcttgaagg  119280
cagcgcatgc gtcttcactc aaggggccca tgcaggaaag agggccccac agaaggacga  119340
ggccagtgca gaatgggctg gaggggacga tgctgactgt gaagcaagtg tagagaaatc  119400
ccaggaaacc tggaggaacc agagacaggg cattagaact catcgttgtg acctggtctg  119460
tattctctga gtgtgctgct gcttttagct cgcttcctta gtctcaggtt gtagtttaag  119520
gcattgtgga gccctaaaaa gcctctactc tgttttttgcc tgtttcggga ccctttcact  119580
tcggggatgt gttgaatttt ttgttttttgt ttttaatttt tttgagatag agtcttgctc  119640
cattgcctag gctggagtgc aatggcacaa tcttggccca ctgcagcccc tgcctcctgg  119700
gttcaagcga ttcttgtgcc tctgcctccc aagtacctgg gattacaggc gcccgccacc  119760
acgcctgacc aattttttata ttttttagtgg agacagagtt ttgccatgtt ggccaagctg  119820
gtctcgaact cctgacctca agtgatccac ccacctcggc ctcccaaagt gctgggatta  119880
taggcatgag ccaccatgcc cggcctgaaa tttaatcaga aataaaattt tgaccccaac  119940
aatgatgcta ggaggcccag atctggggga gagggcaacc ttggccagat gggcctgtct  120000
ctgtttccca agtcttgctg cctctcccgt ctgtgctttg cagcctgtgc atgtctctgt  120060
gcctctgatc ttgttcatcc agaggagagg atagaatcaa gtcatgattc ctggagccct  120120
gagaagaatg ctgtggagaa acttgcaggt agactctaac tgagtgtgtg gctgaggtgc  120180
cagcattgtg tgtggggagg ctgaccgctt ggcctgccca ggcccaggat gctccatggc  120240
cgggcacaga ggcaacttgg ctgtcaggtg tcaggagcct gcagagagca cacagcctgg  120300
accgcagggc gctgcccatg ttcttccagc acctgtcctg cttgctcacc tggcctctta  120360
cagcatttct gtccctcagt tcttagcaag cccaggagct gttcaggttg gcaggtgccg  120420
agtgctgttc ctgcctgtgt agctgtggct cagtcctgtg gggggccccg ctgtggcctg  120480
agtgcagtga ttcgaggtgc cgagtgttcc ctgactcgtt ctgcaggagc tgtgttcaga  120540 cttttcacagc tcttggcttg gagcttctgg agggcttggc attgccaacc agtgcagggg  120600
tggacagtgg gagaggagga atgctagctt tcttgaccag tccattaaat aaatgggata  120660
ttggccgggc acggtggctc acgcctgaat cccagcactt gggaggctg aggcgggtgg  120720 atcacgaagt caggagttcg agaccagcct ggccaacatg gggaaacccc ctctattcta  120780
aaaatacaaa aattagctgg gcgtggtggc agacacctgt aatcctagct actcgggaga  120840
ctgaggcagg agaataggtt gaaaccagaa ggcggaggtt gcagtgagcc aagatcatgc  120900
cactgtactc ccacctgggc aacaagagtg aaactccatc tcacaaaaaa aaagcagaa  120960 tgtctgtttc tgcttagaaa aatcagaatt ttctaaatgc caggtgcttt gaatatgtaa  121020
```

```
gtatgggaaa caactcagcc tgtttcattt ttatgtaaaa tctccacgta gccatgtggc  121080
actggaccga gatgaaagca aagacatttc tccttctgaa ctttgtttct aggaatgttc  121140
cggagaatca cagcagctgc cactagactg ttccgcagtg atggctgtgg cggcagtttc  121200
tacaccctgg acagcttgaa tttgcgggct cgttccatga tcaccaccca cccggccctg  121260
gtgctgctct ggtgtcagat cctgctgctt gtcaaccaca ccgactaccg ctggtgggca  121320
gaagtgcagc agaccccgaa gtaggttcat aatgcccaca gcccagggcg ctggcccagc  121380
actctgtcct gagactccca gtaacctgag attgggccac cgttacagca ttttcatttt  121440 ccatttttg tgagggcttg taaaatttct gctgcatatt aatattcctt tcatggacag  121500
catattgtag agacaaacat gcggtccagc caaaggcatt cagaatagca attgctttct  121560
aaatgtgatt ttctttggca agttctttga caccattcca tcttgtggat tatgcttgtc  121620
atgctgtgtg gctcctacta agttctagtc cttcagttgg ttccatagcc agacatgttg  121680
caatgtctta acttcattat aaattaaatg tggttctggt tattcttaga taatggagta  121740
acgatttagc aaatttcaaa acctcttgga aatattattt gaccattcaa aaagacttac  121800
taagtctctc attatgggtg ccctctttt tgtaaaaggt tttcaggctt aagctccatt  121860
tctaggtgct ccaacactct gttatttgta tacacgtgga aataaaagct gtgacatccc  121920
cgccctagct gaatcctcag cacagtgttt ctggaaggct caagatccca cactggggaa  121980
aagaagttcc agagagaaaa gagggcaggt gctgccgtgc ctctctgctc agtatggata  122040
ctgggccatg tgcggccagg gcttgcagta gggccagttc atggcactca gctggaaagt  122100
ccactgttgg cgggcattcg taaccatcca ctctgtgccg tatgtagtgg ggtgtggcat  122160
ccaagtattt gaaatcagcc gcgtgcagag aaatcagccg cggatgcagc agatcactct  122220
ttttctgaca ggcctgctca ctctgatgtt atatcagaaa gctctgaatc tgggaattgt  122280
gttccctgaa ttggaataac agaaatgctt agatgatcag tgtttaaaag aaataaacca  122340
aaggtaaatt tagtttggaa ttcagcaagc gtcttcattc agccctctga gggcaaacta  122400
cagcttttca taaatgtagg taaattctct gtttcttgac cccttctgac ccagttttcc  122460
tttataacct tctgtattgt tccattatcc tgaaataaca ttaatagatt aggctgggtg  122520
tggtggctca tgcctataat cccagcacct gggaggcca aggcgggagg atcacctgag  122580
gccaggactt cgagaccagc ccagcctggc aacatggtg aaaccctgtc tctactgaaa  122640
ataacaaaaa ttagccaagc gtggtgacag gtgcctgtag tcccagctac tcagaaggct  122700
gaggcaggag aattgcttga acccaggagg caaaggttgc agcgagctga gatcacgcca  122760
ctgcactcta ggctgggtga cagagtgaga ctccatctca aaaaaaaaaa aaaaattaa  122820 tggatcaatg gatttttaac ctaatagtta aattaaaaaa atatcattct ttaatggtaa  122880
tgtaaaggta aaattaagag aagataatat gtaacaagca ttttagtatg tgagtgtcca  122940
aggtctccct gtggtggaag gaaaaaataa atccccataa gtgtccacga tgctcataga  123000
gagcagagct gttccggttt aaaccgctgc tcttaggact gtgttttttcc agctatgggt  123060 ggtgggggat gagtaccttt ttatttccat gagatgagaa aaatgaatta ctagaagtat  123120
gaagcacaaa acacagctgc tctttttta tctggactca gcagctataa aattgctcta  123180
tccagttgca gaagttcctg ctgcttaccc ttgatgcccc ctcggttagt gtgcatctcc  123240
tttcaggctg gctcccagat gggagctggc tccaggcgac actgggtgct ctgctccagg  123300
aggtccttgt gtgggcccta ccccggccta gcccctctct tatggactct gtcaccatgg  123360
gtttgattca ctcaatctgt cttacctttt ggtgagctgt tagagtcctg cctatacttc  123420
```

```
agcacttgtg ggtgtgttgt ggtacacatg acatgttggt cacttcccag ctcatcttgt  123480
tctgagtcac cctggatttg gtacgttcat tcgccactag tagctggcgg tatatggcct  123540
gcgatttgga ggacttgtgc tgctacaaat tggggctgaa tttgagttga cactggccct  123600
tctttatgtc tactgctaat atttgaattg caaatgctgc ctcttctctt tcagaggctc  123660
attaccctat agctgtatta ttgcaaagta cataattaca gcttgagtgt aagtcacgct  123720
gggctggcag gacagccaac tgagaaaggg caagtttcct gttagttttc acattgacac  123780
ataatttaca atacagtaga atgtacttt gtatcaactg tagtcagtaa cagccccctc   123840
ccccaaccac ataagatata gagcagtgct gtcgcttcac atagttccct cttcctctgc  123900
catgtcccgc cctccccagg tctaaccacc aatccgtgct ctattcagcc cattgcagag  123960
ggtcatagaa atagaatcta caggctgggt gtggtggctc atgcctgtaa tcccagtgct  124020
ttgagaggct gaagtggaag gatcacttga ggctaggagt tcgagactag cctgggctac  124080
ctagcaagac cccatctcca gaaaaaaaaa atttgaaaat tacaagcatg tccctgtagt  124140
tccagctgct tgggaagctg aggcgggagg atctcttgtt gaggttacag tgagctatga  124200
tcgtgccact gtgctccagc ctgggtgaca cagcaagacc ttgtctttgg gaaaaaaatt  124260
aagaaagaga tggaaccaca cagtgtgcag ccttttgagt ctggcccctt gcagtgagcg  124320
gtgtctaccg tcatgcgttg cacacgtgtt ggtggctggc ttcttgtgac tgctgagcat  124380
tatatggctg ggctgtagat tgctttcact tcaccagttg ggaaacagag aaaaggcagt  124440
ttttaaaaag tttaaatctg tagaattttg gtttttacca gttctcttct aaatcctgag  124500
ggattacagg aaaagttgtt gtatttcaga atattcttag cttgatgtga cctctctccc  124560
tgttaaggcc ctttgctgca atgggaagga cgtcgtcctc ggtcagaccc tgaaggtcag  124620
aggggcactt tgggagtgtg tcaacatttt aactgtatgg actagagcca agagtctcaa  124680
gatttataat tcccacctat tcaaaaagaa aaaataataa taataaagtg agaagaagtc  124740
aatgtaaagt gaaataaacct gtgttggtgg ggaagaagtg ttttaaaca gaatttccat   124800 aatgtatacc ctgaacgtgt ttagagtggt gatgtttcat tgggaaacga acagtaaaac  124860
atgaaagcag ggagattttc tttctggcag ttggcaactt tcatggcaga tggggaattt  124920
gaaaagcaat tgctcaatta tcaaacatag ccagtgtgag ttctgaaata aaggtgctga  124980
ttgaatgtgc agctttatgg tggattttgt cattcaggca agcattttaa ttttctgcct  125040
gttaaattct gttttctttta gttttttcata tgtggtttat tgtagcttgg gaatagataa  125100
ctgagagtat atattacaca tacaacattc tgatatggca atatttaaac caacttgtct  125160
gttttagaac tagaattaaa cataatcatc ttcagtattt tgcaaataag ctcactgcca  125220
tccagaaaca ttgtcaatgc atctgttgct ccttctagaa gacacagtct gtccagcaca  125280
aagttactta gtccccagat gtctggagaa gaggaggatt ctgacttggc agccaaactt  125340
ggaatgtgca atagagaaat agtacgaaga ggggctctca ttctcttctg tgattatgtc  125400
gtaagtttga aatgcctgta aacggggttg agggaggtgg ggaccgggag aacatcctga  125460
gtagatgaca cttgcctgga ccctctggaa cccagactgc ccagtgtcct gccagctcca  125520
tcaaaactaa atctggaatg aatgtttact tctgctctga catataattg gagaccgggc  125580
ctggccttcc agtcactgga ttctaagctg gactgtgaga gttgatgcag ctgactcatt  125640
tatcaaatgc ccagctattg gcttcacgcc tacacgatgc tgggcatatt tgttaattca  125700
agggaagcaa tggaataata ataactaatg atttgaaaaa caagataagt gcattgacta  125760
```

```
tagtggggtt ctgattttaa atttttaaa aaagtaatac caggagcagt ggcttacgcc   125820
taaattctag caactcgaga ggctgaggtg gaaagatcac ttgagcccag gagtttgaga   125880
caagcctggg ctacggtgta agacccccat ctctaaaaaa ataaaaaatg aaaaattatc   125940
caagtgtggt ggctcgtgcc tgcaatcaca gcttcttgag aagctgaggc cagaggatgg   126000
ctagagcgtg ggagttcgag accagcctgg caacacagag aaaccctgcc cctaccgaaa   126060
gaaagaaaaa ttagcctgat ggtggtgcgt gcctgtggtc ccagctacct gagagactga   126120
gaagggagga ttgcttgagc ccagaagttt gaggctgcgg tgagccgtga ctgtgtcact   126180
gcactttagc ctgggtgaca aggcgagacc cctgctctaa aaacaatttt ttttaagtta   126240
atttgtagaa aaggtgttag atgttcattg ccgtatttta tgatggattc ctgtttaaat   126300
gccattctct taaaaaaaaa aaaataactt gtaggagttt ttaaccgtaa aattagcatc   126360
acatgtttac catggagaat ttacaaaaaa caaacagagg aaaataaaac ctctgtaatc   126420
atactactca gagataactt gctgttagat ttcggtgtag atctaatact ttttctgtat   126480
ttatattaaa aatacttaaa acatatacat ttctttgtta caaacatggt atcttataga   126540
tagtgctgtc acatagcaaa acagtgttaa atattctgaa tcagaaaagg aagccgactc   126600
tccaactgaa agaggtgtta tcctagagac ttttttctggt gatggcaatt tgttaatatt   126660 cacttttgc tttacattct gtattgaaat agttttctg ttttgttcta cttttaagga   126720
taatataatt gtatcatgct gttttttcaca gaaatgtaag aaaaaaagat attaattttg   126780
taagttaata gaggttgagc atcccaaatc caaaaatctg aaatcccaga tgctccaaat   126840
tctgaagctt tttgagtgct gacattatgt tcaaaggaaa tgttcattgg aagatttcag   126900 atttttgat ttagggagct caacaaataa gtataatgca catattccaa aacctgaaaa   126960
aaatcctaca ttcagaatac ttctgatccc aaacatttca gataagggtt attcaacctt   127020
tactgtcaga tgatcccaaa tgaaaaatat taatcgttaa ccaaatgtca aggaattgat   127080 cacatttac agtttctgcc taggattatg aatcaagatg aaaaggctct gcgtgtttaa   127140
aaatatatat atttttattt tcttataaat cttaaatgta tcaacactta agatgtattt   127200
gatatgtgga atccattcat attttggatt aaacaattct gtcaagaccg tggcagtgat   127260
agaggatttt ttttttcccac tgaactatca caaaattgga aaaagagtaa ttggagaacc   127320
ccactggctt ggccagctcg aagccccgga gggggcaggc agtgctgtgg atgggagcgt   127380
cgcagtacca cgctgcccct cctgcccatg gatctctgag gcctgccttt gtcctttgac   127440
ccttggccat ttgttagtgt ctctgagagc tggactgctg tacccctactt ccccaggggg   127500 gcctgacttc acacagcctc tgctgcagtg cgtggttgga ggtgacggcc ttggtaaatc   127560
cagtttcctg cctcctcaat tatttgtgct catacactgt atattttta gtgaggttta   127620 tatttgagat gtgttttctc cttcttaccc tttctggcct ttctatggat taatacctgg   127680
tctcttcttg tgtacttgaa agtgaatctc tcatcgtatt tttccttagt gtcagaacct   127740
ccatgactcc gagcacttaa cgtggctcat tgtaaatcac attcaagatc tgatcagcct   127800
ttcccacgag cctccagtac aggacttcat cagtgctgtt catcggaact ccgctgccag   127860
cggcctcttc atccaggcaa ttcagtctcg ttgtgaaaac ctttcaactg tacgtcttca   127920
tcctgccaac aattgccagt tgcagttttc tctgccttaa aaatggagta ttgaaatttt   127980
taactttaat ttctgactgg caaaatagtc atcttttgtt cttttccttc tcgctgttag   128040
ccaaccactc tgaagaaaac tcttcagtgc ttggagggga tccatctcag ccagtcggga   128100
gctgtgctca cgttgtatgt ggacaggctg ctgtgcaccc cttccgtgt gctggctcgc   128160
```

```
atggtcgaca tccttgcttg tcgccgggta gaaatgcttc tggctgcaaa tttacaggta  128220
ttgggaaaag aaaccctgat attgatttat attgaaaatt tagcaggcca agcaaaacag  128280
gtggctgcct ttttcctcca taggtgtggt cttgacacgg tcaccaatag aaacatggaa  128340
atatctgcaa acttgccatt cctcgtgtgt ctgatctgtt tcttgaactt ttttctagtc  128400
tgtccttact aggatgaact gtacacatca gtttatcctt tttaaatgag catgaggtta  128460 ttttggggttg tacagtgtca caaacacact aatgtgtttt tgtctattag agcagcatgg  128520
cccagttgcc aatggaagaa ctcaacagaa tccaggaata ccttcagagc agcgggctcg  128580
ctcagaggta atgctggaaa cacaggtcat ccttgtgtta ggagaaccca ggatataaaa  128640
gatatagatt tgtgcgggaa taaattcaca ggacaagaaa ttgatgtgcg ttataggtgg  128700
gtttgctgca gaagtgccat aatagaaagc ttcctacttt taaaacaacc agatctcact  128760
ttatatggag taaaggacaa ccagcaggat cacgtctatg acatgagtgg aggcagtttg  128820
cactcctttt ggctgtttga gaggtagtat ttagaatgcc tgtattcact gtcctgtgat  128880
gagtgggaaa ataggttatc agctttatct tagcaaaatc aaagcatatc atctaattgc  128940
taaacaagag ttggcaaatc tgaaagacat tactgaatcc ttggcatgca ggacttacat  129000
ctgcatcccg ttgccatttt ttctcttcaa agcatttaat cacttagttg tgtttgcaaa  129060
gtcttttaga agcctttatc agaaatcctt acatctccta tgtgagtgta tttccatgac  129120
tgcaaaataa gttaaacttt tacctttttt cttcccttgg tggggcgga aattgtgtgt  129180 gtgaaaggga aagagagaca gcagagaagg agaatataat tatcatgctg tgtcctttga  129240
gctgaaattg caaaaaagaa aacacacaca cacatgcttt gatttcagtc ttaagagtac  129300
cttgttgatg gtgttttttaa atgggattgg gcacaattag gtggacagtt tgggggcgatt  129360 tttcggtctg tagggccaag ctgttttgta atttgcttta taaagttgtc actctcatag  129420
catatggtgg cagataaact attattactt tttgacccta gacttagtct tcagtccaga  129480
tgagggagat taaaagatta taaatatctt gtgccagatg aggtgatttt attttgaaat  129540
gaccataaat tcctatcagt tgtcttactg ggatatttga tagtggagtt tgtgcatttg  129600
agtcttagat gatctgtttt acgtttatta agaaagcctt tattagccttt tataccatgt  129660 atggactgtt gcaatgtttg agtataaatg aaatttctgg acaatattaa tggagtacaa  129720
actgtgatac cttagaagta aactagggcc tgcgtttata tcatgacctg tttgagtgtt  129780
gatgagaaaa tagctgtgaa gaaaaagttt taaacaagtt tcattttcct ttaagaagcc  129840
actaatagtg catccttagg gtgtatattt ctagaatcct agtgtgcaga gtttagacta  129900
agactaaaaa aaaaattgca ctgtaatttc cttttttgttt gtattttaga caccagaggc  129960
tctattccct gctggacagg tttcgtctct ccaccatgca agactcactt agtccctctc  130020
ccccagtctc ttcccaccccg ctggacgggg atgggcacgt gtcactggaa acagtgagtc  130080
cggacaaagt aagtgtccag cgtgtctgca tgcgaggcac agggcagagt gcctctgtca  130140
cctgaggcag atacagagag tgcagaggag gtgcggtgga cccaaggagt gctggcgctc  130200
tgctcggctc aatgaagccg tggttagaga cctggggggga ccatcaatgt ccgagggagc  130260
aaagcagtgc tgatgtggga ccgtttcggt aggagtgcga ggtgagtcgt tagtgggtga  130320
ctcaagggaa agtcaattgt ggcctgcagg cccctgactg cacaggcctt caagcacatg  130380
tcagtgcatt tagcctcccct ccatcgcctc ataccttctg gccacctgtg agttgcactg  130440
ccactgccag ccatactggt atgttgtcag cacctccact gctcataccct caccgttagg  130500
```

```
gaccacttgg ggccttggta gagccttggt actctacttt cctggagaga gttcagctta 130560
tgaatatgaa tttagatttc aaaaaccagc agcccaagta taagaaagcg aaggttcagt 130620
cctgccgcct taggctctat ttgctaagca tctgccctgc cctgccctgg ttgctgggaa 130680
gagatgagca aagcagacag cccaggagag gatggcaaag gggccgctaa cccttagtag 130740
tttagctata tttggaagga ctattagaaa ttcaccaggt gaaggggag gccgtgagag 130800
tacccaggta ggtaacagaa gtccaaagag gaagacctgt ggtgtggtga gctgtatagc 130860
cacaacatgc cggccggagg ccctctcagt tagcctagtg cagtgttccc aagcactggc 130920
ctaggcctgt agctccaggg atgtgaagtc cccttgaacg ccacccatca tgttcccctt 130980
attcatcttt ttcttcccag gactggtaca ttcatcttgt caaatcccag tgttggacca 131040
ggtcagattc tgcgctgctg gaaggtgcag agctggtgaa tcggattcct gctgaagata 131100
tgagtgcctt catgatgaac tcggtacggg gggagcagcg gaagcaagga atcctcagct 131160
tttcttgtga cttccaagtg ggatttgtct cctcatgtga cccacttgtt gacaacacat 131220
gttgaggact ccactctgga tggggacggg atgacgagga gactccactc tgaatggggc 131280
tgggaactgg ggaggactcc atttcagggg gccgggacat gggggatatg ctgatcgaga 131340
ttgtttcagc cacattagaa tccaaggagg caagtcgatt tcactcaacc tttcatgcat 131400
ttaaagaaaa tggaggtggt cttagattac agtcatttca ctggtttgtt ctcatggcag 131460
tgaggaaggg tattgggatt ggtgtctgtc ttaattcagg atctttgaga agatggagag 131520
cactccctca gggattagga gagactcgag atggaaatga agatttact acttacaggt 131580
cctggcgggt acatggcatg cccagaggcc cctcacacgt ggaagttggg ggcatgtgag 131640
ggaatgaagt gtggtcctgg gcactagggt gggggacctg agcggnnnnn nnnnnnnnnn 131700
nnnnnnnnnn nnnnnnnnnn nnnnnnnnnn nnnnnnnnnn nnnnnnnnnn nnnnnnnnnn 131760
nnnnnnnnnn nnnnnnnnnn nnnnnnnnnn nnnnnnnnnn nnnnnnnnnn nnnnnnnnnn 131820
nnnnnnnnnn nnnnnnnnnn nnnnnnnnnn nnnnnnnnnn nnnnnnnnnn nnnnnnnnnn 131880
nnnnnnnnnn nnnnnnnnnn nnnnnnnnnn nnnnnnnnnn nnnnnnnnnn nnnnnnnnnn 131940
nnnnnnnnnn nnnnnnnnnn nnnnnnnnnn nnnnnnnnnn nnnnnnnnnn nnnnnnnnnn 132000
nnnnnnnnnn nnnnnnnnnn nnnnnnnnnn nnnnnnnnnn nnnnnnnnnn nnnnnnnnnn 132060
nnnnnnnnnn nnnnnnnnnn nnnnnnnnnn nnnnnnnnnn nnnnnnnnnn nnnnnnnnnn 132120
nnnnnnnnnn nnnnnnnnnn nnnnnnnnnn nnnnnnnnnn nnnnnnnnnn nnnnnnnnnn 132180
nnnnnnnnnn nnnnnnnnnn nnnnnnnnnn nnnnnnnnnn nnnnnnnnnn nnnnnnnnnn 132240
nnnnnnnnnn nnnnnnnnnn nnnnnnnnnn nnnnngagaa acctcctggt gctttagccg 132300
tgcgttgata cacagcagat gggagggaag tgggcacccg ggaggacaaa tgcatgtaga 132360
ggctggggt ggaggcaggt gttcatgaaa agagaccta caggagggc aacacaacag 132420
tgtgttctga tgtactgaag agctagactg aaaagaacag gagaattcac ccaaaatcca 132480
tttactaaaa ttgtttatcc ttttttttt tgagacgaag tctcgctctt gtccccagg 132540
ctggagtgcg atggtagatc ttggctcact gcaacctctg cctcctggat ttaaacaatt 132600
ctcctgcctc agcctcccga gtacaggcat gcgcccacca cgcccggcta attttttgtat 132660
ttttagtaga dacgcggttt caccgtgttg gccaggcttg tcttaaactc ctgacctcag 132720
gtgatctccc tgcctcagcc tcccaaagtg ctgggattac aggcctgagc cactgcgccc 132780
ggcctaaaat tgtttatctt aagattcatg cagtgaaaac taacttactg agtgataaat 132840
ttgcttagtg atctgtttat taggttttct aaatttgcta attgggcttt gaacagctgt 132900
```

```
aaaagttctg actgtaaaag aaagctgcaa cttttggcat tcatgatgct tttctgaata   132960
ttaaactaag atagatgttt tacctgaaga attggccccc aatcttataa atggctaaac   133020
aaaaaaggtt gctaaaacat aatccaaatt gtcataggaa ataccatttt tccaaccaaa   133080
attttgtcat tcatatggct acttttactt atttcagctg catttgacca tcttttcaa    133140 acttcaggga tggctggtgt atcaccgaga tcttggatga cactttagct ttgattttct   133200 gttttttatga attaaaattg tcataccaaa attttactt caagcaaatc caagagcata   133260
aaaaattaaa atatcactta aagtaccaag agagaacaga aatatatttt actaagcgta   133320
cgttgaatga agttgttcaa atatttgtaa caggcataga gtagaatttt cttaaaaaca   133380
tttttgatgg tataccaatc tgtgttttct cagaaacatt tgccttattc ttttttctgt   133440 tgtgttttc ttacctgatt gaaagctcct aatctgttgt tattgtttgt ttaaccttta    133500
atgctctgat ttcaggagtt caacctaagc ctgctagctc catgcttaag cctagggatg   133560
agtgaaattt ctggtggcca gaagagtccg ctttttgaag cagcctgtga ggtgactctg   133620
gcccgcgtga gcagcaccgt gcagcagctc cctgctgtcc accacgtctt ccagtccgac   133680
ctgcctgcag agccggcggc ctactggagc aagttgaatg atctatttgg taattaaaat   133740
taaaatttat cttattttta gaaaggttcc agggccagta tagtactttg caccaagtaa   133800
atatacaata aaggcggtgg atctaataca gcgaaagcgt ttacagaggc agctaaagag   133860
cagcactggt ggcctcagcg cagaatttct tcctgcgtgt ttgccacttt gccgttcatt   133920
gacgtggtca cggacatagg gctctaagcc cttgaggaag gctgggccag acctcagggg   133980
agatgcagcc ccaaactaca tgcagtcatg tggatggatg cgtagatgtg ccattgagga   134040
gcaatgtctt gtgctttcat cagattctca aagaattgct tgactgcctt tcgaaggtgt   134100
tgcatctgtg ctcatgtttg cacccaccca cgagggcctt ctgtttcagg ggatgctgcg   134160
ctgtatcagt ccctgaccac tctggcccgg gccctggcac agtacctggt ggcggtctcc   134220
aaactgccca gtcacttgca ccttcctcct gagaaagaga aggacaccat gaaattcgtg   134280
gtggcaaccc ttgaggtaag aggcagctcc ggagctcatt gttgctgtgg gaggggacac   134340
ggggctgaca ctggagaggg taaagcagtt ttatttgaaa agcaagagct ctgaccaatc   134400
cagtcactat tctgtctcag cctggcagta agtcttgtca ccgtcaagtt attgtagcca   134460
gccttcaccc ttgcctcgcc actcctcacg gtggcctgtg aggtcagcca ggtcccttc   134520 tcatctgcac ctccagtgtt atgtggatcg taattttaga gacttgaaaa ataaccatct   134580
gtaggtactt tgtgtcttaa gttggcctgg acatgtcagc caaggaatac ttggtttgtg   134640
ttagtgcttg taattagccc ccaaaacatg tacacattct ggatgcatta aactcaggcc   134700
tgtatcctta aagggccatc tctgtgctgc ctgccctcag cagggacaca ctttgcagac   134760
ccacagaggc tccgcctcca cctcacacca aagaaaggga ggagtccaaa gggcatcagt   134820
gccgttactc acaaaatgat aaatacaccc ttattctgaa ccaggtggag tcagatggtt   134880
tgtgatccct gtcctttagg tttcagctta gtggggaagt gggaaagcca gcgtgtgatc   134940
acagcacagg gtgattgctg ccgattatat tatgtgcctg ctgtgtgcag gacaacatac   135000
tttacacgca tcatccttatt tgactctcac aactccctgt gagataggct ctgttactcc   135060
catttgacag gtgaggagag caaggcttag agaatttcag tgacttgccc aggtccactg   135120
agctaggaag tagccattct ggcgtttgaa ctcaaggcct gctatcccta gaacccacgc   135180
tctcaaattc aacctctgag gctatgccag aggcaagccc cagtgctgtg ggcgccccag   135240
```

```
ggaagaacct ctggcctggt ggccacgtag cccaggagag atgtctacag gagcccacag    135300
cgctgaagga gagaagggca gcagagttaa gggggcattc tggcagagag gggactggca    135360
ccttggggaa tagctgggtc aggactgaat gtcatggagt caggtcagag ctgtccttct    135420
ggagggcaag ggcatctgga cctgcttccc ctcaatgctt tggacggttc caccacaact    135480
gattcacacg gcctcccaa atgaaggtac acgagcgggc attctgtgac ttggtacttc      135540
cctttaggcc ctgtcctggc atttgatcca tgagcagatt ccgctgagtc tggatctcca    135600
ggcagggctg gactgctgct gcctggccct gcagctgcct ggcctctgga gcgtggtctc    135660
ctccgcagag tttgtgaccc acgcctgctc cctcatccac tgtgtgcact tcatcctgga    135720
ggccggtgag tccccatccg tgaacaatgg gttcctatcc tagttcctgt ctagttcacc    135780
atgtttatat tttgtgctgc ctgttttgcca ggtactaagc taggaattgg ggatggagag    135840
gtagataaaa tacgcattag aagggctgg gctccatctc tttttttttt tttttttttt     135900
tgagacggag tctcgctctg tcgcccaggc tggagtgcag tggccagatc tcagctcact    135960
gcaagctccg cctcccgggt tcacgccatt ctcttgcctc agcctcccga gtagctggga    136020
ctacaggtgc ccgccacctc gcccagctag ttttttcgtat ttttttagtag agacggggtt    136080 tcaccgtgtt agccaggatg gtctcgatct cctgacctcg tgatccgccc gtctcggcct    136140
cccaaagtgc tgggattaca ggcttgagcc accgcgcccg gccggctcca tctcttactc    136200
tccaatatat tggagtctac actggaattt aacttgaatt tgcttttta gtcatttttat    136260 ttagattttg gaatttcagc tttcatcaaa attacttcta aattttatgt ctctgtgatc    136320
tttggtctta gctgactgtt ttatgcattt agtcttatat gatcgaaagg ttagtaagat    136380
tacgttcaga agattgtttt ctgttcaaat gcttgtttct atactgcact ataatattaa    136440
cgtactgtaa aataaaagtg cttattctt ttcaaggaac agtatcctca acaagggtta     136500
ttagccacaa ttttaaaaa attggacatc atggtttaca tgttggaggg cattttgaag    136560 cttttgtattt tcaaattaaa cattatagag tgatgttttg atgtttcata attgttttca    136620
tctgtgcatt tgtggccagc ttgaaaacaa agatccaggg attaatactt aaaagccaga    136680
cttcttgggg gttatagaga tgattttggt agtaatgaat cttgagccgt ctgataataa    136740
cctcggggtg agagatggcc aacaggagag agtcgaggga cttacaaatc tgaatgaaat    136800
ctgaagtaca atcttcaga catatgccac taaccaagag attggtacct cagtctaata    136860
ttgtctgttt gtctaaaatt ggttctaaga aatctaggct catctgtcta tcccttgaa     136920 cttttgtgag gctgcacaaa tgtaaaattt tgaatgaaaa gcactgatgg aagtctgtgg    136980
aaattcttct gtttgttctg ttgtaatttt agttgcagtg cagcctggag agcagcttct    137040
tagtccagaa agaaggacaa ataccccaaa agtcatcaga gaggaggagg aggaaataga    137100
tcctaacaca cagagtaagt ctcaggaccc attctttctt acatgtggtt cctccaagac    137160
ttaaaagtca ttcacagaga cgtgcgccgt ggtgagtgtg cactcctgga agcgcaccgt    137220
agctcggctg tgtcctgctg ctcctccctc gccgtgggag gctttagtcc attgctttgc    137280
cacactcttt tgtttcaccg tatccctgtg catgcggctg tttctgaccc tacagagcag    137340
ctgggatgcc tctggggggag cccttccccg ctccagcact tccacatgcg gttactctgg    137400
gctcctggag ggcagggagc aggtttgtct tctctgtgtt ctcagaaatt aatgcttggc    137460
ccctggtcag caagcagcaa cctttttgttg agtgatactg aataaataca tgtttcccac    137520
atgagtattc agtaacctca gtgtcaggtt caggcatctg ttttggtgga tatttaaaag    137580
aaaattccac ttttcctaca gaaaaaaaaa aataaataaa tctaaatccc agtgatttaa    137640
```

```
gccagttata gacttagaca tatactacgg cttttcatgc cctttcctcc cagttctaga 137700
gtagtatttt actaggaaaa tggtggcaat gcctgttgag aggaaaagtt tttggccaag 137760
tgtctttcgt tcttgccagg ggccctaggc tgctggggct acttcagttt ctttagccca 137820
gtgtctggca gggaatgctc cctgtagcct gtcccacaga ggcagggatg cctcacctgg 137880
ggcctgtcca cgcattttac acagcaccct tacttggagc atcaggcatc ttttccgcgt 137940
tccgtggctc aggaaacaca ccttttcaat catgagttcg ccagtgcttt tgggcttttt 138000
ctcccagctt ttgtgcaatc ctagttatgg atggagtttt cctgccttta gtcttctgca 138060
tagtactttt ttcttctggt tcccggttcg aggttttgta attaaagaat gacccagaag 138120
cagtggcatt ttcttttctt ttctttcttt ttttttttg agacagagtc tggctctgtc 138180
gtccaggctg gagtgcagtg gccggatctc agctcactgc aagctccgcc tcccgggttc 138240
acgccattct cccgcctcag cctcccgagt agctgggact acaggcgccc gccacctcgc 138300
ccggctagtt ttttgtattt tttagtagag acggggtttc accgtgttag ccaggatggt 138360
ctcgatctcc tgacctcgtg attcacccgt cttggcctcc caaagtgctg ggattacagg 138420
cttgagccac cacgcctggc cagcagtggc attttcatac acagccaagg tcttctctga 138480
atttttatct cgaacctctg tgggtccttc aggcttcagt ttgtgatttc atgatttctt 138540
gttgctacct aaggaatatg aaaacaccca cctccctact ctgcgtcttc cagccgatgg 138600
cacctcaggc tcttggtcct gtgcttctgt ggcgaggata agaatagtgc caaccatgtg 138660
gattgagata gatcagttag tccatccatg tcaagcacct ggaatggatg acagtcttgt 138720
tgtgaatact caacagatgc taccatgact ttagttagat ttccattgct ttgaaacagt 138780
tgagacatct cagagctttg agccagagca gtgggccctg atgcaggttc tgtttggttg 138840
aagatgattg tgcttattcc ctgtggccct tgtagaccgg agtgggaagc ttgcttgatt 138900
ttaatcacct cgataggatc ttacttctta aaggtcatcc aataaataat gagccaactc 138960
attagcctgg ggcttaattg cttaagtcca atgagaagtc attctctatc ctaggaagtt 139020
gcccaaactg tagaatctcg tggcctgtgg gtagtagcca cttactacac attcactgac 139080
tcaacgaatc atattttag tagatacaat attctagact caagacacca tgatgtggat 139140
cttcccaggg gtgtgacgtg ttcctcggcg tctgccttgg gagtttccat ttccatcaga 139200
accatgcccc agggccctca aacactctga tctaggaaag ccagtgaagc aaggatgaca 139260
gcgtggccct ttgataccag ctgagggaca gacacaggtc ctgggagacc agagaaagac 139320
aaggggcaga ggaagtgtcc tagagggtgg gccagggg tgggaacgaa ggccagagct 139380
caggttcagg accattccag caatcccagc agaaaatggg gaggattgta tggtataggc 139440
ggatatgaag gaggtagact ctgcaagctt tcagtggcca actcattcta ggtgattcca 139500
caattacagc ttgagcagct gcttgtcggt catgcttctt acactgggca gtagaatgt 139560 gttttttaaa aagtcttctc ttaaccattg cttgtttaga tccgaagtat atcaccgcag 139620
cctgtgagat ggtggcagaa atggtggagt ctctgcagtc ggtgttggct ttgggtcata 139680
aaaggaatag tggcgtgccg gcgtttctca cgtcagtgct caggaacatc gtcgtcagcc 139740
tggcccgcct gccccttgtc aacagctaca cacgtgtgcc cccactggtg agtctggtcg 139800
ttccgtgtag aagaccaagt acggtgaaac gcatgggtaa gccctgggct gggcacaccg 139860
gagagggcag ggcagagtcc ccgcggccca gaggctgcca gctgtggttc tggtgccagc 139920
tgtggttctg gtgccagctg tggttctggt gccagctgtg gttctcgtgc caggctgctt 139980
```

```
tcctcaggca ccgtatgtgg aggtcgctag tagaaatact gggttttcta aaatgaagtg 140040
aggccccaca tccctaagag attagtgtta gacttgattc taaagcaact agaccacttt 140100
gcttactggt agaccagaaa ccacactccc tcgagtgagt gagattttcc tttggaaata 140160
attcatgttt ttctacacaa ttttgctgtt gtcttcagaa tcggtttaaa gtaggtgtta 140220
ttgctgggca cagtaactca tgcctgtaat cccagcactt tgggaagcca aggcgggcag 140280
atcacttgag gtcaggagtt tgagaccagc ctggccaaca tggtgaaacc ccgtctctac 140340
taaaaataca aaaattagcc aggtgtggtg gtgtgcacct gtaatcccag ctactcagga 140400
gactgagaca ggagaatggc ttgaacccag gaggcggagg ttgcagtgag ccagatcac 140460
gctactgcac tccagcctgg gcaacagagc aatattttgt ttcaaaaaaa aaaaaaaaa 140520
aaaaaaaaaa aaagtaggtg ttattgatca ggatgcttgt ttcagataac gaagagctta 140580
gcttgaggag agtgagggtt gatggaaggg gactggcttc tgctcagtga aatggcatca 140640
tcccccacca gcctgctgaa gtaagatgat gggacctgtt ccttagggac tgcagcatcc 140700
tcaggcaaga aagaaaggcc gaccggcagg gtgtgagcca gcaggtatag gtcagtgaca 140760
atggagctgg gtcccaggga agaggcttgt ggctgcttga aagggcgcg tgcccgtctg 140820
cgtgcgcgtg tgtgtatgta cgctggagag tctgggagg cttgctccaa ggacacagta 140880
tttgatcctg agacatgagg agggttctgc cgcaggcgat gaaggtattc agatggagag 140940
ctcattcgga agaagaggcc agggcctggt ggtgctggaa gcagttgcag aacagggagt 141000
tgtaagcttt cctaggaaga gcagcaggag tgctggagaa gcaggccacc cttgctgcat 141060
gggggttgct cttggcccca ctcttggtgc acggcgagtc actgtgagtt cgttagcatc 141120
tggttctgaa acagtaactg ctcctttgga ggggctcggg gagaccatgt aggagggcac 141180
agtcaagagg tcatgctatc tggaacacac ttgaggatat gccaggacgg actgcatgct 141240
gtagataaaa ttcctctagc aagctcttaa ccggcattga ggagttccct gagtgcggtc 141300
atctggaagg cagctgtgaa aggcactgca gtctccccc gggcaggtac caggagcaca 141360
ggggagcaga actgatttaa agagagggct ttcctgtggt gaggtgagag atgagctggt 141420
cattatcata gaacccctct gcctgtgtgc agatgcgctg tgggaatcct ggggttccgt 141480
tgggtcctct gtcacctcac tgaaggcatg tcagctgagc tggccagacc ttcagctgat 141540
cctgccactt gaacagcatc aagcctgcct ctggattctt ctgtgcacgg tgcttgtcta 141600
atcacctcat gcacagagaa ctgtacttca gagtttacag aaataagctg tatggttcat 141660
tttcgtgcct gcttgccaac aaacatatct gagctgaact tcattgaacg cctgccttta 141720
ttctaacaca ccatctgctg tttgtgggcg aggggtgctg tctctaactc ctgcctgcct 141780
ctcccagcat ccctgagtgg ggtgtgccag cagcctcagg gtgaggacag gaagtgggag 141840
ggcagagcag atttggaagg gccacttgat ggggaaggaa gtcccaggaa gcagttggag 141900
ctgttttctg ggggagaagg tgccagcttg ggacagtgt tgtagtgagg aggaagccca 141960
gtggagagaa gtgggcttc ctgcttcctc acagtgtgtc tgtcctgact cagctcgggt 142020
gatgtcactt cctttcatc ttctcaggtg tggaagcttg gatggtcacc caaaccggga 142080
ggggattttg gcacagcatt ccctgagatc ccgtgtgagt tcctccagga aaaggaagtc 142140
tttaaggagt tcatctaccg catcaacacg ctaggtactc ttggggcctc tttcaggtca 142200
ccatcgtcgg gcatgtaccg ggaggaaatc cagagcccca gtactgggat cttctcattt 142260
gactccagaa aagatttaag catgataata atacaaacct gtgtgaatac atttttgcagt 142320
gtcagcaaaa ctccttttac tgagaaaata gatcccagtt cctgtgtttt gtggcttgaa 142380
```

```
tcccagcttt ttatattctg ggcttgtttg aagtcaggaa agattcatgt gtaacagaca  142440
acgtgaggcc aaattctgcc ttcgattttg catttaggct caacagtggc agcgcttgtc  142500
tcggagtgtg ttctcgtgtt caccagtctg atcctgttgt gtctcactgg tgcgttttct  142560
cacatgggaa caagcagacg ggagcagatg gagtcaagtc tcttagcact cgccttcctc  142620
agagcctaga ggcagcatgg ggagaaagcg ggcttggggc tcagacagtc ctggtctgct  142680
tccagccctc tgtagctgag cagcgcggaa caagtccttc taacctctag agaccctcag  142740
ttttgtcaaa tgtaaaatgg gagtcacgtc tatttcatag aattgttgca gatttagaaa  142800
ttacatttct ttttttttt tgagacggag tctcggctct gtcacccagg ctggagtgca  142860
gtggcgcgat ctcggctcac tccaaactcc gcctcctggg ttcacgccat tctcctgcct  142920
cagcctcccg agtagctggg actacaggcg cccgctgcca cgcctggcta atttttttgta  142980
tttttagtag agacagggtt tcattgtatt aaccaggatg gtctcgatct cctgacctcg  143040
tgatccgccc acctcggtct cccaaagtgc tgggattaca ggagtgagcc accgtgcctg  143100
gcctagaaat tgcatttcta aacaagtgtt agcccttatt tctaaataag tgtcgaaatg  143160
aataagtcac cactttcgcc cctatttgat ggcaagaggt gtgatcttgt ggtgggattg  143220
taatcagtca gtcctcagtg actgtgccct gctgtggtgt ttcctggaaa gttcttgtct  143280
tgtcctagaa agtctggcag gggcaccctg tctccactgt ccagtcttct ccccaggccc  143340
ttcaggcttc tgcaaatttg aggcttgttt tcatcccaga aggttctggc agcagacgcc  143400
ttgcgtctac tgtccccttt agttaattag ataattcaat gtccaaaggg aaccctgagc  143460
aggaacctca agccagctgc ctcacggagc tcctcctctt cctcactgtg aagattggtg  143520
tcagtggcct cctggtctcc cccttgccta acacgagctc ctttgcttac ttgggtgccc  143580
ttgcccttga actcccggc agacgtgcgt gacccaagac tgtgctacag tccttgtttt  143640
tgttcatgct catcttcttc ttggttcatt gttttccctg taatgtcaat tgttttattt  143700
gtctgtatct gtgtctgaat cagtcctgca cgctctcctt ctctctgtct tttgttctttt  143760
ctttacccag tttatcacag gaccccccga tgtccatttc tctagttctc ctgtcctaag  143820
cacccccatcc tgtctttctg gccttatcac aagtggcgtg tctgcctcag acatcatgat  143880
gggggcatga agcacagctg tcagaaacaa ctgttcgtta ggtacactcg aattcagctc  143940
atcaatagga atggagggtc tatcagatgt gttttcactg aatccctgtt cnnnnnnnnn  144000
nnnnnnnnnn nnnnnnnnnn nnnnnnnnnn nnnnnnnnnn nnnnnnnnnn nnnnnnnnnn  144060
nnnnnnnnnn nnnnnnnnnn nnnnnnnnnn nnnnnnnnnn nnnnnnnnnn nnnnnnnnnn  144120
nnnnnnnnnn nnnnnnnnnn nnnnnnnnnn nnnnnnnnnn nnnnnnnnnn nnnnnnnnnn  144180
nnnnnnnnnn nnnnnnnnnn nnnnnnnnnn nnnnnnnnnn nnnnnnnnnn nnnnnnnnnn  144240
nnnnnnnnnn nnnnnnnnnn nnnnnnnnnn nnnnnnnnnn nnnnnnnnnn nnnnnnnnnn  144300
nnnnnnnnnn nnnnnnnnnn nnnnnnnnnn nnnnnnnnnn nnnnnnnnnn nnnnnnnnnn  144360
nnnnnnnnnn nnnnnnnnnn nnnnnnnnnn nnnnnnnnnn nnnnnnnnnn nnnnnnnnnn  144420
nnnnnnnnnn nnnnnnnnnn nnnnnnnnnn nnnnnnnnnn nnnnnnnnnn nnnnnnnnnn  144480
nnnnnnnnnn nnnnnnnnnn nnnnnnnnnn nnnnnnnnnn nnnnnnnnnn nnnnnnnnnn  144540
nnnnnnnnnn nnnnnnnnnn nnnnnnnnnn nnnnnnnnnn nnnnnnnnnn nnnnnnnnnn  144600
nnnnnnnnnn nnnnnnnnnn nnnnnnnnnn nnnnnnnnnn nnnnnnnnnn nnnnnnnnnn  144660
nnnnnnnnnn nnnnnnnnnn nnnnnnnnnn nnnnnnnnnn nnnnnnnnnn nnnnnnnnnn  144720
```

```
nnnnnnnnnn nnnnnnnnnn nnnnnnnnnn nnnnnnnnnn nnnnnnnnnn nnnnnnnnnn    144780
nnnnnnnnnn nnnnnnnnnn nnnnnnnnnn nnnnnnnnnn nnnnnnnnnn nnnnnnnnnn    144840
nnnnnnnnnn nnnnnnnnnn nnnnnnnnnn nnnnnnnnnn nnnnnnnnnn nnnnnnnnnn    144900
nnnnnnnnnn nnnnnnnnnn nnnnnnnnnn nnnnnnnnnn nnnnnnnnnn nnnnnnnnnn    144960
nnnnnnnnnn nnnnnnnnnn nnnnnnnnnn nnnnnnnnnn nnnnnnnnnn nnnnnnnnnn    145020
nnnnnnnnnn nnnnnnnnnn nnnnnnnnnn nnnnnnnnnn nnnnnnnnnn nnnnnnnnnn    145080
nnnnnnnnnn nnnnnnnnnn nnnnnnnnnn nnnnnnnnnn nnnnnnnnnn nnnnnnnnnn    145140
nnnnnnnnnn nnnnnnnnnn nnnagaaaat aaggcagcag actggtgttt ctttctttttt   145200 ttttttctc ctaccttatt ttgagagagt agccagatgg tgtcttgact gatattccag     145260
agcagggaca aagcccactg aggtttgggg gctgcaatta ccaatggctg aatgcatttt    145320
gattacggtg cgttccatgt taaggatcaa taagattgtg ctctttctgg aaagtatctt   145380
ttagttttat ttattggtat tcagaggagt gtaggttgaa ttaaaatgaa aaggcatttt   145440
ataaaggccg tgagtagtac atggtttcat ttttctaatg tcttgcagag attttattag   145500
gcttctcgaa gtgttcacgt acattacgtt aatgtgatac taagagtaac tgtactctgg   145560
cacagcgaag ccagcagaat gggaagttgt ggaatgcagg cccttgattc tgatagaagg   145620
tgtggtatga actcgcagaa atgacagttt ggagggtaga catatgtcac aagtcatcaa   145680
gattgtcttt aaattcatcc atagaagcta acaggttgtc ataagcaaag cctctaaaat   145740
gtatgaggga attcaaggat aatttatcaa aaagtaattc atgtttggag ttttgtgccc   145800
aaaggagtcc ttgatttgaa aaatgggtgt ttgcccatca gattgtttca gggtccgtat   145860
gtgcagaggc cgtgcctcgt gccccgtgag ctcagcctga cagaagtccc ttggtagcac   145920
ttagggactt ggttagcact tcttcccttt gaggcagggt ggactctggg ttctgcattc   145980
agagctggct gtgggtgtct tgctgttctt gttgacctgt gggctctcct tccaggaaga   146040
cacagagagc acgcagatca acgtcctggc cgtgcaggcc atcacctcac tggtgctcag   146100
tgcaatgacc gtgcctgtgg ccggcaaccc agctgtgagc tgcttggagc agcagcctcg   146160
gaacaagcct ctgaaagctc tggacaccag gtttgcctga attcccacgt gtctccagga   146220
catcatgggt gctgcggaca gtggggtccc cgctgaagca tccagcagct tccccaggc    146280 tgttttcctt tgttgctaga attgaaaacg ctgtccatgt ggcctgtgca ggaggtgcag   146340
acccaaaggt ggcctcttgg ccattgagga gctggaaacg cgacgggaac tgacatgggg   146400
ttattgggca tttaggggta aacattagca gagcaagaat gagcgggcaa gtggtagaac   146460
acccacctaa gggctcatgg acaggtgctc acttaggaag tgagtttcgt ttggtattac   146520
accaggttcc tttaggcagg gcggagggaa agttctggcg tttttcactt gtaagatttt   146580
gaaggaaaca aaacactctt tacctttttt ctgaaatgta ggtttgggag aagctgagc    146640 attatcagag ggattgtaga gcaagagatt caagcaatgg tttcaaagag agaacatc    146700 gccacccatc atttatacca ggcgtgggat cctgtcccct tctctgtcccc ggctaccaca  146760 ggtacctgag ggagagggtg gggggtggct gtacttgggc tgggatgaga aaagactggc   146820
gtgctcacca caccagttat gcaggaagac ctgagtgtgg tttgagttgg aggctgtggt   146880
gctaaatagc tgccccattc ataagcagga gtcttattca ggcccaggga ggaaataaaa   146940
tctggaaatg aattaggagc attatctcct gccagtcaat tctcacgggc tgtaagaaca   147000
gcaggattta aaagttgaat gagttcctta tgttaagaac tcaaccgagt tcatctacac   147060
aagctgaatc tccagctttt cctaagaaac caggtgtggc agtggctgca gggcggggca   147120
```

```
cagctgggcc tgagcacccc gctccctgca cctctccect ccctgggccc tgtctgtcgg  147180
tgcccactct cccaccaagc ctgccagttg tgtgcctgcc ctatcacagg catcagagtt  147240
tgtcacctgg tttaaaagaa gggagttgtg tagggatctg gggatgcaca tttttcactg  147300
aacagtattt tagcatagag gtttgtgatt ccctggttat ttaggagttt aagcaccttg  147360
aaggctttaa ttgcagaaag gtctatgtgg acatgcaatg tgttatacgc agtgtctatg  147420
accctcaaat gtttattagg gtattgaaat aaactgagca cttggagggc catggatcca  147480
gcttcaagga gttcataggt caggaggacc caggagcaat gacctgtcgt agacggcaga  147540
aaagaggggc acagaggtgg gttgggggca tacacaggca gctcctggag ctccaaggag  147600
agcaagtgct tccagggaag ggggtgtgga ggctccttgg gaggaggcga gttgatgctg  147660
gggtctggca gagggttagc tggggacatt cggctggagg ctgttgtctg ggaattgggg  147720
ggatgcccag cagaaagaca tgcggaggtt gtttggcctg gggcgtgggg ggtgtgagag  147780
gtcgagtggg ggcattatcc tgctcccgct cctgctggct gtatctggtc agcctgggca  147840
ccgaggcggg ttctggaaag cactgttcac agatgcttat ctgagtcccc cagannnnnn  147900
nnnnnnnnnn nnnnnnnnnn nnnnnnnnnn nnnnnnnnnn nnnnnnnnnn nnnnnnnnnn  147960
nnnnnnnnnn nnnnnnnnnn nnnnnnnnnn nnnnnnnnnn nnnnnnnnnn nnnnnnnnnn  148020
nnnnnnnnnn nnnnnnnnnn nnnnnnnnnn nnnnnnnnnn nnnnnnnnnn nnnnnnnnnn  148080
nnnnnnnnnn nnnnnnnnnn nnnnnnnnnn nnnnnnnnnn nnnnnnnnnn nnnnnnnnnn  148140
nnnnnnnnnn nnnnnnnnnn nnnnnnnnnn nnnnnnnnnn nnnnnnnnnn nnnnnnnnnn  148200
nnnnnnnnnn nnnnnnnnnn nnnnnnnnnn nnnnnnnnnn nnnnnnnnnn nnnnnnnnnn  148260
nnnnnnnnnn nnnnnnnnnn nnnnnnnnnn nnnnnnnnnn nnnnnnnnnn nnnnnnnnnn  148320
nnnnnnnnnn nnnnnnnnnn nnnnnnnnnn nnnnnnnnnn nnnnnnnnnn nnnnnnnnnn  148380
nnnnnnnntt gcagtgagcc aagatcacgc cattgcactc cagcctgggc ggcagagcga  148440
gactctgttt caaaaaaaaa aaaaaaaaaa aaaaaatctt taatgttcat tgtttttgtc  148500 cttttttattc ctaggtccca caagcagaga aaatattact tttgttttta tttatgttct  148560
ttattctaga aagtagttaa gagacctcac atgtagtgat agagatgtat ataagagaca  148620
gtgagagggc ctgagctgga cttaagcaag gaccgtgaga caccaaaagg ggtgaggaca  148680
gagtggagtt agctgagatg ctcaggagga agtagatgcc atgaagggct ctgttgtggg  148740
gggctgcagg cttggccctg agtgtccctg tggccagttg ttgggggggg cccagtgtgc  148800
aggcagacag ctcggccact ttgtggcagg tcacgttggt ctgtgcttct gtttcctcct  148860
caggtaagtg aagggattta agggtccagg tgtggtggct cacacctgta atgtataaca  148920
ttttaggagg ctgaggccgg aggctcacct gagctcaggc ggttgaggct gcagtgagcc  148980
atgattgcac cactgcactc cagcctgggc aacagaccaa tactctgtca cttaaaaaaa  149040
gtgtaaacag aaacacaggg ccatttacat atgatgcac atggcaggag ccccacaggt  149100
gtatgctcag gggagggccc agctttgctg gctgacttgc acctatccct ccaccctgtg  149160
ctgtgtcttt cgctcactgg gttcctggtt tagtgaaacc agttgtgcag gacggttccc  149220
ttggtagctt ttgttgcagt ggaaatgggt caggatatgg tgtgtagaag cacttatgag  149280
ctctgagagt ttcctcttat gacttcctgg cctgcagcct tcacagcaga aaccccatga  149340
tgtcacacgc ctgtttctgt tccctgctct gtgccctgta ctgtcctgtt ctgtgcctgc  149400
tggtttcagt gacaggaggc agggagctgc tggaccagcc tgtatttttc tagacatagt  149460
```

```
tggaaaaaga agtcacgctc ttctgtcctc tcacctttga cagatgtttc cacctcaaga    149520
taagtggaca tggccaatag gacgcactgt acttttcctg gatgtgtttc tgaagggcag    149580
gctgagagtg agaggcctgg agctcactgg gtgcctgtgg ccttgtcctg ccccggggga    149640
cactggtctg tgcccgagat actccctatt ccccacgccc cactgcattt gcccacatcc    149700
ttcgatgttt gccctgtgtc caatgtctgc aaaccgactg tcatgggatt atactggggc    149760
tgaagtatag tgccacccct gccctgtcgg ggacgttcag ccccagatgc cactggactg    149820
agccactgct tgcttttagg aaaggggtg ggggttatgg gtctgggctt ggggagcaca    149880
ggggctgctc cttggcctga gaattgttca tacagactcc ctgcccactc cctgcagggg    149940
tgctgggtcc caggggggaa atggcccttg gtgccaagaa cgtgagttgg gcctagggcc    150000
agtgatgatg gagaacagct ttttatgggc acacagccca tagcactgtg ccaagtgctc    150060
gaggctccca gagaagcagg cagaaaggag gacagtcgag gtgtgctgag cacgtggtgg    150120
ctgtgtgatc tggagcgcgg gtcacagagg cgcgggacg ctctggcctg gggtttacca    150180
caatgactgc cagtggcgga gatcggaaaa gaaatctcac gcgttggttc cgtgttttgg    150240
ggggttccgt gtttttggggg gttccgtgtt ttggggggtt ccgtgttttg gggactgcat    150300
tgagatctca cttacgagtg agagcgtccc cttcgtagag cctcttctg tgtcgcctcc    150360 tcagccgctc ctggggctgg ctgactcctg atccaggccc ttagcgtgtg ctggagcttc    150420
ccagcagcag tccagccccc accccaccct ctctgtggac tcccttgcct gtaagctggg    150480
gtgtctgaac gaccccttgca aaggggcaga ctgttcaacg gtaggcatgt gctgagtccc    150540
ggcggccgca cccgcccacc aggagcctgg cactgtggct gcagcgctga gcagcaccct    150600
gtttctgtgg caggtgtcca tacactctgt gtggctgggg aacagcatca cacccctaag    150660
ggaggaggaa tgggacgagg aggaggagga ggaggccgac gcccctgcac cttcatcacc    150720
acccacgtct ccagtcaact ccaggttttc caatggcctt tttcttttct acagaaattt    150780
gaaatttctt atcagtcatt tgatttgttt gaggtgcttc ttgaaatgag cctctcatct    150840
tctgtaccca gaaaacaccc atcttgcata ttctacagga aacaccgggc tggagttgac    150900
atccattcct gttcgcagtt tttactcgag ttgtacagcc gctggatcct gccatccaac    150960
tcagccagga ggaccccggc catcctgatc agtgaggtgg ttcgatccgt aagtgagcct    151020
tcccattccc ctcacactgg cacatgccac acgcaccaca cacgctgcac acacagacac    151080
gccacaccac acgtaccaca tgcaccacac acgtcaca tcacacatac cccacatgca    151140
cggaacacac acacgccaca tgcacacgta cccacatgc atgcaccaca cacacacacc    151200
acatgcacac gtaccccaaa tgcacgcccc atacacctca catgcacaca taccccacat    151260
gcacacaaca cacacatgcc acatgcacac gtaccccgca tgcacacaac acacacatgc    151320
cacatgcaca cataccccac atgcacacaa cacacacacg ccacacgtgc acacacatac    151380
accacatgca ccacgcacag cacacatgcc acacgcacac acacaccaca cacacccac    151440 acagcccata caccactttc atgcaacaca caccacacac aatgccacac tcgccacatg    151500
cacacacacc acatgtacat accacacaca tgccacacgc accacacaca tgccacatgc    151560
accacacaca tgccacacca cacacaccac acacaatgcc acactcacca catgcacaca    151620
caccacatgt acataccaca cacatgccac atgcaccaca cacatgccac atgcaccaca    151680
cacaccacac acatcacata catgcaccac gtgtactatg tacacacaca gacacaccac    151740
acgcgtacac cacacacaga cgcacacacg cgtcccgcgc agtcatgtct cttaggtgta    151800
agaacacgac ttgccagtag cggcgttctg gatgtgttgc ctggattcta actgcgctac    151860
```

```
tctcccttg ctttcctggt gttccacatc tccagcttct ggtggtctca gacttgttca 151920
ctgagcgcaa ccagtttgag ctgatgtatg tgacgctgac agaactgcga agggtgcatc 151980
cttcagaaga cgagatcctc gctcagtacc tggtgcccgc cacctgcaag gcagctgccg 152040
tccttgggat ggtaagtgac aggtggtaca gaggttcctg tcctgaagcc atgtgggccc 152100
atctgccttg ggacctggtg ttggccagag gtgccaggtg cggctgcctc cttccaagag 152160
ttgacccgag ccggactcca cagcccacgt gagctgcagt gcttctcagc tggaggggt 152220 tcagcgacgg tcagtgccat ccacaggcca ccgtgatgtg ggtcgtggcg gccaagccat 152280
ggtttggggt cccgtgtccc tgggcttgtg acatcattgt agtagcccat ccccacagaa 152340
ccatggtgtg tggtagcact gaagcatcgt agatggtgga aacgcgactg gcttccccat 152400
gctctgccct gaggcctgac tgcctcactc cccctcagtt atgttccagg cccccgaac 152460 ttcctgactg gacagcttct ctcctggggg ccattttgtc acagtgaccc tgcgtttcca 152520
gtcccaagtc tgggtgctat agtgtcttct tagcatggtt tttctcttag tctatttcgg 152580
ctgctaccac aaggtacctt agactgggtg atttataaac agtggaaatt cacttctcat 152640
agttctgggg gctggaagtt catggtcaag gtgccaacag atttggtgtt tggtgagggc 152700
tgctctctgc ttcatagatg gcatgttctc actgggtcct cacggtgaaa ggagtgaaca 152760
agctccctca ggccttttcaa aagggcccca atccacaagg gctcacccct catgacttca 152820
tcaccacccg aggccccacc ttctagtact gtggcactgc aaattagttg tcagtgtaag 152880
agtttcgggg gggatacatt cattcagacc atcccaaggg tcaagtgttc atcctcttga 152940
gctcctcctt attctgcttc tggtttatca ggattcagcc cgtgcagcac ggtacctgtg 153000
ttctgtgggc acatcaccac atggcatttc ccaagcatcc atcagctgta cacatgaaat 153060
cgctacctgt gggccccgac tgctggcaaa gcctattcaa ggatgtcaga actgtcagag 153120
ctggagcctc tgggtctttg tcatgtggca ttacctagta atccatttta tgatagcaat 153180
agaaacgcgt gtcttcaaca acacctcag tggctgccgt gtgccagccg tctggagccc 153240
ttggtgagaa tggcatggta gtgcccatca gggcctgctt accccatgct ctggatgggc 153300
tcctgtcagt aacaacgctg tcgtgacagt gatgatgttt ttttgccgtc actccagctg 153360
ctaacatttg cggagctctt cctcctgcac cccacctgac aaaggcaccc taggcggcca 153420
gcgtcagagg ttagctggct tgtctgggtc acacaaaatg cggcagaggt gggactgagc 153480
ccatgtctgt gacctgaagc ctgactccct gcgagtcttg actactcttg cctggactct 153540
gtcctccccg agcccaaact ccagtcatct tcccttgtgg gtggccgtca gcctggtgcc 153600
gtgctggtga cttggcagcc atccaggag tggaaacaat gaacgcgtgg gctccctgtg 153660
tgggcatctc tcttcactgc gagcaccctc tgggtgttgc ccacatgatg tcaaagcggc 153720
tctcggaagg ggtccttctc ctttatgggg agtttcagct gctgggctaa cttgaattgt 153780
aatgtggttt tgtgctcagg cccagagctc cttaggcaag tgttgtgcca tcagtaatca 153840
aatgagaaat aatcattttg aaaagcagat cctaaggcag gatggtcatg ggcactaatt 153900
cccagctctg tgcatctttc ttgaagacgg tgatcctctg tgaaggtttt cagcatgtca 153960
tgcttggtac cagcgtatcc agagcatgtc attttgaggt atttgcctcc tgttgtgaaa 154020
tccgtgccac ctgagagcag gtcctgatgt gggactttca gaggtgggac caggggccgt 154080
gggagcgcag tccttaggga ggtgccgcgt ggcgttgtgt gtatgagggg atagcacagg 154140
gtgaggtggg ggcccaagaa ggaagtgatc caccaaagaa cagcctcttt cggtcctcat 154200
```

```
tcctgggatg ggtgggagcg gcttctgtgt cttccggtca tttccctgc ggagaagctc    154260
ctgccactgc caagaacctc atcttgttcc acaacaagaa gaggctgcct ggccatccag    154320
cgctccatgg gaattctgtg tccccatagt cttgggctga agagagcga catacctgg    154380
tgacttctgc aggggtctcc tcactgttaa agagcagatt gaaagtgaag aatgtgggct    154440
aagtgtttag gtcgatattt aaccccatta ggttttggat actaagtgaa attgaggcca    154500
ttttggttga aggttggcat aaactactat cagggatccc caagactacc cccaggcttt    154560
tctagaagga ctctcagcta agatgtaata cagtaaaagc acacaaaaca caatcagcaa    154620
accaaatcag caagggcaga ggcccatggg gcggtgtccc gaggaaacca ggcccgagct    154680
tccagaatcc tctcccggcg gggtcgtgca ggacacactg agctccccca gagtgagccg    154740
tgacagcgtg tgcagtgtcg tcaccaggct caagcttcca gaatcctctc ccagtggggt    154800
cgtgcaggac gcactgagct ccccccagagt gagctgtgac agtgtgtgca gtgttgtcac    154860
cagggaagcc cactagagac tcggtgccag ggttttgact gcgggctggg cacgtgggca    154920
ccttctgcct gcttcgtgcc catactctgg actcccagag ggaaggcaga ttctcagcac    154980
aaacaccgtt gcccacacaa gcagctgagc acagagagcc cctcctcagt gaggatggtg    155040
ggcaccgtcc cgacaccagc caggggccag ccttgcacac agacctctca ggatggtctt    155100
gggccgtgca cacaagcatg agggcagcgc accgcccccg cccctccttg gctgtgggga    155160
ggagccactg gggcgtgagc tctggtggca tcagcagctt ttgtctgtgt gtgtctagga    155220
caaggtcgtg gcggagcctg tcagccgcct gctggagagc acactcagga gcagccacct    155280
gcccagcagg gtcggagccc tgcacggcat cctctatgtg ctggagtgcg acctgctgga    155340
cgatactgcc aagcagctca tcccagtcat cagtgactat ctcctctcca acctgaaagg    155400
gatcgcccag tgagtgggag cctggctggg gctaggacgg gggtctcgga atgagctgcg    155460
aaggaagcag catcaccctc tccaagtgcc caggtccctg gccagatggc aggcaggtgt    155520
cagtgggaac ccaggtgggc gccatggctg aggttggtga gacgcaaggg cacaggtgtg    155580
tcctagaggc ttcctcgggc accccagtg agctagagct cctgcctctg ctgctgtctc    155640
atgtggcgct gagcacattt ccccatgtgc ccattcctga ctctgctcgc gaggccagcg    155700
gttctcattc tctgctctca gaaccctctc ctcattaccc aggccagcct cctctctgca    155760
ccttccccgc cctggcccag cacctccctc ctgtttccac tgtgactccg acctcacttt    155820
atcttaaagc tgctgggcgg caggttctgc acagatgtgt ccttgacaaa gcacggctgg    155880
tgccacaacc ccttaacgag caagtcaagc tcttcacaac gatgtcttgt gagtgcggag    155940
ggctctgtga caccctggtc tcacctccgc tctcccgaag tcgcagaggc tttagcagag    156000
atgggcccag cctctctgag tcacaggctt tagagctgtc tgtagaggga gggtagaatt    156060
tcatcagcca cccacatggg ggagttgagg gcaagaattt ggagcaaaga tgggaaaggg    156120
gctgggaaga atggccagtg atcccctttg acaagtgggc aggagatggg ggccgggtca    156180
aagttgagtg gaagacttgg agggagatgg gaagatctct gtaggcacag ttcagacagg    156240
agggaggtgt gagccagggc actggctggt ggctgtctgg caggatttgg gacatcctgg    156300
agcagggaca gtggctcaac aggggccatt gccctcatcc aggccagagt ggcacaagct    156360
tgtggggagg cccttctcgt ctgtcatcct tgctgggcgg tgggtgctgt gctagcagga    156420
cgcaggacag gcggacagct ggcaactgtc tctgcatccc tggagcctgg cataggcaa    156480
gtcacacggg gacacaggc ctgcaaatca ggcacatgcg ttggtgcagc gaggtgattt    156540
tgggggcag ccccacaaca ggccccaggc acaggccaaa gccctggctg tgctggcgtg    156600
```

```
ttgggccgtc tatggctctt gctgtgggca tggaggactc aggaaaggag agttgaggtg 156660
gcccaggagt tgcgtttggg atgcagagag cttgtggcat ccaggtagaa atggtgtgtg 156720
gggctggcct cagtgccatg ggcacgggct gtgtcacatg cctccgaggt agaggtggga 156780
ccacgtggtg atggatataa gcatcactgg gcacatttct gtgggtggag gggggcatct 156840
tactggctcc tctgttcaca gtggccactc attcagtccc tggctaccgg gtccccattg 156900
tgccatgggg aaggcaggtg ctgtcggggg atcacacaag gcagcacgtc atggtggaat 156960
gtgccacgaa ggaaaagcac agggcactca ggaagtagag gggactggcc tggggtgtgg 157020
gaatccaggg cctctttgag ggacagagag aggaagtctg tggtggccag tatggaggtg 157080
gccacagggg aggctgggcc aggccgagag ggcagggcgt ggaggaggta gacgggctca 157140
gctatccagg gaggggtcga gcagaggctg aagggtcagg ccaggttaca ggggcctggg 157200
gagccacaca gggtaggtgc ttccgggagc cagcctggcc cgcagctctt cactcccgcg 157260
tggggccggg catgctgcga agccctctct acgttggatg gggcggctg agcctggctg 157320 ctgtctcccg ttttcagctg cgtgaacatt cacagccagc agcacgtact ggtcatgtgt 157380
gccactgcgt tttacctgat tgagaactat cctctggacg tagggccaga attttcagca 157440
tcaataatac aggtgagtgg gccctggctg tcttcctctg cacacgggga gtgggcttcc 157500
cttctctttt ccttgcggga tcataccagt gggccagttt tgacttggtg gggaggaggc 157560
atgaacacct gagaccatgc agcgacagaa acctttctcc ctgtgcagat gtgtggggtg 157620
atgctgtccg gaagtgagga gtccaccccc tctatcattt accactgtgc cctcagaggc 157680
ctggagcgcc tcctgctctc tgagcagctc tcccgcctgg atgcagaatc cctggtcaag 157740
ctgagtgtgg acagagtgaa cgtgcacagc ccgcaccgcg ccatggcggc tctgggcttg 157800
atgctcacct gcatgtacac aggtgagcag gtacacagtg cccgcaaggc cagcccaagt 157860
cctgttcaag ggagacagga gcatgctcgc tcaaggaacc tagactaggt gtcctctgat 157920
ttgacacttt tagtgttgcc ccaagctggc cccatcacct gcaagagag gctctggagc 157980 ccccagggct ggagtacctg gtcagggttg accacccctc tggtcactca tcccatgtgg 158040
ctgagctgtg ctgggtcctg ggctagcgag gggctcacat cacctgctgt caggtcttct 158100
ccagtgattc attggactcc tgtgtacaaa gcactatcta cagagcctgt tgggttgtat 158160
agatgtaacc ttcgtactga acactttat tacaggaaag gagaaagtca gtccgggtag 158220
aacttcagac cctaatcctg cagccccaga cagcgagtcg gtgattgttg ctatggagcg 158280
ggtgtctgtt cttttttgata ggtaagaaac gaagccccat ccctcagccg ttagcttccc 158340
tagaattttg gcctgaagct gagcgtttgt gtgtgttggc tgatcccctg gcgctgttgc 158400
tggagtcccg ccagtgattc ctgaccacag cctgaccgtg ggctgccttg gctcagggtt 158460
ccactggcga gctggtggtc cttggacccc agcgctcagg tgtagtgttg accagttcca 158520
aggttgtccc agcgcctgcc catctctcct gagggctcag gcaccgcacc tggccgtgtg 158580
gggtatggca gggggcagga atgaccagtc tctgggaggg tgcggcagaa gcctgcgcag 158640
tgatgaggag ttggctcagc ctggctgcct gtcgtgagag gggagcccac gggggtctgt 158700
gggagggggt ccatggtgcc tgtgagcagg gtgaggggca gcagcaggag gaggaaggtg 158760
aaacccacac atgcatcttt gagacccgtg tggtcagtgg cttctcctcg ctaccctcc 158820 gccccactgc tgtgcgtgaa ttggtgttga gaattggctt cgctcccctg ctctggaagt 158880
gggttaggag cttcgtaggg cttttctca aggacaaggc tccctgattg ctctcaggcc 158940
```

```
tcagtcctgg cgacatggcg gatctggggc gttgttgtgc tgccttgcct gtgctctcca 159000
atcagggtgt cccagtcctg gcgacatggc ggatctgggg cgttgttgca ctgccttgcc 159060
tgtgctctcc aatcagggtg tccagtgggg agccatttgg cttttctcaa gagcatactc 159120
aggtggactt tgctctattc tttggccaga tgaggtgttc tgaacagctg agcctgtgct 159180
tgtctgtttt catgtttttt tttttttttg agatggagtt ttgcccttgt cacccaggct 159240
ggagtgcaat ggcgcgatct cggctcactg caacctccac ctcccgggtt caagcgattc 159300
tcctgcctca gcctcccaag tagctgggat tacaggcacg tgccaccacg cccagctaat 159360
ttttgtgttt ttagtagaga cagtgcttca ccgtgttggc cgaactggtc tcgaacttct 159420
gaactcaagt gatccaccct cctcggcctc ccaaagtgct gggattgcag gcatgagcca 159480
ccgtgcctgg cccccatgtc gattttaaaa cgcacctctg catcattctt cagttcccac 159540
atgctcactg agcaccacca cagctggcag acggacacag ggaggcgcca cgaccagtcc 159600
tggccttcaa ggggcttgtg gtctagtgga cccagtgcta ggtggcgagt gctccagaga 159660
gcgtggtgta tgccttccgc tctaccgccc tccagacgcc gcaggaggc accttggagc 159720 tgaccacaga tctccctccg tggagcactg tcttcagcgc agccgccatg ccactgctgg 159780
gcgagggtct gcgggcgggt agagccagga gcacctctga gaaagtgcac tgccgttct 159840 tggctgcttc ctgtgcatct cagttacaca cagctggcat gtgtgcactg atgagacagg 159900
aacatgatgg ttgcttttca gcactaaaaa ggatactgct caggggggcgt gtttcaggat 159960 ctggttaggg aaaaagcagc gagagcacag atggggccct gtttggtaac aagaaaaaag 160020
tcccggttga caacagtgct acaaagtgtt agaacacata gaaatgttta tggagcattt 160080
ggatgtggaa agcagcaaaa acataatgag aaggggttct tttgttagga ttttaaaaa 160140 tctcttttgt aacatccttc cggctgcacc atttctgcat attctttat gtagctttca 160200 gactcttagg atttctggtc actgcagggc gtgggagcca acagagcct atgcctagca 160260 gcctgtcttc acgagctgga cagaggagga gctggggttt tgccttttta gcctcaaatt 160320
tcatactcca gttgcttagg ctctgacttt ccccacttgg aaagtccctc acggccaagg 160380
gtacctccca gccctgattt cacatcagca ttttccccag agccaaggcc ctccgcgggc 160440
aggtggggca gctgtgggag ctggtgccag gctctgacct gtgtccctcc tcccaggatc 160500
aggaaaggct ttccttgtga agccagagtg gtggcgagga tcctgcccca gtttctagac 160560
gacttcttcc caccccagga catcatgaac aaagtcatcg gagagtttct gtccaaccag 160620
cagccatacc cccagttcat ggccaccgtg gtgtataagg tgaggttgca tgtgggatgg 160680
ggatggagtg gggaagcctg gaggtggaat tgaccccgac ttgccagcag attcgccaga 160740
agaacccagc cctccccctt taaagcagca atgcctctgg cccccacccc accccaccca 160800
cccgggcaca gcaggtgctt cccgccccc agccctgaca ctcaggcgcc cgcttgctcc 160860
tggcaggtgt ttcagactct gcacagcacc gggcagtcat ccatggtccg ggactgggtc 160920
atgctgtccc tctccaactt cacacagagg acccagtcg ccatgccac atggagcctc 160980 tcctgcttct tcgtcagcgc gtccaccagc ccatgggttg cggcgatgta tcctctctgg 161040
gtccctggtg ctggccccgt ttccctcgtc aacaccgagg ctcatgtttc atgataaagt 161100
tttgaaacct aacctttgca aaagccccac agatgccaag gtgacaggcc ctcagcccca 161160
gggaagtaca atgctgacag ggatacagaa aggagcacat ccagacattt gctgaccagg 161220
gcctctcaga ggggcccgtg tatggcagaa gggtcgaagc tgctaagggg cccttctgtg 161280
gagggcctgg gtgaggggag cgagggtggg cggcggtctc tgcagacctc ccgcccactc 161340
```

```
gcgggctctg tgtggctggg cttctcctga cactgcttct cattagcttt ggtcattgtg 161400
cctcgatcac cctctcgggg aaaggcttaa gtaaagatcc agttcccacc cccagatgct 161460
ggctgccagg agtttccctt tccacagccc tcccccaaga cagaccacaa gagcctccga 161520
gcagcacggt tgtcctggtg ctgacagcac agcctcgccc agtgtgcctg gcgtggtctc 161580
gcccgcactg tactggagca gggctcgtgg gggccagcag gacagcagga gcatcggcca 161640
ccagcgctac acaggagcca ggccaggtga gtgctgccga gtgggtgcct gcctgcaggc 161700
ctcctgcttc cttggccagc tctgcccagc tcacttctgc cctgctggcc ttccagcagg 161760
gtgtccagcc agccaagggt tgcaggaatg aaggtggagg cgctgctgca gctggagcca 161820
tccaggtagc ccttccgggg ctctgctggc tctccaggct ccctgggccc cttcgtaggc 161880
tgtttcagga gaggagctcc caggtgagga cagggaggca gcattcccct catttgccgg 161940
cctttttcct taactcctgc accagcctcc cacatgtcat cagcaggatg ggaaagctgg 162000
agcaggtgga cgtcaacctt ttctgcctgg ttgccacaga cttttacaga caccagatag 162060
aggaggagct cgaccgcagg gccttccagt ctgtgtttga ggtggttgca gctccaggaa 162120
gcccatatca ccggctgctg acttgtttac gaaatgtcca caaggtcacc acctgctgag 162180
cgccatggtg ggagagactg tgaggcggca gctggggctg gagcctccag aaatctgcgc 162240
cctgtgccct gcctccaccg agccagcttg gtccctgtgg gcttccgcac atgccgcggg 162300
cggccaggca acgtgcgtgt ctctgccata tggcagaagt gctcttttgtg gtacagtggc 162360
caggcaagga gtatctgcag tcccggtggg gctgagcctg aggccttccg gagagcagga 162420
gcagctgtgc tgcacgccat gtgggtgacc aggtcctttc cctgatgct cacctgttgg 162480
gtgttgccag gctgcagctg ctcttgcatc tgggccggaa gtcctccctc ctgcaggctg 162540
gctgtgggcc cctctgctgt cctgcagtag aaggtgccgt gagcaggctt tgggaacact 162600
ggcctgtgtc ttcctggtgg ggtgtgcatg ccacgccctg tgtctgtatg cacagatgcc 162660
atggcatgtg ctgggccagt ggctgggggt gctagacacc cagcaccatt ctcccttctc 162720
tcttttcttc tcaggattta aaatttaatt atatcagtaa agagattaat tttaacgtaa 162780
ctctttctat gcccgtgtaa agtatgtgaa ttgcaaggcc tgtgctgcat gcgacagtgt 162840
tcggggaggt gggcagggcc cctggccacg ctccctctcc tgtagccact ggcatagcct 162900
tcctgagcac ccgctgacat ttccgttgta catgttcctg tttatgcatt cacaaggtga 162960
ctgggatgta gagaggcgct agtgtgcagg tggccacagc aggactaagg acaggcccc 163020
actgtcctag gggcatgctc gcctgcagcc cctccttctt gggcacagac aactgttgtt 163080
ctccacccac attagggaca gcagcctccc tatcagctga gaaggccagc cctccctggc 163140
tgtgagcagc ctccgctgtg tccagagaca tgggcctccc actcctgttc cttgctagcc 163200
ctggggcggt gtctgcccag gagctggctg gccggtgatg ggatctgccg ttccatggat 163260
gcatgcccca agggtgtcac tgagctgtgt tttgtctgag cctctcttgg tcaacagcaa 163320
agcttggcgt cttggcactg ttagtgacag agcctggcat cccttctgcc cccgttccag 163380
ctgacatctt gcacggggac cccttttagt caggagagtg cagatctgtg ctcattggag 163440
actgccccac tgccctgtca gagccgccac tcctatcccc aggccaggtc cctgaccag 163500
cctcttgttt gcaggcccag aggagccaag tcattaaaat ggaagtggat tctggatggc 163560
cggctgctgc tgcatatagg actggatttg ggagctctga gatggggcag gagctctgct 163620
tcctcagccc ttgaggcgag ccaggcgagg ttggcgactg tcatgtggct tggtttgctc 163680
```

```
atgcctgttg atgttttggg tattgaatat ggtaagtgga ggaaatgctt ttctggagtc 163740
tgtgcaggtg ctgccttgag accctcaagc ttccacctgt ccctctccta tgtggcagct 163800
gaggagcagc tgacatgtgg acttgtgtgc tgcccacata catgaggggg cgctgaaagg 163860
gagcccctgc tcaaagggag cccctcctct gagcagcctt tgacaggcct gtatgaggct 163920
tttcccacca gctcccaaca gaggcctccc ccagccagga ccacctcgtc ctcgtggcag 163980
ggcagcagga gcggtagaaa gggtctgat gtttgaggag gcccttaagg gaagctactg 164040
aattttaaca agaaagccac cattcttccg tattggttgg gggctcctgt ttctcatcct 164100
agcttcttcc tggaaagcct gctagaagct tgggaatga ggggaaagtt ctcagaaccg 164160
ttgctgctcc ccacccacct cccctgcagt aagttatgtc aacagctcgg agacagaagt 164220
atcacaggcc agatgttgtt ctgctagatg tttacatttg taagaaataa cactgtgaat 164280
gtaaaacgga gccattcccc ttggaatgca tatcgctggg ctcaacacag agtttgtctt 164340
ccttttgttt acgacgtgat ctaaaacagt ccttagcaag gggctcagaa caccccgctc 164400
tggcagtggg tgtcccccac tcccaaaggc ctgcctgtgt gctccagaga tgaatatgag 164460
ctcattagta aaatgacttt acccatgcgt aagtcaagta cacgtgcacg tgcatatgga 164520
cacatctgta gttttataca cgcacatctc aagacagaga tgcatggcct ccaagagtgc 164580
ccgtgtcggt tcttcctgga agttgacttt cctcagacct gccaggtaaa gttagctgtg 164640
tgacgggcgt ccaggcgcgg gcttggtca gagcagggct cattcatggc tcactaggat 164700
cccaccggag aaaacggtct ccatatcaac tctgccgaag ggaggaagac tttgtcgcgt 164760
tcctaaaaaa cctatggcaa gcaccaatca tattatccaa attgtgttga aaatgtgatt 164820
aatttggttg tcaagttttg ggggtgagct gcggggagac tgcttttgtt ttgctgctgg 164880
taatatcagg aaagacttta atgaaaccag ggtagaattg tttggcaatg cactgaagcg 164940
cgtttctgtc ccaaaacgtg cctcccttcc gctgcgggcc cagctgagtc tgtgtaggtg 165000
acgtttccgc tgccaagcg ctctttgtta ctgtccaccc ccatttctgc cagcacacgt 165060
gtcctttcag gaggaaaatg tgaagctgaa acccctccag acacccagaa tgtagcatct 165120
gagaaggccc tgtgccctaa aggacacccc cgccccacc ttcatggagg ggtcattcca 165180
gagccctcgg agccgatgaa cagctcgtcc tcttggagct gagctgagcc ccccacggag 165240
ctcgggacga atagtaaaca gcaataactc ggtctgtggc tgcctggcag gtggaagttc 165300 ctcccctga ggggcggagt gaggttagtt ctgtgtgtct gtggggtgga gtcagcctgc 165360
tcctgctacc tgtgagcatc ctgcccagca gacatcctca cccggctttg tccctcccca 165420
cttcctccct ctgcggggag gacccaggac cacagctgct ggcagggta ggcttggagc 165480 tgtgctccgg aggggccacc tgtgggagcg agaagaagga agatcttgag agctgccgag 165540
gcaccctgga gagctcagga tggtccaggc gagaagagga cactcgctcg ccaggcctgg 165600
gcctcctggg aaggagggag ccgctcagag cgccgcatga caactgaagg caacctggaa 165660
ggttcagagg ccactcttcc cccgtgtgcc tgtcacgctc tggtgcagtc caaggaacgc 165720
cttcccctca gttgtttcca aaagcagagt ctcccgctgc aatctgggtg gtgattgcca 165780
gccttggagg attgtggcca acgtggacct gcctacggag ggtgggctct gacccacgtg 165840
gggcctcctt gtccaggtct cattgctttg tgctgtggtc agagggactg tcagctgagc 165900
ctgagctccc ctggagccag cagggctgtg atgggcgagt cccggagccc acccagacc 165960 tgactgcttc tgagagcaaa gggaaggact gacgagagat gtatatttaa ttttttaaac 166020
tgctgcaaac attgtacatc caaattaaag gaaaaacatt gaaaccatca gttgttgctg 166080
```

-continued

```
tgtgaggctt gctttacttc atgagaacct agaccttgct gagctggagt cttaggaaac   166140
tgtctcctaa gtgcttatcc agcaggggca gaaactgtcc caccagctaa catctgacat   166200
tacggagggt cccgcaggca gctgccagca aggacaagcc ctgtgttttc tgtagccagg   166260
gatgaggaag tggccccagg ggcctggctg ggtgctgctt caagggcctt cgcaaaccac   166320
agtacaggtg gtcttcctgc actgcagatg ggagctgtgg gagctgctgg atccttcatg   166380
gtcaagtgac atcataagct tatatgacac acacaagcct caggacttgg cccatggcac   166440
tggagcaggt catcaggccc agcagactag agctgtgttc tcacagggcc catgaccctt   166500
ctagctcctt ggccattgaa acctgtgtcc ctgacccagc tgctcccagg tacccccaa    166560 agcagctggc acatcccacc tctggtgtgg cctgggctgc tgtgtgtccg cagggcctgc   166620
cccgtctgtt ctagcttgtt tctcctgtct gaaccagcgc ctactccaag aaggctctgc   166680
tcagcccagc ggggatgctt ctaagctcgg cccagcctct gggaagcctt ggtggtcggt   166740
ggtgtagtca tcctgggatg cagaacgaaa acctgcaaga acaaaactgt ggcttcgtct   166800
ggtgcagggt atttagttac tgtttgctga ggtcctgtct ggttctggcg aatgggcagg   166860
ggtcgcccac ccattctttc cctgctctgc tgtccgtgcc aggagagacg ggggcctgtt   166920
ggccaagggg gcagctcctg ctgcctgctg tccttaggca cgtgcaggga ccccctttct   166980
ctgagcagga tggggatcag tctgccagag ggatgtggtg gacaggccca gccgggtaaa   167040
aaattccccc agttgctcaa agcatttggg gcggggcatg ccacttgagc tccttaaatc   167100
tgtctcatag gtgacaccgc tccagggcgc cccaggggct tctcccttca gagctaccaa   167160
agttctggtc acttcagaaa aatggagcac ccccttctcc ctggtccaga tgtggacagc   167220
cagacccttg gcacacctag cacacctggc atggctggta atttcagaaa gaaaagggc    167280 cggggtccag tgggaagcag tggcgaaccc ctcatgcgtg ggctttgcga tccctccccc   167340
tgccacggca gagctgccct cagcacagcc ttcctcttcc tcatcggaga gcacaccctg   167400
tccccttgcc ggggctgtgc tctgtgcctg cagtggtatt tggttttggc tgctactggc   167460
tttgttccaa agaggatctg gaagtcgctt ccctgtgtg gagcgtggag cactgtgagt    167520
cagatgaggg aagtagccag ggggaggtga gtacccggcg gagccgccac agaaaggact   167580 gggtagggg ccttgcctcc acgtgatgtg acacggccag ccgaggacag aggaagcccc    167640
gttcctgggg gtgtggggtg caccctcag gaagcctgc agtgggccc aagggaaggc     167700 gttctctgcg agcccacgag tctgctctgt gggcaccgtg acaatgcccg tgggcagagg   167760
tgggcccggc cttgtgtcgt caccaggacc tcttttggga aaccatgtgg gcatcccttg   167820
cgggtccccc aggttctgca gtcccagcgg cctggctgcc tgttgggcac atggcttgag   167880
ccgcccagag ggcccagccc tgttggcagc cacatcctct ggaggccctg ccggtggggc   167940
tggctttctc taccccacac caggcctcca agtatactgg tcggggtgt ctgggccctg    168000 gg                                                                  168002
```

<210> SEQ ID NO 5
<211> LENGTH: 10295
<212> TYPE: DNA
<213> ORGANISM: Rattus norvegicus

<400> SEQUENCE: 5

```
gcactcgccg cgagggttgc cgggacgggc ccaagatggc tgggagcttt ggttccgctt     60
cggtctacct cgtagagccc cattcattac cttgctgcta agtggcgctg cgtagtgcga    120
```

```
ataggctcca agccttcagg gtctgtcctg tcgggcagga ggccgtcatg gcaaccctgg      180
aaaaactgat gaaggctttc gagtcgctca agtcgttcca gcagcaacag cagcagcagc      240
agccgccgcc gcaggcgccg ccaccaccgc cgccgccgcc gcctcaaccc cctcagccgc      300
cgcctcaggg gcagccgccg ccaccaccgc cgctgccagg tccggccgag gagccgctgc      360
accgaccaaa gaaggaactc tcagccacca agaaggaccg tgtgaatcac tgtctaacaa      420
tatgtgaaaa cattgtggca cagtctctca gaaattctcc agaatttcag aaactcttgg      480
gcattgctat ggaactgttt ctgctgtgca gcgacgatgc ggagtcagac gtcagaatgg      540
tggctgatga gtgcctcaac aaagtcatca agctttgat ggactctaat cttccaaggc       600
tacagttaga actctataag gaaattaaaa agaatggtgc tcctcgaagt ttgcgtgcag      660
ctctgtggag gtttgctgag ctggctcacc tggttcgacc tcagaagtgc aggccttatc      720
tggtgaatct tcttccatgt ttgacccgaa caagcaaacg accggaggag tcagttcagg      780
agactttggc tgcagctgtt cctaaaatta tggcctcttt tggcaatttc gcgaatgaca      840
atgaaattaa ggttctattg aaagctttca tagcaaatct gaagtcaagc tctcccactg      900
tgcggcggac agcagctggg tcagcagtga gtatctgcca gcactctagg aggacacagt      960
acttctacaa ctggctcctg aatgtgctcc taggtttgct ggttcccatg gaggaagacc     1020
accccactct cctgatcctt ggtgtgttgc tcacactgag gtgtctagtg cccttgctcc     1080
agcagcaggt caaggacaca agtctaaagg gcagctttgg ggtaacacgg aaagaaatgg     1140
aagtctctcc ttctgcagag cagcttgtcc aggtttatga actgactttg catcacacac     1200
agcaccaaga ccataatgtg gtgacagggg cattggagct cctgcagcag ctcttccgta     1260
cccctccacc tgagctgctg caagcactga ccacaccagg agggctcggg cagctcactc     1320
tggttcgaga ggaagccggg ggccgaggcc gcagcgggga tatcgtggag cttttagctg     1380 gaggggttc ctcatgcagc cctgttctct caagaaagca aaaaggcaaa gtgctcttag     1440
gagaggaaga agccttggag gatgactcgg agtccaggtc agatgtcagc agctcagcct     1500
ttgcagcctc tgtgaagagt gagattggtg gagagctcgc tgcttcttct tcgggtgtct     1560
ccactcccgg ttctgtaggt cacgacatca tcactgagca gcctcgatcc cagcacacac     1620
ttcaagcaga ctctgtggat ttgtcaggct gtgacttgac cagtgctgct actgatggag     1680
atgaggaaga catcttgagc cacagctcca gccagttcag tgctgttcca tccgaccctg     1740
ccatggacct gaatgatggg acccaggcct cctcacccat cagtgacagt tctcagacca     1800
ccactgaagg acctgattca gctgtgactc cttctgacag ttctgaaatt gtcttagatg     1860
gtgctgacag ccagtattta ggcgtgcaga taggacagcc acaggaggaa gacgaggagg     1920
aagctgcagg tgttctttct ggtgaagtct cagacgtttt cagaaactct tctctggccc     1980
ttcagcaggc acacttgttg gaaagaatgg gtcatagccg gcagccttct gacagcagtg     2040
ttgataagtt tgtttcaaaa gatgaggttg ctgaagctgg ggacccagaa agcaagcctt     2100
gccgaatcaa aggtgacata ggacagccta atgatgatga ttctgctcct ctggtacatt     2160
gtgtccgtct tttatccgct tcctttttgt taactggcga aaagaaagca ctggttccag     2220
acagagatgt gagagtcagt gtgaaggccc tggccctcag ctgtattggt gcagctgtgg     2280
cccttcatcc agagtcgttc ttcagcaaac tctacaaagt acctctcagt accatggaaa     2340
gtactgagga acagtatgtc tctgacatcc tgaactacat cgatcatgga gaccctcagg     2400
tgcgaggagc tactgccatt ctctgtggga cccttgtcta ctccatcctc agcaggtccc     2460
gtctccgtgt tggtgactgg ctgggcacca tcagggccct gacaggaaat acattttctc     2520
```

-continued

```
tggtggactg cattcctttta ctgcagaaaa ctttgaagga tgaatcttct gttacttgca    2580
agttggcttg tacagctgtg aggcactgtg tcctgagtct ttgcagcagc agctacagtg    2640
acttgggatt acaactgctt attgacatgc tgcctctgaa gaacagctcc tactggctgg    2700
tgaggactga actgctggaa actcttgcag agattgattt caggctggtg agttttttgg    2760
aggcaaaagc agaaagttta caccgagggg ctcatcatta tacagggttt ctaaaactac    2820
aagaacgagt actcaataat gtggtcattt atttgcttgg agatgaagac cccagggttc    2880
gacatgttgc tgcgacgaca ttgacaagac ttgtcccaaa gctgttttat aagtgtgacc    2940
aaggacaggc tgacccagtc gtggctgtag caagagatca aagtagtgtt tacctgaagc    3000
tcctcatgca tgagacccag ccaccatccc acttctccgt cagcaccata accagaatct    3060
atagaggcta cagcttacta ccaagtgtaa cagatgtcac catggaaaac aacctctcaa    3120
gagtcgttgc cgcagtttct catgaactca ttacgtcaac tacacgggca ctcacatttg    3180
ggtgctgtga agccttgtgt gttctttcag ccgcctttcc agtttgcact ggagtctag     3240
gatggcactg tggagtgccc ccactgagtg cctctgatga gtccaggaag agctgcactg    3300
ttgggatggc ctccatgatt ctcaccttgc tttcatcagc ttggttccca ctggatctct    3360
cagcccatca ggatgccttg attttggctg gaaacttgct agcagcgagt gcccccaagt    3420
ctctgagaag ctcatgggcc tcggaagaag aaggcagctc agcagccacc agacaggagg    3480
agatctggcc tgccctgggg gatcggactc tggtgcccat ggtggagcag cttttctccc    3540
acctgctgaa ggtgatcaat atctgtgctc atgtcttgga tgacgtgact cctggaccag    3600
caatcaaggc agctttgcct tctctcacaa acccccttc tctaagtcct attcgacgga    3660
aagggaagga gaaagagccc ggagaacaaa catccactcc gatgagtccc aagaaaggtg    3720
gagaggccag tacagcctct cgacagtcag acacctcagg acctgtcaca gcgagtaaat    3780
catcttcact tgggagtttc taccatctcc cttcctacct cagactgcat gatgtcctga    3840
aagccactca cgccaactat aaggtcacct tagatcttca aacagcact gaaaagtttg     3900
gggggttcct gcgctctgcc ttggacgtcc tttctcagat tctagagctg gcgacactgc    3960
aggacattgg aaagtgtgtt gaagaggtcc ttggatactt gaaatcctgc tttagtcgag    4020
aaccaatgat ggcgactgtc tgtgttcagc agctattgaa gactctcttt gggacaaact    4080
tagcctcaca gtttgatggc ttatcttcca accccagcaa gtctcagtgc cgagcacagc    4140
gccttggctc ttccagtgtg aggcccggct tatatcacta ctgcttcatg gcaccataca    4200
cgcacttcac gcaggctttg gctgatgcca gcctgaggaa catggtacag gcggaccagg    4260
agcacgatgc ctcagggtgg tttgatgtac tccagaaagt gtctgctcag ttgaagacga    4320
accttacaag tgtcacaaag aaccgtgcag ataagaacgc tattcataac acattaggt    4380
tatttgagcc tcttgttata aaagcattga agcagtacac cacgacaaca tcagtacaac    4440
tgcagaagca ggttttggat ttgctggcac agctggttca gctacgggtc aattactgtc    4500
tactggattc agatcaggtg ttcatcgggt ttgtgctgaa gcagtttgag tacattgaag    4560
tgggccagtt cagggaatca gaggcaatta ttccaaatat attttttcttc ctggtactat    4620
tatcttatga gcgctaccat tcaaaacaga tcattggaat tcctaaaatc atccagctgt    4680
gtgatggcat catggccagt ggaaggaagg ctgtcacaca tgctattcct gcgctgcagc    4740
ccattgtcca tgacctcttt gtgttaagag gaacaaataa agctgatgca gggaagagc    4800
ttgaaaccca gaaggaggtg gtggtctcaa tgctgttacg actcatccag taccatcagg    4860
```

```
tgctagagat gttcatcctc gtcctgcagc agtgccacaa agagaatgag gacaagtgga    4920
aacggctctc tcggcaggtc gcagacatca tcctgcccat gttagccaag cagcagatgc    4980
atattgactc tcatgaagcc cttggagtat taaatacctt gtttgagatt ttggctcctt    5040
cctccctacg tcctgtggac atgcttttgc ggagtatgtt catcactcca agcacaatgg    5100
catctgtaag cactgtgcag ctgtggatat ctggaatcct agccattctg agggttctca    5160
tttcccagtc aaccgaagac attgttcttt ctcgtattca ggagctctcc ttctctccat    5220
atttaatttc ctgtccagta attaacaggt taagggatgg agacagtaat ccaacactag    5280
gagaacgcag tgaagggaaa caagtaaaga atttgccaga agatacattc tcaaggtttc    5340
tcttacagct ggttggtatt cttctggaag acattgttac aaaacagctc aaagtggaca    5400
tgagtgaaca gcagcataca ttctattgcc aagagctcgg cacactgctc atgtgtctga    5460
tccacatatt caaatctgga atgttccgga gaatcacagc cgctgccact agactcttca    5520
ccagtgatgg ctgtgaaggc agcttctata ctctagatag cctgaatgca cgggtgcgag    5580
ccatggtgcc cacacaccca gctctggtac tgctctggtg tcagatccta ctgctcatca    5640
accacactga ccaccgatgg tgggccgagg tgcagcagac gcccaagaga cacagtctgt    5700
cctgcacgaa gtcactaaac ccccagatat ctgctgaaga ggattctggc tcagcagctc    5760
agcttggaat gtgcaataga gaaatagtac gaagagggggc ccttattctc ttctgtgatt    5820
atgtctgtca gaatctccat gactcagaac acttaacatg gctcattgtg aatcacattc    5880
aagatctgat cagcttgtcc cacgagcctc cagttcaaga cttttattagt gccattcatc    5940 gtaattctgc agctagtggt cttttatcc aggcaattca gtctcgctgt gaaaatcttt    6000
caactccaac cactctgaag aaaacacttc agtgcttgga aggcatccat ctcagccagt    6060
ctggtgctgt gctcacactg tatgtggaca ggctactggg caccccttc cgtgcgctgg    6120 ctcgcatggt cgacaccctg gcctgtcgcc gagtagaaat gcttttggct gcaaatttac    6180
agagcagcat ggcccagttg ccagaggagg aactgaacag aatccaggaa cacctccaga    6240
acactgggct tgcacaaaga caccaaaggc tctattcact gctggacaga ttccgactct    6300
ctactgtgca ggactcactt agcccctttgc ccccagtcac ttcccaccct ctggatgggg    6360
atgggcacac atccctggaa acagtgaatc cggacaaaga ctggtacctc cagcttgtca    6420
gatcccagtg ttggaccagg tcagattctg cactgctgga aggtgcagag ctggtgaacc    6480
gtatccctgc tgaagatatg agtgacttca tgatgagctc ggagttcaac ctaagccttt    6540
tggctccctg cttaagcctt ggcatgagcg agattgctaa tggccaaaag agtcccctt    6600 ttgaagcggc tcgtagggtg actctggacc gggtgaccaa tgtggttcag cagctgcctg    6660
cagtccatca agtcttccag cctttcctgc ctacagaacc cacagcctac tggagcaagc    6720
tgaatgatct ctttggtgat accacatcat accagtctct gaccacactt gcccgtgccc    6780
tggcacagta cctggtggtg ctctccaaag tgcctgctcc tttgcacctt cctcctgaga    6840 aggagggggca cacggtgaag tttgtggtaa tgacacttga ggccctgtca tggcatttga    6900
tccatgagca gatcccactg agtctggacc tccaagccgg cctagactgc tgctgcctgg    6960
cactgcaggt gcctggcctc tggggggtgc tgtcctcccc agagtacgtg actcatactt    7020 gctccctat ccactgtgtg cgattcatcc tggaagccat tgcagtacaa cctggagacc    7080
aacttcttgg tccggaaagc aggtcacata ctccaagggc tgtcagaaag gaggaagtag    7140
actcagatat acaaaacctc agtcacatca cttcggcctg cgagatggtg gcagacatgg    7200
tggaatccct gcagtcggtg ctggccctgg gccacaagag gaacagcacc ctaccttcat    7260
```

```
ttctcacagc tgtgctgaag aacattgttg tcagtctggc ccgcctcccc ctcgttaaca   7320
gctatactcg tgtgcctcct ctggtatgga aactcgggtg gtcacccaag cctggagggg   7380
atttcggcac agtgtttcct gagatccctg tagagttcct ccaggagaag gaggtcctca   7440
aggagttcat ctaccgcatc aacaccctag ggtggaccag tcgtactcaa ttcgaagaaa   7500
cttgggccac cctccttggt gtcctggtga ctcagccctt ggtgatggaa caggaagaga   7560
gcccaccaga ggaagacacc gaaaggaccc agatccacgt cctggctgta caggccatca   7620
cctctctagt gctcagcgca atggctgtgc ctgtggctgg caatccagct gtaagctgct   7680
tggagcaaca gccccggaac aagccactga aggctctcga taccagattt ggaagaaagt   7740
tgagcatgat cagagggatt gtagaacaag aaatccaaga gatggtttcc caaagagaga   7800
atactgccac tcatcattct caccaggcat gggatcctgt cccttctctg ttaccagcta   7860
ctacaggtgc tcttatcagc catgacaagc tgctgctgca gatcaactca gagcgggagc   7920
caggcaacat gagctacaag ctgggccagg tgtccataca ctccgtgtgg ctggggaaca   7980
acatcacacc cctgagagag gaggaatggg atgaggagga ggaggaagaa gcggatgccc   8040
ctgcgccaac atcaccacct gtgtctccag tcaattccag aaaacaccgt gctggggttg   8100
atattcactc ctgttcgcag tttctgcttg aattatacag ccgttggatc ctgccatcca   8160
gtgcagccag aaggacccct gtcatcctga tcagtgaagt ggttcgatct cttcttgtgg   8220
tgtcagactt attcactgaa cgtacccagt ttgaaatgat gtatctgacg ctgacagaac   8280 tacgagagt gcacccttca gaagatgaga tcctcattca atacctggtg cctgccacct   8340
gtaaggcagc tgctgttctt ggaatggaca aaactgtggc agagccggtc agccgcctac   8400
tggagagcac actcaggagc acccacctgc ccagccagat cggagccctg catggcatcc   8460
tctatgtgtt ggagtgtgac ctcttggatg acactgtaaa gcagctcatt ccagttgtta   8520
gtgactatct gctgtccaac ctcaaaggaa tagcccactg cgtgaacatt cacagccagc   8580
agcatgtgct ggtgatgtgt gccactgcat tctacctgat ggaaaactac cctctggatg   8640
tggggccaga attctcagca tctgtgatac agatgtgtgg agtaatgctg tctggaagtg   8700
aggagtccac cccctccatc atttaccact gtgccctccg gggtctggaa cggctcctgc   8760
tgtctgagca gctctctcgg ctagacacgg agtccttggt caagctaagt gtggacagag   8820
tgaatgtaca aagcccacac agggccatgg cagccctagg cctgatgctt acctgcatgt   8880
acacaggaaa ggaaaaagcc agtccaggca gagcttctga ccccagccct gctaccccctg   8940 acagcgagtc tgtgattgta gctatggagc gagtgtctgt gctctttgac aggatccgca   9000
agggatttcc ctgtgaagcc agggtcgtgg caaggatcct gcctcagttt ctagatgact   9060
tctttccacc tcaagatgtc atgaacaaag tcattggaga gttcctgtcc aaccagcagc   9120 cataccaca gttcatggcc actgtagtat acaaggtttt tcagactctg cacagtgctg   9180
ggcagtcatc catggtccgg gactgggtta tgctgtctct gtccaacttc acacaaagaa   9240
ctccagttgc catggccatg tggagcctct cctgcttcct tgtcagtgca tctaccagcc   9300
catgggtttc tgcaatcctt ccacacgtca tcagcaggat gggcaaactg gagcaggtgg   9360
atgtgaacct tttctgcctg gttgccacag acttctacag acaccagata gaggaggaat   9420
tcgaccgcag ggctttccag tctgtgtttg aggtggtggc agcaccagga agtccatacc   9480
acaggctgct tgcttgtttg caaaatgttc acaaggtcac cgcctgctga gtagtacctg   9540
tggaacaaga ggctgagagg aggcaactgc tgtggctaca gcctccaggg gcctgcacca   9600
```

-continued

```
agcttctgct aaggctgcct tggacgtgca ggcttccact tgtgtcaagt ggacagccag    9660
gcaatggcag gagtgctttg caatgagagc tatgcaggga acatgcacta tgttggggtt    9720
gagcctgagt cctgggtcct ggcatcactg cagctggtgg cagtgctagg ttgaccaggt    9780
gtttgtcttt ttcttagtgt tgccctggcc atagttgcca ggttcagct gccctggtat      9840
gtggaacaga atccgagctc ttgtaagatg gttctgagcc ccctgtccc actgggctgg      9900
agagctccct cccacattta cccagcaggt gtacctgcca caccagtgtc tggacacaaa    9960
gtgaatggtg tgggggctgg gaactgggac tgccaggtgt ccagcatcat tttccctttc   10020
tctgttttct tctcaggagt taaaatttaa ttatatcagt aaagagatta attttaatgt   10080
aactcttcct atgcccgtgt aaagtgtgtg acttggcaag gcctgtgctg catgtgacaa   10140
agtttatgga agtggatgcg ccttctggcc accactctct ctcctgtagc tactcagtct   10200
agtcgggcag gtccctcatg tagccctccc aacaccctat ggcacttgca cttcacacgg   10260
ctccttttttc ttatgcattc catttgacta gcaca                              10295

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
tagcattctt atctgcacgg                                                 20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
acccgtaact gaaccagctg                                                 20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ttccctgaac tggcccactt                                                 20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ctctgattcc ctgaactggc                                                 20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 10
gcctctgatt ccctgaactg                                              20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
tgcctctgat tccctgaact                                              20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
ttgcctctga ttccctgaac                                              20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
attgcctctg attccctgaa                                              20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
tggaatgatt gcctctgatt                                              20

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
gtttggaatg attgcctc                                                18

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
ccaatgatct gttttgaatg                                              20

<210> SEQ ID NO 17
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
gccttccttc cactggccat                                               20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ctgcatcagc tttatttgtt                                               20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
cctgcatcag ctttatttgt                                               20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
agctcttttc ctgcatcagc                                               20

<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 21
gtaacattga caccacca                                                 18

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
ctcagtaaca ttgacaccac                                               20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
```
atgagtctca gtaacattga								20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
tccttgtggc actgctgcag								20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ttctccttgt ggcactgctg								20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
tcattctcct tgtggcactg								20

<210> SEQ ID NO 27
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 27
attctccttg tggcactg								18

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
cgagacagtc gcttccactt								20

<210> SEQ ID NO 29
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 29
tgtcgagaca gtcgcttc								18

<210> SEQ ID NO 30
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 30
ttgcacattc caagtttggc                                               20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
tctctattgc acattccaag                                               20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
tttctctatt gcacattcca                                               20

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
tctctattgc acattcca                                                 18

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
gcagggttac cgccatcccc                                               20

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 35
accttatctg cacggttc                                                 18

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
ctctctgtgt atcaccttcc                                               20
```

<210> SEQ ID NO 37
<211> LENGTH: 20
<212> TYPE: DNA
<213> ORGANISM: Artificial sequence
<220> FEATURE:
<223> OTHER INFORMATION: Primer

<400> SEQUENCE: 37
ctccgtccgg tagacatgct                                          20

<210> SEQ ID NO 38
<211> LENGTH: 23
<212> TYPE: DNA
<213> ORGANISM: Artificial sequence
<220> FEATURE:
<223> OTHER INFORMATION: Primer

<400> SEQUENCE: 38
ggaaatcaga accctcaaaa tgg                                      23

<210> SEQ ID NO 39
<211> LENGTH: 29
<212> TYPE: DNA
<213> ORGANISM: Artificial sequence
<220> FEATURE:
<223> OTHER INFORMATION: Probe

<400> SEQUENCE: 39
tgagcactgt tcaactgtgg atatcggga                                29

<210> SEQ ID NO 40
<211> LENGTH: 21
<212> TYPE: DNA
<213> ORGANISM: Artificial sequence
<220> FEATURE:
<223> OTHER INFORMATION: Primer

<400> SEQUENCE: 40
gtctgagcct ctctcggtca a                                        21

<210> SEQ ID NO 41
<211> LENGTH: 19
<212> TYPE: DNA
<213> ORGANISM: Artificial sequence
<220> FEATURE:
<223> OTHER INFORMATION: Primer

<400> SEQUENCE: 41
aagggatgct gggctctgt                                           19

<210> SEQ ID NO 42
<211> LENGTH: 30
<212> TYPE: DNA
<213> ORGANISM: Artificial sequence
<220> FEATURE:
<223> OTHER INFORMATION: Probe

<400> SEQUENCE: 42
agcaaagctt ggtgtcttgg cactgttagt                               30

<210> SEQ ID NO 43
<211> LENGTH: 21
<212> TYPE: DNA
<213> ORGANISM: Artificial sequence
<220> FEATURE:

```
<223> OTHER INFORMATION: Primer

<400> SEQUENCE: 43
cagagctggt caaccgtatc c                                              21

<210> SEQ ID NO 44
<211> LENGTH: 21
<212> TYPE: DNA
<213> ORGANISM: Artificial sequence
<220> FEATURE:
<223> OTHER INFORMATION: Primer

<400> SEQUENCE: 44
ggcttaaaca gggagccaaa a                                              21

<210> SEQ ID NO 45
<211> LENGTH: 26
<212> TYPE: DNA
<213> ORGANISM: Artificial sequence
<220> FEATURE:
<223> OTHER INFORMATION: Probe

<400> SEQUENCE: 45
acttcatgat gagctcggag ttcaac                                         26

<210> SEQ ID NO 46
<211> LENGTH: 25
<212> TYPE: DNA
<213> ORGANISM: Artificial sequence
<220> FEATURE:
<223> OTHER INFORMATION: Primer

<400> SEQUENCE: 46
aggagaaaaa caaagaacac cagaa                                          25

<210> SEQ ID NO 47
<211> LENGTH: 25
<212> TYPE: DNA
<213> ORGANISM: Artificial sequence
<220> FEATURE:
<223> OTHER INFORMATION: Primer

<400> SEQUENCE: 47
caattagggc aactcagaaa tagct                                          25

<210> SEQ ID NO 48
<211> LENGTH: 22
<212> TYPE: DNA
<213> ORGANISM: Artificial sequence
<220> FEATURE:
<223> OTHER INFORMATION: Probe

<400> SEQUENCE: 48
ccaactggtc ccccagccaa ga                                             22

<210> SEQ ID NO 49
<211> LENGTH: 21
<212> TYPE: DNA
<213> ORGANISM: Artificial sequence
<220> FEATURE:
<223> OTHER INFORMATION: Primer

<400> SEQUENCE: 49
cagagctggt gaaccgtatc c                                              21
```

```
<210> SEQ ID NO 50
<211> LENGTH: 21
<212> TYPE: DNA
<213> ORGANISM: Artificial sequence
<220> FEATURE:
<223> OTHER INFORMATION: Primer

<400> SEQUENCE: 50
ggcttaagca gggagccaaa a                                              21

<210> SEQ ID NO 51
<211> LENGTH: 26
<212> TYPE: DNA
<213> ORGANISM: Artificial sequence
<220> FEATURE:
<223> OTHER INFORMATION: Probe

<400> SEQUENCE: 51
acttcatgat gagctcggag ttcaac                                         26

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
tcctagtgtt acattaccgc                                                20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
ctcgactaaa gcaggatttc                                                20

<210> SEQ ID NO 54
<211> LENGTH: 17
<212> TYPE: DNA
<213> ORGANISM: Artificial sequence
<220> FEATURE:
<223> OTHER INFORMATION: Primer

<400> SEQUENCE: 54
tggtccccca gccaaga                                                   17

<210> SEQ ID NO 55
<211> LENGTH: 18
<212> TYPE: DNA
<213> ORGANISM: Artificial sequence
<220> FEATURE:
<223> OTHER INFORMATION: Primer

<400> SEQUENCE: 55
cccaccgtgt gacatcca                                                  18

<210> SEQ ID NO 56
<211> LENGTH: 26
<212> TYPE: DNA
<213> ORGANISM: Artificial sequence
<220> FEATURE:
<223> OTHER INFORMATION: Probe
```

```
<400> SEQUENCE: 56
agctatctcc gagctgccct gattgg                                        26
```